United States Patent
Jia et al.

(10) Patent No.: US 8,846,928 B2
(45) Date of Patent: Sep. 30, 2014

(54) BENZAMIDES AND NICOTINAMIDES AS SYK MODULATORS

(75) Inventors: Zhaozhong J. Jia, San Mateo, CA (US); Yonghong Song, Foster City, CA (US); Qing Xu, Foster City, CA (US); Brian Kane, Oakland, CA (US); Shawn M. Bauer, Pacifica, CA (US); Anjali Pandey, Fremont, CA (US)

(73) Assignee: Portola Pharmaceuticals, Inc., South San Francisco, CA (US)

( * ) Notice: Subject to any disclaimer, the term of this patent is extended or adjusted under 35 U.S.C. 154(b) by 217 days.

(21) Appl. No.: 13/287,005

(22) Filed: Nov. 1, 2011

(65) Prior Publication Data

US 2012/0142671 A1 Jun. 7, 2012

Related U.S. Application Data

(60) Provisional application No. 61/409,077, filed on Nov. 1, 2010.

(51) Int. Cl.
| | | |
|---|---|---|
| C07D 249/06 | (2006.01) | |
| C07D 231/38 | (2006.01) | |
| C07D 417/12 | (2006.01) | |
| C07D 257/04 | (2006.01) | |
| C07D 471/04 | (2006.01) | |
| C07D 249/08 | (2006.01) | |
| C07D 275/03 | (2006.01) | |
| C07D 417/14 | (2006.01) | |
| C07D 405/12 | (2006.01) | |
| C07D 495/04 | (2006.01) | |
| C07D 401/12 | (2006.01) | |
| C07D 233/56 | (2006.01) | |
| C07D 213/82 | (2006.01) | |
| C07D 405/14 | (2006.01) | |
| C07D 261/14 | (2006.01) | |
| C07D 209/08 | (2006.01) | |
| C07D 401/14 | (2006.01) | |
| C07D 413/12 | (2006.01) | |
| C07D 231/12 | (2006.01) | |
| C07D 239/48 | (2006.01) | |

(52) U.S. Cl.
CPC ............ *C07D 213/82* (2013.01); *C07D 231/38* (2013.01); *C07D 417/12* (2013.01); *C07D 257/04* (2013.01); *C07D 471/04* (2013.01); *C07D 249/08* (2013.01); *C07D 275/03* (2013.01); *C07D 417/14* (2013.01); *C07D 405/12* (2013.01); *C07D 495/04* (2013.01); *C07D 401/12* (2013.01); *C07D 233/56* (2013.01); *C07D 405/14* (2013.01); *C07D 261/14* (2013.01); *C07D 209/08* (2013.01); *C07D 401/14* (2013.01); *C07D 413/12* (2013.01); *C07D 249/06* (2013.01); *C07D 231/12* (2013.01); *C07D 239/48* (2013.01)
USPC ........ 546/159; 546/114; 546/121; 546/277.1; 546/268.4

(58) Field of Classification Search
CPC ... C07D 249/06; C07D 231/12; C07D 239/48
USPC .................... 546/159, 114, 121, 277.1, 268.1
See application file for complete search history.

(56) References Cited

U.S. PATENT DOCUMENTS 6,797,706 B1 * 9/2004 Hisamichi et al. ............ 514/183
2006/0217417 A1 9/2006 Brunette et al.

FOREIGN PATENT DOCUMENTS

| EP | 1184376 A1 | 3/2002 |
|---|---|---|
| WO | 0046980 | * 12/2000 |
| WO | WO0076980 A1 | 12/2000 |
| WO | WO2005009443 A1 | 2/2005 |
| WO | 2008/024963 | * 2/2008 |
| WO | WO2009136995 A2 | 11/2009 |

OTHER PUBLICATIONS

CAPLus 2000:900621, abstract of WO 2000076980, Dec. 2000.*
International Search Report and Written Opinion, mailed Jun. 21, 2012 for International Application No. PCT/US2011/058826, 16 pages.

* cited by examiner

*Primary Examiner* — D Margaret M. Seaman
(74) *Attorney, Agent, or Firm* — Kilpatrick Townsend & Stockton LLP

(57) ABSTRACT

The present invention is directed to compounds of formula I and pharmaceutically acceptable salts, esters, and prodrugs thereof which are inhibitors of Syk kinase. The present invention is also directed to intermediates used in making such compounds, the preparation of such a compound, pharmaceutical compositions containing such a compound, methods of inhibition Syk kinase activity, methods of inhibition the platelet aggregation, and methods to prevent or treat a number of conditions mediated at least in part by Syk kinase activity, such as Non Hodgkin's Lymphoma.

26 Claims, No Drawings

BENZAMIDES AND NICOTINAMIDES AS SYK MODULATORS

CROSS-REFERENCES TO RELATED APPLICATIONS

This application claims priority under 35 U.S.C. §119(e) from U.S. Provisional Application 61/409,077, filed Nov. 1, 2010, which is incorporated by reference in its entirety herewith.

BACKGROUND OF THE INVENTION

This invention is directed to pyrimidine, pyrrolopyrimidine and purine-based analogs which act as inhibitors of Spleen tyrosine kinase (Syk). This invention is also directed to pharmaceutical compositions containing the pyrimidine compounds and methods of using the compounds or compositions to treat a condition mediated at least in part by syk activity. The invention is also directed to methods of making the compounds described herein.

Protein kinases constitute a large family of structurally related enzymes that are responsible for the control of a variety of signal transduction processes within cells (see, e.g., Hardie and Hanks, The Protein Kinase Facts Book, I and II, Academic Press, San Diego, Calif., 1995). Protein kinases are thought to have evolved from a common ancestral gene due to the conservation of their structure and catalytic function. Almost all kinases contain a similar 250-300 amino acid catalytic domain. The kinases can be categorized into families by the substrates they phosphorylate (e.g., protein-tyrosine, protein-serine/threonine, lipids, etc.). Sequence motifs have been identified that generally correspond to each of these families (see, e.g., Hanks & Hunter, (1995), FASEB J. 9:576-596; Knighton et al., (1991), Science 253:407-414; Hiles et al., (1992), Cell 70:419-429; Kunz et al., (1993), Cell 73:585-596; Garcia-Bustos et al., (1994), EMBO J. 13:2352-2361).

Many diseases are associated with abnormal cellular responses triggered by protein kinase-mediated events. These diseases include autoimmune diseases, inflammatory diseases, bone diseases, metabolic diseases, neurological and neurodegenerative diseases, cancer, cardiovascular diseases, allergies, asthma, alzheimer's disease and hormone-related diseases. As a consequence, there has been substantial efforts in medicinal chemistry to find inhibitors of protein kinases for use as therapeutic agents.

Immunoreceptor tyrosine activation motif (ITAM)-mediated signaling has emerged as a primary event in signaling pathways responsible for human pathologies. ITAM-mediated signaling is responsible for relaying activation signals initiated at classical immune receptors such as T-cell receptors, B-cell receptors, Fc receptors in immune cells and at GPVI and FcγRIIa in platelets to downstream intracellular molecules such as Syk and ZAP-70 (Underhill, D. M and Goodridge, H. S., *Trends Immunol.*, 28:66-73, 2007).

The binding of a ligand to an ITAM-containing receptor triggers signaling events which allows for the recruitment of proteins from a family of nonreceptor tyrosine kinases called the Src family. These kinases phosphorylate tyrosine residues within the ITAM sequence, a region with which the tandem SH2 domains on either Syk or ZAP-70 interact.

Syk, along with Zap-70, is a member of the Syk family of protein tyrosine kinases. The interaction of Syk or ZAP-70 with diphosphorylated ITAM sequences induces a conformation change in the kinases that allows for tyrosine phosphorylation of the kinase itself. Phosphorylated Syk family members activate a multitude of downstream signaling pathway proteins which include Src homology 2 (SH2) domain containing leukocyte-specific phosphoprotein of 76 kDa (SLP-76), Linker of Activation of T-cells (LAT) and PLC (phospholipase C)γ2.

Human pathologies attributed to dysfunctional ITAM-mediated signaling include autoimmune diseases such as rheumatoid arthritis, systemic lupus, multiple sclerosis, hemolytic anemia, immune-thrombocytopenia purpura, and heparin-induced thrombocytopenia and arteriosclerosis. Interestingly, many of the above mentioned diseases are thought to occur through crosslinking of Fc receptors by antibodies which, via Syk, activate a signaling cascade in mast, basophil and other immune cells that result in the release of cell mediators responsible for inflammatory reactions. The release of mediators and the production of cytokines in IgE stimulation-dependent allergic and inflammatory reactions from mast cells and basophiles can be controlled by inhibiting the tyrosine kinase activity of Syk (Rossi, A. B. et al., *J Allergy Clin Immunol.*, 118:749-755, 2006). In immune-thrombocytopenia, antibody bound platelets are cleared by the spleen by an Fc receptor/ITAM/Syk-mediated process (Crow, A. R. et al., *Blood*, 106: abstract 2165, 2005). Drug-induced thrombocytopenia, caused by heparin-platelet factor 4 immune complexes that activate platelet FcγRIIa, also involve Syk signaling downstream of receptor engagement (Reilly, M. P., *Blood*, 98:2442-2447, 2001).

Platelet agonists induce inside-out integrin signaling resulting in fibrinogen binding and platelet aggregation. This initiates outside-in signaling which produces further stimulation of platelets. Syk is activated during both phases of integrin signaling, and inhibition of Syk is shown to inhibit platelet adhesion to immobilized proteins (Law, D. A. et al., *Blood*, 93:2645-2652, 1999). Release of arachidonic acid and serotonin and platelet aggregation induced by collagen are markedly inhibited in platelets derived from Syk deficient mouse (Poole, A. et al., *EMBO J.*, 16:2333-2341, 1997). Thus Syk inhibitors may also possess anticoagulation action.

Because of the role Syk plays in Ig-induced platelet activation, it is likely to be important in arteriosclerosis and restenosis. Arteriosclerosis is a class of diseases characterized by the thickening and hardening of the arterial walls of blood vessels. Although all blood vessels are susceptible to this serious degenerative condition, the aorta and the coronary arteries serving the heart are most often affected. Arteriosclerosis is of profound clinical importance since it can increase the risk of heart attacks, myocardial infarctions, strokes, and aneurysms.

The traditional treatment for arteriosclerosis includes vascular recanalization procedures for less-serious blockages and coronary bypass surgery for major blockages. A serious shortcoming of intravascular procedures is that, in a significant number of treated individuals, some or all of the treated vessels restenose (i.e., re-narrow). For example, restenosis of an atherosclerotic coronary artery after PTCA occurs in 10-50% of patients undergoing this procedure and subsequently requires either further angioplasty or a coronary artery bypass graft. Furthermore, restenosis of an atherosclerotic coronary artery after stenting occurs in 10-20% of patients undergoing this procedure and subsequently requires repeat treatments to maintain adequate blood flow through the affected artery. Restenosis generally occurs in a relatively brief time period, e.g., roughly less than six months, after treatment.

While the exact hormonal and cellular processes promoting restenosis have not been determined, restenosis is thought to be due in part to mechanical injury to the walls of the blood vessels caused by the balloon catheter or other intravascular device. For example, the process of PTCA, in addition to opening the obstructed artery, also injures resident coronary arterial smooth muscle cells (SMCs). In response to this injury, adhering platelets, infiltrating macrophages, leukocytes, or the smooth muscle cells themselves release cell-derived growth factors such as platelet-derived growth factor (PDGF), with subsequent proliferation and migration of medial SMCs through the internal elastic lamina to the area of the vessel intima. Further proliferation and hyperplasia of intimal SMCs and, most significantly, production of large amounts of extracellular matrix over a period of three to six months results in the filling in and narrowing of the vascular space sufficient to significantly obstruct blood flow.

In addition to the role Syk plays in Ig-induced platelet activations, Syk plays a very important role in collagen-mediated signaling. The primary adhesive protein responsible for platelet adhesion and activation is collagen. Collagen is a filamentous protein contained within the fibrotic caps of atheromas which becomes exposed to blood during plaque rupture. Collagen functions initially by binding von Willebrand factor which tethers platelets through binding platelet membrane GPIb. Collagen functions secondarily by engaging the two collagen receptors on platelets, GPVI and integrin α2β1.

GPVI exists in platelet membranes as a complex with FcRγ, an interaction required for the expression of GPVI. Activation of FcγRIIa on platelets results in platelet shape change, secretion and thrombosis. Signaling by the GPVI/FcRγ complex is initiated by tyrosine phosphorylation of the ITAM domain of FCRγ followed by the recruitment of Syk. Activation of GPVI leads to induction of multiple platelet functions including: activation of integrins β2β1 to achieve firm platelet adhesion, and GP IIb-IIIa which mediates platelet aggregation and thrombosis growth; platelet secretion, allowing for the delivery of inflammatory proteins such as CD40L, RANTES and TGFβ to the vessel wall; and the expression of P-selectin which allows for the recruitment of leukocytes. Therefore, it is believed that Syk inhibitors can inhibit thrombotic events mediated by platelet adhesion, activation and aggregation.

It has been reported that the tyrosine phosphorylation of intracellular protein (activation) induced by stimulation of a receptor for IgG antibody, FcγR, and the phagocytosis mediated by FcγR are considerably inhibited in macrophages derived from Syk deficient mouse (Crowley, M. T. et al., *J. Exp. Med.*, 186:1027-1039, 1997). This suggests that Syk has a markedly important role in the FcγR-mediated phagocytosis of macrophages.

It has also been reported that an antisense oligonucleotide of Syk suppresses the apoptosis inhibition of eosinophils induced by GM-CSF (Yousefi, S. et al., *J. E. Med.*, 183:1407-1414, 1996), showing that Syk is essential for the life extending signal of eosinophils caused by GM-CSF and the like. Since life extension of eosinophils is closely related to the transition of diseases into a chronic state in allergic disorders, such as asthma, Syk inhibitors can also serve as therapeutic agents for chronic eosinophilic inflammation.

Syk is important for the activation of B-cells via a B-cell antigen receptor and is involved in the phosphatidylinositol metabolism and increase in the intracellular calcium concentration caused by the antigen receptor stimulation (Hutchcroft, J E. et al., *J. Biol. Chem.*, 267:8613-8619, 1992; and Takata, M. et al., *EMBO J.*, 13:1341-1349, 1994). Thus, Syk inhibitors may be used to control the function of B-cells and are, therefore, expected to serve as therapeutic agents for antibody-related diseases.

Syk binds to a T-cell antigen receptor, quickly undergoes tyrosine phosphorylation through crosslinking of the receptor and synergistically acts upon intracellular signals mediated by Src tyrosine kinases such as Lck (Couture, C. et al., *Proc. Natl. Acad. Sci. USA,* 91:5301-5305, 1994; and Couture, C. et al., *Mol. Cell. Biol.,* 14:5249-5258, 1994). Syk is present in mature T-cell populations, such as intraepithelial γδ T-cells and naïve αβ T-cells, and has been reported to be capable of phosphorylation of multiple components of the TCR signaling cascade (Latour, S. et. al., *Mol Cell Biol.,* 17:4434-4441, 1997). As a consequence, Syk inhibitors may serve as agents for inhibiting cellular immunity mediated by T-cell antigen receptor.

Recent comparative genomic hybridization studies have identified Syk as another gene important in the pathogenesis of Mantle Cell Lymphoma (MCL) (Chen, R. et al. *Journal of Clinical Oncology,* 2007 ASCO Annual Meeting Proceedings (Post-Meeting Edition). Vol 25, No 18S (June 20 Supplement), 2007: 8056). MCL represents 5-10% of all non-Hodgkins lymphomas and it is a difficult form of lymphoma to treat. It has the worst prognosis among the B cell lymphomas with median survival of three years. It has been reported that Syk is overexpressed in MCL (Rinaldi, A, et. al, *Br. J. Haematol.,* 2006; 132:303-316) and that Syk mediates mTOR (mammalian target of Rapamycin) survival signals in follicular, mantel cell, Burkitt's, and diffuse large B-cell non-Hodgkin's lymphomas (Leseux, L., et. al, Blood, 2006; 108: 4156-4162).

Several lines of evidence suggest that many B-cell lymphomas depend upon B-cell receptor (BCR)-mediated survival signals. BCR signaling induces receptor oligomerization and phosphorylation of Igα and β immunoreceptor tyrosine-based activated motifs by SRC family kinases. ITAM phosphorylation results in the recruitment and activation of Syk that initiates downstream events and amplifies the original BCR signal. Given the role of tonic BCR signaling in normal B cell and Syk-dependent survival of non-Hodgkins lymphoma cell lines in vitro (Chen, L., et. al, *Blood,* 2006; 108:3428-3433), Syk inhibition is a promising rational treatment target for certain B-cell lymphomas and chronic lymphocytic leukemia (CLL) (Stefania Gobessi, Luca Laurenti, Pablo Longo, Laura Carsetti, Giuseppe Leone, Dimitar G. Efremov, Constitutive activation of the protein tyrosine kinase Syk in Chronic Lymphocytic Leukemia B-cells, Blood, 2007, 110, Abstract 1123). Recent data shows that administration of a multikinase inhibitor which inhibits Syk, may have significant clinical activity in CLL patients (Friedberg J W et al, Blood 2010; 115(13),).

The oncogenic potential of the spleen tyrosine kinase (Syk) has been described in a number of different settings. Clinically, Syk over-expression is reported in Mantle Cell Lymphoma (Rinaldi, A, et. al, *Br. J. Haematol.,* 2006; 132:303-316) and the TEL-Syk fusion protein (Translocated ETS Leukemia) generated by a chromosomal translocation (t(9; 12)(q22;p12)) leads to increased Syk activity and is associated with myelodysplastic syndrome (Kuno, Y., et. al, Blood, 2001; 97:1050-1055). Leukemia is induced in mice by adoptively transferring bone marrow cells that express human TEL-Syk (Wossning, T., JEM, 2006; 203:2829-2840). Further, in mouse primary bone marrow cells, over-expression of Syk results in IL-7 independent growth in culture (Wossning, T., et. al, JEM, 2006; 203:2829-2840). Additional recent studies also suggest that Syk-dependant survival signals may play a role in B-cell malignancies, including DLBCL, mantle cell lymphoma and follicular lymphoma (Gururajan, Jennings et al. 2006; Irish, Czerwinski et al. J Immunol 176(10): 5715-9 (2006). Given the role of tonic BCR signaling in normal B cells and Syk-dependent survival of NHL cell lines in vitro, the specific inhibition of Syk may prove promising for the treatment of certain B-cell lymphomas.

Interestingly, Syk signaling appears to be required for B-cell development and survival in humans and mouse. Inducible loss of the B-cell receptor (Lam, K., et. al, Cell, 1997; 90:1073-1083) or Igα (Kraus, M., et. al, Cell, 2004; 117:787-800) results in loss of peripheral B-cells in mice. Over-expression of the protein tyrosine phosphatase PTP-RO, which is known to negatively regulate Syk activity, inhibits proliferation and induces apoptosis in cell lines derived from non-Hodgkin's lymphomas (Chen, L., et. al, Blood, 2006; 108:3428-3433). Finally, B-cell lymphomas rarely exhibit loss of BCR expression, and anti-idiotype therapy rarely leads to resistance (Kuppers, R. Nat Rev Cancer, 2005; 5:251-262).

Engagement of the antigen-specific B cell receptor (BCR) activates multiple signaling pathways that ultimately regulate the cells activation status, promoting survival and clonal expansion. Signaling through the BCR is made possible by its association with two other members of the immunoglobulin super-family; Igα and Igβ, each bearing an immuno-tyrosine based activation motif (ITAM) (Jumaa, Hendriks et al. Annu Rev Immunol 23: 415-45 (2005). The ITAM domain is directly phosphorylated by Src family kinases in response to BCR engagement. The spleen tyrosine kinase (Syk) docks with and phosphorylates the ITAM, a process that enhances its kinase activity, resulting in Syk autophosphorylation and tyrosine phosphorylation of multiple downstream substrates (Rolli, Gallwitz et al. Mol Cell 10(5): 1057-69 (2002). This signaling pathway is active in B cells beginning at the transition from pro- to pre-B cell stage of development, when the newly formed pre-BCR is expressed. In fact, B cell development arrests at the pro-B cell stage in Syk knockout mice (Cheng, Rowley et al. 1995; Turner, Mee et al. Nature 378 (6554): 303-6 (1995). Inducible loss of the B cell receptor (Lam, Kuhn et al. Cell 90(6): 1073-83 (1997) or Igα (Kraus, Alimzhanov et al. Cell 117(6): 787-800 (2004) results in loss of peripheral B cells in mice. Human B cells also appear to require Syk for proliferation and survival. Over-expression of the protein tyrosine phosphatase PTP-RO, a negative regulator of Syk activity, inhibits proliferation and induces apoptosis in cell lines derived from non-Hodgkin's lymphomas (NHL) (Chen, Juszczynski et al. Blood 108(10): 3428-33 (2006). Knock down of Syk by siRNA in the NHL line SUDHL-4 led to a block in the G1/S transition of the cell cycle (Gururajan, Dasu et al. J Immunol 178(1): 111-21 (2007). Together, these data suggest that Syk signaling is required for the development, proliferation, and even survival of human and mouse B cells.

Recently, R406 (Rigel Pharmaceuticals) was reported to inhibit ITAM signaling in response to various stimuli, including FcεR1 and BCR induced Syk activation (Braselmann, Taylor et al. J Pharmacol Exp Ther 319(3): 998-1008 (2006). Interestingly, this ATP-competitive inhibitor of Syk was also active against Flt3, cKit, and JAK kinases, but not against Src kinase (Braselmann, Taylor et al. 2006). Activating mutations to Flt3 are associated with AML and inhibition of this kinase is currently under clinical development (Burnett and Knapper Hematology Am Soc Hematol Educ Program 2007: 429-34 (2007). Over-activation of the tyrosine kinase cKit is also associated with hematologic malignancies, and a target for cancer therapy (Heinrich, Griffith et al. Blood 96(3): 925-32 (2000). Similarly, JAK3 signaling is implicated in leukemias and lymphomas, and is currently exploited as a potential therapeutic target (Heinrich, Griffith et al. 2000). Importantly, the multi-kinase inhibitory activity of R406 attenuates BCR signaling in lymphoma cell lines and primary human lymphoma samples, resulting in apoptosis of the former (Chen, Monti et al. Blood 111(4): 2230-7 (2008). Further, a phase II clinical trial reported favorable results by this compound in refractory NHL and chronic lymphocytic leukemia (Friedberg J W et al, Blood 2010; 115(13)). Although the precise mechanism of action is unclear for R406, the data suggest that inhibition of kinases that mediate survival signaling in lymphocytes is clinically beneficial.

Additional recent studies also suggest that Syk-dependant survival signals may play a role in B-cell malignancies, including DLBCL, mantle cell lymphoma and follicular lymphoma (see e.g., S. Linfengshen et al. Blood, February 2008; 111: 2230-2237; J. M. Irish et al. Blood, 2006; 108: 3135-3142; A. Renaldi et al. Brit J. Haematology, 2006; 132: 303-316; M. Guruoajan et al. J. Immunol, 2006; 176: 5715-5719; L. Laseux et al. Blood, 2006; 108: 4156-4162.

Patents and patent applications describing substituted pyrimidinediamine compounds include: U.S. application Ser. No. 10/355,543 filed Jan. 31, 2003 (US2004/0029902A1), international application Serial No. PCT/US03/03022 filed Jan. 31, 2003 (WO 03/063794), U.S. application Ser. No. 10/631,029 filed Jul. 29, 2003, international application Serial No. PCT/US03/24087 (WO 04/014382), U.S. application Ser. No. 10/903,263 filed Jul. 30, 2004, and international application Serial No. PCT/US2004/24716 (WO 05/016893), the disclosures of which are incorporated herein by reference. Substituted pyrimidinediamine compounds are also described in international patent application publication numbers: WO 02/059110, WO 03/074515, WO 03/106416, WO 03/066601, WO 03/063794, WO 04/046118, WO 05/016894, WO 05/122294, WO 05/066156, WO 03/002542, WO 03/030909, WO 00/39101, WO 05/037800 and U.S. Pat. Pub. No. 2003/0149064.

While progress has been made in this field, there remains a need in the art for compounds that inhibit Syk kinase, as well as for methods for treating conditions in a patient, such as restenosis, and/or inflammation that can benefit from such inhibition. Moreover, the availability of compounds that selectively inhibit one of these kinases as compared to other kinases would also be desirable. The present invention satisfies this and other needs.

BRIEF SUMMARY OF THE INVENTION

The present invention provides novel compounds having activity as inhibitors of Syk activity (also referred to herein as "Syk inhibitors") as well as to methods for their preparation and use, and to pharmaceutical compositions containing the same. Such compounds have the following structure (I):

The present invention provides in one embodiment, a compound of having the formula (I):

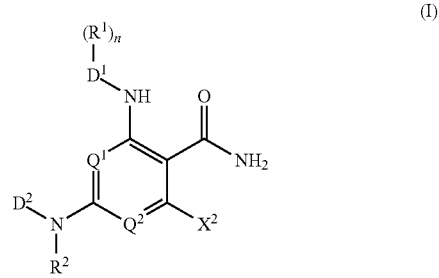

or a tautomer thereof or a pharmaceutically acceptable salt or hydrate thereof, wherein $D^1$, $R^1$, $D^2$, $R^2$, $Q^1$, $Q^2$, $X^2$ and n are as defined below.

The present invention also provides a pharmaceutical composition comprising a therapeutically effective amount of a compound of formula I, or a pharmaceutical acceptable salt thereof, and a pharmaceutically acceptable carrier and/or diluent.

The compounds of the present invention have utility over a wide range of therapeutic applications, and may be used to treat a variety of conditions, mediated at least in part by Syk activity, in both men and women, as well as a mammal in general (also referred to herein as a "subject"). For example, such conditions include, but are not limited to, those associated with cardiovascular disease, inflammatory disease or autoimmune disease. More specifically, the compounds of the present invention have utility for treating conditions or disorders including, but not limited to: restenosis, inflammation, heparin induced thrombocytopenia, dilated cardiomyopathy, sickle cell disease, atherosclerosis, myocardial infarction, vascular inflammation, unstable angina, acute coronary syndromes, allergy, asthma, rheumatoid arthritis, B-cell mediated diseases such as Non Hodgkin's lymphoma, Crohn's disease, anti-phospholipid syndrome, lupus, psoriasis, multiple sclerosis, and chronic lymphocytic leukemia. Thus, in one embodiment, methods are disclosed which include the administration of an effective amount of a compound of formula (I), typically in the form of a pharmaceutical composition, to a subject in need thereof.

The present invention also provides a method for inhibiting the Syk activity of a blood sample comprising contacting said sample with a compound of the present invention.

The present invention further provides compounds in purified forms, as well as chemical intermediates.

These and other aspects, objects, features and advantages of the invention will be apparent upon reference to the following detailed description and figures. To this end, various references are set forth herein which describe in more detail certain background information, procedures, compounds and/or compositions, and are each hereby incorporated by reference in their entirety.

DETAILED DESCRIPTION OF THE INVENTION

As used herein, the below terms have the following meanings unless specified otherwise:

1. Abbreviations and Definitions

The abbreviations used herein are conventional, unless otherwise defined. The following abbreviations are used: AcOH=acetic acid, AIBN=azobisisobutyronitrile (also azobisisobutylonitrile), aq.=aqueous, Boc=t-butylcarboxy, Bz-benzyl, BOP=benzotriazol-1-yloxytris(dimethylamino)-phosphonium hexafluorophosphate, BPO=benzoyl peroxide, nBuOH=n-butanol, $CBr_4$=tetrabromomethane, mCPBA=m-chloroperoxybenzoic acid, $CH_2Cl_2$ or DCM=dichloromethane, $Cs_2CO_3$=cesium carbonate, $CuCl_2$=copper chloride; DIBAL=diisobutylaluminum hydride, DIEA=Hunig's base or diisopropyl ethylamine, DME=dimethoxy-ethane, DMF=dimethyl formamide, DMSO=dimethyl sulfoxide, DPPA=diphenyl phosphoryl azide, $Et_3N$=triethylamine, EtOAc=ethyl acetate, g=gram, HATU=2-(1H 7-Azabenzotriazol-1-yl)-1,1,3,3-tetramethyl uronium hexafluorophosphate, $H_2$=hydrogen; $H_2O$=water; HBr=hydrogen bromide; HCl=hydrogen chloride, HIV=human immunodeficiency virus, HPLC=high pressure liquid chromatography, h=hour, IgE=immunoglobulin E, $IC_{50}$=The concentration of an inhibitor that is required for 50% inhibition of an enzyme in vitro, IPA=isopropyl alcohol, kg=kilogram, KCN=potassium cyanide, KOH=potassium hydroxide, $K_2PO_4$=potassium phosphate, LDA=lithium diisopropylamide, $LiAlH_4$=lithium aluminum hydride=LiOH: lithium hydroxide; MeCN=acetonitrile; MS=Mass Spec, m/z=mass to charge ratio, MHz=Mega Hertz, MeOH=methanol, μM=micromolar, μL=microliter, mg=milligram, mm=millimeter, mM=millimolar, mmol=millimole, mL=milliliter, mOD/min=millioptical density units per minute, min=minute, M=molar, $Na_2CO_3$=sodium carbonate, ng=nanogram, $NaHCO_3$=sodium bicarbonate; $NaNO_2$=sodium nitrite; NaOH=sodium hydroxide; $Na_2S_2O_3$=sodium thiosulfate; $Na_2SO_4$=sodium sulfate; NBS=N-bromosuccinimide; $NH_4Cl$=ammonium chloride; $NH_4OAc$=ammonium acetate; NaSMe=sodium methylthiolate, NBS=N-bromosuccinamide, n-BuLi=n-butyl lithium, nm=nanometer, nM=nanomolar, N=Normal, NMP=N-methylpyrrolidone, NMR=nuclear magnetic resonance, Pd/C=palladium on carbon, $Pd(PPh_3)_4$=Tetrakis-(triphenyl-phosphine)-palladium, pM=picomolar, Pin=pinacolato, PEG=polyethylene glycol, $PPh_3$ or $Ph_3P$=triphenyl phosphine, RLV=Raucher leukemia virus, Ra—Ni=Rainey Nickel, $SOCl_2$=thionyl chloride, RT=room temperature, TEA=triethylamine, THF=tetrahydrofuran, TFA=trifluoroacetic acid, TLC=thin layer chromatography, TMS=trimethylsilyl, Tf=trifluoromethylsulfonyl and TSC=trisodium citrate.

It is noted here that as used in this specification and the appended claims, the singular forms "a," "an," and "the" include plural reference unless the context clearly dictates otherwise.

"Alkyl," by itself or as part of another substituent, means, unless otherwise stated, a straight or branched chain, fully saturated aliphatic hydrocarbon radical having the number of carbon atoms designated. For example, "$C_{1-8}$alkyl" refers to a hydrocarbon radical straight or branched, containing from 1 to 8 carbon atoms that is derived by the removal of one hydrogen atom from a single carbon atom of a parent alkane. The phrase "unsubstituted alkyl" refers to alkyl groups that do not contain groups other than fully saturated aliphatic hydrocarbon radicals. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups such as isopropyl, t-butyl, isobutyl, sec-butyl, and the like. Representative alkyl groups include straight and branched chain alkyl groups having 1, 2, 3, 4, 5, 6, 7, 8, 9, 10, 11 or 12 carbon atoms. Further representative alkyl groups include straight and branched chain alkyl groups having 1, 2, 3, 4, 5, 6, 7 or 8 carbon atoms.

"Alkylene" by itself or as part of another substituent means a divalent radical derived from an alkane, as exemplified by —$CH_2CH_2CH_2CH_2$—. Typically, an alkylene group will have from 1, 2, 3, 4, 5, 6, 7 or 8 carbon atoms that is derived by the removal of one hydrogen atom from a single carbon atom of a parent alkyl.

"Cycloalkyl" or "carbocycle", by themselves or in combination with other terms, represent, unless otherwise stated, cyclic versions of "alkyl", "alkenyl" and "alkynyl" in which all ring atoms are carbon. "Cycloalkyl" or "carbocycle" refers to a mono- or polycyclic group. When used in connection with cycloalkyl substituents, the term "polycyclic" refers herein to fused and non-fused alkyl cyclic structures. "Cycloalkyl" or "carbocycle" may faun a bridged ring or a spiro ring. The cycloalkyl group may have one or more double or triple bond(s). The term "cycloalkenyl" refers to a cycloalkyl group that has at least one site of alkenyl unsaturation between the ring vertices. The term "cycloalkynyl" refers to a cycloalkyl group that has at least one site of alkynyl unsaturation between the ring vertices. When "cycloalkyl" is used in combination with "alkyl", as in $C_{3-8}$cycloalkyl$C_{3-8}$ alkylene-, the cycloalkyl portion is meant to have the stated number of carbon atoms (e.g., from three to eight carbon atoms), while the alkylene portion has from one to eight carbon atoms. Typical cycloalkyl substituents have from 3 to 8 ring atoms. Examples of cycloalkyl include cyclopentyl, cyclohexyl, 1-cyclohexenyl, 3-cyclohexenyl, cycloheptyl, and the like.

"Aryl" by itself or as part of another substituent refers to a polyunsaturated, aromatic, hydrocarbon group containing from 6 to 14 carbon atoms, which can be a single ring or multiple rings (up to three rings) which are fused together or linked covalently. Thus the phrase includes, but is not limited to, groups such as phenyl, biphenyl, anthracenyl, naphthyl by way of example. Non-limiting examples of unsubstituted aryl groups include phenyl, 1-naphthyl, 2-naphthyl and 4-biphenyl. "Substituted aryl group" includes, for example, —CH$_2$OH (one carbon atom and one heteroatom replacing a carbon atom) and —CH$_2$SH. The term "heteroalkylene" by itself or as part of another substituent means a divalent radical derived from heteroalkyl, as exemplified by —CH$_2$—CH$_2$—S—CH$_2$CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "heterocycle", "heterocyclyl" or "heterocyclic" refer to a saturated or unsaturated non-aromatic cyclic group containing at least one heteroatom. As used herein, the term "heteroatom" is meant to include oxygen (O), nitrogen (N), sulfur (S) and silicon (Si). Each heterocycle can be attached at any available ring carbon or heteroatom. Each heterocycle may have one or more rings. When multiple rings are present, they can be fused together or linked covalently. Each heterocycle typically contains 1, 2, 3, 4 or 5, independently selected heteroatoms. Preferably, these groups contain 1, 2, 3, 4, 5, 6, 7, 8, 9 or 10 carbon atoms, 0, 1, 2, 3, 4 or 5 nitrogen atoms, 0, 1 or 2 sulfur atoms and 0, 1 or 2 oxygen atoms. More preferably, these groups contain 1, 2 or 3 nitrogen atoms, 0-1 sulfur atoms and 0-1 oxygen atoms. Non-limiting examples of heterocycle groups include morpholin-3-one, piperazine-2-one, piperazin-1-oxide, pyridine-2-one, piperidine, morpholine, piperazine, isoxazoline, pyrazoline, imidazoline, pyrazol-5-one, pyrrolidine-2,5-dione, imidazolidine-2,4-dione, pyrrolidine, tetrahydroquinolinyl, decahydroquinolinyl, tetrahydrobenzooxazepinyl dihydrodibenzooxepin and the like.

"Heteroaryl" refers to a cyclic or polycyclic aromatic radical that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom or through a carbon atom and can contain 5 to 10 carbon atoms. Non-limiting examples of heteroaryl groups include 1-pyrrolyl, 2-pyrrolyl, 3-pyrrolyl, 1-pyrazolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl and 4-pyrimidyl. If not specifically stated, substituents for each of the above noted aryl and heteroaryl ring systems are selected from the group of acceptable substituents described herein. "Substituted heteroaryl" refers to a unsubstituted heteroaryl group as defined above in which one or more of the ring members is bonded to a non-hydrogen atom such as described above with respect to substituted alkyl groups and substituted aryl groups. Representative substituents include straight and branched chain alkyl groups —CH$_3$, —C$_2$H$_5$, —CH$_2$OH, —OH, —OCH$_3$, —OC$_2$H$_5$, —OCF$_3$, —OC(=O)CH$_3$, —OC(=O)NH$_2$, —OC(=O)N(CH$_3$)$_2$, —CN, —NO$_2$, —C(=O)CH$_3$, —CO$_2$H, —CO$_2$CH$_3$, —CONH$_2$, —NH$_2$, —N(CH$_3$)$_2$, —NHSO$_2$CH$_3$, —NHCOCH$_3$, —NHC(=O)OCH$_3$, —NHSO$_2$CH$_3$, —SO$_2$CH$_3$, —SO$_2$NH$_2$ and halo.

"Bicyclic heteroaryl" refers to bicyclic aromatic radical that contain from one to five heteroatoms selected from N, O, and S, wherein the nitrogen and sulfur atoms are optionally oxidized, and the nitrogen atom(s) are optionally quaternized. A bicyclic heteroaryl group can be attached to the remainder of the molecule through a heteroatom or through a carbon atom and can contain 5 to 10 carbon atoms. Non-limiting examples of bicyclic heteroaryl groups include 5-benzothiazolyl, purinyl, 2-benzimidazolyl, benzopyrazolyl, 5-indolyl, azaindole, 1-isoquinolyl, 5-isoquinolyl, 2-quinoxalinyl, 5-quinoxalinyl, 3-quinolyl and 6-quinolyl. If not specifically stated, substituents for each of the above noted aryl and heteroaryl ring systems are selected from the group of acceptable substituents described herein.

In each of the above embodiments designating a number of atoms e.g. "$C_{1-8}$" is meant to include all possible embodiments that have one fewer atom. Non-limiting examples include $C_{1-7}$, $C_{2-8}$, $C_{2-7}$, $C_{3-8}$, $C_{3-7}$ and the like.

Each of the terms herein (e.g., "alkyl," "cycloalkyl", "heteroalkyl," "aryl" and "heteroaryl") is meant to include both "unsubstituted" and optionally "substituted" forms of the indicated radical, unless otherwise indicated. Typically each radical is substituted with 0, 1, 2,3,4 or 5 substituents, unless otherwise indicated. Examples of substituents for each type of radical are provided below.

"Substituted" refers to a group as defined herein in which one or more bonds to a carbon(s) or hydrogen(s) are replaced by a bond to non-hydrogen and non-carbon atom "substituents" such as, but not limited to, a halogen atom such as F, Cl, Br, and I; an oxygen atom in groups such as hydroxyl groups, alkoxy groups, aryloxy, and acyloxy groups; a sulfur atom in groups such as thiol groups, alkyl and aryl sulfide groups, sulfone groups, sulfonyl groups, and sulfoxide groups; a nitrogen atom in groups such as amino, alkylamines, dialkylamines, arylamines, alkylarylamines, diarylamines, alkoxyamino, hydroxyamino, acylamino, sulfonylamino, N-oxides, imides, and enamines; and other heteroatoms in various other groups. "Substituents" also include groups in which one or more bonds to a carbon(s) or hydrogen(s) atom is replaced by a higher-order bond (e.g., a double- or triple-bond) to a heteroatom such as oxygen in oxo, acyl, amido, alkoxycarbonyl, aminocarbonyl, carboxyl, and ester groups; nitrogen in groups such as imines, oximes, hydrazones, and nitriles. "Substituents" further include groups in which one or more bonds to a carbon(s) or hydrogen(s) atoms is replaced by a bond to a cycloalkyl, heterocyclyl, aryl, and heteroaryl groups. Representative "substituents" include, among others, groups in which one or more bonds to a carbon or hydrogen atom is/are replaced by one or more bonds to fluoro, chloro, or bromo group. Another representative "substituent" is the trifluoromethyl group and other groups that contain the trifluoromethyl group. Other representative "substituents" include those in which one or more bonds to a carbon or hydrogen atom is replaced by a bond to an oxygen atom such that the substituted alkyl group contains a hydroxyl, alkoxy, or aryloxy group. Other representative "substituents" include alkyl groups that have an amine, or a substituted or unsubstituted alkylamine, dialkylamine, arylamine, (alkyl)(aryl)amine, diarylamine, heterocyclylamine, diheterocyclylamine, (alkyl)(heterocyclyl)amine, or (aryl)(heterocyclyl)amine group. Still other representative "substituents" include those in which one or more bonds to a carbon(s) or hydrogen(s) atoms is replaced by a bond to an alkyl, cycloalkyl, aryl, heteroaryl, or heterocyclyl group.

The herein-defined groups may include prefixes and/or suffixes that are commonly used in the art to create additional well-recognized substituent groups. As examples, "alkylamino" refers to a group of the formula —$NR^aR^b$. Unless stated otherwise, for the following groups containing $R^a$, $R^b$, $R^c$, $R^d$ and $R^e$: $R^a$, and $R^b$ are each independently selected from H, alkyl, alkoxy, thioalkoxy, cycloalkyl, aryl, heteroaryl, or heterocyclyl or are optionally joined together with the atom(s) to which they are attached to form a cyclic group. When $R^a$ and $R^b$ are attached to the same nitrogen atom, they can be combined with the nitrogen atom to form a 5-, 6- or 7-membered ring. For example, —$NR^aR^b$ is meant to include 1-pyrrolidinyl and 4-morpholinyl.

$R^c$, $R^d$, $R^e$ and $R^f$ are each independently selected from alkyl, alkenyl, alkynyl, cycloalkyl, cycloalkenyl, aryl, heteroaryl, heterocyclyl or alkylenearyl as defined herein.

Typically, a particular radical will have 0, 1, 2 or 3 substituents, with those groups having two or fewer substituents being preferred in the present invention. More preferably, a radical will be unsubstituted or monosubstituted. Most preferably, a radical will be unsubstituted.

"Substituents" for the alkyl and heteroalkyl radicals (as well as those groups referred to as alkylene, alkenyl, heteroalkylene, heteroalkenyl, alkynyl, cycloalkyl, heterocyclyl) can be a variety of groups selected from: —$OR^a$, =O, =$NR^a$, =N—$OR^a$, —$NR^aR^b$, —$SR^a$, halogen, —$SiR^aR^b R^c$, —OC(O)$R^a$, —C(O)$R^a$, —$CO_2R^a$, —CONR$^a$R$^b$, —OC(O)NR$^a$R$^b$, —NR$^b$C(O)R$^a$, —NR$^a$—C(O)NR$^b$R$^c$, —NR$^a$—SO$_2$NR$^b$R$^c$, —NR$^b$CO$_2$R$^a$, —NH—C(NH$_2$)=NH, —NR$^a$C(NH$_2$)=NH, —NH—C(NH$_2$)=NR$^a$, —S(O)R$^a$, —SO$_2$R$^a$, —SO$_2$NR$^a$R$^b$, —NR$^b$SO$_2$R, —CN and —NO$_2$, in a number ranging from zero to three, with those groups having zero, one or two substituents being particularly preferred.

In some embodiments, "substituents" for the alkyl and heteroalkyl radicals are selected from: —OR$^a$, =O, —NR$^a$R$^b$, —SR$^a$, halogen, —SiR$^a$R$^b$R$^c$, —OC(O)R$^a$, —C(O)R$^a$, —CO$_2$R$^a$, —CONR$^a$R$^b$, —OC(O)NR$^a$R$^b$, —NR$^b$C(O)R$^a$, —N R$^b$CO$_2$R$^a$, —NR$^a$—SO$_2$NR$^b$R$^c$, —S(O)R$^a$, —SO$_2$R$^a$, —SO$_2$NR$^a$R$^b$, —NR$^c$SO$_2$R, —CN and —NO$_2$, where R$^a$ and R$^b$ are as defined above. In some embodiments, substituents are selected from: —OR$^a$, =O, —NR$^a$R$^b$, halogen, —OC(O) R$^a$, —CO$_2$R$^a$, —CONR$^a$R$^b$, —OC(O)NR$^a$R$^b$, —NR$^b$C(O)R$^a$, —NR$^b$CO$_2$R$^a$, —NR$^a$—SO$_2$NR$^b$R$^c$, —SO$_2$R$^a$, —SO$_2$NR$^a$R$^b$, —NR"SO$_2$R, —CN and —NO$_2$.

Examples of substituted alkyl are: —(CH$_2$)$_3$NH$_2$, —(CH$_2$)$_3$NH(CH$_3$), —(CH$_2$)$_3$NH(CH$_3$)$_2$, —CH$_2$C(=CH$_2$) CH$_2$NH$_2$, —CH$_2$C(=O)CH$_2$NH$_2$, —CH$_2$S(=O)$_2$CH$_3$, —CH$_2$OCH$_2$NH$_2$, —CO$_2$H. Examples of substituents of substituted alkyl are: CH$_2$OH, —OH, —OCH$_3$, —OC$_2$H$_5$, —OCF$_3$, —OC(=O)CH$_3$, —OC(=O)NH$_2$, —OC(=O)N (CH$_3$)$_2$, —CN, —NO$_2$, —C(=O)CH$_3$, —CO$_2$H, —CO$_2$CH$_3$, —CONH$_2$, —NH$_2$, —N(CH$_3$)$_2$, —NHSO$_2$CH$_3$, —NHCOCH$_3$, —NHC(=O)OCH$_3$, —NHSO$_2$CH$_3$, —SO$_2$CH$_3$, —SO$_2$NH$_2$, and halo.

Similarly, "substituents" for the aryl and heteroaryl groups are varied and are selected from: -halogen, —OR$^a$, —OC(O) R$^a$, —NR$^a$R$^b$, —SR$^a$, —R$^a$, —CN, —NO$_2$, —CO$_2$R$^a$, —CONR$^a$R$^b$, —C(O)R$^a$, —OC(O)NR$^a$R$^b$, —NR$^b$C(O)R$^a$, —NR$^b$C(O)$_2$R$^a$, —NR$^a$—C(O)NR$^b$R$^c$, —NH—C(NH$_2$)=NH, —NR$^a$C(N H$_2$)=NH, —NH—C(NH$_2$)=NR$^a$, —S(O)R$^a$, —S(O)$_2$R$^a$, —S(O)$_2$NR$^a$R$^b$, —N$_3$, —CH(Ph)$_2$, perfluoroC$_{1-8}$alkoxy, and perfluoroC$_{1-8}$alkyl, in a number ranging from zero to the total number of open valences on the aromatic ring system; and where R$^a$, R$^b$ and R$^c$ are independently selected from hydrogen, C$_{1-6}$alkyl and heteroalkyl, unsubstituted aryl and heteroaryl, (unsubstituted aryl)-C$_{1-8}$alkyl, and (unsubstituted aryl)oxy-C$_{1-8}$alkyl.

Two of the "substituents" on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is 0, 1 or 2. Alternatively, two of the substituents on adjacent atoms of the aryl or heteroaryl ring may optionally be replaced with a substituent of the formula -A-(CH$_2$)$_r$—B—, wherein A and B are independently —CH$_2$—, —O—, —NH—, —S—, —S(O)—, —S(O)$_2$—, —S(O)$_2$NR$^a$— or a single bond, and r is 1, 2 or 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_S$—X—(CH$_2$)$_t$—, where s and t are independently integers of from 0 to 3, and X is —O—, —NR$^a$—, —S—, —S(O)—, —S(O)$_2$—, or —S(O)$_2$NR$^a$—. The substituent R$^a$ in —NR$^a$— and —S(O)$_2$NR$^a$— is selected from hydrogen or unsubstituted C$_{1-6}$alkyl. Otherwise, R' is as defined above.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

The term "acyl" refers to the group —C(=O)R$^c$ where R$^c$ is alkyl, alkenyl, alkynyl, cycloalkyl, cycloalkenyl, aryl, heteroaryl or heterocyclyl. Acyl includes the "acetyl" group —C(=O)CH$_3$.

"Acylamino-" refers to the group —NR$^a$C(=O)R$^c$ where R$^c$ is alkyl, alkenyl, alkynyl, cycloalkyl, cycloalkenyl, aryl, heteroaryl or heterocyclyl.

"Acyloxy" refers to —OC(=O)—R$^c$ where R$^c$ is alkyl, alkenyl, alkynyl, cycloalkyl, cycloalkenyl, aryl, heteroaryl or heterocyclyl.

"Alkoxy" refers to —OR$^d$ wherein R$^d$ is alkyl as defined herein. Representative examples of alkoxy groups include methoxy, ethoxy, t-butoxy, trifluoromethoxy, and the like.

"Alkoxyamino" refers to the group —NHOR$^d$ where R$^d$ is alkyl.

"Alkoxyalkyleneamino" refers to the group —NR$^a$-alkylene-OR$^d$ where R$^d$ is alkyl and —NR$^a$— is defined in amino.

"Alkoxycarbonyl" refers to —C(=O)OR$^d$ wherein R$^d$ is alkyl. Representative alkoxycarbonyl groups include, for example, those shown below.

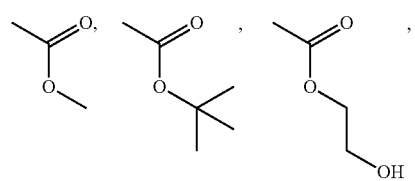

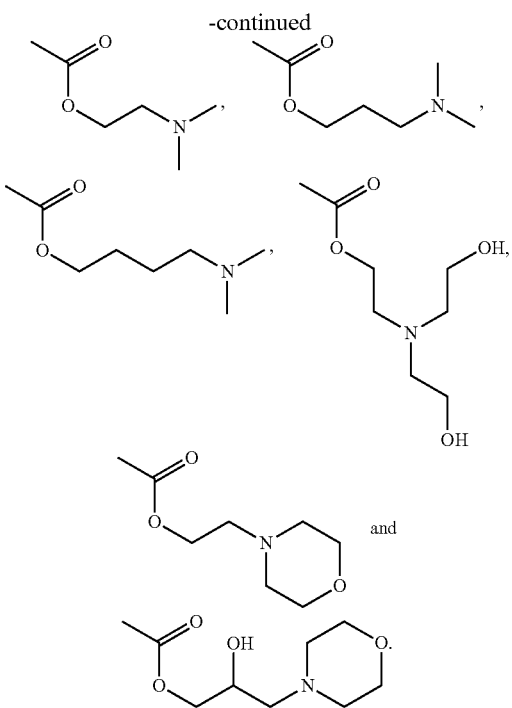

These alkoxycarbonyl groups can be further substituted as will be apparent to those having skill in the organic and medicinal chemistry arts in conjunction with the disclosure herein.

"Alkoxycarbonylalkylene" refers to the group -alkylene-C(=O)OR$^d$ wherein R$^d$ is alkyl.

"Alkoxycarbonylamino" refers to —NR$^a$C(=O)OR$^d$ wherein R$^d$ is alkyl.

"Alkoxycarbonylaminoalkylene" refers to -alkylene-NR$^a$C(=O)OR$^d$ wherein R$^d$ is alkyl.

"Alkoxycarbonylalkyleneaminosulfonyl" refers to —SO$_2$NR$^a$-alkyleneC(=O)OR$^d$ wherein R$^d$ is alkyl.

"Alkoxysulfonylamino" refers to the group —NR$^a$S(=O)$_2$—OR$^d$ where R$^d$ is alkyl.

"Alkylcarbonyl" refers to the group —C(=O)R$^c$ where R$^c$ is alkyl.

"Alkylcarbonyloxy" refers to —OC(=O)—R$^c$ where R$^c$ is alkyl.

"Alkylcarbonylamino" refers to —NR$^a$C(=O)R$^c$ wherein R$^c$ is alkyl. Representative alkylcarbonylamino groups include, for example, —NHC(=O)CH$_3$, —NHC(=O)CH$_2$CH$_3$, —NHC(=O)CH$_2$NH(CH$_3$), —NHC(=O)CH$_2$N(CH$_3$)$_2$, or —NHC(=O)(CH$_2$)$_3$OH.

"Alkylheterocyclyl" refers to the group -heterocyclyl-R$^d$, where R$^d$ is alkyl.

"Alkylheterocyclylalkylene" refers to the group -alkylene-heterocyclyl-R$^d$, where R$^d$ is alkyl.

"Alkylsulfanyl", "alkylthio", or "thioalkoxy" refers to the group S—R$^d$, where R$^d$ is alkyl.

"Alkylsulfinyl" refers to —S(=O)R$^e$ where R$^e$ is alkyl. Alkylsulfonyl groups employed in compounds of the present invention are typically C$_{1-6}$alkylsulfinyl groups.

"Alkylsulfonyl" refers to —S(=O)$_2$R$^e$ where R$^e$ is alkyl. Alkylsulfonyl groups employed in compounds of the present invention are typically C$_{1-6}$alkylsulfonyl groups.

"Alkylsulfonylalkylene" refers to -alkylene-S(=O)$_2$R$^e$ where R$^e$ is alkyl. Alkylsulfonyl groups employed in compounds of the present invention are typically C$_{1-6}$alkylsulfonyl groups.

"Alkylsulfonylamino" refers to —NR$^a$S(=O)$_2$—R$^e$ wherein R$^e$ is alkyl.

"Alkynyloxy" refers to the group —O-alkynyl, wherein alkynyl is as defined herein. Alkynyloxy includes, by way of example, ethynyloxy, propynyloxy, and the like.

"Amidino" refers to the group —C(=NR$^a$)NR$^b$R$^c$, wherein R$^b$ and R$^c$ independently are selected from the group consisting of hydrogen, alkyl, substituted alkyl, alkenyl, alkynyl, aryl, cycloalkyl, cycloalkenyl, heteroaryl, heterocyclic, and where R$^b$ and R$^c$ are optionally joined together with the nitrogen bound thereto to form a heterocyclic or substituted heterocyclic group. R$^a$ is selected from the group consisting of hydrogen, alkyl, alkenyl, alkynyl, cycloalkynyl, aryl, cycloalkyl, cycloalkenyl, heteroaryl, heterocyclic, substituted heterocyclic, nitro, nitroso, hydroxy, alkoxy, cyano, —N=N—N-alkyl, —N(alkyl)SO$_2$-alkyl, —N—N=N=N-alkyl, acyl and —SO$_2$-alkyl.

"Amino" refers to a monovalent radical —NR$^a$R$^b$ or divalent radical —NR$^a$—. The term includes "alkylamino" which refers to the group —NR$^a$R$^b$ where R$^a$ is alkyl and R$^b$ is H or alkyl. The term also includes "arylamino" which refers to the group —NR$^a$R$^b$ where at least one R$^a$ or R$^b$ is aryl. The term also includes "(alkyl)(aryl)amino" which refers to the group —NR$^a$R$^b$ where R$^a$ is alkyl and R$^b$ is aryl. Additionally, for dialkylamino groups, the alkyl portions can be the same or different and can also be combined to form a 3-7 membered ring with the nitrogen atom to which each is attached. Accordingly, a group represented as —NR$^a$R$^b$ is meant to include piperidinyl, pyrrolidinyl, morpholinyl, azetidinyl and the like.

"Aminoalkoxy" refers to —O-alkylene-NR$^a$R$^b$.

"Aminoalkylene" refers to -alkylene-NR$^a$R$^b$.

"Aminoalkylenecarbonyl" refers to —C(=O)-alkylene-NR$^a$R$^b$.

"Aminoalkyleneaminocarbonyl" refers to —C(=O)NR$^a$-alkylene-NR$^a$R$^b$.

"Aminoaryl" refers to -aryl-NR$^a$R$^b$.

"Aminocarbonyl" or "aminoacyl" refers to the amide —C(=O)—NR$^a$R$^b$. The term "alkylaminocarbonyl" refers herein to the group —C(=O)—NR$^a$R$^b$ where R$^a$ is alkyl and R$^b$ is H or alkyl. The term "arylaminocarbonyl" refers herein to the group —C(=O)—NR$^a$R$^b$ where R$^a$ or R$^b$ is aryl. Representative aminocarbonyl groups include, for example, those shown below. These aminocarbonyl group can be further substituted as will be apparent to those having skill in the organic and medicinal chemistry arts in conjunction with the disclosure herein.

"Aminocarbonylalkoxy" refers to —O-alkylene-C(=O)—NR$^a$R$^b$ wherein R$^a$ is hydrogen or alkyl and R$^a$ and R$^b$ independently are selected from the group consisting of hydrogen, alkyl, alkenyl, alkynyl, aryl, cycloalkyl, cycloalkenyl, heteroaryl, heterocyclic, and where R$^a$ and R$^b$ are optionally joined together with the nitrogen bound thereto to form a heterocyclic or substituted heterocyclic group.

"Aminocarbonylalkylene" refers to -alkylene-C(=O)—NR$^a$R$^b$ wherein R$^a$ is hydrogen or alkyl and R$^a$ and R$^b$ independently are selected from the group consisting of hydrogen, alkyl, alkenyl, alkynyl, aryl, cycloalkyl, cycloalkenyl, heteroaryl, heterocyclic, and where R$^a$ and R$^b$ are optionally joined together with the nitrogen bound thereto to form a heterocyclic or substituted heterocyclic group.

"Aminocarbonylalkyleneaminosulfonyl" refers to —S(O)$_2$NR$^a$-alkylene-C(=O)—NR$^a$R$^b$ wherein each R$^a$ is hydrogen or alkyl and R$^a$ and R$^b$ independently are selected from the group consisting of hydrogen, alkyl, alkenyl, alkynyl, aryl, cycloalkyl, cycloalkenyl, heteroaryl, heterocyclic, and where R$^a$ and R$^b$ of the amino group are optionally joined together with the nitrogen bound thereto to form a heterocyclic or substituted heterocyclic group.

"Aminocarbonylamino" refers to the group —NR$^a$C(O)NR$^a$R$^b$, wherein R$^a$ is hydrogen or alkyl and R$^a$ and R$^b$ independently are selected from the group consisting of hydrogen, alkyl, alkenyl, alkynyl, aryl, cycloalkyl, cycloalkenyl, heteroaryl, heterocyclic, and where R$^a$ and R$^b$ are optionally joined together with the nitrogen bound thereto to form a heterocyclic or substituted heterocyclic group.

"Aminocarbonylaminoalkylene" refers to the group -alkylene-NR$^a$C(O)NR$^a$R$^b$, wherein R$^a$ is hydrogen or alkyl and R$^a$ and R$^b$ independently are selected from the group consisting of hydrogen, alkyl, alkenyl, alkynyl, aryl, cycloalkyl, cycloalkenyl, heteroaryl, heterocyclic, and where R$^a$ and R$^b$ are optionally joined together with the nitrogen bound thereto to form a heterocyclic or substituted heterocyclic group.

"Aminocarboxyalkylene" refers to the group -alkylene-OC(O)NR$^a$R$^b$, wherein R$^a$ is hydrogen or alkyl and R$^a$ and R$^b$ independently are selected from the group consisting of hydrogen, alkyl, alkenyl, alkynyl, aryl, cycloalkyl, cycloalkenyl, heteroaryl, heterocyclic, and where R$^a$ and R$^b$ are optionally joined together with the nitrogen bound thereto to form a heterocyclic or substituted heterocyclic group.

"Aminosulfonyl" refers to —S(O)$_2$NR$^a$R$^b$ where R is independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic and where R$^a$ and R$^b$ are optionally joined together with the nitrogen bound thereto to form a heterocyclic or substituted heterocyclic group and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminosulfonylalkylene" refers to -alkylene-S(O)$_2$NR$^a$R$^b$ where R is independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic and where R$^a$ and R$^b$ are optionally joined together with the nitrogen bound thereto to form a heterocyclic or substituted heterocyclic group and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

The term "alkylaminosulfonyl" refers herein to the group —S(O)$_2$NR$^a$R$^b$ where R$^a$ is alkyl and R$^b$ is H or alkyl. The term "alkylarylsulfonyl" refers herein to the group —S(O)$_2$NR$^a$R$^b$ where R$^a$ or R$^b$ is alkylaryl.

"Aminosulfonyloxy" refers to the group —O—SO$_2$NR$^a$R$^b$, wherein R$^a$ and R$^b$ independently are selected from the group consisting of hydrogen, alkyl, alkenyl, alkynyl, aryl, cycloalkyl, cycloalkenyl, heteroaryl and heterocyclic; R$^a$ and R$^b$ are optionally joined together with the nitrogen bound thereto to form a heterocyclic or substituted heterocyclic group.

"Aminosulfonylamino" refers to the group —NR$^a$—SO$_2$NR$^b$R$^c$, wherein R$^a$ is hydrogen or alkyl and R$^b$ and R$^c$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^b$ and R$^c$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Aminothiocarbonyl" refers to the group —C(S)NR$^a$R$^b$, wherein R$^a$ and R$^b$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^a$ and R$^b$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminothiocarbonylamino" refers to the group —NR$^a$C(S)NR$^a$R$^b$, wherein R$^a$ is hydrogen or alkyl and R$^b$ and R$^c$ are optionally joined together with the nitrogen bound thereto to form a heterocyclic or substituted heterocyclic group.

"Arylalkoxycarbonylamino" refers to the group —NR$^a$C(=O)O-alkylene-R$^c$ where R$^c$ is aryl.

"Arylcarbonyl" refers to the group —C(O)R$^c$ where R$^c$ is aryl.

"Arylcarbonylamino" refers to —NR$^a$C(=O)R$^c$ wherein R$^c$ is aryl.

"Arylcarbonyloxy" refers to —OC(=O)—R$^c$ where R$^c$ is aryl.

"Aryloxy" refers to —OR$^d$ where R$^d$ is aryl. Representative examples of aryloxy groups include phenoxy, naphthoxy, and the like.

"Aryloxycarbonyl" refers to —C(=O)OR$^d$ wherein R$^d$ is aryl.

"Aryloxycarbonylamino" refers to —NR$^a$C(=O)OR$^d$ wherein R$^d$ is aryl.

"Arylsulfanyl", "arylthio", or "thioaryloxy" refers to the group S—R$^d$, where R$^d$ is aryl.

"Arylsulfonyl" refers to —S(=O)$_2$R$^e$ where R$^e$ is aryl.

"Arylsulfonylamino" refers to —NR$^a$S(=O)$_2$—R$^e$ wherein R$^e$ is aryl.

"Arylthio" refers to the group —S-aryl, wherein aryl is as defined herein. In other embodiments, sulfur may be oxidized to —S(O)— or —SO$_2$— moieties. The sulfoxide may exist as one or more stereoisomers.

"Bond" when used a element in a Markush group means that the corresponding group does not exist, and the groups of both sides are directly linked.

"Carbonyl" refers to the divalent group —C(=O)—.

"Carboxy" or "carboxyl" refers to the group —CO$_2$H.

"Carboxyalkylene" refers to the group -alkylene-CO$_2$H.

"Carboxyalkylenesulfonylamino" refers to the group —NR$^a$SO$_2$-alkylene-CO$_2$H.

"Carboxyl ester", "carbonylalkoxy" or "carboxy ester" refers to the group —C(=O)OR$^c$.

"Cycloalkylalkylene" refers to a radical —R$^x$R$^y$ wherein R$^x$ is an alkylene group and R$^y$ is a cycloalkyl group as defined herein, e.g., cyclopropylmethyl, cyclohexenylpropyl, 3-cyclohexyl-2-methylpropyl, and the like.

"Ester" refers to —C(=O)OR$^d$ wherein R$^d$ is alkyl, cycloalkyl, aryl, heteroaryl, or heterocyclyl.

"Halo" or "halogen" by themselves or as part of another substituent, mean, unless otherwise stated, a fluorine, chlorine, bromine, or iodine atom. Additionally, terms such as "haloalkyl", are meant to include alkyl in which one or more hydrogen is substituted with halogen atoms which can be the same or different, in a number ranging from one up to the maximum number of halogens permitted e.g. for alkyl, (2m'+1), where m' is the total number of carbon atoms in the alkyl group. For example, the term "haloC$_{1-8}$alkyl" is meant to include trifluoromethyl, 2,2,2-trifluoroethyl, 4-chlorobutyl, 3-bromopropyl, and the like. The term "perhaloalkyl" means, unless otherwise stated, alkyl substituted with (2m'+1) halogen atoms, where m' is the total number of carbon atoms in the alkyl group. For example, the term "perhaloC$_{1-8}$alkyl", is meant to include trifluoromethyl, pentachloroethyl, 1,1,1-trifluoro-2-bromo-2-chloroethyl, and the like. Additionally, term "haloalkoxy" refers to an alkoxy radical substituted with one or more halogen atoms.

"Heterocyclylcarbonyl" refers to the —C(=O)R$^c$ where R$^c$ is heterocyclyl.

"Hydroxy" or "hydroxyl" refers to the group —OH.

"Hydroxyalkylene" refers to the group -alkylene-OH.

"Hydroxyalkyleneamino" refers to the group —NR$^a$-alkylene-OH.

"Hydroxyalkyleneaminocarbonyl" refers to the group —C(=O)NR$^a$-alkylene-OH.

"Hydroxyalkyleneaminosulfonyl" refers to the group —SO$_2$NR$^a$-alkylene-OH.

"Hydroxyamino" refers to the group —NHOH.

"Hydroxyalkylenecarbonylamino" refers to the group —NR$^a$C(=O)-alkylene-OH.

"Imino" refers to the group =NR$^a$.

"Nitro" refers to —NO$_2$.

"Nitroso" refers to the group —NO.

The terms "optional" or "optionally" as used throughout the specification means that the subsequently described event or circumstance may but need not occur, and that the description includes instances where the event or circumstance occurs and instances in which it does not. For example, "heterocyclo group optionally mono- or di-substituted with an alkyl group means that the alkyl may but need not be present, and the description includes situations where the heterocyclo group is mono- or disubstituted with an alkyl group and situations where the heterocyclo group is not substituted with the alkyl group.

"Optionally substituted" means a ring which is optionally substituted independently with substituents. A site of a group that is unsubstituted may be substituted with hydrogen.

"Oxo" refers to the divalent group =O.

"Sulfanyl" refers to the group —SR$^f$ where R$^f$ is as defined herein.

"Sulfinyl" refers to the group —S(=O)—R$^e$ where R$^e$ is as defined herein.

"Sulfonic acid" refers to the group —S(O)$_2$—OH.

"Sulfonyl" refers to the group —S(O)$_2$—R$^e$ where R$^e$ is as defined herein.

"Sulfonylamino" refers to —NR$^a$S(=O)$_2$—R$^e$ where R$^a$ is selected from the group consisting of hydrogen, alkyl, alkenyl, alkynyl, aryl, cycloalkyl, cycloalkenyl, heteroaryl and heterocyclyl and R$^e$ is as defined herein.

"Sulfonyloxy" refers to the group —OSO$_2$—R$^c$.

Compounds that have the same molecular formula but differ in the nature or sequence of bonding of their atoms or the arrangement of their atoms in space are termed "isomers". Isomers that differ in the arrangement of their atoms in space are termed "stereoisomers". "Stereoisomer" and "stereoisomers" refer to compounds that exist in different stereoisomeric forms if they possess one or more asymmetric centers or a double bond with asymmetric substitution and, therefore, can be produced as individual stereoisomers or as mixtures. Stereoisomers include enantiomers and diastereomers. Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture". Unless otherwise indicated, the description is intended to include individual stereoisomers as well as mixtures. The methods for the determination of stereochemistry and the separation of stereoisomers are well-known in the art (see discussion in Chapter 4 of ADVANCED ORGANIC CHEMISTRY, 4th edition J. March, John Wiley and Sons, New York, 1992) differ in the chirality of one or more stereocenters.

"Thioacyl" refers to the groups R$^a$—C(S)—.

"Thiol" refers to the group —SH.

"Tautomer" refers to alternate forms of a molecule that differ in the position of a proton, such as enol-keto and imine-enamine tautomers, or the tautomeric forms of heteroaryl groups containing a —N=C(H)—NH— ring atom arrangement, such as pyrazoles, imidazoles, benzimidazoles, triazoles, and tetrazoles. A person of ordinary skill in the art would recognize that other tautomeric ring atom arrangements are possible.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups are limited to -substituted aryl-(substituted aryl)-substituted aryl.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, Protective Groups in Organic Chemistry, 3$^{rd}$ Ed., 1999, John Wiley & Sons, NY and Harrison et al., Compendium of Synthetic Organic Methods, Vols. 1-8, 1971-1996, John Wiley & Sons, NY. Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl and trityl ethers, as well as alkyl ethers, tetrahydropyranyl ethers, trialkylsilyl ethers (e.g., TMS or TIPPS groups) and allyl ethers.

The term "pharmaceutically acceptable salts" is meant to include salts of the active compounds which are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of salts derived from pharmaceutically-acceptable inorganic bases include aluminum, ammonium, calcium, copper, ferric, ferrous, lithium, magnesium, manganic, manganous, potassium, sodium, zinc and the like. Salts derived from pharmaceutically-acceptable organic bases include salts of primary, secondary and tertiary amines, including substituted amines, cyclic amines, naturally-occurring amines and the like, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge, S. M. et al., "Pharmaceutical Salts," *Journal of Pharmaceutical Science*, 66:1-19, 1977). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug ester form. "Prodrug"s of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent. Prodrugs are frequently, but not necessarily, pharmacologically inactive until converted into the active drug. Prodrugs are typically obtained by masking a functional group in the drug believed to be in part required for activity with a progroup (defined below) to form a promoiety which undergoes a transformation, such as cleavage, under the specified conditions of use to release the functional group, and hence the active drug. The cleavage of the promoiety may proceed spontaneously, such as by way of a hydrolysis reaction, or it may be catalyzed or induced by another agent, such as by an enzyme, by light, by acid or base, or by a change of or exposure to a physical or environmental parameter, such as a change of temperature. The agent may be endogenous to the conditions of use, such as an enzyme present in the cells to which the prodrug is administered or the acidic conditions of the stomach, or it may be supplied exogenously.

"Progroup" refers to a type of protecting group that, when used to mask a functional group within an active drug to form a promoiety, converts the drug into a prodrug. Progroups are typically attached to the functional group of the drug via bonds that are cleavable under specified conditions of use. Thus, a progroup is that portion of a promoiety that cleaves to release the functional group under the specified conditions of use. As a specific example, an amide promoiety of the formula —NH—C(O)CH$_3$ comprises the progroup —C(O)CH$_3$.

A wide variety of progroups, as well as the resultant promoieties, suitable for masking functional groups in the active Syk selective inhibitory compounds to yield prodrugs are well-known in the art. For example, a hydroxyl functional group may be masked as a sulfonate, ester (such as acetate or maleate) or carbonate promoiety, which may be hydrolyzed in vivo to provide the hydroxyl group. An amino functional group may be masked as an amide, carbamate, imine, urea, phosphenyl, phosphoryl or sulfenyl promoiety, which may be hydrolyzed in vivo to provide the amino group. A carboxyl group may be masked as an ester (including methyl, ethyl, pivaloyloxymethyl, silyl esters and thioesters), amide or hydrazide promoiety, which may be hydrolyzed in vivo to provide the carboxyl group. The invention includes those esters and acyl groups known in the art for modifying the solubility or hydrolysis characteristics for use as sustained-release or prodrug formulations. Other specific examples of suitable progroups and their respective promoieties will be apparent to those of skill in the art.

Certain compounds of the present invention can exist in unsolvated forms as well as solvated forms, including hydrated forms. "Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers, regioisomers and individual isomers (e.g., separate enantiomers) are all intended to be encompassed within the scope of the present invention. These isomers can be resolved or asymmetrically synthesized using conventional methods to render the isomers "optically pure", i.e., substantially free of its other isomers. If, for instance, a particular enantiomer of a compound of the present invention is desired, it may be prepared by asymmetric synthesis, or by derivation with a chrial auxilliary, where the resulting diastereomeric mixture is separated and the auxilliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diasteromers thus formed by fractional crystallization or chromatographic means well known in the art, and subsequent recovery of the pure enantiomers.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are intended to be encompassed within the scope of the present invention.

The term "administering" refers to oral administration, administration as a suppository, topical contact, intravenous, intraperitoneal, intramuscular, intralesional, intranasal or subcutaneous administration, or the implantation of a slow-release device e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

An "agonist" or "activator" refers to an agent or molecule that binds to a receptor of the invention, stimulates, increases, opens, activates, facilitates, enhances activation or enzymatic activity, sensitizes or up regulates the activity of a receptor of the invention.

An "antagonist" or "inhibitor" refers to an agent or molecule that inhibits or binds to, partially or totally blocks stimulation or activity, decreases, closes, prevents, delays activation or enzymatic activity, inactivates, desensitizes, or down regulates the activity of a receptor of the invention. As used herein, "antagonist" also includes a reverse or inverse agonist.

As used herein, the term "condition or disorder responsive to modulation of Syk" and related terms and phrases refer to a condition or disorder associated with inappropriate, e.g., less than or greater than normal, activity of Syk and at least partially responsive to or affected by modulation of Syk (e.g., Syk antagonist or agonist results in some improvement in patient well-being in at least some patients). Inappropriate functional activity of Syk might arise as the result of expression of Syk in cells which normally do not express the receptor, greater than normal production of Syk, or slower than normal metabolic inactivation or elimination of Syk or its active metabolites, increased expression of Syk or degree of intracellular activation (leading to, e.g., inflammatory and immune-related disorders and conditions) or decreased expression of Syk. A condition or disorder associated with Syk may include a "Syk-mediated condition or disorder".

As used herein, the phrases "a condition or disorder mediated at least in part by Syk kinase activity", and related phrases and terms refer to a condition or disorder characterized by inappropriate, e.g., greater than normal, Syk activity. Inappropriate Syk functional activity might arise as the result of Syk expression in cells which normally do not express Syk or increased Syk expression or degree of intracellular activation (leading to, e.g., inflammatory and immune-related disorders and conditions). A condition or disorder mediated at least in part by Syk or JAK kinase activity may be completely or partially mediated by inappropriate Syk functional activity. However, a condition or disorder mediated at least in part by Syk kinase activity is one in which modulation of Syk results in some effect on the underlying condition or disorder (e.g., an Syk antagonist results in some improvement in patient well-being in at least some patients).

The term "inflammation" as used herein refers to infiltration of white blood cells (e.g., leukocytes, monocytes, etc.) into the area being treated for restenosis.

The term "intervention" refers to an action that produces an effect or that is intended to alter the course of a disease process. For example, "vascular intervention" refers to the use of an intravascular procedure such as angioplasty or a stent to open an obstructed blood vessel.

The term "intravascular device" refers to a device useful for a vascular recanalization procedure to restore blood flow through an obstructed blood vessel. Examples of intravascular devices include, without limitation, stents, balloon catheters, autologous venous/arterial grafts, prosthetic venous/arterial grafts, vascular catheters, and vascular shunts.

As used herein, the term "JAK" refers to a Janus kinase (RefSeq Accession No. P-43408) or a variant thereof that is capable of mediating gene expression in vitro or in vivo. JAK variants include proteins substantially homologous to native JAK, i.e., proteins having one or more naturally or non-naturally occurring amino acid deletions, insertions or substitutions (e.g., JAK derivatives, homologs and fragments). The amino acid sequence of JAK variant preferably is at least about 80% identical to a native JAK, more preferably at least about 90% identical, and most preferably at least about 95% identical.

The term "leukocyte" refers to any of the various blood cells that have a nucleus and cytoplasm, separate into a thin white layer when whole blood is centrifuged, and help protect the body from infection and disease. Examples of leukocytes include, without limitation, neutrophils, eosinophils, basophils, lymphocytes, and monocytes.

The term "mammal" includes, without limitation, humans, domestic animals (e.g., dogs or cats), farm animals (cows, horses, or pigs), monkeys, rabbits, mice, and laboratory animals.

The terms "modulate", "modulation" and the like refer to the ability of a compound to increase or decrease the function and/or expression of Syk, where such function may include transcription regulatory activity and/or protein-binding. Modulation may occur in vitro or in vivo. Modulation, as described herein, includes the inhibition, antagonism, partial antagonism, activation, agonism or partial agonism of a function or characteristic associated with Syk, either directly or indirectly, and/or the upregulation or downregulation of the expression of Syk, either directly or indirectly. In a preferred embodiment, the modulation is direct. Inhibitors or antagonists are compounds that, e.g., bind to, partially or totally block stimulation, decrease, prevent, inhibit, delay activation, inactivate, desensitize, or downregulate signal transduction. Activators or agonists are compounds that, e.g., bind to, stimulate, increase, open, activate, facilitate, enhance activation, activate, sensitize or upregulate signal transduction. The ability of a compound to inhibit the function of Syk can be demonstrated in a biochemical assay, e.g., binding assay, or a cell-based assay, e.g., a transient transfection assay.

"Modulators" of activity are used to refer to "ligands", "antagonists" and "agonists" identified using in vitro and in vivo assays for activity and their homologs and mimetics. Modulators include naturally occurring and synthetic ligands, antagonists, agonists, molecules and the like. Assays to identify antagonists and agonists include, e.g., applying putative modulator compounds to cells, in the presence or absence of a receptor of the invention and then determining the functional effects on a receptor of the invention activity. Samples or assays comprising a receptor of the invention that are treated with a potential activator, inhibitor, or modulator are compared to control samples without the inhibitor, activator, or modulator to examine the extent of effect. Control samples (untreated with modulators) are assigned a relative activity value of 100%. Inhibition is achieved when the activity value of a receptor of the invention relative to the control is about 80%, optionally 50% or 25-1%. Activation is achieved when the activity value of a receptor of the invention relative to the control is 110%, optionally 150%, optionally 200-500%, or 1000-3000% higher.

"Patient" refers to human and non-human animals, especially mammals. Examples of patients include, but are not limited to, humans, cows, dogs, cats, goats, sheep, pigs and rabbits.

Turning next to the compositions of the invention, the term "pharmaceutically acceptable carrier or excipient" means a carrier or excipient that is useful in preparing a pharmaceutical composition that is generally safe, non-toxic and neither biologically nor otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

The terms "pharmaceutically effective amount", "therapeutically effective amount" or "therapeutically effective dose" refers to the amount of the subject compound that will elicit the biological or medical response of a tissue, system, animal or human that is being sought by the researcher, veterinarian, medical doctor or other clinician. The term "therapeutically effective amount" includes that amount of a compound that, when administered, is sufficient to prevent development of, or alleviate to some extent, one or more of the symptoms of the condition or disorder being treated. The therapeutically effective amount will vary depending on the compound, the disorder or condition and its severity and the age, weight, etc., of the mammal to be treated.

The term "platelet" refers to a minute, nonnucleated, disklike cell found in the blood plasma of mammals that functions to promote blood clotting.

The terms "prevent", "preventing", "prevention" and grammatical variations thereof as used herein, refers to a method of partially or completely delaying or precluding the onset or recurrence of a disorder or condition and/or one or more of its attendant symptoms or barring a subject from acquiring or reacquiring a disorder or condition or reducing a subject's risk of acquiring or reacquiring a disorder or condition or one or more of its attendant symptoms.

The term "recanalization" refers to the process of restoring flow to or reuniting an interrupted channel of the body, such as a blood vessel.

The term "restenosis" refers to a re-narrowing or blockage of an artery at the same site where treatment, such as an angioplasty or a stent procedure, has been performed.

The phrase "selectively" or "specifically" when referring to binding to a receptor, refers to a binding reaction that is determinative of the presence of the receptor, often in a heterogeneous population of receptors and other biologics. Thus, under designated conditions, the compounds bind to a particular receptor at least two times the background and more typically more than 10 to 100 times background. Specific binding of a compound under such conditions requires a compound that is selected for its specificity for a particular receptor. For example, small organic molecules can be screened to obtain only those compounds that specifically or selectively bind to a selected receptor and not with other receptors or proteins. A variety of assay formats may be used to select compounds that are selective for a particular receptor. For example, High-throughput screening assays are routinely used to select compounds that are selective for a particular a receptor.

As used herein, the term "Sickle cell anemia" refers to an inherited disorder of the red blood cells in which both hemoglobin alleles encode the sickle hemoglobin (S) protein, i.e., the S/S genotype. The presence of abnormal hemoglobin results in the production of unusually shaped cells, which do not survive the usual length of time in the blood circulation. Thus, anemia results. "Anemia" refers to a decrease in the number of red blood cells and/or hemoglobin in the blood.

The term "Sickle cell disease" refers to an inherited disorder of the red blood cells in which one hemoglobin allele encodes the sickle hemoglobin (S) protein, and the other allele encodes another unusual hemoglobin protein, such as hemoglobin (S), (C), (D), (E), and (βThal). Examples of sickle cell disease genotypes include, without limitation, the S/S, S/C, S/D, S/E, and S/βThal genotypes. The most common types of sickle cell disease include sickle cell anemia, sickle-hemoglobin C disease, sickle beta-plus thalassemia, and sickle beta-zero thalassemia.

The "subject" is defined herein to include animals such as mammals, including, but not limited to, primates (e.g., humans), cows, sheep, goats, horses, dogs, cats, rabbits, rats, mice and the like. In preferred embodiments, the subject is a human.

As used herein, the term "Syk" refers to a spleen tyrosine kinase (RefSeq Accession No. P-043405) or a variant thereof that is capable of mediating a cellular response to T-cell receptors in vitro or in vivo. Syk variants include proteins substantially homologous to native Syk, i.e., proteins having one or more naturally or non-naturally occurring amino acid deletions, insertions or substitutions (e.g., Syk derivatives, homologs and fragments). The amino acid sequence of Syk variant preferably is at least about 80% identical to a native Syk, more preferably at least about 90% identical, and most preferably at least about 95% identical.

The term "Syk inhibitor" refers to any agent that inhibits the catalytic activity of spleen tyrosine kinase.

The terms "treat", "treating", "treatment" and grammatical variations thereof as used herein, includes partially or completely delaying, alleviating, mitigating or reducing the intensity of one or more attendant symptoms of a disorder or condition and/or alleviating, mitigating or impeding one or more causes of a disorder or condition. Treatments according to the invention may be applied preventively, prophylactically, palliatively or remedially.

The term "vessel" refers to any channel for carrying a fluid, such as an artery or vein. For example, a "blood vessel" refers to any of the vessels through which blood circulates in the body. The lumen of a blood vessel refers to the inner open space or cavity of the blood vessel.

2. Embodiments of the Invention a. Compounds

The present invention provides in one embodiment, a compound of having the formula (I):

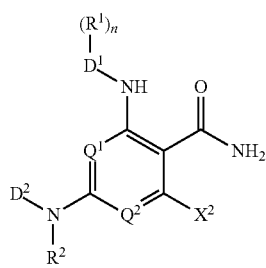

(I)

or a tautomer thereof or a pharmaceutically acceptable salt or hydrate thereof,
wherein:
each $Q^1$ and $Q^2$ are selected from the group consisting of $CX^1$ or N; wherein at least one of $Q^1$ or $Q^2$ is $CX^1$;
each $X^1$ is independently selected from the group consisting of: hydrogen, $C_{1-8}$ alkyl, halogen, cyano, and aminocarbonyl;
$X^2$ is H or halogen;
$D^1$ is selected from the group consisting of:
(a) aryl;
(b) heteroaryl; and
(c) heterocyclyl;
each $R^1$ is independently selected from the group consisting of $C_{1-8}$ alkyl, $C_{2-8}$-alkenyl, $C_{2-8}$alkynyl, $C_{1-8}$alkoxy, $C_{1-8}$alkylthio, aminocarbonyl, $C_{1-8}$alkoxycarbonyl$C_{1-8}$alkylene, $C_{1-8}$alkoxycarbonyl$C_{1-8}$alkoxy, $C_{1-8}$alkoxycarbonylamino, oxo, halo, cyano, halo$C_{1-8}$alkyl, halo$C_{1-8}$alkoxy, aminosulfonyl, heteroarylsulfinyl; amino, hydroxyl, $C_{1-8}$arylalkylene, phenyl, amino$C_{1-8}$alkyl, amino$C_{3-8}$cycloalkyl, heterocyclyl, heteroaryl, heterocyclyl$C_{1-8}$alkylene and hydroxy$C_{1-8}$alkylene;
$D^2$ is selected from the group consisting of:

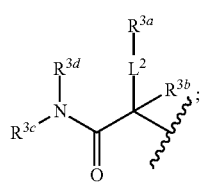

(a)

$R^{3a}$ is selected from the group consisting of: H, $C_{1-8}$alkenyl, $C_{1-8}$alkynyl, hydroxyl, oxo, amino, thio, halo, carboxy, aminocarbonyl, $C_{1-8}$alkoxy, halo$C_{1-8}$alkoxy, $C_{1-8}$alkylamino, di$C_{1-8}$alkylamino, cyano, $C_{1-8}$alkylthio, $C_{1-8}$alkylsulfonyl, aminocarbonyl, $C_{1-8}$alkoxycarbonylamino, $C_{1-8}$alkyl$C_{3-8}$cycloalkyl, $C_{3-8}$cycloalkyl, $C_{3-8}$cycloalkyloxy, $C_{3-8}$cycloalkylamino, $C_{3-8}$cycloalkylthio; heteroaryl, heteroarylalkoxy, aryl, arylalkoxy, heterocyclyl and heterocyclyloxy; wherein the aryl is optionally substituted by hydroxyl, $C_{1-8}$alkyl, $C_{1-8}$alkoxy, halo, halo$C_{1-8}$alkyl, $C_{1-8}$alkylsulfonyl or heteroaryl;
$R^{3b}$ is selected from the group consisting of: H, and $C_{1-8}$alkyl; or may be combined with $R^{3a}$ to form a 3 to 8 membered carbocyclic or heterocyclic ring
$R^{3c}$ is selected from the group consisting of: H, $C_{1-8}$alkyl and $C_{3-8}$cycloalkyl; or taken together with $R^{3d}$ and the atoms to which they are attached to form a heterocyclyl ring;
$R^{3d}$ is selected from the group consisting of H, $C_{1-8}$alkyl and $C_{3-8}$cycloalkyl;
$L^2$ is selected from the group consisting of a bond and $C_{1-8}$alkylene;

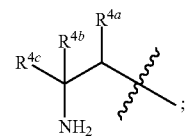

(b)

$R^{4a}$ is independently selected from the group consisting of: H, $C_{1-8}$alkyl, hydroxy$C_{1-8}$alkyl, $C_{1-8}$haloalkyl, amino, $C_{1-8}$alkylamino, $C_{1-8}$ alkoxycarbonylamino$C_{1-8}$ alkylene, $C_{3-8}$cycloalkyl, heteroaryl, $C_{1-8}$ alkyl$C_{3-8}$cycloalkyl, $C_{1-8}$alkylthio$C_{1-8}$ alkyl, $C_{1-8}$alkylsulfonyl$C_{1-8}$ alkylene, aminocarbonyl, $C_{1-8}$alkoxy$C_{1-8}$alkyl, $C_{1-8}$alkoxy$C_{1-8}$alkoxy, halo$C_{1-8}$alkyl, aryl and heterocyclyl; wherein the aryl is optionally substituted by hydroxyl, $C_{1-8}$alkoxy, halo or halo$C_{1-8}$alkyl; or taken together with $R^{4b}$ and the atoms to which they are attached to form a $C_{3-8}$ cycloalkyl or heterocycloalkyl ring;
$R^{4b}$ is selected from the group consisting of H, $C_{1-8}$alkylamino, amino, amino$C_{1-8}$alkyl, carboxy, $C_{1-8}$alkylamino$C_{1-8}$alkyl, $C_{1-8}$alkoxy$C_{1-8}$alkyl, hydroxy$C_{1-8}$alkyl; carboxy$C_{1-8}$alkyl, $C_{3-8}$cycloalkyl$C_{1-8}$alkyl, aryloxy$C_{1-8}$alkyl, aryl$C_{1-8}$alkyl, heteroaryl$C_{1-8}$alkyl, and hydroxy$C_{1-8}$alkoxy; or may be combined with $R^{4a}$ or $R^{4c}$ and the atoms to which they are attached to form a $C_{3-8}$ cycloalkyl or heterocyclyl ring;
$R^{4c}$ is H or alkyl or may be combined with $R^{4b}$ and the atoms to which they are attached to form a $C_{3-8}$cycloalkyl or heterocyclyl ring;
(c) $C_{3-8}$cycloalkyl; optionally substituted with from 1 to 3 substituents, $R^{6a}$, independently selected from the group consisting of $C_{1-8}$alkyl; $C_{1-8}$alkoxy$C_{1-8}$alkyl, aminocarbonyl-, hydroxy, oxo, halogen, $C_{1-8}$alkoxy and $C_{1-8}$alkylsulfonyl;
(d) heterocycloalkyl; optionally substituted with from 1 to 3 substituents, $R^{6a}$, independently selected from the group consisting of $C_{1-8}$alkyl, $C_{1-8}$alkoxy$C_{1-8}$alkyl, aminocarbonyl-, hydroxy, oxo, halogen, $C_{1-8}$alkoxy and $C_{1-8}$alkylsulfonyl; and
(e) arylalkylene; optionally substituted with from 1 to 3 substituents, $R^{6a}$, independently selected from the group consisting of $C_{1-8}$alkyl, $C_{1-8}$alkoxy$C_{1-8}$alkyl, aminocarbonyl-, hydroxy, oxo, halogen, $C_{1-8}$alkoxy and $C_{1-8}$alkylsulfonyl;
each $R^2$ is independently selected from the group consisting of H and $C_{1-8}$ alkyl;
the subscript n is 0, 1, 2, 3 or 4; and
the wavy line indicates the point of attachment to the rest of the molecule.

The present invention provides in another group of embodiments, a compound, having formula (Ia):

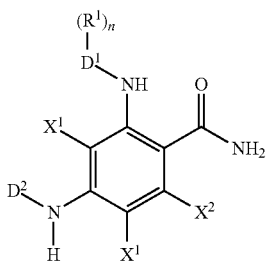

or a tautomer thereof or a pharmaceutically acceptable salt or hydrate thereof.

The present invention provides in another group of embodiments, a compound, having formula (Ib) or (Ic):

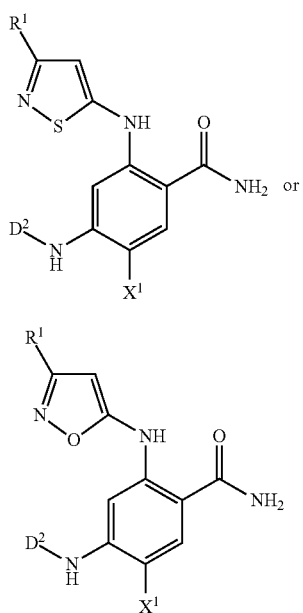

or a tautomer thereof or a pharmaceutically acceptable salt or hydrate thereof.

The present invention provides in another group of embodiments, a compound, having formula (Id):

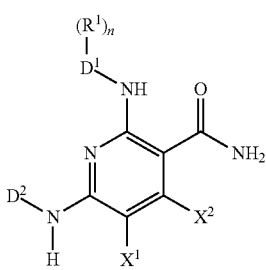

or a tautomer thereof or a pharmaceutically acceptable salt or hydrate thereof.

The present invention provides in another group of embodiments, a compound, having formula (Ie):

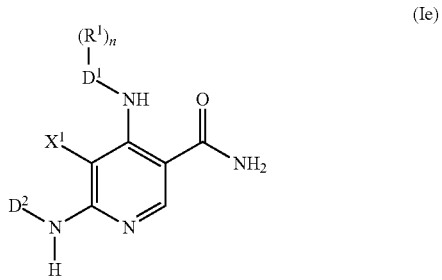

or a tautomer thereof or a pharmaceutically acceptable salt or hydrate thereof.

The present invention provides in another group of embodiments, a compound, wherein $X^1$ is selected from the group consisting of H, halo, cyano and aminocarbonyl. The present invention provides in another group of embodiments, a compound, wherein $X^1$ is F.

The present invention provides in another group of embodiments, a compound, wherein $D^1$ is H. The present invention provides in another group of embodiments, a compound, wherein $D^1$ is aryl. The present invention provides in another group of embodiments, a compound, wherein $D^1$ is phenyl or naphthyl. The present invention provides in another group of embodiments, a compound, wherein $D^1$ is cycloalkyl. The present invention provides in another group of embodiments, a compound, wherein $D^1$ is selected from the group consisting of cyclopentyl, cyclobutyl and cyclopropyl. The present invention provides in another group of embodiments, a compound, wherein $D^1$ is heteroaryl.

The present invention provides in another group of embodiments, a compound, wherein the heteroaryl group, alone or when part of a group containing a heteroaryl moiety is selected from the group consisting of:

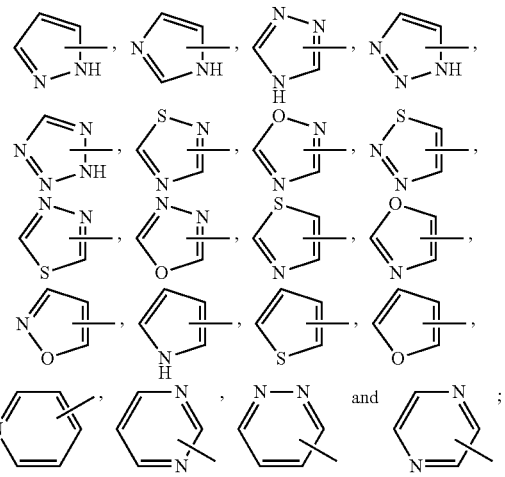

each of which is optionally substituted with from 1 to 2 substituents independently selected from the group consisting of: $C_{1-8}$ alkyl, amino, hydroxyl, oxo, halo, $C_{1-8}$alkoxy, hydroxy$C_{1-8}$alkyl-, amino$C_{1-8}$alkyl, $C_{1-8}$alkylcarbonyl, halo$C_{1-8}$alkyl, $C_{3-8}$cycloalkyl, $C_{1-8}$-aminocycloalkyl, amino$C_{1-8}$alkylenecarbonyl, aminocarbonyl, $C_{1-8}$alkyleneamino$C_{1-8}$alkylenecarbonyl, $C_{1-8}$alkoxy$C_{1-8}$alkylenecarbonyl, hydroxy$C_{1-8}$alkylenecarbonyl, hydroxy$C_{1-8}$alkoxycarbonyl, $C_{1-8}$ alkoxycarbonylamino, aryl, aryl$C_{1-8}$alkoxycarbonylamino, $C_{1-8}$alkylsulfonyl, amino$C_{1-8}$alkylenesulfonyl, aminosulfonyl, $C_{1-8}$alkyleneamino$C_{1-8}$alkylenesulfonyl, $C_{1-8}$alkoxy$C_{1-8}$alkylenesulfonyl, hydroxy$C_{1-8}$alkylenesulfonyl, hydroxy$C_{1-8}$alkoxysulfonyl, aminosulfonyl, and $C_{1-8}$alkylheterocyclyl.

The present invention provides in another group of embodiments, a compound, wherein the heteroaryl group, alone or when part of a group containing a heteroaryl moiety is selected from the group consisting of:

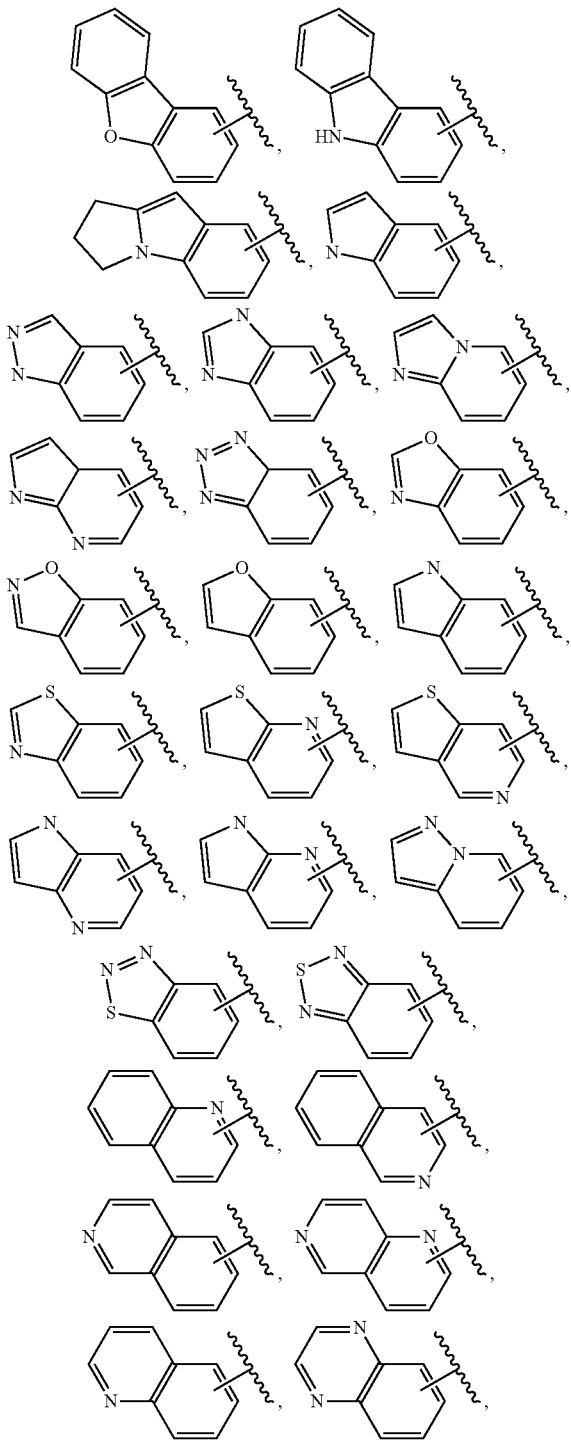

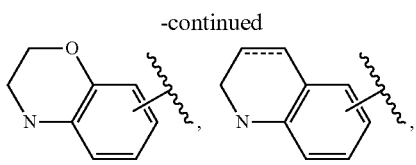

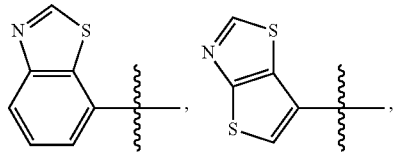

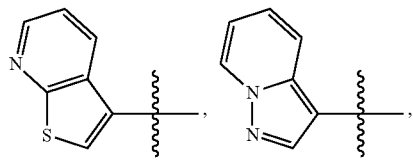

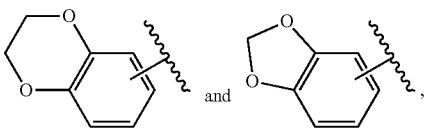

optionally substituted with from 1 to 3 $R^7$ substituents independently selected from the group consisting of: $C_{1-8}$ alkyl, $C_{1-8}$alkylcarbonyl, $C_{1-8}$aminocycloalkyl, amino$C_{1-8}$alkylenecarbonyl, aminocarbonyl, $C_{1-8}$alkyleneamino$C_{1-8}$alkylenecarbonyl, $C_{1-8}$alkoxy$C_{1-8}$alkylenecarbonyl, hydroxy$C_{1-8}$ alkylenecarbonyl, hydroxy$C_{1-8}$alkoxycarbonyl, aminocarbonyl, amino, $C_{1-8}$ alkoxycarbonylamino, aryl, aryl$C_{1-8}$ alkoxycarbonylamino, hydroxyl, $C_{1-8}$ alkoxy, $C_{1-8}$alkylsulfonyl, amino$C_{1-8}$alkylenesulfonyl, aminosulfonyl, $C_{1-8}$alkyleneamino$C_{1-8}$alkylenesulfonyl, $C_{1-8}$alkoxy$C_{1-8}$alkylenesulfonyl, hydroxy$C_{1-8}$alkylenesulfonyl, hydroxy$C_{1-8}$alkoxysulfonyl, aminosulfonyl, oxo, halo, phenyl and $C_{1-8}$alkylheterocyclyl; and the wavy line indicates the point of attachment to the rest of the molecule.

The present invention provides in another group of embodiments, a compound, wherein $D^1$ is selected from the group consisting of:

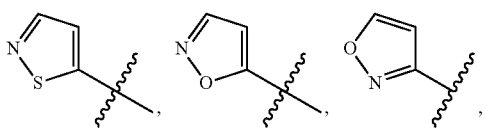

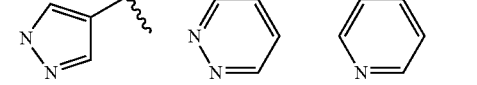

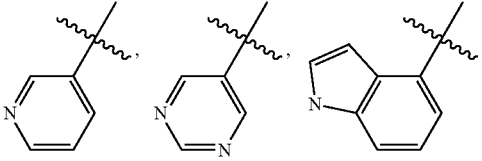

-continued

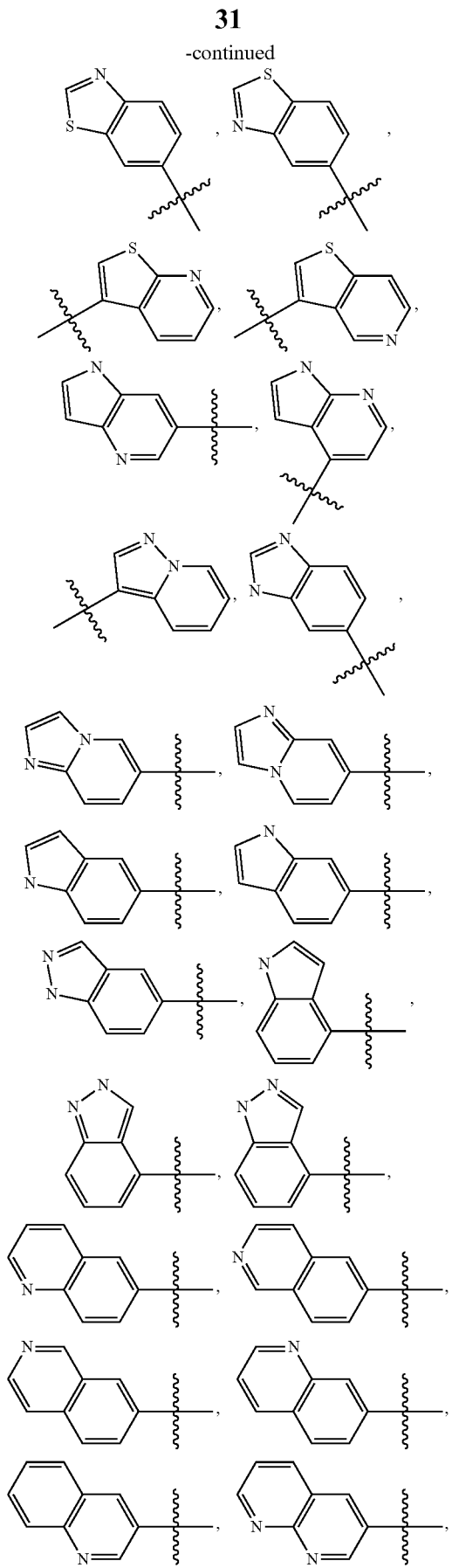

-continued

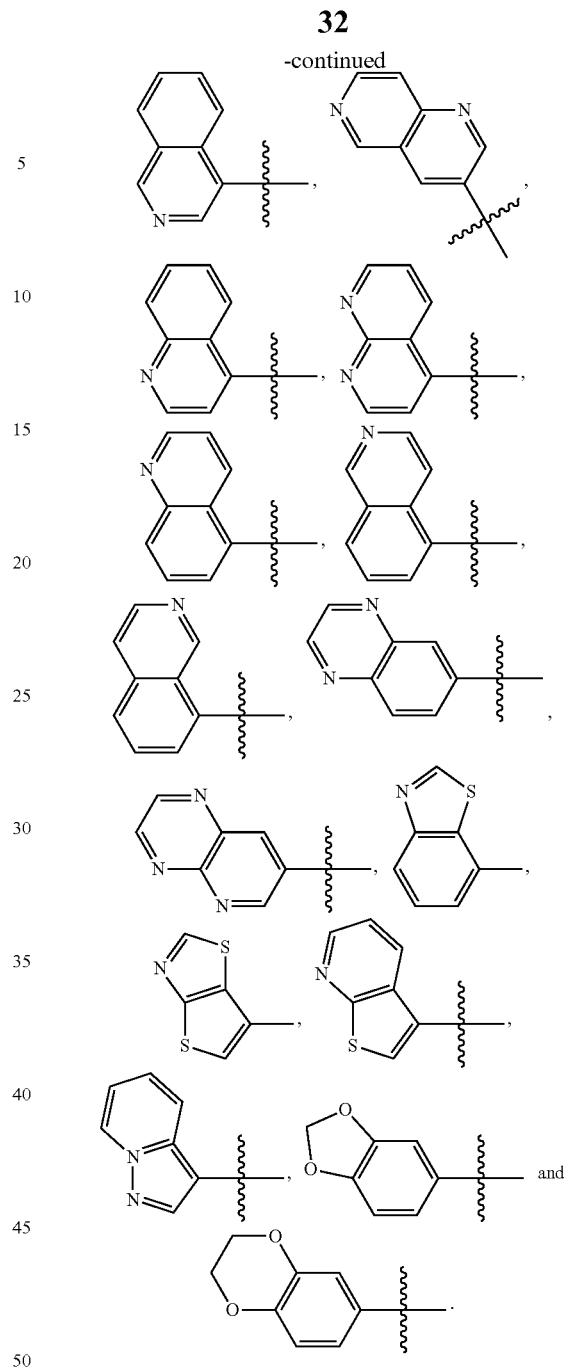

The present invention provides in another group of embodiments, a compound, wherein $D^1$ is heterocyclyl (or heterocycloalkyl).

The present invention provides in another group of embodiments, a compound, wherein n is 2. The present invention provides in another group of embodiments, a compound, wherein n is 1. The present invention provides in another group of embodiments, a compound, wherein n is 0.

The present invention provides in another group of embodiments, a compound, wherein each $R^1$ is independently selected from the group consisting of $C_{1-8}$alkyl, $C_{1-8}$alkoxy, $C_{1-8}$alkoxy$C_{1-8}$alkyl, $C_{1-8}$alkoxy$C_{1-8}$alkoxy, halo, phenyl, aminocarbonyl, heteroaryl, heterocyclyl, heteroaryloxy and heterocyclyloxy wherein the heteroaryl group is selected from the group consisting of:

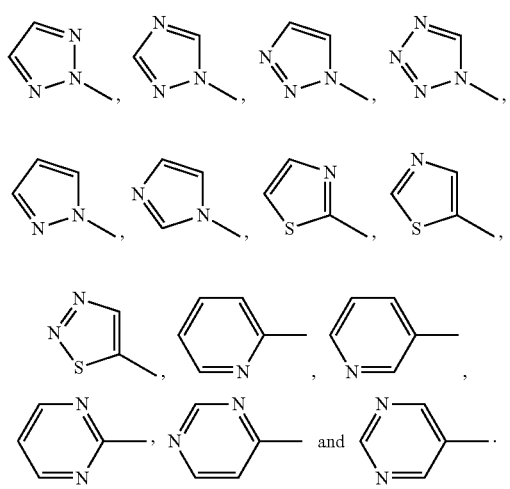

The present invention provides in another group of embodiments, a compound, wherein the heterocyclyl group is selected from the group consisting of:

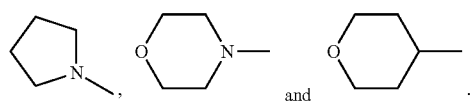

The present invention provides in another group of embodiments, a compound, wherein $D^2$ is:

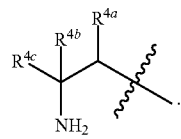

The present invention provides in another group of embodiments, a compound, wherein $D^2$ is:

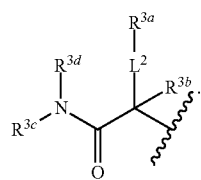

The present invention provides in another group of embodiments, a compound, wherein $D^2$ is cycloalkyl. The present invention provides in another group of embodiments, a compound, wherein $D^2$ is selected from the group consisting of cyclopentyl, cyclobutyl and cyclopropyl. The present invention provides in another group of embodiments, a compound, wherein $D^2$ is cyclopentyl.

The present invention provides in another group of embodiments, a compound, wherein the heteroaryl group, alone or when part of a group containing a heteroaryl moiety is selected from the group consisting of:

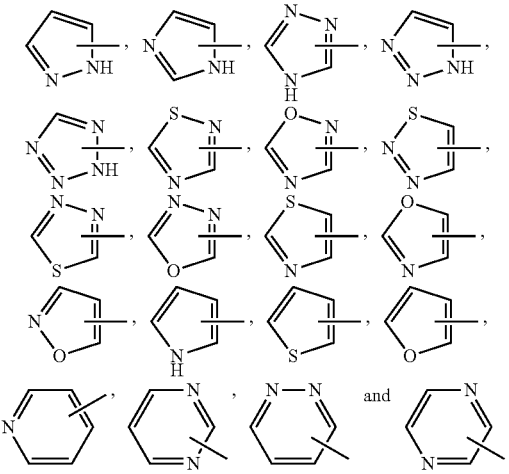

each of which is optionally substituted with from 1 to 2 substituents independently selected from the group consisting of: $C_{1-8}$ alkyl, amino, hydroxyl, oxo, halo, $C_{1-8}$ alkoxy, hydroxy$C_{1-8}$alkyl-, amino$C_{1-8}$alkyl, $C_{1-8}$alkylcarbonyl, halo$C_{1-8}$alkyl, $C_{3-8}$cycloalkyl, $C_{1-8}$aminocycloalkyl, amino$C_{1-8}$alkylenecarbonyl, aminocarbonyl, $C_{1-8}$alkyleneamino$C_{1-8}$alkylenecarbonyl, $C_{1-8}$alkoxy$C_{1-8}$alkylenecarbonyl, hydroxy$C_{1-8}$alkylenecarbonyl, hydroxy$C_{1-8}$alkoxycarbonyl, $C_{1-8}$ alkoxycarbonylamino, aryl, aryl$C_{1-8}$alkoxycarbonylamino, $C_{1-8}$alkylsulfonyl, amino$C_{1-8}$alkylenesulfonyl, aminosulfonyl, $C_{1-8}$alkyleneamino$C_{1-8}$alkylenesulfonyl, $C_{1-8}$alkoxy$C_{1-8}$alkylenesulfonyl, hydroxy$C_{1-8}$alkylenesulfonyl, hydroxy$C_{1-8}$alkoxysulfonyl, aminosulfonyl, and $C_{1-8}$alkylheterocyclyl.

The present invention provides in another group of embodiments, a compound, wherein the heteroaryl group, alone or when part of a group containing a heteroaryl moiety is selected from the group consisting of:

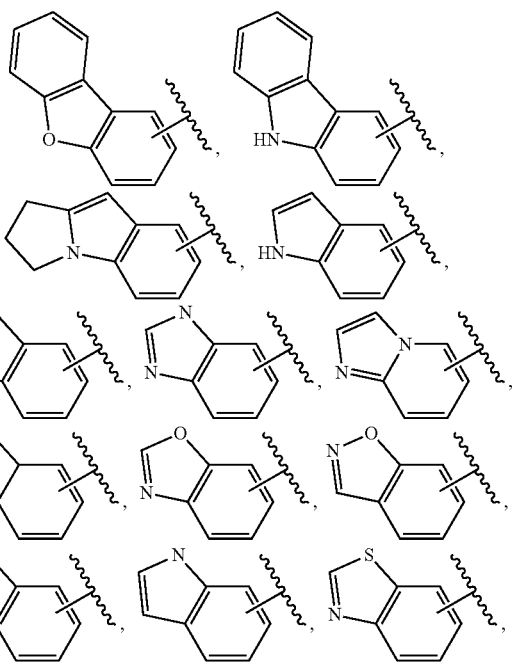

-continued

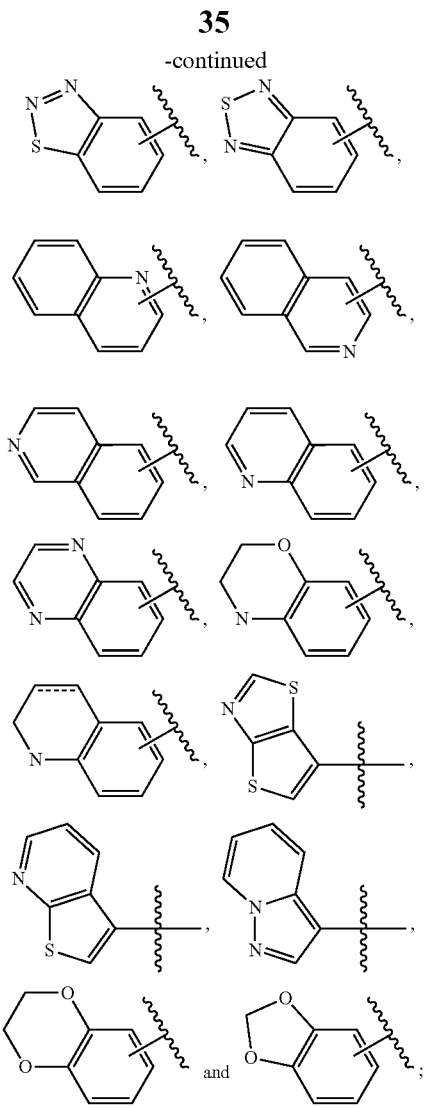

each of which is optionally substituted with from 1 to 3 R[7] substituents independently selected from the group consisting of: $C_{1-8}$ alkyl, $C_{1-8}$alkylcarbonyl, $C_{1-8}$aminocycloalkyl, amino$C_{1-8}$alkylenecarbonyl, aminocarbonyl, $C_{1-8}$alkyleneamino$C_{1-8}$alkylenecarbonyl, $C_{1-8}$alkoxy$C_{1-8}$alkylenecarbonyl, hydroxy$C_{1-8}$alkylenecarbonyl, hydroxy$C_{1-8}$alkoxycarbonyl, aminocarbonyl, amino, $C_{1-8}$ alkoxycarbonylamino, aryl, aryl$C_{1-8}$alkoxycarbonylamino, hydroxyl, $C_{1-8}$ alkoxy, $C_{1-8}$alkylsulfonyl, amino$C_{1-8}$alkylenesulfonyl, aminosulfonyl, $C_{1-8}$alkyleneamino$C_{1-8}$alkylenesulfonyl, $C_{1-8}$ alkoxy$C_{1-8}$ alkylenesulfonyl, hydroxy$C_{1-8}$alkylenesulfonyl, hydroxy$C_{1-8}$alkoxysulfonyl, aminosulfonyl, oxo, halo, phenyl and $C_{1-8}$alkylheterocyclyl; and the wavy line indicates the point of attachment to the rest of the molecule.

The present invention provides in another group of embodiments, a compound, wherein $D^2$ is heterocycloalkyl. The present invention provides in another group of embodiments, a compound, wherein $D^2$ is arylalkylene.

The present invention provides in another group of embodiments, a compound, wherein $R^2$ is selected from the group consisting of H and $C_{1-8}$alkyl.

The present invention provides in another group of embodiments, a compound, wherein the moiety:

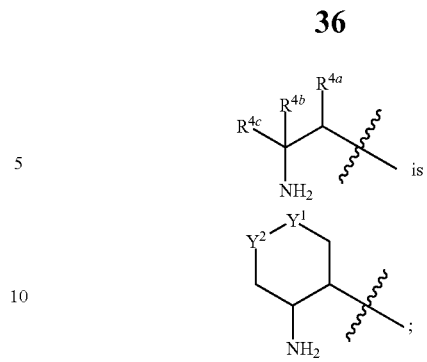

wherein $Y^1$ and $Y^2$ is each independently selected from the group consisting of: O, $CR_2$, NH, $NCOCH_3$ and S.

The present invention provides in another group of embodiments, a compound, wherein the moiety:

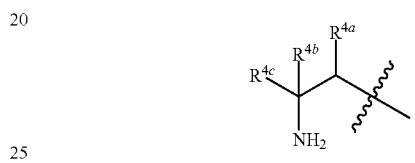

is selected from the group consisting of:

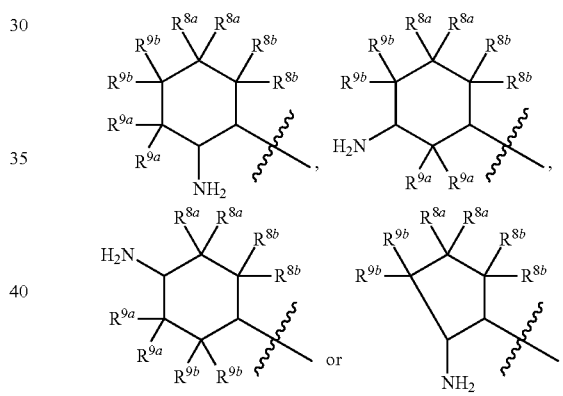

wherein each $R^{8a}$ and $R^{8b}$ is independently H, hydroxyl, $CO_2H$, $CO_2R$ (where R is a $C_1$-$C_6$ alkyl group), $CONR_1R_2$ (where $R_1$ and $R_2$ are independently $C_1$-$C_6$ alkyl groups), halo or if on adjacent carbon atoms, may be combined with the atoms to which they are attached to form a fused benzene ring; and each $R^{9a}$ and $R^{9b}$ is independently H, hydroxyl, $CO_2H$, $CO_2R$ (where R is a $C_1$-$C_6$ alkyl group), $CONR_1R_2$ (where $R_1$ and $R_2$ are independently $C_1$-$C_6$ alkyl groups), halo or, if on adjacent carbon atoms, may be combined with the atoms to which they are attached to form a fused benzene ring; and the wavy line indicates the point of attachment to the rest of the molecule.

The present invention provides in another group of embodiments, a compound, wherein: the moiety:

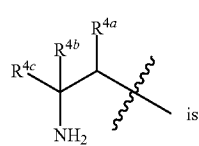 is

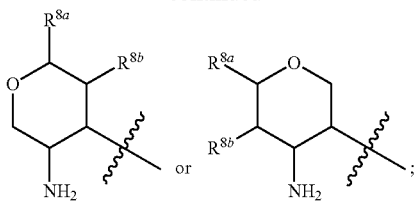

wherein each $R^{8a}$ and $R^{8b}$ is independently H, $CO_2H$, $CO_2R$ (where R is a $C_1$-$C_6$ alkyl group), $CONR_1R_2$ (where $R_1$ and $R_2$ are independently $C_1$-$C_6$ alkyl groups), or may be combined with the atoms to which they are attached to form a fused benzene ring; and the wavy line indicates the point of attachment to the rest of the molecule.

The present invention provides in another group of embodiments, a compound, wherein the compound has the formula (If):

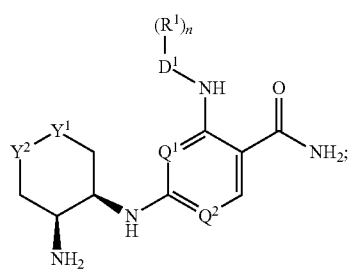

(If)

wherein each $Y^1$ and $Y^2$ is each independently selected from the group consisting of: O, $CR_2$, NH, $NCOCH_3$ and S.

The present invention provides in another group of embodiments, a compound, wherein the compound has the formula (Ig):

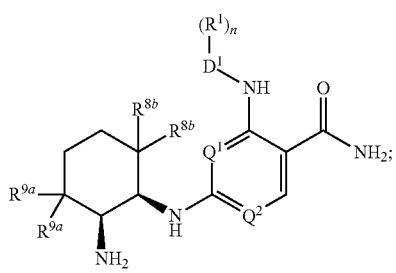

(Ig)

Wherein each $R^{9a}$ and $R^{8b}$ is independently H or F. In one group of embodiments $R^{8b}$ is H. In another group of embodiments $R^{8b}$ is F. In one group of embodiments $R^{9a}$ is H. In another group of embodiments $R^{9a}$ is F.

The present invention provides in another group of embodiments, a compound wherein $D^1$ is selected from the group consisting of:

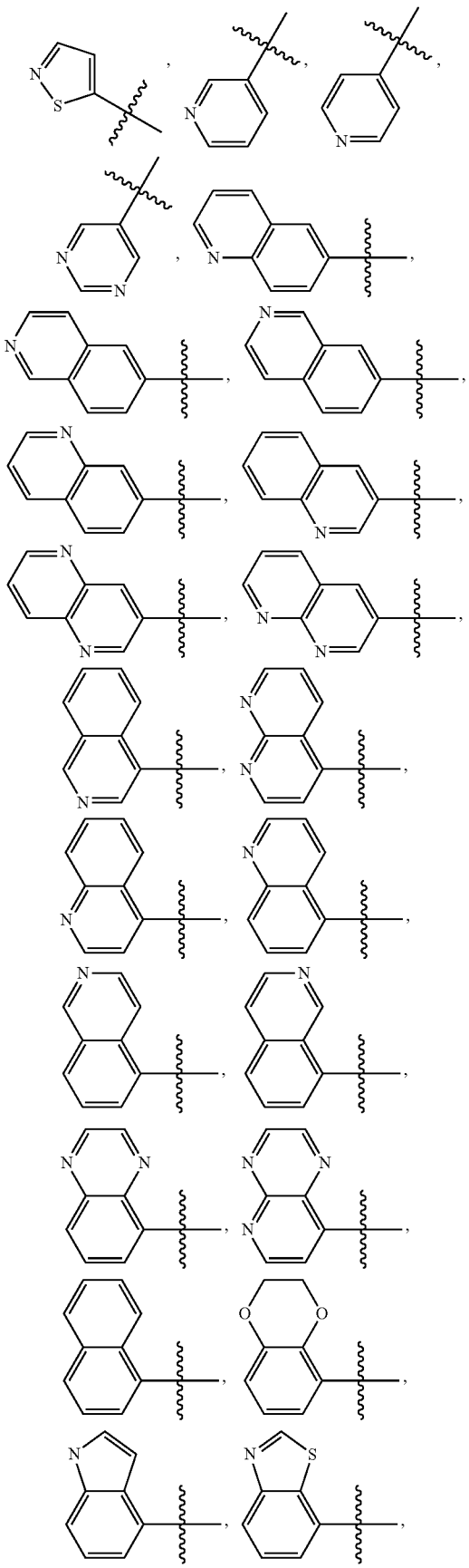

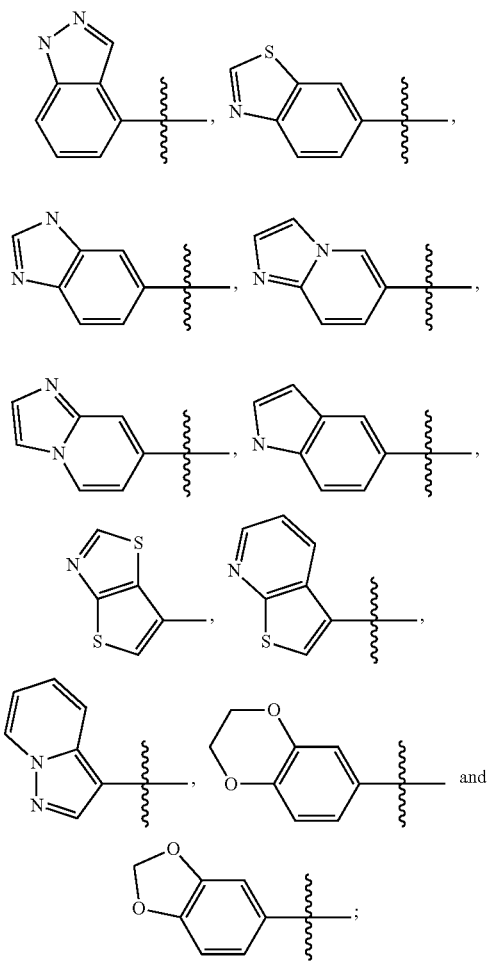

and $R^1$ is alkyl, alkoxy or halo. In one group of embodiments, $R^1$ is methyl. In one group of embodiments, $R^1$ is methoxy. In one group of embodiments, $R^1$ if fluoro.

The present invention provides in another group of embodiments, a compound wherein the compound has the formula (Ih):

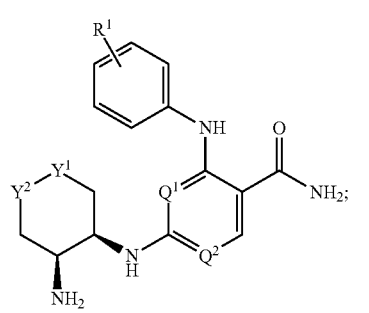

wherein each $Y^1$ and $Y^2$ is each independently selected from the group consisting of: O, $CR_2$, NH, $NCOCH_3$ and S.

The present invention provides in another group of embodiments, a compound, wherein the compound has the formula (Ii):

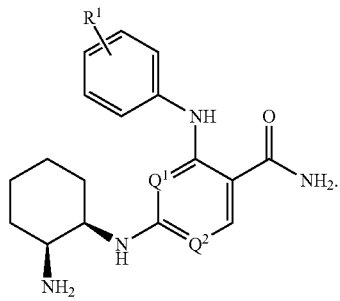

The present invention provides in another group of embodiments, a compound, wherein the compound has the formulae (Ija-la):

(Ija)

(Ika)

(IIa)

The present invention provides in another group of embodiments, a compound, wherein the compound has the formulae (Ijb-lb):

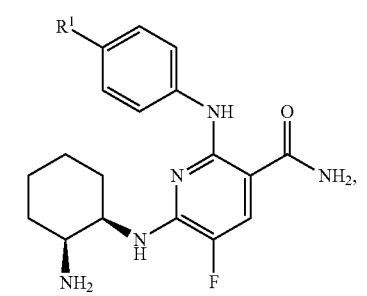 (Ijb)

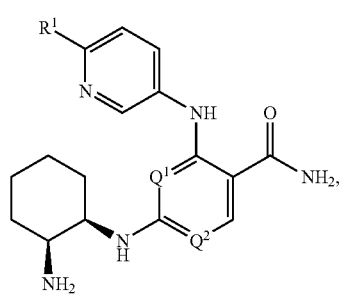 (In)

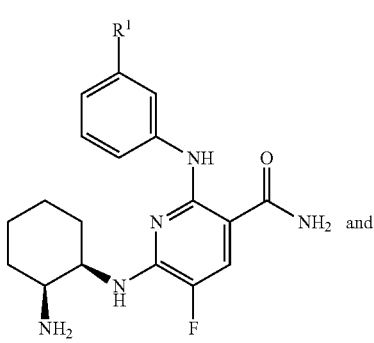 (Ikb)

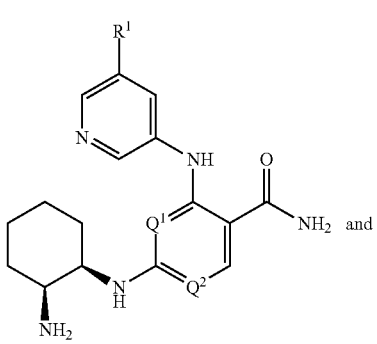 (Io)

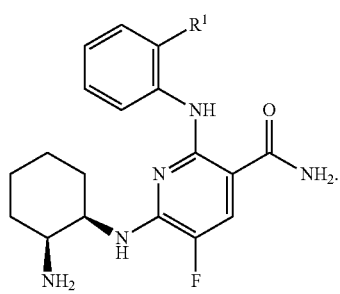 (IIb)

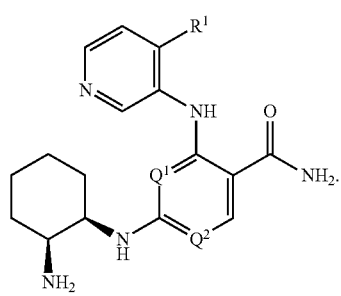 (Ip)

The present invention provides in another group of embodiments, a compound having the formula (Im):

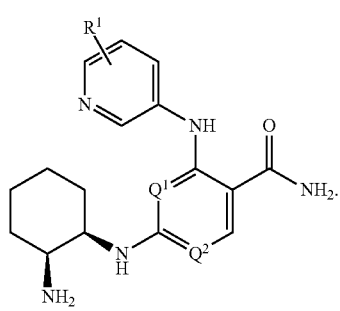 (Im)

The present invention provides in another group of embodiments, a compound, wherein the compound has the formula (Ii):

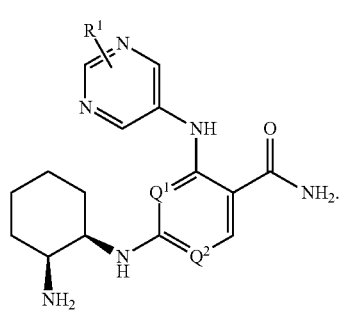 (Iq)

The present invention provides in another group of embodiments, a compound, wherein the compound has the formulae (In-p):

The present invention provides in another group of embodiments, a compound, wherein the compound has the formulae (Ir):

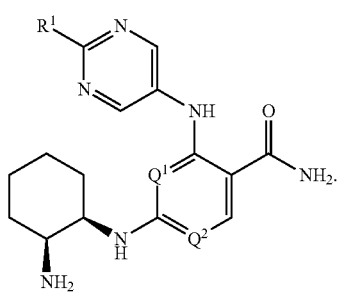
(Ir)

The present invention provides in another group of embodiments, a compound, wherein the compound has the formula (Ii):

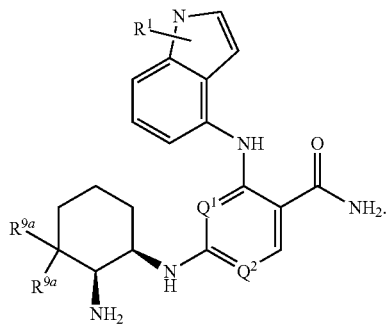
(Is)

The present invention provides in another group of embodiments, a compound, wherein the compound has the formulae (Ir):

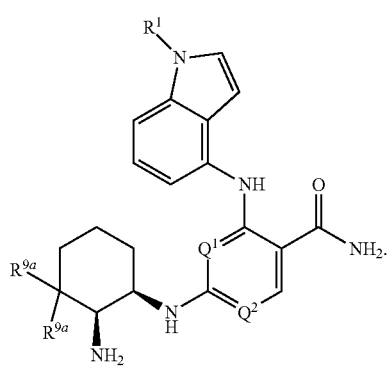
(It)

The present invention provides in another group of embodiments, a compound wherein $R^1$ is selected from the group consisting of:

$C_{1-8}$alkoxy, $C_{1-8}$alkoxy$C_{1-8}$alkoxy,

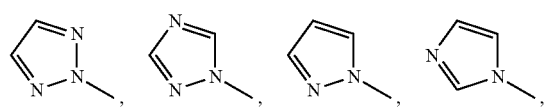

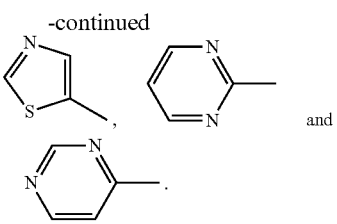

-continued

In another group of embodiments, $R^1$ is methyl. In another group of embodiments, $R^1$ is methoxy. In another group of embodiments, $R^1$ is fluoro.

The present invention provides in another group of embodiments, a compound, wherein a compound having the formula (Is):

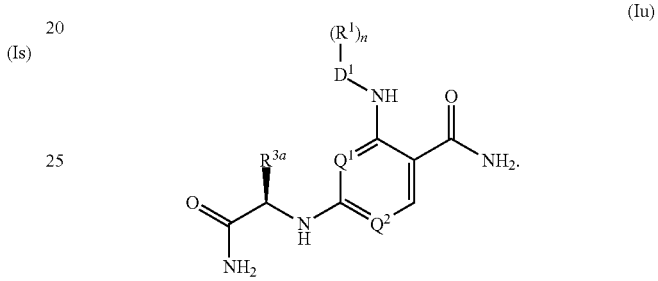
(Iu)

The present invention provides in another group of embodiments, a compound, wherein the compound has the formula (It):

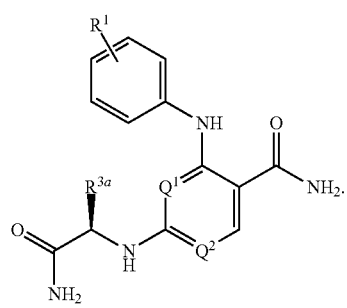
(Iv)

The present invention provides in another group of embodiments, a compound wherein the compound has a formula selected from the group consisting of:

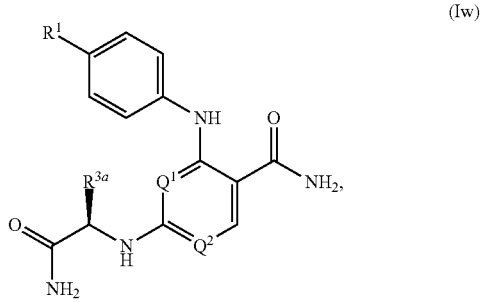
(Iw)

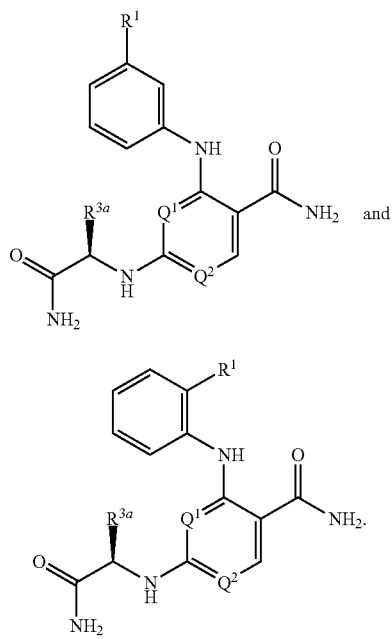

The present invention provides in another group of embodiments, a compound, wherein $R^{3a}$ is selected from the group consisting of $C_{1-8}$alkyl, $C_{3-8}$cycloalkyl, aryl, heteroaryl and heterocyclyl.

The present invention provides in another group of embodiments, a compound, wherein $R^{3a}$ is selected from the group consisting of methyl, ethyl, isopropyl, isobutyl, benzyl, benzyloxymethyl, hydroxymethyl, methoxymethyl, cyclohexylmethyl, phenyl, cyclopropyl, cyclohexyl, cyclopropylmethyl, ethyl, 4-fluorophenylmethyl, 3-fluorophenylmethyl, 4-pyridinylmethyl, 3-pyridinylmethyl, 4-hydroxyphenylmethyl and 4-methoxyphenylmethyl.

The present invention provides in another group of embodiments, a compound, wherein the moiety:

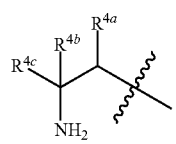

is selected from the group consisting of:

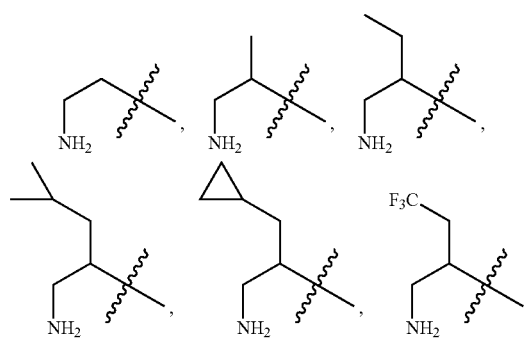

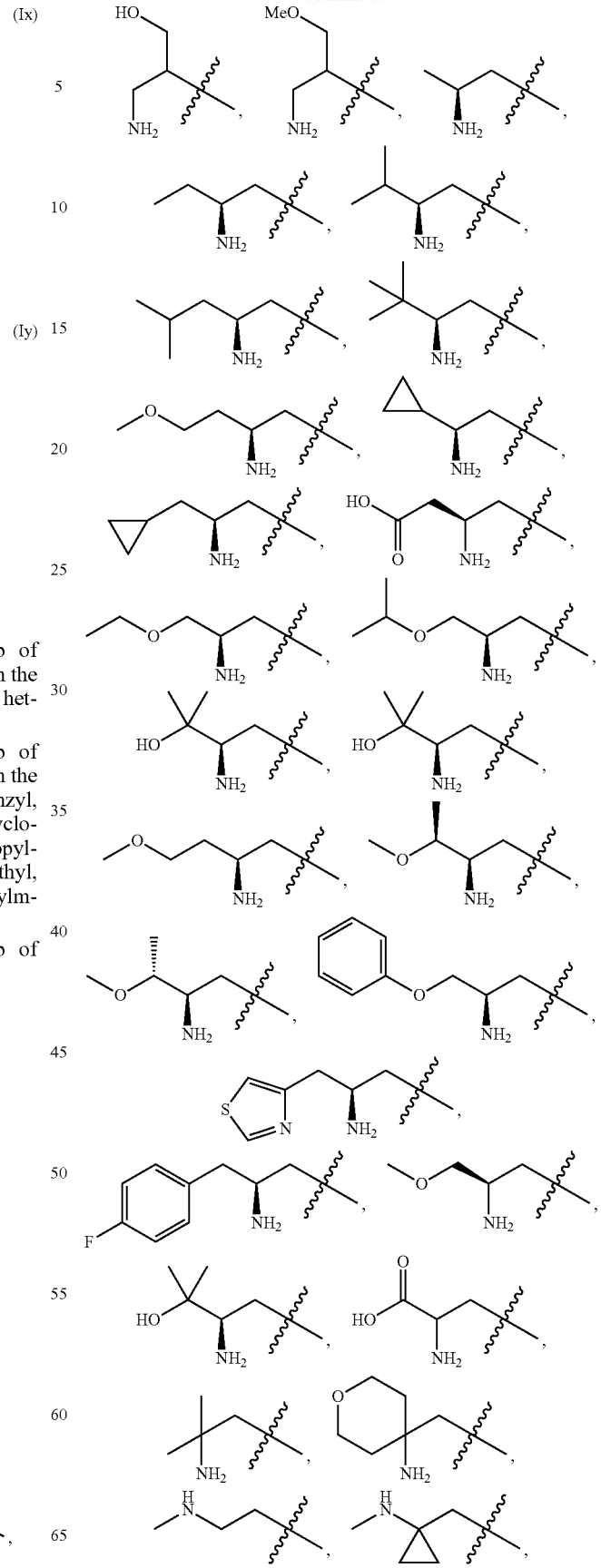

-continued

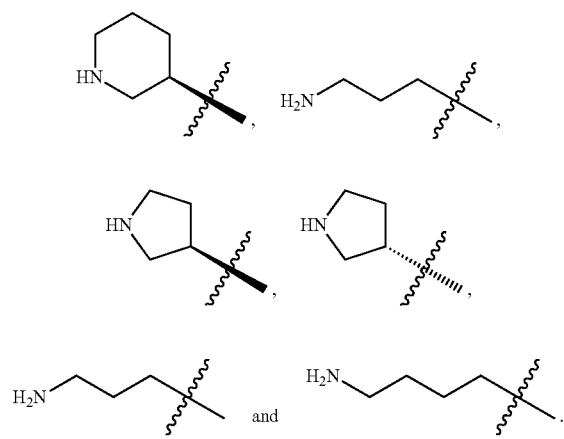

The present invention provides in another group of embodiments, a compound, wherein the moiety:

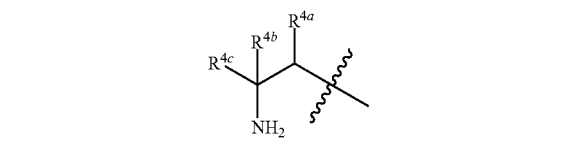

is selected from the group consisting of:

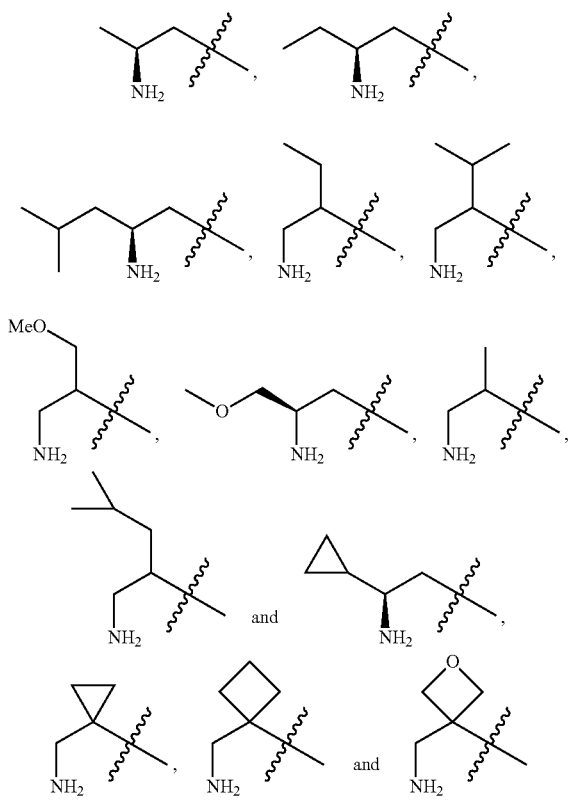

The present invention provides in another embodiment, a compound having the formula (Iz):

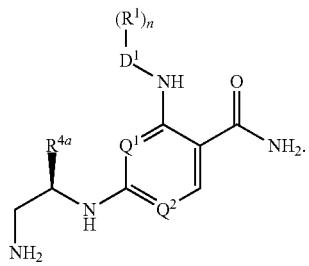

The present invention provides in another embodiment, a compound selected from the group consisting of: 4-(1R,2S)-2-aminocyclohexylamino)-2-(m-tolylamino)benzamide; 4-((1R,2S)-2-aminocyclohexylamino)-2-(1-methyl-1H-indol-4-ylamino)benzamide; 4-((1R,2S)-2-aminocyclohexylamino)-2-(4-fluorophenylamino)benzamide; 4-(1R,2S)-2-aminocyclohexylamino)-2-(3,5-dimethylphenylamino)benzamide; 2-(3-(2H-1,2,3-triazol-2-yl)phenylamino)-4-(1R,2S)-2-aminocyclohexylamino)benzamide; 4-(1R,2S)-2-aminocyclohexylamino)-2-(3-methylisothiazol-5-ylamino)benzamide; 4-((1R,2S)-2-aminocyclohexylamino)-2-(3-phenylisoxazol-5-ylamino)benzamide; 4-((1R,2S)-2-aminocyclohexylamino)-2-(1-methyl-1H-pyrazol-4-ylamino)benzamide; (R)-4-(1-amino-4-methyl-1-oxopentan-2-ylamino)-2-(3-methylisothiazol-5-ylamino)benzamide; (R)-4-(1-amino-1-oxopropan-2-ylamino)-2-(3-methylisothiazol-5-ylamino)benzamide; (R)-4-(1-amino-3-methyl-1-oxobutan-2-ylamino)-2-(3-methylisothiazol-5-ylamino)benzamide; (R)-4-(1-amino-4-methyl-1-oxopentan-2-ylamino)-2-(5-methylisoxazol-3-ylamino)benzamide; (R)-4-(1-amino-4-methyl-1-oxopentan-2-ylamino)-2-(3-methylisoxazol-5-ylamino)benzamide; (R)-4-(1-amino-1-oxo-3-phenylpropan-2-ylamino)-2-(3-methylisothiazol-5-ylamino)benzamide; (R)-4-(1-amino-3-(benzyloxy)-1-oxopropan-2-ylamino)-2-(3-methylisothiazol-5-ylamino)benzamide; (R)-4-(1-amino-3-hydroxy-1-oxopropan-2-ylamino)-2-(3-methylisothiazol-5-ylamino)benzamide; (R)-4-(1-amino-3-cyclohexyl-1-oxopropan-2-ylamino)-2-(3-methylisothiazol-5-ylamino)benzamide; (R)-4-(2-amino-2-oxo-1-phenylethylamino)-2-(3-methylisothiazol-5-ylamino)benzamide; (R)-4-(1-amino-4-methyl-1-oxopentan-2-ylamino)-2-fluoro-6-(3-methylisothiazol-5-ylamino)benzamide; (R)-4-(1-amino-4-methyl-1-oxopentan-2-ylamino)-5-fluoro-2-(3-methylisothiazol-5-ylamino)benzamide; 4-((1R,2S)-2-aminocyclohexylamino)-5-fluoro-2-(3-methylisothiazol-5-ylamino)benzamide; (R)-4-(2-amino-1-cyclohexyl-2-oxoethylamino)-2-(3-methylisothiazol-5-ylamino)benzamide; (R)-4-(1-amino-4-methyl-1-oxopentan-2-ylamino)-3-fluoro-2-(3-methylisothiazol-5-ylamino)benzamide; (R)-4-(1-amino-1-oxo-3-phenylpropan-2-ylamino)-5-fluoro-2-(3-methylisothiazol-5-ylamino)benzamide; (R)-4-(1-amino-3-cyclopropyl-1-oxopropan-2-ylamino)-5-fluoro-2-(3-methylisothiazol-5-ylamino)benzamide; (R)-4-(1-amino-1-oxobutan-2-ylamino)-5-fluoro-2-(3-methylisothiazol-5-ylamino)benzamide; (R)-4-(1-amino-3-(4-fluorophenyl)-1-oxopropan-2-ylamino)-5-fluoro-2-(3-methylisothiazol-5-ylamino)benzamide; (R)-4-(1-amino-3-(4-hydroxyphenyl)-1-oxopropan-2-ylamino)-5-fluoro-2-(3-methylisothiazol-5-ylamino)benzamide; (R)-4-(2-amino-3-methoxypropylamino)-2-(3-methylisothiazol-5-ylamino)benzamide; (S)-4-(2-aminobutylamino)-2-(3-methylisothiazol-5-ylamino)benzamide; (S)-4-(2- aminopropylamino)-2-(3-methylisothiazol-5-ylamino)benzamide; (S)-4-(2-amino-4-methylpentylamino)-2-(3-methylisothiazol-5-ylamino)benzamide; (R)-4-(1-amino-1-oxobutan-2-ylamino)-2-(3-methylisothiazol-5-ylamino)benzamide; (R)-4-(1-amino-1-oxobutan-2-ylamino)-2-(3-methylisothiazol-5-ylamino)benzamide; (R)-4-(1-amino-3-cyclopropyl-1-oxopropan-2-ylamino)-2-(3-methylisothiazol-5-ylamino)benzamide; (R)-4-(1-amino-3-(4-methoxyphenyl)-1-oxopropan-2-ylamino)-5-fluoro-2-(3-methylisothiazol-5-ylamino)benzamide; (R)-4-(1-amino-3-(3-fluorophenyl)-1-oxopropan-2-ylamino)-5-fluoro-2-(3-methylisothiazol-5-ylamino)benzamide; (R)-4-(1-amino-1-oxo-3-(pyridin-4-yl)propan-2-ylamino)-5-fluoro-2-(3-methylisothiazol-5-ylamino)benzamide; (R)-4-(1-amino-1-oxo-3-(pyridin-3-yl)propan-2-ylamino)-5-fluoro-2-(3-methylisothiazol-5-ylamino)benzamide; (R)-4-(1-amino-3-methoxy-1-oxopropan-2-ylamino)-5-fluoro-2-(3-methylisothiazol-5-ylamino)benzamide; 2-(3-(2H-1,2,3-triazol-2-yl)phenylamino)-6-((1R,2S)-2-aminocyclohexylamino)-5-fluoronicotinamide; 2-(3-(1H-1,2,4-triazol-1-yl)phenylamino)-6-((1R,2S)-2-aminocyclohexylamino)-5-fluoronicotinamide; 2-(3-(1H-1,2,3-triazol-1-yl)phenylamino)-6-((1R,2S)-2-aminocyclohexylamino)-5-fluoronicotinamide; 2-(3-(1H-tetrazol-1-yl)phenylamino)-6-(1R,2S)-2-aminocyclohexylamino)-5-fluoronicotinamide; 2-(3-(1H-pyrazol-1-yl)phenylamino)-6-((1R,2S)-2-aminocyclohexylamino)-5-fluoronicotinamide; 2-(3-(1H-imidazol-1-yl)phenylamino)-6-((1R,2S)-2-aminocyclohexylamino)-5-fluoronicotinamide; 6-((1R,2S)-2-aminocyclohexylamino)-5-fluoro-2-(3-(pyrrolidin-1-yl)phenylamino)nicotinamide; 6-((1R,2S)-2-aminocyclohexylamino)-5-fluoro-2-(3-morpholinophenylamino)nicotinamide; 2-(4-(2H-1,2,3-triazol-2-yl)phenylamino)-6-(1R,2S)-2-aminocyclohexylamino)-5-fluoronicotinamide; 2-(4-(1H-1,2,4-triazol-1-yl)phenylamino)-6-((1R,2S)-2-aminocyclohexylamino)-5-fluoronicotinamide; 2-(4-(1H-imidazol-1-yl)phenylamino)-6-((1R,2S)-2-aminocyclohexylamino)-5-fluoronicotinamide; 2-(4-(1H-pyrazol-1-yl)phenylamino)-6-((1R,2S)-2-aminocyclohexylamino)-5-fluoronicotinamide; 6-(1R,2S)-2-aminocyclohexylamino)-5-fluoro-2-(4-(pyrrolidin-1-yl)phenylamino)nicotinamide; 6-((1R,2S)-2-aminocyclohexylamino)-5-fluoro-2-(4-morpholinophenylamino)nicotinamide; 6-((1R,2S)-2-aminocyclohexylamino)-5-fluoro-2-(3-(pyrimidin-2-yl)phenylamino)nicotinamide; 6-((1R,2S)-2-aminocyclohexylamino)-5-fluoro-2-(3-(pyrimidin-4-yl)phenylamino)nicotinamide; 6-((1R,2S)-2-aminocyclohexylamino)-5-fluoro-2-(3-(pyrimidin-5-yl)phenylamino)nicotinamide; 6-((1R,2S)-2-aminocyclohexylamino)-5-fluoro-2-(4-(pyrimidin-2-yl)phenylamino)nicotinamide; 6-((1R,2S)-2-aminocyclohexylamino)-5-fluoro-2-(4-(pyrimidin-4-yl)phenylamino)nicotinamide; 6-((1R,2S)-2-aminocyclohexylamino)-2-(benzo[d]thiazol-6-ylamino)-5-fluoronicotinamide; 6-((1R,2S)-2-aminocyclohexylamino)-5-fluoro-2-(imidazo[1,2-a]pyridin-6-ylamino)nicotinamide; 6-((1R,2S)-2-aminocyclohexylamino)-5-fluoro-2-(imidazo[1,2-a]pyridin-7-ylamino)nicotinamide; 6-((1R,2S)-2-aminocyclohexylamino)-5-fluoro-2-(1-methyl-1H-indol-5-ylamino)nicotinamide; 6-((1R,2S)-2-aminocyclohexylamino)-5-fluoro-2-(1-methyl-1H-indol-4-ylamino)nicotinamide; 6-((1R,2S)-2-aminocyclohexylamino)-5-fluoro-2-(2-methyl-2H-indazol-4-ylamino)nicotinamide; 6-((1R,2S)-2-aminocyclohexylamino)-5-fluoro-2-(quinolin-6-ylamino)nicotinamide; 6-((1R,2S)-2-aminocyclohexylamino)-5-fluoro-2-(isoquinolin-6-ylamino)nicotinamide; 6-((1R,2S)-2-aminocyclohexylamino)-5-fluoro-2-(isoquinolin-7-ylamino)nicotinamide; 6-((1R,2S)-2-aminocyclohexylamino)-5-fluoro-2-(quinolin-7-ylamino)nicotinamide; 6-((1R,2S)-2-aminocyclohexylamino)-5-fluoro-2-(quinolin-3-ylamino)nicotinamide; 6-((1R,2S)-2-aminocyclohexylamino)-5-fluoro-2-(isoquinolin-4-ylamino)nicotinamide; 6-((1R,2S)-2-aminocyclohexylamino)-5-fluoro-2-(quinolin-4-ylamino)nicotinamide; 6-((1R,2S)-2-aminocyclohexylamino)-5-fluoro-2-(quinolin-5-ylamino)nicotinamide; 6-((1R,2S)-2-aminocyclohexylamino)-5-fluoro-2-(isoquinolin-5-ylamino)nicotinamide; 6-((1R,2S)-2-aminocyclohexylamino)-5-fluoro-2-(isoquinolin-8-ylamino)nicotinamide; 6-((1R,2S)-2-aminocyclohexylamino)-5-fluoro-2-(quinoxalin-6-ylamino)nicotinamide; 6-((1R,2S)-2-aminocyclohexylamino)-5-fluoro-2-(pyrido[3,2-b]pyrazin-7-ylamino)nicotinamide; 6-((1R,2S)-2-aminocyclohexylamino)-2-(2,3-dihydrobenzo[b][1,4]dioxin-6-ylamino)-5-fluoronicotinamide; 6-(1R,2S)-2-aminocyclohexylamino)-5-fluoro-2-(3-(2-methoxyethoxy)phenylamino)nicotinamide; 6-((1R,2S)-2-aminocyclohexylamino)-5-fluoro-2-(3-(tetrahydro-2H-pyran-4-yloxy)phenylamino)nicotinamide; 6-((1R,2S)-2-aminocyclohexylamino)-5-fluoro-2-(4-(tetrahydro-2H-pyran-4-yloxy)phenylamino)nicotinamide; 6-((1R,2S)-2-aminocyclohexylamino)-5-fluoro-2-(3-methylisothiazol-5-ylamino)nicotinamide; 6-((1R,2S)-2-aminocyclohexylamino)-5-fluoro-2-(1-methyl-1H-pyrazol-4-ylamino)nicotinamide; 6-((1R,2S)-2-aminocyclohexylamino)-5-fluoro-2-(pyridazin-4-ylamino)nicotinamide; 6-((1R,2S)-2-aminocyclohexylamino)-5-fluoro-2-(2-methylpyridin-4-ylamino)nicotinamide; 6-((1R,2S)-2-aminocyclohexylamino)-2-(2,6-dimethylpyridin-4-ylamino)-5-fluoronicotinamide; 6-((1R,2S)-2-aminocyclohexylamino)-5-fluoro-2-(5-methylpyridin-3-ylamino)nicotinamide; 6-((1R,2S)-2-aminocyclohexylamino)-5-fluoro-2-(5-methoxypyridin-3-ylamino)nicotinamide; 6-((1R,2S)-2-aminocyclohexylamino)-5-fluoro-2-(5-fluoropyridin-3-ylamino)nicotinamide; (R)-2-(3-(2H-1,2,3-triazol-2-yl)phenylamino)-6-(1-aminobutan-2-ylamino)-5-fluoronicotinamide; (S)-2-(3-(2H-1,2,3-triazol-2-yl)phenylamino)-6-(1-amino-3-methoxypropan-2-ylamino)-5-fluoronicotinamide; (R)-6-(1-aminobutan-2-ylamino)-5-fluoro-2-(3-(pyrimidin-2-yl)phenylamino)nicotinamide; (R)-6-(1-aminobutan-2-ylamino)-2-(benzo[d]thiazol-6-ylamino)-5-fluoronicotinamide; (R)-6-(1-aminobutan-2-ylamino)-5-fluoro-2-(quinolin-6-ylamino)nicotinamide; (R)-6-(1-aminobutan-2-ylamino)-5-fluoro-2-(5-methylpyridin-3-ylamino)nicotinamide; (R)-6-(1-aminobutan-2-ylamino)-5-fluoro-2-(5-methoxypyridin-3-ylamino)nicotinamide; (R)-6-(1-amino-1-oxobutan-2-ylamino)-5-fluoro-2-(quinolin-7-ylamino)nicotinamide; (R)-6-(1-amino-1-oxobutan-2-ylamino)-5-fluoro-2-(isoquinolin-7-ylamino)nicotinamide; (R)-6-(1-amino-1-oxobutan-2-ylamino)-5-fluoro-2-(isoquinolin-6-ylamino)nicotinamide; (R)-6-(1-amino-1-oxobutan-2-ylamino)-5-fluoro-2-(quinolin-6-ylamino)nicotinamide; 6-(4-(4-acetylpiperazin-1-yl)phenylamino)-2-(cyclobutylamino)nicotinamide; 6-((1R,2S)-2-aminocyclohexylamino)-2-(m-tolylamino)nicotinamide; tert-butyl (1S,2R)-2-(5-carbamoyl-6-(m-tolylamino)pyridin-2-ylamino)cyclohexylcarbamate; tert-butyl (1S,2R)-2-(5-carbamoyl-6-(m-tolylamino)pyridin-2-ylamino)cyclohexylcarbamate; (R)-6-(1-amino-4-methyl-1- oxopentan-2-ylamino)-2-(m-tolylamino)nicotinamide; 2-(3-(2H-1,2,3-triazol-2-yephenylamino)-6-(1R,2S)-2-aminocyclohexylamino)-5-cyanonicotinamide; 6-((1R,2S)-2-aminocyclohexylamino)-5-cyano 2-(m-tolylamino) nicotinamide; (S)-2-(3-(2H-1,2,3-triazol-2-yl)phenylamino)-6-(2-aminopropylamino)-5-cyanonicotinamide; (R)-2-(3-(2H-1,2,3-triazol-2-yl)phenylamino)-6-(1-aminopropan-2-ylamino)-5-cyanonicotinamide; (R)-2-(3-(2H-1,2,3-triazol-2-yl)phenylamino)-6-(1-amino-4-methylpentan-2-ylamino)-5-cyanonicotinamide; (S)-2-(3-(2H-1,2,3-triazol-2-yl)phenylamino)-6-(2-amino-2-cyclopropylethylamino)-5-cyanonicotinamide; (R)-6-(1-aminopropan-2-ylamino)-5-cyano-2-(2-methyl-2H-indazol-4-ylamino)nicotinamide; 6-(1R,2S)-2-aminocyclohexylamino)-5-cyano-2-(quinolin-6-ylamino)nicotinamide; (R)-6-(1-aminopropan-2-ylamino)-5-cyano-2-(quinolin-6-ylamino)nicotinamide; 6-((1R,2S)-2-aminocyclohexylamino)-5-cyano-2-(2-methyl-2H-indazol-4-ylamino)nicotinamide; 2-(3-(2H-1,2,3-triazol-2-yl)phenylamino)-6-((1R,2S)-2-aminocyclohexylamino)pyridine-3,5-dicarboxamide; 2-(1H-indazol-5-ylamino)-6-(1R,2S)-2-aminocyclohexylamino)-5-cyanonicotinamide; 6-(1R,2S)-2-aminocyclohexylamino)-2-(benzo[d]thiazol-6-ylamino)-5-cyanonicotinamide; (S)-6-(2-amino-2-cyclopropylethylamino)-2-(benzo[d]thiazol-6-ylamino)-5-cyanonicotinamide; 6-((1R,2S)-2-aminocyclohexylamino)-5-cyano-2-(1-methyl-1H-indazol-4-ylamino)nicotinamide; 2-(4-(1H-pyrazol-1-yl)phenylamino)-6-((1R,2S)-2-aminocyclohexylamino)-5-cyanonicotinamide; (R)-6-(1-amino-4-methylpentan-2-ylamino)-5-cyano-2-(quinolin-6-ylamino)nicotinamide; (R)-6-(1-amino-4-methylpentan-2-ylamino)-2-(benzo[d]thiazol-6-ylamino)-5-cyanonicotinamide; (R)-6-(1-amino-4-methyl-1-oxopentan-2-ylamino)-2-(quinolin-6-ylamino)-5-cyanonicotinamide; (R)-2-(3-(2H-1,2,3-triazol-2-yl)phenylamino)-6-(1-amino-4-methyl-1-oxopentan-2-ylamino)-5-cyanonicotinamide; (R)-2-(3-(2H-1,2,3-triazol-2-yl)phenylamino)-6-(1-amino-3-methyl-1-oxobutan-2-ylamino)-5-cyanonicotinamide; (R)-2-(1H-indazol-5-ylamino)-6-(1-amino-4-methyl-1-oxopentan-2-ylamino)-5-cyanonicotinamide; (R)-6-(1-amino-3-methylbuttan-2-ylamino)-5-cyano-2-(quinolin-6-ylamino)nicotinamide; 6-((1R,2S)-2-aminocyclohexylamino)-5-cyano-2-(quinolin-3-ylamino)nicotinamide; 6-((1R,2S)-2-aminocyclohexylamino)-5-cyano-2-(3-(pyrimidin-2-yl)phenylamino)nicotinamide; 6-((1R,2S)-2-aminocyclohexylamino)-5-cyano-2-(3-(pyridin-2-yl)phenylamino)nicotinamide; 2-(3-(2H-1,2,3-triazol-2-yl)phenylamino)-6-((1R,2S)-2-aminocyclohexylamino)nicotinamide; 2-(3-(pyrimidin-2-yl)phenylamino)-6-((1R,2S)-2-aminocyclohexylamino)nicotinamide; 2-(quinolin-6-ylamino)-6-((1R,2S)-2-aminocyclohexylamino)nicotinamide; 2-(isoquinolin-6-ylamino)-6-((1R,2S)-2-aminocyclohexylamino)nicotinamide; 2-(1-methyl-1H-indazol-4-ylamino)-6-((1R,2S)-2-aminocyclohexylamino)-5-fluoronicotinamide; 2-(isoquinolin-7-ylamino)-6-((1R,2S)-2-aminocyclohexylamino)nicotinamide; 2-(3-(1H-1,2,4-triazol-1-yl)phenylamino)-6-((1R,2S)-2-aminocyclohexylamino)nicotinamide; 2-(1-methyl-1H-indazol-5-ylamino)-6-((1R,2S)-2-aminocyclohexylamino)-5-fluoronicotinamide; 6-(cis-2-aminocyclohexylamino)-2-(4-(1H-pyrazol-1-yl)phenylamino)nicotinamide; 6-(cis-2-aminocyclohexylamino)-2-(1H-indazol-5-ylamino)nicotinamide; 6-(cis-2-aminocyclohexylamino)-4-(3-toluidino)nicotinamide; 6-(4-(4-acetylpiperazin-1-yl)phenylamino)-4-(benzylamino)nicotinamide; (S)-4-(benzylamino)-6-(4-(3-(methylcarbamoyl)piperidin-1-yl)phenylamino)nicotinamide; 6-(4-(4-acetylpiperazin-1-yl)-3-methylphenylamino)-4-(benzylamino)nicotinamide; (R)-4-(benzylamino)-6-(4-(3-(methylcarbamoyl)piperidin-1-yl)phenylamino)nicotinamide.

The present invention provides in another embodiment, a compound selected from the group consisting of: (R)-4-(4-(6-(1-amino-1-oxobutan-2-ylamino)-3-carbamoyl-5-fluoropyridin-2-ylamino)phenyl)-1-methylpiperidine 1-oxide, 6-((1R,2S)-2-aminocyclohexylamino)-5-fluoro-2-(4-(1-methylpiperidin-4-yl)phenylamino)nicotinamide, 6-((1R,2S)-2-aminocyclohexylamino)-2-(benzo[d]thiazol-5-ylamino)-5-fluoronicotinamide, 6-((1R,2S)-2-aminocyclohexylamino)-2-(benzo[d]thiazol-7-ylamino)-5-fluoronicotinamide, 6-((1R,2S)-2-aminocyclohexylamino)-5-fluoro-2-(phenylamino)nicotinamide, 6-((1R,2S)-2-aminocyclohexylamino)-5-fluoro-2-(o-tolylamino)nicotinamide, 6-((1R,2S)-2-aminocyclohexylamino)-5-fluoro-2-(m-tolylamino)nicotinamide, 6-((1R,2S)-2-aminocyclohexylamino)-5-fluoro-2-(p-tolylamino)nicotinamide, 6-((1R,2S)-2-aminocyclohexylamino)-5-fluoro-2-(3-fluorophenylamino)nicotinamide, 6-((1R,2S)-2-aminocyclohexylamino)-2-(3-chlorophenylamino)-5-fluoronicotinamide, 6-((1R,2S)-2-aminocyclohexylamino)-2-(4-chlorophenylamino)-5-fluoronicotinamide, 6-((1R,2S)-2-aminocyclohexylamino)-2-(2,3-dimethylphenylamino)-5-fluoronicotinamide, 6-((1R,2S)-2-aminocyclohexylamino)-2-(3,5-dimethylphenylamino)-5-fluoronicotinamide, 6-((1R,2S)-2-aminocyclohexylamino)-5-fluoro-2-(3-fluoro-5-methylphenylamino)nicotinamide, 6-((1R,2S)-2-aminocyclohexylamino)-5-fluoro-2-(4-fluoro-3-methylphenylamino)nicotinamide, 6-((1R,2S)-2-aminocyclohexylamino)-5-fluoro-2-(3-fluoro-4-methylphenylamino)nicotinamide, 6-((1R,2S)-2-aminocyclohexylamino)-2-(3,5-difluorophenylamino)-5-fluoronicotinamide, 6-((1R,2S)-2-aminocyclohexylamino)-2-(3-chloro-5-fluorophenylamino)-5-fluoronicotinamide, 6-((1R,2S)-2-aminocyclohexylamino)-5-fluoro-2-(3-fluoro-5-methoxyphenylamino)nicotinamide, 6-((1R,2R)-2-amino-3,3-difluorocyclohexylamino)-5-fluoro-2-(quinolin-5-ylamino)nicotinamide, 6-((1R,2R)-2-amino-3,3-difluorocyclohexylamino)-2-(benzo[d]thiazol-6-ylamino)-5-fluoronicotinamide, 6-((1R,2R)-2-amino-3,3-difluorocyclohexylamino)-2-(benzo[d]thiazol-7-ylamino)-5-fluoronicotinamide, 6-((1R,2R)-2-amino-3,3-difluorocyclohexylamino)-5-fluoro-2-(1-methyl-1H-indol-4-ylamino)nicotinamide, 6-((1R,2R)-2-amino-3,3-difluorocyclohexylamino)-5-fluoro-2-(1-methyl-1H-indol-5-ylamino)nicotinamide, 6-((1R,2R)-2-amino-3,3-difluorocyclohexylamino)-5-fluoro-2-(5-methylpyridin-3-ylamino)nicotinamide, 6-((1R,2R)-2-amino-3,3-difluorocyclohexylamino)-5-fluoro-2-(3-methylisothiazol-5-ylamino)nicotinamide, 6-((1R,2R)-2-amino-3,3-difluorocyclohexylamino)-5-fluoro-2-(p-tolylamino)nicotinamide, 6-((1R,2R)-2-amino-3,3-difluorocyclohexylamino)-5-fluoro-2-(m-tolylamino)nicotinamide, 6-((1R,2R)-2-amino-3,3-difluorocyclohexylamino)-2-(3-chlorophenylamino)-5-fluoronicotinamide, 6-((1R,2R)-2-amino-3,3-difluorocyclohexylamino)-2-(3,5-difluorophenylamino)-5-fluoronicotinamide, 6-((1R,2R)-2-amino-3,3-difluorocyclohexylamino)-5-fluoro-2-(3-fluoro-5-methoxyphenylamino)nicotinamide, 6-((1R,2R)-2-amino-3,3-difluorocyclohexylamino)-5-fluoro-2-(3-fluoro-5-methylphenylamino)nicotinamide, 2-(3-(2H-1,2,3-triazol-2-yl)phenylamino)-6-((1S,6S)-6-amino-2,2-difluorocyclohexylamino)-5-fluoronicotinamide, 2-(3-(1H-pyrazol-1-yl)phenylamino)-6-((1S,6S)-6-amino-2,2- difluorocyclohexylamino)-5-fluoronicotinamide, 6-((1S,6S)-6-amino-2,2-difluorocyclohexylamino)-5-fluoro-2-(3-(pyrimidin-2-yl)phenylamino)nicotinamide, 6-((1S,6S)-6-amino-2,2-difluorocyclohexylamino)-5-fluoro-2-(quinolin-6-ylamino)nicotinamide, 6-((1S,6S)-6-amino-2,2-difluorocyclohexylamino)-5-fluoro-2-(quinolin-3-ylamino)nicotinamide, 6-((1S,6S)-6-amino-2,2-difluorocyclohexylamino)-2-(benzo[d]thiazol-6-ylamino)-5-fluoronicotinamide, 6-((1S,6S)-6-amino-2,2-difluorocyclohexylamino)-5-fluoro-2-(p-tolylamino)nicotinamide, 6-((1S,6S)-6-amino-2,2-difluorocyclohexylamino)-5-fluoro-2-(pyridin-3-ylamino)nicotinamide, 6-((1S,6S)-6-amino-2,2-difluorocyclohexylamino)-5-fluoro-2-(5-fluoropyridin-3-ylamino)nicotinamide, 6-(3R,4R)-3-aminotetrahydro-2H-pyran-4-ylamino)-5-fluoro-2-(p-tolylamino)nicotinamid, (S)-6-(1-(1-aminocyclopropyl)propylamino)-5-fluoro-2-(m-tolylamino)nicotinamide, (S)-6-[(1-(1-aminocyclopropyl)propylamino)-5-fluoro-2-(p-tolylamino)nicotinamide,(S)-6-(1-(1-aminocyclopropyl)propylamino)-5-fluoro-2-(pyridin-3-ylamino)nicotinamide, (R)-6-(1-(1-aminocyclopropyl)propylamino)-5-fluoro-2-(p-tolylamino)nicotinamide, (R)-6-(1-(1-aminocyclopropyl)propylamino)-5-fluoro-2-(m-tolylamino)nicotinamide, (R)-6-(1-(1-aminocyclopropyl)propylamino)-5-fluoro-2-(5-fluoropyridin-3-ylamino)nicotinamide, 6-((1R,2S)-2-aminocyclohexylamino)-5-fluoro-2-(3-methylisoxazol-5-ylamino)nicotinamide, (R)-4-(1-amino-3-cyclopropyl-1-oxopropan-2-ylamino)-5-fluoro-2-(3-phenylisoxazol-5-ylamino)benzamide, 6-(1-carbamoylcyclopentylamino)-5-fluoro-2-(quinolin-3-ylamino)nicotinamide, 6-(1-amino-4,4,4-trifluoro-1-oxobutan-2-ylamino)-5-fluoro-2-(quinolin-3-ylamino)nicotinamide, 6-(1-carbamoylcyclohexylamino)-5-fluoro-2-(quinolin-3-ylamino)nicotinamide, 6-(1-carbamoylcyclopentylamino)-5-fluoro-2-(quinolin-3-ylamino)nicotinamide, 6-(1-carbamoylcyclobutylamino)-5-fluoro-2-(quinolin-3-ylamino)nicotinamide, (S)-2-(m-toluidino)-6-(2-amino-4,4-difluorobutylamino)-5-fluoronicotinamide, (S)-2-(p-toluidino)-6-(2-amino-4,4-difluorobutylamino)-5-fluoronicotinamide, and (S)-6-(2-amino-4,4-difluorobutylamino)-5-fluoro-2-(5-fluoropyridin-3-ylamino)nicotinamide.

The present invention provides in another embodiment, a compound selected from the group consisting of: 6-((1R,2S)-2-aminocyclohexylamino)-2-(1H-imidazol-1-yl)nicotinamide; 6-((3R,4R)-3-aminotetrahydro-2H-pyran-4-ylamino)-2-(benzo[d]thiazol-6-ylamino)-5-fluoronicotinamide; 6-((3R,4R)-3-aminotetrahydro-2H-pyran-4-ylamino)-5-fluoro-2-(m-tolylamino)nicotinamide; 6-((3R,4R)-3-aminotetrahydro-2H-pyran-4-ylamino)-2-(3-chlorophenylamino)-5-fluoronicotinamide; 6-((1R,2R)-2-amino-3,3-difluorocyclohexylamino)-5-fluoro-2-(1-methyl-1H-indazol-4-ylamino)nicotinamide; 6-((1S,6S)-6-amino-2,2-difluorocyclohexylamino)-2-(3-chlorophenylamino)-5-fluoronicotinamide; 6-((1S,6S)-6-amino-2,2-difluorocyclohexylamino)-2-(1-methyl-1H-indazol-4-ylamino)nicotinamide; 6-((1R,2R)-2-amino-3,3-difluorocyclohexylamino)-2-(1-ethyl-1H-indol-4-ylamino)-5-fluoronicotinamide; 6-((1R,2R)-2-amino-3,3-difluorocyclohexylamino)-5-fluoro-2-(1-isopropyl-1H-indol-4-ylamino)nicotinamide; 6-((1R,2R)-2-amino-3,3-difluorocyclohexylamino)-5-fluoro-2-(1-isobutyl-1H-indol-4-ylamino)nicotinamide; 6-((1R,2S)-2-aminocyclohexylamino)-5-fluoro-2-(thieno[2,3-b]pyridin-3-ylamino)nicotinamide; 6-((1R,2S)-2-aminocyclohexylamino)-5-fluoro-2-(thieno[3,2-c]pyridin-3-ylamino)nicotinamide; 6-((1R,2R)-2-amino-3,3-difluorocyclohexylamino)-5-fluoro-2-(1-methyl-2-oxoindolin-4-ylamino)nicotinamide; 6-((1R,2S)-2-aminocyclohexylamino)-2-(1-methyl-1H-indol-4-ylamino)nicotinamide; 6-((1R,2S)-2-aminocyclohexylamino)-2-(1-methyl-1H-indol-5-ylamino)nicotinamide; 6-((1R,2S)-2-aminocyclohexylamino)-2-(1-methyl-1H-indazol-4-ylamino)nicotinamide; 6-((1R,2S)-2-aminocyclohexylamino)-2-(1-methyl-1H-indazol-5-ylamino)nicotinamide; 6-((1R,2S)-2-aminocyclohexylamino)-2-(benzo[d]thiazol-5-ylamino)nicotinamide; 6-((1R,2S)-2-aminocyclohexylamino)-2-(benzo[d]thiazol-7-ylamino)nicotinamide; 6-((1R,2S)-2-aminocyclohexylamino)-2-(thieno[2,3-b]pyridin-3-ylamino)nicotinamide; 6-((1R,2S)-2-aminocyclohexylamino)-2-(benzo[d]thiazol-6-ylamino)nicotinamide; 6-((1R,2S)-2-aminocyclohexylamino)-2-(2-hydroxybenzo[d]thiazol-6-ylamino)nicotinamide; 6-((1R,2R)-2-amino-3,3-difluorocyclohexylamino)-5-fluoro-2-(thieno[2,3-b]pyridin-3-ylamino)nicotinamide; 2-(1,6-naphthyridin-3-ylamino)-6-((1R,2S)-2-aminocyclohexylamino)nicotinamide; 2-(1H-pyrrolo[3,2-b]pyridin-6-ylamino)-6-((1R,2S)-2-aminocyclohexylamino)nicotinamide; 3-(6-((1R,2S)-2-aminocyclohexylamino)-3-carbamoyl-5-fluoropyridin-2-ylamino)-5-fluoropyridine 1-oxide; 2-(5-methoxypyridin-3-ylamino)-6-((3aS,7aR)-2-oxo-octahydrobenzo[d]imidazol-1-yl)nicotinamide; 2-(5-methylpyridin-3-ylamino)-6-((3aS,7aR)-2-oxo-octahydrobenzo[d]imidazol-1-yl)nicotinamide; 6-((1R,2S)-2-aminocyclohexylamino)-5-fluoro-2-(1-methyl-1H-pyrrolo[2,3-b]pyridin-4-ylamino)nicotinamide; 6-((1S,6S)-6-amino-2,2-difluorocyclohexylamino)-2-(thieno[2,3-b]pyridin-3-ylamino)nicotinamide; 6-((1S,6S)-6-amino-2,2-difluorocyclohexylamino)-2-(3-(thiazol-2-yl)phenylamino)nicotinamide; 2-(3-(2H-1,2,3-triazol-2-yl)phenylamino)-6-((1S,6S)-6-amino-2,2-difluorocyclohexylamino)nicotinamide; 6-((1S,6S)-6-amino-2,2-difluorocyclohexylamino)-2-(quinolin-6-ylamino)nicotinamide; 6-((1R,2R)-2-amino-3,3-difluorocyclohexylamino)-2-(quinolin-6-ylamino)nicotinamide; 6-((1R,2R)-2-amino-3,3-difluorocyclohexylamino)-2-(quinolin-7-ylamino)nicotinamide; 6-((1R,2R)-2-amino-3,3-difluorocyclohexylamino)-2-(1-methyl-1H-indol-4-ylamino)nicotinamide; 6-((1R,2S)-2-aminocyclohexylamino)-2-(pyrazolo[1,5-a]pyridin-3-ylamino)nicotinamide; 6-((1R,2R)-2-amino-3,3-difluorocyclohexylamino)-5-fluoro-2-(pyrazolo[1,5-a]pyridin-3-ylamino)nicotinamide; 6-((1R,2S)-2-aminocyclohexylamino)-4-(pyrazolo[1,5-a]pyridin-3-ylamino)nicotinamide; 6-((1R,2S)-2-aminocyclohexylamino)-4-(thieno[2,3-b]pyridin-3-ylamino)nicotinamide; (R)-6-(1-amino-1-oxobutan-2-ylamino)-5-fluoro-2-(thieno[2,3-b]pyridin-3-ylamino)nicotinamide; (R)-6-(1-amino-1-oxobutan-2-ylamino)-5-fluoro-2-(pyrazolo[1,5-a]pyridin-3-ylamino)nicotinamide; (R)-6-(1-amino-1-oxobutan-2-ylamino)-2-(thieno[2,3-b]pyridin-3-ylamino)nicotinamide; and 6-(1-(aminomethyl)cyclopropylamino)-2-(quinolin-6-ylamino)nicotinamide.

The present invention provides in another embodiment, a compound of the examples.

The present invention provides in another embodiment, a compound of any one of the tables.

The present invention provides in another embodiment, a compound of any one of the figures.

The present invention in another group of embodiments, does not include a compound disclosed in WO 2010/058846.

It is understood that in another group of embodiments, any of the above embodiments may also be combined with other embodiments listed herein, to form other embodiments of the invention. Similarly, it is understood that in other embodiments, listing of groups includes embodiments wherein one or more of the elements of those groups is not included.

b. Methods of Synthesis

The compounds of the present invention may be prepared by known organic synthesis techniques, including the methods described in more detail in the Examples.

One skilled in the art will recognize that in certain embodiments of structures (I) when D1, $R^1$, $D^2$ or $R^2$ comprises a terminal heteroatom, it may be advantageous to use a protecting group strategy. The protecting group can be removed using methods known to those skilled in the art to yield compounds of structure (I).

The compounds of the present invention may generally be utilized as the free base. Alternatively, the compounds of this invention may be used in the form of acid addition salts as described below.

c. Inhibition of Syk Kinases

The activity of a specified compound as an inhibitor of a Syk kinase may be assessed in vitro or in vivo. In some embodiments, the activity of a specified compound can be tested in a cellular assay. Selectivity could also be ascertained in biochemical assays with isolated kinases. Exemplary assays of this type are described in greater detail in the Examples.

d. Compositions and Methods of Administration

The present invention further provides compositions comprising one or more compounds of formula (I) or a pharmaceutically acceptable salt, ester or prodrug thereof, and a pharmaceutically acceptable carrier or diluent. It will be appreciated that the compounds of formula (I)) in this invention may be derivatized at functional groups to provide prodrug derivatives which are capable of conversion back to the parent compounds in vivo. Examples of such prodrugs include the physiologically acceptable and metabolically labile ester derivatives, such as methoxymethyl esters, methylthiomethyl esters, or pivaloyloxymethyl esters derived from a hydroxyl group of the compound or a carbamoyl moiety derived from an amino group of the compound. Additionally, any physiologically acceptable equivalents of the compounds of formula (I), similar to metabolically labile esters or carbamates, which are capable of producing the parent compounds of formula (I) in vivo, are within the scope of this invention.

As used herein, the term "pharmaceutically acceptable salts" refers to any acid or base addition salt whose counterions are non-toxic to the patient in pharmaceutical doses of the salts. A host of pharmaceutically acceptable salts are well known in the pharmaceutical field. If pharmaceutically acceptable salts of the compounds of this invention are utilized in these compositions, those salts are preferably derived from inorganic or organic acids and bases. Included among such acid salts are the following: acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, lucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate, undecanoate, hydrohalides (e.g., hydrochlorides and hydrobromides), sulphates, phosphates, nitrates, sulphamates, malonates, salicylates, methylene-bis-b-hydroxynaphthoates, gentisates, isethionates, di-p-toluoyltartrates, ethanesulphonates, cyclohexylsulphamates, quinates, and the like. Pharmaceutically acceptable base addition salts include, without limitation, those derived from alkali or alkaline earth metal bases or conventional organic bases, such as triethylamine, pyridine, piperidine, morpholine, N-methylmorpholine, ammonium salts, alkali metal salts, such as sodium and potassium salts, alkaline earth metal salts, such as calcium and magnesium salts, salts with organic bases, such as dicyclohexylamine salts, N-methyl-D-glucamine, and salts with amino acids such as arginine, lysine, and so forth.

Furthermore, the basic nitrogen-containing groups may be quaternized with agents like lower alkyl halides, such as methyl, ethyl, propyl and butyl chlorides, bromides and iodides; dialkyl sulfates, such as dimethyl, diethyl, dibutyl and diamyl sulfates, long chain halides, such as decyl, lauryl, myristyl and stearyl chlorides, bromides and iodides; aralkyl halides, such as benzyl and phenethyl bromides and others. Water or oil-soluble or dispersible products are thereby obtained.

The compounds utilized in the compositions and methods of this invention may also be modified by appending appropriate functionalities to enhance selective biological properties. Such modifications are known in the art and include those which increase biological penetration into a given biological system (e.g., blood, lymphatic system, central nervous system, etc.), increase oral availability, increase solubility to allow administration by injection, alter metabolism and alter rate of excretion.

The pharmaceutical compositions of the invention can be manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, tablets, capsules, syrup, suppositories, injections, emulsions, elixirs, suspensions or solutions. Formulations may optionally contain stabilizers, pH modifiers, surfactants, bioavailability modifiers and combinations of these.

The term "unit dosage form" refers to physically discrete units suitable as unitary dosages for human subjects and other mammals, each unit containing a predetermined quantity of drug calculated to produce the desired onset, tolerability, and/or therapeutic effects, in association with a suitable pharmaceutical excipient (e.g., an ampoule). In addition, more concentrated compositions may be prepared, from which the more dilute unit dosage compositions may then be produced. The more concentrated compositions thus will contain substantially more than, e.g., at least 1, 2, 3, 4, 5, 6, 7, 8, 9, 10, or more times the amount of one or more Syk inhibitors.

Methods for preparing such dosage forms are known to those skilled in the art (see, for example, *REMINGTON'S PHARMACEUTICAL SCIENCES,* 18TH ED., Mack Publishing Co., Easton, Pa. (1990)). In addition, pharmaceutically acceptable salts of the Syk inhibitors of the present invention (e.g., acid addition salts) may be prepared and included in the compositions using standard procedures known to those skilled in the art of synthetic organic chemistry and described, e.g., by J. March, Advanced Organic Chemistry: Reactions, Mechanisms and Structure, 4th Ed. (New York: Wiley-Interscience, 1992).

The compositions typically include a conventional pharmaceutical carrier or excipient and may additionally include other medicinal agents, carriers, adjuvants, diluents, tissue permeation enhancers, solubilizers, and the like. Preferably, the composition will contain about 0.01% to about 90%, preferably about 0.1% to about 75%, more preferably about 0.1% to 50%, still more preferably about 0.1% to 10% by weight of one or more Syk inhibitors, with the remainder consisting of suitable pharmaceutical carrier and/or excipients. Appropriate excipients can be tailored to the particular composition and route of administration by methods well known in the art, e.g., REMINGTON'S PHARMACEUTICAL SCIENCES, supra.

Pharmaceutically acceptable carriers that may be used in these compositions include ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Examples of suitable excipients include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, and polyacrylic acids such as Carbopols. The compositions can additionally include lubricating agents such as talc, magnesium stearate, and mineral oil; wetting agents; emulsifying agents; suspending agents; preserving agents such as methyl-, ethyl-, and propyl-hydroxy-benzoates; pH adjusting agents such as inorganic and organic acids and bases; sweetening agents; and flavoring agents.

Administration of a composition comprising one or more Syk inhibitors with one or more suitable pharmaceutical excipients as advantageous can be carried out via any of the accepted modes of administration. Thus, administration can be, for example, oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally or intravenously. The formulations of the invention may be designed as short-acting, fast-releasing, or long-acting. Still further, compounds can be administered in a local rather than systemic means, such as administration (e.g., injection) as a sustained release formulation. According to a representative embodiment, the compositions of this invention are formulated for pharmaceutical administration to a mammal, preferably a human being.

The compositions of the present invention containing one or more Syk inhibitors can be administered repeatedly, e.g., at least 2, 3, 4, 5, 6, 7, 8, or more times, or the composition may be administered by continuous infusion. Suitable sites of administration include, but are not limited to, skin, bronchial, gastrointestinal, anal, vaginal, eye, and ear. The formulations may take the form of solid, semi-solid, lyophilized powder, or liquid dosage forms, such as, for example, tablets, pills, capsules, powders, solutions, suspensions, emulsions, suppositories, retention enemas, creams, ointments, lotions, gels, aerosols, or the like, preferably in unit dosage forms suitable for simple administration of precise dosages.

The pharmaceutical compositions of this invention may be in any orally acceptable dosage form, including tablets, capsules, cachets, emulsions, suspensions, solutions, syrups, elixirs, sprays, boluses, lozenges, powders, granules, and sustained-release formulations. Suitable excipients for oral administration include pharmaceutical grades of mannitol, lactose, starch, magnesium stearate, sodium saccharine, talcum, cellulose, glucose, gelatin, sucrose, magnesium carbonate, and the like. In the case of tablets for oral use, carriers that are commonly used include lactose and corn starch. Lubricating agents, such as magnesium stearate, are also typically added. For a capsule form, useful diluents include lactose and dried cornstarch. When aqueous suspensions are required for oral use, the active ingredient is combined with emulsifying and suspending agents. If desired, certain sweetening, flavoring or coloring agents may also be added.

In some embodiments, the compositions take the form of a pill, tablet, or capsule, and thus, the composition can contain, along with one or more Syk inhibitors, a diluent such as lactose, sucrose, dicalcium phosphate, and the like; a disintegrant such as starch or derivatives thereof; a lubricant such as magnesium stearate and the like; and/or a binder such a starch, gum acacia, polyvinylpyrrolidone, gelatin, cellulose and derivatives thereof. A tablet can be made by any compression or molding process known to those of skill in the art. Compressed tablets may be prepared by compressing in a suitable machine the Syk inhibitors in a free-flowing form, e.g., a powder or granules, optionally mixed with accessory ingredients, e.g., binders, lubricants, diluents, disintegrants, or dispersing agents. Molded tablets can be made by molding in a suitable machine a mixture of the powdered Syk inhibitors with any suitable carrier.

Alternatively, the pharmaceutical compositions of this invention may be in the form of suppositories for rectal administration. These may be prepared by mixing the agent with a suitable non-irritating excipient which is solid at room temperature but liquid at rectal temperature and therefore will melt in the rectum to release the drug. Such materials include cocoa butter, beeswax, polyethylene glycol (PEG), hard fat, and/or hydrogenated cocoglyceride. Compositions suitable for rectal administration may also comprise a rectal enema unit containing one or more Syk inhibitors and pharmaceutically-acceptable vehicles (e.g., 50% aqueous ethanol or an aqueous salt solution) that are physiologically compatible with the rectum and/or colon. The rectal enema unit contains an applicator tip protected by an inert cover, preferably comprised of polyethylene, lubricated with a lubricant such as white petrolatum, and preferably protected by a one-way valve to prevent back-flow of the dispensed formula. The rectal enema unit is also of sufficient length, preferably two inches, to be inserted into the colon via the anus.

Liquid compositions can be prepared by dissolving or dispersing one or more Syk inhibitors and optionally one or more pharmaceutically acceptable adjuvants in a carrier such as, for example, aqueous saline, aqueous dextrose, glycerol, ethanol, and the like, to form a solution or suspension, e.g., for oral, topical, or intravenous administration. Pharmaceutical formulations may be prepared as liquid suspensions or solutions using a sterile liquid, such as oil, water, alcohol, and combinations thereof. Pharmaceutically suitable surfactants, suspending agents or emulsifying agents, may be added for oral or parenteral administration. Suspensions may include oils, such as peanut oil, sesame oil, cottonseed oil, corn oil and olive oil. Suspension preparation may also contain esters of fatty acids, such as ethyl oleate, isopropyl myristate, fatty acid glycerides and acetylated fatty acid glycerides. Suspension formulations may include alcohols, such as ethanol, isopropyl alcohol, hexadecyl alcohol, glycerol and propylene glycol. Ethers, such as poly(ethyleneglycol), petroleum hydrocarbons, such as mineral oil and petrolatum, and water may also be used in suspension formulations.

The pharmaceutical compositions of this invention may also be in a topical form, especially when the target of treatment includes areas or organs readily accessible by topical application, including diseases of the eye, the skin, or the lower intestinal tract. Suitable topical formulations are readily prepared for each of these areas or organs. For topical administration, the composition containing one or more Syk inhibitors can be in the form of emulsions, lotions, gels, foams, creams, jellies, solutions, suspensions, ointments, and transdermal patches.

Topical application for the lower intestinal tract may be effected in a rectal suppository formulation (see above) or in a suitable enema formulation. Topically-transdermal patches may also be used. For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers include mineral oil, sorbitan monostearate, polysorbate 60, cetyl esters, wax, cetyl alcohol, 2-octyldodecanol, benzyl alcohol and water.

The pharmaceutical compositions of this invention may also be administered by nasal aerosol or inhalation. For delivery by inhalation, the compositions can be delivered as a dry powder or in liquid form via a nebulizer. Such compositions are prepared according to techniques known in the art of pharmaceutical formulation and may be prepared as solutions in saline, employing benzyl alcohol or other suitable preservatives, absorption promoters to enhance bioavailability, fluorocarbons and/or other conventional solubilizing or dispersing agents.

For ophthalmic use, the pharmaceutical compositions may be formulated as micronized suspensions in isotonic, pH adjusted sterile saline, or, preferably, as solutions in isotonic, pH adjusted sterile saline, either with our without a preservative, such as benzylalkonium chloride. Alternatively, for ophthalmic uses, the pharmaceutical compositions may be formulated in an ointment, such as petrolatum.

For parenteral administration, the compositions can be in the form of sterile injectable solutions and sterile packaged powders. Preferably, injectable solutions are formulated at a pH of about 4.5 to about 7.5.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. Compounds may be formulated for parenteral administration by injection such as by bolus injection or continuous infusion. A unit dosage form for injection may be in ampoules or in multi-dose containers.

The compositions of the present invention can also be provided in a lyophilized form. Such compositions may include a buffer, e.g., bicarbonate, for reconstitution prior to administration, or the buffer may be included in the lyophilized composition for reconstitution with, e.g., water. The lyophilized composition may further comprise a suitable vasoconstrictor, e.g., epinephrine. The lyophilized composition can be provided in a syringe, optionally packaged in combination with the buffer for reconstitution, such that the reconstituted composition can be immediately administered to a patient.

Any of the above dosage forms containing effective amounts are within the bounds of routine experimentation and within the scope of the invention. A therapeutically effective dose may vary depending upon the route of administration and dosage form. The representative compound or compounds of the invention is a formulation that exhibits a high therapeutic index. The therapeutic index is the dose ratio between toxic and therapeutic effects which can be expressed as the ratio between $LD_{50}$ and $ED_{50}$. The $LD_{50}$ is the dose lethal to 50% of the population and the $ED_{50}$ is the dose therapeutically effective in 50% of the population. The $LD_{50}$ and $ED_{50}$ are determined by standard pharmaceutical procedures in animal cell cultures or experimental animals.

Besides those representative dosage forms described above, pharmaceutically acceptable excipients and carriers and dosage forms are generally known to those skilled in the art and are included in the invention. It should be understood that a specific dosage and treatment regimen for any particular patient will depend upon a variety of factors, including the activity of the specific compound employed, the age, body weight, general health, sex and diet of the patient, and the time of administration, rate of excretion, drug combination, judgment of the treating physician and severity of the particular disease being treated. The amount of active ingredient(s) will also depend upon the particular compound and other therapeutic agent, if present, in the composition.

e. Methods of Use

The invention provides methods of inhibiting or decreasing Syk activity as well as treating or ameliorating a Syk associated state, symptom, condition, disorder or disease in a patient in need thereof (e.g., human or non-human). In one embodiment, the Syk associated state, symptom, condition, disorder or disease is mediated, at least in part by Syk kinase activity. In more specific embodiments, the present invention provides a method for treating a condition or disorder mediated at least in part by Syk kinase activity is cardiovascular disease, inflammatory disease or autoimmune disease.

In one embodiment, the invention provides methods for preventing or treating a condition in a mammal mediated at least in part by syk activity comprising the step of administering to the mammal a therapeutically effective amount of a compound of the present invention. Such conditions include, but are not limited, to restenosis, acute coronary syndrome, myocardial infarction, unstable angina, refractory angina, occlusive coronary thrombosis occurring post-thrombolytic therapy or post-coronary angioplasty, a thrombotically mediated cerebrovascular syndrome, embolic stroke, thrombotic stroke, transient ischemic attacks, venous thrombosis, deep venous thrombosis, pulmonary embolism, coagulopathy, disseminated intravascular coagulation, thrombotic thrombocytopenic purpura, thromboangiitis obliterans, thrombotic disease associated with heparin-induced thrombocytopenia, thrombotic complications associated with extracorporeal circulation, thrombotic complications associated with instrumentation such as cardiac or other intravascular catheterization, intra-aortic balloon pump, coronary stent or cardiac valve, conditions requiring the fitting of prosthetic devices, and the like.

In a further embodiment, the present invention provides a method for treating thrombosis, immune thrombocytic purura, heparin induced thrombocytopenia, dilated cardiomypathy, sickle cell disease, atherosclerosis, myocardial infarction, vascular inflammation, unstable angina or acute coronary syndromes.

In another embodiment, the present invention also provides a method for treating allergy, asthma, theumatoid arthritis, B Cell mediated disease such as Non-Hodgkin's Lymphoma, anti phospholipids syndrome, lupus, psoriasis, multiple sclerosis, end stage renal disease or chronic lymphocytic leukemia.

In another embodiment, the present invention provides a method for treating hemolytic anemia or immune thrombocytopenic purpura.

In another embodiment, the present invention provides a method for treating vasculitis, including but not limited to: Large vessel vasculitis, such as Giant cell arteritis and Takayasu's arteritis; Medium vessel vasculitis, such as Polyarteritis nodosa (PAN) and Kawasaki Disease; Small vessel vasculitis, such as Wegener's granulomatosis, Churg-Strauss syndrome, Microscopic polyangiitis, Henoch-Schonlein purpura, Cryoglobulinaemic vasculitis, and Cutaneous leucocytoclastic angiitis.

In another embodiment, the present invention provides a method for treating a Auto-immune blistering skin disease including but not limited to: Pemphigus, such as Pemphigus vulgaris, Pemphigus foliaceus, Paraneoplastic pemphigus, and IgA pemphigus; and Subepidermal autoimmune blistering skin disease, such as Bullous pemphigoid, Pemphigoid gestationis, Linear IgA dermatosis, Mucous membrane pemphigoid, Lichen planus pemphigoides, Anti-laminin g1/p200 pemphigoid, Epidermolysis bullosa acquisita and Dermatitis herpetiformis.

Therapy using the compounds described herein can be applied alone, or it can be applied in combination with or adjunctive to other common immunosuppressive therapies, such as, for example, the following: mercaptopurine; corticosteroids such as prednisone; methylprednisolone and prednisolone; alkylating agents such as cyclophosphamide; calcineurin inhibitors such as cyclosporine, sirolimus, and tacrolimus; inhibitors of inosine monophosphate dehydrogenase (IMPDH) such as mycophenolate, mycophenolate mofetil, and azathioprine; and agents designed to suppress cellular immunity while leaving the recipient's humoral immunologic response intact, including various antibodies (for example, antilymphocyte globulin (ALG), antithymocyte globulin (ATG), monoclonal anti-T-cell antibodies (OKT3)) and irradiation. These various agents can be used in accordance with their standard or common dosages, as specified in the prescribing information accompanying commercially available forms of the drugs (see also: the prescribing information in the 2006 Edition of The Physician's Desk Reference), the disclosures of which are incorporated herein by reference. Azathioprine is currently available from Salix Pharmaceuticals, Inc., under the brand name AZASAN; mercaptopurine is currently available from Gate Pharmaceuticals, Inc., under the brand name PURINETHOL; prednisone and prednisolone are currently available from Roxane Laboratories, Inc.; Methyl prednisolone is currently available from Pfizer; sirolimus (rapamycin) is currently available from Wyeth-Ayerst under the brand name RAPAMUNE; tacrolimus is currently available from Fujisawa under the brand name PROGRAF; cyclosporine is current available from Novartis under the brand dame SANDIMMUNE and from Abbott under the brand name GENGRAF; IMPDH inhibitors such as mycophenolate mofetil and mycophenolic acid are currently available from Roche under the brand name CELLCEPT and from Novartis under the brand name MYFORTIC; azathioprine is currently available from Glaxo Smith Kline under the brand name IMURAN; and antibodies are currently available from Ortho Biotech under the brand name ORTHOCLONE, from Novartis under the brand name SIMULECT (basiliximab), and from Roche under the brand name ZENAPAX (daclizumab).

In another embodiment, the compounds could be administered either in combination or adjunctively with an inhibitor of a Syk kinase. Syk kinase is a tyrosine kinase known to play a critical role in Fcγ receptor signaling, as well as in other signaling cascades, such as those involving B-cell receptor signaling (Turner et al., (2000), Immunology Today 21:148-154) and integrins beta(1), beta (2), and beta (3) in neutrophils (Mocsai et al., (2002), Immunity 16:547-558). For example, Syk kinase plays a pivotal role in high affinity IgE receptor signaling in mast cells that leads to activation and subsequent release of multiple chemical mediators that trigger allergic attacks. However, unlike the JAK kinases, which help regulate the pathways involved in delayed or cell-mediated Type IV hypersensitivity reactions, Syk kinase helps regulate the pathways involved in immediate IgE-mediated, Type I hypersensitivity reactions. Certain compounds that affect the Syk pathway may or may not also affect the JAK pathways.

Suitable Syk inhibitory compounds are described, for example, in Ser. No. 10/355,543 filed Jan. 31, 2003 (publication no. 2004/0029902); WO 03/063794; Ser. No. 10/631,029 filed Jul. 29, 2003; WO 2004/014382; Ser. No. 10/903,263 filed Jul. 30, 2004; PCT/US2004/24716 filed Jul. 30, 2004 (WO005/016893); Ser. No. 10/903,870 filed Jul. 30, 2004; PCT/US2004/24920 filed Jul. 30, 2004, the disclosures of which are incorporated herein by reference. The described herein and Syk inhibitory compounds could be used alone or in combination with one or more conventional transplant rejection treatments, as described above.

In a specific embodiment, the compounds can be used to treat or prevent these diseases in patients that are either initially non-responsive (resistant) to or that become non-responsive to treatment with a Syk inhibitory compound or one of the other current treatments for the particular disease. The compounds could also be used in combination with Syk inhibitory compounds in patients that are Syk-compound resistant or non-responsive. Suitable Syk-inhibitory compounds with which the compounds can be administered are provided infra.

In another embodiment, this invention provides a method of treating a T-cell mediated autoimmune disease, comprising administering to a patient suffering from such an autoimmune disease an amount of a compound effective to treat the autoimmune disease wherein the compound is selected from the compounds of the invention, as described herein, and the compound is administered in combination with or adjunctively to a compound that inhibits Syk kinase with an $IC_{50}$ in the range of at least 10 μM.

When used to treat or prevent such diseases, the compounds can be administered singly, as mixtures of one or more compounds, or in mixture or combination with other agents useful for treating such diseases and/or the symptoms associated with such diseases. The compounds may also be administered in mixture or in combination with agents useful to treat other disorders or maladies, such as steroids, membrane stabilizers, 5-lipoxygenase (5LO) inhibitors, leukotriene synthesis and receptor inhibitors, inhibitors of IgE isotype switching or IgE synthesis, IgG isotype switching or IgG synthesis, beta.-agonists, tryptase inhibitors, aspirin, cyclooxygenase (COX) inhibitors, methotrexate, anti-TNF drugs, anti CD20 antibody, PD4 inhibitors, p38 inhibitors, PDE4 inhibitors, and antihistamines, to name a few. The compounds can be administered per se in the form of prodrugs or as pharmaceutical compositions, comprising an active compound or prodrug.

Active compounds of the invention typically inhibit the Syk and/or JAK/Stat pathway. The activity of a specified compound as an inhibitor of a Syk kinase can be assessed in vitro or in vivo. In some embodiments, the activity of a specified compound can be tested in a cellular assay.

"Cell proliferative disorder" refers to a disorder characterized by abnormal proliferation of cells. A proliferative disorder does not imply any limitation with respect to the rate of cell growth, but merely indicates loss of normal controls that affect growth and cell division. Thus, in some embodiments, cells of a proliferative disorder can have the same cell division rates as normal cells but do not respond to signals that limit such growth. Within the ambit of "cell proliferative disorder" is neoplasm or tumor, which is an abnormal growth of tissue. Cancer refers to any of various malignant neoplasms characterized by the proliferation of cells that have the capability to invade surrounding tissue and/or metastasize to new colonization sites.

Generally, cell proliferative disorders treatable with the compounds disclosed herein relate to any disorder characterized by aberrant cell proliferation. These include various tumors and cancers, benign or malignant, metastatic or non-metastatic. Specific properties of cancers, such as tissue invasiveness or metastasis, can be targeted using the methods described herein. Cell proliferative disorders include a variety of cancers, including, among others, ovarian cancer, renal cancer, gastrointestinal cancer, kidney cancer, bladder cancer, pancreatic cancer, lung squamous carcinoma, and adenocarcinoma.

In some embodiments, the cell proliferative disorder treated is a hematopoietic neoplasm, which is aberrant growth of cells of the hematopoietic system. Hematopoietic malignancies can have its origins in pluripotent stem cells, multipotent progenitor cells, oligopotent committed progenitor cells, precursor cells, and terminally differentiated cells involved in hematopoiesis. Some hematological malignancies are believed to arise from hematopoietic stem cells, which have the ability for self renewal. For instance, cells capable of developing specific subtypes of acute myeloid leukemia (AML) (Cynthia K. Hahn, Kenneth N. Ross, Rose M. Kakoza, Steven Karr, Jinyan Du, Shao-E Ong, Todd R. Golub, Kimberly Stegmaier, Syk is a new target for AML differentiation, Blood, 2007, 110, Abstract 209) upon transplantation display the cell surface markers of hematopoietic stem cells, implicating hematopoietic stem cells as the source of leukemic cells. Blast cells that do not have a cell marker characteristic of hematopoietic stem cells appear to be incapable of establishing tumors upon transplantation (Blaire et al., 1997, Blood 89:3104-3112). The stem cell origin of certain hematological malignancies also finds support in the observation that specific chromosomal abnormalities associated with particular types of leukemia can be found in normal cells of hematopoietic lineage as well as leukemic blast cells. For instance, the reciprocal translocation t(9q34;22q11) associated with approximately 95% of chronic myelogenous leukemia appears to be present in cells of the myeloid, erythroid, and lymphoid lineage, suggesting that the chromosomal aberration originates in hematopoietic stem cells. A subgroup of cells in certain types of CML displays the cell marker phenotype of hematopoietic stem cells.

Although hematopoietic neoplasms often originate from stem cells, committed progenitor cells or more terminally differentiated cells of a developmental lineage can also be the source of some leukemias. For example, forced expression of the fusion protein Bcr/Abl (associated with chronic myelogenous leukemia) in common myeloid progenitor or granulocyte/macrophage progenitor cells produces a leukemic-like condition. Moreover, some chromosomal aberrations associated with subtypes of leukemia are not found in the cell population with a marker phenotype of hematopoietic stem cells, but are found in a cell population displaying markers of a more differentiated state of the hematopoietic pathway (Turhan et al., 1995, Blood 85:2154-2161). Thus, while committed progenitor cells and other differentiated cells may have only a limited potential for cell division, leukemic cells may have acquired the ability to grow unregulated, in some instances mimicking the self-renewal characteristics of hematopoietic stem cells (Passegue et al., Proc. Natl. Acad. Sci. USA, 2003, 100:11842-9).

In some embodiments, the hematopoietic neoplasm treated is a lymphoid neoplasm, where the abnormal cells are derived from and/or display the characteristic phenotype of cells of the lymphoid lineage. Lymphoid neoplasms can be subdivided into B-cell neoplasms, T and NK-cell neoplasms, and Hodgkin's lymphoma. B-cell neoplasms can be further subdivided into precursor B-cell neoplasm and mature/peripheral B-cell neoplasm. Exemplary B-cell neoplasms are precursor B-lymphoblastic leukemia/lymphoma (precursor B-cell acute lymphoblastic leukemia) while exemplary mature/peripheral B-cell neoplasms are B-cell chronic lymphocytic leukemia/small lymphocytic lymphoma, B-cell prolymphocytic leukemia, lymphoplasmacytic lymphoma, splenic marginal zone B-cell lymphoma, hairy cell leukemia, plasma cell myeloma/plasmacytoma, extranodal marginal zone B-cell lymphoma of MALT type, nodal marginal zone B-cell lymphoma, follicular lymphoma, mantle-cell lymphoma, diffuse large B-cell lymphoma, mediastinal large B-cell lymphoma, primary effusion lymphoma, and Burkitt's lymphoma/Burkitt cell leukemia. T-cell and Nk-cell neoplasms are further subdivided into precursor T-cell neoplasm and mature (peripheral) T-cell neoplasms. Exemplary precursor T-cell neoplasm is precursor T-lymphoblastic lymphoma/leukemia (precursor T-cell acute lymphoblastic leukemia) while exemplary mature (peripheral) T-cell neoplasms are T-cell prolymphocytic leukemia T-cell granular lymphocytic leukemia, aggressive NK-cell leukemia, adult T-cell lymphoma/leukemia (HTLV-1), extranodal NK/T-cell lymphoma, nasal type, enteropathy-type T-cell lymphoma, hepatosplenic gamma-delta T-cell lymphoma, subcutaneous panniculitis-like T-cell lymphoma, Mycosis fungoides/Sezary syndrome, Anaplastic large-cell lymphoma, T/null cell, primary cutaneous type, Peripheral T-cell lymphoma, not otherwise characterized, Angioimmunoblastic T-cell lymphoma, Anaplastic large-cell lymphoma, T/null cell, primary systemic type. The third member of lymphoid neoplasms is Hodgkin's lymphoma, also referred to as Hodgkin's disease. Exemplary diagnosis of this class that can be treated with the compounds include, among others, nodular lymphocyte-predominant Hodgkin's lymphoma, and various classical forms of Hodgkin's disease, exemplary members of which are Nodular sclerosis Hodgkin's lymphoma (grades 1 and 2), Lymphocyte-rich classical Hodgkin's lymphoma, Mixed cellularity Hodgkin's lymphoma, and Lymphocyte depletion Hodgkin's lymphoma. In various embodiments, any of the lymphoid neoplasms that are associated with aberrant Syk activity can be treated with the Syk inhibitory compounds.

In some embodiments, the hematopoietic neoplasm treated is a myeloid neoplasm. This group comprises a large class of cell proliferative disorders involving or displaying the characteristic phenotype of the cells of the myeloid lineage. Myeloid neoplasms can be subdivided into myeloproliferative diseases, myelodysplastic/myeloproliferative diseases, myelodysplastic syndromes, and acute myeloid leukemias. Exemplary myeloproliferative diseases are chronic myelogenous leukemia (e.g., Philadelphia chromosome positive (t(9; 22)(qq34;q11)), chronic neutrophilic leukemia, chronic eosinophilic leukemia/hypereosinophilic syndrome, chronic idiopathic myelofibrosis, polycythemia vera, and essential thrombocythemia. Exemplary myelodysplastic/myeloproliferative diseases are chronic myelomonocytic leukemia, atypical chronic myelogenous leukemia, and juvenile myelomonocytic leukemia. Exemplary myelodysplastic syndromes are refractory anemia, with ringed sideroblasts and without ringed sideroblasts, refractory cytopenia (myelodysplastic syndrome) with multilineage dysplasia, refractory anemia (myelodysplastic syndrome) with excess blasts, 5q-syndrome, and myelodysplastic syndrome. In various embodiments, any of the myeloid neoplasms that are associated with aberrant Syk activity can be treated with the Syk inhibitory compounds.

In some embodiments, the compounds can be used to treat Acute myeloid leukemias (AML), which represent a large class of myeloid neoplasms having its own subdivision of disorders. These subdivisions include, among others, AMLs with recurrent cytogenetic translocations, AML with multilineage dysplasia, and other AML not otherwise categorized. Exemplary AMLs with recurrent cytogenetic translocations include, among others, AML with t(8;21)(q22;q22), AML1 (CBF-alpha)/ETO, Acute promyelocytic leukemia (AML with t(15;17)(q22;q11-12) and variants, PML/RAR-alpha), AML with abnormal bone marrow eosinophils (inv(16) (p13q22) or t(16;16)(p13;q11), CBFb/MYH11X), and AML with 11q23 (MLL) abnormalities. Exemplary AML with multilineage dysplasia are those that are associated with or without prior myelodysplastic syndrome. Other acute myeloid leukemias not classified within any definable group include, AML minimally differentiated, AML without maturation, AML with maturation, Acute myelomonocytic leukemia, Acute monocytic leukemia, Acute erythroid leukemia, Acute megakaryocytic leukemia, Acute basophilic leukemia, and Acute panmyelosis with myelofibrosis.

"Treating" within the context of the invention means an alleviation of symptoms associated with a disorder or disease, or halt of further progression or worsening of those symptoms, or prevention or prophylaxis of the disease or disorder.

The term "mammal" includes organisms which express Syk and/or JAK. Examples of mammals include mice, rats, cows, sheep, pigs, goats, horses, bears, monkeys, dogs, cats and, preferably, humans. Transgenic organisms which express Syk are also included in this definition.

The inventive methods comprise administering an effective amount of a compound or composition described herein to a mammal or non-human animal. As used herein, "effective amount" of a compound or composition of the invention includes those amounts that antagonize or inhibit Syk and/or JAK. An amount which antagonizes or inhibits Syk is detectable, for example, by any assay capable of determining Syk activity, including the one described below as an illustrative testing method. Effective amounts may also include those amounts which alleviate symptoms of a Syk associated disorder treatable by inhibiting Syk and/or JAK. Accordingly, "antagonists of Syk" or "antagonists of JAK" include compounds which interact with the Syk or JAK, respectively, and modulate, e.g., inhibit or decrease, the ability of a second compound, e.g., another Syk or JAK ligand, to interact with the Syk or JAK, respectively. The Syk or JAK binding compounds are preferably antagonists of Syk or JAK, respectively. The language "Syk binding compound" and "JAK-binding compound" (e.g., exhibits binding affinity to the receptor) includes those compounds which interact with Syk or JAK resulting in modulation of the activity of Syk or JAK, respectively. Syk binding compounds may be identified using an in vitro (e.g., cell and non-cell based) or in vivo method. A description of in vitro methods are provided below.

The amount of compound present in the methods and compositions described herein should be sufficient to cause a detectable decrease in the severity of the disorder, as measured by any of the assays described in the examples. The amount of Syk modulator needed will depend on the effectiveness of the modulator for the given cell type and the length of time required to treat the disorder. In certain embodiments, the compositions of this invention may further comprise another therapeutic agent. When a second agent is used, the second agent may be administered either as a separate dosage form or as part of a single dosage form with the compounds or compositions of this invention. While one or more of the inventive compounds can be used in an application of monotherapy to treat a disorder, disease or symptom, they also may be used in combination therapy, in which the use of an inventive compound or composition (therapeutic agent) is combined with the use of one or more other therapeutic agents for treating the same and/or other types of disorders, symptoms and diseases. Combination therapy includes administration of the two or more therapeutic agents concurrently or sequentially. The agents may be administered in any order. Alternatively, the multiple therapeutic agents can be combined into a single composition that can be administered to the patient. For instance, a single pharmaceutical composition could comprise the compound or pharmaceutically acceptable salt, ester or prodrug thereof according to the formula I, another therapeutic agent (e.g., methotrexate) or a pharmaceutically acceptable salt, ester or prodrug thereof, and a pharmaceutically acceptable excipient or carrier.

The invention comprises a compound having the formula I, a method for making an inventive compound, a method for making a pharmaceutical composition from at least one inventive compound and at least one pharmaceutically acceptable carrier or excipient, and a method of using one or more inventive compounds to treat a variety of disorders, symptoms and diseases (e.g., inflammatory, autoimmune, neurological, neurodegenerative, oncology and cardiovascular). In certain groups of embodiments the inflammatory disease and autoimmune disease is selected from the group consisting of organ transplants, osteoarthritis, irritable bowel disease (IBD), asthma, chronic obstructive pulmonary disease (COPD), systemic lupus erythematosus, multiple sclerosis, rheumatoid arthritis (RA), Crohn's disease, Type I diabetes, conjunctivitis, uveitis and psoriasis. In certain groups of embodiments the inflammatory disease is selected from the group consisting of allergy, asthma, rheumatoid arthritis, B Cell mediated diseases such as Non Hodgkin's Lymphoma, anti phospholipid syndrome, lupus, psoriasis, multiple sclerosis and end stage renal disease. In certain groups of embodiments the cardiovascular disease is selected from the group consisting of immune thrombocytopenic purpura, hemolytic anemia and heparin induced thrombocytopenia. In certain groups of embodiments the inflammatory disease is rheumatoid arthritis. In certain groups of embodiments the sickle cell disease is selected from the group consisting of sickle cell anemia, sickle-hemoglobin C disease, sickle beta-plus thalassemia, and sickle beta-zero thalassemia. In certain groups of embodiments the autoimmune disease is selected from the group consisting of organ transplants, chronic obstructive pulmonary disease (COPD), hemolytic anemia, immune thrombocytopenic purpura (ITP), multiple sclerosis, Sjogren's syndrome Type I diabetes, rheumatoid arthritis, lupus (including systemic lupus erythematosus (SLE), vasculitis, glomerular nephritis (GN), auto-immune-blistering disease, atopic dermatitis (eczema), atherosclerosis and psoriasis. In certain groups of embodiments the cell proliferative disorder is leukemia, a lymphoma, myeloproliferative disorders, hematological malignancies, and chronic idiopathic myelofibrosis. In certain groups of embodiments the disorder is acute myeloid leukemia (AML), chronic lymphocytic leukemia (CLL), acute lymphoblastic leukemia (ALL) or non-Hodgkin's lymphoma.

The inventive compounds and their pharmaceutically acceptable salts and/or neutral compositions may be formulated together with a pharmaceutically acceptable excipient or carrier and the resulting composition may be administered in vivo to mammals, such as men, women and animals, to treat a variety of disorders, symptoms and diseases. Furthermore, the inventive compounds can be used to prepare a medicament that is useful for treating a variety of disorders, symptoms and diseases.

All of the compounds of the present invention are potent inhibitors of Syk kinases, exhibiting $IC_{50}$s in the respective assay in the range of less than 5 µM, with most being in the nanomolar, and several in the sub-nanomolar, range.

f. Kits

Still another aspect of this invention is to provide a kit comprising separate containers in a single package, wherein the inventive pharmaceutical compounds, compositions and/or salts thereof are used in combination with pharmaceutically acceptable carriers to treat states, disorders, symptoms and diseases where Syk plays a role.

EXAMPLES

The following examples are offered to illustrate, but not to limit, the claimed invention.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1967-2004, Volumes 1-22; *Rodd's Chemistry of Carbon Compounds*, Elsevier Science Publishers, 1989, Volumes 1-5 and Supplementals; and Organic Reactions, Wiley & Sons: New York, 2005, Volumes 1-65.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C. to about 75° C.

Referring to the examples that follow, compounds of the present invention were synthesized using the methods described herein, or other methods, which are well known in the art.

The compounds and/or intermediates may be characterized by high performance liquid chromatography (HPLC) using a Waters Alliance chromatography system with a 2695 Separation Module (Milford, Mass.). The analytical columns may be C-18 SpeedROD RP-18E Columns from Merck KGaA (Darmstadt, Germany). Alternately, characterization may be performed using a Waters Unity (HPLC) system with Waters Acquity HPLC BEH C-18 2.1 mm×15 mm columns. A gradient elution may be used, typically starting with 5% acetonitrile/95% water and progressing to 95% acetonitrile over a period of 5 minutes for the Alliance system and 1 minute for the Acquity system. All solvents may contain 0.1% trifluoroacetic acid (TFA). Compounds may be detected by ultraviolet light (UV) absorption at either 220 nm or 254 nm. HPLC solvents may be from EMD Chemicals, Inc. (Gibbstown, N.J.). In some instances, purity may be assessed by thin layer chromatography (TLC) using glass backed silica gel plates, such as, for example, EMD Silica Gel 60 2.5 cm×7.5 cm plates. TLC results may be readily detected visually under ultraviolet light, or by employing well known iodine vapor and other various staining techniques.

Mass spectrometric analysis may be performed on one of two Agilent 1100 series LCMS instruments with acetonitrile/water as the mobile phase. One system may use TFA as the modifier and measure in positive ion mode [reported as MH+, (M+1) or (M+H)+] and the other may use either formic acid or ammonium acetate and measure in both positive [reported as MH$^+$, (M+1) or (M+H)$^+$] and negative [reported as M−, (M−1) or (M−H)$^-$] ion modes.

Nuclear magnetic resonance (NMR) analysis may be performed on some of the compounds with a Varian 400 MHz NMR (Palo Alto, Calif.). The spectral reference may be either TMS or the known chemical shift of the solvent.

The purity of some of the invention compounds may be assessed by elemental analysis (Robertson Microlit, Madison, N.J.).

Melting points may be determined on a Laboratory Devices Mel-Temp apparatus (Holliston, Mass.).

Preparative separations may be carried out as needed, using either an Sq16x or an Sg100c chromatography system and prepackaged silica gel columns all purchased from Teledyne Isco, (Lincoln, Nebr.). Alternately, compounds and intermediates may be purified by flash column chromatography using silica gel (230-400 mesh) packing material, or by HPLC using a C-18 reversed phase column. Typical solvents employed for the Isco systems and flash column chromatography may be dichloromethane, methanol, ethyl acetate, hexane, acetone, aqueous hydroxyamine and triethyl amine. Typical solvents employed for the reverse phase HPLC may be varying concentrations of acetonitrile and water with 0.1% trifluoroacetic acid.

General Methods

The following synthetic reaction schemes are merely illustrative of some methods by which the compounds of the present invention can be synthesized, and various modifications to these synthetic reaction schemes can be made and will be suggested to one skilled in the art having referred to the disclosure contained in this application.

Example 1

4-((1R,2S)-2-aminocyclohexylamino)-2-(m-tolylamino)benzamide

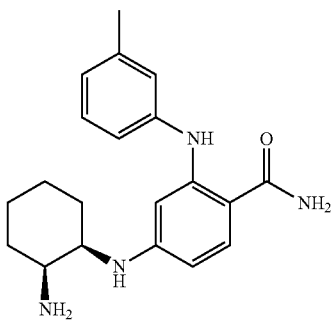 [SMILES: Cc1cccc(Nc2cc(N[C@@H]3CCCC[C@@H]3N)ccc2C(N)=O)c1]

A solution of 2-bromo-4-fluorobenzonitrile (0.761 g, 3.80 mmol), tert-butyl (1S,2R)-2-aminocyclohexylcarbamate (1.00 g, 0.808 mmol) and DIEA (1.00 mL, 5.76 mmol) in DMSO (6 mL) was stirred at 100 C for 18 h. EtOAc and water were added. The organic phase was separated, washed with 1N HCl, then with 5% $NaHCO_3$, dried over $Na_2SO_4$, concentrated in vacuo to give tert-butyl (1S,2R)-2-(3-bromo-4-cyanophenylamino)cyclohexylcarbamate (1.48 g) as an off-white solid.

A mixture of tert-butyl (1S,2R)-2-(3-bromo-4-cyanophenylamino)cyclohexylcarbamate (98 mg, 0.25 mmol), m-toluidine (54 uL, 0.50 mmol), BINAP (31 mg, 0.050 mmol), $Pd(OAc)_2$ (12 mg, 0.053 mmol) and $Cs_2CO_3$ (160 mg, 0.49 mmol) in toluene (3 mL) was degassed with Ar, then was stirred at 100 C for 3 h. EtOAc and water were added. The organic phase was separated, washed with 1N HCl, then with brine, dried over $Na_2SO_4$, concentrated in vacuo to give tert-butyl (1S,2R)-2-(4-cyano-3-(m-tolylamino)phenylamino) cyclohexylcarbamate as a residue.

The residue was dissolved in DMSO (2 mL), $K_2CO_3$ (200 mg, 1.45 mmol) was added; then $H_2O_2$ (50% aq., 0.500 mL) was added dropwise (gas evolved). The mixture was stirred at 100 C for 15 min. Water was added. The product was extracted with nBuOH. The nBuOH extract was concentrated in vacuo. The residue was dissolved in TFA (2 mL). After being stirred for 16 h, TFA was removed in vacuo. The residue was purified by HPLC to give the titled compound (32 mg). MS 339.2 (M+H); UV 205.8, 275.4 nm Scheme 1

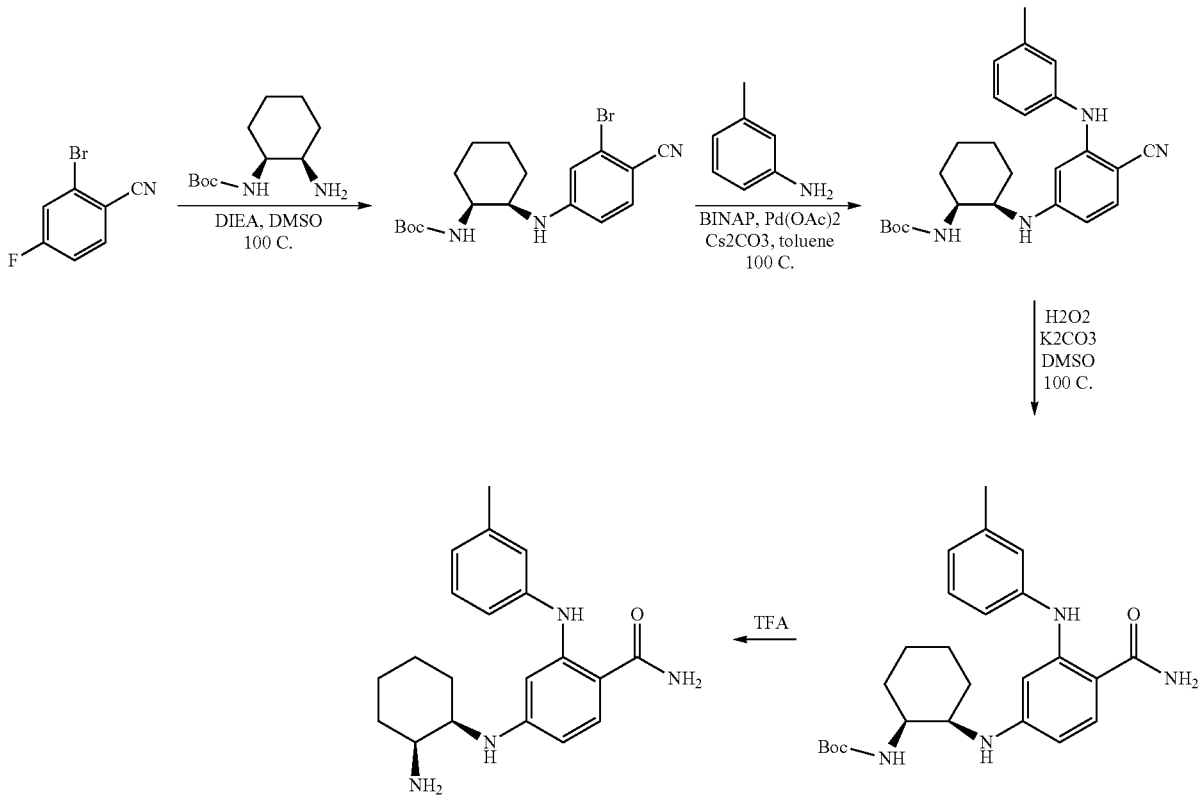

Example 2

4-((1R,2S)-2-aminocyclohexylamino)-2-(1-methyl-1H-indol-4-ylamino)benzamide

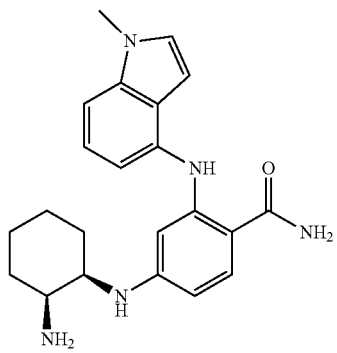 [SMILES: Cn1ccc2c(Nc3cc(N[C@@H]4CCCC[C@@H]4N)ccc3C(N)=O)cccc21]

Scheme 2

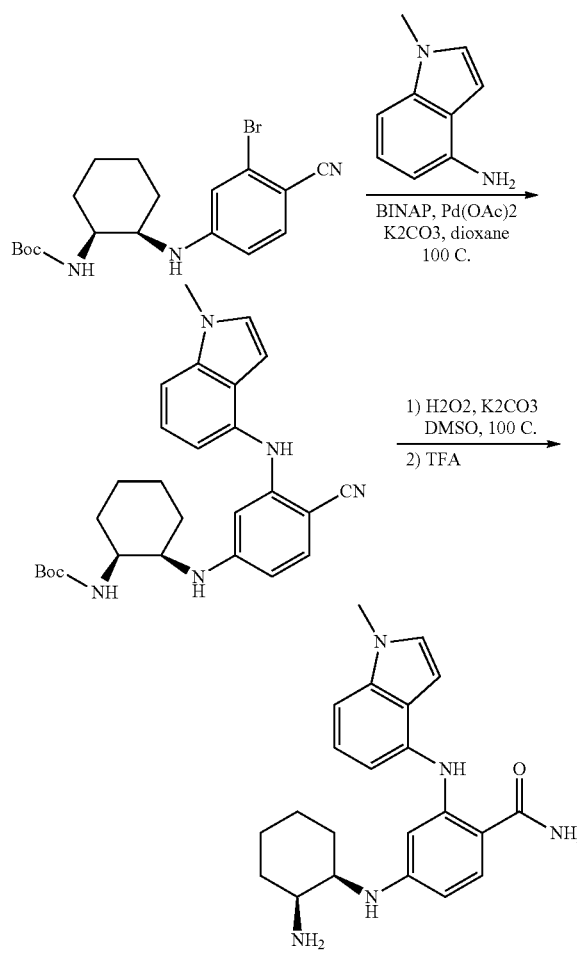

A mixture of tert-butyl (1S,2R)-2-(3-bromo-4-cyanophenylamino)cyclohexylcarbamate (200 mg, 0.507 mmol), 1-methyl-1H-indol-4-amine (160 mg, 1.09 mmol), BINAP (50 mg, 0.080 mmol), Pd(OAc)$_2$ (25 mg, 0.11 mmol) and K$_2$CO$_3$ (150 mg, 1.08 mmol) in dioxane (4 mL) was degassed with Ar, then was stirred at 100 C for 16 h. EtOAc and water were added. The organic phase was separated, washed with 1N HCl, then with 5% NaHCO$_3$, dried over Na$_2$SO$_4$, concentrated in vacuo. The residue was purified by a silica gel column, eluted with 10-40% EtOAc in hexane to give tert-butyl (1S,2R)-2-(4-cyano-3-(1-methyl-1H-indol-4-ylamino)phenylamino)cyclohexylcarbamate (92 mg) as an oil.

To a solution of tert-butyl (1S,2R)-2-(4-cyano-3-(1-methyl-1H-indol-4-ylamino)phenylamino)cyclohexylcarbamate (90 mg, 0.19 mmol) in DMSO (2 mL). K$_2$CO$_3$ (130 mg, 0.94 mmol) and H$_2$O$_2$ (50% aq., 0.500 mL) were added. The mixture was stirred at 100 C for 10 min. Water and EtOAc were added. The organic phase was separated, dried over Na$_2$SO$_4$, concentrated in vacuo. The residue was dissolved in TFA (2 mL). After 10 min of standing, TFA was removed in vacuo. The residue was purified by HPLC to give the titled compound (10 mg). MS 378.3 (M+H); UV 224.7, 291.5 nm

Example 3

4-((1R,2S)-2-aminocyclohexylamino)-2-(4-fluorophenylamino)benzamide

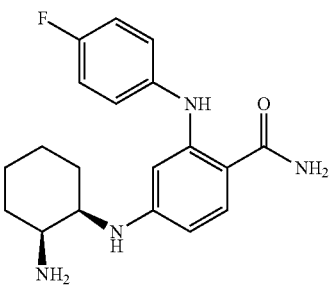 [SMILES: NC(=O)c1ccc(N[C@@H]2CCCC[C@@H]2N)cc1Nc1ccc(F)cc1]

Scheme 3

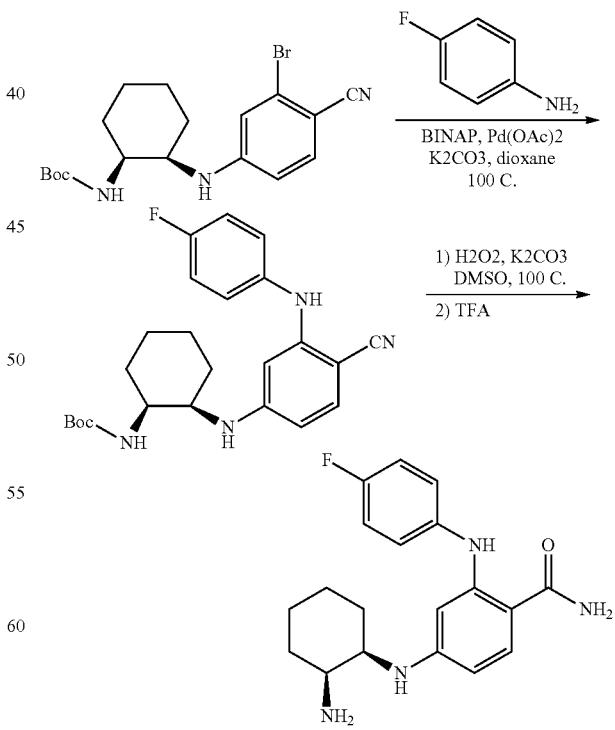

A mixture of tert-butyl (1S,2R)-2-(3-bromo-4-cyanophenylamino)cyclohexylcarbamate (150 mg, 0.380 mmol), 4-fluoroaniline (75 uL, 0.792 mmol), BINAP (40 mg, 0.064 mmol), Pd(OAc)$_2$ (25 mg, 0.11 mmol) and K$_2$CO$_3$ (150 mg, 1.08 mmol) in dioxane (3 mL) was degassed with Ar, then was stirred at 100 C for 16 h. EtOAc and water were added. The organic phase was separated, washed with 1N HCl, then with 5% NaHCO$_3$, dried over Na$_2$SO$_4$, concentrated in vacuo to give tert-butyl (1S,2R)-2-(4-cyano-3-(4-fluorophenylamino)phenylamino)cyclohexylcarbamate as a crude residue.

The crude residue was dissolved in DMSO (2 mL), K$_2$CO$_3$ (150 mg, 1.08 mmol) and H$_2$O$_2$ (50% aq., 0.500 mL) were added. The mixture was stirred at 100 C for 10 min. More H$_2$O$_2$ (50% aq., 1.00 mL) was added, stirred at 100 C for another 5 min. Water and EtOAc were added. The organic phase was separated, dried over Na$_2$SO$_4$, concentrated in vacuo. The residue was dissolved in TFA (3 mL). After 16 h of standing, TFA was removed in vacuo. The residue was purified by HPLC to give the titled compound (10 mg). MS 343.4 (M+H); UV 201.0, 279.2 nm Example 4

4-((1R,2S)-2-aminocyclohexylamino)-2-(3,5-dimethylphenylamino)benzamide

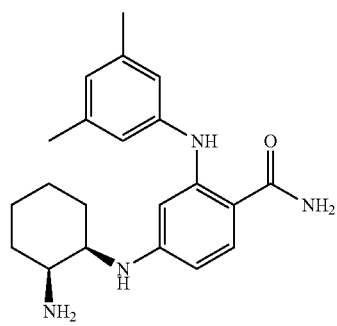 [SMILES: Cc1cc(C)cc(Nc2cc(N[C@@H]3CCCC[C@@H]3N)ccc2C(N)=O)c1]

Scheme 4

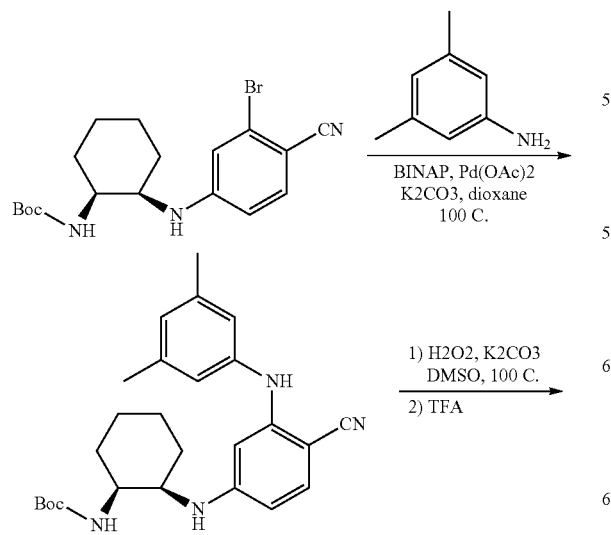

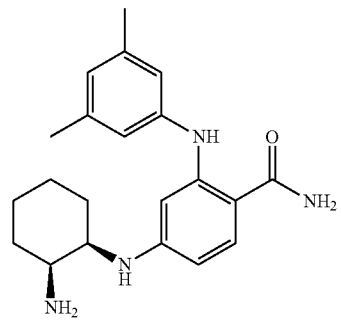

A mixture of tert-butyl (1S,2R)-2-(3-bromo-4-cyanophenylamino)cyclohexylcarbamate (150 mg, 0.380 mmol), 3,5-dimethylaniline (95 uL, 0.761 mmol), BINAP (40 mg, 0.064 mmol), Pd(OAc)$_2$ (25 mg, 0.11 mmol) and K$_2$CO$_3$ (150 mg, 1.08 mmol) in dioxane (4 mL) was degassed with Ar, then was stirred at 100 C for 4 h. EtOAc and water were added. The organic phase was separated, washed with 1N HCl, then with 5% NaHCO$_3$, dried over Na$_2$SO$_4$, concentrated in vacuo to give tert-butyl (1S,2R)-2-(4-cyano-3-(3,5-dimethylphenylamino)phenylamino)cyclohexylcarbamate as a crude residue.

The crude residue was dissolved in DMSO (2 mL), K$_2$CO$_3$ (200 mg, 1.45 mmol) and H$_2$O$_2$ (50% aq., 1.00 mL) were added. The mixture was stirred at 100 C for 10 min. Water and EtOAc were added. The organic phase was separated, dried over Na$_2$SO$_4$, concentrated in vacuo. The residue was dissolved in TFA (3 mL). After 16 h of standing, TFA was removed in vacuo. The residue was purified by HPLC to give the titled compound (11 mg). MS 353.5 (M+H); UV 202.9, 283.5 nm Example 5

2-(3-(2H-1,2,3-triazol-2-yl)phenylamino)-4-(1R,2S)-2-aminocyclohexylamino)benzamide

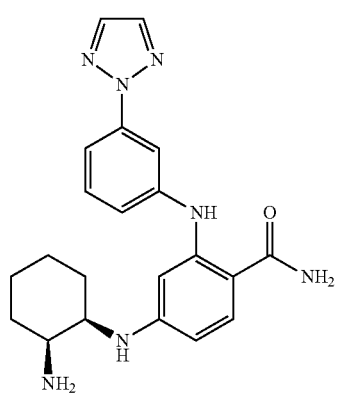 [SMILES: NC(=O)c1ccc(N[C@@H]2CCCC[C@@H]2N)cc1Nc1cccc(-n2nccn2)c1]

Scheme 5

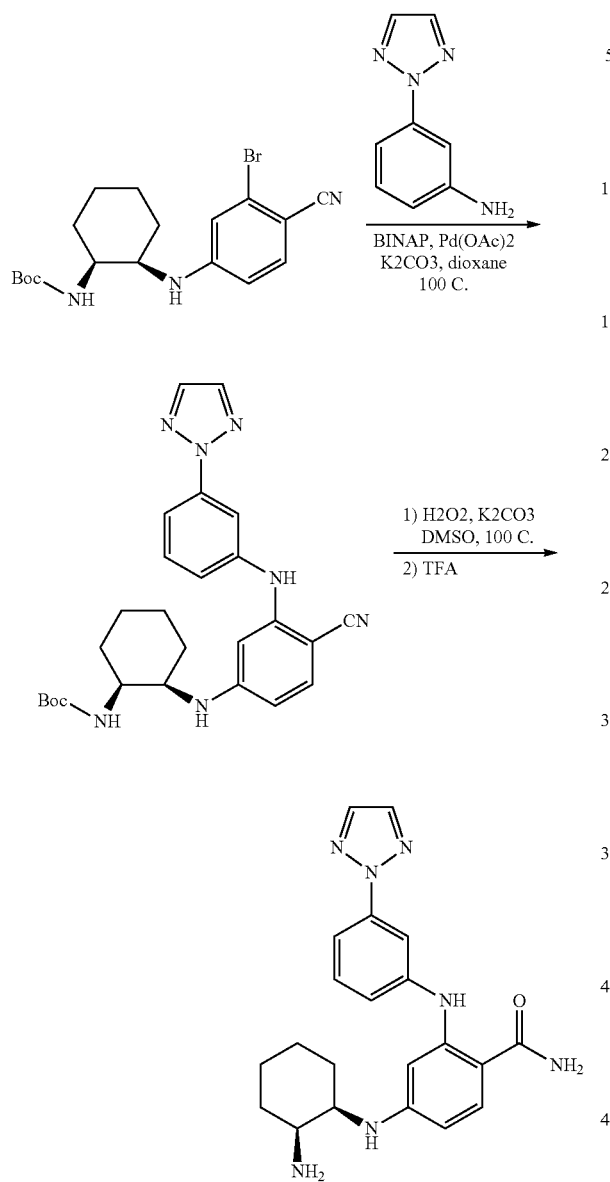

A mixture of tert-butyl (1S,2R)-2-(3-bromo-4-cyanophenylamino)cyclohexylcarbamate (150 mg, 0.380 mmol), 3-(2H-1,2,3-triazol-2-yl)aniline (100 mg, 0.625 mmol), BINAP (40 mg, 0.064 mmol), Pd(OAc)$_2$ (25 mg, 0.11 mmol) and K$_2$CO$_3$ (150 mg, 1.08 mmol) in dioxane (3 mL) was degassed with Ar, then was stirred at 100 C for 4 h. EtOAc and water were added. The organic phase was separated, washed with 1N HCl, then with 5% NaHCO$_3$, dried over Na$_2$SO$_4$, concentrated in vacuo to give tert-butyl (1S,2R)-2-(3-(3-(2H-1,2,3-triazol-2-yl)phenylamino)-4-cyanophenylamino)cyclohexylcarbamate as a crude residue.

The crude residue was dissolved in DMSO (2 mL), K$_2$CO$_3$ (200 mg, 1.45 mmol) and H$_2$O$_2$ (50% aq., 1.00 mL) were added. The mixture was stirred at 100 C for 10 min. Water and EtOAc were added. The organic phase was separated, dried over Na$_2$SO$_4$, concentrated in vacuo. The residue was dissolved in TFA (3 mL). After 16 h of standing, TFA was removed in vacuo. The residue was purified by HPLC to give the titled compound (12 mg). MS 392.5 (M+H); UV 202.9, 276.8 nm

Example 6

4-((1R,2S)-2-aminocyclohexylamino)-2-(3-methylisothiazol-5-ylamino)benzamide

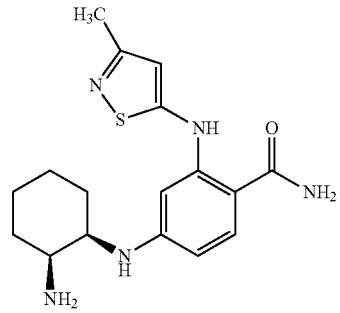 [SMILES: Cc1cc(Nc2cc(N[C@@H]3CCCC[C@@H]3N)ccc2C(N)=O)sn1]

Scheme 6

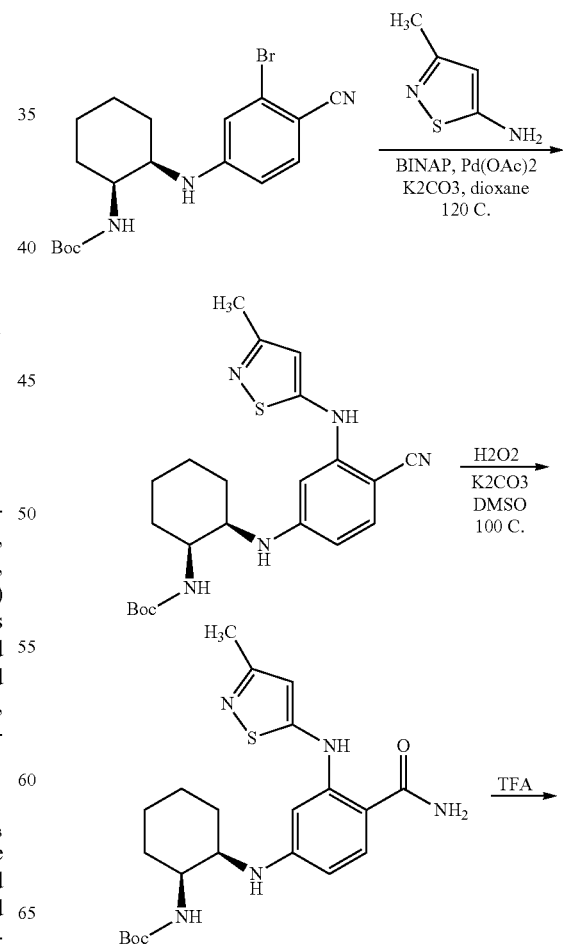

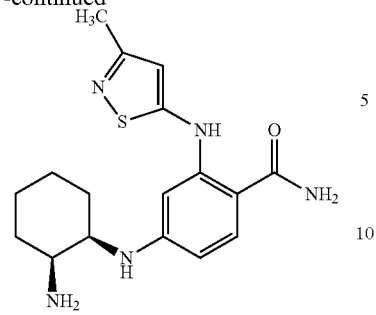

A mixture of tert-butyl (1S,2R)-2-(3-bromo-4-cyanophenylamino)cyclohexylcarbamate (150 mg, 0.380 mmol), 5-amino-3-methylisothiazole hydrochloride (100 mg, 0.664 mmol), BINAP (40 mg, 0.064 mmol), Pd(OAc)$_2$ (30 mg, 0.13 mmol) and K$_2$CO$_3$ (300 mg, 2.17 mmol) in dioxane (4 mL) was degassed with Ar, then was stirred at 120 C for 18 h. EtOAc and water were added. The organic phase was separated, washed with 1N HCl, dried over Na$_2$SO$_4$, concentrated in vacuo to give tert-butyl (1S,2R)-2-(4-cyano-3-(3-methylisothiazol-5-ylamino)phenylamino)cyclohexylcarbamateas a crude residue.

The crude residue was dissolved in DMSO (2 mL), K$_2$CO$_3$ (240 mg, 1.73 mmol) and H$_2$O$_2$ (50% aq., 1.00 mL) were added. The mixture was stirred at 100 C for 10 min. Water and EtOAc were added. The organic phase was separated, dried over Na$_2$SO$_4$, concentrated in vacuo. The residue was dissolved in TFA (3 mL). After 10 min of standing, TFA was removed in vacuo. The residue was purified by HPLC to give the titled compound (33 mg). MS 346.4 (M+H); UV 205.3, 299.5 nm

Example 7

4-((1R,2S)-2-aminocyclohexylamino)-2-(3-phenylisoxazol-5-ylamino)benzamide

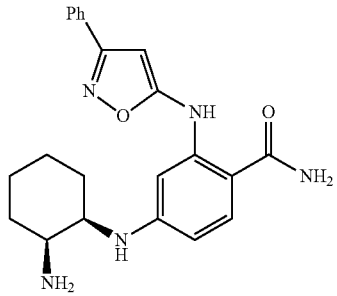 [SMILES: NC(=O)c1ccc(N[C@@H]2CCCC[C@@H]2N)cc1Nc1cc(-c2ccccc2)no1]

Scheme 7

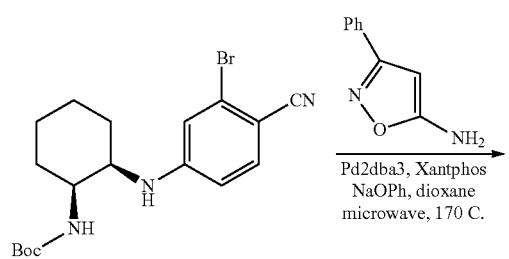

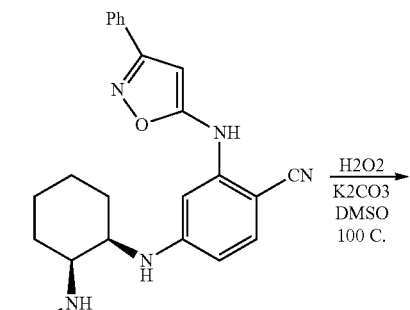

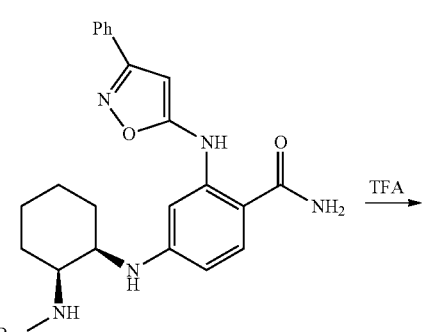

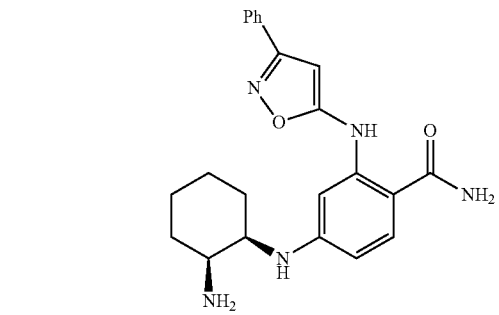

A mixture of tert-butyl (1S,2R)-2-(3-bromo-4-cyanophenylamino)cyclohexylcarbamate (150 mg, 0.380 mmol), 5-amino-3-phenylisoxazole (130 mg, 0.812 mmol), sodium phenoxide trihydrate (100 mg, 0.588 mmol), xantphos (30 mg, 0.051 mmol) and Pd$_2$(dba)$_3$ (30 mg, 0.032 mmol) in dioxane (2 mL) was degassed with Ar, then was heated at 170 C for 30 min by microwave. It was concentrated in vacuo. The residue was purified by HPLC to give tert-butyl (1S,2R)-2-(4-cyano-3-(3-phenylisoxazol-5-ylamino)phenylamino)cyclohexylcarbamate (38 mg).

To a solution of tert-butyl (1S,2R)-2-(4-cyano-3-(3-phenylisoxazol-5-ylamino)phenylamino)cyclohexylcarbamate (38 mg, 0.080 mmol) in DMSO (1 mL), K$_2$CO$_3$ (100 mg, 0.724 mmol) and H$_2$O$_2$ (50% aq., 0.800 mL) were added. After being stirred at 100 C for 10 min, the mixture was purified by HPLC to give tert-butyl (1S,2R)-2-(4-carbamoyl-3-(3-phenylisoxazol-5-ylamino)phenylamino)cyclohexylcarbamate (6 mg).

Compound tert-butyl (1S,2R)-2-(4-carbamoyl-3-(3-phenylisoxazol-5-ylamino)phenylamino)cyclohexylcarbamate (6 mg) was dissolved in TFA (1 mL). After 10 min of standing, TFA removed in vacuo. The residue was purified by HPLC to give the titled compound (1 mg). MS 392.4 (M+H); UV 202.9, 294.0 nm

Example 8

4-((1R,2S)-2-aminocyclohexylamino)-2-(1-methyl-1H-pyrazol-4-ylamino)benzamide

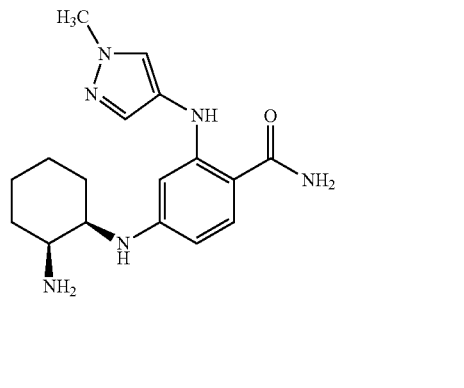 [SMILES: Cn1cc(Nc2cc(N[C@@H]3CCCC[C@@H]3N)ccc2C(N)=O)cn1]

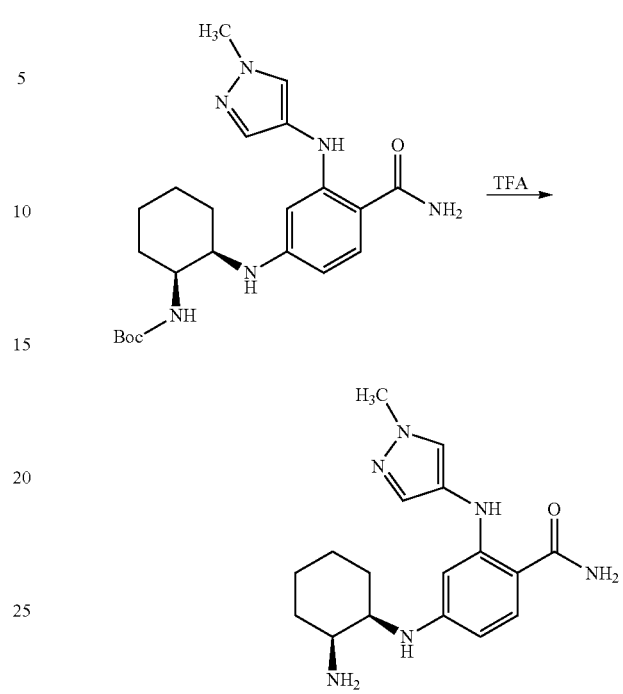

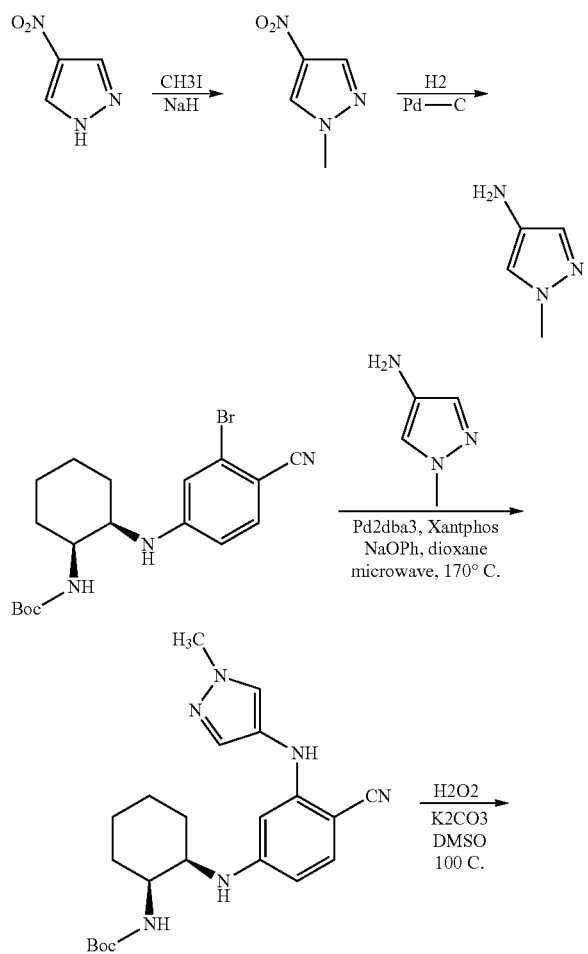

To a solution of 4-nitro-1H-pyrazole (1.13 g, 10.0 mmol) and iodomethane (1.25 mL, 20.0 mmol) in DMF (12 mL), NaH (60% in mineral oil, 0.600 g, 15.0 mmol) was added. The mixture was stirred for 18 h. Water and EtOAc were added. The organic phase was separated, washed with water, dried over $Na_2SO_4$, concentrated in vacuo to give 1-methyl-4-nitro-1H-pyrazole as a solid (1.11 g).

A mixture of 1-methyl-4-nitro-1H-pyrazole (1.10 g, 8.66 mmol) and Pd—C (10%, 190 mg) in EtOAc (20 mL) (containing 8 drops of 6N HCl) was hydrogenated under balloon $H_2$ for 18 h. After being filtered through celite, the filtrate was concentrated in vacuo. The residue was dissolved in 1N HCl (20 mL), then washed with hexane, concentrated in vacuo to give 1-methyl-1H-pyrazol-4-amine dihydrochloride as a solid (0.918 g).

A mixture of tert-butyl (1S,2R)-2-(3-bromo-4-cyanophenylamino)cyclohexylcarbamate (150 mg, 0.380 mmol), 1-methyl-1H-pyrazol-4-amine dihydrochloride (80 mg, 0.470 mmol), sodium phenoxide trihydrate (300 mg, 1.76 mmol), xantphos (30 mg, 0.051 mmol) and $Pd_2(dba)_3$ (30 mg, 0.032 mmol) in dioxane (3 mL) was degassed with Ar, then was heated at 170 C for 30 min by microwave. It was concentrated in vacuo. The residue was purified by HPLC to give tert-butyl (1S,2R)-2-(4-cyano-3-(1-methyl-1H-pyrazol-4-ylamino)phenylamino)cyclohexylcarbamate (50 mg).

To a solution of tert-butyl (1S,2R)-2-(4-cyano-3-(1-methyl-1H-pyrazol-4-ylamino)phenylamino)cyclohexylcarbamate (50 mg, 0.12 mmol) in DMSO (1 mL), $K_2CO_3$ (100 mg, 0.724 mmol) and $H_2O_2$ (50% aq., 0.800 mL) were added. The mixture was stirred at 100 C for 10 min. Water and EtOAc were added. The organic phase was separated, dried over $Na_2SO_4$, concentrated in vacuo. The residue was dissolved in TFA (1 mL). After 10 min of standing, TFA was removed in vacuo. The residue was purified by HPLC to give the titled compound (31 mg). MS 329.4 (M+H); UV 205.3, 258.4, 280.5, 327.9 nm Example 9

(R)-4-(1-amino-4-methyl-1-oxopentan-2-ylamino)-2-(3-methylisothiazol-5-ylamino)benzamide

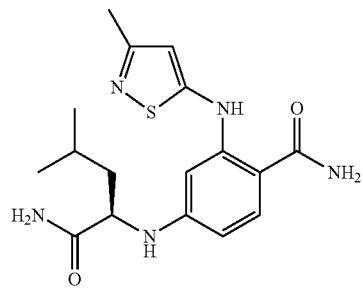 [SMILES: Cc1cc(Nc2cc(N[C@H](CC(C)C)C(N)=O)ccc2C(N)=O)sn1]

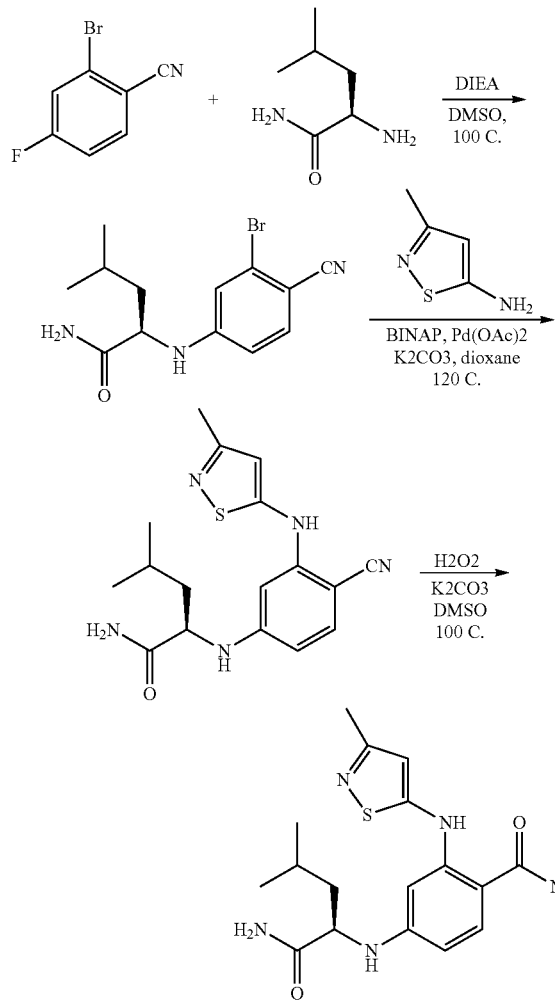

A solution of 2-bromo-4-fluorobenzonitrile (200 mg, 1.00 mmol), D-leucine amide hydrochloride (200 mg, 1.20 mmol) and DIEA (0.620 mL, 3.56 mmol) in DMSO (3 mL) was stirred at 100 C for 18 h. EtOAc and water were added. The organic phase was separated, dried over $Na_2SO_4$, concentrated in vacuo. The residue was purified by a silica gel column, eluted first with 30% EtOAc in hexane, then with 80% EtOAc to give (R)-2-(3-bromo-4-cyanophenylamino)-4-methylpentanamide (187 mg).

A mixture of (R)-2-(3-bromo-4-cyanophenylamino)-4-methylpentanamide (187 mg, 0.603 mmol), 5-amino-3-methylisothiazole hydrochloride (115 mg, 0.763 mmol), BINAP (40 mg, 0.064 mmol), Pd(OAc)$_2$ (30 mg, 0.13 mmol) and $K_2CO_3$ (300 mg, 2.17 mmol) in dioxane (4 mL) was degassed with Ar, then was stirred at 120 C for 18 h. The mixture was concentrated in vacuo. The residue was purified by HPLC to give (R)-2-(4-cyano-3-(3-methylisothiazol-5-ylamino)phenylamino)-4-methylpentanamide (102 mg).

To a solution of (R)-2-(4-cyano-3-(3-methylisothiazol-5-ylamino)phenylamino)-4-methylpentanamide (102 mg, 0.297 mmol) in DMSO (2 mL), $K_2CO_3$ (200 mg, 1.45 mmol) and $H_2O_2$ (50% aq., 1.00 mL) were added. After being stirred at 100 C for 5 min, the mixture was purified by HPLC to give the titled compound (32 mg). MS 362.4 (M+H); UV 226.6, 275.5, 303.2 nm Example 10

(R)-4-(1-amino-1-oxopropan-2-ylamino)-2-(3-methylisothiazol-5-ylamino)benzamide

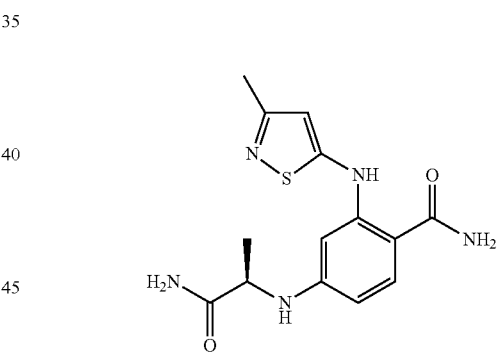

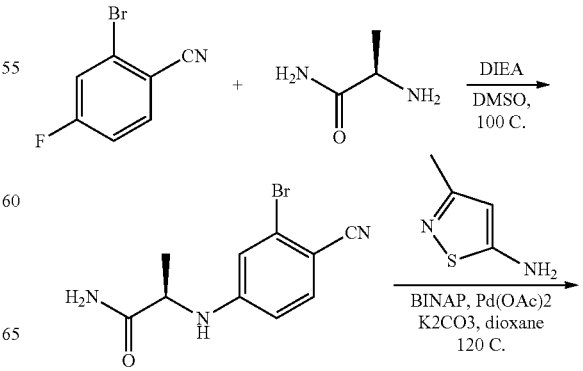

-continued

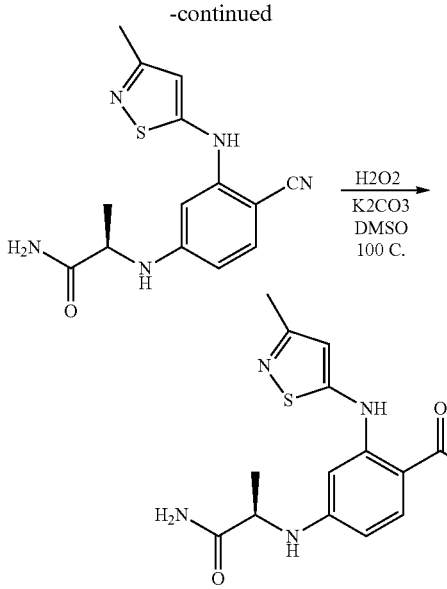

A solution of 2-bromo-4-fluorobenzonitrile (200 mg, 1.00 mmol), D-alanine amide hydrochloride (148 mg, 1.19 mmol) and DMA (0.620 mL, 3.56 mmol) in DMSO (3 mL) was stirred at 100 C for 18 h. EtOAc and water were added. The organic phase was separated, dried over Na₂SO₄, concentrated in vacuo. The residue was purified by a silica gel column, eluted first with 30% EtOAc in hexane, then with 100% EtOAc to give (R)-2-(3-bromo-4-cyanophenylamino) propanamide (185 mg).

A mixture of (R)-2-(3-bromo-4-cyanophenylamino)propanamide (185 mg, 0.690 mmol), 5-amino-3-methylisothiazole hydrochloride (133 mg, 0.883 mmol), BINAP (40 mg, 0.064 mmol), Pd(OAc)₂ (30 mg, 0.13 mmol) and K₂CO₃ (300 mg, 2.17 mmol) in dioxane (4 mL) was degassed with Ar, then was stirred at 120 C for 18 h. The mixture was concentrated in vacuo. The residue was purified by HPLC to give ((R)-2-(4-cyano-3-(3-methylisothiazol-5-ylamino)phenylamino)propanamide (127 mg).

To a solution of (R)-2-(4-cyano-3-(3-methylisothiazol-5-ylamino)phenylamino)propanamide (127 mg, 0.421 mmol) in DMSO (2 mL), K₂CO₃ (200 mg, 1.45 mmol) and H₂O₂ (50% aq., 1.00 mL) were added. After being stirred at 100 C for 5 min, the mixture was purified by HPLC to give the titled compound (34 mg). MS 320.3 (M+H); UV 205.3, 294.6 nm Example 11

(R)-4-(1-amino-3-methyl-1-oxobutan-2-ylamino)-2-(3-methylisothiazol-5-ylamino)benzamide

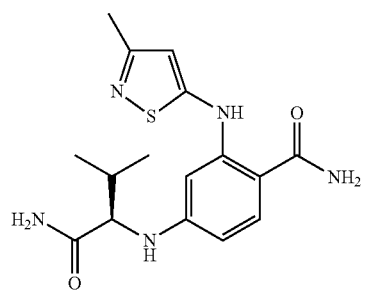 [SMILES: Cc1cc(Nc2cc(N[C@@H](C(N)=O)C(C)C)ccc2C(N)=O)sn1]

The titled compound was synthesized analogously according to the procedures described for (R)-4-(1-amino-4-methyl-1-oxopentan-2-ylamino)-2-(3-methylisothiazol-5-ylamino)benzamide in Example 9. MS 348.3 (M+H); UV 205.9, 300.8 nm Example 12

(R)-4-(1-amino-4-methyl-1-oxopentan-2-ylamino)-2-(5-methylisoxazol-3-ylamino)benzamide

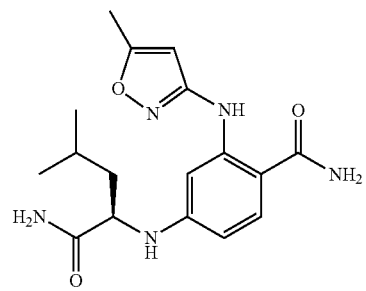 [SMILES: Cc1cc(Nc2cc(N[C@H](CC(C)C)C(N)=O)ccc2C(N)=O)no1]

Scheme 11

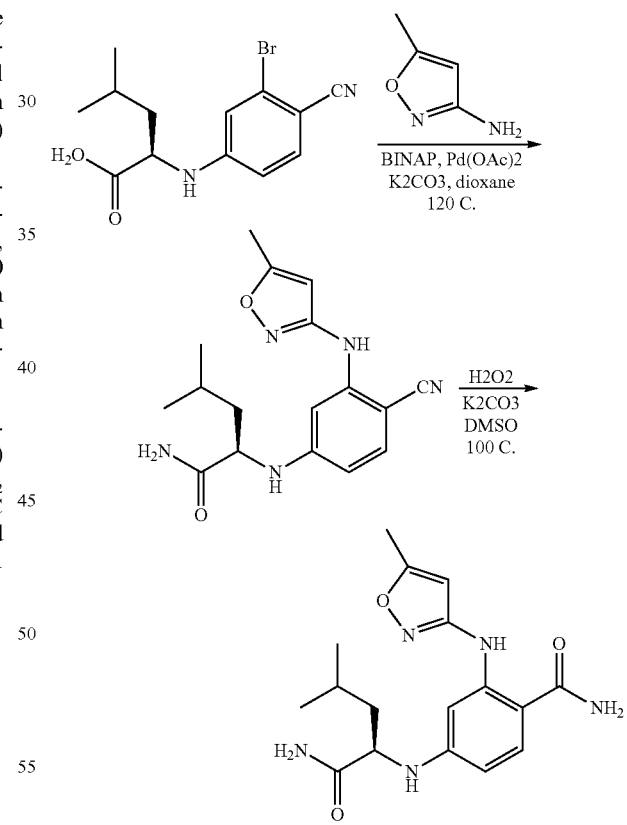

A mixture of (R)-2-(3-bromo-4-cyanophenylamino)-4-methylpentanamide (120 mg, 0.387 mmol), 3-amino-5-methylisoxazole (60 mg, 0.612 mmol), BINAP (40 mg, 0.064 mmol), Pd(OAc)₂ (30 mg, 0.13 mmol) and K₂CO₃ (150 mg, 1.08 mmol) in dioxane (3 mL) was degassed with Ar, then was stirred at 120 C for 18 h. The mixture was concentrated in vacuo. The residue was purified by HPLC to give (R)-2-(4-cyano-3-(5-methylisoxazol-3-ylamino)phenylamino)-4-methylpentanamide (25 mg).

To a solution of (R)-2-(4-cyano-3-(5-methylisoxazol-3-ylamino)phenylamino)-4-methylpentanamide (15 mg, 0.045 mmol) in DMSO (1 mL), K$_2$CO$_3$ (150 mg, 1.08 mmol) and H$_2$O$_2$ (50% aq., 0.800 mL) were added. After being stirred at 90 C for 5 min, the mixture was purified by HPLC to give the titled compound (6 mg). MS 346.3 (M+H); UV 203.5, 270.0, 293.4 nm Example 13

(R)-4-(1-amino-4-methyl-1-oxopentan-2-ylamino)-2-(3-methylisoxazol-5-ylamino)benzamide

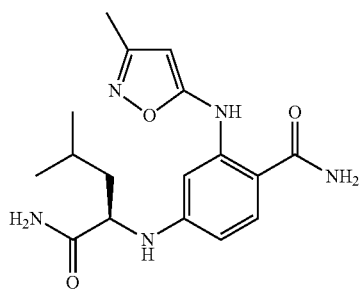 [SMILES: Cc1cc(Nc2cc(N[C@H](CC(C)C)C(N)=O)ccc2C(N)=O)on1]

Scheme 12

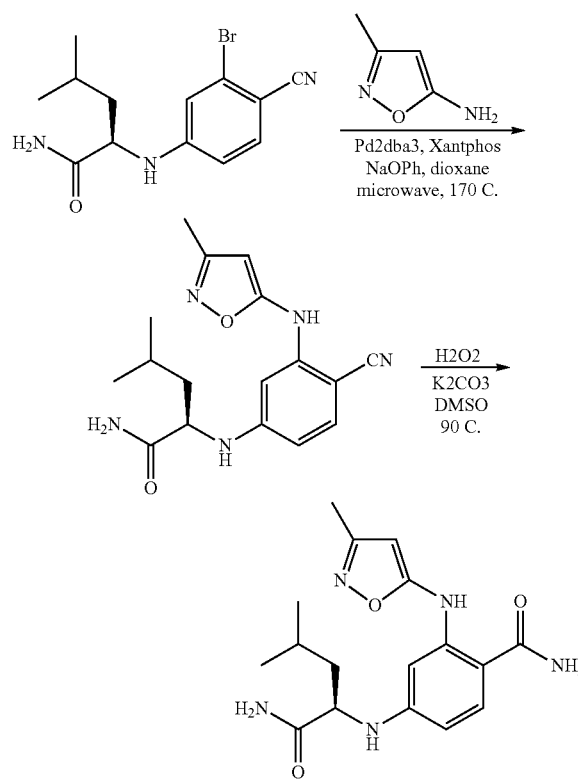

A mixture of (R)-2-(3-bromo-4-cyanophenylamino)-4-methylpentanamide (120 mg, 0.387 mmol), 5-amino-3-methylisoxazole (60 mg, 0.612 mmol), sodium phenoxide trihydrate (100 mg, 0.588 mmol), xantphos (25 mg, 0.043 mmol) and Pd$_2$(dba)$_3$ (20 mg, 0.021 mmol) in dioxane (3 mL) was degassed with Ar, then was heated at 170 C for 15 min by microwave. It was concentrated in vacuo. The residue was purified by HPLC to give (R)-2-(4-cyano-3-(3-methylisoxazol-5-ylamino)phenylamino)-4-methylpentanamide (20 mg).

To a solution of (R)-2-(4-cyano-3-(3-methylisoxazol-5-ylamino)phenylamino)-4-methylpentanamide (20 mg, 0.061 mmol) in DMSO (1 mL), K$_2$CO$_3$ (150 mg, 1.08 mmol) and H$_2$O$_2$ (50% aq., 0.800 mL) were added. After being stirred at 90 C for 5 min, the mixture was purified by HPLC to give the titled compound (1 mg). MS 346.3 (M+H); UV 202.2, 279.2 nm Example 14

(R)-4-(1-amino-1-oxo-3-phenylpropan-2-ylamino)-2-(3-methylisothiazol-5-ylamino)benzamide

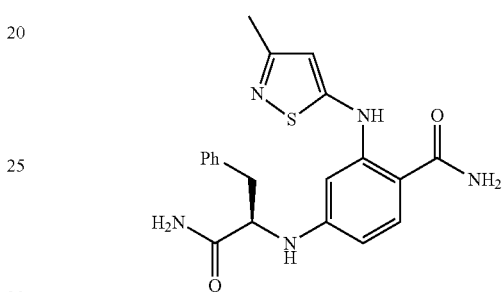

Scheme 13

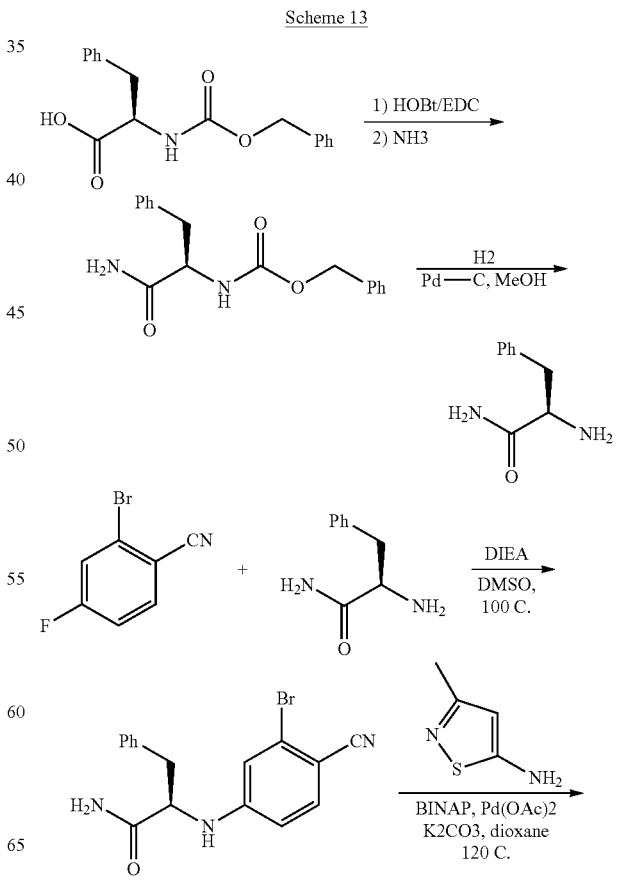

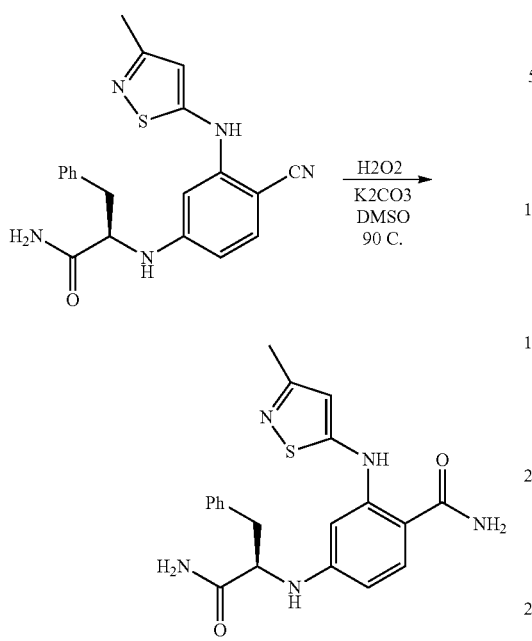

purified by HPLC to give the titled compound (22 mg). MS 396.4 (M+H); UV 200.4, 295.8 nm Example 15

(R)-4-(1-amino-3-(benzyloxy)-1-oxopropan-2-ylamino)-2-(3-methylisothiazol-5-ylamino)benzamide

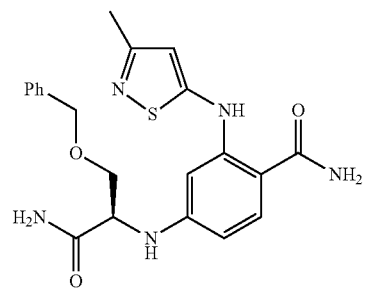 [SMILES: Cc1cc(Nc2cc(N[C@H](COCc3ccccc3)C(N)=O)ccc2C(N)=O)sn1]

To a solution of N-Cbz-D-phenylalanine (1.00 g, 3.34 mmol) and HOBt hydrate (0.614 g, 4.01 mmol) in DMF (9 mL), EDC (0.834 g, 4.34 mmol) was added. The mixture was stirred for 40 min. Then conc. NH₄OH (1.00 mL, ~14 mmol) was added. It was stirred for 72 h. Water and EtOAc were added. The organic phase was separated, washed with 5% NaHCO₃, dried over Na₂SO₄, concentrated in vacuo to give (R)-benzyl 1-amino-1-oxo-3-phenylpropan-2-ylcarbamate as a solid (0.910 g).

A mixture of (R)-benzyl 1-amino-1-oxo-3-phenylpropan-2-ylcarbamate (910 mg, 3.05 mmol) and Pd—C (10%, 200 mg) in MeOH (20 mL) was hydrogenated under balloon H₂ for 16 h. It was filtered through celite. The filtrate was concentrated in vacuo to give D-phenylalanine amide as a white solid (493 mg).

A solution of 2-bromo-4-fluorobenzonitrile (255 mg, 1.27 mmol), D-phenylalanine amide (220 mg, 1.34 mmol) and DIEA (0.466 mL, 2.68 mmol) in DMSO (3 mL) was stirred at 100 C for 18 h. The mixture was then purified by HPLC to give (R)-2-(3-bromo-4-cyanophenylamino)-3-phenylpropanamide (102 mg).

A mixture of (R)-2-(3-bromo-4-cyanophenylamino)-3-phenylpropanamide (102 mg, 0.296 mmol), 5-amino-3-methylisothiazole hydrochloride (58 mg, 0.385 mmol), BINAP (25 mg, 0.040 mmol), Pd(OAc)₂ (20 mg, 0.089 mmol) and K₂CO₃ (150 mg, 1.08 mmol) in dioxane (3 mL) was degassed with Ar, then was stirred at 120 C for 18 h. Water and EtOAc were added. After being filtered, the organic phase was separated, washed with 1N HCl, dried over Na₂SO₄, concentrated in vacuo to give (R)-2-(4-cyano-3-(3-methylisothiazol-5-ylamino)phenylamino)-3-phenylpropanamide as a crude residue.

To a solution of the crude residue in DMSO (2 mL), K₂CO₃ (200 mg, 1.44 mmol) and H₂O₂ (50% aq., 1.00 mL) were added. After being stirred at 90 C for 5 min, the mixture was Scheme 14

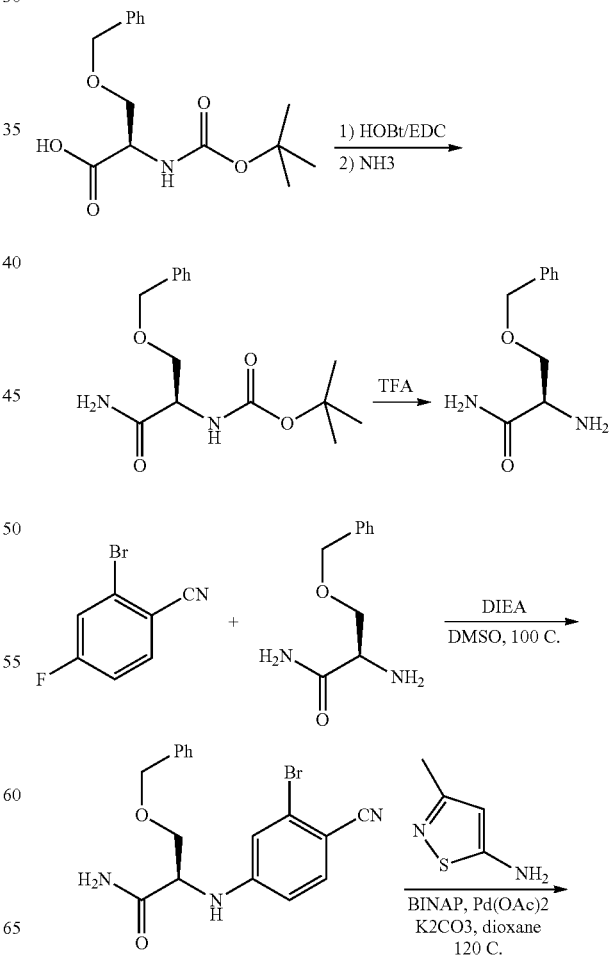

-continued

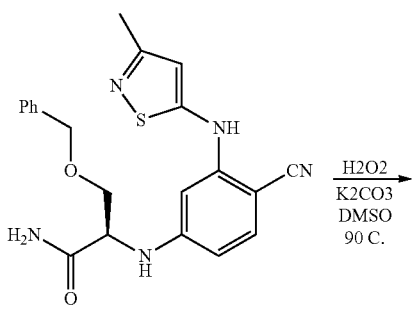

To a solution of (R)-3-(benzyloxy)-2-(4-cyano-3-(3-methylisothiazol-5-ylamino)phenylamino)propanamide (73 mg, 0.18 mmol) in DMSO (2 mL), K₂CO₃ (200 mg, 1.44 mmol) and H₂O₂ (50% aq., 1.00 mL) were added. After being stirred at 90 C for 15 min, the mixture was purified by HPLC to give the titled compound (6 mg). MS 426.3 (M+H); UV 200.4, 293.4 nm Example 16

(R)-4-(1-amino-3-hydroxy-1-oxopropan-2-ylamino)-2-(3-methylisothiazol-5-ylamino)benzamide

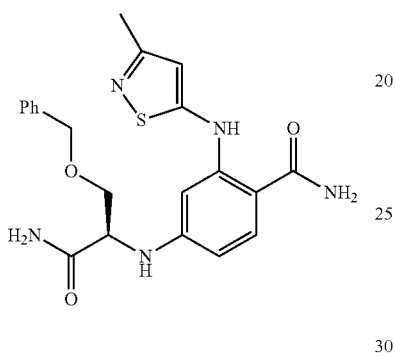

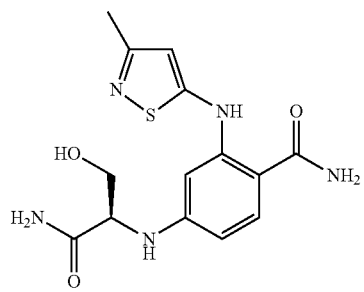 [SMILES: Cc1cc(Nc2cc(N[C@H](CO)C(N)=O)ccc2C(N)=O)sn1]

To a solution of N-Boc-O-benzyl-D-serine (510 mg, 1.72 mmol) and HOBt hydrate (317 mg, 2.07 mmol) in DMF (9 mL), EDC (432 mg, 2.25 mmol) was added. The mixture was stirred for 60 min. Then conc. NH₄OH (0.600 mL, ~8.40 mmol) was added. It was stirred for 18 h. Water and EtOAc were added. The organic phase was separated, washed with 5% NaHCO₃, dried over Na₂SO₄, concentrated in vacuo to give (R)-tert-butyl 1-amino-3-(benzyloxy)-1-oxopropan-2-ylcarbamate (444 mg).

Compound (R)-tert-butyl 1-amino-3-(benzyloxy)-1-oxopropan-2-ylcarbamate (444 mg, 1.51 mmol) was dissolved in TFA (8 mL). After 20 min of standing, TFA was removed in vacuo. To the residue, nBuOH and aq. 5% NaHCO₃ were added. The nBuOH phase was separated, and concentrated in vacuo to O-benzyl-D-serinamide (290 mg).

A solution of 2-bromo-4-fluorobenzonitrile (200 mg, 1.00 mmol), O-benzyl-D-serinamide (290 mg, 1.49 mmol) and DIEA (0.466 mL, 2.68 mmol) in DMSO (3 mL) was stirred at 100 C for 18 h. Water and EtOAc were added. The organic phase was separated, washed with 1N HCl, dried over Na₂SO₄, concentrated in vacuo. The residue was purified by a silica gel column, eluted with 0-60% EtOAc in hexane to give (R)-3-(benzyloxy)-2-(3-bromo-4-cyanophenylamino) propanamide (66 mg).

A mixture of (R)-3-(benzyloxy)-2-(3-bromo-4-cyanophenylamino)propanamide (66 mg, 0.176 mmol), 5-amino-3-methylisothiazole hydrochloride (35 mg, 0.232 mmol), BINAP (20 mg, 0.032 mmol), Pd(OAc)₂ (15 mg, 0.066 mmol) and K₂CO₃ (100 mg, 0.724 mmol) in dioxane (2 mL) was degassed with Ar, then was stirred at 120 C for 18 h. Water and EtOAc were added. After being filtered, the organic phase was separated, dried over Na₂SO₄, concentrated in vacuo to give (R)-3-(benzyloxy)-2-(4-cyano-3-(3-methylisothiazol-5-ylamino)phenylamino)propanamide as a crude residue (73 mg).

Scheme 15

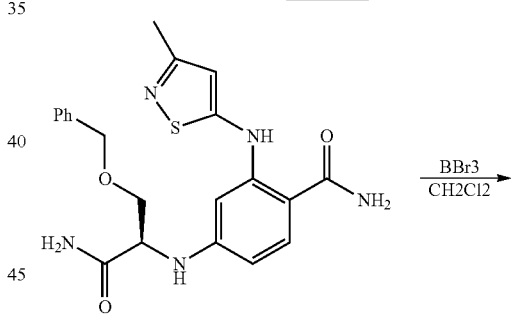

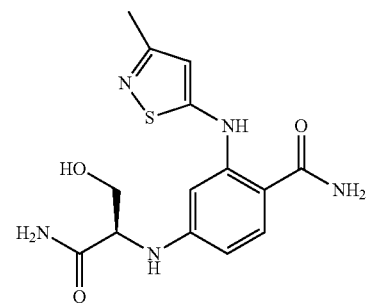

To a suspension of (R)-4-(1-amino-3-(benzyloxy)-1-oxopropan-2-ylamino)-2-(3-methylisothiazol-5-ylamino)benzamide (4 mg, 0.009 mmol) in CH₂Cl₂ (1 mL), BBr₃ (0.050 mL, 0.53 mmol) was added. After being stirred and swirled for 1 h, the mixture was purified by HPLC to give the titled compound (1 mg). MS 336.3 (M+H); UV 202.9, 294.6 nm Example 17

(R)-4-(1-amino-3-cyclohexyl-1-oxopropan-2-ylamino)-2-(3-methylisothiazol-5-ylamino)benzamide

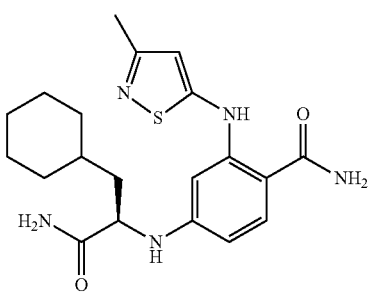 [SMILES: Cc1cc(Nc2cc(N[C@H](CC3CCCCC3)C(N)=O)ccc2C(N)=O)sn1]

Scheme 16

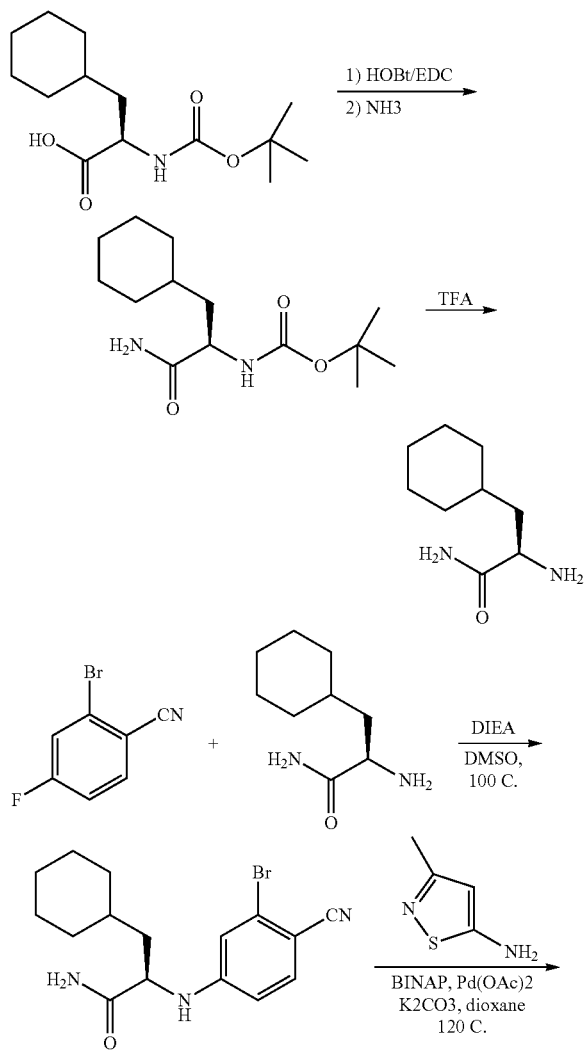

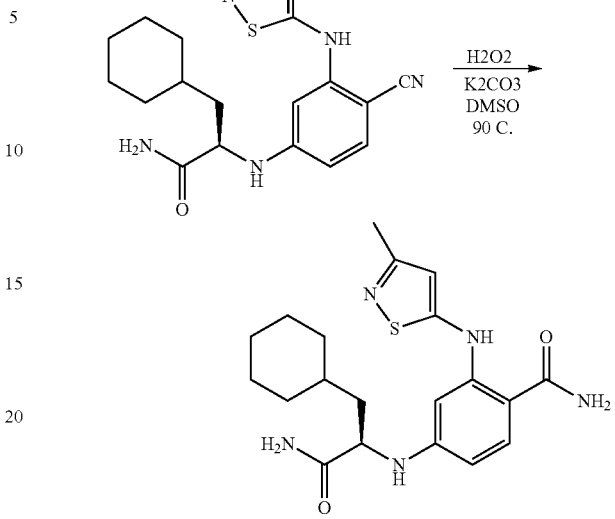

To a solution of N-Boc-β-cyclohexyl-D-alanine (1.00 g, 3.69 mmol) and HOBt hydrate (0.678 g, 4.43 mmol) in DMF (10 mL), EDC (0.850 g, 4.43 mmol) was added. The mixture was stirred for 60 min. Then conc. NH₄OH (1.00 mL, ~14.0 mmol) was added. It was stirred for 18 h. Water and EtOAc were added. The organic phase was separated, washed with 5% NaHCO₃, dried over Na₂SO₄, concentrated in vacuo to give (R)-tert-butyl 1-amino-3-cyclohexyl-1-oxopropan-2-yl-carbamate as a white solid (0.917 g).

The white solid (0.917 g, 3.40 mmol) was dissolved in TFA (10 mL). After 2 h of standing, TFA was removed in vacuo. To the residue, nBuOH and aq. 5% NaHCO₃ were added. The nBuOH phase was separated, washed with water, concentrated in vacuo to give (R)-2-amino-3-cyclohexylpropanamide (0.519 g)

A solution of 2-bromo-4-fluorobenzonitrile (200 mg, 1.00 mmol), (R)-2-amino-3-cyclohexylpropanamide (280 mg, 1.64 mmol) and DIEA (0.500 mL, 2.87 mmol) in DMSO (3 mL) was stirred at 120 C for 18 h. Water and EtOAc were added. The organic phase was separated, washed with 1N HCl, dried over Na₂SO₄, concentrated in vacuo. The residue was purified by a silica gel column, eluted with 0-70% EtOAc in hexane to give (R)-2-(3-bromo-4-cyanophenylamino)-3-cyclohexylpropanamide (222 mg).

A mixture of (R)-2-(3-bromo-4-cyanophenylamino)-3-cyclohexylpropanamide (222 mg, 0.634 mmol), 5-amino-3-methylisothiazole hydrochloride (126 mg, 0.840 mmol), BINAP (60 mg, 0.096 mmol), Pd(OAc)₂ (45 mg, 0.200 mmol) and K₂CO₃ (360 mg, 2.60 mmol) in dioxane (4 mL) was degassed with Ar, then was stirred at 120 C for 18 h. Water and EtOAc were added. After being filtered, the organic phase was separated, washed with 1N HCl, then with 5% NaHCO₃, dried over Na₂SO₄, concentrated in vacuo to give (R)-2-(4-cyano-3-(3-methylisothiazol-5-ylamino)phenylamino)-3-cyclohexylpropanamide as a solid (241 mg).

To a solution of (R)-2-(4-cyano-3-(3-methylisothiazol-5-ylamino)phenylamino)-3-cyclohexylpropanamide (241 mg, 0.629 mmol) in DMSO (2 mL), K₂CO₃ (300 mg, 2.17 mmol) and H₂O₂ (50% aq., 1.00 mL) were added. After being stirred at 90 C for 10 min, the mixture was purified by HPLC to give the titled compound (81 mg). MS 402.4 (M+H); UV 204.7, 298.3 nm

Example 18

(R)-4-(2-amino-2-oxo-1-phenylethylamino)-2-(3-methylisothiazol-5-ylamino)benzamide

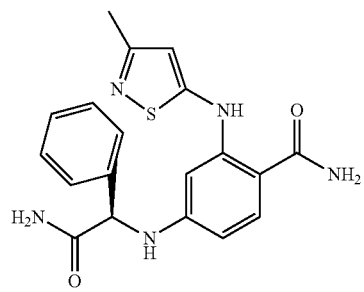 [SMILES: Cc1cc(Nc2cc(N[C@@H](C(N)=O)c3ccccc3)ccc2C(N)=O)sn1]

Scheme 17

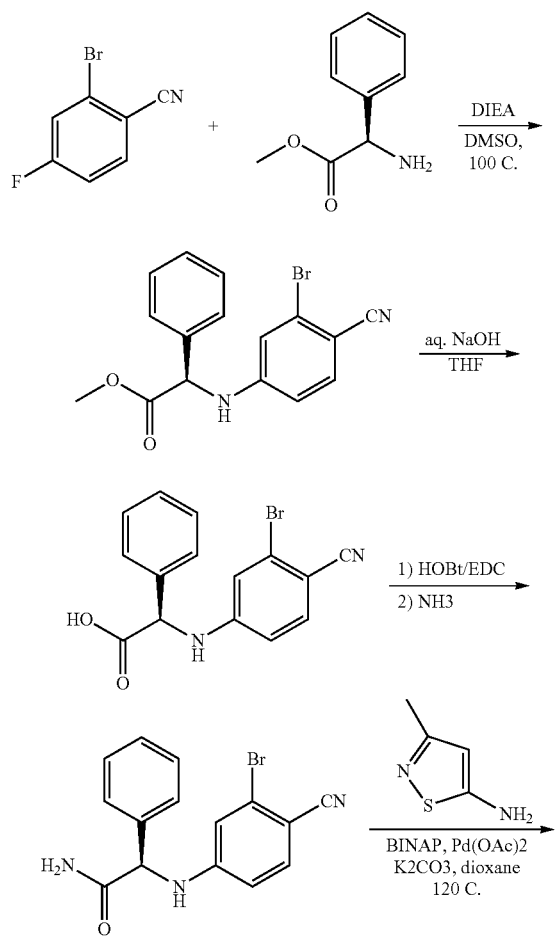

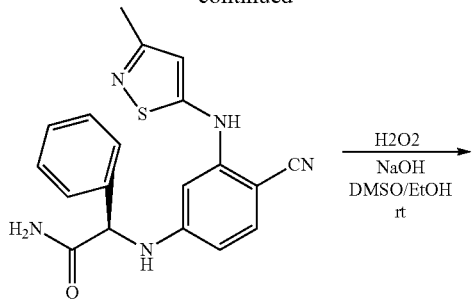

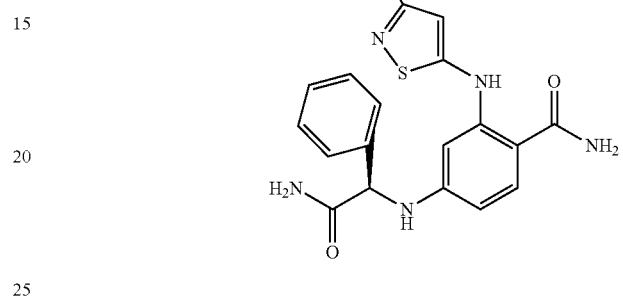

A solution of 2-bromo-4-fluorobenzonitrile (200 mg, 1.00 mmol), (R)-phenylglycine methyl ester hydrochloride (202 mg, 1.00 mmol) and DIEA (0.600 mL, 3.45 mmol) in DMSO (3 mL) was stirred at 100 C for 18 h. Water and EtOAc were added. The organic phase was separated, washed with 1N HCl, dried over $Na_2SO_4$, concentrated in vacuo. The residue was purified by a silica gel column, eluted with 0-35% EtOAc in hexane to give (R)-methyl 2-(3-bromo-4-cyanophenylamino)-2-phenylacetate (98 mg).

To a solution of (R)-methyl 2-(3-bromo-4-cyanophenylamino)-2-phenylacetate (98 mg, 0.28 mmol) in THF (2 mL), 1N aq. NaOH (1.00 mL, 1.00 mmol) was added. After being stirred for 18 h, the solution was acidified with 1N HCl to pH 1-2. Water and EtOAc were added. The organic phase was separated, dried over $Na_2SO_4$, concentrated in vacuo to give (R)-2-(3-bromo-4-cyanophenylamino)-2-phenylacetic acid (90 mg).

To a solution of (R)-2-(3-bromo-4-cyanophenylamino)-2-phenylacetic acid (90 mg, 0.27 mmol) and HOBt hydrate (62 mg, 0.40 mmol) in DMF (2 mL), EDC (74 mg, 0.38 mmol) was added. The mixture was stirred for 60 min. Then conc. $NH_4OH$ (0.100 mL, ~1.40 mmol) was added. It was stirred for 18 h. Water and EtOAc were added. The organic phase was separated, washed with 5% $NaHCO_3$, dried over $Na_2SO_4$, concentrated in vacuo to give (R)-2-(3-bromo-4-cyanophenylamino)-2-phenylacetamide (78 mg).

A mixture of (R)-2-(3-bromo-4-cyanophenylamino)-2-phenylacetamide (78 mg, 0.236 mmol), 5-amino-3-methylisothiazole hydrochloride (47 mg, 0.312 mmol), BINAP (30 mg, 0.048 mmol), $Pd(OAc)_2$ (20 mg, 0.089 mmol) and $K_2CO_3$ (134 mg, 0.971 mmol) in dioxane (3 mL) was degassed with Ar, then was stirred at 120 C for 18 h. Water and EtOAc were added. After being filtered, the organic phase was separated, washed with brine, dried over $Na_2SO_4$, concentrated in vacuo to give (R)-2-(4-cyano-3-(3-methylisothiazol-5-ylamino)phenylamino)-2-phenylacetamide as a crude residue.

To a solution of the crude residue in EtOH (2 mL) and DMSO (0.5 mL), 1N aq. NaOH (0.5 mL) and $H_2O_2$ (50% aq., 0.5 mL) were added. After being stirred at room temperature for 1 h, the mixture was concentrated in vacuo. The residue was acidified with HOAc (0.5 mL), and then was purified by HPLC to give the titled compound (12 mg). MS 382.3 (M+H); UV 208.3, 302.0 nm Example 19

(R)-4-(1-amino-4-methyl-1-oxopentan-2-ylamino)-2-fluoro-6-(3-methylisothiazol-5-ylamino)benzamide

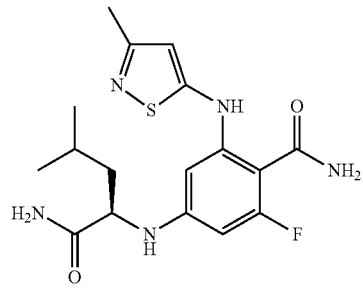 [SMILES: Cc1cc(Nc2cc(N[C@H](CC(C)C)C(N)=O)cc(F)c2C(N)=O)sn1]

Scheme 18

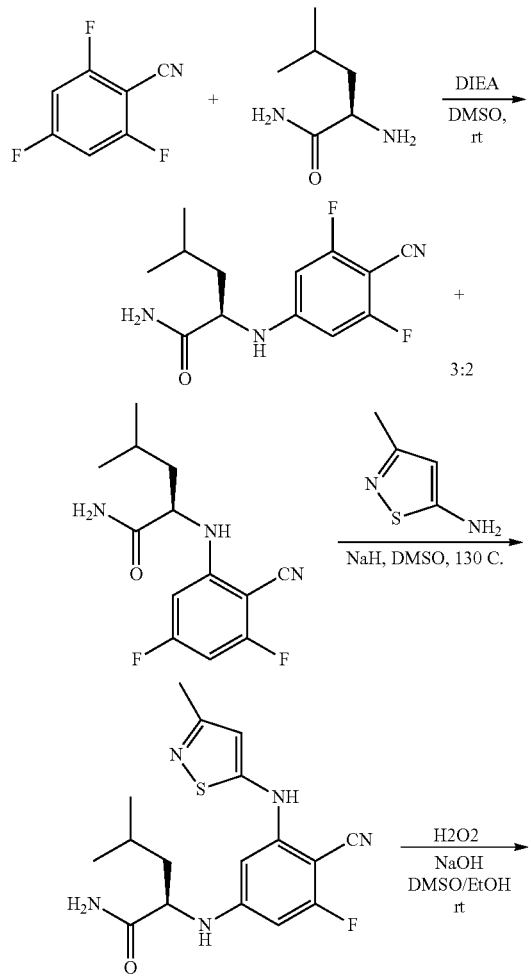

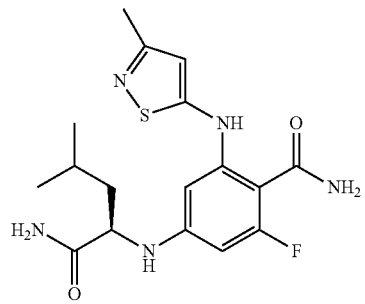

To a solution of 2,4,6-trifluorobenzonitrile (208 mg, 1.32 mmol) in DMSO (2 mL), a solution of D-leucine amide hydrochloride (220 mg, 1.32 mmol) and DIEA (0.688 mL, 3.96 mmol) in DMSO (5 mL) was added. After being stirred at room temperature for 18 h, water and EtOAc were added. The organic phase was separated, washed with water, dried over $Na_2SO_4$, concentrated in vacuo. The residue was purified by a silica gel column, eluted with 20-80% EtOAc in hexane to give (R)-2-(4-cyano-3,5-difluorophenylamino)-4-methylpentanamide (92 mg).

To a solution of (R)-2-(4-cyano-3,5-difluorophenylamino)-4-methylpentanamide (92 mg, 0.34 mmol) and 5-amino-3-methylisothiazole hydrochloride (70 mg, 0.46 mmol) in DMSO (2 mL), NaH (60% in mineral oil, 80 mg, 2.00 mmol) was added. $H_2$ gas evolved. The mixture was stirred at 130 C for 1 h. After being acidified with HOAc (1.0 mL), the mixture was purified by HPLC to give (R)-2-(4-cyano-3-fluoro-5-(3-methylisothiazol-5-ylamino)phenylamino)-4-methylpentanamide (38 mg).

To a solution of (R)-2-(4-cyano-3-fluoro-5-(3-methylisothiazol-5-ylamino)phenylamino)-4-methylpentanamide (38 mg, 0.105 mmol) in EtOH (1 mL) and DMSO (0.5 mL), 1N aq. NaOH (0.4 mL) and $H_2O_2$ (50% aq., 0.4 mL) were added. After being stirred at room temperature for 1 h, the mixture was concentrated in vacuo. The residue was acidified with HOAc (0.5 mL), and then was purified by HPLC to give the titled compound (18 mg). MS 380.3 (M+H); UV 221.1, 282.9, 297.7 nm Example 20

(R)-4-(1-amino-4-methyl-1-oxopentan-2-ylamino)-5-fluoro-2-(3-methylisothiazol-5-ylamino)benzamide

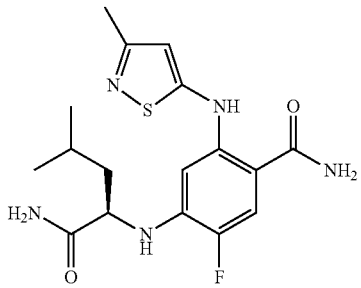 [SMILES: Cc1cc(Nc2cc(N[C@H](CC(C)C)C(N)=O)c(F)cc2C(N)=O)sn1]

Scheme 19

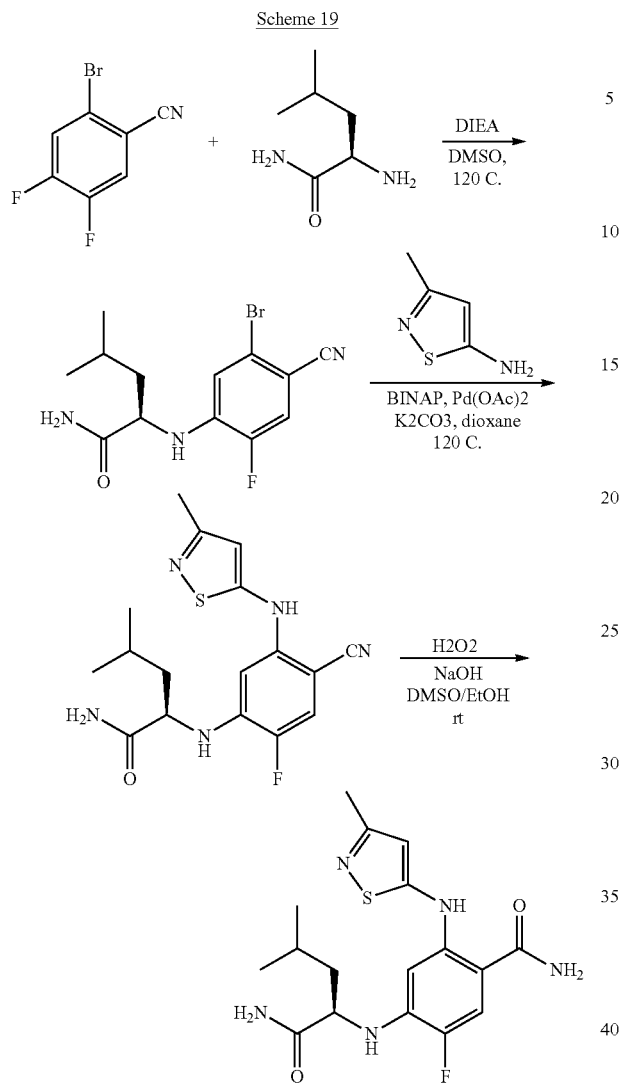

A solution of 2-bromo-4,5-difluorobenzonitrile (218 mg, 1.00 mmol), D-leucine amide hydrochloride (185 mg, 1.10 mmol) and DIEA (0.600 mL, 3.45 mmol) in DMSO (3 mL) was stirred at 120 C for 18 h. Water and EtOAc were added. The organic phase was separated, washed with water, dried over $Na_2SO_4$, concentrated in vacuo. The residue was purified by a silica gel column, eluted with 0-50% EtOAc in hexane to give (R)-2-(5-bromo-4-cyano-2-fluorophenylamino)-4-methylpentanamide (175 mg).

A mixture of (R)-2-(5-bromo-4-cyano-2-fluorophenylamino)-4-methylpentanamide (175 mg, 0.533 mmol), 5-amino-3-methylisothiazole hydrochloride (97 mg, 0.644 mmol), BINAP (50 mg, 0.080 mmol), $Pd(OAc)_2$ (35 mg, 0.156 mmol) and $K_2CO_3$ (250 mg, 1.81 mmol) in dioxane (4 mL) was degassed with Ar, then was stirred at 120 C for 18 h. Water and EtOAc were added. After being filtered, the filtrate was washed with water, dried over $Na_2SO_4$, concentrated in vacuo to give (R)-2-(4-cyano-2-fluoro-5-(3-methylisothiazol-5-ylamino)phenylamino)-4-methylpentanamide as a crude residue.

To a solution of the crude residue in EtOH (2 mL) and DMSO (0.5 mL), 1N aq. NaOH (0.5 mL) and $H_2O_2$ (50% aq., 0.5 mL) were added. After being stirred at room temperature for 1 h, the mixture was concentrated in vacuo. The residue was acidified with HOAc (0.5 mL), and then was purified by HPLC to give the titled compound (26 mg). MS 380.3 (M+H); UV 219.3, 278.0, 302.6 nm

Example 21

4-((1R,2S)-2-aminocyclohexylamino)-5-fluoro-2-(3-methylisothiazol-5-ylamino)benzamide

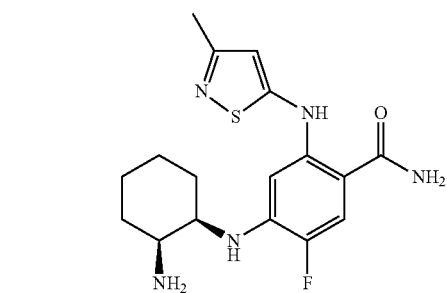

Scheme 20

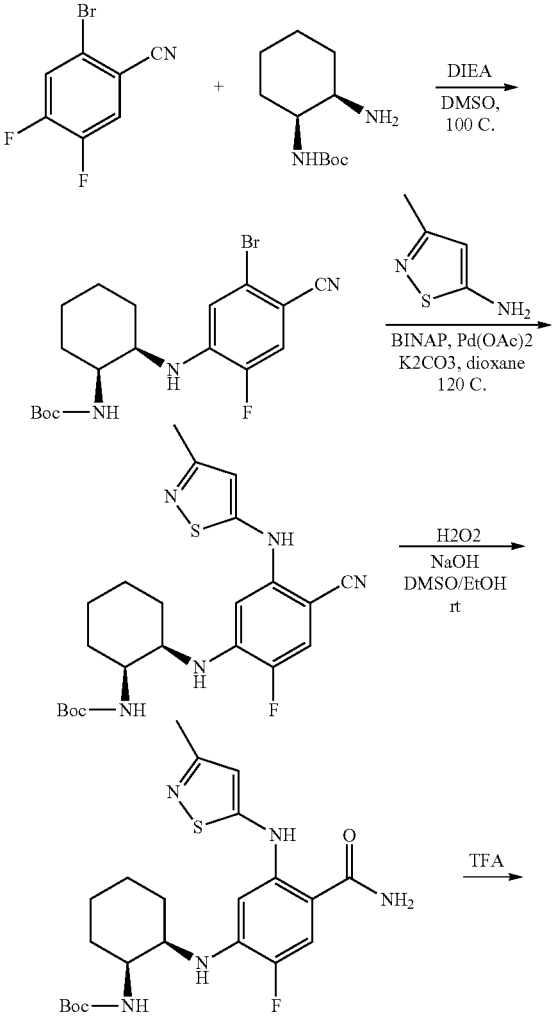

-continued

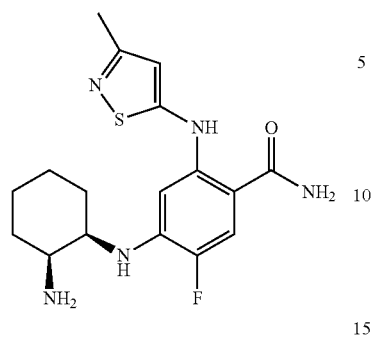

A solution of 2-bromo-4,5-difluorobenzonitrile (218 mg, 1.00 mmol), tert-butyl (1S,2R)-2-aminocyclohexylcarbamate (214 mg, 1.00 mmol) and DIEA (0.300 mL, 1.72 mmol) in DMSO (2 mL) was stirred at 100 C for 18 h. Water was added to induce precipitation. The precipitate was collected and dried on vacuum to give tert-butyl (1S,2R)-2-(5-bromo-4-cyano-2-fluorophenylamino)cyclohexylcarbamate as a solid (385 mg).

A mixture of tert-butyl (1S,2R)-2-(5-bromo-4-cyano-2-fluorophenylamino)cyclohexylcarbamate (220 mg, 0.534 mmol), 5-amino-3-methylisothiazole hydrochloride (97 mg, 0.644 mmol), BINAP (50 mg, 0.080 mmol), Pd(OAc)$_2$ (35 mg, 0.156 mmol) and K$_2$CO$_3$ (250 mg, 1.81 mmol) in dioxane (4 mL) was degassed with Ar, then was stirred at 120 C for 18 h. After the mixture was filtered, the filtrate was concentrated in vacuo. To a solution of the residue in EtOH (2 mL) and DMSO (0.5 mL), 1N aq. NaOH (0.5 mL) and H$_2$O$_2$ (50% aq., 0.5 mL) were added. After being stirred at room temperature for 3 h, water and EtOAc were added. The organic phase was separated, dried over Na$_2$SO$_4$, concentrated in vacuo. The residue was dissolved in TFA (5 mL). After 30 min of standing, TFA was removed in vacuo. The residue was purified by HPLC to give the titled compound (144 mg). MS 364.4 (M+H); UV 204.7, 292.8 nm Example 22

(R)-4-(2-amino-1-cyclohexyl-2-oxoethylamino)-2-(3-methylisothiazol-5-ylamino)benzamide

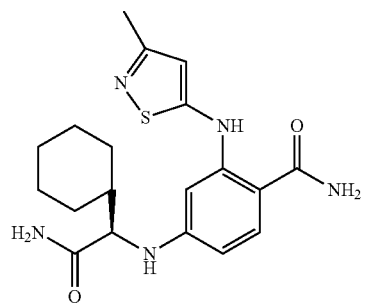 [SMILES: Cc1cc(Nc2cc(N[C@@H](C(N)=O)C3CCCCC3)ccc2C(N)=O)sn1]

The titled compound was synthesized analogously according to the procedures described for (R)-4-(1-amino-3-cyclohexyl-1-oxopropan-2-ylamino)-2-(3-methylisothiazol-5-ylamino)benzamide in Example 17. MS 388.4 (M+H); UV 202.2, 300.2 nm Example 23

(R)-4-(1-amino-4-methyl-1-oxopentan-2-ylamino)-3-fluoro-2-(3-methylisothiazol-5-ylamino)benzamide

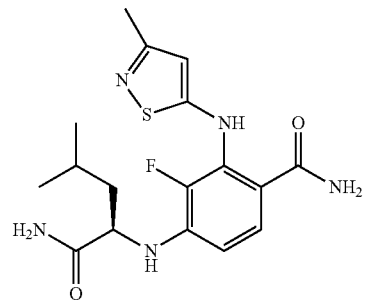 [SMILES: Cc1cc(Nc2c(C(N)=O)ccc(N[C@H](CC(C)C)C(N)=O)c2F)sn1]

Scheme 21

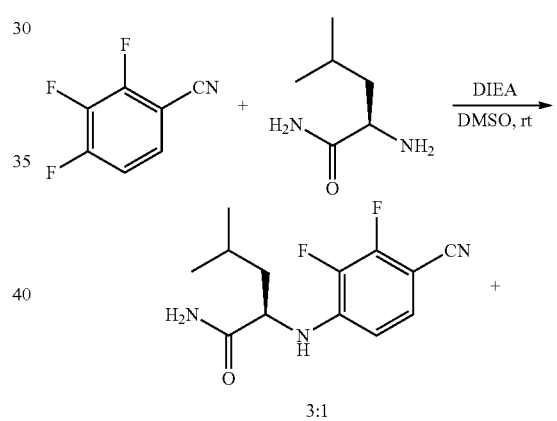

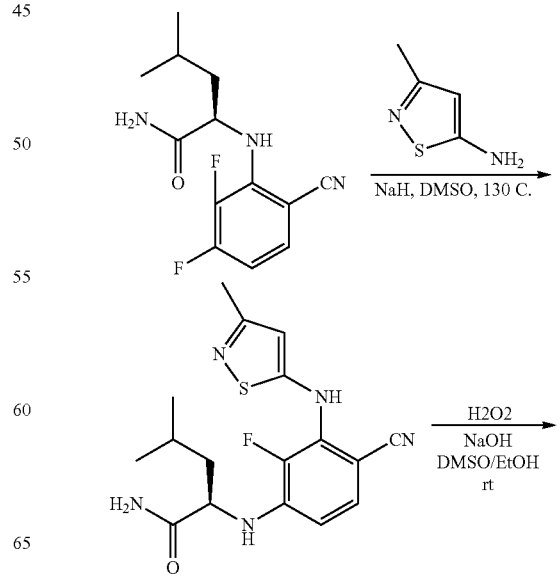

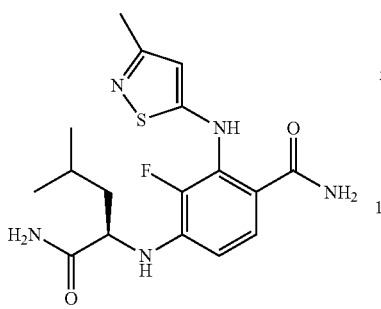

To 2,3,4-trifluorobenzonitrile (265 mg, 1.68 mmol) in a flask, a solution of D-leucine amide hydrochloride (282 mg, 1.68 mmol) and DIEA (0.880 mL, 5.06 mmol) in DMSO (5 mL) was added. After being stirred at room temperature for 68 h, water and EtOAc were added. The organic phase was separated, washed with water, dried over $Na_2SO_4$, concentrated in vacuo. The residue was purified by a silica gel column, eluted with 0-70% EtOAc in hexane to give (R)-2-(4-cyano-2,3-difluorophenylamino)-4-methylpentanamide (113 mg).

To a solution of (R)-2-(4-cyano-2,3-difluorophenylamino)-4-methylpentanamide (113 mg, 0.423 mmol) and 5-amino-3-methylisothiazole hydrochloride (70 mg, 0.464 mmol) in DMSO (3 mL), NaH (60% in mineral oil, 100 mg, 2.50 mmol) was added. $H_2$ gas evolved. The mixture was stirred at 130 C for 30 min. Water and EtOAc were added. The organic phase was separated, dried over $Na_2SO_4$, concentrated in vacuo. To a solution of the residue in EtOH (2 mL) and DMSO (0.5 mL), 1N aq. NaOH (0.5 mL) and $H_2O_2$ (50% aq., 0.5 mL) were added. After being stirred at room temperature for 30 min, the mixture was concentrated in vacuo. The residue was acidified with HOAc (0.5 mL), and then was purified by HPLC to give the titled compound (36 mg). MS 380.4 (M+H); UV 202.2, 280.5 nm Example 24

(R)-4-(1-amino-1-oxo-3-phenylpropan-2-ylamino)-5-fluoro-2-(3-methylisothiazol-5-ylamino)benzamide

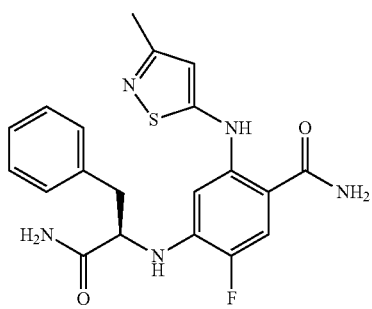

Scheme 22

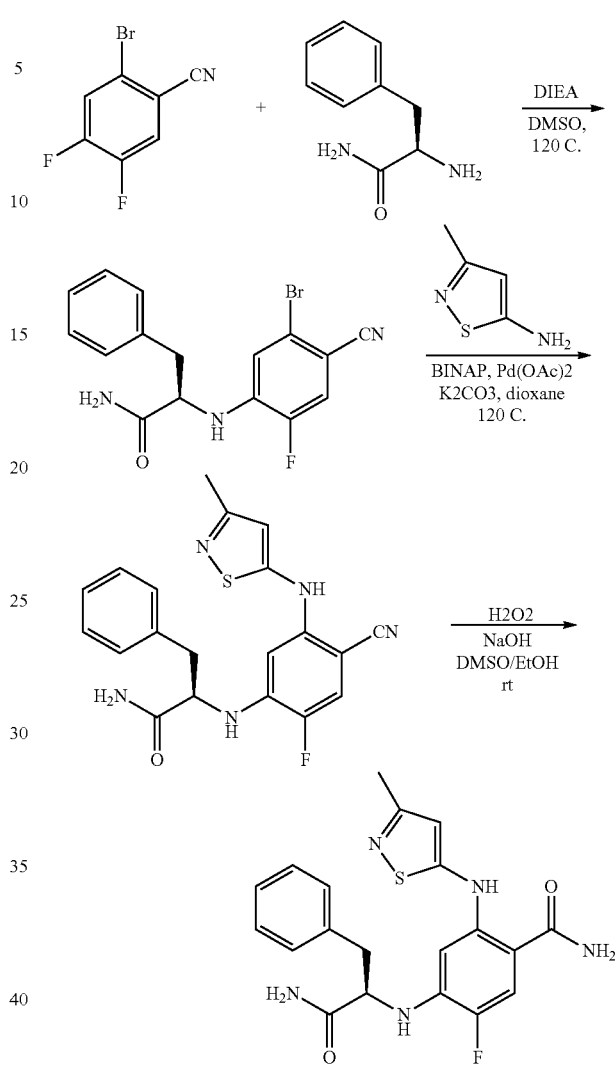

A solution of 2-bromo-4,5-difluorobenzonitrile (218 mg, 1.00 mmol), D-phenylalanine amide (185 mg, 1.12 mmol) and DIEA (0.600 mL, 3.45 mmol) in DMSO (3 mL) was stirred at 120 C for 18 h. Water and EtOAc were added. The organic phase was separated, washed with water, dried over $Na_2SO_4$, concentrated in vacuo to give (R)-2-(5-bromo-4-cyano-2-fluorophenylamino)-3-phenylpropanamide (362 mg).

A mixture of (R)-2-(5-bromo-4-cyano-2-fluorophenylamino)-3-phenylpropanamide (362 mg, 1.00 mmol), 5-amino-3-methylisothiazole hydrochloride (166 mg, 1.10 mmol), BINAP (70 mg, 0.112 mmol), Pd(OAc)$_2$ (35 mg, 0.156 mmol) and $K_2CO_3$ (430 mg, 3.11 mmol) in dioxane (5 mL) was degassed with Ar, then was stirred at 120 C for 18 h. More Pd(OAc)$_2$ (35 mg, 0.156 mmol) was added. The mixture was stirred at 120 C for another 18 h. Water and EtOAc were added. After being filtered, the filtrate was washed with water, dried over $Na_2SO_4$, concentrated in vacuo to give (R)-2-(4-cyano-2-fluoro-5-(3-methylisothiazol-5-ylamino)phenylamino)-3-phenylpropanamide as a crude residue.

To a solution of the crude residue in EtOH (4 mL) and DMSO (1 mL), 1N aq. NaOH (1.0 mL) and $H_2O_2$ (50% aq., 1.0 mL) were added. After being stirred at room temperature for 1 h, the mixture was concentrated in vacuo. The residue was acidified with HOAc (0.5 mL), and then was purified by HPLC to give the titled compound (39 mg). MS 414.3 (M+H); UV 201.5, 293.3 nm

Example 25

(R)-4-(1-amino-3-cyclopropyl-1-oxopropan-2-ylamino)-5-fluoro-2-(3-methylisothiazol-5-ylamino)benzamide

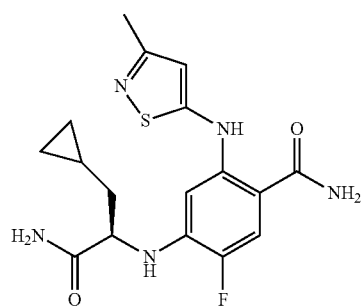 [SMILES: Cc1cc(Nc2cc(N[C@H](CC3CC3)C(N)=O)c(F)cc2C(N)=O)sn1]

Scheme 23

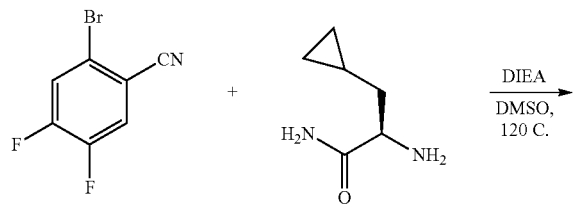

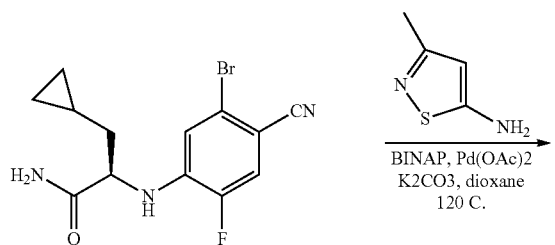

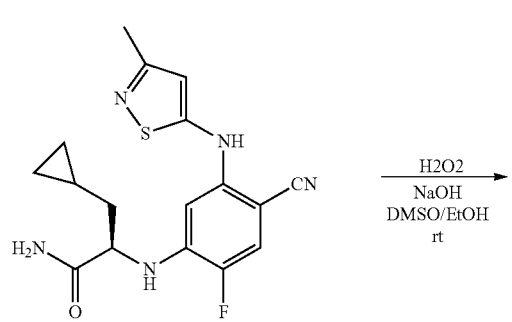

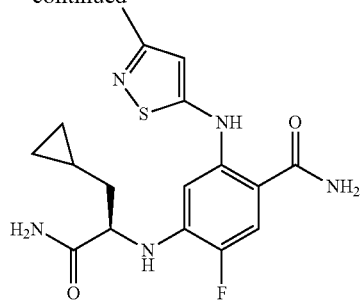

A solution of 2-bromo-4,5-difluorobenzonitrile (218 mg, 1.00 mmol), (R)-2-amino-3-cyclopropylpropanamide (188 mg, 1.14 mmol) and DIEA (0.600 mL, 3.45 mmol) in DMSO (3 mL) was stirred at 120 C for 18 h. Water and EtOAc were added. The organic phase was separated, washed with water, dried over Na$_2$SO$_4$, concentrated in vacuo to give (R)-2-(5-bromo-4-cyano-2-fluorophenylamino)-3-cyclopropylpropanamide (326 mg).

A mixture of (R)-2-(5-bromo-4-cyano-2-fluorophenylamino)-3-phenylpropanamide (362 mg, 1.00 mmol), 5-amino-3-methylisothiazole hydrochloride (166 mg, 1.10 mmol), BINAP (70 mg, 0.112 mmol), Pd(OAc)$_2$ (35 mg, 0.156 mmol) and K$_2$CO$_3$ (430 mg, 3.11 mmol) in dioxane (5 mL) was degassed with Ar, then was stirred at 120 C for 18 h. More Pd(OAc)$_2$ (35 mg, 0.156 mmol) was added. The mixture was stirred at 120 C for another 18 h. Water and EtOAc were added. After being filtered, the filtrate was washed with water, dried over Na$_2$SO$_4$, concentrated in vacuo to give (R)-2-(4-cyano-2-fluoro-5-(3-methylisothiazol-5-ylamino)phenylamino)-3-cyclopropylpropanamide as a crude residue.

To a solution of the crude residue in EtOH (4 mL) and DMSO (1 mL), 1N aq. NaOH (1.0 mL) and H$_2$O$_2$ (50% aq., 1.0 mL) were added. After being stirred at room temperature for 1 h, the mixture was concentrated in vacuo. The residue was acidified with HOAc (0.5 mL), and then was purified by HPLC to give the titled compound (54 mg). MS 378.3 (M+H); UV 200.0, 292.7 nm

Example 26

(R)-4-(1-amino-1-oxobutan-2-ylamino)-5-fluoro-2-(3-methylisothiazol-5-ylamino)benzamide

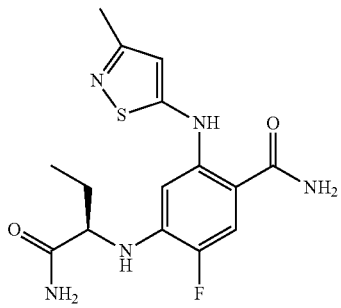 [SMILES: CC[C@@H](Nc1cc(Nc2cc(C)ns2)c(C(N)=O)cc1F)C(N)=O]

The titled compound was synthesized analogously according to the procedures described for (R)-4-(1-amino-3-cyclopropyl-1-oxopropan-2-ylamino)-5-fluoro-2-(3-methyl-isothiazol-5-ylamino)benzamide in Example 25. MS 352.4 (M+H); UV 207.1, 292.8 nm Example 27

(R)-4-(1-amino-3-(4-fluorophenyl)-1-oxopropan-2-ylamino)-5-fluoro-2-(3-methylisothiazol-5-ylamino)benzamide

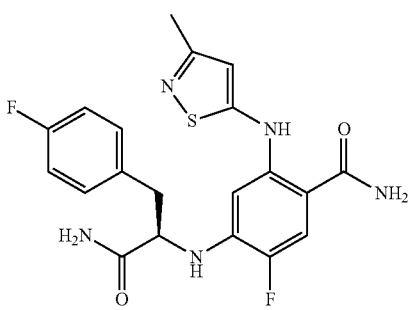 [SMILES: Cc1cc(Nc2cc(N[C@H](Cc3ccc(F)cc3)C(N)=O)c(F)cc2C(N)=O)sn1]

The titled compound was synthesized analogously according to the procedures described for (R)-4-(1-amino-1-oxo-3-phenylpropan-2-ylamino)-5-fluoro-2-(3-methylisothiazol-5-ylamino)benzamide in Example 24. MS 432.2 (M+H); UV 207.1, 295.2 nm Example 28

(R)-4-(1-amino-3-(4-hydroxyphenyl)-1-oxopropan-2-ylamino)-5-fluoro-2-(3-methylisothiazol-5-ylamino)benzamide

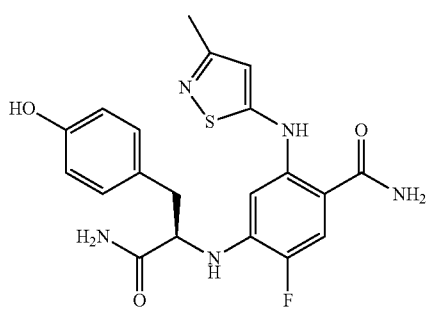 [SMILES: Cc1cc(Nc2cc(N[C@H](Cc3ccc(O)cc3)C(N)=O)c(F)cc2C(N)=O)sn1]

The titled compound was synthesized analogously according to the procedures described for (R)-4-(1-amino-1-oxo-3-phenylpropan-2-ylamino)-5-fluoro-2-(3-methylisothiazol-5-ylamino)benzamide in Example 24. MS 430.3 (M+H); UV 224.1, 280.5, 302.6 nm Example 29

(R)-4-(2-amino-3-methoxypropylamino)-2-(3-methylisothiazol-5-ylamino)benzamide

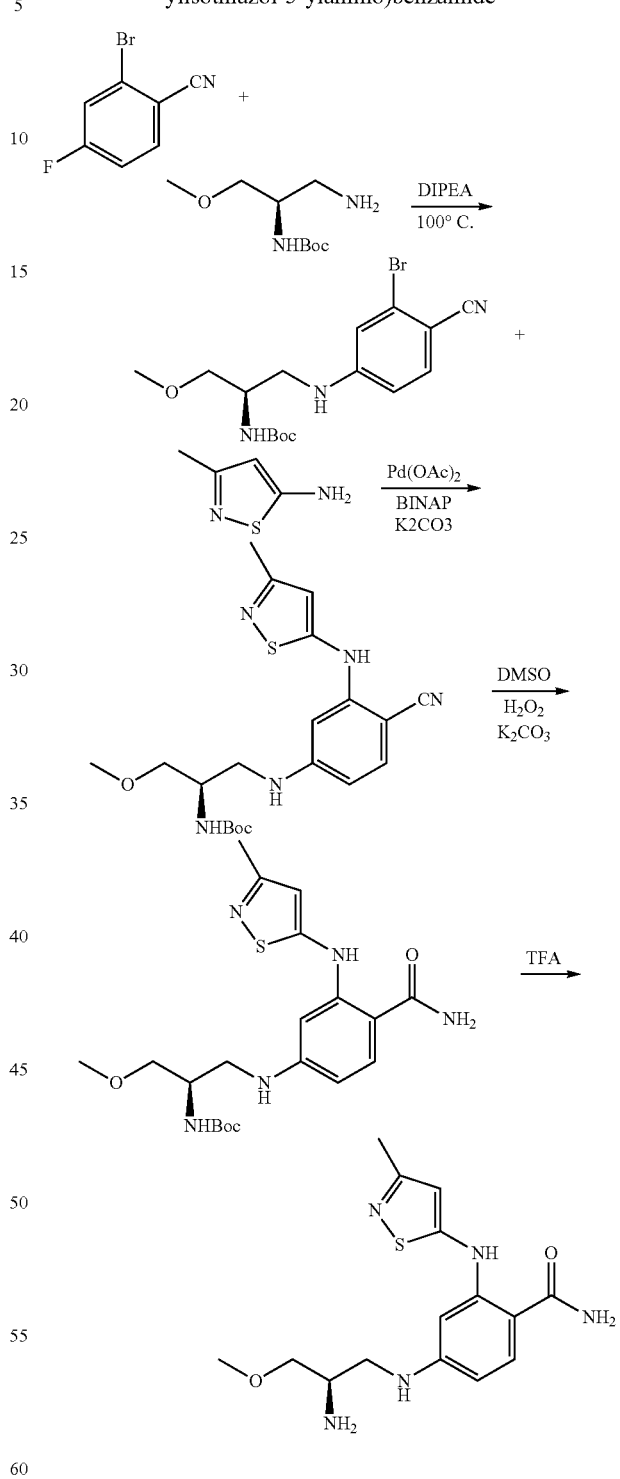

Step 1: To a solution of 2-bromo-4-fluorobenzonitrile (0.2 g, 1 mmol) in DMSO (3 mL) was added (R)-tert-butyl 1-amino-3-methoxypropan-2-ylcarbamate (0.22 g, 1.08 mmol) and DIPEA (0.267 mL, 1.5 mmol). The mixture was heated at 100° C. for 15 h, and was diluted with EtOAc and washed with 1N HCl and Sat. NaHCO₃. The organic phase was separated, dried over Na₂SO₄, concentrated in vacuo to give (R)-tert-butyl 1-(3-bromo-4-cyanophenylamino)-3-methoxypropan-2-ylcarbamate (0.3 g).

Step 2: A mixture of (R)-tert-butyl 1-(3-bromo-4-cyanophenylamino)-3-methoxypropan-2-ylcarbamate (150 mg, 0.39 mmol), 5-amino-3-methylisothiazole hydrochloride (76 mg, 0.51 mmol), BINAP (25 mg, 0.04 mmol), Pd(OAc)$_2$ (18 mg, 0.08 mmol) and K$_2$CO$_3$ (188 mg, 1.37 mmol) p-dioxane (3 mL) was degassed with Ar, then was heated at 120° C. for 15 h. the mixture was filtered, filter cake was washed with EtOAc, and the filtrated was concentrated in vacuo to give (R)-tert-butyl 1-(4-cyano-3-(3-methylisothiazol-5-ylamino)phenylamino)-3-methoxypropan-2-ylcarbamate as crude oil.

Step 3: The above mentioned crude oil from step 2 was dissolved in DMSO (2 mL), K$_2$CO$_3$ (500 mg, 3.6 mmol) was added; then H$_2$O$_2$ (50% aq., 2 mL) was added dropwise (gas evolved). The mixture was stirred at 80° C. for 15 min, cooled and was diluted with water, the resulting precipitate was collected by filtration, dried in vacuo to give (R)-tert-butyl 1-(4-carbamoyl-3-(3-methylisothiazol-5-ylamino)phenylamino)-3-methoxypropan-2-ylcarbamate as solid.

Step 4: The above product from step 3 was added TFA in DCM (1:1, 2 mL), 30 min later, the solution was concentrated under vacuum and was purified by preparative HPLC to give (R)-4-(2-amino-3-methoxypropylamino)-2-(3-methylisothiazol-5-ylamino)benzamide as TFA salt. MS 336.2 (M+H); UV 293.8 nm.

Example 30

(S)-4-(2-aminobutylamino)-2-(3-methylisothiazol-5-ylamino)benzamide

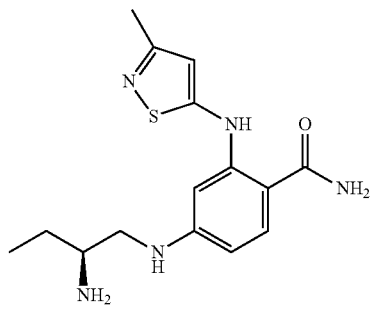 [SMILES: CC[C@H](N)CNc1ccc(C(N)=O)c(Nc2cc(C)ns2)c1]

The title compound was prepared similar to Example 29 using (S)-tert-butyl 1-aminobutan-2-ylcarbamate to replace (R)-tert-butyl 1-amino-3-methoxypropan-2-ylcarbamate. MS 320.2 (M+H); UV 293.9 nm.

Example 31

(S)-4-(2-aminopropylamino)-2-(3-methylisothiazol-5-ylamino)benzamide

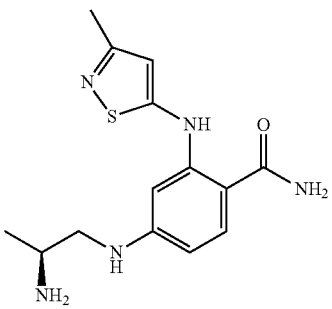 [SMILES: Cc1cc(Nc2cc(NC[C@H](C)N)ccc2C(N)=O)sn1]

The title compound was prepared similar to Example 29 using (S)-tert-butyl 1-aminopropan-2-ylcarbamate to replace (R)-tert-butyl 1-amino-3-methoxypropan-2-ylcarbamate. MS 306.2 (M+H); UV 294.9 nm.

Example 32

(S)-4-(2-amino-4-methylpentylamino)-2-(3-methylisothiazol-5-ylamino)benzamide

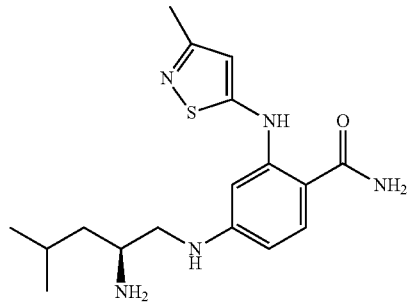 [SMILES: Cc1cc(Nc2cc(NC[C@@H](N)CC(C)C)ccc2C(N)=O)sn1]

The title compound was prepared similar to Example 29 using (S)-tert-butyl 1-amino-4-methylpentan-2-ylcarbamate to replace (R)-tert-butyl 1-amino-3-methoxypropan-2-ylcarbamate. MS 348.2 (M+H); UV 284.2 nm.

Example 33

(R)-4-(1-amino-1-oxobutan-2-ylamino)-2-(3-methylisothiazol-5-ylamino)benzamide

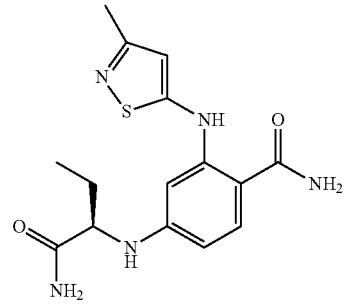 [SMILES: CC[C@@H](Nc1ccc(C(N)=O)c(Nc2cc(C)ns2)c1)C(N)=O]

The title compound was prepared similar to Example 9 using (R)-2-aminobutanamide hydrochloride salt to replace D-leucinamide hydrochloride salt. MS 334.1 (M+H); UV 295.7 nm.

Example 34

(R)-4-(1-amino-1-oxobutan-2-ylamino)-2-(3-methylisothiazol-5-ylamino)benzamide

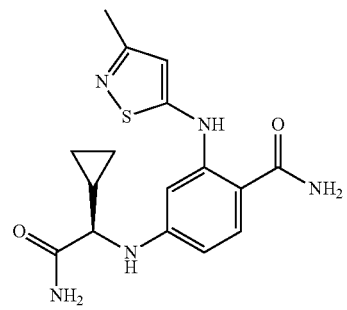 [SMILES: Cc1cc(Nc2cc(N[C@@H](C(N)=O)C3CC3)ccc2C(N)=O)sn1]

Synthesis of (R)-2-amino-2-cyclopropylacetamide hydrochloride salt

To a solution of (R)-2-(tert-butoxycarbonylamino)-2-cyclopropylacetic acid (430 mg, 2 mmol) in DMF (6 ml) was added EDC (461 mg, 2.4 mmol) and HOBt.H$_2$O (367 mg, 2.4 mmol) at room temperature, 20 min later, it was added ammonia in MeOH (7N, 0.6 mL, 4 mmol) at room temperature. After stirring for 30 min, it was diluted with water and EtOAc, organic layer was separated and washed with Sat. NaHCO$_3$, brine, dried and concentrated to give (R)-tert-butyl-2-amino-1-cyclopropyl-2-oxoethylcarbamate (330 mg) as crude oil, which was treated with 4N HCl in Dioxane (2 mL). 30 min later, it was concentrated to give (R)-2-amino-2-cyclopropylacetamide hydrochloride salt.

The title compound was prepared similar to Example 9 using (R)-2-amino-2-cyclopropylacetamide hydrochloride salt to replace D-leucinamide hydrochloride salt. MS 346.2 (M+H); UV 295.7 nm.

Example 35

(R)-4-(1-amino-3-cyclopropyl-1-oxopropan-2-ylamino)-2-(3-methylisothiazol-5-ylamino)benzamide

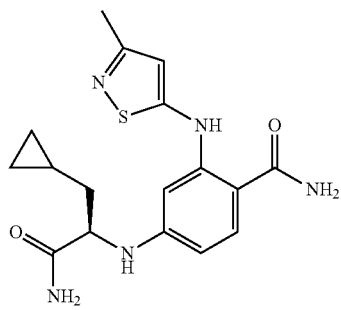 [SMILES: Cc1cc(Nc2cc(N[C@H](CC3CC3)C(N)=O)ccc2C(N)=O)sn1]

Synthesis of (R)-2-amino-3-cyclopropylpropanamide hydrochloride salt

To a solution of (R)-2-amino-3-cyclopropylpropanoic acid (1.0 g, 7.7.4 mmol) in Ethanol (15 mL) and water (8 mL) was added 1N NaOH (10 mL) and Di-tert-butyl carbonate (1.86 g, 8.52 mmol) in THF (8 mL). After stirring at room temperature for 15 h, the solution was diluted with water, extracted with ether, the aqueous layer was separated and was acidified to pH 2 with conc. HCl, the aqueous layer was extracted with EtOAc, organic layer was separated, washed with brine, dried and concentrated to give (R)-2-(tert-butoxycarbonylamino)-3-cyclopropylpropanoic acid (1.0 g).

To a solution of above mentioned (R)-2-(tert-butoxycarbonylamino)-3-cyclopropylpropanoic acid (1.0 g, 4.36 mmol) in DMF (10 ml) was added EDC (1.0 g, 5.24 mmol) and HOBt.H$_2$O (367 mg, 2.4 mmol) at room temperature, 20 min later, it was added ammonia in (7N, 0.6 mL, 4 mmol) at room temperature. After stirring for 30 min, it was diluted with water and EtOAc, organic layer was separated and washed with Sat. NaHCO$_3$, brine, dried and concentrated to give (R)-tert-butyl-1-amino-3-cyclopropyl-1-oxopropan-2-ylcarbamate (750 mg) as crude oil, which was treated with 4N HCl in Dioxane (5 mL). 30 min later, it was concentrated to give (R)-2-amino-2-cyclopropylacetamide hydrochloride salt.

The title compound was prepared similar to Example 9 using (R)-2-amino-3-cyclopropylpropanamide hydrochloride salt to replace D-leucinamide hydrochloride salt. MS 360.2 (M+H); UV 291.4 nm.

Example 36

(R)-4-(1-amino-3-(4-methoxyphenyl)-1-oxopropan-2-ylamino)-5-fluoro-2-(3-methylisothiazol-5-ylamino)benzamide

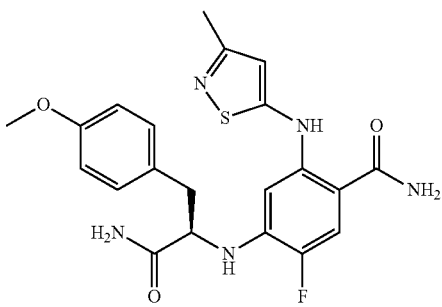 [SMILES: COc1ccc(C[C@@H](Nc2cc(Nc3cc(C)ns3)c(C(N)=O)cc2F)C(N)=O)cc1]

The titled compound is synthesized analogously according to the procedures described for (R)-4-(1-amino-1-oxo-3-phenylpropan-2-ylamino)-5-fluoro-2-(3-methylisothiazol-5-ylamino)benzamide in Example 24. M+H found: 444.2. UV: 224.1, 295.2 nm.

Example 37

(R)-4-(1-amino-3-(3-fluorophenyl)-1-oxopropan-2-ylamino)-5-fluoro-2-(3-methylisothiazol-5-ylamino)benzamide

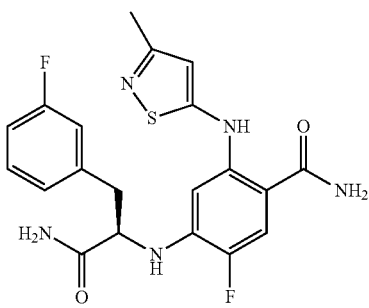

The titled compound is synthesized analogously according to the procedures described for (R)-4-(1-amino-1-oxo-3-phenylpropan-2-ylamino)-5-fluoro-2-(3-methylisothiazol-5-ylamino)benzamide in Example 24. M+H found: 232.2. UV: 212.0, 297.7 nm.

Example 38

(R)-4-(1-amino-1-oxo-3-(pyridin-4-yl)propan-2-ylamino)-5-fluoro-2-(3-methylisothiazol-5-ylamino)benzamide

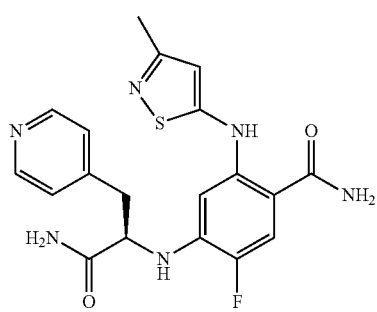 [SMILES: Cc1cc(Nc2cc(N[C@H](Cc3ccncc3)C(N)=O)c(F)cc2C(N)=O)sn1]

The titled compound is synthesized analogously according to the procedures described for (R)-4-(1-amino-1-oxo-3-phenylpropan-2-ylamino)-5-fluoro-2-(3-methylisothiazol-5-ylamino)benzamide in Example 24. M+H found: 415.1. UV: 216.8, 253.5, 295.2 nm.

Example 39

(R)-4-(1-amino-1-oxo-3-(pyridin-3-yl)propan-2-ylamino)-5-fluoro-2-(3-methylisothiazol-5-ylamino)benzamide

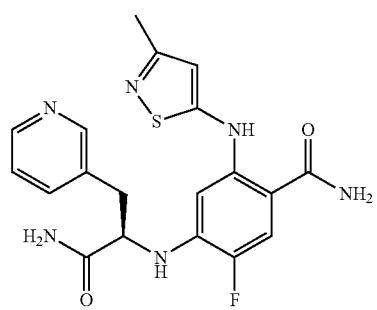 [SMILES: Cc1cc(Nc2cc(N[C@H](Cc3cccnc3)C(N)=O)c(F)cc2C(N)=O)sn1]

The titled compound is synthesized analogously according to the procedures described for (R)-4-(1-amino-1-oxo-3-phenylpropan-2-ylamino)-5-fluoro-2-(3-methylisothiazol-5-ylamino)benzamide in Example 24. M+H found: 415.1. UV: 216.8, 278.0, 302.6 nm.

Example 40

(R)-4-(1-amino-3-methoxy-1-oxopropan-2-ylamino)-5-fluoro-2-(3-methylisothiazol-5-ylamino)benzamide

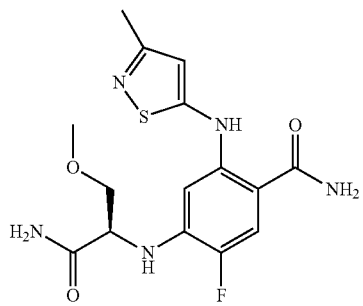 [SMILES: COC[C@@H](Nc1cc(Nc2cc(C)ns2)c(C(N)=O)cc1F)C(N)=O]

Scheme 24

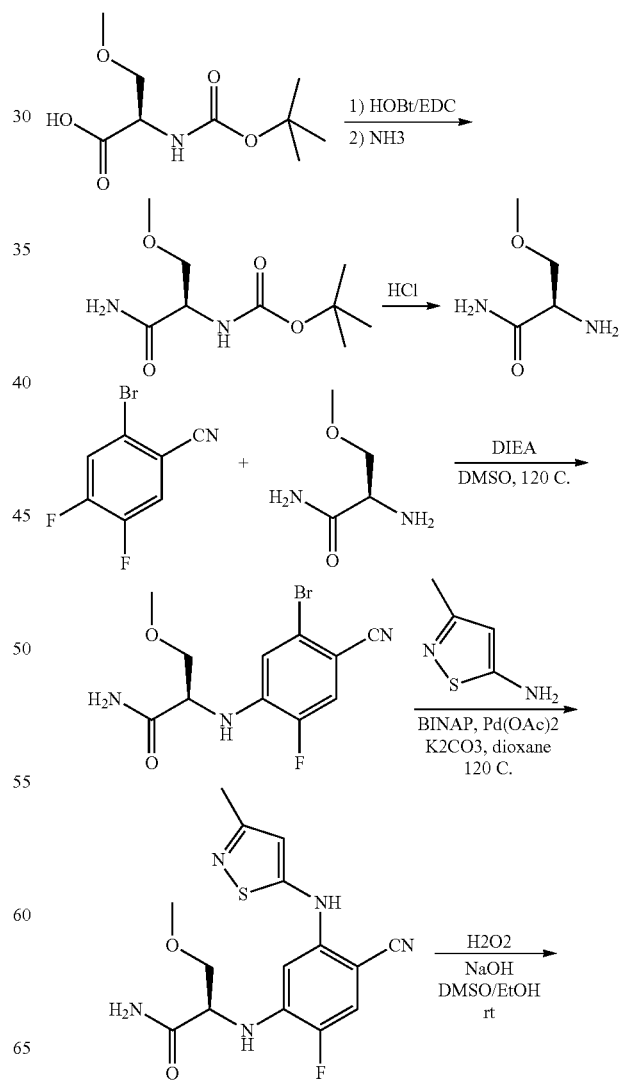

-continued

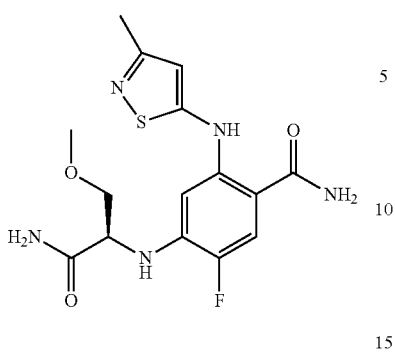

A solution of N-Boc-O-methyl-D-serine (438 mg, 2.00 mmol), HOBt monohydrate (364 mg, 2.38 mmol) and EDC (460 mg, 2.39 mmol) in DMF (9 mL) was stirred at room temperature for 2 h, conc. NH₄OH (0.700 mL, ca. 9.80 mmol) was added. The mixture was stirred for 18 h. Water and EtOAc were added. The organic phase was washed with 5% NaHCO₃, dried over Na₂SO₄, concentrated in vacuo to give (R)-tert-butyl 1-amino-3-methoxy-1-oxopropan-2-ylcarbamate (100 mg). The aqueous phase was further extracted with nBuOH (30 mL). The nBuOH solution was washed with 5% NaHCO₃, then was concentrated in vacuo to give another portion of (R)-tert-butyl 1-amino-3-methoxy-1-oxopropan-2-ylcarbamate (242 mg).

A solution of (R)-tert-butyl 1-amino-3-methoxy-1-oxopropan-2-ylcarbamate (342 mg, 1.57 mmol) in 4N HCl in dioxane (5 mL) was stirred at room temperature for 18 h. It was then concentrated in vacuo to give (R)-2-amino-3-methoxypropanamide hydrochloride (260 mg).

A solution of 2-bromo-4,5-difluorobenzonitrile (168 mg, 0.770 mmol), (R)-2-amino-3-methoxypropanamide hydrochloride (120 mg, 0.776 mmol) and DIEA (0.500 mL, 2.87 mmol) in DMSO (3 mL) was stirred at 120 C for 18 h. Water and EtOAc were added. The organic phase was separated, dried over Na₂SO₄, concentrated in vacuo. The residue was purified by a silica gel column, which was eluted with 0-70% EtOAc in hexane to give (R)-2-(5-bromo-4-cyano-2-fluorophenylamino)-3-methoxypropanamide (52 mg).

A mixture of (R)-2-(5-bromo-4-cyano-2-fluorophenylamino)-3-methoxypropanamide (52 mg, 0.164 mmol), 5-amino-3-methylisothiazole hydrochloride (40 mg, 0.265 mmol), K₂CO₃ (110 mg, 0.797 mmol), BINAP (30 mg, 0.048 mmol) and Pd(OAc)₂ (25 mg, 0.111 mmol) in dioxane (2 mL) was degassed with argon, then was stirred at 120 C for 18 h. The mixture was concentrated in vacuo. The residue was purified by HPLC to give (R)-2-(4-cyano-2-fluoro-5-(3-methylisothiazol-5-ylamino)phenylamino)-3-methoxypropanamide (16 mg).

To a solution of (R)-2-(4-cyano-2-fluoro-5-(3-methylisothiazol-5-ylamino)phenylamino)-3-methoxypropanamide (10 mg, 0.028 mmol) in EtOH (1 mL) and DMSO (0.5 mL), aq. 1N NaOH (0.5 mL, 0.50 mmol) and aq. H₂O₂ (50%, 0.5 mL) were added. The mixture was stirred at room temperature for 20 min. HOAc (0.5 mL) was added. The mixture was purified by HPLC to give the titled compound (9 mg). MS 368.2 (M+H); UV 219.3, 282.9, 302.6 nm.

Example 41

Preparation of 2-(3-(2H-1,2,3-triazol-2-yephenylamino)-6-(1R,2S)-2-aminocyclohexylamino)-5-fluoronicotinamide

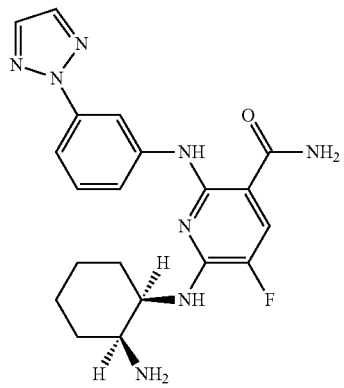 [SMILES: NC(=O)c1cc(F)c(N[C@@H]2CCCC[C@@H]2N)nc1Nc1cccc(-n2nccn2)c1]

Scheme 25:

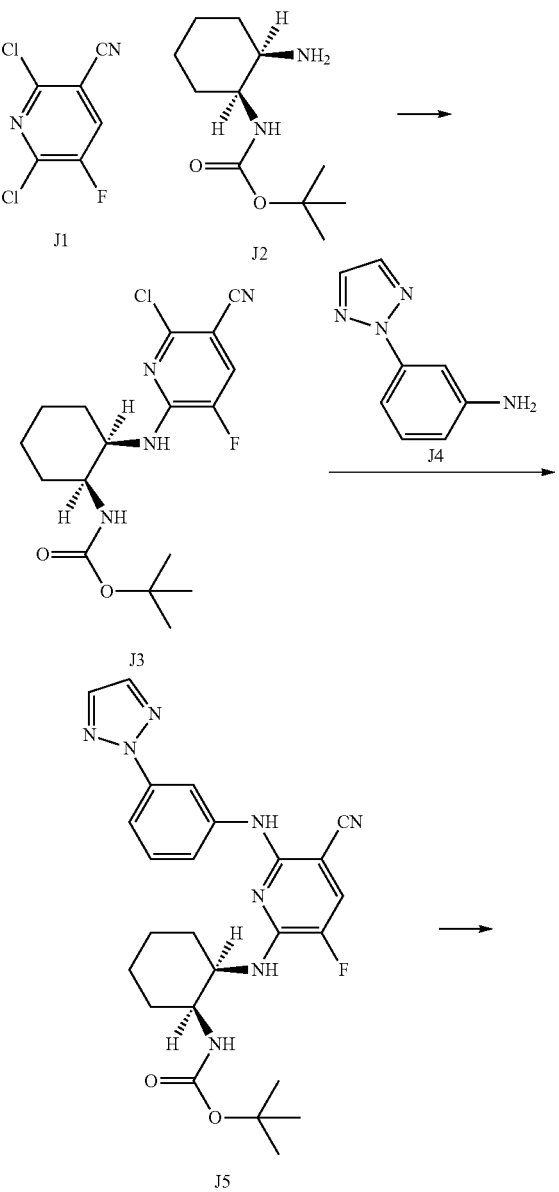

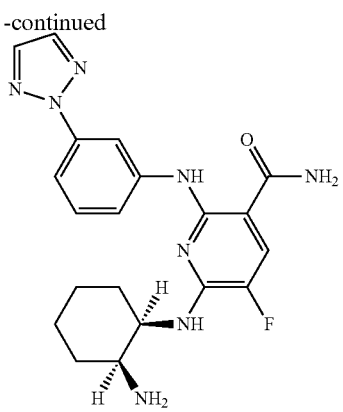

Step 1: 2,6-Dichloro-5-fluoro-3-pyridinecarbonitrile (J1, Aldrich 422169, 2.00 g, 10.5 mmol) was dissolved in 50 mL NMP in a 500 mL flask and stirred at RT. To it was added compound J2 (tert-butyl (1S,2R)-2-aminocyclohexylcarbamate, 2.69 g, 12.5 mmol) in waxy solid form in multiple portions. Then DIEA (3.65 mL, 21.0 mmol) was added a few minutes later. The mixture was heated to 80° C. gradually and stirred at this temperature for 2 hours (very clean reaction; complete by analytical HPLC analysis). The mixture was cooled down to RT. To the flask then was added 400 mL cold water. A light yellow solid (tert-butyl (1S,2R)-2-(6-chloro-5-cyano-3-fluoropyridin-2-ylamino)cyclohexylcarbamate, compound J3 crashed out. It was isolated using Buchner funnel and washed with cold water multiple times (to wash away NMP completely). The solid was dried in vacuum oven at RT for two overnights. No other purification was necessary. Yield was over 90%.

Step 2: To a clean 500 mL flask were added to following reagents: compound J3 (300 mg, 0.82 mmol), 3-(2H-1,2,3-triazol-2-yl)aniline (compound J4, 261 mg, 1.63 mmol), fine-powder cesium carbonate (802 mg, 2.46 mmol), Q-Phos (1,2,3,4,5-pentaphenyl-1'-(di-tert-butylphosphino)ferrocene) (58 mg, 0.082 mmol; Aldrich #675784) and Pd(dba)$_2$ (bis(dibenzylideneacetone)palladium(0)) (92 mg, 0.16 mmol; Aldrich #227994). To the mixture was then added 30 mL toluene. The resulting slurry was degassed using argon stream gently for 3 min. It was then sent to 110° C. bath with an air-cooled condenser on top and stirred under argon for overnight. The mixture was then cooled to RT and concentrated on rotovap to remove all the solvent. To the residue were added 300 mL EtOAc and 100 mL water. After vigorously stirring for 15-30 min, the organic phase was separated, and the aq phase and the black junks between org and aq phases were all discarded. The EtOAc phase was then washed with brine twice. The organic phase was dried over MgSO$_4$, concentrated and subjected to flash column with 0%-15% EtOAc in DCM to isolate the desired product, compound J5.

Step 3: To the above-prepared compound J5 was added 6 mL TFA at RT. After stirring for 3 min, 1 mL conc. H$_2$SO$_4$ was added. The mixture was then sent to pre-heated 80° C. bath and stirred for 30 min. It was then cooled to RT. To it was added 10 mL water. The mixture was stirred for 10 min, filtered and directly subjected to prep HPLC (running with 3 mM HCl in water as solvent A and neat acetonitrile as solvent B) in two injections to isolate the title compound as HCl salt (lyophilized). Yield: 141 mg, 42% overall yield for Step 2 and Step 3. UV: 268, 306 nm. M+H found for C$_{20}$H$_{23}$FN$_8$O: 411.4. NMR (CD$_3$OD): 8.86 (1H, t, J=2.4 Hz), 7.96 (2H, s), 7.79 (1H, d, J=12.4 Hz), 7.68 (1H, dm, J=8.0 Hz), 7.41 (1H, t, J=8.4 Hz), 7.16 (1H, dm, J=8.4 Hz), 4.70 (1H, m), 3.81 (1H, m), 1.88-1.51 (8H, m) ppm.

Example 42

Preparation of 2-(3-(1H-1,2,4-triazol-1-yl)phenylamino)-6-((1R,2S)-2-aminocyclohexylamino)-5-fluoronicotinamide

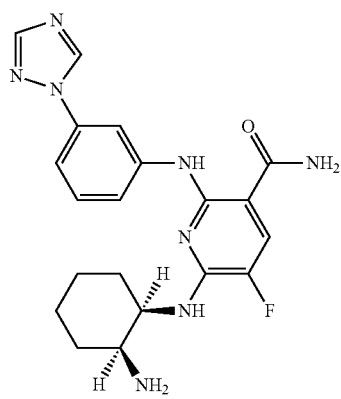 [SMILES: NC(=O)c1cc(F)c(N[C@@H]2CCCC[C@@H]2N)nc1Nc1cccc(-n2cncn2)c1]

The title compound was prepared using the same chemistry shown in Example 41. UV: 237, 307 nm. M+H found for C$_{20}$H$_{23}$FN$_8$O: 411.4. NMR (CD$_3$OD): 9.13 (1H, d, J=1.2 Hz), 8.58 (1H, m), 8.23 (1H, d, J=0.8 Hz), 7.80 (1H, d, J=12.0 Hz), 7.45 (1H, t, J=8.4 Hz), 7.37 (1H, m), 7.27 (1H, m), 4.61 (1H, m), 3.79 (1H, m), 1.85-1.55 (8H, m) ppm.

Example 43

Preparation of 2-(3-(1H-1,2,3-triazol-1-yephenylamino)-6-((1R,2S)-2-aminocyclohexylamino)-5-fluoronicotinamide

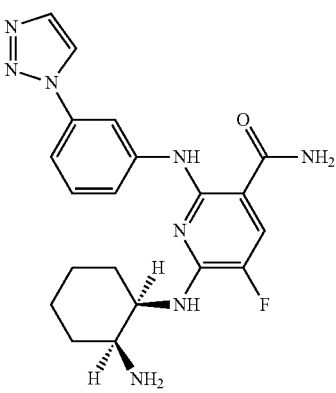

The title compound was prepared using the same chemistry shown in Example 41. UV: 259, 306 nm. M+H found for C$_{20}$H$_{23}$FN$_8$O: 411.4. NMR (CD$_3$OD): 8.88 (1H, m), 8.58 (1H, d, J=1.2 Hz), 7.94 (1H, d, J=1.2 Hz), 7.80 (1H, d, J=12.0

Hz), 7.47 (1H, t, J=8.0 Hz), 7.33 (1H, m), 7.22 (1H, m), 4.71 (1H, m), 3.83 (1H, m), 1.84-1.50 (8H, m) ppm.

Example 44

Preparation of 2-(3-(1H-tetrazol-1-yl)phenylamino)-6-((1R,2S)-2-aminocyclohexylamino)-5-fluoronicotinamide

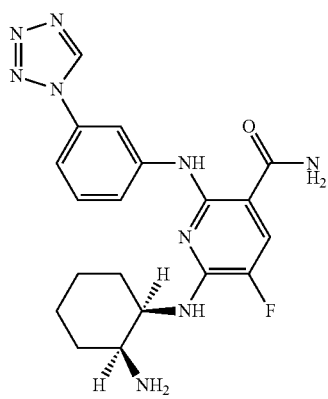 [SMILES: NC(=O)c1cc(F)c(N[C@@H]2CCCC[C@@H]2N)nc1Nc1cccc(-n2cnnn2)c1]

The title compound was prepared using the same chemistry shown in Example 41. UV: 238, 262, 306 nm. M+H found for $C_{19}H_{22}FN_9O$: 412.4. NMR ($CD_3OD$): 9.82 (1H, d, J=1.2 Hz), 8.82 (1H, s), 7.80 (1H, dd, J=12.0; 1.2 Hz), 7.51 (1H, t, J=6.8 Hz), 7.38 (1H, m), 7.32 (1H, m), 4.73 (1H, m), 3.79 (1H, m), 1.86-1.55 (8H, m) ppm.

Example 45

Preparation of 2-(3-(1H-pyrazol-1-yl)phenylamino)-6-((1R,2S)-2-aminocyclohexylamino)-5-fluoronicotinamide

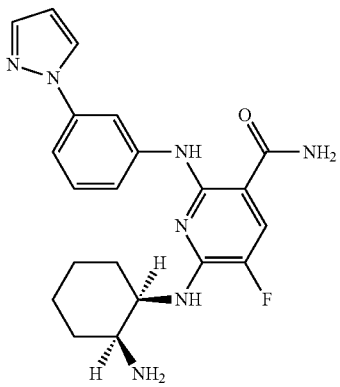 [SMILES: NC(=O)c1cc(F)c(N[C@@H]2CCCC[C@@H]2N)nc1Nc1cccc(-n2cccn2)c1]

The title compound was prepared using the same chemistry shown in Example 41. UV: 262, 306 nm. M+H found for $C_{21}H_{24}FN_7O$: 410.4. NMR ($CD_3OD$): 8.58 (1H, t, J=2.0 Hz), 8.24 (1H, d, J=2.0 Hz), 7.78 (1H, d, J=12.0 Hz), 7.77 (1H, d, J=1.2 Hz), 7.39 (1H, t, J=7.6 Hz), 7.27 (1H, m), 7.13 (1H, m), 6.56 (1H, t, J=2.0 Hz), 4.56 (1H, m), 3.78 (1H, m), 1.81-1.46 (8H, m) ppm.

Example 46

Preparation of 2-(3-(1H-imidazol-1-yl)phenylamino)-6-((1R,2S)-2-aminocyclohexylamino)-5-fluoronicotinamide

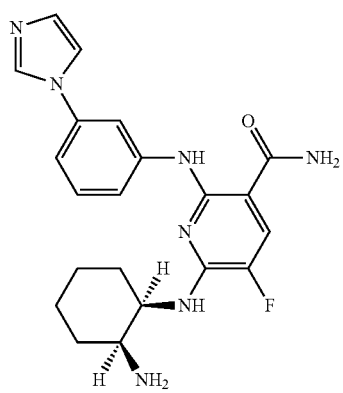

The title compound was prepared using the same chemistry shown in Example 41. UV: 265, 306 nm. M+H found for $C_{21}H_{24}FN_7O$: 410.5. NMR ($CD_3OD$): 9.40 (1H, s), 8.08 (1H, t, J=1.2 Hz), 7.94 (1H, m), 7.88 (1H, t, J=2.0 Hz), 7.81 (1H, d, J=12.0 Hz), 7.76 (1H, t, J=1.6 Hz), 7.56 (1H, t, J=8.0 Hz), 7.27 (1H, m), 4.38 (1H, m), 3.81 (1H, m), 1.87-1.50 (8 h, m) ppm.

Example 47

Preparation of 6-((1R,2S)-2-aminocyclohexylamino)-5-fluoro-2-(3-(pyrrolidin-1-yl)phenylamino)nicotinamide

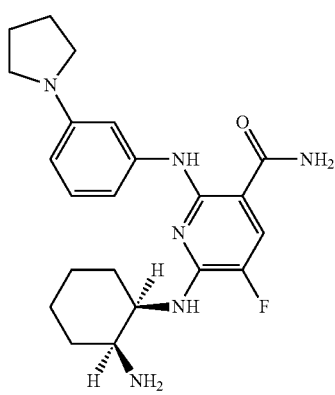 [SMILES: NC(=O)c1cc(F)c(N[C@@H]2CCCC[C@@H]2N)nc1Nc1cccc(N2CCCC2)c1]

The title compound was prepared using the same chemistry shown in Example 41. UV: 265, 307 nm. M+H found for $C_{22}H_{29}FN_6O$: 413.4. NMR ($CD_3OD$): 7.76 (1H, d, J=12.0

Hz), 7.55 (1H, m), 7.32 (1H, m), 7.00 (1H, m), 6.75 (1H, m), 4.41 (1H, m), 3.81 (1H, m), 3.55 (4H, m), 2.18 (4H, m), 1.84-1.61 (8H, m) ppm.

Example 48

Preparation of 6-((1R,2S)-2-aminocyclohexylamino)-5-fluoro-2-(3-morpholinophenylamino)nicotinamide

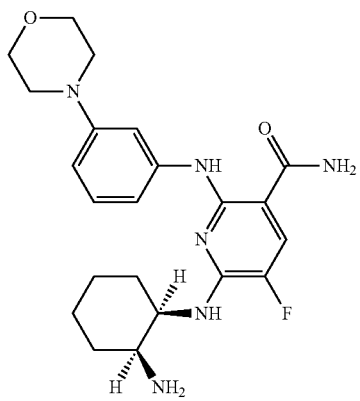 [SMILES: NC(=O)c1cc(F)c(N[C@@H]2CCCC[C@@H]2N)nc1Nc1cccc(N2CCOCC2)c1]

The title compound was prepared using the same chemistry shown in Example 41. UV: 263, 308 nm. M+H found for $C_{22}H_{29}FN_6O_2$: 429.4. NMR (CD$_3$OD): 7.78 (1H, d, J=12.0 Hz), 7.74 (1H, m), 7.40 (1H, m), 7.34 (1H, m), 7.02 (1H, m), 4.45 (1H, m), 4.01 (4H, m), 3.82 (1H, m), 3.48 (4H, m), 1.86-1.61 (8H, m) ppm.

Example 49

Preparation of 2-(4-(2H-1,2,3-triazol-2-ylphenylamino)-6-(1R,2S)-2-aminocyclohexylamino)-5-fluoronicotinamide

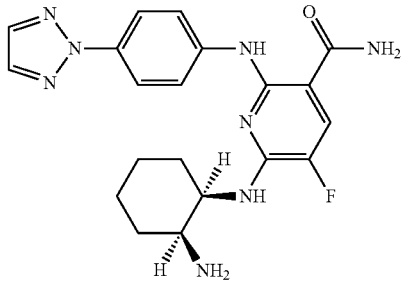 [SMILES: NC(=O)c1cc(F)c(N[C@@H]2CCCC[C@@H]2N)nc1Nc1ccc(-n2nccn2)cc1]

The title compound was prepared using the same chemistry shown in Example 41. UV: 268, 325 nm. M+H found for $C_{20}H_{23}FN_8O$: 411.5. NMR (CD$_3$OD): 7.98 (2H, dt, J=8.8; 2.0 Hz), 7.88 (2H, s), 7.77 (1H, d, J=11.6 Hz), 7.72 (2H, dt, J=8.8; 1.8 Hz), 4.42 (1H, m), 3.93 (1H, m), 1.90-1.64 (8H, m) ppm.

Example 50

Preparation of 2-(4-(1H-1,2,4-triazol-1-yl)phenylamino)-6-(1R,2S)-2-aminocyclohexylamino)-5-fluoronicotinamide

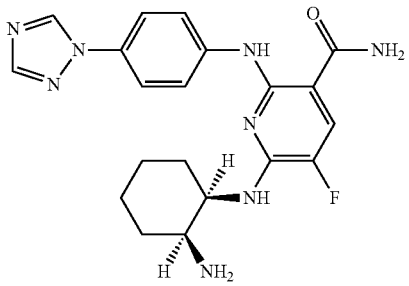 [SMILES: NC(=O)c1cc(F)c(N[C@@H]2CCCC[C@@H]2N)nc1Nc1ccc(-n2cncn2)cc1]

The title compound was prepared using the same chemistry shown in Example 41. UV: 268, 316 nm. M+H found for $C_{20}H_{23}FN_8O$: 411.4. NMR (CD$_3$OD): 9.01 (1H, s), 8.15 (1H, s), 7.78 (1H, d, J=12.0 Hz), 7.77-7.72 (4H, m), 4.42 (1H, m), 3.92 (1H, m), 1.89-1.64 (8H, m) ppm.

Example 51

Preparation of 2-(4-(1H-imidazol-1-yl)phenylamino)-6-((1R,2S)-2-aminocyclohexylamino)-5-fluoronicotinamide

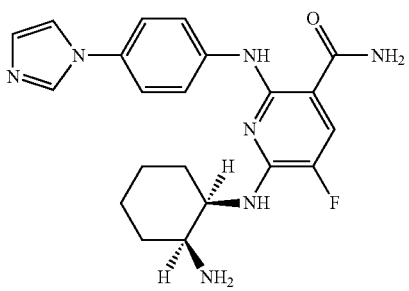 [SMILES: NC(=O)c1cc(F)c(N[C@@H]2CCCC[C@@H]2N)nc1Nc1ccc(-n2ccnc2)cc1]

The title compound was prepared using the same chemistry shown in Example 41. UV: 268, 316 nm. M+H found for $C_{21}H_{24}FN_7O$: 410.4. NMR (CD$_3$OD): 9.27 (1H, s), 7.98 (1H, t, J=1.6 Hz), 7.85 (2H, dt, J=8.8; 2.0 Hz), 7.81 (1H, d, J=12.0 Hz), 7.70 (1H, t, J=2.0 Hz), 7.64 (2H, dt, J=8.8; 2.0 Hz), 4.46 (1H, m), 3.92 (1H, m), 1.94-1.65 (8H, m) ppm.

Example 52

Preparation of 2-(4-(1H-pyrazol-1-yl)phenylamino)-6-((1R,2S)-2-aminocyclohexylamino)-5-fluoronicotinamide

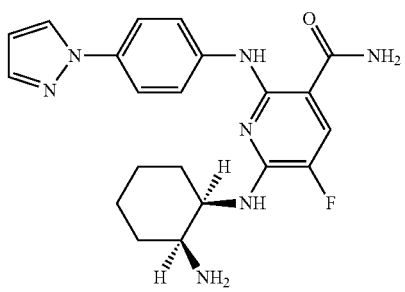 [SMILES: NC(=O)c1cc(F)c(N[C@@H]2CCCC[C@@H]2N)nc1Nc1ccc(-n2cccn2)cc1]

The title compound was prepared using the same chemistry shown in Example 41. UV: 273, 316 nm. M+H found for $C_{21}H_{24}FN_7O$: 410.5. NMR (CD$_3$OD): 8.14 (1H, d, J=2.0 Hz), 7.77 (1H, d, J=12.0 Hz), 7.70-7.64 (5H, m), 6.52 (1H, t, J=2.0 Hz), 4.40 (1H, m), 3.91 (1H, m), 1.89-1.63 (8H, m) ppm.

Example 53

Preparation of 6-((1R,2S)-2-aminocyclohexylamino)-5-fluoro-2-(4-(pyrrolidin-1-yl)phenylamino)nicotinamide

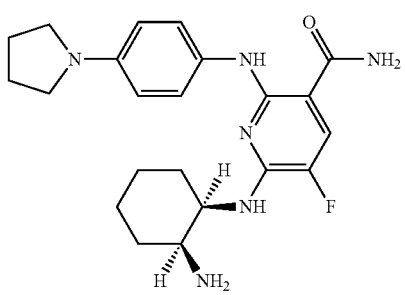 [SMILES: NC(=O)c1cc(F)c(N[C@@H]2CCCC[C@@H]2N)nc1Nc1ccc(N2CCCC2)cc1]

The title compound was prepared using the same chemistry shown in Example 41. UV: 263, 306 nm. M+H found for $C_{22}H_{29}FN_6O$: 413.5. NMR (CD$_3$OD): 7.80-7.30 (5H, m), 4.38 (1H, m), 3.84 (1H, m), 3.69 (4H, m), 2.24 (4H, m), 1.89-1.63 (8H, m) ppm.

Example 54

Preparation of 6-((1R,2S)-2-aminocyclohexylamino)-5-fluoro-2-(4-morpholinophenylamino)nicotinamide

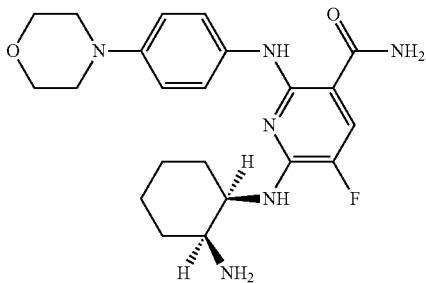 [SMILES: NC(=O)c1cc(F)c(N[C@@H]2CCCC[C@@H]2N)nc1Nc1ccc(N2CCOCC2)cc1]

The title compound was prepared using the same chemistry shown in Example 41. UV: 265, 308 nm. M+H found for $C_{22}H_{29}FN_6O_2$: 429.5. NMR (CD$_3$OD): 7.77 (1H, d, J=12.0 Hz), 7.59 (2H, m), 7.26 (2H, m), 4.33 (1H, m), 3.96 (4H, m), 3.85 (1H, m), 3.35 (4H, m), 1.85-1.63 (8H, m) ppm.

Example 55

Preparation of 6-((1R,2S)-2-aminocyclohexylamino)-5-fluoro-2-(3-(pyrimidin-2-yl)phenylamino)nicotinamide

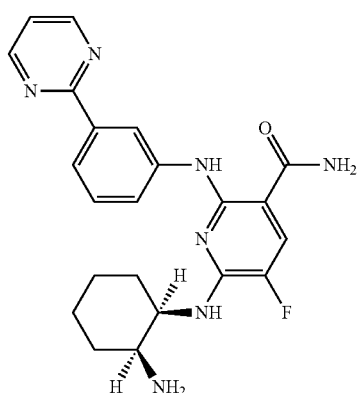

Scheme 26:

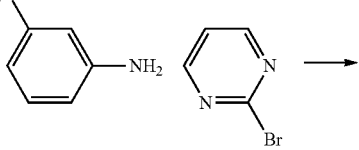

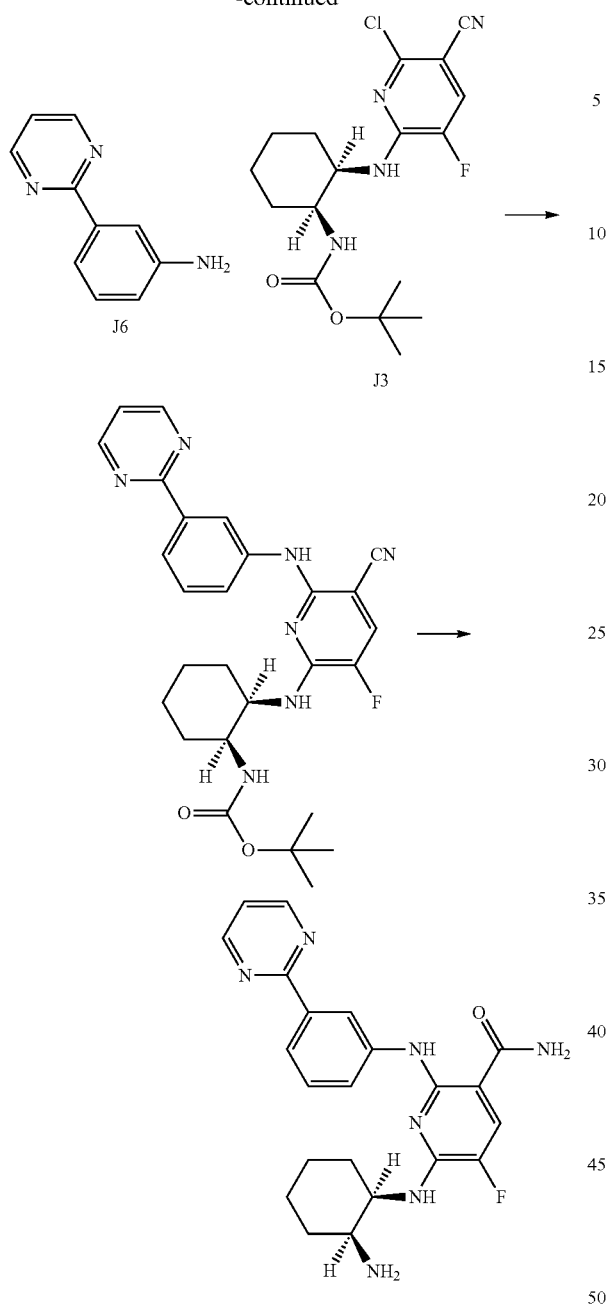

1.6 Hz), 7.78 (1H, d, J=12.0 Hz), 7.49 (1H, m), 7.44 (1H, d, J=7.6 Hz), 7.41 (1H, t, J=4.8 Hz), 4.58 (1H, m), 3.77 (1H, m), 1.88-1.48 (8H, m).

Example 56

Preparation of 6-((1R,2S)-2-aminocyclohexylamino)-5-fluoro-2-(3-(pyrimidin-4-yl)phenylamino)nicotinamide

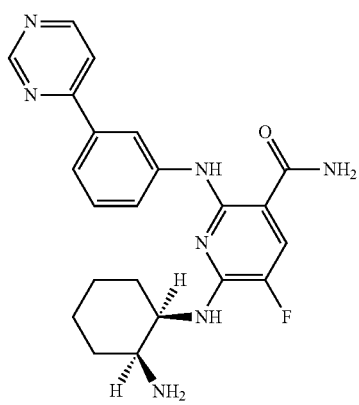 [SMILES: NC(=O)c1cc(F)c(N[C@@H]2CCCC[C@@H]2N)nc1Nc1cccc(-c2ccncn2)c1]

The title compound was prepared using the same chemistry shown in Example 55. UV: 278, 301 nm. M+H found for C$_{22}$H$_{29}$FN$_6$O$_2$: 422.5. NMR (CD$_3$OD): 9.24 (1H, s), 8.83 (1H, d, J=5.2 Hz), 8.58 (1H, t, J=2.0 Hz), 8.05 (1H, dd, J=5.6; 1.2 Hz), 7.76 (1H, d, J=12.0 Hz), 7.74 (1H, m), 7.61 (1H, m), 7.49 (1H, t, J=7.6 Hz), 4.51 (1H, m), 3.77 (1H, m), 1.85-1.47 (8H, m) ppm.

Example 57

Preparation of 6-((1R,2S)-2-aminocyclohexylamino)-5-fluoro-2-(3-(pyrimidin-5-yl)phenylamino)nicotinamide

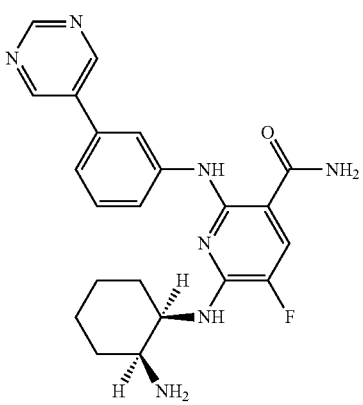 [SMILES: NC(=O)c1cc(F)c(N[C@@H]2CCCC[C@@H]2N)nc1Nc1cccc(-c2cncnc2)c1]

The mixture of 3-aminophenylboronic acid (6.0 g, 43.8 mmol), 2-bromopyrimidine (7.0 g, 43.8 mmol), Pd(PPh$_3$)$_2$Cl$_2$ (1.54 g, 2.19 mml) and potassium carbonate (18.1 g, 131 mmol) in 200 mL dioxane and 100 mL water was degassed using argon stream for 3 min. It was then stirred at 85° C. in argon atmosphere for 5 h. It was concentrated in vacuo to remove dioxane. To the residue was added 200 mL water, and the mixture was extracted using chloroform three times. The extracts were combined, dried, concentrated and purified using flash column with 1:3 EtOAc/DCM to afford aniline J6 (5.25 g, 70% yield).

With aniline J6, the title compound was prepared using the same chemistry shown in Example 41. UV: 263, 301 nm. M+H found for C$_{22}$H$_{24}$FN$_7$O: 422.4. NMR (CD$_3$OD): 8.88 (2H, d, J=5.2 Hz), 8.80 (1H, t, J=2.0 Hz), 8.03 (1H, dt, J=6.0;

The title compound was prepared using the same chemistry shown in Example 55. UV: 245, 265, 303 nm. M+H found for C$_{22}$H$_{29}$FN$_6$O$_2$: 422.4. NMR (CD$_3$OD): 9.17 (1H, s), 9.09 (2H, s), 8.06 (1H, t, J=2.0 Hz), 7.77 (1H, d, J=12.0 Hz), 7.61

(1H, m), 7.48 (1H, t, J=8.0 Hz), 7.33 (1H, m), 4.38 (1H, m), 3.74 (1H, m), 1.83-1.46 (8H, m) ppm.

Example 58

Preparation of 6-((1R,2S)-2-aminocyclohexylamino)-5-fluoro-2-(4-(pyrimidin-2-yl)phenylamino)nicotinamide

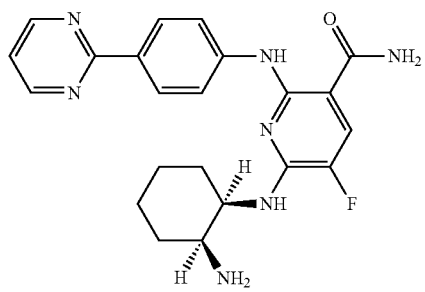 [SMILES: NC(=O)c1cc(F)c(N[C@@H]2CCCC[C@@H]2N)nc1Nc1ccc(-c2ncccn2)cc1]

The title compound was prepared using the same chemistry shown in Example 55. UV: 268 nm. M+H found for $C_{22}H_{29}FN_6O_2$: 422.5. NMR (CD$_3$OD): 8.82 (2H, d, J=4.8 Hz), 8.33 (2H, dt, J=8.8; 2.0 Hz), 7.78 (1H, d, J=12.0 Hz), 7.75 (2H, dt, J=9.2; 2.0 Hz), 7.33 (1H, t, J=4.4 Hz), 4.47 (1H, m), 3.98 (1H, m), 1.95-1.66 (8H, m) ppm.

Example 59

Preparation of 6-(1R,2S)-2-aminocyclohexylamino)-5-fluoro-2-(4-(pyrimidin-4-yephenylamino)nicotinamide

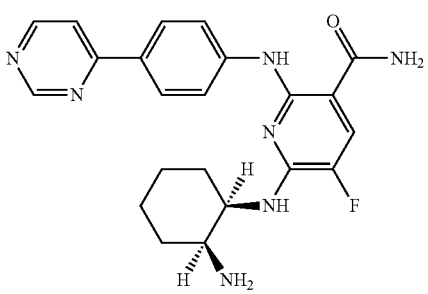 [SMILES: NC(=O)c1cc(F)c(N[C@@H]2CCCC[C@@H]2N)nc1Nc1ccc(-c2ccncn2)cc1]

The title compound was prepared using the same chemistry shown in Example 55. UV: 268 nm. M+H found for $C_{22}H_{29}FN_6O_2$: 422.5. NMR (CD$_3$OD): 9.19 (1H, s), 8.76 (1H, d, J=6.0 Hz), 8.25 (2H, dt, J=8.8; 2.0 Hz), 8.13 (1H, dd, J=6.0; 1.2 Hz), 7.83 (2H, dt, J=8.8; 2.0 Hz), 7.81 (1H, d, J=12.0 Hz), 4.49 (1H, m), 3.98 (1H, m), 1.96-1.67 (8H, m) ppm.

Example 60

Preparation of 6-((1R,2S)-2-aminocyclohexylamino)-2-(benzo[d]thiazol-6-ylamino)-5-fluoronicotinamide

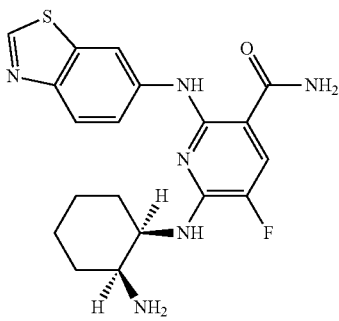

The title compound was prepared using the same chemistry shown in Example 41. UV: 258, 325 nm. M+H found for $C_{19}H_{21}FN_6OS$: 400.4. NMR (CD$_3$OD): 9.10 (1H, s), 8.49 (1H, d, J=2.0 Hz), 7.96 (1H, d, J=8.8 Hz), 7.78 (1H, d, J=12.0 Hz), 7.57 (1H, dd, J=8.8; 2.0 Hz), 4.41 (1H, m), 3.89 (1H, m), 1.88-1.63 (8H, m) ppm.

Example 61

Preparation of 6-((1R,2S)-2-aminocyclohexylamino)-5-fluoro-2-(imidazo[1,2-a]pyridin-6-ylamino)nicotinamide

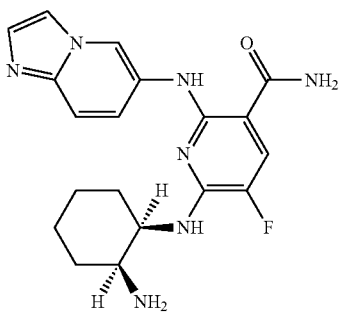 [SMILES: NC(=O)c1cc(F)c(N[C@@H]2CCCC[C@@H]2N)nc1Nc1ccc2nccn2c1]

The title compound was prepared using the same chemistry shown in Example 41. UV: 295 nm. M+H found for $C_{19}H_{22}FN_7O$: 384.4. NMR (CD$_3$OD): 9.31 (1H, t, J=0.8 Hz), 8.13 (1H, d, J=2.0 Hz), 7.96 (1H, d, J=10.0 Hz), 7.95 (1H, d, J=9.6 Hz), 7.86 (1H, d, J=11.6 Hz), 7.84 (1H, d, J=10.0 Hz), 4.55 (1H, m), 3.80 (1H, m), 1.90-1.62 (8H, m) ppm.

Example 62

Preparation of 6-((1R,2S)-2-aminocyclohexylamino)-5-fluoro-2-(imidazo[1,2-a]pyridin-7-ylamino)nicotinamide

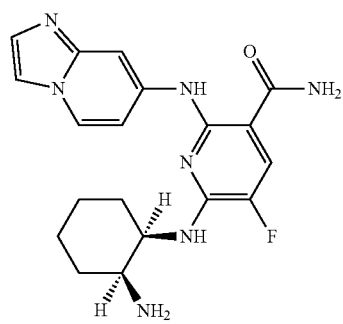 [SMILES: NC(=O)c1cc(F)c(N[C@@H]2CCCC[C@@H]2N)nc1Nc1ccn2ccnc2c1]

The title compound was prepared using the same chemistry shown in Example 41. UV: 240, 282 nm. M+H found for $C_{19}H_{22}FN_7O$: 384.4. NMR (CD$_3$OD): 8.53 (1H, d, J=7.6 Hz), 8.38 (1H, s), 7.90 (1H, d, J=0.8 Hz), 7.89 (1H, d, J=11.6 Hz), 7.76 (1H, d, J=2.0 Hz), 7.36 (1H, dd, J=7.2; 2.0 Hz), 4.68 (1H, m), 3.89 (1H, m), 1.99-1.64 (8H, m) ppm.

Example 63

Preparation of 6-((1R,2S)-2-aminocyclohexylamino)-5-fluoro-2-(1-methyl-1H-indol-5-ylamino)nicotinamide

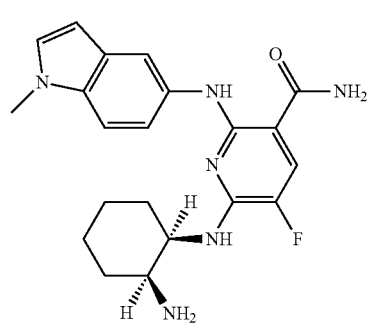

The title compound was prepared using the same chemistry shown in Example 41. UV: 282 nm. M+H found for $C_{21}H_{25}FN_6O$: 397.4. NMR (CD$_3$OD): 7.71 (1H, d, J=11.6 Hz), 7.71 (1H, d, J=2.0 Hz), 7.34 (1H, d, J=8.8 Hz), 7.17-7.14 (2H, m), 6.39 (1H, dd, J=3.2; 0.8 Hz), 4.19 (1H, m), 3.81 (3H, m), 3.67 (1H, m), 1.81-1.54 (8H, m) ppm.

Example 64

Preparation of 6-((1R,2S)-2-aminocyclohexylamino)-5-fluoro-2-(1-methyl-1H-indol-4-ylamino)nicotinamide

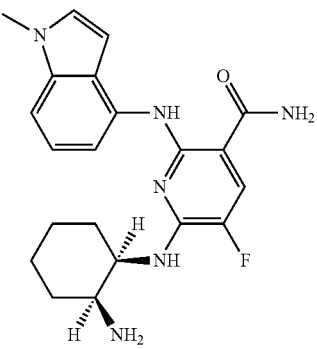 [SMILES: Cn1ccc2c(Nc3nc(N[C@@H]4CCCC[C@@H]4N)c(F)cc3C(N)=O)cccc21]

The title compound was prepared using the same chemistry shown in Example 41. UV: 325 nm. M+H found for $C_{21}H_{25}FN_6O$: 397.4. NMR (CD$_3$OD): 7.78-7.75 (2H, m), 7.18-7.08 (3H, m), 6.55 (1H, d, J=3.2 Hz), 4.33 (1H, m), 3.84 (1H, m), 3.81 (3H, s), 1.84-1.59 (8H, m) ppm.

Example 65

Preparation of 6-((1R,2S)-2-aminocyclohexylamino)-5-fluoro-2-(2-methyl-2H-indazol-4-ylamino)nicotinamide

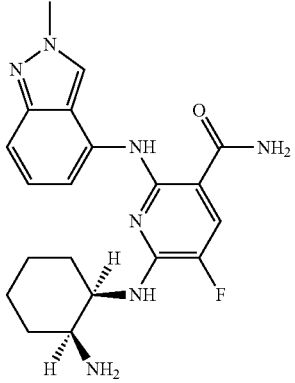 [SMILES: Cn1cc2c(Nc3nc(N[C@@H]4CCCC[C@@H]4N)c(F)cc3C(N)=O)cccc2n1]

The title compound was prepared using the same chemistry shown in Example 41. UV: 282 nm. M+H found for $C_{20}H_{24}FN_7O$: 398.5. NMR (CD$_3$OD): 8.13 (1H, d, J=6.8

Hz), 8.01 (1H, d, J=7.6 Hz), 7.77 (1H, m), 7.28 (1H, m), 7.03 (1H, m), 4.36 (1H, m), 4.22 (3H, m), 3.94 (1H, m), 1.88-1.62 (8H, m) ppm.

Example 66

Preparation of 6-((1R,2S)-2-aminocyclohexylamino)-5-fluoro-2-(quinolin-6-ylamino)nicotinamide

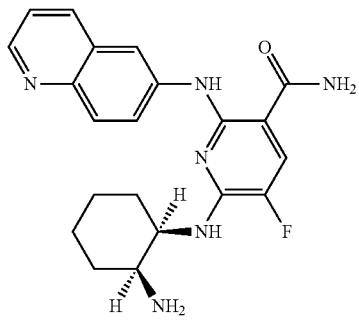

The title compound was prepared using the same chemistry shown in Example 41. UV: 266, 303, 330 nm. M+H found for $C_{21}H_{23}FN_6O$: 395.4. NMR ($CD_3OD$): 8.91-8.88 (2H, m), 8.64 (1H, d, J=2.4 Hz), 8.19 (1H, dd, J=9.6; 2.4 Hz), 8.12 (1H, d, J=9.2 Hz), 7.93 (1H, dd, J=8.0; 4.8 Hz), 7.87 (1H, d, J=11.6 Hz), 4.65 (1H, m), 3.88 (1H, m), 2.00-1.66 (8H, m) ppm.

Example 67

Preparation of 6-((1R,2S)-2-aminocyclohexylamino)-5-fluoro-2-(isoquinolin-6-ylamino)nicotinamide

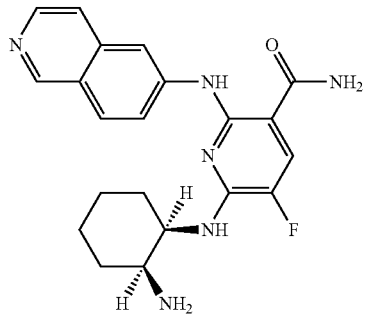 [SMILES: NC(=O)c1cc(F)c(N[C@@H]2CCCC[C@@H]2N)nc1Nc1ccc2cnccc2c1]

The title compound was prepared using the same chemistry shown in Example 41. UV: 217, 258, 335 nm. M+H found for $C_{21}H_{23}FN_6O$: 395.4. NMR ($CD_3OD$): 9.28 (1H, s), 8.59 (1H, s), 8.31 (1H, d, J=7.2 Hz), 8.26 (1H, d, J=9.2 Hz), 8.02-7.94 (2H, m), 7.90 (1H, d, J=12.0 Hz), 4.66 (1H, m), 3.92 (1H, m), 1.99-1.71 (8H, m) ppm.

Example 68

Preparation of 6-((1R,2S)-2-aminocyclohexylamino)-5-fluoro-2-(isoquinolin-7-ylamino)nicotinamide

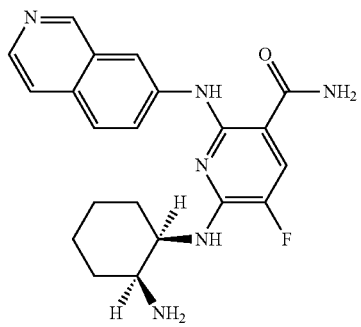 [SMILES: NC(=O)c1cc(F)c(N[C@@H]2CCCC[C@@H]2N)nc1Nc1ccc2ccncc2c1]

The title compound was prepared using the same chemistry shown in Example 41. UV: 264, 325 nm. M+H found for $C_{21}H_{23}FN_6O$: 395.4. NMR ($CD_3OD$): 9.49 (1H, s), 8.68 91H, d, J=2.0 Hz), 8.37 (1H, d, J=6.4 Hz), 8.33 (1H, dd, J=8.8; 2.0 Hz), 8.29 (1H, d, J=6.0 Hz), 8.19 (1H, d, J=9.2 Hz), 7.87 (1H, d, J=12.0 Hz), 4.64 (1H, m), 3.88 (1H, m), 1.99-1.65 (8H, m) ppm.

Example 69

Preparation of 6-((1R,2S)-2-aminocyclohexylamino)-5-fluoro-2-(quinolin-7-ylamino)nicotinamide

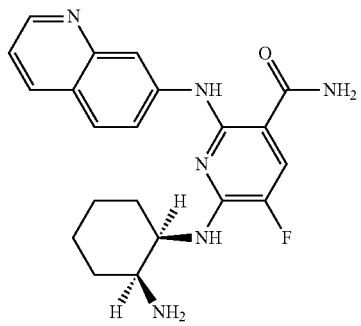 [SMILES: NC(=O)c1cc(F)c(N[C@@H]2CCCC[C@@H]2N)nc1Nc1ccc2cccnc2c1]

The title compound was prepared using the same chemistry shown in Example 41. UV: 264, 297 nm. M+H found for $C_{21}H_{23}FN_6O$: 395.4. NMR ($CD_3OD$): 8.89 (1H, dd, J=5.6; 1.6 Hz), 8.78 (1H, d, J=7.2 Hz), 8.43 (1H, s), 8.09 (1H, d, J=9.2 Hz), 7.89 (1H, m), 7.88 (1H, d, J=12.0 Hz), 7.65 (1H, m), 4.76 (1H, m), 3.91 (1H, m), 1.92-1.61 (8H, m) ppm.

Example 70

Preparation of 6-((1R,2S)-2-aminocyclohexylamino)-5-fluoro-2-(quinolin-3-ylamino)nicotinamide

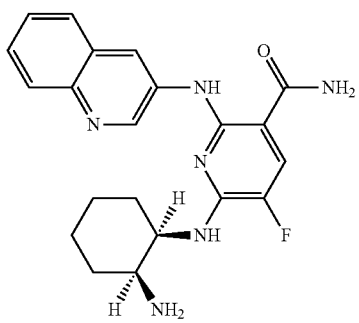 [SMILES: NC(=O)c1cc(F)c(N[C@@H]2CCCC[C@@H]2N)nc1Nc1cnc2ccccc2c1]

The title compound was prepared using the same chemistry shown in Example 41. UV: 225, 244, 297, 327 nm. M+H found for C$_{21}$H$_{23}$FN$_6$O: 395.4. NMR (CD$_3$OD): 9.38 (1H, d, J=2.8 Hz), 8.95 (1H, s), 8.08-8.05 (2H, m), 7.87 (1H, d, J=12.0 Hz), 7.83 (1H, m), 7.76 (1 h, m), 4.55 (1H, m), 3.76 (1H, m), 1.92-1.62 (8H, m) ppm.

Example 71

Preparation of 6-((1R,2S)-2-aminocyclohexylamino)-5-fluoro-2-(isoquinolin-4-ylamino)nicotinamide

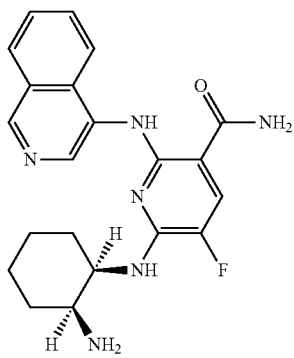 [SMILES: NC(=O)c1cc(F)c(N[C@@H]2CCCC[C@@H]2N)nc1Nc1cncc2ccccc12]

The title compound was prepared using the same chemistry shown in Example 41. UV: 221 nm. M+H found for C$_{21}$H$_{23}$FN$_6$O: 395.5. NMR (CD$_3$OD): 9.62 (1H, s), 9.22 (1H, s), 8.50 (1H, d, J=8.4 Hz), 8.42 (1H, d, J=8.0 Hz), 8.21 (1H, m), 8.02 (1H, m), 7.96 (1H, d, J=12.4 Hz), 4.60 (1H, m), 3.82 (1H, m), 1.94-1.66 (8H, m) ppm.

Example 72

Preparation of 6-(1R,2S)-2-aminocyclohexylamino)-5-fluoro-2-(quinolin-4-ylamino)nicotinamide

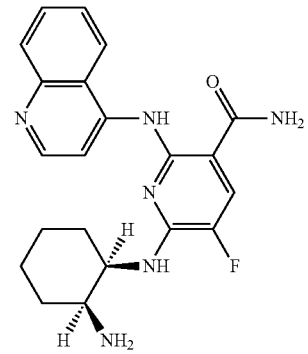 [SMILES: NC(=O)c1cc(F)c(N[C@@H]2CCCC[C@@H]2N)nc1Nc1ccnc2ccccc12]

The title compound was prepared using the same chemistry shown in Example 41. UV: 263, 325 nm. M+H found for C$_{21}$H$_{23}$FN$_6$O: 395.4. NMR (CD$_3$OD): 8.99 (1H, d, J=7.2 Hz), 8.81 (1H, d, J=7.2 Hz), 8.56 (1H, d, J=8.4 Hz), 8.10-8.02 (3H, m), 7.91 (1H, m), 4.60 (1H, m), 3.93 (1H, m), 2.02-1.70 (8H, m) ppm.

Example 73

Preparation of 6-((1R,2S)-2-aminocyclohexylamino)-5-fluoro-2-(quinolin-5-ylamino)nicotinamide

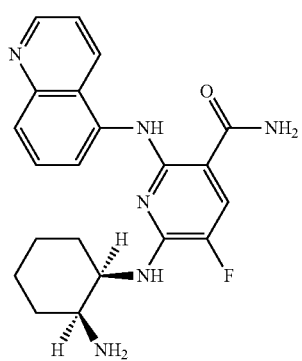 [SMILES: NC(=O)c1cc(F)c(N[C@@H]2CCCC[C@@H]2N)nc1Nc1cccc2ncccc12]

The title compound was prepared using the same chemistry shown in Example 41. UV: 239, 273 nm. M+H found for C$_{21}$H$_{23}$FN$_6$O: 395.4. NMR (CD$_3$OD): 9.17 (1H, d, J=8.8 Hz), 9.08 (1H, dd, J=8.8; 1.6 Hz), 8.63 (1H, d, J=7.2 Hz), 8.05

(1H, t, J=8.4 Hz), 7.94 (1H, m), 7.90 (1H, d, J=11.6 Hz), 7.79 (1H, d, J=8.8 Hz), 4.27 (1H, m), 3.74 (1H, m), 1.89-1.56 (8H, m) ppm.

Example 74

Preparation of 6-((1R,2S)-2-aminocyclohexylamino)-5-fluoro-2-(isoquinolin-5-ylamino)nicotinamide

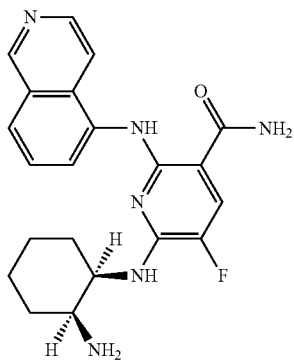 [SMILES: NC(=O)c1cc(F)c(N[C@@H]2CCCC[C@@H]2N)nc1Nc1cccc2cnccc12]

The title compound was prepared using the same chemistry shown in Example 41. UV: 249 nm. M+H found for C₂₁H₂₃FN₆O: 395.4. NMR (CD₃OD): 9.61 (1H, s), 8.86 (1H, d, J=7.6 Hz), 8.56 (1H, d, J=6.4 Hz), 8.46 (1H, d, J=6.8 Hz), 8.05 (1H, d, J=8.4 Hz), 7.96 91H, t, d=8.0 Hz), 7.88 (1H, d, J=11.6 Hz), 4.27 (1H, m), 3.73 (1H, m), 1.87-1.54 (8H, m) ppm.

Example 75

Preparation of 6-((1R,2S)-2-aminocyclohexylamino)-5-fluoro-2-(isoquinolin-8-ylamino)nicotinamide

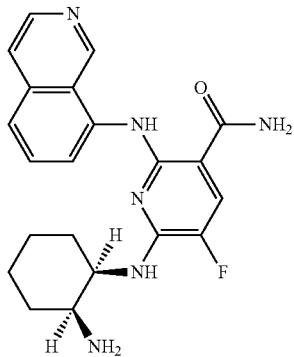 [SMILES: NC(=O)c1cc(F)c(N[C@@H]2CCCC[C@@H]2N)nc1Nc1cccc2ccncc12]

The title compound was prepared using the same chemistry shown in Example 41. UV: 273 nm. M+H found for C₂₁H₂₃FN₆O: 395.4. NMR (CD₃OD): 9.65 (1H, s), 8.67 (1H, d, J=7.6 Hz), 8.50 (1H, d, J=6.8 Hz), 8.30 (1H, d, J=6.4 Hz), 8.13 (1H, t, J=8.0 Hz), 7.90 (1H, d, J=11.6 Hz), 7.82 (1H, d, J=8.0 Hz), 4.27 (1H, m), 3.74 (1H, m), 1.90-1.54 (8H, m) ppm.

Example 76

Preparation of 6-((1R,2S)-2-aminocyclohexylamino)-5-fluoro-2-(quinoxalin-6-ylamino)nicotinamide

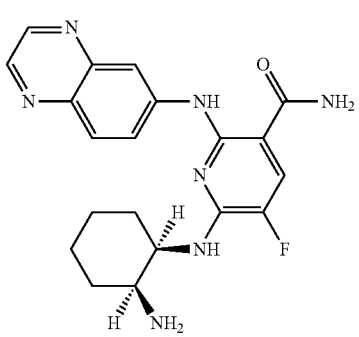 [SMILES: NC(=O)c1cc(F)c(N[C@@H]2CCCC[C@@H]2N)nc1Nc1ccc2nccnc2c1]

The title compound was prepared using the same chemistry shown in Example 41. UV: 263, 292 nm. M+H found for C₂₀H₂₂FN₇O: 396.4. NMR (CD₃OD): 8.79 (1H, d, J=2.0 Hz), 8.77 (1H, d, J=2.4 Hz), 8.68 (1H, d, J=2.4 Hz), 7.97 (1H, d, J=9.2 Hz), 7.85 (1H, d, J=12.0 Hz), 7.71 (1H, dd, J=8.8; 2.4 Hz), 4.63 (1H, m), 4.00 (1H, m), 2.16-1.67 (8H, m) ppm.

Example 77

Preparation of 6-((1R,2S)-2-aminocyclohexylamino)-5-fluoro-2-(pyrido[3,2-b]pyrazin-7-ylamino)nicotinamide

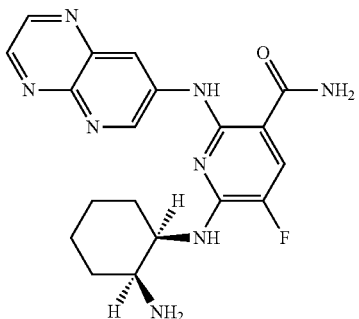

The title compound was prepared using the same chemistry shown in Example 41. UV: 301 nm. M+H found for C₁₉H₂₁FN₈O: 397.4. NMR (CD₃OD): 9.04 (1H, d, J=2.8

Hz), 9.00 (1H, d, J=2.4 Hz), 8.88 (1H, d, J=2.0 Hz), 8.79 (1H, d, J=2.0 Hz), 7.85 (1H, d, J=11.6 Hz), 4.58 (1H, m), 3.99 (1H, m), 1.86-1.69 (8H, m) ppm.

Example 78

Preparation of 6-(1R,2S)-2-aminocyclohexylamino)-2-(2,3-dihydrobenzo[b][1,4]dioxin-6-ylamino)-5-fluoronicotinamide

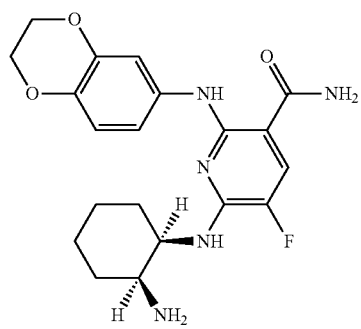 [SMILES: NC(=O)c1cc(F)c(N[C@@H]2CCCC[C@@H]2N)nc1Nc1ccc2c(c1)OCCO2]

Scheme 27:

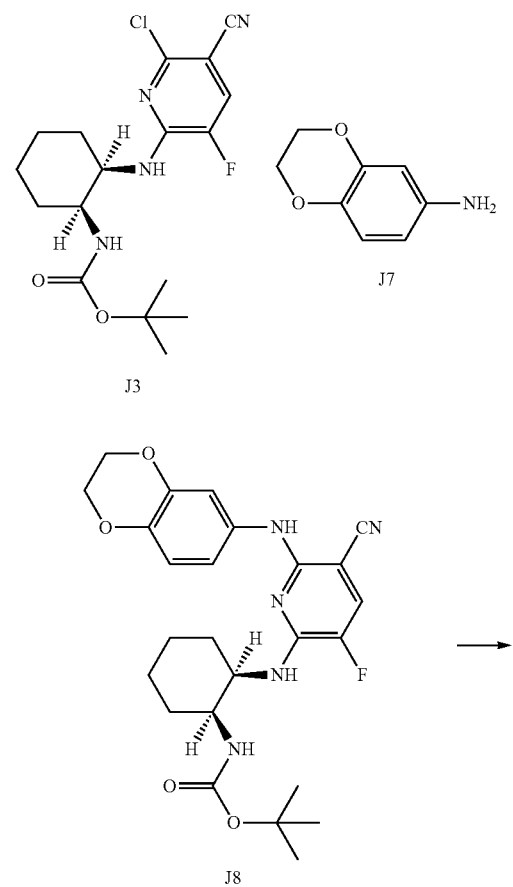

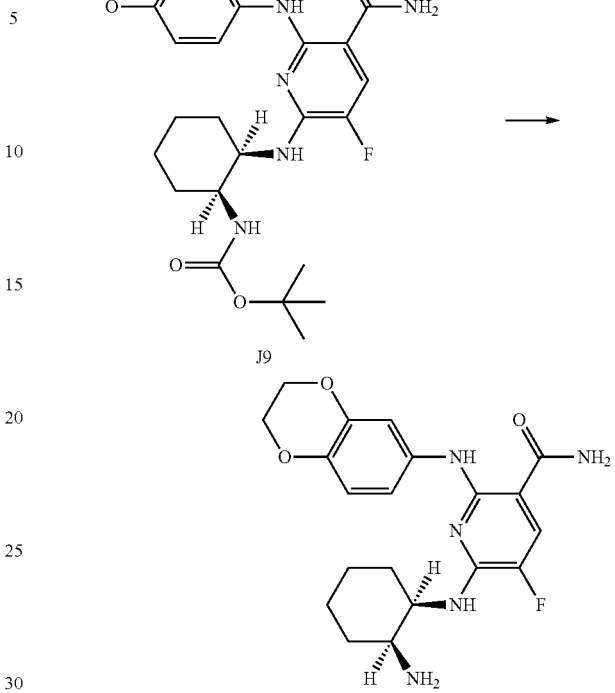

Step 1: To a clean 200 mL flask were added to following chemical reagents: compound J3 (shown in Example 41, 100 mg, 0.27 mmol), 1,4-benzodioxan-6-amine (compound J7, 82 mg, 0.54 mmol), fine-powder cesium carbonate (264 mg, 0.81 mmol), Q-Phos (1,2,3,4,5-pentaphenyl-1'-(di-tert-butylphosphino)ferrocene) (20 mg, 0.027 mmol; Aldrich #675784) and Pd(dba)$_2$ (bis(dibenzylideneacetone)palladium(0)) (32 mg, 0.054 mmol; Aldrich #227994). To the mixture was then added 15 mL toluene. The resulting slurry was degassed using argon stream gently for 3 min. It was then sent to 110° C. bath with an air-cooled condenser on top and stirred under argon for overnight. The mixture was then cooled to RT and concentrated on rotovap to remove all the solvent. To the residue were added 150 mL EtOAc and 100 mL water. After vigorously stirring for 15-30 min, the organic phase was separated, and the aq phase and the black junks between org and aq phases were all discarded. The EtOAc phase was then washed with brine twice. The organic phase was dried over MgSO$_4$, concentrated and subjected to flash column with 0%-10% EtOAc in DCM to isolate the desired product, compound J8.

Step 2: The above prepared compound J8 was dissolved in 2 mL DMSO. To it were added 1 mL 50% H$_2$O$_2$ and then powder potassium carbonate (74 mg, 0.54 mmol). The mixture was stirred at RT for 30 min. To it was poured 150 mL EtOAc and 50 mL water. The organic phase was separated and washed with brine twice, dried over MgSO$_4$, and concentrated in vacuo to offer crude compound J9. Compound J9 was then treated with 1:1 DCM and TFA at RT for 30 min. The mixture was concentrated and subjected to prep HPLC (running with 3 mM HCl in water as solvent A and neat acetonitrile as solvent B) to isolate the title compound as HCl salt (lyophilized). UV: 294 nm. M+H found for C$_{20}$H$_{24}$FN$_5$O$_3$: 402.4. NMR (CD$_3$OD): 7.70 (1H, d, J=12.4 Hz), 7.30 (1H, t, J=1.2 Hz), 6.75 (2H, d, J=1.2 Hz), 4.28-4.20 (5H, m), 3.92 (1H, m), 1.91-1.60 (8H, m) ppm.

Example 79

Preparation of 6-((1R,2S)-2-aminocyclohexylamino)-5-fluoro-2-(3-(2-methoxyethoxy)phenylamino)nicotinamide

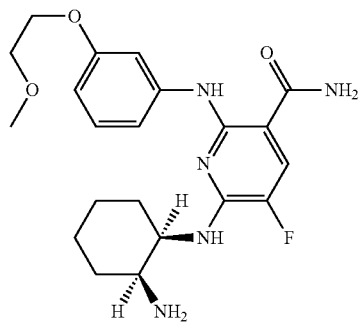 [SMILES: COCCOc1cccc(Nc2nc(N[C@@H]3CCCC[C@@H]3N)c(F)cc2C(N)=O)c1]

The title compound was prepared using the same chemistry shown in Example 78. UV: 246, 306 nm. M+H found for $C_{21}H_{28}FN_5O_3$: 418.5. NMR (CD$_3$OD): 7.73 (1H, d, J=12.0 Hz), 7.51 (1H, t, J=2.4 Hz), 7.18 (1H, t, J=8.0 Hz), 6.88 (1H, dd, J=8.0; 2.4 Hz), 6.58 (1H, dd, J=8.0; 2.4 Hz), 4.36 (1H, m), 4.11 (2H, m), 3.94 (1H, m), 3.75 (2H, m), 3.43 (3H, s), 2.04-1.60 (8H, m) ppm.

Example 80

Preparation of 6-((1R,2S)-2-aminocyclohexylamino)-5-fluoro-2-(3-(tetrahydro-2H-pyran-4-yloxy)phenylamino)nicotinamide

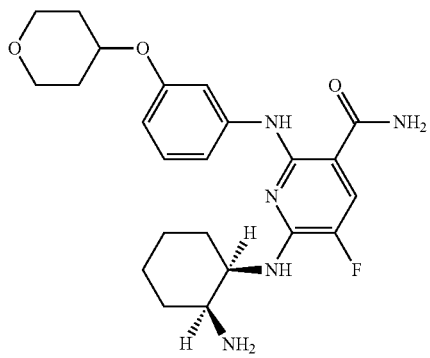 [SMILES: NC(=O)c1cc(F)c(N[C@@H]2CCCC[C@@H]2N)nc1Nc1cccc(OC2CCOCC2)c1]

Scheme 28:

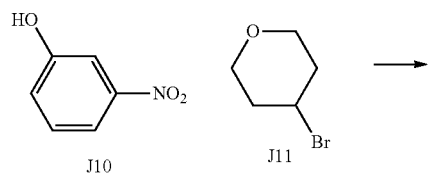

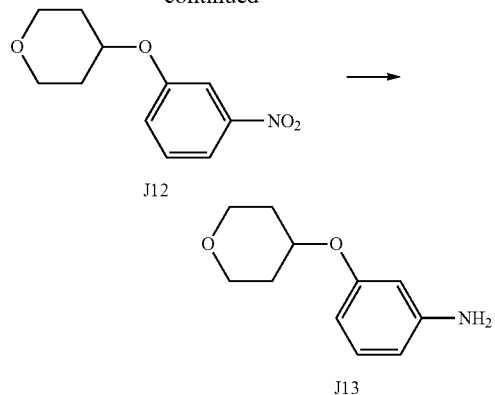

The mixture of 3-nitrophenol (J10, 500 mg, 3.6 mmol), 4-bromotetrahydropyran (J11, 3.0 g, 18 mmol) and Cs$_2$CO$_3$ (2.35 g, 7.2 mmol) in 15 mL DMF was stirred in a sealed tube at 100° C. for overnight. The ratio of desired compound J12 and starting material J10 was found to be 1:1.3 by HPLC. The mixture was cooled to RT, and to it was poured 200 mL EtOAc. It was washed with saturated Na$_2$CO$_3$ twice and brine twice. The organic phase was dried over MgSO$_4$, concentrated in vacuo and purified using silica flash column with 1:3 EtOAc and DCM to yield J12. Compound J12 was dissolved in 200 mL EtOAc. To it was added 10% Pd/C (200 mg). The mixture was stirred for overnight under a hydrogen balloon. The mixture was then filtered through celite. The celite layer was thoroughly washed with methanol. The filtrate was concentrated in vacuo and subjected to silica flash column with 0-11% MeOH in DCM to isolate desired aniline, compound J13 (248 mg, overall 36% yield).

The title compound was prepared using the same chemistry shown in Example 78 with aniline J13 to replace aniline J7. UV: 306 nm. M+H found for $C_{23}H_{30}FN_5O_3$: 444.5. NMR (CD$_3$OD): 7.63 (1H, d, J=12.0 Hz), 7.33 (1H, t, J=2.4 Hz), 7.07 (1H, t, J=8.0 Hz), 6.83 (1H, dd, J=8.0; 1.6 Hz), 6.51 (1H, dd, J=8.0; 2.4 Hz), 4.46 (1H, m), 4.25 (1H, m), 3.88-3.83 (3H, m), 3.49 (2H, m), 1.98-1.51 (12H, m) ppm.

Example 81

Preparation of 6-((1R,2S)-2-aminocyclohexylamino)-5-fluoro-2-(4-(tetrahydro-2H-pyran-4-yloxy)phenylamino)nicotinamide

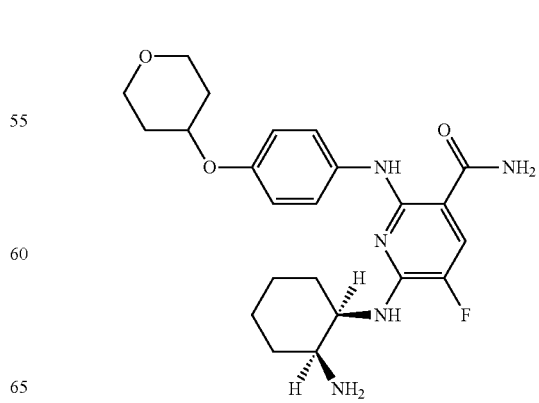

The title compound was prepared using the same chemistry shown in Example 80. UV: 297 nm. M+H found for $C_{23}H_{30}FN_5O_3$: 444.5. NMR (CD$_3$OD): 7.70 (1H, d, J=12.4 Hz), 7.40 (2H, dt, J=9.2; 2.4 Hz), 6.93 (2H, dt, J=8.8; 2.4 Hz), 4.51 (1H, m), 4.24 (1H, m), 3.99-3.93 (2H, m), 3.83 (1H, m), 3.59 (2H, m), 2.05-1.55 (12H, m) ppm.

Example 82

Preparation of 6-((1R,2S)-2-aminocyclohexylamino)-5-fluoro-2-(3-methylisothiazol-5-ylamino)nicotinamide

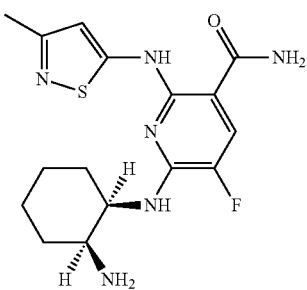 [SMILES: Cc1cc(Nc2nc(N[C@@H]3CCCC[C@@H]3N)c(F)cc2C(N)=O)sn1]

Scheme 29:

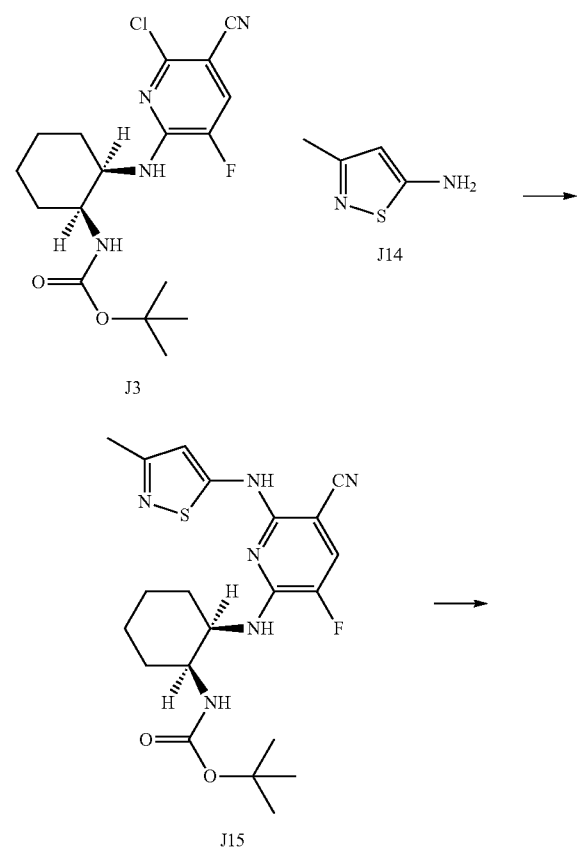

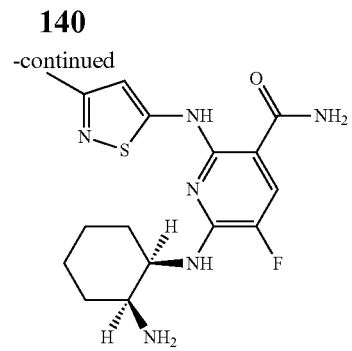

Step 1: The mixture of compound J3 (shown in Example 41, 100 mg, 0.27 mmol), 5-amino-3-methyl-isothiazole hydrochloride (J14, 122 mg, 0.81 mmol), sodium tert-butoxide (156 mg, 1.62 mmol), Q-Phos (1,2,3,4,5-pentaphenyl-1'-(di-tert-butylphosphino)ferrocene) (20 mg, 0.027 mmol; Aldrich #675784) and Pd(dba)$_2$ (bis(dibenzylideneacetone) palladium(0)) (32 mg, 0.054 mmol; Aldrich #227994) in 15 mL toluene was degassed using argon stream gently for 3 min. It was then sent to 110° C. bath with an air-cooled condenser on top and stirred under argon for 7 h. The mixture was then cooled to RT and concentrated on rotovap to remove all the solvent. To the residue were added 150 mL EtOAc and 100 mL water. After vigorously stirring for 15-30 min, the organic phase was separated, and the aq phase and the black junks between org and aq phases were all discarded. The EtOAc phase was then washed with brine twice. The organic phase was dried over MgSO$_4$, concentrated and subjected to flash column to isolate the desired product, compound J15.

Step 2: To the above prepared compound J15 was added 5 mL TFA at RT. After stirring for 3 min, 1 mL conc. H$_2$SO$_4$ was added. The mixture was then sent to pre-heated 80° C. bath and stirred for 20 min. It was the cooled to RT. To it was added 10 mL water. The mixture was stirred for 10 min, filtered and directly subjected to prep HPLC (running with 3 mM HCl in water as solvent A and neat acetonitrile as solvent B) to isolate the title compound as HCl salt (lyophilized). Yield: 10 mg, 10% overall yield for Step 1 and Step 2. UV: 244, 273, 340 nm. M+H found for $C_{16}H_{21}FN_6OS$: 365.3. NMR (CD$_3$OD): 7.98 (1H, d, J=11.6 Hz), 6.88 (1H, s), 4.73 (1H, m), 3.92 (1H, m), 2.51 (3H, s), 2.06-1.70 (8H, m) ppm.

Example 83

Preparation of 6-((1R,2S)-2-aminocyclohexylamino)-5-fluoro-2-(1-methyl-1H-pyrazol-4-ylamino)nicotinamide The title compound was prepared using the same chemistry shown in Example 41 with 1-methyl-1H-pyrazol-4-ylamine dihydrochloride to replace aniline J4. UV: 281 nm. M+H found for $C_{16}H_{22}FN_7O$: 348.4. NMR (CD$_3$OD): 7.71 (1H, d, J=12.0 Hz), 7.71 (1H, s), 7.61 (1H, s), 4.39 (1H, m), 3.88 (1H, m), 3.87 (3H, s), 1.86-1.64 (8H, m) ppm.

Example 84

Preparation of 6-(1R,2S)-2-aminocyclohexylamino)-5-fluoro-2-(pyridazin-4-ylamino)nicotinamide

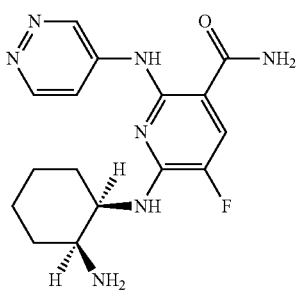 [SMILES: NC(=O)c1cc(F)c(N[C@@H]2CCCC[C@@H]2N)nc1Nc1ccnnc1]

The title compound was prepared using the same chemistry shown in Example 41 with 4-aminopyridazine to replace aniline J4. UV: 249, 320 nm. M+H found for $C_{16}H_{20}FN_7O$: 346.4. NMR (CD$_3$OD): 9.31 (1H, s), 9.03 (1H, d, J=7.2 Hz), 8.52 (1H, m), 7.98 (1H, d, J=11.2 Hz), 4.52 (1H, m), 3.84 (1H, m), 1.98-1.66 (8H, m) ppm.

Example 85

Preparation of 6-((1R,2S)-2-aminocyclohexylamino)-5-fluoro-2-(2-methylpyridin-4-ylamino)nicotinamide

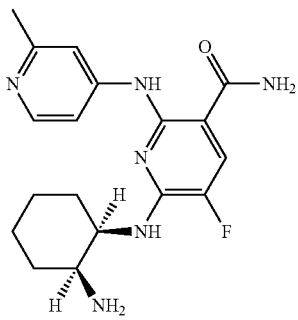

The title compound was prepared using the same chemistry shown in Example 41 with 4-amino-2-methylpyridine to replace aniline J4. UV: 273 nm. M+H found for $C_{18}H_{23}FN_6O$: 359.4. NMR (CD$_3$OD): 8.32 (1H, d, J=7.2 Hz), 8.00 (1H, s), 7.93 (1H, d, J=11.2 Hz), 7.81 (1H, s), 4.53 (1H, m), 3.85 (1H, m), 2.65 (3H, s), 1.98-1.65 (8H, m) ppm.

Example 86

Preparation of 6-((1R,2S)-2-aminocyclohexylamino)-2-(2,6-dimethylpyridin-4-ylamino)-5-fluoronicotinamide

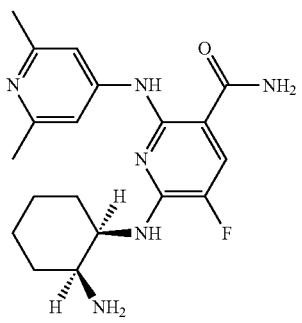 [SMILES: Cc1cc(Nc2nc(N[C@@H]3CCCC[C@@H]3N)c(F)cc2C(N)=O)cc(C)n1]

The title compound was prepared using the same chemistry shown in Example 41 with 4-amino-2,6-dimethylpyridine to replace aniline J4. UV: 273, 330 nm. M+H found for $C_{19}H_{25}FN_6O$: 373.4. NMR (CD$_3$OD): 7.92 (1H, d, J=12.0 Hz), 7.72 (2H, s), 4.55 (1H, m), 3.82 (1H, m), 2.61 (6H, s), 1.99-1.64 (8H, m) ppm.

Example 87

Preparation of 6-((1R,2S)-2-aminocyclohexylamino)-5-fluoro-2-(5-methylpyridin-3-ylamino)nicotinamide

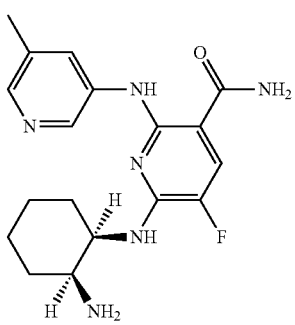

The title compound was prepared using the same chemistry shown in Example 41 with 3-amino-5-methylpyridine to replace aniline J4. UV: 230, 263 nm. M+H found for $C_{18}H_{23}FN_6O$: 359.4. NMR (CD$_3$OD): 9.23 (1H, d, J=2.4

Hz), 8.29 (1H, s), 8.22 (1H, d, J=0.8 Hz), 7.88 (1H, d, J=12.4 Hz), 4.54 (1H, m), 3.77 (1H, m), 2.53 (3H, s), 1.94-1.65 (8H, m) ppm.

Example 88

Preparation of 6-((1R,2S)-2-aminocyclohexylamino)-5-fluoro-2-(5-methoxypyridin-3-ylamino)nicotinamide

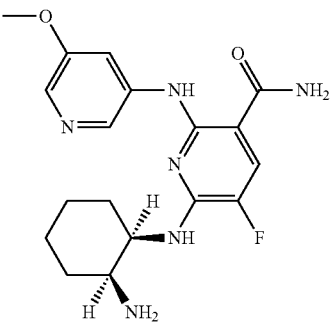 [SMILES: COc1cncc(Nc2nc(N[C@@H]3CCCC[C@@H]3N)c(F)cc2C(N)=O)c1]

The title compound was prepared using the same chemistry shown in Example 41 with 3-amino-5-methoxypyridine to replace aniline J4. UV: 278 nm. M+H found for $C_{18}H_{23}FN_6O_2$: 375.4. NMR (CD$_3$OD): 8.82 (1H, d, J=1.6 Hz), 8.10 (1H, t, J=2.0 Hz), 8.06 (1H, d, J=2.4 Hz), 7.86 (1H, d, J=12.0 Hz), 4.48 (1H, m), 4.01 (3H, s), 3.78 (1H, m), 1.94-1.64 (8H, m) ppm.

Example 89

Preparation of 6-((1R,2S)-2-aminocyclohexylamino)-5-fluoro-2-(5-fluoropyridin-3-ylamino)nicotinamide

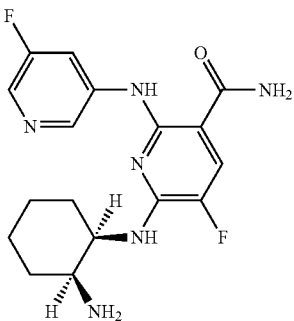 [SMILES: NC(=O)c1cc(F)c(N[C@@H]2CCCC[C@@H]2N)nc1Nc1cncc(F)c1]

Step 1: 2,6-Dichloro-5-fluoro-3-pyridinecarbonitrile (Aldrich 422169, 2.00 g, 10.5 mmol) was dissolved in 50 mL NMP in a 500 mL flask and stirred at RT. To it was added tert-butyl (1S,2R)-2-aminocyclohexylcarbamate (2.69 g, 12.5 mmol) in waxy solid form in multiple portions. Then DIEA (3.65 mL, 21.0 mmol) was added a few minutes later. The mixture was heated to 80° C. gradually and stirred at this temperature for 2 hours (very clean reaction; complete by analytical HPLC analysis). The mixture was cooled down to RT. To the flask then was added 400 mL cold water. A light yellow solid, (tert-butyl (1S,2R)-2-(6-chloro-5-cyano-3-fluoropyridin-2-ylamino)cyclohexylcarbamate, crashed out. It was isolated using Buchner funnel and washed with cold water multiple times (to wash away NMP completely). The solid was dried in vacuum oven at RT for two overnights. No other purification was necessary. Yield was over 90%.

Step 2: To a clean 100 mL flask were added to following reagents: (tert-butyl (1S,2R)-2-(6-chloro-5-cyano-3-fluoropyridin-2-ylamino)cyclohexylcarbamate (100 mg, 0.27 mmol), 3-amino-5-fluoropyridine (61 mg, 0.54 mmol), fine-powder cesium carbonate (264 mg, 0.81 mmol), Q-Phos (1,2,3,4,5-pentaphenyl-1'-(di-tert-butylphosphino)ferrocene) (40 mg, 0.054 mmol; Aldrich #675784) and Pd(dba)$_2$ (bis(dibenzylideneacetone)palladium(0)) (64 mg, 0.11 mmol; Aldrich #227994). To the mixture was then added 15 mL toluene. The resulting slurry was degassed using argon stream gently for 3 min. It was then sent to 110° C. bath with an air-cooled condenser on top and stirred under argon for overnight. The mixture was then cooled to RT and concentrated on rotovap to remove all the solvent. To the residue were added 300 mL EtOAc and 100 mL water. After vigorously stirring for 15-30 min, the organic phase was separated, and the aq phase and the black junks between org and aq phases were all discarded. The EtOAc phase was then washed with brine twice. The organic phase was dried over MgSO$_4$, concentrated and subjected to flash column with 0%-35% EtOAc in DCM to isolate the desired product, tert-butyl (1S,2R)-2-(5-cyano-3-fluoro-6-(5-fluoropyridin-3-ylamino)pyridin-2-ylamino)cyclohexylcarbamate. It was added 4 mL TFA at RT. After stirring for 3 min, 1 mL conc. H$_2$SO$_4$ was added. The mixture was then sent to pre-heated 80° C. bath and stirred for 90 min. It was then cooled to RT. To it was added 10 mL water. The mixture was stirred for 10 min, filtered and directly subjected to prep HPLC (running with 3 mM HCl in water as solvent A and neat acetonitrile as solvent B) in two injections to isolate the title compound as HCl salt (lyophilized). Yield: 58 mg, 59% yield for Step 2. UV: 258, 330 nm. M+H found for $C_{17}H_{20}F_2N_6O$: 363.3. NMR (CD$_3$OD): 8.56 (1H, m), 8.20 (1H, dd, J=11.2; 2.0 Hz), 8.06 (1H, m), 7.82 (1H, d, J=11.6 Hz), 4.42 (1H, m), 3.86 (1H, m), 1.93-1.63 (8H, m) ppm.

Example 90

Preparation of (R)-2-(3-(2H-1,2,3-triazol-2-yephenylamino)-6-(1-aminobutan-2-ylamino)-5-fluoronicotinamide

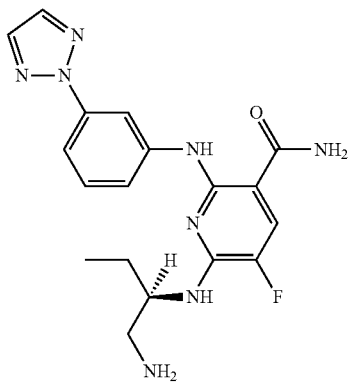 [SMILES: CC[C@H](CN)Nc1nc(Nc2cccc(-n3nccn3)c2)c(C(N)=O)cc1F]

Scheme 30:

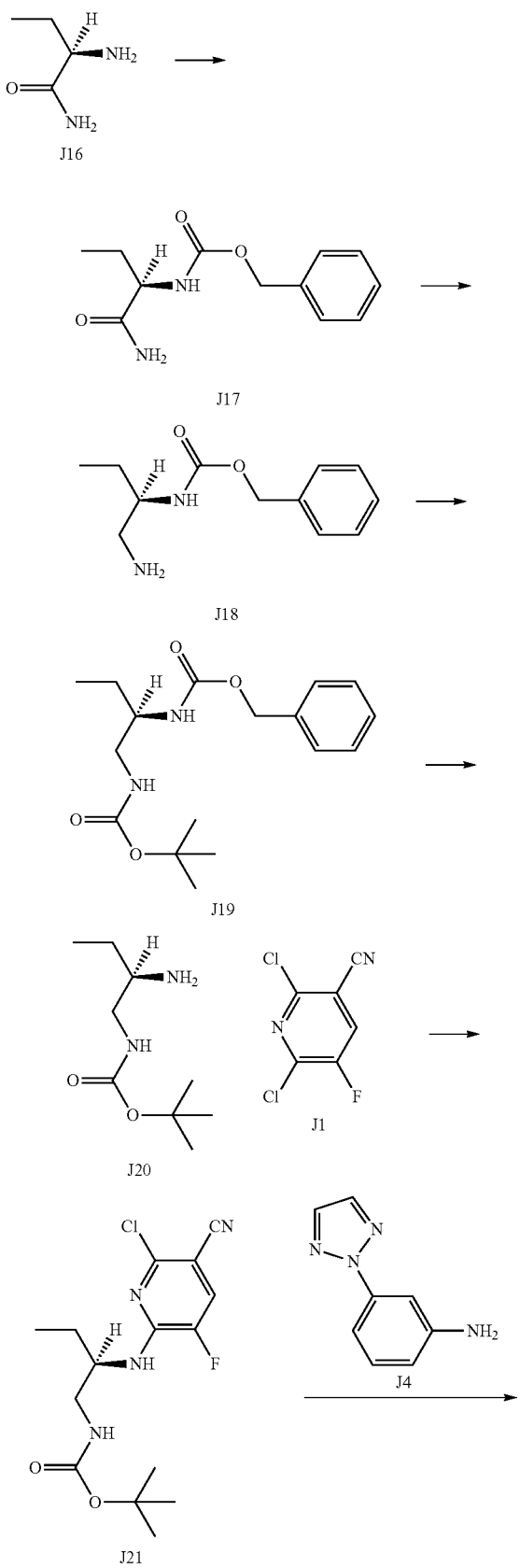

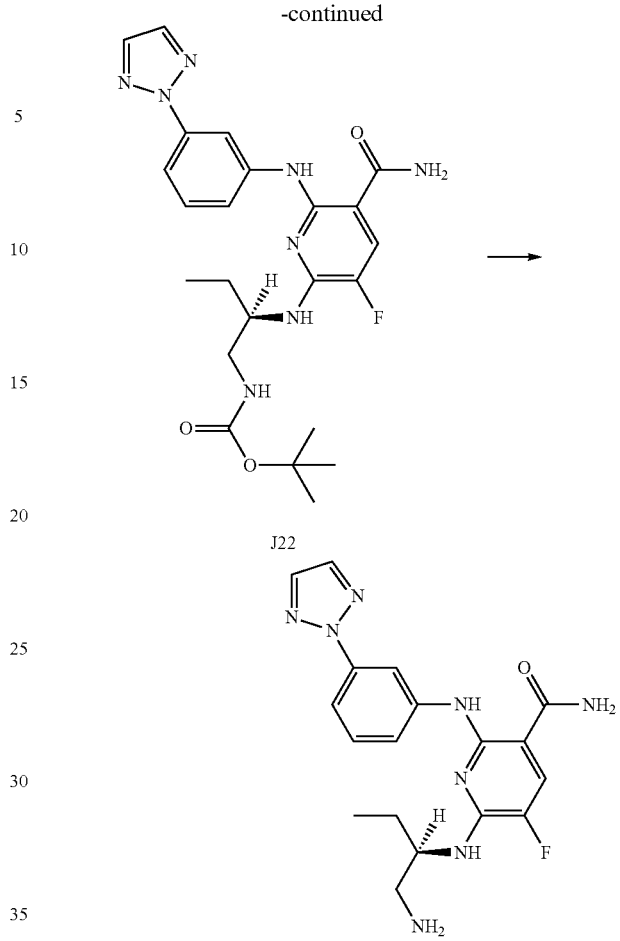

Step 1: (R)-(−)-2-aminobutanamide hydrochloride (J16, Aldrich, 3.30 g, 23.8 mmol) was dissolved in 100 mL dioxane. To it were added 30 mL water, sodium carbonate (7.57 g, 71.4 mmol) and benzyl chloroformate (4.03 mL, 28.6 mmol, dropwise by syringe). The mixture was stirred at RT for overnight. To it was poured 500 mL EtOAc. The mixture was washed with water and twice with brine. The organic phase was dried, concentrated in vacuo. To the solid residue were added 400 mL hexane and 50 mL DCM. The slurry was rotated slowly on rotovap at RT for 2 h. The solid in the slurry was isolated using a Buchner funnel and washed with hexane three times. The white solid, very pure compound J17 (nearly quantitative yield), was then dried in vacuo.

Step 2: The above-prepared compound J17 was dissolved in 200 mL THF. To it was added $BH_3.Me_2S$ (5.46 mL, 57.5 mmol) at RT. The stirred mixture was then gently refluxed under argon for 5 h to give compound J18. It was cooled to RT. To it was added 200 mL water very slowly. The resulting mixture was then stirred for 1 h at RT. To it were added potassium carbonate (9.53 g, 69 mmol) and $Boc_2O$ (10.03 g, 46 mmol). The mixture was stirred at RT for overnight to afford J19. To it was poured 500 mL EtOAc. The mixture was washed with brine three times. The organic phase was dried, concentrated and subjected to flash column (35% EtOAc in hexane) to isolate J19.

Step 3: The above-prepared J19 was dissolved in 250 mL EtOAc. To it was added 2.0 g 10% Pd/C. The mixture was sent to a Parr shaker for hydrogenation at 35 psi pressure for overnight. The mixture was filtered through celite. The celite layer was thoroughly washed with methanol. The filtrate was concentrated in vacuo and subjected to flash column (20%

MeOH in DCM) to isolate compound J20 (1.44 g, 32% overall yield from compound J16) as a thick oil.

Step 4: 2,6-Dichloro-5-fluoro-3-pyridinecarbonitrile (J1, Aldrich 422169, 1.22 g, 6.38 mmol) was dissolved in 20 mL NMP in a 200 mL flask and stirred at RT. To it was added above-prepared compound J20 (1.44 g, 7.66 mmol) and DIEA (2.22 mL, 12.8 mmol). The mixture was heated to 80° C. gradually and stirred at this temperature for 90 min. The mixture was cooled down to RT. To the flask then was added 200 mL cold water. A light yellow solid (compound J21) crashed out. It was isolated using Buchner funnel and washed with cold water multiple times. The solid was dried in vacuum oven at 40° C. for overnight. No other purification was necessary. Yield: 1.85 g, 71%.

Step 5: To a clean 150 mL flask were added to following reagents: compound J21 (100 mg, 0.29 mmol), 3-(2H-1,2,3-triazol-2-yl)aniline (compound J4, 94 mg, 0.58 mmol), fine-powder cesium carbonate (293 mg, 0.90 mmol), Q-Phos (1,2,3,4,5-pentaphenyl-1'-(di-tert-butylphosphino)ferrocene) (21 mg, 0.03 mmol; Aldrich #675784) and Pd(dba)$_2$ (bis(dibenzylideneacetone)palladium(0)) (35 mg, 0.06 mmol; Aldrich #227994). To the mixture was then added 20 mL toluene. The resulting slurry was degassed using argon stream gently for 3 min. It was then sent to 110° C. bath with an air-cooled condenser on top and stirred under argon for overnight. The mixture was then cooled to RT and concentrated on rotovap to remove all the solvent. To the residue were added 150 mL EtOAc and 50 mL water. After vigorously stirring for 15-30 min, the organic phase was separated, and the aq phase and the black junks between org and aq phases were all discarded. The EtOAc phase was then washed with brine twice. The organic phase was dried over MgSO$_4$, concentrated and subjected to flash column with 0%-10% EtOAc in DCM to isolate the desired product, compound J22.

Step 6: To the above-prepared compound J22 was added 4 mL TFA at RT. After stirring for 3 min, 1 mL conc. H$_2$SO$_4$ was added. The mixture was then sent to pre-heated 80° C. bath and stirred for 45 min. It was the cooled to RT. To it was added 10 mL water. The mixture was stirred for 10 min, filtered and directly subjected to prep HPLC (running with 3 mM HCl in water as solvent A and neat acetonitrile as solvent B) to isolate the title compound as HCl salt (lyophilized). Yield: 71 mg, 63% overall yield for Step 5 and Step 6. UV: 263, 301 nm. M+H found for C$_{18}$H$_{21}$FN$_8$O: 385.4. NMR (CD$_3$OD): 9.06 (1H, t, J=2.0 Hz), 7.95 (2H, s), 7.78 (1H, d, J=12.0 Hz), 7.65 (1H, dm, J=8.4 Hz), 7.40 (1H, t, J=8.0 Hz), 7.15 (1H, dm, J=8.0 Hz), 4.80 (1H, s), 3.33 (1H, m), 3.09 (1H, m), 1.77 (2H, m), 1.03 (3H, t, J=7.6 Hz) ppm.

Example 91

Preparation of (S)-2-(3-(2H-1,2,3-triazol-2-yl)phenylamino)-6-(1-amino-3-methoxypropan-2-ylamino)-5-fluoronicotinamide

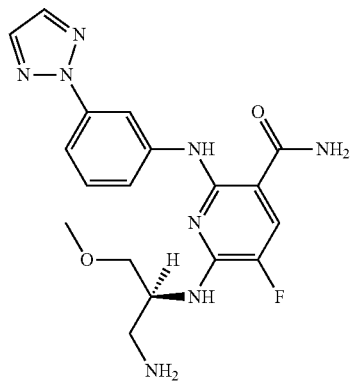 [SMILES: COC[C@H](CN)Nc1nc(Nc2cccc(-n3nccn3)c2)c(C(N)=O)cc1F]

Scheme 31:

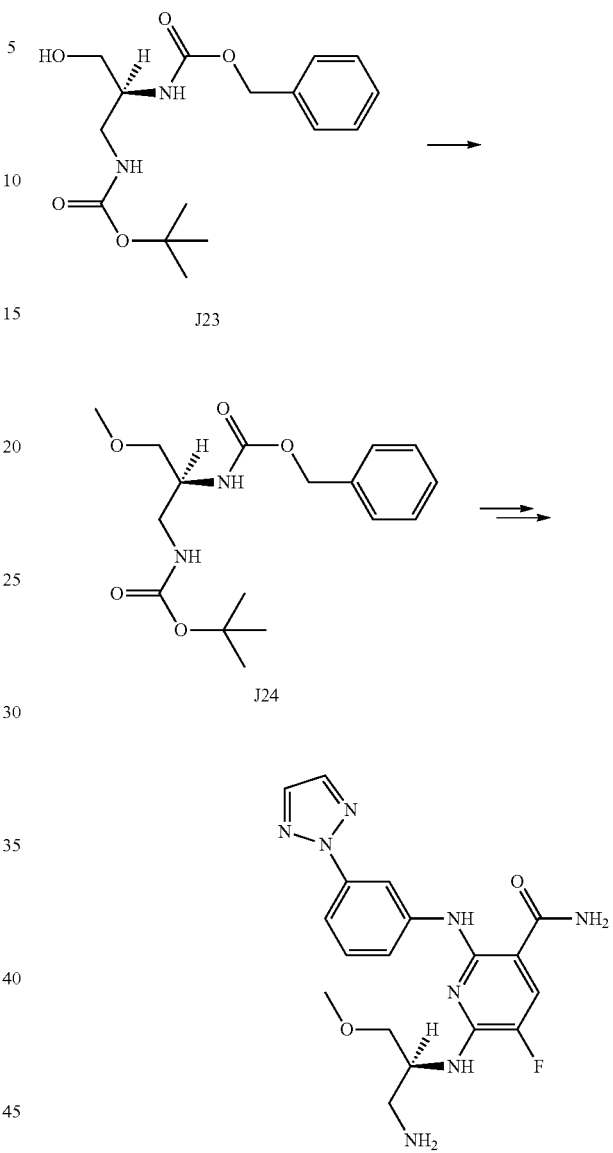

Compound J23 ((S)-2-(Z-amino)-3-(Boc-amino)-1-propanol, Chem-Impex #16241, 2.0 g, 6.0 mmol) was dissolved in 100 mL dry DCM. To it were added proton sponge (1,8-bis(dimethylamino)naphthalene, 3.21 g, 15 mmol). After 3 min, Me$_3$O$^+$BF$_4^-$ (2.22 g, 15 mmol) was added in small portions. The mixture was stirred at RT for three days; the ratio of J24 and J23 was 10:1 by HPLC in the end. To it was added 50 mL sat sodium carbonate solution and 200 mL chloroform. The mixture was stirred and the organic phase was separated. It was washed with brine twice, dried, concentrated in vacuo and purified using flash column to get pure compound J24 (1.77 g, 87% yield).

The title compound was prepared using the same chemistry shown in Example 90 with the Cbz-deprotected J24 to replace J19. UV: 268, 306 nm. M+H found for C$_{18}$H$_{21}$FN$_8$O$_2$: 401.5. NMR (CD$_3$OD): 8.97 (1H, t, J=2.4 Hz), 7.95 (2H, s), 7.80 (1H, d, J=12.0 Hz), 7.65 (1H, dm, J=8.0 Hz), 7.40 (1H, t, 8.0

Hz), 7.18 (1H, dm, J=8.0 Hz), 4.97 (1H, m), 3.72 (2H, m), 3.45 (1H, m), 3.39 (3H, s), 3.29 (1H, m) ppm.

Example 92

Preparation of (R)-6-(1-aminobutan-2-ylamino)-5-fluoro-2-(3-(pyrimidin-2-yl)phenylamino)nicotinamide

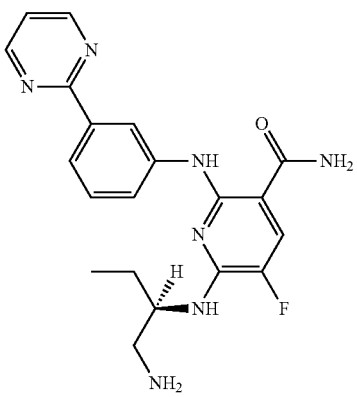 [SMILES: CC[C@H](CN)Nc1nc(Nc2cccc(-c3ncccn3)c2)c(C(N)=O)cc1F]

The title compound was prepared using the same chemistry shown in Example 90 with aniline J6 (see Example 55) to replace aniline J4. UV: 268, 306 nm. M+H found for $C_{20}H_{22}FN_7O$: 396.4. NMR (CD$_3$OD): 8.99 (1H, m), 8.86 (2H, d, J=4.8 Hz), 8.02 (1H, m), 7.77 (1H, d, J=12.0 Hz), 7.44-7.38 (3H, m), 4.70 (1H, m), 3.28 (1H, m), 3.06 (1H, m), 1.74 (2H, m), 1.03 (3H, t, J=7.6 Hz) ppm.

Example 93

Preparation of (R)-6-(1-aminobutan-2-ylamino)-2-(benzo[d]thiazol-6-ylamino)-5-fluoronicotinamide

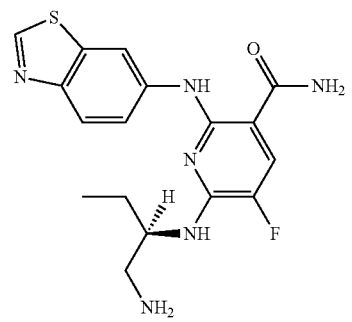 [SMILES: CC[C@H](CN)Nc1nc(Nc2ccc3ncsc3c2)c(C(N)=O)cc1F]

The title compound was prepared using the same chemistry shown in Example 90. UV: 259, 325 nm. M+H found for $C_{17}H_{19}FN_6OS$: 375.3. NMR (CD$_3$OD): 9.06 (1H, m), 8.46 (1H, d, J=2.4 Hz), 7.95 (1H, d, J=8.8 Hz), 7.76 (1H, d, J=12.0 Hz), 7.61 (1H, dd, J=8.8; 1.6 Hz), 4.41 (1H, m), 3.26 (1H, m), 3.09 (1H, m), 1.76 (2H, m), 1.09 (3H, t, J=6.8 Hz) ppm.

Example 94

Preparation of (R)-6-(1-aminobutan-2-ylamino)-5-fluoro-2-(quinolin-6-ylamino)nicotinamide

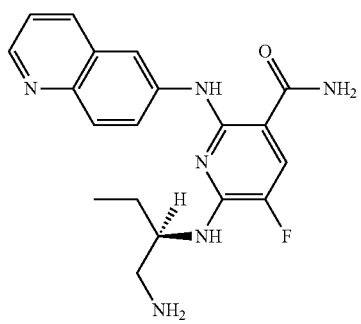 [SMILES: CC[C@H](CN)Nc1nc(Nc2ccc3ncccc3c2)c(C(N)=O)cc1F]

The title compound was prepared using the same chemistry shown in Example 90. UV: 268, 297 nm. M+H found for $C_{19}H_{21}FN_6O$: 369.4. NMR (CD$_3$OD): 8.85 (1H, dd, J=5.2; 1.2 Hz), 8.75 (1H, d, 8.0 Hz), 8.62 (1H, d, J=1.6 Hz), 8.13 (1H, dd, J=9.2; 2.0 Hz), 8.08 (1H, d, J=9.2 Hz), 7.83 (1H, d, J=12.0 Hz), 7.82 (1H, m), 4.57 (1H, m), 3.35 (1H, m), 3.16 (1H, m), 1.82 (2H, m), 1.08 (3H, t, J=7.6 Hz) ppm.

Example 95

Preparation of (R)-6-(1-aminobutan-2-ylamino)-5-fluoro-2-(5-methylpyridin-3-ylamino)nicotinamide

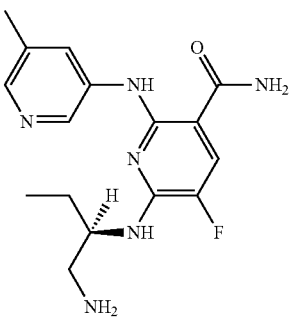 [SMILES: CC[C@H](CN)Nc1nc(Nc2cncc(C)c2)c(C(N)=O)cc1F]

The title compound was prepared using the same chemistry shown in Example 90. UV: 263, 330 nm. M+H found for $C_{16}H_{21}FN_6O$: 333.3. NMR (CD$_3$OD): 9.37 (1H, s), 8.20 (2H, m), 7.85 (1H, dd, J=11.6; 1.6 Hz), 4.48 (1H, m), 3.26 (1H, m), 3.11 (1H, m), 2.52 (3H, s), 1.73 (2H, m), 1.01 (3H, t, J=7.2 Hz) ppm.

Example 96

Preparation of (R)-6-(1-aminobutan-2-ylamino)-5-fluoro-2-(5-methoxypyridin-3-ylamino)nicotinamide

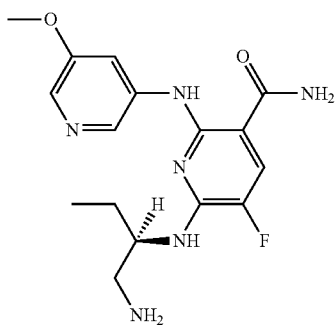 [SMILES: CC[C@H](CN)Nc1nc(Nc2cncc(OC)c2)c(C(N)=O)cc1F]

The title compound was prepared using the same chemistry shown in Example 90. UV: 272, 282 nm. M+H found for $C_{16}H_{21}FN_6O_2$: 349.3. NMR (CD$_3$OD): 9.04 (1H, s), 8.06 (1H, d, J=2.4 Hz), 7.96 (1H, d, J=2.4 Hz), 7.84 (1H, d, J=12.4 Hz), 4.47 (1H, m), 4.00 (3H, s), 3.26 (1H, m), 3.11 (1H, m), 1.71 (2H, m), 1.01 (3H, t, J=6.8 Hz) ppm.

Example 97

Preparation of (R)-6-(1-amino-1-oxobutan-2-ylamino)-5-fluoro-2-(quinolin-7-ylamino)nicotinamide

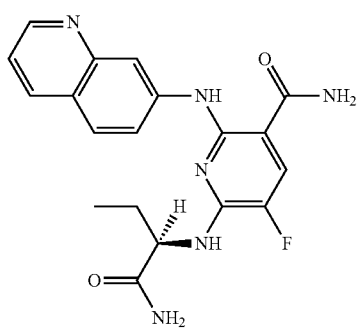

Scheme 32:

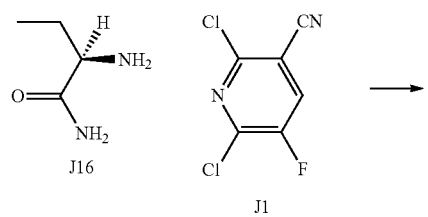

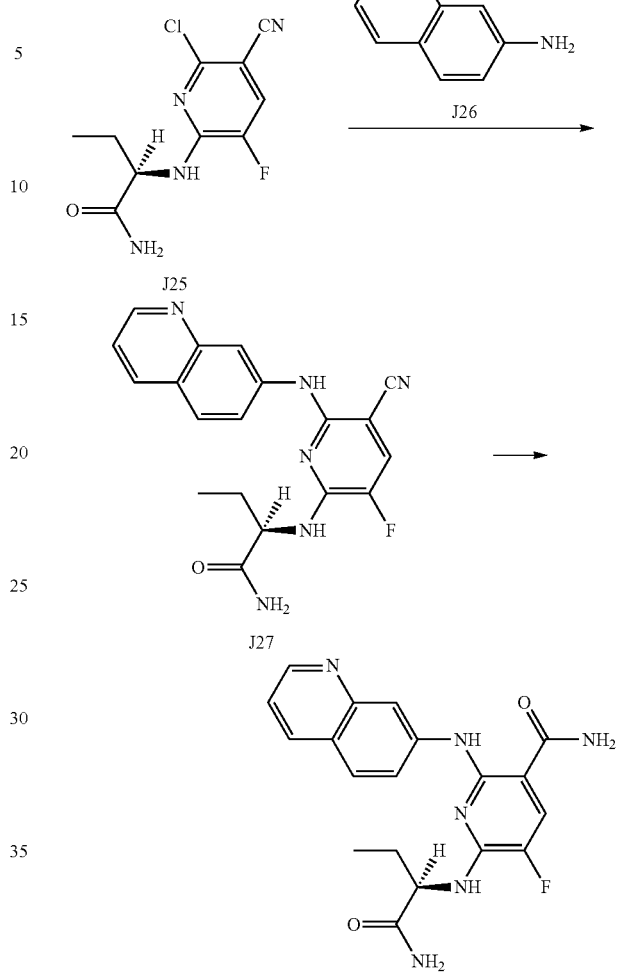

Step 1: To the mixture of (R)-(−)-2-aminobutanamide hydrochloride (J16, Aldrich, 1.00 g, 7.2 mmol) and 2,6-dichloro-5-fluoro-3-pyridinecarbonitrile (J1, Aldrich, 0.92 g, 4.8 mmol) in 40 mL NMP added DIEA (2.5 mL, 14.4 mmol). The mixture was then sent to 100° C. for stirring for 1 h. The mixture was cooled to RT, and to it was poured 300 mL EtOAc. The mixture was washed with brine four times. The organic phase was dried, concentrated and purified using silica flash column (70% EtOAc-30% DCM) to isolate compound J25 (1.21 g, 98% yield).

Step 2: The mixture of compound J25 (140 mg, 0.55 mmol), 7-aminoquinoline (J26, 158 mg, 1.1 mmol), Pd(OAc)$_2$ (25 mg, 0.11 mmol), racemic BINAP (68 mg, 0.11 mmol) and fine-powder cesium carbonate (540 mg, 1.65 mmol) in 30 mL dioxane was degassed using argon stream for 3 min. It was then stirred at 100° C. in argon atmosphere for overnight (22 h). The ratio of compound J27 and J25 was found to be 1.8:1 by HPLC. The mixture was cooled to RT, concentrated in vacuo, taken into 200 mL EtOAc and 50 mL water. The organic phase was separated and washed with brine. It was dried, concentrated and purified using silica flash column (35% EtOAc in DCM) to give compound J27.

Step 3: The above-prepared compound J27 was dissolved in 4 mL DMSO. To it were added 2 mL 50% H$_2$O$_2$ and then powder potassium carbonate (91 mg, 0.66 mmol). The mixture was stirred at RT for 30 min. It was diluted with 4 mL 1N HCl. The mixture was subjected to reverse prep HPLC to isolate the title compound as HCl salt (31 mg). UV: 263, 294 nm. M+H found for $C_{19}H_{19}FN_6O_2$: 383.3. NMR (CD$_3$OD): 9.27 (1H, s), 8.95 (1H, d, J=4.4 Hz), 8.84 (1H, m), 8.09 (1H, d, J=9.2 Hz), 7.90 (1H, d, J=11.6 Hz), 7.70 (1H, m), 7.60 (1H, dd, J=9.2; 2.0 Hz), 4.39 (1H, m), 2.09 (2H, m), 1.16 (3H, t, J=7.6 Hz) ppm.

Example 98

Preparation of (R)-6-(1-amino-1-oxobutan-2-ylamino)-5-fluoro-2-(isoquinolin-7-ylamino)nicotinamide

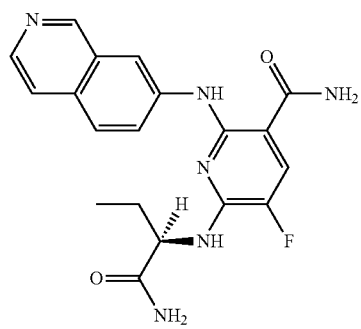 [SMILES: CC[C@@H](Nc1nc(Nc2ccc3ccncc3c2)c(C(N)=O)cc1F)C(N)=O]

Scheme 33:

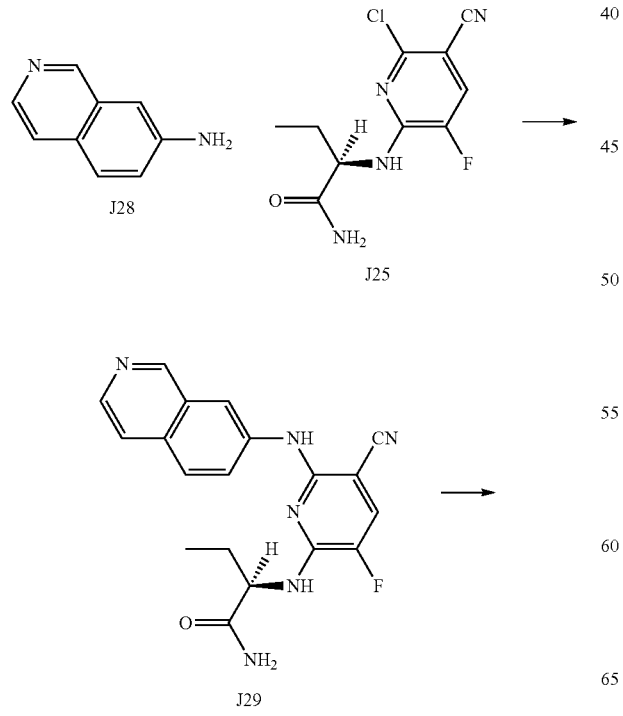

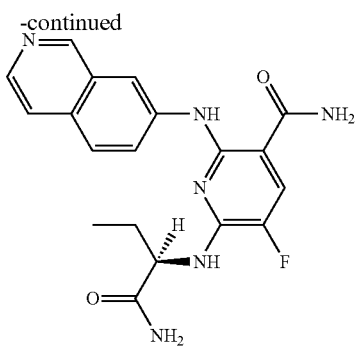

Step 1: The mixture of compound J25 (shown in Example 97, 150 mg, 0.59 mmol), 7-aminoisoquinoline (J28, 170 mg, 1.18 mmol), fine-powder cesium carbonate (577 mg, 1.77 mmol), Q-Phos (1,2,3,4,5-pentaphenyl-1'-(di-tert-butylphosphino)ferrocene) (43 mg, 0.06 mmol) and Pd(dba)$_2$ (69 mg, 0.12 mmol) in 20 mL toluene was degassed using argon stream for 3 min. It was then stirred at 110° C. in argon atmosphere for overnight. The ratio of compound J29 and J25 was found to be 1.5:1 by HPLC. The mixture was cooled to RT, concentrated in vacuo, taken into 200 mL EtOAc and 50 mL water. The organic phase was separated and washed with brine. It was dried, concentrated and purified using silica flash column (10% MeOH in DCM) to give compound J29.

Step 2: The above-prepared compound J29 was dissolved in 4 mL DMSO. To it were added 2 mL 50% H$_2$O$_2$ and then powder potassium carbonate (97 mg, 0.70 mmol). The mixture was stirred at RT for 30 min. It was diluted with 4 mL 1N HCl. The mixture was subjected to reverse prep HPLC to isolate the title compound as HCl salt (33 mg). UV: 262 nm. M+H found for $C_{19}H_{19}FN_6O_2$: 383.5. NMR (CD$_3$OD): 9.79 (1H, s), 9.23 (1H, d, J=2.4 Hz), 8.32 (1H, d, J=6.4 Hz), 8.26 (1H, d, J=6.4 Hz), 8.13 (1H, d, J=8.8 Hz), 7.89 (1H, dd, J=8.8; 2.4 Hz), 7.86 (1H, d, J=11.6 Hz), 4.37 (1H, m), 2.07 (2H, m), 1.15 (3H, t, J=7.6 Hz) ppm.

Example 99

Preparation of (R)-6-(1-amino-1-oxobutan-2-ylamino)-5-fluoro-2-(isoquinolin-6

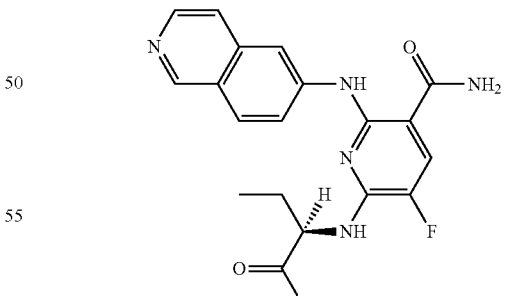

The title compound was prepared using the same chemistry shown in Example 98. UV: 257, 282, 334 nm. M+H found for $C_{19}H_{19}FN_6O_2$: 383.4. NMR (CD$_3$OD): 9.25 (1H, s), 8.90 (1H, d, J=2.0 Hz), 8.41 (1H, d, J=6.8 Hz), 8.26 (1H, d, J=6.8 Hz), 8.22 (1H, d, J=6.8 Hz), 7.88 (1H, d, J=12.0 Hz), 7.72 (1H, dd, J=8.8; 2.4 Hz), 4.43 (1H, m), 2.09 (2H, m), 1.14 (3H, t, J=7.6 Hz) ppm.

Example 100

Preparation of (R)-6-(1-amino-1-oxobutan-2-ylamino)-5-fluoro-2-(quinolin-6

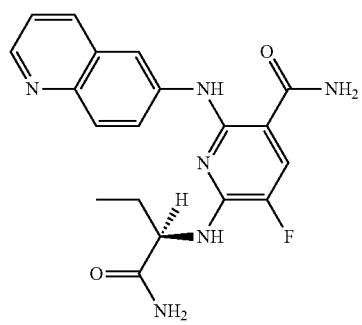

Step 1: To the mixture of (R)-(−)-2-aminobutanamide hydrochloride (1.00 g, 7.2 mmol) and 2,6-dichloro-5-fluoro-3-pyridinecarbonitrile (0.92 g, 4.8 mmol) in 40 mL NMP added DIEA (2.5 mL, 14.4 mmol). The mixture was then sent to 100° C. for stirring for 1 h. The mixture was cooled to RT, and to it was poured 300 mL EtOAc. The mixture was washed with brine four times. The organic phase was dried, concentrated and purified using silica flash column (70% EtOAc-30% DCM) to isolate (R)-2-(6-chloro-5-cyano-3-fluoropyridin-2-ylamino)butanamide (1.21 g, 98% yield).

Step 2: The mixture of (R)-2-(6-chloro-5-cyano-3-fluoropyridin-2-ylamino)butanamide (235 mg, 0.92 mmol), 6-aminoquinoline (288 mg, 2.0 mmol), Pd(OAc)$_2$ (44 mg, 0.22 mmol), racemic BINAP (136 mg, 0.22 mmol) and fine-powder cesium carbonate (1.0 g, 3.1 mmol) in 30 mL dioxane was degassed using argon stream for 3 min. It was then stirred at 100° C. in argon atmosphere for overnight. The mixture was cooled to RT, concentrated in vacuo, taken into 200 mL EtOAc and 50 mL water. The organic phase was separated and washed with brine. It was dried, concentrated and purified using silica flash column (35% EtOAc in DCM) to give (R)-2-(5-cyano-3-fluoro-6-(quinolin-6-ylamino)pyridin-2-ylamino)butanamide. It was dissolved in 4 mL DMSO. To it were added 2 mL 50% H$_2$O$_2$ and then powder potassium carbonate (91 mg, 0.66 mmol). The mixture was stirred at RT for 30 min. It was diluted with 4 mL 1N HCl. The mixture was subjected to reverse prep HPLC to isolate the title compound as HCl salt (210 mg). UV: 268, 297, 330 nm. M+H found for C$_{19}$H$_{19}$FN$_6$O$_2$: 383.4. NMR (CD$_3$OD): 9.12 (1H, d, J=8.8 Hz), 8.90 (1H, s), 8.82 (1H, d, J=5.2 Hz), 8.03 (1H, d, J=8.8 Hz), 7.92 (1H, d, J=10.0 Hz), 7.85-7.82 (2H, m), 4.39 (1H, m), 2.09 (2H, m), 1.16 (3H, t, J=7.6 Hz) ppm.

Example 101

The Synthesis of Pyridine Analogs as Syk Inhibitor in Solid Phase Chemistry

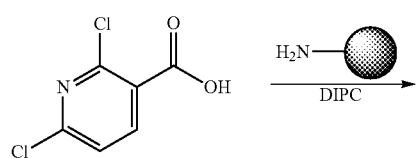

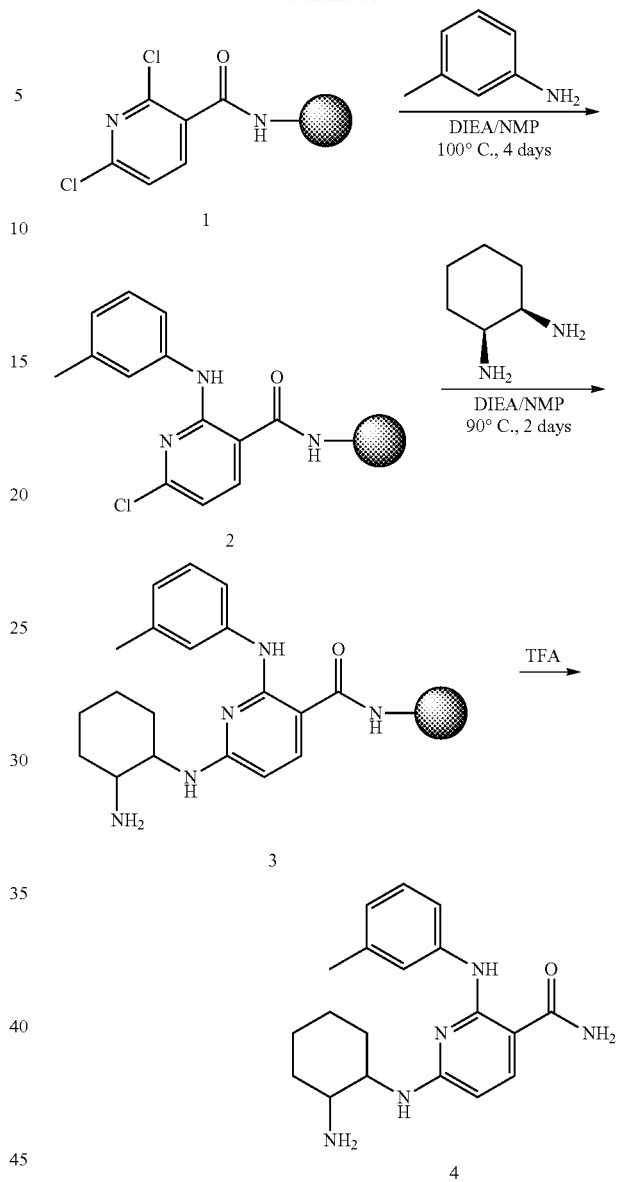

2,6-dichloronicotinamide on solid support (1). To Rink amide AM resin (0.62 mmol) in a reaction vessel, a solution of 2,6-dichloronicotinic acid (580 mg, 3 mmol), N,N-diisopropylcarbodiimide (378 mg, 3 mmol) in DCM was added. After shaking for 2 days, the resin was washed with DCM, acetonitrile and DCM.

2-(m-toluidino)-6-chloronicotinamide on solid support (2). To the resin 1 (0.12 mmol), m-toluidine (64 mg, 0.60 mmol), DIEA (0.66 mmol) in NMP was added. After shaking at 100° C. for 4 days, the resin was washed with DCM, acetonitrile and DCM.

2-(m-toluidino)-6-(2-aminocyclohexylamino)nicotinamide on solid support (4). To the resin 2 (0.03 mmol), cis-cyclohexane-1,2-diamine (60 μL, 0.50 mmol), DIEA (0.60 mmol) in NMP was added. After shaking at 90° C. for 2 days, the resin was washed with DCM, acetonitrile and DCM, and then treated with TFA/DCM (1/3) for 30 min. The collected TFA/DCM solution was concentrated. After purification with Prep-HPLC, the desired product was obtained (overall yield 31%). MS+ 340.3; UV: λ=201.6, 279.2 nm.

Example 102

6-((1R,2S)-2-aminocyclohexylamino)-2-(m-tolylamino)nicotinamide

Scheme 34:

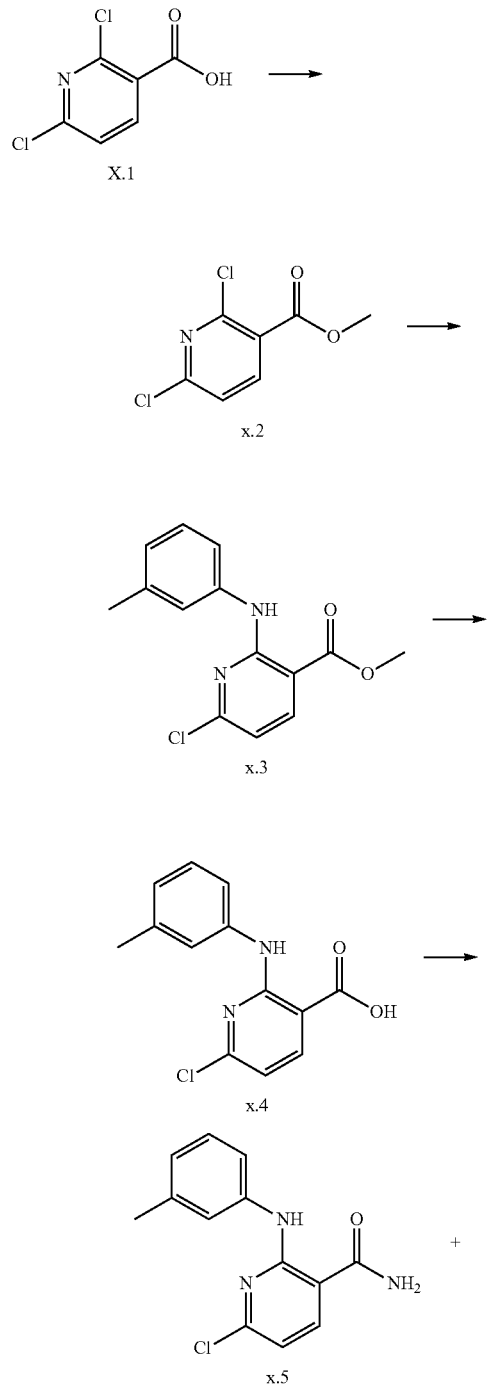

Step 1:

Dichlorocarboxylic acid X.1 (2.0 g, 10 mmol) was diluted with 10 mL each of 1,4-dioxane and methanol, then treated with a 2.0M TMSCHN$_2$ in diethyl ether solution (7.5 mL, 15 mmol) resulting in vigorous gas evolution and a light green solution. After stirring overnight the reaction was checked by UPLC which showed complete conversion to the desired product. The reaction was concentrated to near dryness, then diluted with water and stirred vigorously. The resulting granular precipitate was then filtered and dried under vacuum affording the desired methyl ester as a light beige solid (2.01 g, 97%). MS found for $C_7H_5Cl_2NO_2$ as $(M+H)^+$ 206.0, 208.0. UV λ=276.

Step 2:

Dichloro ester X.2 (2.0 g, 9.7 mmol) was diluted with 20 mL of acetonitrile then treated with diisopropyl ethyl amine (1.9 mL, 10.7 mmol) followed by meta-toluidine (0.75 mL, 9.7 mmol). The reaction as then stirred at a temperature of 50° C. for two days during which time a precipitate formed. When the progress was checked by UPLC the reaction was found to be only 50% complete with an 4:1 ratio of the 2-amino to 6-amino isomers. The solids were removed by filtration affording 0.40 g of the desired product. The filtrate was then diluted with water to 100 mL total volume affording an additional 0.50 g of the desired product. MS found for $C_{11}H_{13}ClN_2O_2$ as $(M+H)^+$ 241.0, 243.0. UV λ=263 (major), 288 (minor).

Step 3:

Methyl ester X.3 (0.5 g, 2.1 mmol) was diluted with 10 mL of 1,4-dioxane and then treated with 1.0 M LiOH (2.5 mL, 2.5 mmol) and stirred at room temperature for two hours. The reaction as diluted with ca. 30 mL of water and acidified to pH=2 with 1.0 M hydrochloric acid, and extracted twice with ethyl acetate. Concentration of the combined organic layers afforded the desired carboxylic acid which was used immediately for the next step.

Step 4:

Carboxylic acid X.4 from the previous step was dissolved in 10 mL of N,N-dimethylformamide then treated with hydroxybenzotriazole (0.54 g 4.0 mmol) and EDC (0.77 g, 4.0 mmol). The reaction was stirred until all solids dissolved (ca. 15 min), then treated with 0.5 M ammonia in dioxane (13 mL, 6.5 mmol), capped, and stirred overnight. The following morning the reaction was checked by UPLC which consumption of the starting material and the formation of two new peaks. The reaction was diluted with water and the solids isolated by filtration affording the desired product as a light beige solid (no yield calculated). UV λ=207, 265.

Step 5:

Chloropyridine X.5 (20 mg, 0.089 mmol) was treated with 4 equivalents of Boc protected cyclohexanediamine and 4 equivalents of diisopropylethylamine in N-methylpyrroldinone. The reaction was then capped and heated to 150° C. for three days. The reaction was checked by HPLC and found to be 30% complete. It was then diluted with water and purified by preparative HPLC, affording the desired product as a white solid after lyophilization. MS found for $C_{24}H_{33}N_5O_3$ as $(M+H)^+$ 440.5. UV λ=203, 282. The Boc protecting group was then removed using 4 M HCl in dioxane and the final product purified by preparative HPLC affording the desired product as a light brown solid. $C_{19}H_{25}N_5O$ as $(M+H)^+$ 340.4. UV λ=210, 281, 301. $^1$H NMR (CD$_3$OD-d$_4$, 400 MHz): δ 7.79 (d, 1H), 7.38 (d, 1H), 7.32 (s, 1H), 7.21 (t, 1H), 6.86 (d, 1H), 6.10 (d, 1H), 4.38 (m, 1H), 3.63 (m, 1H), 2.36 (s, 3H), 1.50-1.89 (m, 8H).

Example 103

(R)-2-(m-toluidino)-6-(2-amino-3-methoxypropylamino)nicotinamide

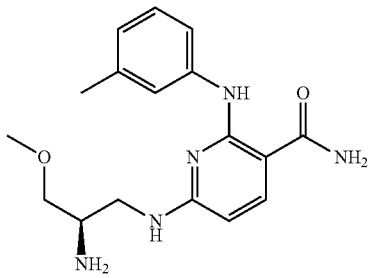 [SMILES: COC[C@H](N)CNc1ccc(C(N)=O)c(Nc2cccc(C)c2)n1]

The titled compound was prepared in a manner similar to Example 102 using Boc protected (R)-3-methoxypropane-1,2-diamine in place of cyclohexanediamine. $C_{17}H_{23}N_5O_2$ as $(M+H)^+$ 330.4. UV λ=201, 301. $^1$H NMR (CD$_3$OD-d$_4$, 400 MHz): δ 7.79 (d, 1H), 7.44 (d, 1H), 7.23 (s, 1H), 7.19 (t, 1H), 6.82 (d, 1H), 6.02 (d, 1H), 3.69 (m, 2H), 3.50 (m, 3H), 3.37 (s, 3H), 2.38 (s, 3H).

Example 104

(R)-2-(m-toluidino)-6-(1-amino-1-oxopropan-2-ylamino)nicotinamide

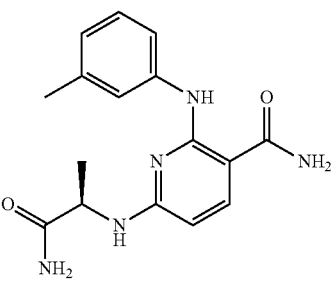 [SMILES: Cc1cccc(Nc2nc(N[C@H](C)C(N)=O)ccc2C(N)=O)c1]

The titled compound was prepared in a manner similar to Example 102 using (R)-alaninamide in place of cyclohexanediamine. $C_{16}H_{19}N_5O_2$ as $(M+H)^+$ 314.3. UV λ=201, 301. $^1$H NMR (CD$_3$OD-d$_4$, 400 MHz): δ 7.91 (br s, 1H), 7.41 (broad d, 1H), 7.30 (s, 1H), 7.14 (broad t, 1H), 6.92 (broad s, 1H), 6.00 (d, 1H), 4.41 (m, 1H), 2.38 (s, 3H), 1.43 (d, 3H).

Example 105

(R)-6-(1-amino-4-methyl-1-oxopentan-2-ylamino)-2-(m-tolylamino)nicotinamide

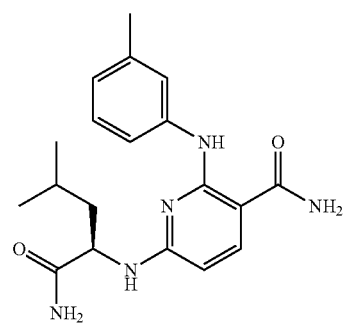 [SMILES: Cc1cccc(Nc2nc(N[C@H](CC(C)C)C(N)=O)ccc2C(N)=O)c1]

The titled compound was prepared in a manner similar to Example 102 using (R)-leucinamide in place of cyclohexanediamine. $C_{19}H_{25}N_5O_2$ as $(M+H)^+$ 356.4. UV λ=208, 279. $^1$H NMR (CD$_3$OD-d$_4$, 400 MHz): δ 7.91 (br s, 1H), 7.42 (broad d, 1H), 7.35 (s, 1H), 7.18 (broad t, 1H), 6.92 (broad s, 1H), 6.00 (d, 1H), 4.41 (m, 1H), 2.38 (s, 3H), 1.61-1.83 (m, 2H), 0.98 (d, 3H), 0.93 (d, 3H).

Example 106

Preparation of 2-(3-(2H-1,2,3-triazol-2-yl)phenylamino)-6-((1R,2S)-2-aminocyclohexylamino)-5-cyanonicotinamide

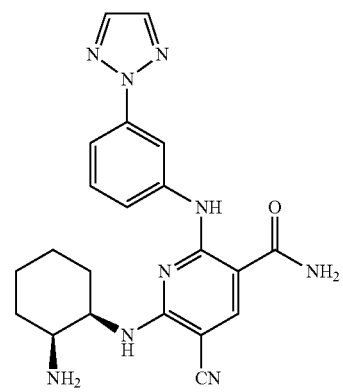 [SMILES: N#Cc1cc(C(N)=O)c(Nc2cccc(-n3nccn3)c2)nc1N[C@@H]1CCCC[C@@H]1N]

Scheme 35:

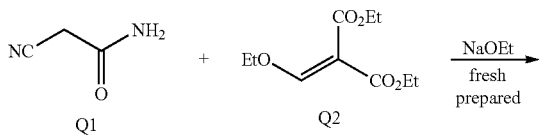

-continued

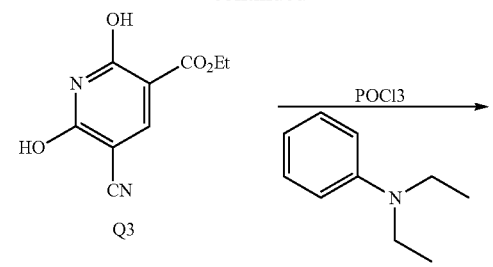

Q3

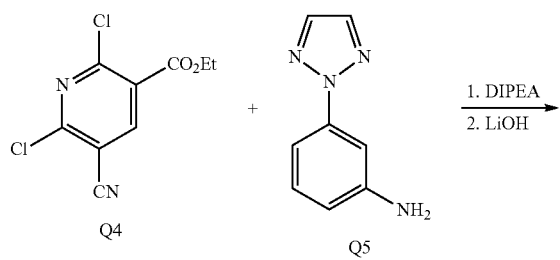

Q4    Q5

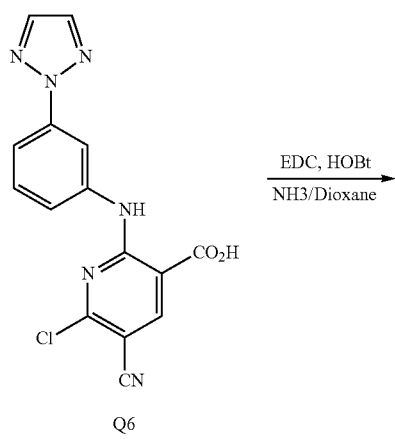

Q6

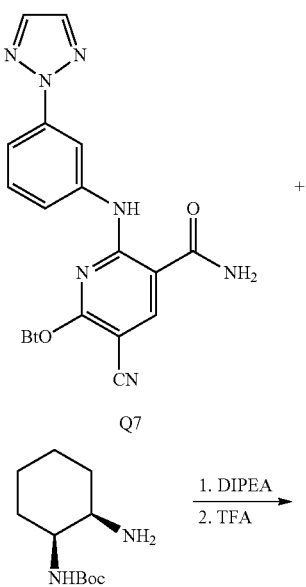

Q7

-continued

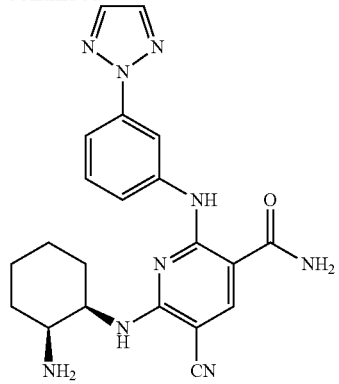

Step 1: To sodium (2.25 g, 0.1 mol) was added absolute ethanol (45 mL), the mixture was heated at 80° C. for 1 h when all the sodium has been consumed. The solution was then added 2-cyanoacetamide Q1 (3.15 g, 0.038 mol) and diethyl 2-(ethoxymethylene)malonate Q2 (8.1 g, 0.038 mol) followed by Ethanol (15 mL), the mixture was heated at reflux for 15 h, the resulting suspension was collected by filtration, the filter cake was triturated with ether and hexane, and collected by filtration, dried to give ethyl 5-cyano-2,6-dihydroxynicotinate Q3 (10.0 g).

Step 2: To a solution of ethyl 5-cyano-2,6-dihydroxynicotinate Q3 (2.06 g, 10 mmol) in $POCl_3$ (15 mL) was added N,N-diethylaniline (2.2 mL). The mixture was heated at 100° C. for 8 h, and was transferred to ice water slowly, the resulting dark red precipitate was collected by filtration and dried to give ethyl 5-cyano-2,6-dichloronicotinate Q4 (1.10 g).

Step 3: To a suspension of ethyl 5-cyano-2,6-dichloronicotinate Q4 (1.10 g, 4.4 mmol) in ACN (20 ml) was added 3-(2H-1,2,3-triazol-2-yl)aniline Q5 (774 mg, 4.84 mmol) and DIPEA (1.18 mL, 6.6 mmol). The mixture was stirred at ambient temperature for 15 h, and diluted with water; the resulting precipitate was collected by filtration to give intermediate, which was added THF (12 mL) and a solution of LiOH (106 mg, 8.8 mmol) in water (6 mL). After stirring at ambient temperature for 2 h, THF was removed by concentration and the residue was acidified to pH 2, the resulting precipitate was collected by filtration to give 2-(3-(2H-1,2,3-triazol-2-yl)phenylamino-6-chloro-5-cyanonicotinic acid Q6 (870 mg).

Step 4: To a suspension of 2-(3-(2H-1,2,3-triazol-2-yephenylamino-6-chloro-5-cyanonicotinic acid Q6 (870 mg, 2.56 mmol) in DMF (12 mL) was added EDC (1.08 g, 5.63 mmol) and HOBt monohydrate (822 mg, 5.38 mmol) at ambient temperature, after stirring for 30 min, the mixture was added Ammonia in Dioxane (0.5 M, 12 mL, 6 mmol). After stirring for 10 min, dioxane was removed and the residue was diluted with water, the resulting precipitate was collected by filtration, dried under vacuum to give 6-(1H-benzo[d][1,2,3]triazol-1-yloxy)-2-(3-(2H-1,2,3-trazol-2-yephenylamino)-5-cyanonicotinamide Q7 (1.18 g).

Step 5: To a solution of 6-(1H-benzo[d][1,2,3]triazol-1-yloxy)-2-(3-(2H-1,2,3-triazol-2-yephenylamino)-5-cyanonicotinamide Q7 (66 mg, 0.15 mmol) in ACN (1 mL) was added tert-butyl (1S,2R)-2-aminocyclohexylcarbamate (48 mg, 0.225 mmol) and DIPEA (0.04 mL, 0.225 mmol). After heating at 75° C. for 1 h, the mixture was cooled and diluted with water, the resulting precipitate was collected by filtration, dried to give intermediate 2-(3-(2H-1,2,3-triazol-2-yl)phenylamino)-6-(1R,2S)-2-tert-butyloxycarbonylaminocyclohexylamino)-5-cyanonicotinamide, which was diluted with DCM (1 mL) and added TFA (1 mL). After stirring for 30 min, the mixture was concentrated and purified by preparative HPLC to give 2-(3-(2H-1,2,3-triazol-2-yephenylamino)-6-(1R,2S)-2-aminocyclohexylamino)-5-cyanonicotinamide (35 mg). MS found for $C_{21}H_{23}N_9O$ as M+H: 418.4. λ=264.1, 311.6.

Example 107

Preparation of 6-((1R,2S)-2-aminocyclohexy-lamino)-5-cyano 2-(m-tolylamino)nicotinamide

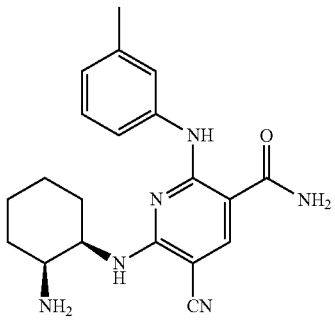 [SMILES: Cc1cccc(Nc2nc(N[C@@H]3CCCC[C@@H]3N)c(C#N)cc2C(N)=O)c1]

The title compound was prepared similar to Example 106 using m-tolylamine to replace 3-(2H-1,2,3-triazol-2-yl)aniline Q5. MS found for $C_{20}H_{24}N_6O$ as M+H: 365.4. λ=260.5, 314.0 nm.

Example 108

Preparation of (S)-2-(3-(2H-1,2,3-triazol-2-yl)phenylamino)-6-(2-aminopropylamino)-5-cyanonicotinamide

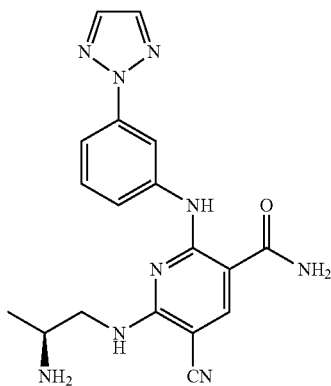 [SMILES: C[C@H](N)CNc1nc(Nc2cccc(-n3nccn3)c2)c(C(N)=O)cc1C#N]

The title compound was prepared similar to Example 106 using (S)-tert-butyl 1-aminopropan-2-ylcarbamate to replace tert-butyl (1S,2R)-2-aminocyclohexylcarbamate MS found for $C_{18}H_{19}N_9O$ as M+H: 378.4. λ=264.1, 310.4 nm.

Example 109

Preparation of (R)-2-(3-(2H-1,2,3-triazol-2-yl)phenylamino)-6-(1-aminopropan-2-ylamino)-5-cyanonicotinamide

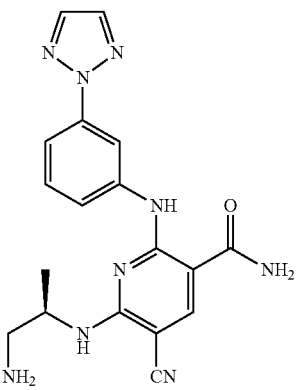 [SMILES: C[C@H](CN)Nc1nc(Nc2cccc(-n3nccn3)c2)c(C(N)=O)cc1C#N]

The title compound was prepared similar to Example 106 using (R)-tert-butyl 2-aminopropylcarbamate to replace tert-butyl (1S,2R)-2-aminocyclohexylcarbamate MS found for $C_{18}H_{19}N_9O$ as M+H: 378.4. λ=264.1, 314.0 nm.

Example 110

Preparation of (R)-2-(3-(2H-1,2,3-triazol-2-yl)phenylamino)-6-(1-amino-4-methylpentan-2-ylamino)-5-cyanonicotinamide

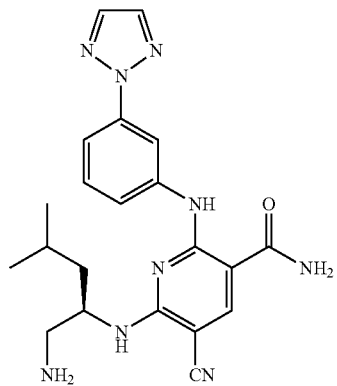 [SMILES: CC(C)C[C@H](CN)Nc1nc(Nc2cccc(-n3nccn3)c2)c(C(N)=O)cc1C#N]

The title compound was prepared similar to Example 106 using (R)-tert-butyl 2-amino-4-methylpentylcarbamate to replace tert-butyl (1S,2R)-2-aminocyclohexylcarbamate. MS found for $C_{21}H_{25}N_9O$ as M+H: 420.4. $\lambda$=265.3, 311.6 nm.

Example 111

Preparation of (S)-2-(3-(2H-1,2,3-triazol-2-yl)phenylamino)-6-(2-amino-2-cyclopropylethylamino)-5-cyanonicotinamide

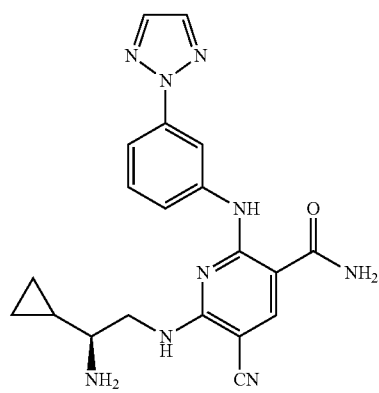 [SMILES: N#Cc1cc(C(N)=O)c(Nc2cccc(-n3nccn3)c2)nc1NC[C@@H](N)C1CC1]

The title compound was prepared similar to Example 106 using (S)-tert-butyl 2-amino-1-cyclopropylethylcarbamate to replace tert-butyl (1S,2R)-2-aminocyclohexylcarbamate. MS found for $C_{20}H_{21}N_9O$ as M+H: 404.4. $\lambda$=264.1, 311.6 nm.

Example 112

Preparation of (R)-6-(1-aminopropan-2-ylamino)-5-cyano-2-(2-methyl-2H-indazol-4-ylamino)nicotinamide

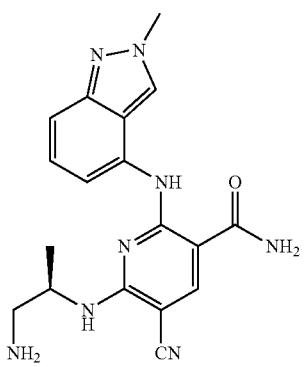 [SMILES: C[C@H](CN)Nc1nc(Nc2cccc3nn(C)cc23)c(C(N)=O)cc1C#N]

The title compound was prepared similar to Example 106 using 2-methyl-2H-indazol-4-amine to replace 3-(2H-1,2,3-triazol-2-yl)aniline Q5 and (R)-tert-butyl 2-aminopropylcarbamate to replace tert-butyl (1S,2R)-2-aminocyclohexylcarbamate. MS found for $C_{18}H_{20}N_8O$ as M+H: 365.3. $\lambda$=249.9, 275.9 nm.

Example 113

Preparation of 6-((1R,2S)-2-aminocyclohexylamino)-5-cyano-2-(quinolin-6-ylamino)nicotinamide

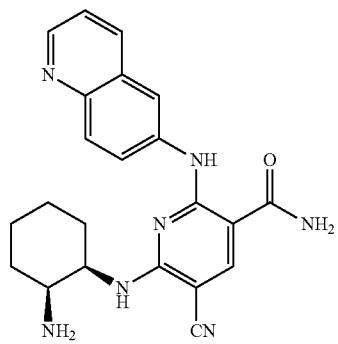

The title compound was prepared similar to Example 106 using 6-aminoquinoline to replace 3-(2H-1,2,3-triazol-2-yl)aniline Q5. MS found for $C_{22}H_{23}N_7O$ as M+H: 402.4. $\lambda$=270.5, 300.7 nm.

Example 114

Preparation of (R)-6-(1-aminopropan-2-ylamino)-5-cyano-2-(quinolin-6-ylamino)nicotinamide

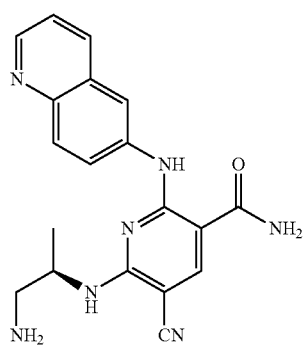

The title compound was prepared similar to Example 106 using 6-aminoquinoline to replace 3-(2H-1,2,3-triazol-2-yl)aniline Q5 and (R)-tert-butyl 2-aminopropylcarbamate to replace tert-butyl (1S,2R)-2-aminocyclohexylcarbamate. MS found for $C_{19}H_{19}N_7O$ as M+H: 362.4. λ=270.0, 300.9 nm.

Example 115

Preparation of 6-((1R,2S)-2-aminocyclohexylamino)-5-cyano-2-(2-methyl-2H-indazol-4-ylamino)nicotinamide

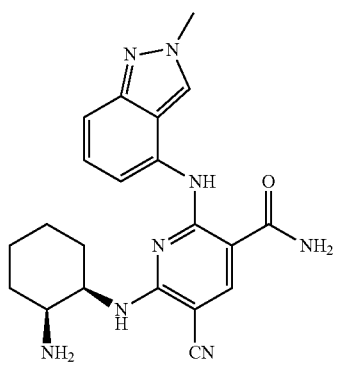 [SMILES: Cn1cc2c(Nc3nc(N[C@@H]4CCCC[C@@H]4N)c(C#N)cc3C(N)=O)cccc2n1]

The title compound was prepared similar to Example 106 using 2-methyl-2H-indazol-4-amine to replace 3-(2H-1,2,3-triazol-2-yl)aniline Q5. MS found for $C_{21}H_{24}N_8O$ as M+H: 405.4. λ=251.1, 275.9 nm.

Example 116

Preparation of 2-(3-(2H-1,2,3-triazol-2-yl)phenylamino)-6-((1R,2S)-2-aminocyclohexylamino)pyridine-3,5-dicarboxamide

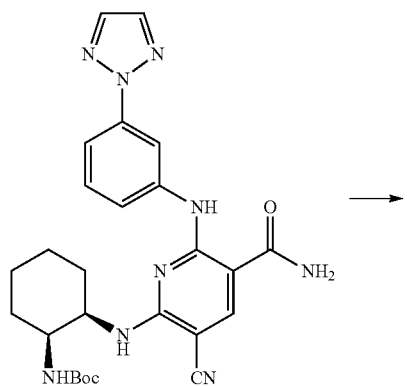

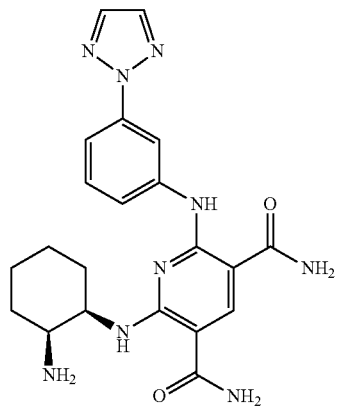

To a solution of 2-(3-(2H-1,2,3-triazol-2-yl)phenylamino)-6-((1R,2S)-2-tert-butyloxycarbonylaminocyclohexylamino)-5-cyanonicotinamide (50 mg, 0.12 mmol) in DMSO (1 mL) was added $K_2CO_3$ (200 mg, 1.45 mmol) and $H_2O_2$ (50% in $H_2O$, 0.8 mL) at ambient temperature (caution: gas evolution). After stirring for 5 min, it was added water, the resulting precipitate was collected by filtration and was treated with TFA in DCM, 10 min later, the solution was concentrated and purified by preparative HPLC to give 2-(3-(2H-1,2,3-triazol-2-yephenylamino)-6-(1R,2S)-2-aminocyclohexylamino)pyridine-3,5-dicarboxamide (20 mg). MS found for $C_{26}H_{33}N_9O_4$ as M+H: 436.4. λ=267.6, 312.8 nm.

Example 117

Preparation of 2-(1H-indazol-5-ylamino)-6-(1R,2S)-2-aminocyclohexylamino)-5-cyanonicotinamide

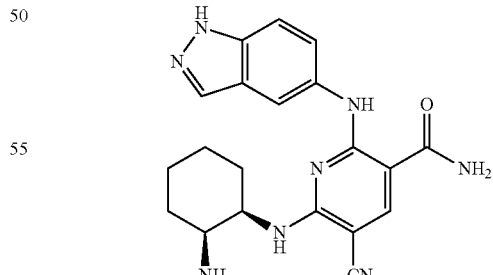

The title compound was prepared similar to Example 106 using 5-aminoindazole to replace 3-(2H-1,2,3-triazol-2-yl)aniline Q5. MS found for $C_{20}H_{22}N_8O$ as M+H: 391.4. λ=253.4, 305.6 nm.

Example 118

Preparation of 6-((1R,2S)-2-aminocyclohexylamino)-2-(benzo[d]thiazol-6-ylamino)-5-cyanonicotinamide

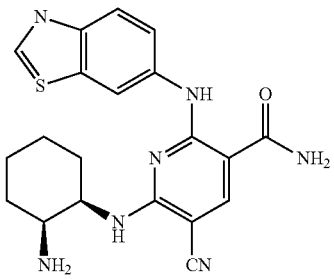

The title compound was prepared similar to Example 106 using 6-aminobenzothiazole to replace 3-(2H-1,2,3-triazol-2-yl)aniline Q5. MS found for $C_{20}H_{21}N_7OS$ as M+H: 408.4. λ=252.3 nm.

Example 119

Preparation of (S)-6-(2-amino-2-cyclopropylethylamino)-2-(benzo[d]thiazol-6-ylamino)-5-cyanonicotinamide

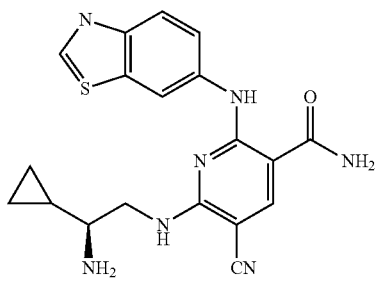

The title compound was prepared similar to Example 106 using 6-aminobenzothiazole to replace 3-(2H-1,2,3-triazol-2-yl)aniline Q5 and using (S)-tert-butyl 2-amino-1-cyclopropylethylcarbamate to replace tert-butyl (1S,2R)-2-aminocyclohexylcarbamate. MS found for $C_{19}H_{19}N_7OS$ as M+H: 394.4. λ=251.1 nm.

Example 120

Preparation of 6-((1R,2S)-2-aminocyclohexylamino)-5-cyano-2-(1-methyl-1H-indazol-4-ylamino)nicotinamide

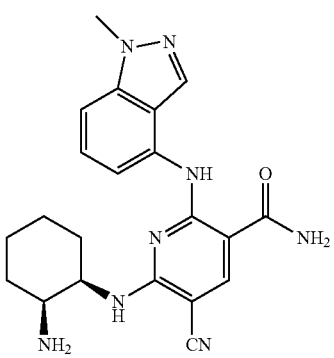 [SMILES: Cn1ncc2c(Nc3nc(N[C@@H]4CCCC[C@@H]4N)c(C#N)cc3C(N)=O)cccc21]

The title compound was prepared similar to Example 106 using 1-methyl-1H-indazol-4-amine to replace 3-(2H-1,2,3-triazol-2-yl)aniline Q5. MS found for $C_{21}H_{24}N_8O$ as M+H: 405.4. λ=264.1, 310.4 nm.

Example 121

Preparation of 2-(4-(1H-pyrazol-1-yephenylamino)-6-(1R,2S)-2-aminocyclohexylamino)-5-cyanonicotinamide

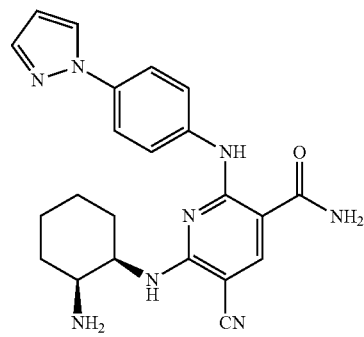 [SMILES: N#Cc1cc(C(N)=O)c(Nc2ccc(-n3cccn3)cc2)nc1N[C@@H]1CCCC[C@@H]1N]

The title compound was prepared similar to Example 106 using 4-(1H-pyrazol-1-yl)aniline to replace 3-(2H-1,2,3-triazol-2-yl)aniline Q5. MS found for $C_{22}H_{24}N_8O$ as M+H: 417.4. λ=267.6 nm.

Example 122

Preparation of (R)-6-(1-amino-4-methylpentan-2-ylamino)-5-cyano-2-(quinolin-6-ylamino)nicotinamide

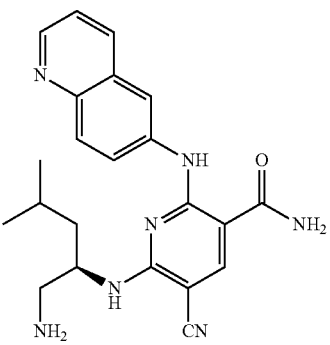 [SMILES: CC(C)C[C@H](CN)Nc1nc(Nc2ccc3ncccc3c2)c(C(N)=O)cc1C#N]

The title compound was prepared similar to Example 106 using 6-aminoqinoline to replace 3-(2H-1,2,3-triazol-2-yl)aniline Q5 and using (R)-tert-butyl 2-amino-4-methylpentylcarbamate to replace tert-butyl (1S,2R)-2-aminocyclohexylcarbamate. MS found for $C_{22}H_{25}N_7O$ as M+H: 404.4. λ=271.2, 300.9 nm.

Example 123

Preparation of (R)-6-(1-amino-4-methylpentan-2-ylamino)-2-(benzo[d]thiazol-6-ylamino)-5-cyanonicotinamide

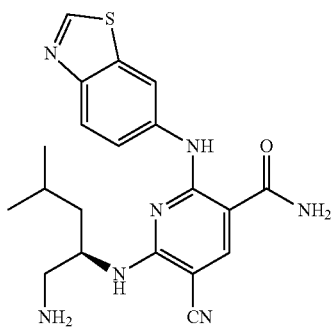 [SMILES: CC(C)C[C@H](CN)Nc1nc(Nc2ccc3ncsc3c2)c(C(N)=O)cc1C#N]

The title compound was prepared similar to Example 106 using 6-aminobenzothiazole to replace 3-(2H-1,2,3-triazol-2-yl)aniline Q5 and using (R)-tert-buty 2-amino-4-methylpentylcarbamate to replace tert-butyl (1S,2R)-2-aminocyclohexylcarbamate. MS found for $C_{20}H_{23}N_7OS$ as M+H: 410.3. λ=252.3 nm.

Example 124

Preparation of (R)-6-(1-amino-4-methyl-1-oxopentan-2-ylamino)-2-(quinolin-6-ylamino)-5-cyanonicotinamide

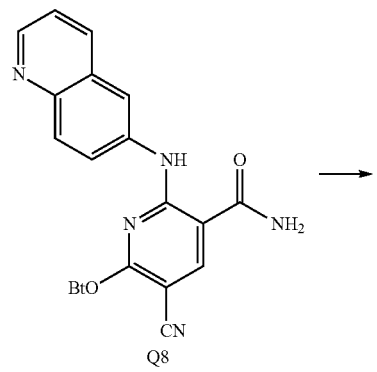

Compound Q8 was prepared similar to compound Q7 using 6-aminoquinoline to replace 3-(2H-1,2,3-triazol-2-yl)aniline Q5.

To a solution of Q8 (62 mg, 0.15 mmol) in NMP (0.8 mL) was added D-leucinamide hydrochloride salt (36 mg, 0.22 mmol) followed by DIPEA (0.078 mL, 0.44 mmol). The mixture was heated at 100° C. for 2 h, and was subjected to preparative HPLC to yield (R)-6-(1-amino-4-methyl-1-oxopentan-2-ylamino)-2-(quinolin-6-ylamino)-5-cyanonicotinamide as TFA salt (28 mg). MS found for $C_{22}H_{23}N_7O_2$ as M+H: 418.4. λ=271.2, 300.9 nm.

Example 125

Preparation of (R)-2-(3-(2H-1,2,3-triazol-2-yl)phenylamino)-6-(1-amino-4-methyl-1-oxopentan-2-ylamino)-5-cyanonicotinamide

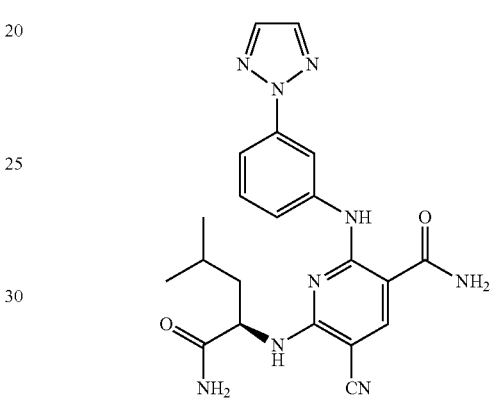

The title compound was prepared similar to Example 124 using compound Q5 to replace compound Q8. MS found for $C_{21}H_{23}N_9O_2$ as M+H: 434.4. λ=265.3, 312.8 nm.

Example 126

Preparation of (R)-2-(3-(2H-1,2,3-triazol-2-yl)phenylamino)-6-(1-amino-3-methyl-1-oxobutan-2-ylamino)-5-cyanonicotinamide

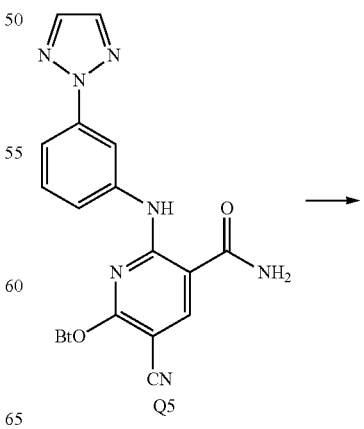

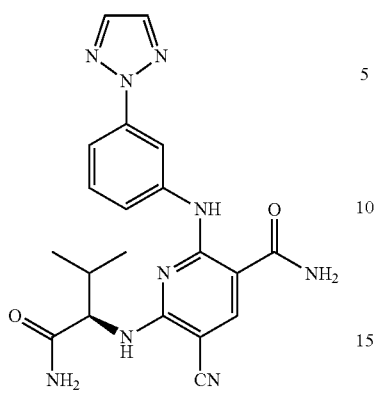

To a solution of Q5 (66 mg, 0.15 mmol) in NMP (0.8 mL) was added D-valinamide hydrochloride salt (36 mg, 0.22 mmol) followed by DIPEA (0.078 mL, 0.44 mmol). The mixture was heated at 100° C. for 2 h, and was subjected to preparative HPLC to yield (R)-2-(3-(2H-1,2,3-triazol-2-yl)phenylamino)-6-(1-amino-3-methyl-1-oxobutan-2-ylamino)-5-cyanonicotinamide as TFA salt (32 mg). MS found for $C_{20}H_{21}N_9O_2$ as M+H: 420.4. $\lambda$=265.0, 313.6 nm.

Example 127

Preparation of (R)-2-(1H-indazol-5-ylamino)-6-(1-amino-4-methyl-1-oxopentan-2-ylamino)-5-cyanonicotinamide

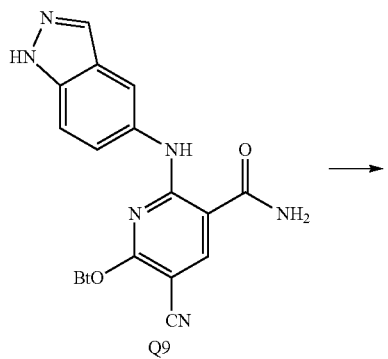

Compound Q9 was prepared similar to compound Q7 using 5-aminoindazole to replace 3-(2H-1,2,3-triazol-2-yl)aniline Q5.

To a solution of Q9 (62 mg, 0.15 mmol) in NMP (0.8 mL) was added D-leucinamide hydrochloride salt (36 mg, 0.22 mmol) followed by DIPEA (0.078 mL, 0.44 mmol). The mixture was heated at 100° C. for 2 h, and was subjected to preparative HPLC to yield (R)-2-(1H-indazol-5-ylamino)-6-(1-amino-4-methyl-1-oxopentan-2-ylamino)-5-cyanonicotinamide as TFA salt (10 mg). MS found for $C_{20}H_{22}N_8O_2$ as M+H: 407.4. $\lambda$=256.8, 311.5 nm.

Example 128

Preparation of (R)-6-(1-amino-3-methylbuttan-2-ylamino)-5-cyano-2-(quinolin-6-ylamino)nicotinamide

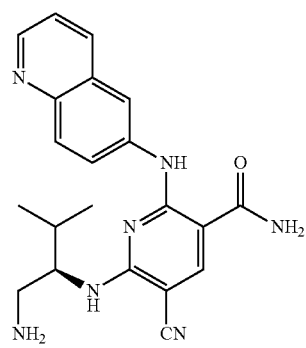 [SMILES: CC(C)[C@H](CN)Nc1nc(Nc2ccc3ncccc3c2)c(C(N)=O)cc1C#N]

The title compound was prepared similar to Example 122 using (R)-tert-butyl-2-amino-3-methylbutylcarbamate to replace (R)-tert-butyl 2-amino-4-methylpentylcarbamate. MS found for $C_{21}H_{23}{-}_7O$ as M+H: 390.4. $\lambda$=271.2, 300.9 nm.

Example 129

Preparation of 6-(1R,2S)-2-aminocyclohexylamino)-5-cyano-2-(quinolin-3-ylamino)nicotinamide

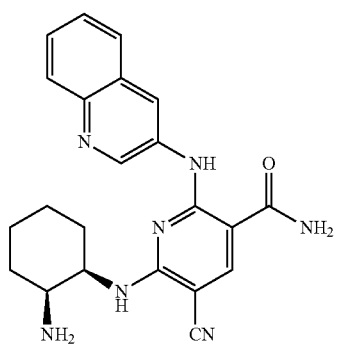 [SMILES: N#Cc1cc(C(N)=O)c(Nc2cnc3ccccc3c2)nc1N[C@@H]1CCCC[C@@H]1N]

The title compound was prepared similar to Example 106 using 3-aminoquinoline to replace 3-(2H-1,2,3-triazol-2-yl)aniline Q5. MS found for $C_{22}H_{23}N_7O$ as M+H: 402.4. λ=298.8 nm.

Example 130

Preparation of 6-(1R,2S)-2-aminocyclohexylamino)-5-cyano-2-(3-(pyrimidin-2-yl)phenylamino)nicotinamide

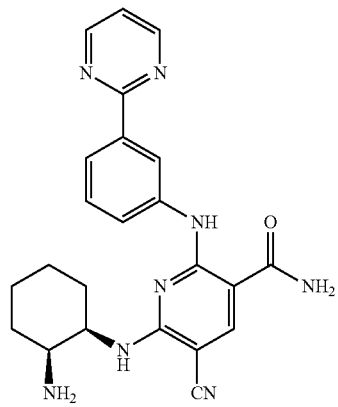 [SMILES: N#Cc1cc(C(N)=O)c(Nc2cccc(-c3ncccn3)c2)nc1N[C@@H]1CCCC[C@@H]1N]

The title compound was prepared similar to Example 106 using 3-(pyrimidin-2-yl)aniline to replace 3-(2H-1,2,3-triazol-2-yl)aniline Q5. MS found for $C_{23}H_{24}N_8O$ as M+H: 429.4. λ=255.8, 310.4 nm.

Example 131

Preparation of 6-((1R,2S)-2-aminocyclohexylamino)-5-cyano-2-(3-(pyridin-2-yl)phenylamino)nicotinamide

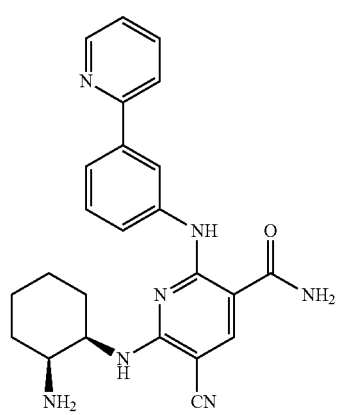 [SMILES: N#Cc1cc(C(N)=O)c(Nc2cccc(-c3ccccn3)c2)nc1N[C@@H]1CCCC[C@@H]1N]

The title compound was prepared similar to Example 106 using 3-(pyridin-2-yl)aniline to replace 3-(2H-1,2,3-triazol-2-yl)aniline Q5. MS found for $C_{24}H_{25}N_7O$ as M+H: 428.3. λ=242.8, 305.6 nm.

Example 132

Preparation of 2-(3-(2H-1,2,3-triazol-2-yl)phenylamino)-6-((1R,2S)-2-aminocyclohexylamino)nicotinamide (4)

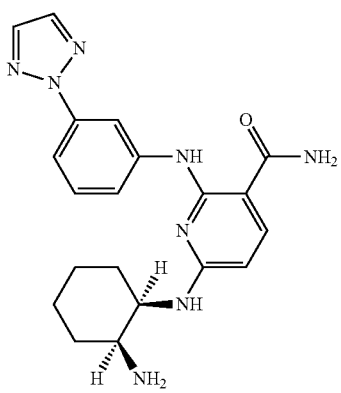

The title compound was prepared according to scheme 36.

Scheme 36.

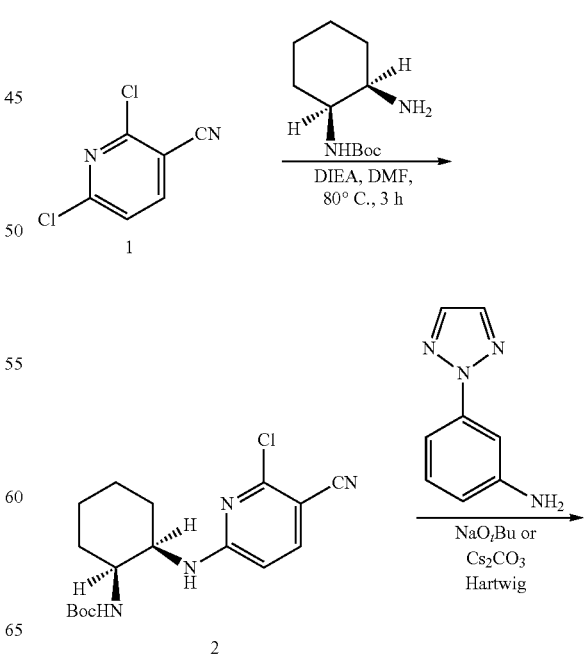

-continued

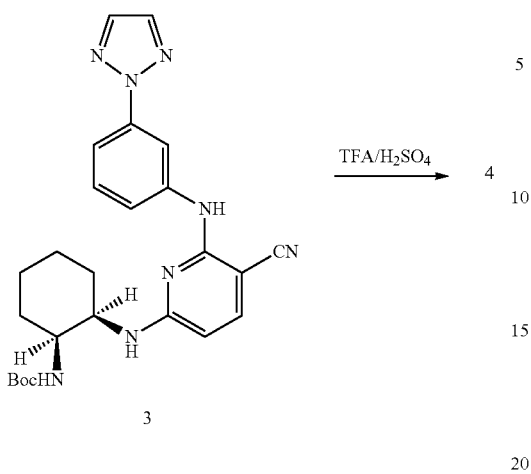

To a solution of 2,6-dichloropyridine-3-carbonitrile (1) (Aldrich 684872, 1.73 g, 0.100 mol) in ~100 mL of DMF was added ~2 ml of DIEA and 2.15 g of tert-butyl (1S,2R)-2-aminocyclohexylcarbamate (0.100 mol, 1 eq). The reaction mixture was stirred at 80° C. for 3 hours. After cooling, ~200 mL of $H_2O$ was added. The mixture was extracted with EtOAc (2×100 mL). The combined organics were washed with $H_2O$ (4×100 mL), brine (2×75 mL), and dried over $MgSO_4$. The solvent was removed in vacuo to provide crude product. The crude was dissolved in $CH_2Cl_2$ and a normal phase column was run as follows:

| Gradient: % EtOAc (in $CH_2Cl_2$) | Minutes |
|---|---|
| 0 | Initial |
| 5 | 30.0 |
| 15 | 10.0 |

Product eluted at ~10% EtOAc. Eluent concentrated to give 2.30 g of 2 (tert-butyl (1S,2R)-2-(6-chloro-5-cyano-pyridin-2-ylamino)cyclohexylcarbamate). 66% yield.

To 130 mg (0.37 mmol) of 2, 118 mg of the 3-(2H-1,2,3-triazol-2-yl)aniline (1.2 eq), 107 mg $NaO_tBu$ (3 eq), 85 mg $Pd(dba)_2$ (0.4 eq), and 53 mg Q-Phos (Aldrich 675784, 0.2 eq) was added ~5 mL dry toluene. The reaction mixture was degassed with Ar for 10 min and then refluxed under argon at 110° C. for 3 hours. The reaction mixture was cooled and diluted with EtOAc, washed with water and brine, dried over $MgSO_4$, and concentrated. The resulting oil was dissolved in a 3:1 mixture of $TFA/H_2SO_4$. The mixture was heated to 80° C. for 1 hour and then cooled to room temperature. Approximately 10 mL $H_2O$ was added to the mixture and the resulting solution was subjected to reverse phase preparative HPLC. Product was isolated by utilizing a mobile phase with 0.1% TFA in water as solvent A and 0.1% TFA in acetonitrile as solvent B and eluting with a 15% to 50% B mixture over 10 minutes.

Yield: 23 mg. UV: 265, 306 nm. M+H found for $C_{20}H_{24}N_8O$: 393.3. NMR ($CD_3OD$): 8.96 (1H, br), 7.96 (2H, s), 7.82 (1H, d, J=8.8 Hz), 7.67 (1H, d, J=6.0 Hz), 7.42 (1H, t, J=6.0 Hz), 7.17 (1H, d, J=5.6 Hz), 6.18 (1H, d, J=8.8 Hz), 4.78 (1H, br), 3.65 (1H, br), 1.90-1.45 (8H, m) ppm.

Example 133

Preparation of 2-(3-(pyrimidin-2-yl)phenylamino)-6-((1R,2S)-2-aminocyclohexylamino)nicotinamide

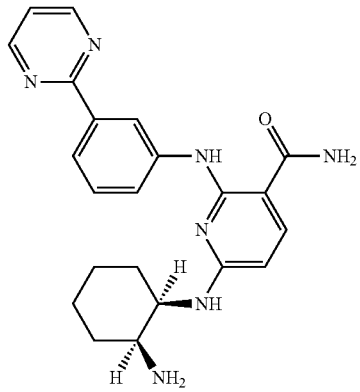 [SMILES: NC(=O)c1ccc(N[C@@H]2CCCC[C@@H]2N)nc1Nc1cccc(-c2ncccn2)c1]

The title compound was prepared by utilizing intermediate 2,3-(pyrimidin-2-yl)aniline and analogous chemistry as shown in Scheme 36. UV: 261, 302, 337 nm. M+H found for $C_{22}H_{25}N_7O$: 404.3. NMR ($CD_3OD$): 8.91 (1H, br), 8.87 (2H, dd, J=2.8 Hz, 4.4 Hz), 8.05-8.02 (1H, m), 7.82 (1H, dd, J=2.8 Hz, 4.8 Hz), 7.46-7.36 (3H, m), 6.17 (1H, dd, J=2.8 Hz, 4.4 Hz), 4.68 (1H, br), 3.59 (1H, br), 1.90-1.40 (8H, m) ppm.

Example 134

Preparation of 2-(quinolin-6-ylamino)-6-((1R,2S)-2-aminocyclohexylamino)nicotinamide

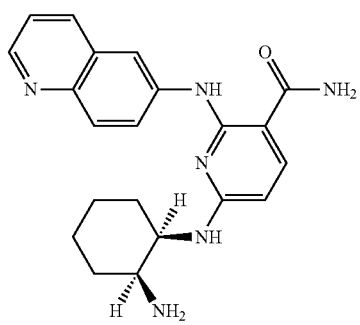 [SMILES: NC(=O)c1ccc(N[C@@H]2CCCC[C@@H]2N)nc1Nc1ccc2ncccc2c1]

The title compound was prepared by utilizing intermediate 2,6-aminoquinoline and analogous chemistry as shown in Scheme 36. UV: 268, 299, 327 nm. M+H found for $C_{21}H_{24}N_6O$: 377.3. NMR ($CD_3OD$): 8.86 (1H, d, J=4.8 Hz), 8.78 (1H, d, J=8.8 Hz), 8.68 (1H, br), 8.18-8.07 (2H, m), 7.90-7.82 (2H, m), 6.28 (1H, d, J=8.8 Hz), 4.62 (1H, br), 3.76 (1H, br), 2.05-1.50 (8H, m) ppm.

Example 135

Preparation of 2-(isoquinolin-6-ylamino)-6-((1R,2S)-2-aminocyclohexylamino)nicotinamide

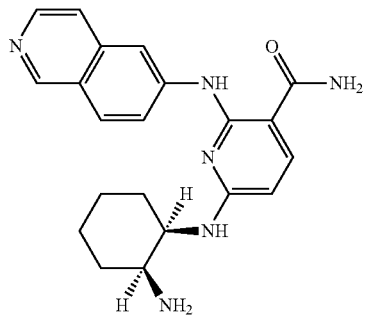 [SMILES: NC(=O)c1ccc(N[C@@H]2CCCC[C@@H]2N)nc1Nc1ccc2cnccc2c1]

The title compound was prepared by utilizing intermediate 2,6-aminoisoquinoline and analogous chemistry as shown in Scheme 35. UV: 216, 261, 285, 326 nm. M+H found for $C_{21}H_{24}N_6O$: 377.2. NMR ($CD_3OD$): 9.31 (1H, s), 8.75 (1H, br), 8.31-8.25 (2H, m), 8.05 (1H, d, J=6.8 Hz), 7.98 (1H, dd, J=2.0 Hz, 8.8 Hz), 7.93 (1H, d, J=8.8 Hz), 6.38 (1H, d, J=9.2 Hz), 4.65 (1H, br), 3.78 (1H, br), 2.05-1.56 (8H, m) ppm.

Example 136

Preparation of 2-(1-methyl-1H-indazol-4-ylamino)-6-((1R,2S)-2-aminocyclohexylamino)-5-fluoronicotinamide

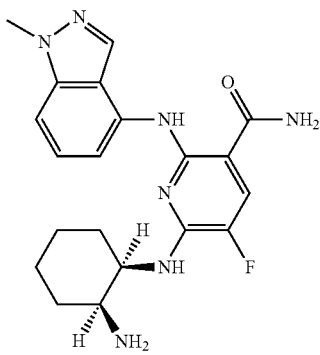 [SMILES: Cn1ncc2c(Nc3nc(N[C@@H]4CCCC[C@@H]4N)c(F)cc3C(N)=O)cccc21]

The title compound was prepared by utilizing the fluoro analog of intermediate 2,4-amino-1-methyl-1H-indazole, and analogous chemistry as shown in Scheme 36. UV: 263, 338 nm. M+H found for $C_{20}H_{24}FN_7O$: 398.3. NMR ($CD_3OD$): 8.06 (1H, s), 7.90 (1H, d, J=7.6 Hz), 7.81 (1H, d, J=11.6 Hz), 7.40-7.36 (1H, m), 7.15 (1H, d, J=8 Hz), 4.40 (1H, br), 4.05 (3H, s), 3.92 (1H, br), 1.94-1.53 (8H, m) ppm.

Example 137

Preparation of 2-(isoquinolin-7-ylamino)-6-((1R,2S)-2-aminocyclohexylamino)nicotinamide

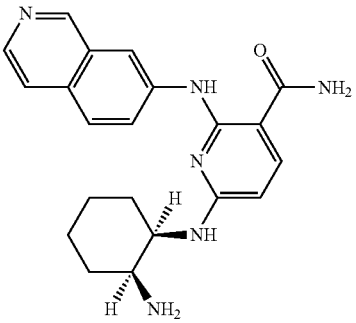

The title compound was prepared by utilizing intermediate 2,7-aminoisoquinoline and analogous chemistry as shown in Scheme 36. UV: 268, 336 nm. M+H found for $C_{21}H_{24}N_6O$: 377.3. NMR ($CD_3OD$): 9.40 (1H, s), 8.76 (1H, br), 8.36 (1H, d, J=6.4 Hz), 8.26 (1H, dd, J=2.4 Hz, 9.2 Hz), 8.20 (1H, d, J=6.0 Hz), 8.13 (1H, d, J=9.2 Hz), 7.89 (1H, d, J=8.4 Hz), 6.29 (1H, d, J=8.8 Hz), 4.62 (1H, br), 3.75 (1H, br), 2.06-1.55 (8H, m) ppm.

Example 138

Preparation of 2-(3-(1H-1,2,4-triazol-1-yepheny-lamino)-6-(1R,2S)-2-aminocyclohexylamino)nicotinamide

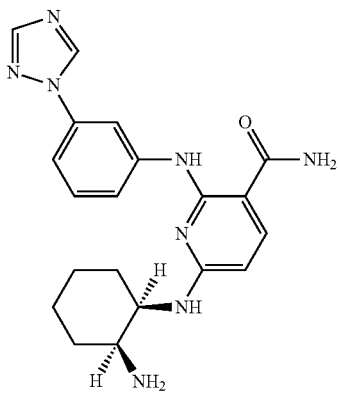

The title compound was prepared by utilizing intermediate 2,3-(1H-1,2,4-triazol-1-yl)aniline, and analogous chemistry as shown in Scheme 36. UV: 237, 262, 307 nm. M+H found for $C_{20}H_{24}N_8O$: 393.3. NMR ($CD_3OD$): 9.12 (1H, s), 8.67 (1H, br), 8.24 (1H, s), 7.82 (1H, d, J=8.8 Hz), 7.44 (1H, t, J=6.0 Hz), 7.37 (1H, dt, J=0.6 Hz, 6.8 Hz) 7.29-7.25 (1H, m), 6.19 (1H, d, J=8.8 Hz), 4.68 (1H, br), 3.69 (1H, br), 1.90-1.45 (8H, m) ppm.

Example 139

Preparation of 2-(1-methyl-1H-indazol-5-ylamino)-6-((1R,2S)-2-aminocyclohexylamino)-5-fluoronicotinamide

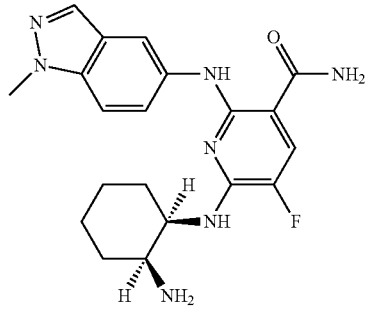 [SMILES: Cn1ncc2cc(Nc3nc(N[C@@H]4CCCC[C@@H]4N)c(F)cc3C(N)=O)ccc21]

The title compound was prepared by utilizing the fluoro analog of intermediate 2,5-amino-1-methyl-1H-indazole, and analogous chemistry as shown in Scheme 36.

UV: 243, 288 nm. M+H found for $C_{20}H_{24}FN_7O$: 398.3. NMR (CD$_3$OD): 8.00 (1H, dd, J=0.8 Hz, 2.0 Hz), 7.93 (1H, d, J=0.6 Hz), 7.74 (1H, d, J=12.4 Hz), 7.51 (1H, dd, J=0.8 Hz, 9.2 Hz), 7.43 (1H, dd, J=2.0 Hz, 8.8 Hz), 4.30 (1H, br), 4.04 (3H, s), 3.79 (1H, br), 1.94-1.53 (8H, m) ppm.

Example 140

Preparation of 6-(cis-2-aminocyclohexylamino)-2-(4-(1H-pyrazol-1-yl)phenylamino)nicotinamide

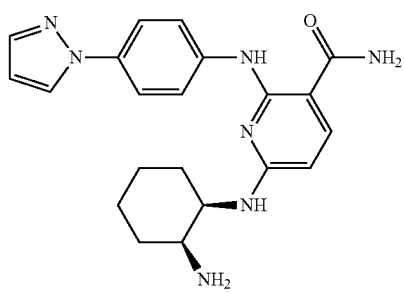 [SMILES: NC(=O)c1ccc(N[C@@H]2CCCC[C@@H]2N)nc1Nc1ccc(-n2cccn2)cc1]

The title compound was prepared according to scheme 37.

Scheme 37:

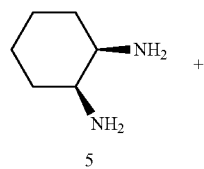

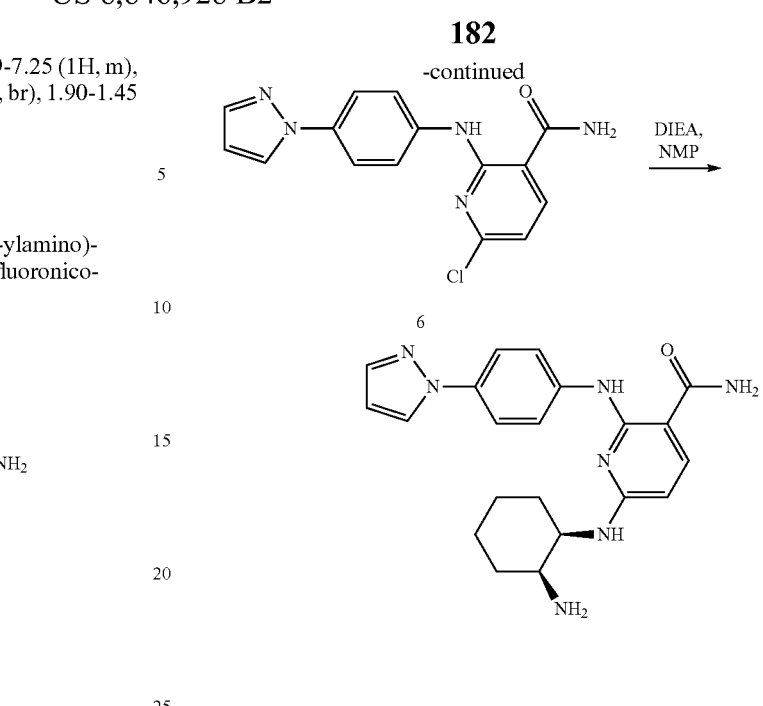

A stirring solution of cis-1,2-diaminocyclohexane (5) (~0.1 mL), 2-(4-(1H-pyrazol-1-yl)phenylamino)-6-chloronicotinamide (6) (30 mg), DIEA (~0.1 mL) in ~5 mL NMP was heated at 150° C. for 18 hours. The reaction mixture was cooled and a H$_2$O/TFA mixture was added. A preparative rpHPLC utilizing a mobile phase with 0.1% TFA in water as solvent A and 0.1% TFA in acetonitrile as solvent B and eluting with a 10% to 50% B mixture over 10 minutes was run. UV: 276, 312 nm. M+H found for $C_{21}H_{25}N_7O$: 392.3. NMR (CD$_3$OD): 8.14 (1H, d, J=2.0 Hz), 7.80 (1H, d, J=8.4 Hz), 7.73-7.63 (5H, m), 6.52 (1H, t, J=2.0 Hz), 6.13 (1H, d, J=8.4 Hz), 4.40 (1H, br), 3.76 (1H, br), 1.92-1.53 (8H, m) ppm.

Example 141

Preparation of 6-(cis-2-aminocyclohexylamino)-2-(1H-indazol-5-ylamino)nicotinamide

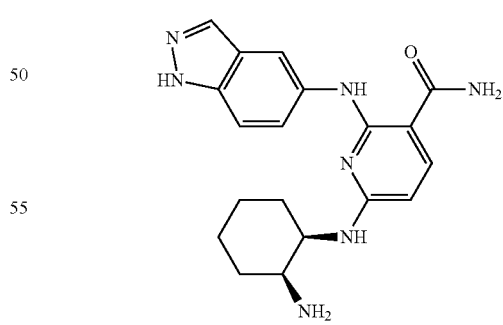

The title compound was prepared by reacting 5 (from scheme 37) and 2-(1H-indazol-5-ylamino)-6-chloronicotinamide (in place of 2-(4-(1H-pyrazol-1-yephenylamino)-6-chloronicotinamide) utilizing analogous chemistry as shown in scheme 37. UV: 277 nm. M+H found for $C_{19}H_{23}N_7O$: 366.2. NMR (CD$_3$OD): 8.02-7.97 (2H, m), 7.81 (1H, d, J=8.8

Hz), 7.53 (1H, d, J=9.2 Hz), 7.42 (1H, dd, J=2.0 Hz, 8.8 Hz), 6.09 (1H, d, J=8.4 Hz), 4.30 (1H, br), 3.60 (1H, br), 1.91-1.48 (8H, m) ppm.

Example 142

Preparation of 6-(cis-2-aminocyclohexylamino)-4-(3-toluidino)nicotinamide

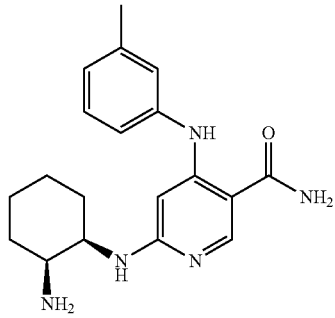

The title compound was prepared with intermediate (7) according to scheme 38 below.

Scheme 38:

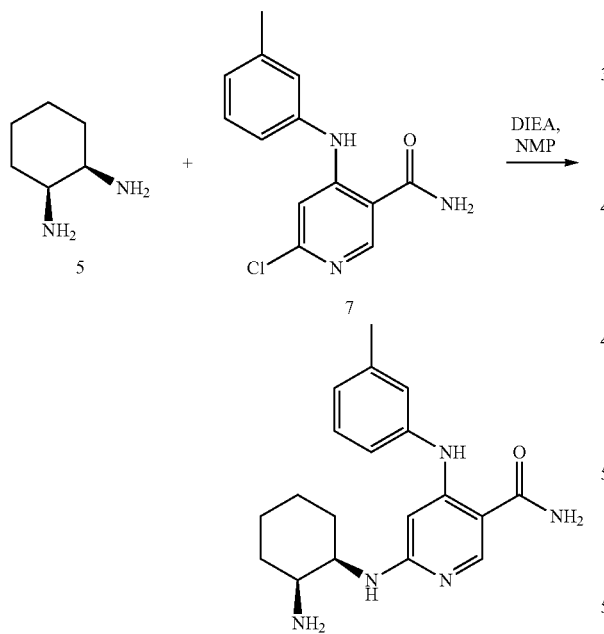

A solution of cis-1,2-diaminocyclohexane (5) (~400 mg), (7) (80 mg), and DIEA (~0.3 mL) in ~5 mL NMP was heated at 150° C. for 80 hours. The reaction mixture was cooled and a H₂O/TFA mixture was added. The resulting solution was purified via preparative rpHPLC. Product was isolated by utilizing a mobile phase with 0.1% TFA in water as solvent A and 0.1% TFA in acetonitrile as solvent B and eluting with a 5% to 40% B mixture over 10 minutes. UV: 254 nm. M+H found for $C_{19}H_{25}N_5O$: 340.3. NMR (CD₃OD): 8.28 (1H, s), 7.36 (1H, t, J=7.6 Hz), 7.17-7.08 (2H, m), 6.24 (1H, s), 4.05 (1H, br), 3.56 (1H, br), 2.39 (3H, s), 1.91-1.52 (8H, m) ppm.

Example 143

Preparation of (S)-5-fluoro-6-(piperidin-3-ylamino)-2-(quinolin-6-ylamino)nicotinamide

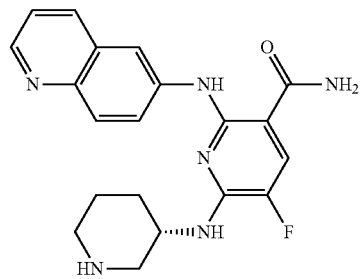 [SMILES: NC(=O)c1cc(F)c(N[C@H]2CCCNC2)nc1Nc1ccc2ncccc2c1]

The title compound can be prepared by methods described in example 90. However (S)-tert-butyl 3-aminopiperidine-1-carboxylate hydrochloride salt can be utilized instead of J20 and 6-aminoquinoline instead of 3-(2H-1,2,3-triazol-2-yl) aniline.

Example 144

6-(cyclopentylamino)-4-(4-morpholinophenylamino)nicotinamide

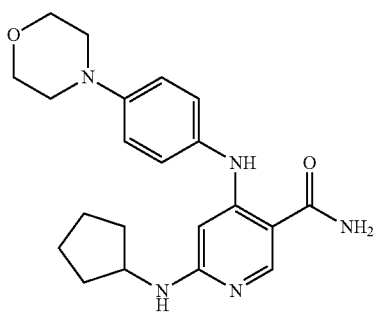

The title compound was prepared according to scheme 40 below.

Scheme 40:

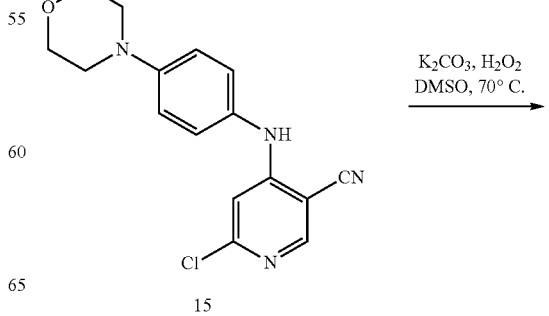

-continued

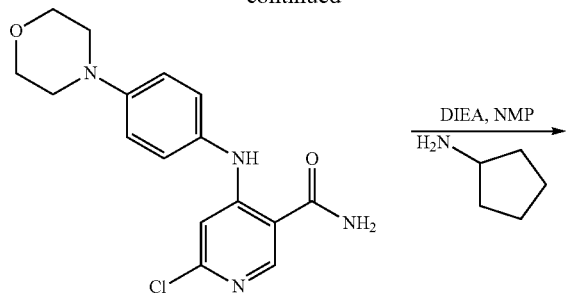

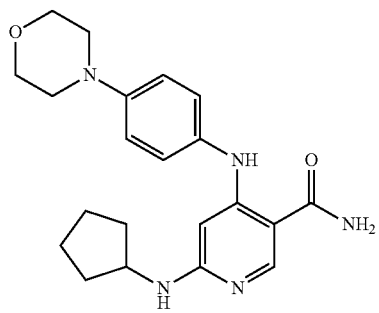 [SMILES: NC(=O)c1cnc(NC2CCCC2)cc1Nc1ccc(N2CCOCC2)cc1]

In addition to the isolation of 14, the first preparative rpHPLC run in scheme 39 resulted in the isolation of 15, mixed with its regioisomer. The mixture of regioisomers were subsequently converted their corresponding amides by utilizing similar chemistry as described in scheme 38. Compound 16 was separated from its regioisomer via preparative rpHPLC utilizing a mobile phase with 0.1% TFA in water as solvent A and 0.1% TFA in acetonitrile as solvent B and eluting with a 5% to 35% B mixture over 10 minutes. Fractions containing 16 were concentrated in vacuo to yield 122 mg which was dissolved in 6 mL NMP. From this ~20 mg/mL stock solution, 2 mL was used in the subsequent reaction. Two equivalents of both cyclopentylamine and DIEA were added. The reaction mixture was stirred at 150° C. for 18 h and then at 190° C. for another 24 hours. The reaction mixture was cooled and a H$_2$O/TFA mixture was added. The resulting solution was subjected to preparative rpHPLC utilizing a mobile phase with 0.1% TFA in water as solvent A and 0.1% TFA in acetonitrile as solvent B and eluting with a 10% to 45% B mixture over 10 minutes. UV: 257 nm. M+H found for C$_{21}$H$_{27}$N$_5$O$_2$: 382.4. NMR (CD$_3$OD): 8.14 (1H, s), 7.18 (2H, d, J=9.2 Hz), 7.06 (2H, d, J=8.8 Hz), 5.91 (1H, s), 3.86-3.80 (5H, m), 3.18 (4H, dd, J=4.8 Hz, 4.8 Hz), 2.03-1.93 (2H, m), 1.78-1.50 (6H, m) ppm.

Example 145

4-(4-carbamoylphenylamino)-6-(cyclopentylamino) nicotinamide

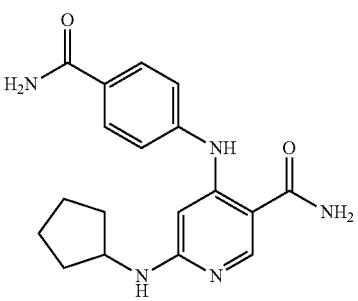 [SMILES: NC(=O)c1ccc(Nc2cc(NC3CCCC3)ncc2C(N)=O)cc1]

The title compound was prepared according to scheme 41 below.

Scheme 41:

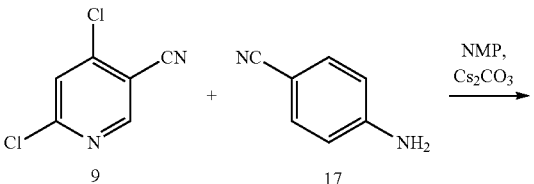

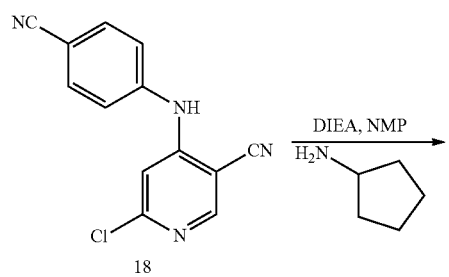

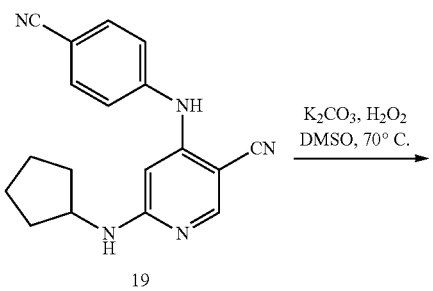

Intermediate 18 was synthesized utilizing similar chemistry as described for the synthesis of 8 in scheme 40. Compound 18 was reacted with pentylamine as described in scheme 41. Finally, 19 was converted to the title compound utilizing similar chemistry as that originally described in scheme 40. UV: 250 nm. M+H found for C$_{18}$H$_{21}$N$_5$O$_2$: 340.4. NMR (CD$_3$OD): 8.19 (1H, s), 7.97 (2H, d, J=8.8 Hz), 7.40 (2H, d, J=8.4 Hz), 6.28 (1H, s), 3.90-3.84 (1H, m), 2.10-1.96 (2H, m), 1.83-1.54 (6H, m) ppm.

Example 146

4-((1R,2S)-2-aminocyclohexylamino)-5-fluoro-2-(3-phenylisoxazol-5-ylamino)benzamide

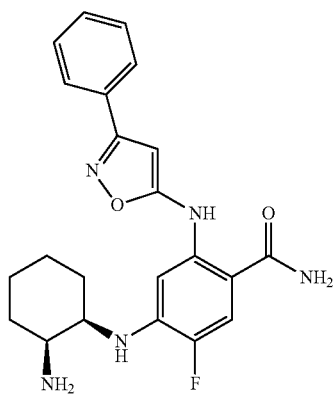 [SMILES: NC(=O)c1cc(F)c(N[C@@H]2CCCC[C@@H]2N)cc1Nc1cc(-c2ccccc2)no1]

Scheme 42

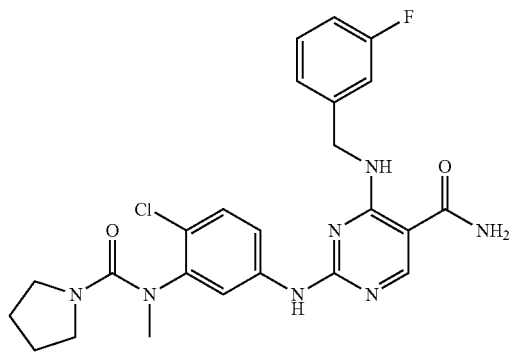

A mixture of tert-butyl (1S,2R)-2-(5-bromo-4-cyano-2-fluorophenylamino)cyclohexylcarbamate (165 mg, 0.400 mmol), 5-amino-3-phenylisoxazole (96 mg, 0.600 mmol), sodium phenoxide trihydrate (136 mg, 0.800 mmol), xantphos (30 mg, 0.051 mmol) and Pd$_2$(dba)$_3$ (30 mg, 0.032 mmol) in dioxane (2 mL) was degassed with Ar, then was heated at 170 C for 30 min by microwave. It was concentrated in vacuo. The residue was purified by HPLC to give tert-butyl (1S,2R)-2-(4-cyano-2-fluoro-5-(3-phenylisoxazol-5-ylamino)phenylamino)cyclohexylcarbamate (40 mg).

The compound tert-butyl (1S,2R)-2-(4-cyano-2-fluoro-5-(3-phenylisoxazol-5-ylamino)phenylamino)cyclohexylcarbamate (40 mg, 0.081 mmol) was dissolved in TFA (1.0 mL). After 20 min, TFA was removed in vacuo to give 4-((1R,2S)-2-aminocyclohexylamino)-5-fluoro-2-(3-phenylisoxazol-5-ylamino)benzonitrile (51 mg).

To a solution of 4-((1R,2S)-2-aminocyclohexylamino)-5-fluoro-2-(3-phenylisoxazol-5-ylamino)benzonitrile in EtOH (1 mL) and DMSO (0.5 mL), 1N aq. NaOH (0.5 mL) and H$_2$O$_2$ (50% aq., 0.5 mL) were added. After being stirred at room temperature for 1 h, the mixture was concentrated in vacuo. The residue was acidified with HOAc (0.5 mL), and then was purified by HPLC to give the titled compound (33 mg). MS 410.3 (M+H); UV 204.7, 246.1, 287.8 nm.

Example 147

4-((1R,2S)-2-aminocyclohexylamino)-2-(3-methylisoxazol-5-ylamino)benzamide

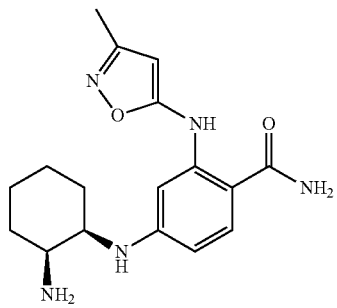 [SMILES: Cc1cc(Nc2cc(N[C@@H]3CCCC[C@@H]3N)ccc2C(N)=O)on1]

The titled compound is synthesized analogously according to the procedures described for 4-((1R,2S)-2-aminocyclohexylamino)-5-fluoro-2-(3-phenylisoxazol-5-ylamino)benzamide. MS 330.3 (M+H); UV 204.7, 278.0 nm

Example 148

4-((1R,2S)-2-aminocyclohexylamino)-5-fluoro-2-(3-methylisoxazol-5-ylamino)benzamide

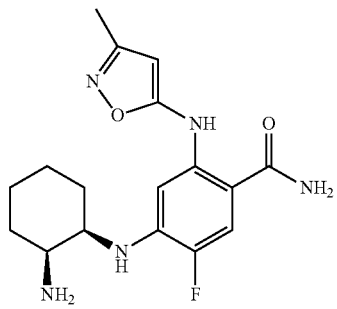 [SMILES: Cc1cc(Nc2cc(N[C@@H]3CCCC[C@@H]3N)c(F)cc2C(N)=O)on1]

The titled compound is synthesized analogously according to the procedures described for 4-((1R,2S)-2-aminocyclohexylamino)-5-fluoro-2-(3-phenylisoxazol-5-ylamino)benzamide. MS 348.2 (M+H); UV 202.2, 280.5 nm.

Example 149

(R)-4-(1-amino-3-(2-fluorophenyl)-1-oxopropan-2-ylamino)-5-fluoro-2-(3-methylisothiazol-5-ylamino)benzamide

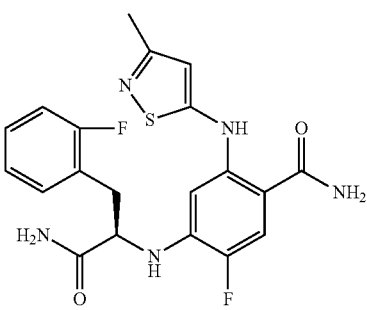

The titled compound is synthesized analogously according to the procedures described for (R)-4-(1-amino-1-oxo-3-phenylpropan-2-ylamino)-5-fluoro-2-(3-methylisothiazol-5- ylamino)benzamide in Example 24. MS 432.2 (M+H); UV 204.7, 292.8 nm.

Example 150

Preparation of 2-(1,8-naphthyridin-3-ylamino)-6-((1R,2S)-2-aminocyclohexylamino)-5-fluoronicotinamide

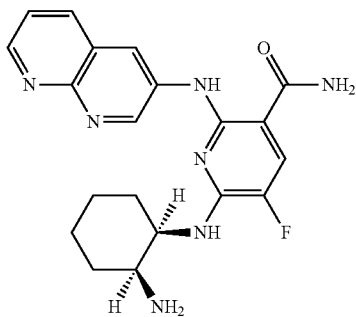

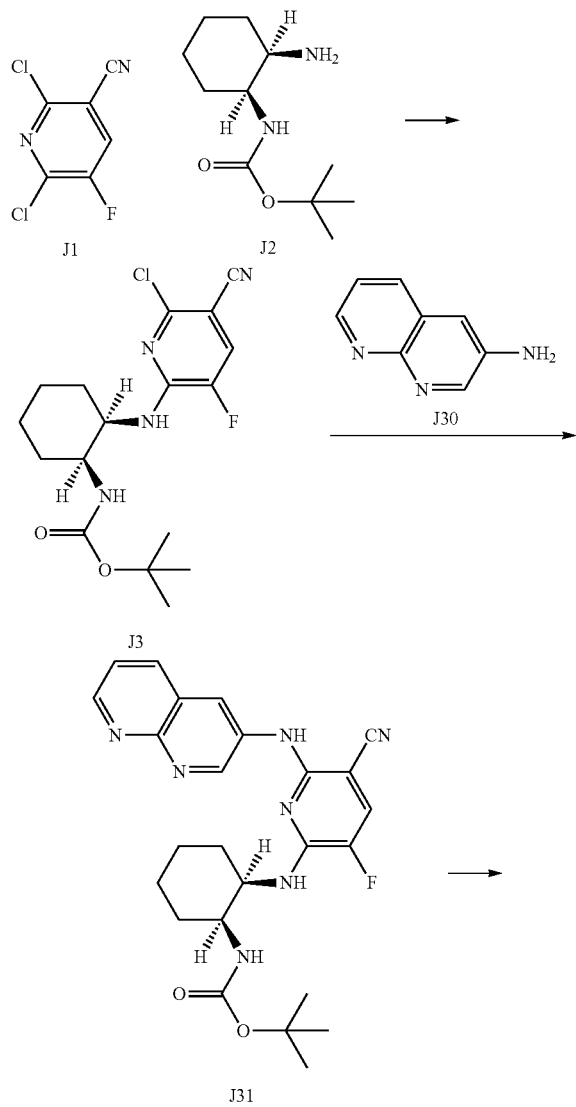

Scheme 43:

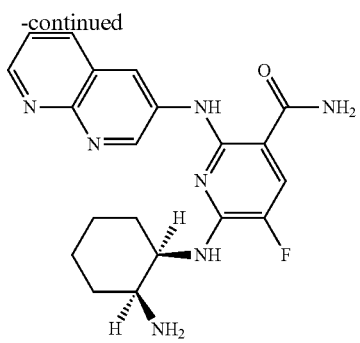

Step 1: 2,6-Dichloro-5-fluoro-3-pyridinecarbonitrile (J1, Aldrich 422169, 2.00 g, 10.5 mmol) was dissolved in 50 mL NMP in a 500 mL flask and stirred at RT. To it was added compound J2 (tert-butyl (1S,2R)-2-aminocyclohexylcarbamate, 2.69 g, 12.5 mmol) in waxy solid form in multiple portions. Then DIEA (3.65 mL, 21.0 mmol) was added a few minutes later. The mixture was heated to 80° C. gradually and stirred at this temperature for 2 hours (very clean reaction; complete by analytical HPLC analysis). The mixture was cooled down to RT. To the flask then was added 400 mL cold water. A light yellow solid (tert-butyl (1S,2R)-2-(6-chloro-5-cyano-3-fluoropyridin-2-ylamino)cyclohexylcarbamate, compound J3 crashed out. It was isolated using Buchner funnel and washed with cold water multiple times (to wash away NMP completely). The solid was dried in vacuum oven at RT for two overnights. No other purification was necessary. Yield was over 90%.

Step 2: To a clean 500 mL flask were added to following reagents: compound J3 (100 mg, 0.27 mmol), 1,8-naphthyridin-3-amine (compound J30, 78 mg, 0.54 mmol), fine-powder cesium carbonate (264 mg, 0.81 mmol), Q-Phos (1,2,3,4,5-pentaphenyl-1'-(di-tert-butylphosphino)ferrocene) (20 mg, 0.027 mmol; Aldrich #675784) and Pd(dba)$_2$ (bis(dibenzylideneacetone)palladium(0)) (32 mg, 0.054 mmol; Aldrich #227994). To the mixture was then added 15 mL toluene. The resulting slurry was degassed using argon stream gently for 3 min. It was then sent to 110° C. bath with an air-cooled condenser on top and stirred under argon for overnight. The mixture was then cooled to RT and concentrated on rotovap to remove all the solvent. To the residue were added 200 mL EtOAc and 70 mL water. After vigorously stirring for 15-30 min, the organic phase was separated, and the aq phase and the black junks between org and aq phases were all discarded. The EtOAc phase was then washed with brine twice. The organic phase was dried over MgSO$_4$, concentrated and subjected to flash column with 0%-80% EtOAc in DCM to isolate the desired product, compound J31.

Step 3: To the above-prepared compound J31 was added 5 mL TFA at RT. After stirring for 3 min, 1 mL conc. H$_2$SO$_4$ was added. The mixture was then sent to pre-heated 80° C. bath and stirred for 45 min. It was the cooled to RT. To it was added 10 mL water. The mixture was stirred for 10 min, filtered and directly subjected to prep HPLC (running with 3 mM HCl in water as solvent A and neat acetonitrile as solvent B) to isolate the title compound as HCl salt (lyophilized). Yield: 49 mg, 46% overall yield for Step 2 and Step 3. UV: 263, 301, 325 nm. M+H found for C$_{20}$H$_{22}$FN$_7$O: 396.2. NMR (CD$_3$OD): 9.40 (1H, d, J=2.4 Hz), 9.02 (1H, dd, J=9.2; 1.6 Hz), 8.91 (1H, d, J=2.8 Hz), 8.88 (1H, dd, J=8.4; 1.6 Hz), 7.95 (1H, dd, J=8.4, 5.2 Hz), 7.89 (1H, d, J=11.6 Hz), 4.61 (1H, m), 3.84 (1H, m), 1.95-1.66 (8H, m) ppm.

Example 151

Preparation of 2-(1,8-naphthyridin-4-ylamino)-6-((1R,2S)-2-aminocyclohexylamino)-5-fluoronicotinamide

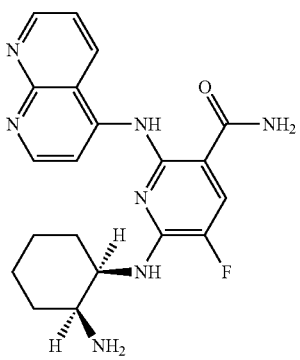

The title compound was prepared using the same chemistry shown in Example 150 using 1,8-naphthyridin-4-amine to replace J30. UV: 254, 273, 320 nm. M+H found for $C_{20}H_{22}FN_7O$: 396.3. NMR (CD$_3$OD): 9.13 (1H, m), 8.92-8.88 (3H, m), 8.03 (1H, dd, J=11.6, 2.4 Hz), 7.87 (1H, m), 4.60 (1H, m), 3.93 (1H, m), 2.02-1.68 (8H, m) ppm.

Example 152

Preparation of 6-((1R,2S)-2-aminocyclohexylamino)-5-fluoro-2-(pyrimidin-5-ylamino)nicotinamide

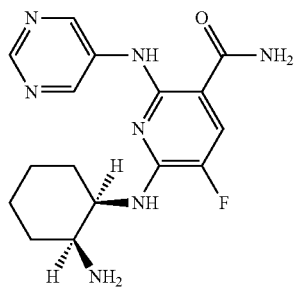

The title compound was prepared using the same chemistry shown in Example 150 using 5-aminopyrimidine to replace J30. UV: 263, 306 nm. M+H found for $C_{16}H_{20}FN_7O$: 346.3. NMR (CD$_3$OD): 9.18 (2H, s), 8.81 (1H, s), 7.85 (1H, d, J=11.6 Hz), 4.44 (1H, m), 3.79 (1H, m), 1.95-1.61 (8H, m) ppm.

Example 153

Preparation of 6-((1R,2S)-2-aminocyclohexylamino)-5-fluoro-2-(1-methyl-1H-benzo[d]imidazol-5-ylamino)nicotinamide

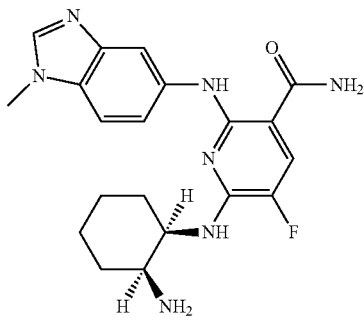 [SMILES: Cn1cnc2cc(Nc3nc(N[C@@H]4CCCC[C@@H]4N)c(F)cc3C(N)=O)ccc21]

The title compound was prepared using the same chemistry shown in Example 150 using 1-methyl-1H-benzo[d]imidazol-5-amine to replace J30. UV: 235, 263, 292 nm. M+H found for $C_{20}H_{24}FN_7O$: 398.3. NMR (CD$_3$OD): 8.15 (1H, s), 7.81 (1H, d, J=11.6 Hz), 7.80-7.71 (3H, m), 4.47 (1H, m), 4.09 (3H, s), 3.84 (1H, m), 1.92-1.62 (8H, m) ppm.

Example 154

Preparation of 2-(5-(2H-1,2,3-triazol-2-yl)pyridin-3-ylamino)-6-((1R,2S)-2-aminocyclohexylamino)-5-fluoronicotinamide

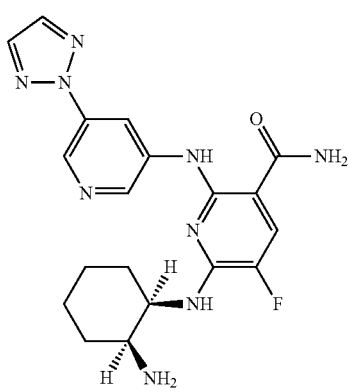

Scheme 44:

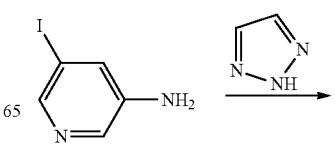

Scheme 45:

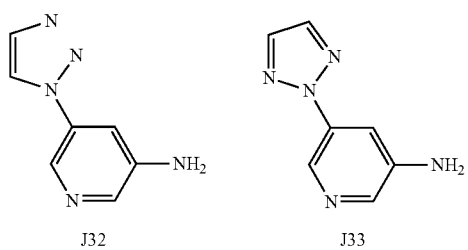

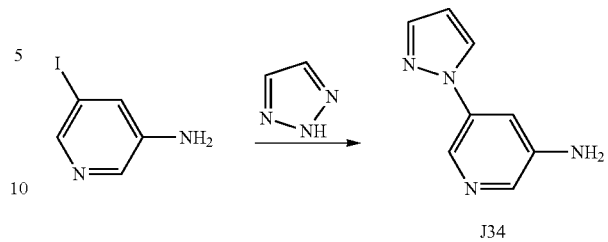

The mixture of 5-iodopyridin-3-ylamine (1.00 g, 4.6 mmol), 1,2,3-triazole (1.06 mL, 18.4 mmol), K$_3$PO$_4$ (1.95 g, 9.2 mmol), CuI (270 mg, 0.14 mmol) and ethylenediamine (0.10 mL, 0.14 mmol) in 20 mL dioxane and 5 mL DMSO was stirred in a sealed tube at 120° C. for 3 days. A 1:1 mixture of J32 and J33 was found. The mixture was cooled to RT, diluted with 200 mL EtOAc, filtered through a short silica plug. The solid cake was thoroughly washed was 300 mL EtOAc. All the filtrate was concentrated in vacuo and subjected to silica flash column using 0-15% MeOH in DCM to isolate compound J33 (300 mg, 40% yield). NMR (CDCl$_3$): 8.76 (1H, d=2.0 Hz), 8.07 (1H, d, J=2.4 Hz), 7.83 (2H, s), 7.65 (1H, t, J=2.0 Hz), 3.94 (2H, bs) ppm. NMR of J32 (CDCl$_3$): 8.31 (1H, d, J=2.0 Hz), 8.14 (1H, d, J=2.8 Hz), 8.01 (1H, d, J=1.2 Hz), 7.87 (1H, d, J=1.2 Hz), 7.49 (1H, t, J=2.0 Hz), 4.02 (2H, bs) ppm.

The title compound was prepared using the same chemistry shown in Example 150 using compound J33 prepared above. UV: 263, 330 nm. M+H found for C$_{19}$H$_{22}$FN$_9$O: 412.3. NMR (CD$_3$OD): 9.26 (1H, t, J=2.4 Hz), 8.84 (1H, d, J=2.4 Hz), 8.52 (1H, d, J=2.4 Hz), 8.06 (2H, s), 7.84 (1H, d, J=11.6 Hz), 4.72 (1H, m), 3.78 (1H, m), 1.92-1.57 (8H, m) ppm.

Example 155

Preparation of 2-(5-(1H-pyrazol-1-yl)pyridin-3-ylamino)-6-((1R,2S)-2-aminocyclohexylamino)-5-fluoronicotinamide

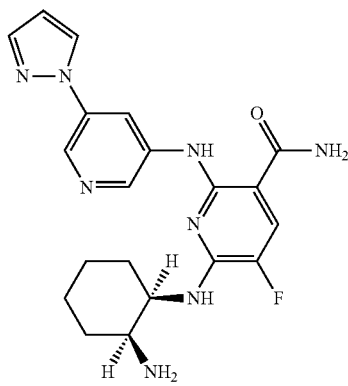

The mixture of 5-iodopyridin-3-ylamine (1.00 g, 4.6 mmol), pyrazole (0.94, 13.8 mmol), K$_3$PO$_4$ (1.95 g, 9.2 mmol), CuI (270 mg, 0.14 mmol) and ethylenediamine (0.10 mL, 0.14 mmol) in 20 mL dioxane and 5 mL DMSO was stirred in a sealed tube at 120° C. for 24 h. The reaction was clean and complete. The mixture was cooled to RT, diluted with 200 mL EtOAc, filtered through a short silica plug. The solid cake was thoroughly washed was 300 mL EtOAc. All the filtrate was concentrated in vacuo and subjected to silica flash column using 0-10% MeOH in DCM to isolate compound J34 (>90% yield).

The title compound was prepared using the same chemistry shown in Example 150 using compound J34 prepared above. UV: 254, 330 nm. M+H found for C$_{20}$H$_{23}$FN$_8$O: 411.3. NMR (CD$_3$OD): 9.29 (1H, t, J=2.0 Hz), 8.73 (1H, s), 8.72 (1H, s), 8.47 (1H, d, J=2.4 Hz), 7.89 (1H, s), 7.88 (1H, d, J=12.8 Hz), 6.66 (1H, t, J=2.0 Hz), 4.67 (1H, m), 3.75 (1H, m), 1.88-1.54 (8H, m) ppm.

Example 156

Preparation of 6-((1R,2S)-2-aminocyclohexylamino)-5-fluoro-2-(5-(pyrimidin-2-yl)pyridin-3-ylamino)nicotinamide

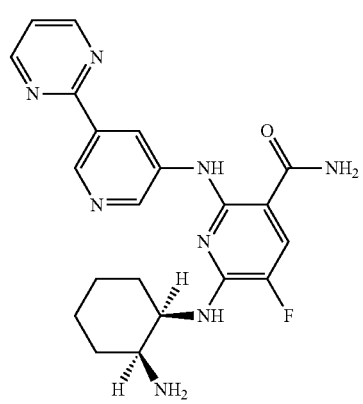 [SMILES: NC(=O)c1cc(F)c(N[C@@H]2CCCC[C@@H]2N)nc1Nc1cncc(-c2ncccn2)c1]

Scheme 46:

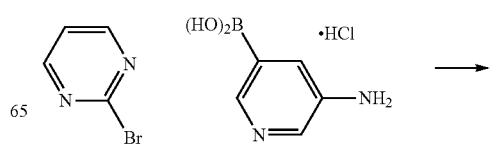

-continued

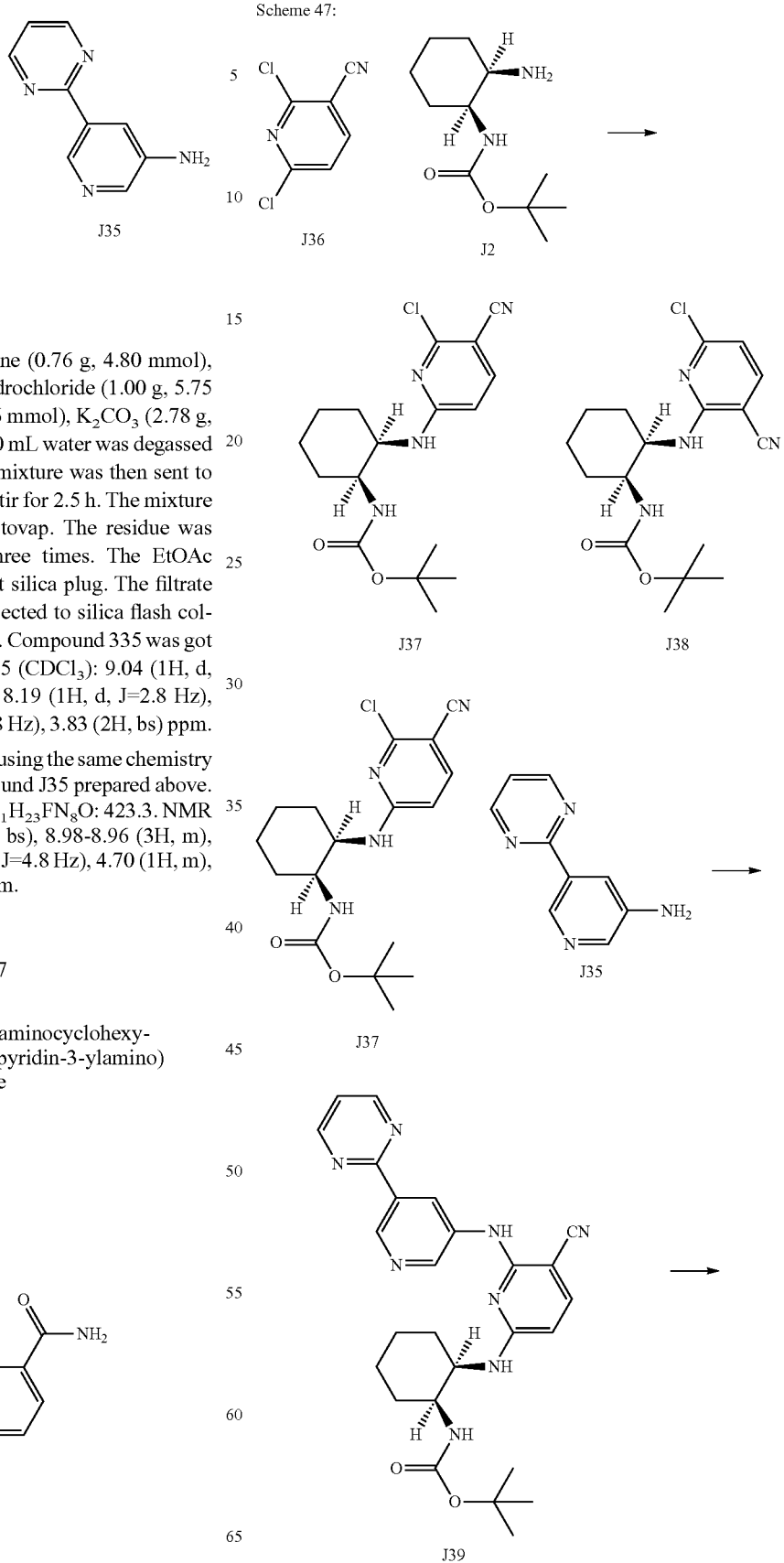

Scheme 47:

The mixture of 2-bromopyrimidine (0.76 g, 4.80 mmol), 5-aminopyridine-3-boronic acid hydrochloride (1.00 g, 5.75 mmol), Pd(Ph$_3$P)$_2$Cl$_2$ (730 mg, 0.96 mmol), K$_2$CO$_3$ (2.78 g, 20.2 mmol) in 40 mL dioxane and 20 mL water was degassed using argon stream for 3 min. The mixture was then sent to 85° C. bath in argon atmosphere to stir for 2.5 h. The mixture was concentrated to dryness on rotovap. The residue was triturated with 200 mL EtOAc three times. The EtOAc decants were forced through a short silica plug. The filtrate was concentrated in vacuo and subjected to silica flash column using 0%-10% MeOH in DCM. Compound 335 was got in 40% yield (330 mg). NMR of J35 (CDCl$_3$): 9.04 (1H, d, J=2.0 Hz), 8.80 (2H, d, J=4.8 Hz), 8.19 (1H, d, J=2.8 Hz), 7.99-7.98 (1H, m), 7.23 (1H, t, J=4.8 Hz), 3.83 (2H, bs) ppm.

The title compound was prepared using the same chemistry shown in Example 150 using compound J35 prepared above. UV: 254, 330 nm. M+H found for C$_{21}$H$_{23}$FN$_8$O: 423.3. NMR (CD$_3$OD): 9.51 (1H, bs), 9.19 (1H, bs), 8.98-8.96 (3H, m), 7.88 (1H, d, J=12.0 Hz), 7.53 (1H, t, J=4.8 Hz), 4.70 (1H, m), 3.77 (1H, m), 1.90-1.56 (8H, m) ppm.

Example 157

Preparation of 6-(((1R,2S)-2-aminocyclohexylamino)-2-(5-(pyrimidin-2-yl)pyridin-3-ylamino)nicotinamide

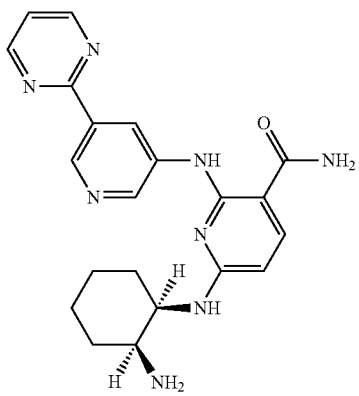 [SMILES: NC(=O)c1ccc(N[C@@H]2CCCC[C@@H]2N)nc1Nc1cncc(-c2ncccn2)c1]

Step 1: 2,6-Dichloro-3-pyridinecarbonitrile (J36, 1.70 g, 9.82 mmol) was dissolved in 30 mL DMF in a 500 mL flask and stirred at RT. To it was added compound J2 (tert-butyl (1S,2R)-2-aminocyclohexylcarbamate, 2.31 g, 10.8 mmol) in waxy solid form in multiple portions. Then DIEA (2.08 mL, 12.0 mmol) was added a few minutes later. The mixture was heated to 80° C. gradually and stirred at this temperature for overnight. A mixture of J37 and J38 (ratio=2.5:1 by analytical HPLC) was got. The mixture was cooled down to RT and concentrated in high vacuum to remove DMF. To the residue was poured 300 mL EtOAc. The organic solution was washed with brine three times. It was dried, concentrated and subjected to silica flash column to isolate the major product J37 (1.77 g, 51%).

Step 2: To a clean 200 mL flask were added to following reagents: compound J37 (145 mg, 0.40 mmol), compound J35 (Example 156, 103 mg, 0.60 mmol), fine-powder cesium carbonate (391 mg, 1.20 mmol), Q-Phos (1,2,3,4,5-pentaphenyl-1'-(di-tert-butylphosphino)ferrocene) (28 mg, 0.040 mmol; Aldrich #675784) and Pd(dba)$_2$ (bis(dibenzylideneacetone)palladium(0)) (46 mg, 0.080 mmol; Aldrich #227994). To the mixture were then added 15 mL toluene and 5 mL dioxane. The resulting slurry was degassed using argon stream gently for 3 min. It was then sent to 110° C. bath with an air-cooled condenser on top and stirred under argon for overnight. The mixture was then cooled to RT and concentrated on rotovap to remove all the solvent. To the residue were added 200 mL EtOAc and 70 mL water. After vigorously stirring for 15-30 min, the organic phase was separated, and the aq phase and the black junks between org and aq phases were all discarded. The EtOAc phase was then washed with brine twice. The organic phase was dried over MgSO$_4$, concentrated and subjected to flash column with 0%-80% EtOAc in DCM to isolate the desired product, compound J39.

Step 3: To the above-prepared compound J39 was added 5 mL TFA at RT. After stirring for 3 min, 1 mL conc. H$_2$SO$_4$ was added. The mixture was then sent to pre-heated 80° C. bath and stirred for 45 min. It was the cooled to RT. To it was added 10 mL water. The mixture was stirred for 10 min, filtered and directly subjected to prep HPLC (running with 3 mM HCl in water as solvent A and neat acetonitrile as solvent B) to isolate the title compound as HCl salt (lyophilized). Yield: 65 mg, 39% overall yield for Step 2 and Step 3. UV: 254, 330 nm. M+H found for C$_{21}$H$_{24}$N$_8$O: 423.3. NMR (CD$_3$OD): 9.56 (1H, bs), 9.18 (1H, bs), 9.05 (1H, bs), 8.97-8.96 (2H, m), 7.89 (1H, dd, J=8.8; 2.4 Hz), 7.52 (1H, td, J=4.8; 2.4 Hz), 6.32 (1H, dd, J=8.8; 2.8 Hz), 4.75 (1H, m), 3.65 (1H, m), 1.90-1.52 (8H, m) ppm.

Example 158

Preparation of 2-(5-(2H-1,2,3-triazol-2-yl)pyridin-3-ylamino)-6-(1R,2S)-2-aminocyclohexylamino)nicotinamide

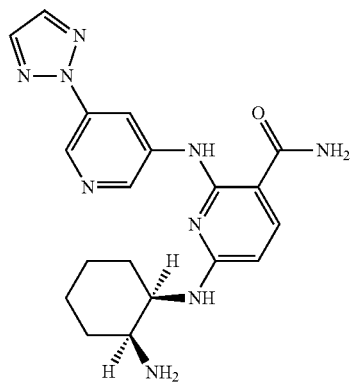

The title compound was prepared using the same chemistry shown in Example 156 and 157 using compound J33 shown in Example 154. UV: 263, 325 nm. M+H found for C$_{19}$H$_{23}$N$_9$O: 394.3. NMR (CD$_3$OD): 9.51 (1H, s), 8.87 (1H, d, J=1.6 Hz), 8.64 (1H, s), 8.09 (2H, s), 7.88 (1H, d, J=9.2 Hz), 6.31 (1H, d, J=8.8 Hz), 4.80 (1H, m), 3.67 (1H, m), 1.88-1.55 (8H, m) ppm.

Example 159

Preparation of 2-(5-(1H-pyrazol-1-yl)pyridin-3-ylamino)-6-((1R,2S)-2-aminocyclohexylamino)nicotinamide

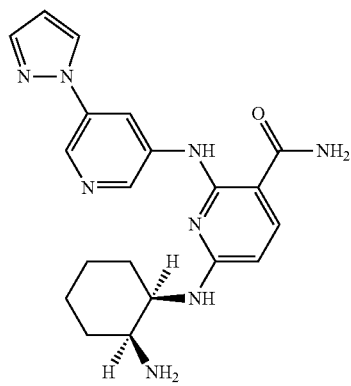

The title compound was prepared using the same chemistry shown in Example 156 using compound J34 shown in Example 154. UV: 259, 325 nm. M+H found for C$_{20}$H$_{24}$N$_8$O: 393.3. NMR (CD$_3$OD): 9.15 (1H, bs), 8.61-8.59 (2H, m), 8.41 (1H, bs), 7.87-7.85 (2H, m), 6.62 (1H, bs), 6.27 (1H, d, J=8.8 Hz), 4.68 (1H, m), 3.66 (1H, m), 1.88-1.54 (8H, m) ppm.

Example 160

Preparation of 2-(5-(1H-imidazol-1-yl)pyridin-3-ylamino)-6-((1R,2S)-2-aminocyclohexylamino)-5-fluoronicotinamide

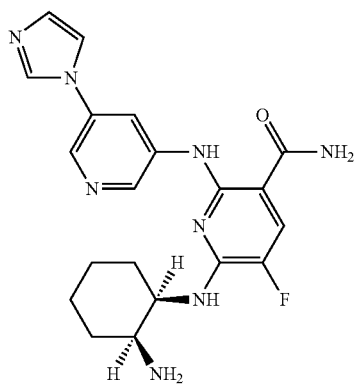 [SMILES: NC(=O)c1cc(F)c(N[C@@H]2CCCC[C@@H]2N)nc1Nc1cncc(-n2ccnc2)c1]

The title compound was prepared using the same chemistry shown in Example 155. UV: 263, 330 nm. M+H found for $C_{20}H_{23}FN_8O$: 411.4. NMR ($CD_3OD$): 9.65 (1H, t, J=1.2 Hz), 9.51 (1H, d, J=2.0 Hz), 8.66 (1H, d, J=2.4 Hz), 8.43 (1H, t, J=2.0 Hz), 8.23 (1H, t, J=2.0 Hz), 7.89 (2H, m), 4.49 (1H, m), 3.77 (1H, m), 1.92-1.57 (8H, m) ppm.

Example 161

Preparation of 2-(5-(1H-imidazol-1-yl)pyridin-3-ylamino)-6-((1R,2S)-2-aminocyclohexylamino)nicotinamide

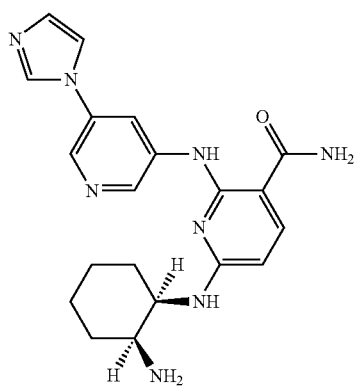

The title compound was prepared using the same chemistry shown in Example 157. UV: 268, 325 nm. M+H found for $C_{20}H_{24}N_8O$: 393.3. NMR ($CD_3OD$): 9.60 (1H, m), 9.50 (1H, m), 8.56 (1H, m), 8.34 (1H, m), 8.19 (1H, m), 7.91-7.86 (2H, m), 6.30 (1H, m), 4.46 (1H, m), 3.67 (1H, m), 1.90-1.52 (8H, m) ppm.

Example 162

Preparation of 6-((1R,2S)-2-aminocyclohexylamino)-5-fluoro-2-(5-(thiazol-2-yl)pyridin-3-ylamino)nicotinamide

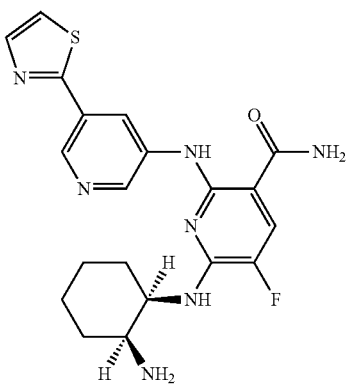 [SMILES: NC(=O)c1cc(F)c(N[C@@H]2CCCC[C@@H]2N)nc1Nc1cncc(-c2nccs2)c1]

Preparation of 5-(thiazol-2-yl)pyridin-3-amine

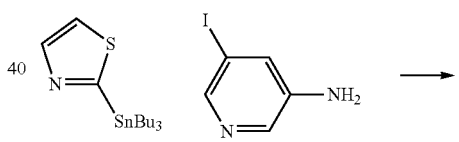

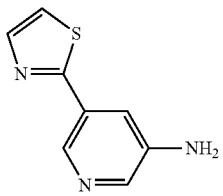

The mixture of 2-tributylstannylthiazole (2.24 g, 6.00 mmol), 5-iodopyridin-3-ylamine (1.10 g, 5.00 mmol) and Pd(Ph$_3$P)$_4$ (580 mg, 0.5 mmol) in 50 mL toluene was degassed using Ar. The mixture was then stirred under Ar at 115° C. for 3 h. The mixture was concentrated and subjected to flash column (0 to 7% MeOH in DCM) to isolate 5-(thiazol-2-yl)pyridin-3-amine (740 mg, 84% yield).

The title compound was prepared using the same chemistry shown in Example 150. UV: 268, 325 nm. M+H found for $C_{20}H_{22}FN_7OS$: 428.1. NMR ($CD_3OD$): 9.39 (1H, s), 8.97

(1H, d, J=2.0 Hz), 8.84 (1H, s), 8.08 (1H, m), 7.91-7.88 (2H, m), 4.68 (1H, m), 3.77 (1H, m), 1.90-1.65 (8H, m) ppm.

Example 163

Preparation of 6-(1R,2S)-2-aminocyclohexylamino)-2-(5-(thiazol-2-yl)pyridin-3-ylamino)nicotinamide

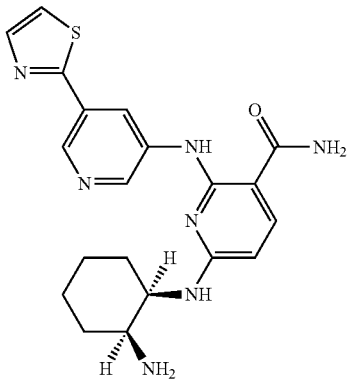 [SMILES: NC(=O)c1ccc(N[C@@H]2CCCC[C@@H]2N)nc1Nc1cncc(-c2nccs2)c1]

The title compound was prepared using the same chemistry shown in Example 157. UV: 273, 315 nm. M+H found for $C_{20}H_{23}N_7OS$: 410.2. NMR ($CD_3OD$): 9.30 (1H, m), 8.89 (1H, m), 8.76 (1H, m), 8.05 (1H, m), 7.90 (1H, d, J=8.4 Hz), 7.82 (1H, m), 6.32 (1H, d, J=8.8 Hz), 4.68 (1H, m), 3.66 (1H, m), 1.86-1.52 (8H, m) ppm.

Example 164

Preparation of 6-(1R,2S)-2-aminocyclohexylamino)-2-(5-methoxypyridin-3-ylamino)nicotinamide

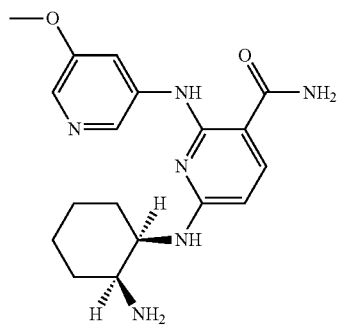 [SMILES: COc1cncc(Nc2nc(N[C@@H]3CCCC[C@@H]3N)ccc2C(N)=O)c1]

The title compound was synthesized utilizing chemistry described in example 157. Note that 3-amino-5-methoxypyridine was utilized instead of J35. Conversion of the nitrile to the amide and Boc-deprotection was performed as shown in scheme 36. UV: 223, 324 nm. M+H found for $C_{18}H_{24}N_6O_2$: 357.3. NMR ($CD_3OD$): 8.98 (1H, br), 8.10-8.04 (2H, m), 7.88 (1H, d, J=8.8 Hz), 6.30 (1H, d, J=8.4 Hz), 4.55-4.45 (1H, m), 3.98 (3H, s), 3.70-3.60 (1H, m), 1.95-1.51 (8H, m) ppm.

Example 165

Preparation of 2-(1,8-naphthyridin-3-ylamino)-6-(1R,2S)-2-aminocyclohexylamino)nicotinamide

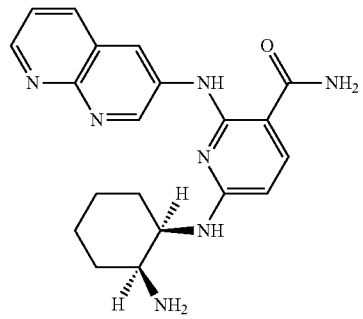 [SMILES: NC(=O)c1ccc(N[C@@H]2CCCC[C@@H]2N)nc1Nc1cnc2ncccc2c1]

The title compound was prepared using the same chemistry shown in Example 157. UV: 263, 297, 325 nm. M+H found for $C_{20}H_{23}N_7O$: 378.3. NMR ($CD_3OD$): 9.43 (1H, s), 9.02 (2H, m), 8.88 (1H, d, J=8.4 Hz), 7.96-7.92 (3H, m), 6.35 (1H, d, J=8.4 Hz), 4.56 (1H, m), 3.73 (1H, m), 1.88-1.62 (8H, m) ppm.

Example 166

Preparation of 6-((1R,2S)-2-aminocyclohexylamino)-5-fluoro-2-(2-methoxypyrimidin-5-ylamino)nicotinamide

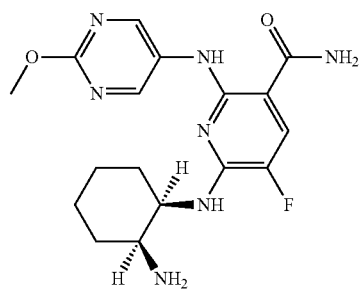 [SMILES: COc1ncc(Nc2nc(N[C@@H]3CCCC[C@@H]3N)c(F)cc2C(N)=O)cn1]

The title compound was prepared using the same chemistry shown in Example 150. UV: 297 nm. M+H found for $C_{17}H_{22}FN_7O_2$: 376.2. NMR ($CD_3OD$): 8.76 (2H, s), 7.76 (1H, d, J=11.6 Hz), 4.28 (1H, m), 3.99 (3H, s), 3.72 (1H, m), 1.86-1.61 (8H, m) ppm.

Examples 167-173

The title compounds was prepared using the same chemistry as shown in the Schemes above unless otherwise noted.

| EXAMPLE NO. | STRUCTURE |
|---|---|
| 167 | 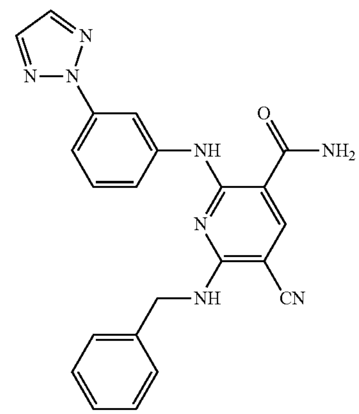 [SMILES: N#Cc1cc(C(N)=O)c(Nc2cccc(-n3nccn3)c2)nc1NCc1ccccc1] |
| 168 | 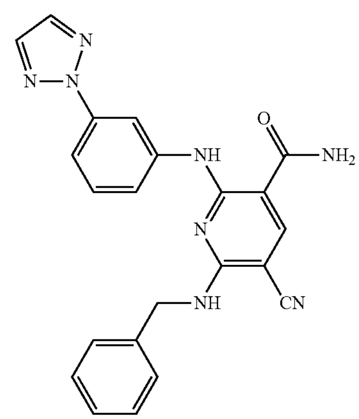 [SMILES: N#Cc1cc(C(N)=O)c(Nc2cccc(-n3nccn3)c2)nc1NCc1ccccc1] |
| 169 | 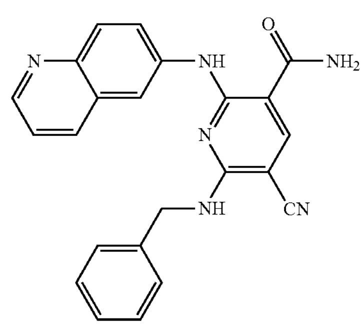 [SMILES: N#Cc1cc(C(N)=O)c(Nc2ccc3ncccc3c2)nc1NCc1ccccc1] |
| 172 | 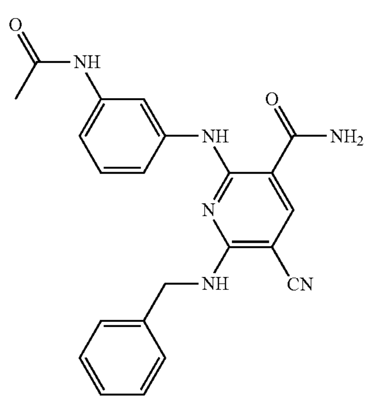 [SMILES: CC(=O)Nc1cccc(Nc2nc(NCc3ccccc3)c(C#N)cc2C(N)=O)c1] |
| 173 | |

Example 174

Preparation of 6-((1R,2S)-2-aminocyclohexylamino)-5-fluoro-2-(pyridin-3-ylamino)nicotinamide Step 1: 2,6-Dichloro-5-fluoro-3-pyridinecarbonitrile (Aldrich 422169, 2.00 g, 10.5 mmol) was dissolved in 50 mL NMP in a 500 mL flask and stirred at RT. To it was added tert-butyl (1S,2R)-2-aminocyclohexylcarbamate (2.69 g, 12.5 mmol) in waxy solid form in multiple portions. Then DIEA (3.65 mL, 21.0 mmol) was added a few minutes later. The mixture was heated to 80° C. gradually and stirred at this temperature for 2 hours (very clean reaction; complete by analytical HPLC analysis). The mixture was cooled down to RT. To the flask then was added 400 mL cold water. A light yellow solid, (tert-butyl (1S,2R)-2-(6-chloro-5-cyano-3-fluoropyridin-2-ylamino)cyclohexylcarbamate, crashed out. It was isolated using Buchner funnel and washed with cold water multiple times (to wash away NMP completely). The solid was dried in vacuum oven at RT for two overnights. No other purification was necessary. Yield was over 90%.

Step 2: To a clean 100 mL flask were added to following reagents: (tert-butyl (1S,2R)-2-(6-chloro-5-cyano-3-fluoro-pyridin-2-ylamino)cyclohexylcarbamate (100 mg, 0.27 mmol), 3-aminopyridine (68 mg, 0.54 mmol), fine-powder cesium carbonate (264 mg, 0.81 mmol), Q-Phos (1,2,3,4,5-pentaphenyl-1'-(di-tert-butylphosphino)ferrocene) (19 mg, 0.03 mmol; Aldrich #675784) and Pd(dba)$_2$ (bis(dibenzylideneacetone)palladium(0)) (16 mg, 0.03 mmol; Aldrich #227994). To the mixture was then added 15 mL toluene. The resulting slurry was degassed using argon stream gently for 3 min. It was then sent to 110° C. bath with an air-cooled condenser on top and stirred under argon for overnight. The mixture was then cooled to RT and concentrated on rotovap to remove all the solvent. To the residue were added 300 mL EtOAc and 100 mL water. After vigorously stirring for 15-30 min, the organic phase was separated, and the aq phase and the black junks between org and aq phases were all discarded. The EtOAc phase was then washed with brine twice. The organic phase was dried over MgSO$_4$, concentrated and subjected to flash column with 0%-40% EtOAc in DCM to isolate the desired product, tert-butyl (1S,2R)-2-(5-cyano-3-fluoro-6-(pyridin-3-ylamino)pyridin-2-ylamino)cyclohexylcarbamate. It was added 5 mL TFA at RT. After stirring for 3 min, 1 mL conc. H$_2$SO$_4$ was added. The mixture was then sent to pre-heated 80° C. bath and stirred for 60 min. It was then cooled to RT. To it was added 10 mL water. The mixture was stirred for 10 min, filtered and directly subjected to prep HPLC (running with 3 mM HCl in water as solvent A and neat acetonitrile as solvent B) in two injections to isolate the title compound as HCl salt (lyophilized). Yield: 62 mg, 67% yield for Step 2. UV: 259, 325 nm. M+H found for C$_{17}$H$_{21}$FN$_6$O: 345.3. NMR (CD$_3$OD): 9.32 (1H, s), 8.43 (1H, m), 8.33 (1H, m), 7.90-7.82 (2H, m), 4.52 (1H, m), 3.79 (1H, m), 1.93-1.64 (8H, m) ppm.

Example 175

Preparation of 6-(1R,2S)-2-aminocyclohexylamino)-5-fluoro-2-(pyridin-4-ylamino)nicotinamide

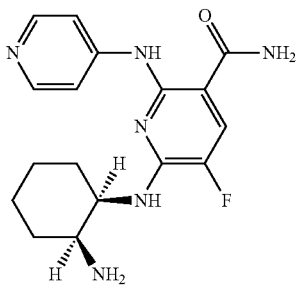 [SMILES: NC(=O)c1cc(F)c(N[C@@H]2CCCC[C@@H]2N)nc1Nc1ccncc1]

The title compound was prepared using the same chemistry shown in Example 174. UV: 273, 325 nm. M+H found for C$_{17}$H$_{21}$FN$_6$O: 345.3. NMR (CD$_3$OD): 8.41 (2H, d, J=6.0 Hz), 8.01-7.92 (3H, m), 4.51 (1H, m), 3.86 (1H, m), 1.93-1.67 (8H, m) ppm.

Example 176

Preparation of 6-((1R,2S)-2-aminocyclohexylamino)-5-fluoro-2-(6-(trifluoromethyl)pyridin-3-ylamino)nicotinamide

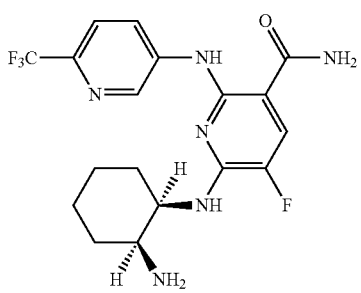 [SMILES: NC(=O)c1cc(F)c(N[C@@H]2CCCC[C@@H]2N)nc1Nc1ccc(C(F)(F)F)nc1]

The title compound was prepared using the same chemistry shown in Example 174. UV: 263, 325 nm. M+H found for C$_{18}$H$_{20}$F$_4$N$_6$O: 413.3. NMR (CD$_3$OD): 9.05 (1H, s), 8.13 (1H, d, J=8.8 Hz), 7.83 (1H, d, J=12.0 Hz), 7.73 (1H, d, J=8.4 Hz), 4.47 (1H, m), 3.83 (1H, m), 1.90-1.66 (8H, m) ppm.

Example 177

Preparation of 6-((1R,2S)-2-aminocyclohexylamino)-5-fluoro-2-(thiazol-5-ylamino)nicotinamide

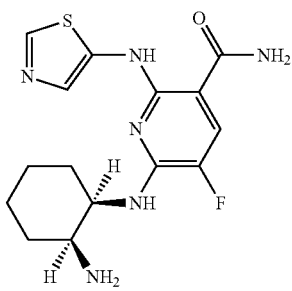 [SMILES: NC(=O)c1cc(F)c(N[C@@H]2CCCC[C@@H]2N)nc1Nc1cncs1]

The title compound was prepared using the same chemistry shown in Example 174. UV: 282, 311 nm. M+H found for C$_{15}$H$_{19}$FN$_6$OS: 351.2. NMR (CD$_3$OD): 9.01 (1H, s), 7.81 (1H, d, J=11.2 Hz), 7.75 (1H, s), 4.78 (1H, m), 3.72 (1H, m), 1.86-1.44 (8H, m) ppm.

Example 178

Preparation of 6-((1R,2S)-2-aminocyclohexylamino)-5-fluoro-2-(isothiazol-4-ylamino)nicotinamide

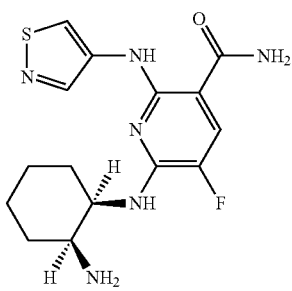 [SMILES: NC(=O)c1cc(F)c(N[C@@H]2CCCC[C@@H]2N)nc1Nc1cnsc1]

The title compound was prepared using the same chemistry shown in Example 174. UV: 273, 311 nm. M+H found for C$_{15}$H$_{19}$FN$_6$OS: 351.3. NMR (CD$_3$OD): 8.66-8.59 (2H, m), 7.76 (1H, m), 4.43 (1H, m), 3.82 (1H, m), 1.86-1.64 (8H, m) ppm.

Example 179

Preparation of 6-(1R,2S)-2-aminocyclohexylamino)-2-(5-fluoropyridin-3-ylamino)nicotinamide

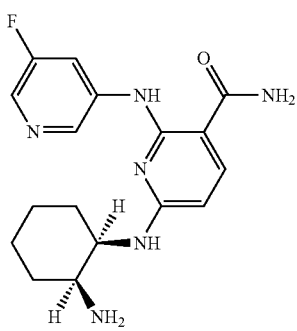 [SMILES: NC(=O)c1ccc(N[C@@H]2CCCC[C@@H]2N)nc1Nc1cncc(F)c1]

The title compound was prepared using the same chemistry shown in Example 157. UV: 235, 263, 320 nm. M+H found for $C_{17}H_{21}FN_6O$: 345.2. NMR (CD$_3$OD): 8.76 (1H, s), 8.40 (1H, m), 8.15 (1H, m), 7.86 (1H, m), 6.28 (1H, dd, J=8.8; 3.2 Hz), 4.43 (1H, m), 3.74 (1H, m), 1.92-1.60 (8H, m) ppm.

Example 180

Preparation of 6-((1R,2S)-2-aminocyclohexylamino)-2-(pyridin-3-ylamino)nicotinamide

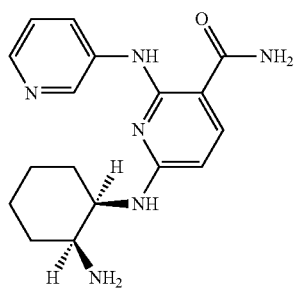 [SMILES: NC(=O)c1ccc(N[C@@H]2CCCC[C@@H]2N)nc1Nc1cccnc1]

The title compound was prepared using the same chemistry shown in Example 157. UV: 235, 263, 297 nm. M+H found for $C_{17}H_{22}N_6O$: 327.2. NMR (CD$_3$OD): 9.52 (1H, s), 8.44 (1H, d, J=8.8 Hz), 8.33 (1H, d, J=5.6 Hz), 7.92-7.84 (2H, m), 6.33 (1H, d, J=9.2 Hz), 4.51 (1H, m), 3.65 (1H, m), 1.90-1.58 (8H, m) ppm.

Example 181

Preparation of 6-((1R,2S)-2-aminocyclohexylamino)-2-(pyridin-4-ylamino)nicotinamide

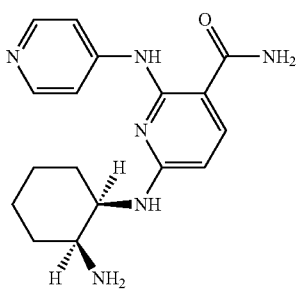 [SMILES: NC(=O)c1ccc(N[C@@H]2CCCC[C@@H]2N)nc1Nc1ccncc1]

The title compound was prepared using the same chemistry shown in Example 157. UV: 282, 316 nm M+H found for $C_{17}H_{22}N_6O$: 327.3. NMR (CD$_3$OD): 8.51-8.41 (2H, m), 8.21-7.95 (3H, m), 6.55 (1H, m), 4.48 (1H, m), 3.75 (1H, m), 2.00-1.60 (8H, m) ppm.

Example 182

Preparation of 6-((1R,2S)-2-aminocyclohexylamino)-2-(3-methylisothiazol-5-ylamino)nicotinamide

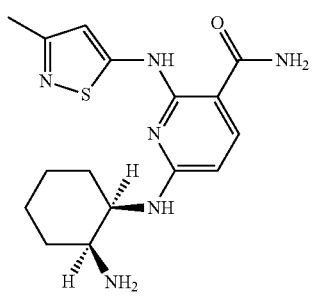

The title compound was prepared using the same chemistry shown in Example 157. UV: 244, 278, 320 nm. M+H found for $C_{16}H_{22}N_6OS$: 347.2. NMR (CD$_3$OD): 8.00 (1H, d, J=8.4 Hz), 6.93 (1H, s), 6.45 (1H, d, J=8.8 Hz), 4.64 (1H, m), 3.79 (1H, m), 2.53 (3H, s), 1.98-1.64 (8H, m) ppm.

Example 183

Preparation of 2-(1,5-naphthyridin-3-ylamino)-6-((1R,2S)-2-aminocyclohexylamino)-5-fluoronicotinamide

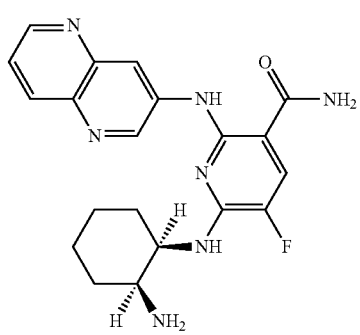 [SMILES: NC(=O)c1cc(F)c(N[C@@H]2CCCC[C@@H]2N)nc1Nc1cnc2cccnc2c1]

Preparation of 1,5-naphthyridin-3-amine

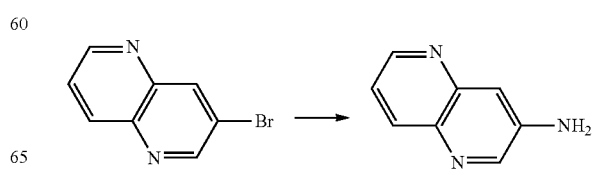

Commercial 3-bromo-[1,5]naphthyridine (1.00 g, 4.8 mmol) was dissolved in 50 mL dioxane. To it were added t-butyl carbamate (0.85 g, 7.2 mmol), cesium carbonate (3.13 g, 9.6 mmol), Pd$_2$(dba)$_3$ (0.22 g, 0.24 mmol) and XantPhos (0.42 g, 0.72 mmol). The mixture was degassed with Ar stream and stirred under Ar in 85° C. bath for 5 h. The mixture was concentrated, taken into 400 mL EtOAc and 200 mL water. The organic phase was separated, dried, concentrated and subjected to flash column (0-30% EtOAc in DCM) to obtain tert-butyl 1,5-naphthyridin-3-ylcarbamate (1.04 g, 88% yield). This compound was treated with 50 mL 4N HCl in dioxane for overnight. To the suspension was poured diethyl ether 300 mL. The suspension was vigorously stirred. The solid product was collected by filtration as 1,5-naphthyridin-3-amine di-HCl salt.

The title compound was prepared using the same chemistry shown in Example 174. UV: 254, 311 nm. M+H found for C$_{20}$H$_{22}$FN$_7$O: 396.3. NMR (CD$_3$OD): 9.18 (1H, d, J=2.4 Hz), 8.98 (1H, dd, J=5.2; 1.6 Hz), 8.89 (1H, d, J=2.0 Hz), 8.72 (1H, d, J=8.4 Hz), 7.90 (1H, d, J=12.0 Hz), 7.84 (1H, dd, J=8.8; 5.2 Hz), 4.74 (1H, m), 3.90 (1H, m), 2.00-1.64 (8H, m) ppm.

Example 184

Preparation of 2-(1,5-naphthyridin-3-ylamino)-6-(1R,2S)-2-aminocyclohexylamino)nicotinamide

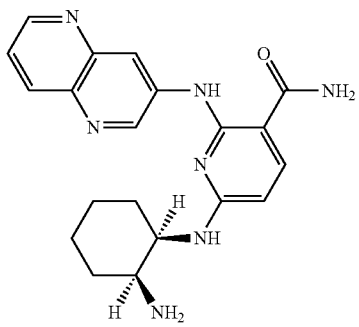 [SMILES: NC(=O)c1ccc(N[C@@H]2CCCC[C@@H]2N)nc1Nc1cnc2cccnc2c1]

The title compound was prepared using the same chemistry shown in Example 157. UV: 259, 320 nm. M+H found for C$_{20}$H$_{23}$N$_7$O: 378.3. NMR (CD$_3$OD): 9.05 (2H, broad s), 8.93 (1H, dd, J=4.8; 1.6 Hz), 8.55 (1H, d, J=8.4 Hz), 7.92 (1H, d, J=9.2 Hz), 7.73 (1H, dd, J=8.8; 4.8 Hz), 6.34 (1H, d, J=8.4 Hz), 4.66 (1H, m), 3.76 (1H, m), 2.00-1.56 (8H, m) ppm.

Example 185

Preparation of 6-((1R,2S)-2-aminocyclohexylamino)-2-(quinolin-3-ylamino)nicotinamide

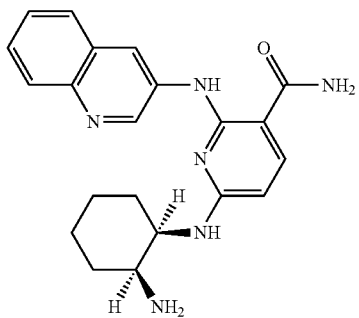 [SMILES: NC(=O)c1ccc(N[C@@H]2CCCC[C@@H]2N)nc1Nc1cnc2ccccc2c1]

The title compound was prepared using the same chemistry shown in Example 157. UV: 226, 249, 301, 332 nm. M+H found for C$_{21}$H$_{24}$N$_6$O: 377.2. NMR (CD$_3$OD): 9.62 (1H, m), 9.10 (1H, s), 8.13-8.10 (2H, m), 7.91 (1H, d, J=9.2 Hz), 7.88 (1H, m), 7.81 (1H, m), 6.34 (1H, d, J=8.8 Hz), 4.57 (1H, m), 3.66 (1H, m), 1.99-1.57 (8H, m) ppm.

Example 186

Preparation of 6-((1R,2S)-2-aminocyclohexylamino)-2-(quinolin-7-ylamino)nicotinamide

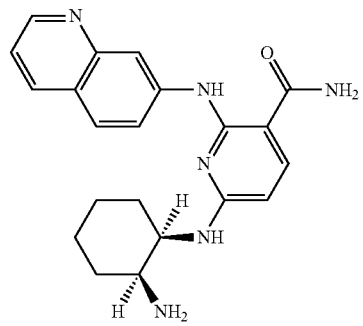 [SMILES: NC(=O)c1ccc(N[C@@H]2CCCC[C@@H]2N)nc1Nc1ccc2cccnc2c1]

The title compound was prepared using the same chemistry shown in Example 157. UV: 268, 297 nm. M+H found for C$_{21}$H$_{24}$N$_6$O: 377.2. NMR (CD$_3$OD): 8.88-8.86 (2H, m), 8.81 (1H, d, J=8.0 Hz), 8.09 (1H, d, J=9.2 Hz), 7.91 (1H, d, J=9.2 Hz), 7.78 (1H, d, J=8.4 Hz), 7.67 (1H, dd, J=8.0; 5.6 Hz), 6.38 (1H, d, J=8.8 Hz), 4.64 (1H, m), 3.78 (1H, m), 1.93-1.57 (8H, m) ppm.

Example 187

Preparation of 2-(3-(1H-pyrrol-1-yl)phenylamino)-6-((1R,2S)-2-aminocyclohexylamino)-5-fluoronicotinamide

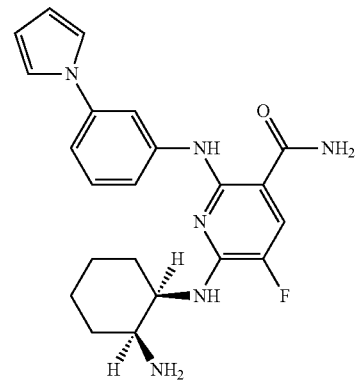 [SMILES: NC(=O)c1cc(F)c(N[C@@H]2CCCC[C@@H]2N)nc1Nc1cccc(-n2cccc2)c1]

The title compound was prepared using the same chemistry shown in Example 174. UV: 259, 306 nm. M+H found for C$_{22}$H$_{25}$FN$_6$O: 409.2. NMR (CD$_3$OD): 8.17 (1H, t, J=2.4 Hz), 7.76 (1H, d, J=12.0 Hz), 7.34 (1H, t, J=7.6 Hz), 7.17 (2H, t, J=2.4 Hz), 7.12-7.05 (2H, m), 6.30 (2H, t, J=2.4 Hz), 4.26 (1H, m), 3.79 (1H, m), 1.82-1.14 (8H, m) ppm.

Example 188

Preparation of 2-(4-(1H-pyrrol-1-yl)phenylamino)-6-((1R,2S)-2-aminocyclohexylamino)-5-fluoronicotinamide

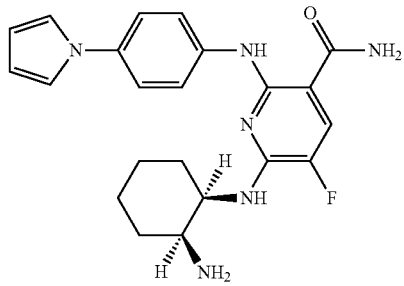 [SMILES: NC(=O)c1cc(F)c(N[C@@H]2CCCC[C@@H]2N)nc1Nc1ccc(-n2cccc2)cc1]

The title compound was prepared using the same chemistry shown in Example 174. UV: 311 nm. M+H found for $C_{22}H_{25}FN_6O$: 409.2. NMR ($CD_3OD$): 7.75 (1H, d, J=12.0 Hz), 7.61 (2H, dd, J=9.2; 2.0 Hz), 7.40 (2H, d, J=8.8; 2.0 Hz), 7.11 (2H, t, J=2.4 Hz), 6.26 (2H, t, J=2.4 Hz), 4.35 (1H, m), 3.89 (1H, m) 1.89-1.62 (8H, m) ppm.

Example 189

Preparation of 6-((1R,2S)-2-aminocyclohexylamino)-5-fluoro-2-(3-(thiazol-2-yl)phenylamino)nicotinamide

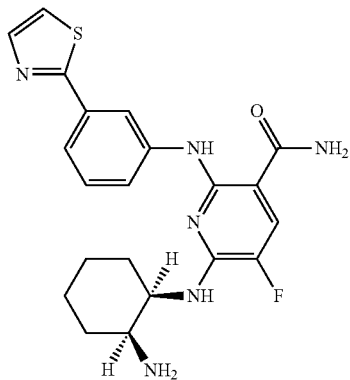 [SMILES: NC(=O)c1cc(F)c(N[C@@H]2CCCC[C@@H]2N)nc1Nc1cccc(-c2nccs2)c1]

Preparation of 3-(thiazol-2-yl)aniline

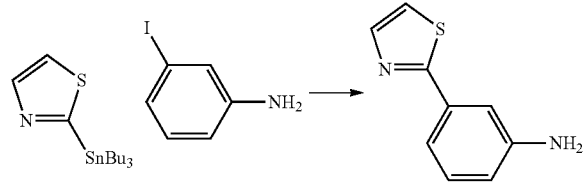

The mixture of 2-tributylstannylthiazole (1.57 mL, 5.00 mmol), 3-iodoaniline (0.50 mL, 4.16 mmol) and Pd(Ph₃P)₄ (465 mg, 0.4 mmol) in 50 mL toluene was degassed using Ar. The mixture was then stirred under Ar at 115° C. for 3 h. The mixture was concentrated and subjected to flash column (0 to 4.5% MeOH in DCM) to isolate 3-(thiazol-2-yl)aniline (709 mg, 95% yield).

The title compound was prepared using the same chemistry shown in Example 174. UV: 301 nm. M+H found for $C_{21}H_{23}FN_6OS$: 427.1. NMR ($CD_3OD$): 8.63 (1H, s), 7.92 (1H, m), 7.80 (1H, d, J=12.0 Hz), 7.65 (1H, m), 7.52 (1H, m), 7.44-7.37 (2H, m), 4.58 (1H, m), 3.81 (1H, m), 1.79-1.56 (8H, m) ppm.

Example 190

Preparation of 2-(2-(1H-pyrazol-1-yl)pyridin-4-ylamino)-6-((1R,2S)-2-aminocyclohexylamino)-5-fluoronicotinamide

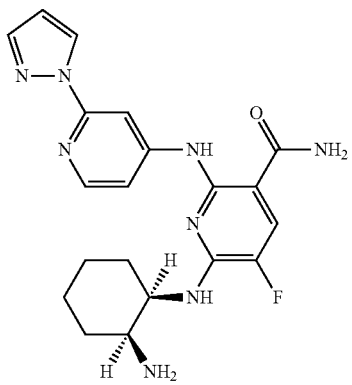 [SMILES: NC(=O)c1cc(F)c(N[C@@H]2CCCC[C@@H]2N)nc1Nc1ccnc(-n2cccn2)c1]

Preparation of 2-(1H-pyrazol-1-yl)pyridin-4-amine

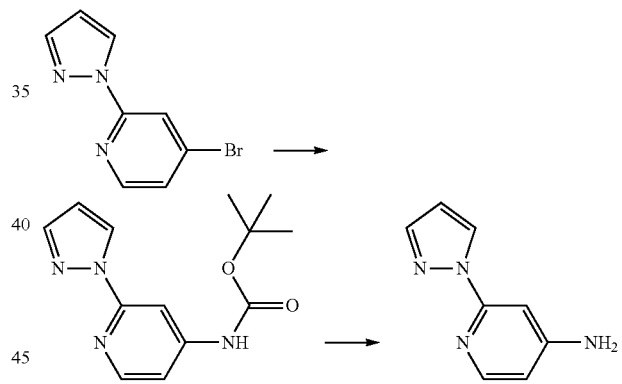

Commercial 4-bromo-2-(1H-pyrazol-1-yl)pyridine (500 mg, 2.23 mmol) was dissolved in 30 mL dioxane. To it were added t-butyl carbamate (392 g, 3.35 mmol), cesium carbonate (1.46 g, 4.46 mmol), Pd₂(dba)₃ (101 mg, 0.11 mmol) and XantPhos (192 mg, 0.33 mmol). The mixture was degassed with Ar stream and stirred under Ar in 85° C. bath for overnight. The mixture was concentrated, taken into 200 mL EtOAc and 100 mL water. The organic phase was separated, dried, concentrated and subjected to flash column (0-20% EtOAc in DCM) to obtain tert-butyl 2-(1H-pyrazol-1-yl)pyridin-4-ylcarbamate. This compound was treated with 2:1 DCM/TFA mixture at RT for 2 h. The mixture was pumped to dryness to afford 2-(1H-pyrazol-1-yl)pyridin-4-amine di-TFA salt.

The title compound was prepared using the same chemistry shown in Example 174 UV: 273, 325 nm. M+H found for $C_{20}H_{23}FN_8O$: 411.2. NMR ($CD_3OD$): 8.75 (1H, s), 8.57 (1H, d, J=2.8 Hz), 8.20 (1H, d, J=6.4 Hz), 7.89 (1H, d, J=11.6 Hz), 7.87 (1H, s), 7.25 (1H, m), 6.63 (1H, m), 4.80 (1H, m), 3.84 (1H, m), 1.91-1.58 (8H, m) ppm.

Example 191

Preparation of 2-(6-(1H-pyrazol-1-yl)pyridin-3-ylamino)-6-((1R,2S)-2-aminocyclohexylamino)-5-fluoronicotinamide

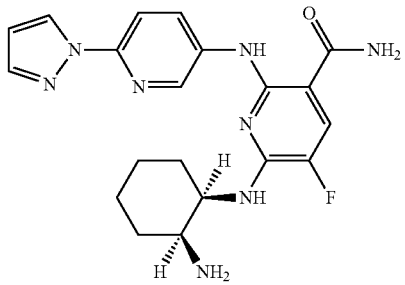 [SMILES: NC(=O)c1cc(F)c(N[C@@H]2CCCC[C@@H]2N)nc1Nc1ccc(-n2cccn2)nc1]

Preparation of 6-(1H-pyrazol-1-yl)pyridin-3-amine

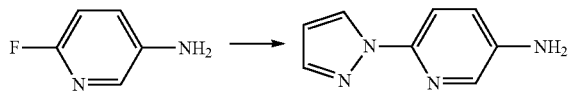 [SMILES: Nc1ccc(F)nc1 ; Nc1ccc(-n2cccn2)nc1]

Commercial 6-fluoropyridin-3-amine (500 mg, 4.46 mmol) was dissolved in 20 mL dry NMP. To it were added pyrazole (910 mg, 13.4 mmol) and cesium carbonate (4.4 g, 13.4 mmol). The mixture was stirred in a sealed tube at 120° C. for over the weekend (3 nights). The mixture was diluted with chloroform, washed with brine (3 times), dried, concentrated and subjected to flash column (0 to 30% EtOAc in DCM) to isolate 6-(1H-pyrazol-1-yl)pyridin-3-amine (120 mg, 17% yield).

The title compound was prepared using the same chemistry shown in Example 174. UV: 273, 325 nm. M+H found for $C_{20}H_{23}FN_8O$: 411.2. NMR (CD$_3$OD): 8.66 (1H, d, J=2.4 Hz), 8.49 (1H, d, J=2.4 Hz), 8.15 (1H, dd, J=8.8; 2.4 Hz), 7.85 (1H, d, J=8.4 Hz), 7.79 (1H, d, J=12.4 Hz), 7.73 (1H, s), 6.52 (1H, t, J=2.0 Hz), 4.40 (1H, m), 3.86 (1H, m), 1.89-1.63 (8H, m) ppm.

Example 192

Preparation of 2-(3-(1H-pyrazol-1-yl)phenylamino)-6-((1R,2S)-2-aminocyclohexylamino)nicotinamide

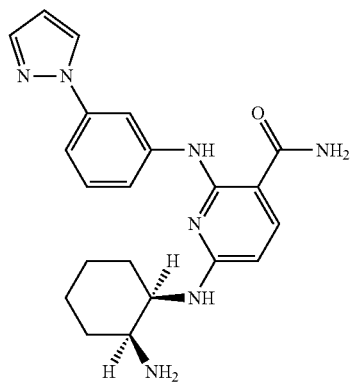 [SMILES: NC(=O)c1ccc(N[C@@H]2CCCC[C@@H]2N)nc1Nc1cccc(-n2cccn2)c1]

The title compound was prepared using the same chemistry shown in Example 157. UV: 263, 306 nm. M+H found for $C_{21}H_{25}N_7O$: 392.2. NMR (CD$_3$OD): 8.63 (1H, s), 8.25 (1H, d, J=2.8 Hz), 7.85 (1H, d, J=8.0 Hz), 7.77 (1H, d, J=2.0 Hz), 7.42 (1H, t, J=8.0 Hz), 7.31 (1H, m), 7.15 (1H, d, J=8.0 Hz), 6.56 (1H, m), 6.20 (1H, d, J=8.8 Hz), 4.62 (1H, m), 3.66 (1H, m), 1.81-1.46 (8H, m) ppm.

Example 193

Preparation of 6-(1R,2S)-2-aminocyclohexylamino)-2-(3-(thiazol-2-yl)phenylamino)nicotinamide

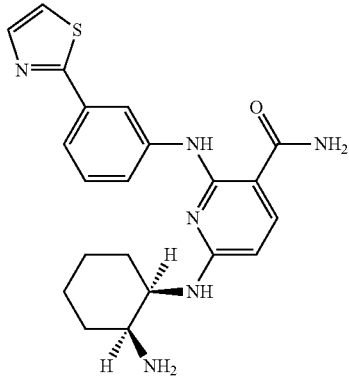

The title compound was prepared using the same chemistry shown in Example 157. UV: 306 nm. M+H found for $C_{21}H_{24}N_6OS$: 409.1. NMR (CD$_3$OD): 8.72 (1H, s), 7.91 (1H, d, J=3.2 Hz), 7.83 (1H, d, J=8.8 Hz), 7.64 (1H, d, J=3.2 Hz), 7.52 (1H, m), 7.41 (1H, m), 7.34 (1H, m), 6.18 (1H, d, J=8.4 Hz), 4.64 (1H, m), 3.65 (1H, m), 1.80-1.47 (8H, m) ppm.

Example 194

Preparation of 4-(3-(2H-1,2,3-triazol-2-yl)phenylamino)-6-(1R,2S)-2-aminocyclohexylamino)nicotinamide

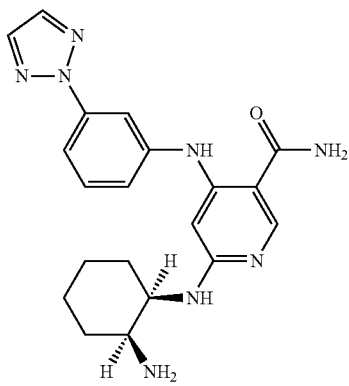 [SMILES: NC(=O)c1cnc(N[C@@H]2CCCC[C@@H]2N)cc1Nc1cccc(-n2nccn2)c1]

Scheme 48:
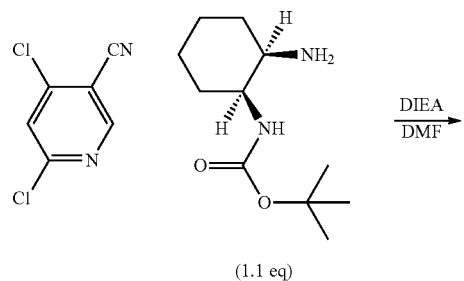
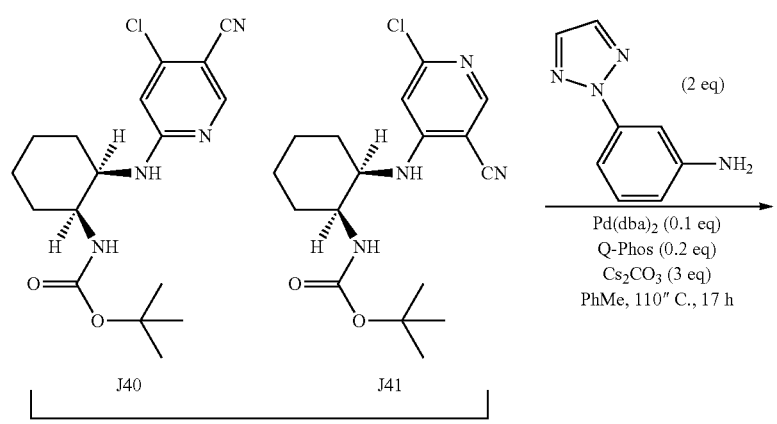
inseparable by silica column
ratio = 1.2:1
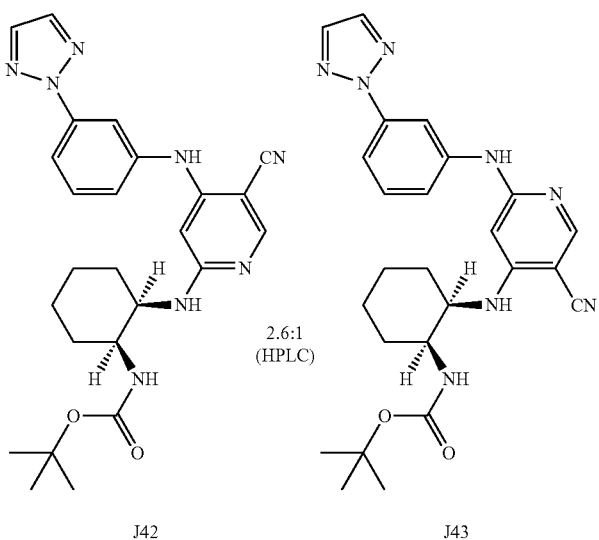
2.6:1
(HPLC)

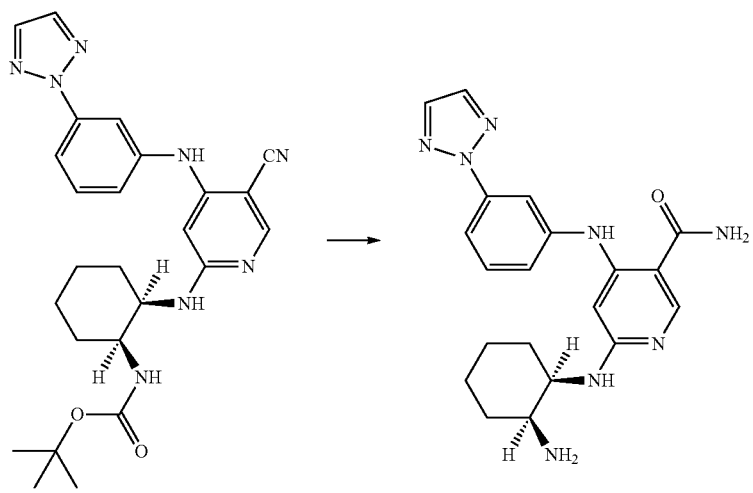

J42

4,6-Dichloronicotinitrile (670 mg, 3.85 mmol) was dissolved in 30 mL dry DMF. To it were added the BOC-protected cyclohexanediamine (990 mg, 4.62 mmol) and DIEA (1.00 mL, 5.78 mmol). The mixture was stirred at 80° C. for 5 h to yield a mixture of J40 and J41. The mixture was diluted with EtOAc, washed with brine 3×, dried and subjected to flash column. No separation between J40 and 341 was achieved. The ratio of J40 and J41 was 1.2:1 based on proton NMR.

The mixture of J40 and J41 (1.2:1) (340 mg, 0.97 mmol), triazolyl aniline (310 mg, 1.94 mmol), cesium carbonate (980 mg, 3.0 mmol), Q-phos (Aldrich #675784, 71 mg, 0.1 mmol), Pd(dba)$_2$ (56 mg, 0.1 mmol) in 30 mL toluene and 10 mL dioxane was degassed with Ar and stirred at 110° C. for overnight to give J42 and J43 in a ratio of 2.6:1 by HPLC. The mixture was concentrated, taken into EtOAc, washed with brine 2×, dried, concentrated and subjected to flash column (0 to 30% EtOAc in DCM) to separate J42 (major, more polar) and J43 (minor, less polar).

Compound J42 was treated with 5 mL TFA and 1 mL concentrated sulfuric acid at 80° C. for 35 min. To it was added 10 mL water. The mixture was concentrated and subjected to reverse phase preparative HPLC to isolate the title compound. UV: 259 nm. M+H found for $C_{20}H_{24}N_8O$: 393.2. NMR (CD$_3$OD): 8.34 (1H, s), 8.08 (1H, s), 8.03 (1H, d, J=7.2 Hz), 7.95 (2H, s), 7.65 (1H, td, J=8.4; 1.6 Hz), 7.36 (1H, m), 6.42 (1H, s), 4.07 (1H, m), 3.56 (1H, m), 1.85-1.52 (8H, m) ppm.

Example 195

Preparation of 6-((1R,2S)-2-aminocyclohexylamino)-4-(3-methylisothiazol-5-ylamino)nicotinamide

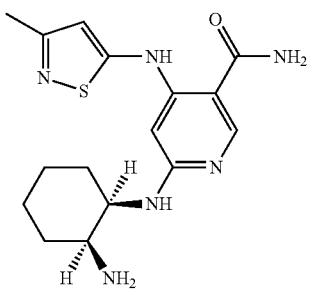 [SMILES: Cc1cc(Nc2cc(N[C@@H]3CCCC[C@@H]3N)ncc2C(N)=O)sn1]

The title compound was prepared using the same chemistry shown in Example 194. UV: 259, 316 nm. M+H found for $C_{16}H_{22}N_6OS$: 347.2. NMR (CD$_3$OD): 8.41 (1H, s), 6.97 (1H, s), 6.62 (1H, s), 4.32 (1H, m), 3.59 (1H, m), 2.44 (3H, s), 1.91-1.60 (8H, m) ppm.

Example 196

Preparation of (R)-6-(2-amino-1-cyclopropyl-2-oxoethylamino)-5-fluoro-2-(quinolin-3-ylamino)nicotinamide

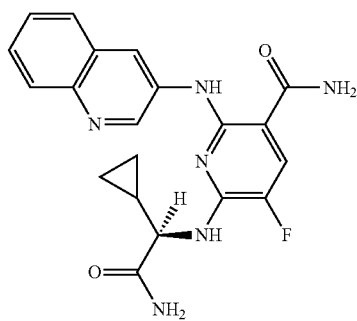 [SMILES: NC(=O)c1cc(F)c(N[C@@H](C(N)=O)C2CC2)nc1Nc1cnc2ccccc2c1]

Scheme 49:

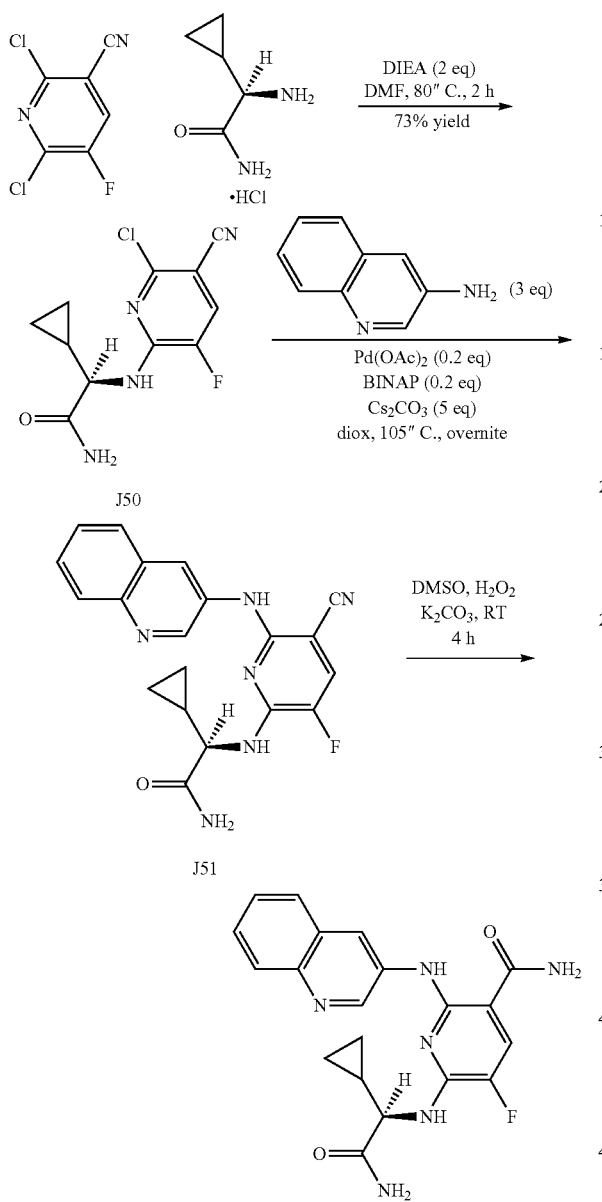

2,6-Dichloro-5-fluoronicotinonitrile (320 mg, 1.66 mmol) was dissolved in 15 mL dry DMF. To it were added D-cyclopropylglycinamide hydrochloride (250 mg, 1.66 mmol) and DIEA (870 μL, 5.0 mmol). The mixture was stirred at 80° C. for 2 h and concentrated in vacuo. The residue was directly subjected to flash column to isolate compound J50 (326 mg, 73% yield).

The mixture of compound J50 (100 mg, 0.37 mmol), 3-aminoquinoline (162 mg, 1.12 mmol), cesium carbonate (605 mg, 1.85 mmol), BINAP (50 mg, 0.08 mmol) and Pd(OAc)$_2$ (18 mg, 0.08 mmol) in 15 mL dioxane was degassed with Ar. The mixture was stirred under Ar at 105° C. for overnight. It was concentrated in vacuo, taken into EtOAc, washed with brine, dried, concentrated in vacuo and subjected to flash column (0 to 10% MeOH in DCM) to isolate compound J51.

Compound J51 was then dissolved in 4 mL DMSO. To it were added 100 mg powder K$_2$CO$_3$ and 2 mL 30% H$_2$O$_2$ in water. The mixture was stirred at RT for 4 h. To it was added 4 mL water, the mixture was vigorously stirred and subjected to reverse phase preparative HPLC to isolate the title compound (96 mg, 66% overall yield from J50). UV: 244, 297 nm. M+H found for C$_{20}$H$_{19}$FN$_6$O$_2$: 395.2. NMR (CD$_3$OD): 9.59 (1H, s), 9.12 (1H, s), 8.31 (1H, d, J=8.4 Hz), 8.09 (1H, d, J=8.4 Hz), 7.94-7.82 (3H, m), 3.69 (1H, m), 1.35 (1H, m), 0.75-0.46 (4H, m) ppm.

Example 197

Preparation of (R)-6-(2-amino-1-cyclopropyl-2-oxoethylamino)-5-fluoro-2-(quinolin-6-ylamino)nicotinamide

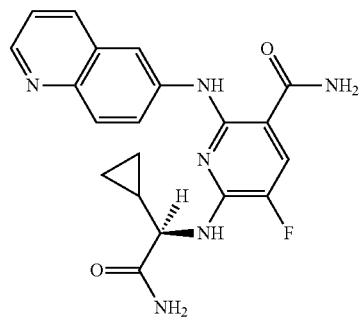

The title compound was prepared using the same chemistry shown in Example 196. UV: 268, 292, 330 nm. M+H found for C$_{20}$H$_{19}$FN$_6$O$_2$: 395.2. NMR (CD$_3$OD): 9.15 (1H, m), 8.87 (1H, m), 8.81 (1H, m), 8.02 (1H, m), 7.92-7.83 (3H, m), 3.83 (1H, m), 1.37 (1H, m), 0.76-0.45 (4H, m) ppm.

Example 198

Preparation of (R)-6-(2-amino-1-cyclopropyl-2-oxoethylamino)-5-fluoro-2-(3-methylisothiazol-5-ylamino)nicotinamide

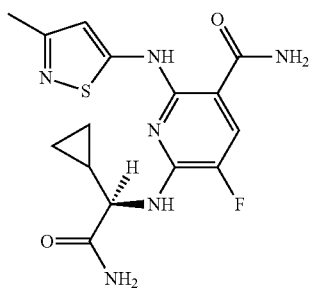 [SMILES: Cc1cc(Nc2nc(N[C@@H](C(N)=O)C3CC3)c(F)cc2C(N)=O)sn1]

2,6-Dichloro-5-fluoronicotinonitrile (320 mg, 1.66 mmol) was dissolved in 15 mL dry DMF. To it were added D-cyclopropylglycinamide hydrochloride (250 mg, 1.66 mmol) and DIEA (870 μL, 5.0 mmol). The mixture was stirred at 80° C. for 2 h and concentrated in vacuo. The residue was directly subjected to flash column to isolate (R)-2-(6-chloro-5-cyano-3-fluoropyridin-2-ylamino)-2-cyclopropylacetamide (326 mg, 73% yield). The mixture of (R)-2-(6-chloro-5-cyano-3-fluoropyridin-2-ylamino)-2-cyclopropylacetamide (100 mg, 0.37 mmol), 3-methylisothiazole hydrochloride (170 mg, 1.12 mmol), cesium carbonate (850 mg, 2.60 mmol), BINAP (50 mg, 0.08 mmol) and Pd(OAc)$_2$ (18 mg, 0.08 mmol) in 15 mL dioxane was degassed with Ar. The mixture was stirred under Ar at 105° C. for overnight. It was concentrated in vacuo, taken into EtOAc, washed with brine, dried, concentrated in vacuo and subjected to flash column (0 to 10% MeOH in DCM) to isolate (R)-2-(5-cyano-3-fluoro-6-(3-methylisothiazol-5-ylamino)pyridin-2-ylamino)-2-cyclopropylacetamide. It was then dissolved in 4 mL DMSO. To it were added 100 mg powder $K_2CO_3$ and 2 mL 30% $H_2O_2$ in water. The mixture was stirred at RT for 3 h. To it was added 4 mL water, the mixture was vigorously stirred and subjected to reverse phase preparative HPLC to isolate the title compound (81 mg). UV: 244, 273, 330 nm. M+H found for $C_{15}H_{17}FN_6O_2S$: 365.1. NMR (CD$_3$OD): 7.97 (1H, d, J=11.2 Hz), 6.89 (1H, s), 4.26 (1H, d, J=8.8 Hz), 2.52 (3H, s), 1.40 (1H, m), 0.78-0.49 (4H, m) ppm.

Example 199

Preparation of (R)-6-(1-amino-1-oxopentan-2-ylamino)-5-fluoro-2-(quinolin-3-ylamino)nicotinamide

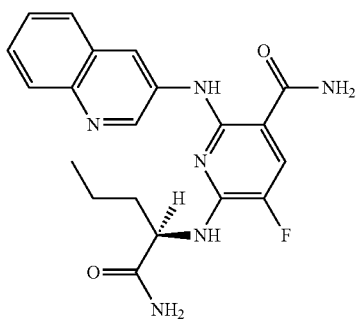

The title compound was prepared using the same chemistry shown in Example 196. UV: 244, 297 nm. M+H found for $C_{20}H_{21}FN_6O_2$: 397.3. NMR (CD$_3$OD): 9.47 (1H, d, J=2.4 Hz), 9.19 (1H, d, J=2.4 Hz), 8.30 (1H, d, J=8.0 Hz), 8.06 (1H, d, J=8.4 Hz), 7.90-7.79 (3H, m), 4.40 (1H, m), 1.96 (2H, m), 1.57 (2H, m), 1.00 (3H, t, J=6.8 Hz) ppm.

Example 200

(R)-6-(1-amino-1-oxopentan-2-ylamino)-5-fluoro-2-(quinolin-6

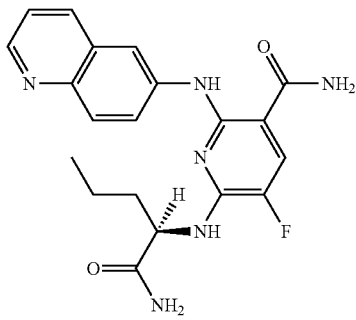

The title compound is prepared using the same chemistry shown in Example 196. UV: 266, 298, 330 nm. M+H found for $C_{20}H_{21}FN_6O_2$: 397.3. NMR (CD$_3$OD): 9.25 (1H, d, J=8.0 Hz), 8.97 (1H, d, J=2.0 Hz), 8.86 (1H, dd, J=5.6; 1.6 Hz), 8.06 (1H, d, J=8.4 Hz), 7.97 (1H, dd, J=8.8; 2.4 Hz), 7.92 (1H, dd, J=8.0; 4.8 Hz), 7.85 (1H, d, J=11.6 Hz), 4.49 (1H, dd, J=9.6; 4.8 Hz), 1.96 (2H, m), 1.56 (2H, m), 0.98 (314, t, J=7.2 Hz) ppm.

Example 201

Preparation of (R)-6-(1-amino-1-oxopentan-2-ylamino)-5-fluoro-2-(quinolin-7-ylamino)nicotinamide

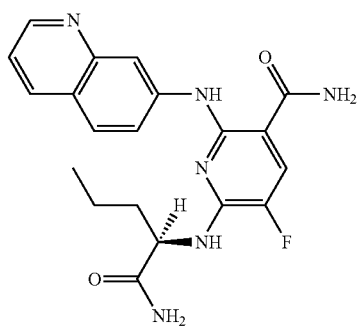 [SMILES: CCC[C@@H](Nc1nc(Nc2ccc3cccnc3c2)c(C(N)=O)cc1F)C(N)=O]

The title compound is prepared using the same chemistry shown in Example 196. UV: 263, 297 nm. M+H found for $C_{20}H_{21}FN_6O_2$: 397.3. NMR (CD$_3$OD): 9.30 (1H, s), 8.97 (1H, dd, J=5.2; 1.6 Hz), 8.88 (1H, d, J=8.4 Hz), 8.11 (1H, d, J=9.2 Hz), 7.90 (1H, d, J=11.6 Hz), 7.73 (1H, dd, J=8.0; 5.6 Hz), 7.61 (1H, dd, J=9.2; 2.4 Hz), 4.42 (1H, m), 1.99 (2H, m), 1.60 (2H, m), 1.00 (3H, t, J=7.6 Hz) ppm.

Example 202

Preparation of (R)-6-(1-amino-1-oxopentan-2-ylamino)-5-fluoro-2-(3-methylisothiazol-5-ylamino)nicotinamide

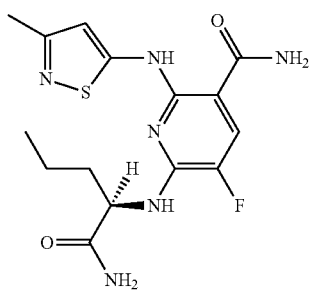 [SMILES: CCC[C@@H](Nc1nc(Nc2cc(C)ns2)c(C(N)=O)cc1F)C(N)=O]

The title compound was prepared using the same chemistry shown in Example 196. UV: 244, 273, 325 nm. M+H found for $C_{15}H_{19}FN_6O_2S$: 367.2. NMR (CD$_3$OD): 7.95 (1H, dd, J=11.6; 2.4 Hz), 6.85 (1H, d, J=4.0 Hz), 4.81 (1H, m), 2.49 (3H, d, J=2.8 Hz), 2.00 (2H, m), 1.53 (2H, m), 1.00 (3H, t, J=6.8 Hz) ppm.

Example 203

Preparation of (R)-6-(1-amino-1-oxobutan-2-ylamino)-2-(quinolin-3-ylamino)nicotinamide

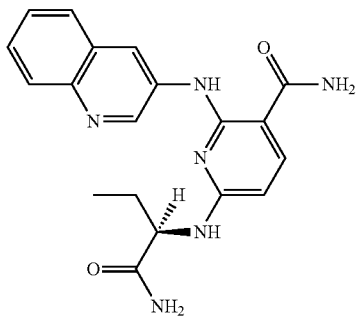

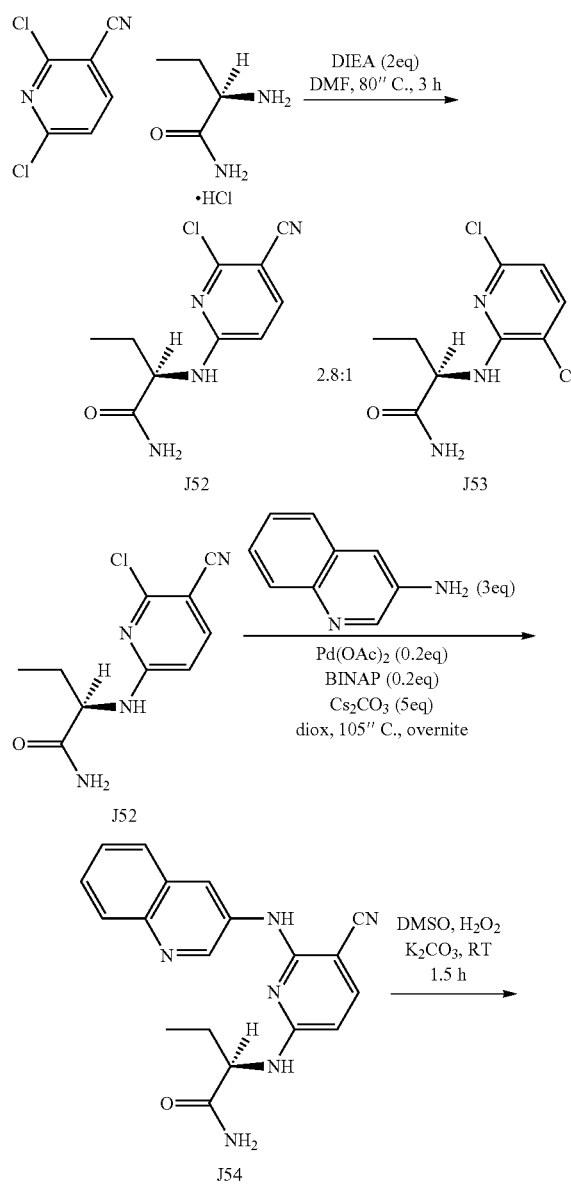

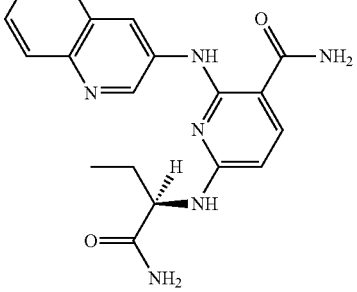

2,6-Dichloronicotinonitrile (940 mg, 5.40 mmol) was dissolved in 30 mL dry DMF. To it were added (R)-(−)-2-aminobutanamide hydrochloride (Aldrich #679830, 1.13 g, 8.15 mmol) and DIEA (2.82 mL, 16.2 mmol). The mixture was stirred at 80° C. for 3 h to give products J52 and J53 in 2.8:1 ratio (by HPLC). The mixture was concentrated in vacuo to remove DMF. EtOAc was poured in. The organic phase was washed with brine 2×, dried and concentrated to dryness. The solid was triturated with 50 mL DCM. The solid was collected by filtration, which was 93% pure J52 with 7% J53.

The mixture of compound J52 (120 mg, 0.50 mmol), 3-aminoquinoline (220 mg, 1.5 mmol), cesium carbonate (820 mg, 2.5 mmol), BINAP (63 mg, 0.1 mmol) and Pd(OAc)$_2$ (23 mg, 0.1 mmol) in 20 mL dioxane was degassed with Ar. The mixture was stirred under Ar at 105° C. for overnight. It was concentrated in vacuo, taken into EtOAc, washed with brine, dried, concentrated in vacuo and subjected to flash column (0 to 5% MeOH in DCM) to isolate compound J54.

Compound J54 was then dissolved in 4 mL DMSO. To it were added 100 mg powder K$_2$CO$_3$ and 2 mL 50% H$_2$O$_2$ in water. The mixture was stirred at RT for 1.5 h. To it was added 4 mL water, the mixture was vigorously stirred and subjected to reverse phase preparative HPLC to isolate the title compound. UV: 226, 249, 301 nm. M+H found for C$_{19}$H$_{20}$N$_6$O$_2$: 365.2. NMR (CD$_3$OD): 9.53 (1H, d, J=2.0 Hz), 9.18 (1H, d, J=2.0 Hz), 8.28 (1H, d, J=8.0 Hz), 8.05 (1H, d, J=8.4 Hz), 7.91-7.78 (3H, m), 6.28 (1H, d, J=8.8 Hz), 4.23 (1H, m), 1.95 (2H, m), 1.13 (3H, t, J=7.2 Hz) ppm.

Example 204

Preparation of (R)-6-(1-amino-1-oxobutan-2-ylamino)-2-(quinolin-7-ylamino)nicotinamide

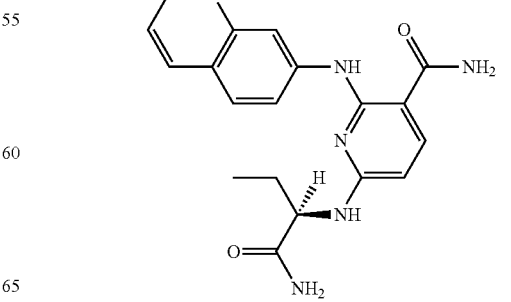

The title compound was prepared using the same chemistry shown in Example 203. UV: 263, 297 nm. M+H found for $C_{19}H_{20}N_6O_2$: 365.2. NMR (CD$_3$OD): 9.43 (1H, s), 8.95 (1H, dd, J=5.6; 1.6 Hz), 8.87 (1H, d, J=7.6 Hz), 8.10 (1H, m), 7.92 (1H, m), 7.72 (1H, m), 7.58 (1H, m), 6.38 (1H, d, J=9.2 Hz), 4.25 (1H, m), 2.02 (2H, m), 1.18 (3H, t, J=7.2 Hz) ppm.

Example 205

Preparation of (R)-6-(1-amino-1-oxobutan-2-ylamino)-2-(quinolin-6-ylamino)nicotinamide

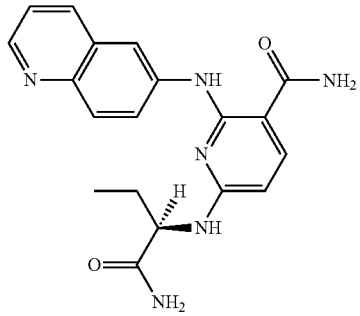

The mixture of (R)-2-(6-chloro-5-cyanopyridin-2-ylamino)butanamide (compound J52 in Example 203) (140 mg, 0.59 mmol), 6-aminoquinoline (260 mg, 1.8 mmol), cesium carbonate (980 mg, 3.0 mmol), BINAP (75 mg, 0.12 mmol) and Pd(OAc)$_2$ (27 mg, 0.12 mmol) in 20 mL dioxane was degassed with Ar. The mixture was stirred under Ar at 105° C. for overnight. It was concentrated in vacuo, taken into EtOAc, washed with brine, dried, concentrated in vacuo and subjected to flash column (0 to 8% MeOH in DCM) to isolate (R)-2-(5-cyano-6-(quinolin-6-ylamino)pyridin-2-ylamino) butanamide. It was then dissolved in 4 mL DMSO. To it were added 100 mg powder K$_2$CO$_3$ and 2 mL 50% H$_2$O$_2$ in water. The mixture was stirred at RT for 1 h. To it was added 4 mL water, the mixture was vigorously stirred and subjected to reverse phase preparative HPLC to isolate the title compound (65 mg). UV: 267, 299, 330 nm. M+H found for $C_{19}H_{20}N_6O_2$: 365.2. NMR (CD$_3$OD): 9.25 (1H, d, J=8.8 Hz), 9.04 (1H, d, J=2.0 Hz), 8.85 (1H, dd, J=6.4; 2.4Hz), 8.06 (1H, d, J=9.6 Hz), 7.99 (1H, dd, J=9.2; 2.41 Hz), 7.92 (1H, m), 7.88 (1H, d, J=8.8 Hz), 6.28 (1H, d, J=9.2 Hz), 4.31 (1H, m), 2.00 (2H, m), 1.14 (3H, t, J=7.6 Hz) ppm.

Example 206

Preparation of (R)-6-(1-amino-1-oxobutan-2-ylamino)-2-(benzo[d]thiazol-6-ylamino)nicotinamide

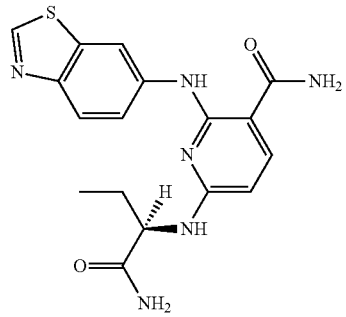

The title compound was prepared using the same chemistry shown in Example 203. UV: 260, 334 nm. M+H found for $C_{17}H_{18}N_6O_2S$: 371.1. NMR (CD$_3$OD): 9.20 (1H, s), 8.65 (1H, m), 8.00 (1H, d, J=8.4 Hz), 7.91 (1H, m), 7.53 (1H, dd, J=8.4; 1.6 Hz), 6.11 (1H, d, J=9.2 Hz), 4.26 (1H, m), 1.92 (2H, m), 1.07 (3H, t, J=7.6 Hz) ppm.

Example 207

Preparation of (R)-6-(1-amino-1-oxobutan-2-ylamino)-2-(benzo[d]thiazol-5-ylamino)nicotinamide

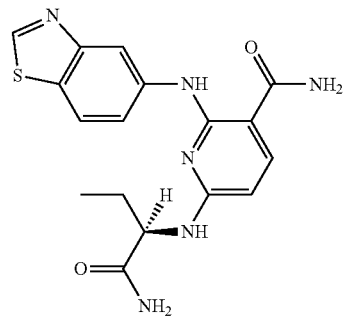 [SMILES: CC[C@@H](Nc1ccc(C(N)=O)c(Nc2ccc3scnc3c2)n1)C(N)=O]

The title compound was prepared using the same chemistry shown in Example 203. UV: 273, 305, 336 nm. M+H found for $C_{17}H_{18}N_6O_2S$: 371.2. NMR (CD$_3$OD): 9.30 (1H, s), 8.63 (1H, m), 7.99 (1H, d, J=8.0 Hz), 7.87 (1H, m), 7.56 (1H, dd, J=8.8; 2.0 Hz), 6.10 (1H, d, J=8.4 Hz), 4.45 (1H, m), 1.92 (2H, m), 1.04 (3H, t, J=7.2 Hz) ppm.

Example 208

Preparation of (R)-6-(1-amino-1-oxobutan-2-ylamino)-2-(1-methyl-1H-indol-5-ylamino)nicotinamide

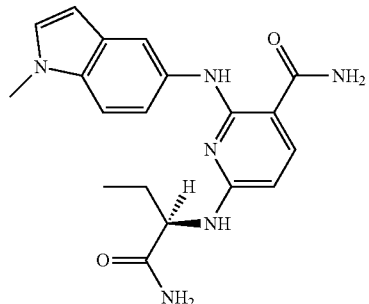

The title compound was prepared using the same chemistry shown in Example 203. UV: 278 nm. M+H found for $C_{19}H_{22}N_6O_2$: 367.3. NMR (CD$_3$OD): 8.23 (1H, dd, J=9.2; 2.0 Hz), 7.61 (1H, d, J=2.0 Hz), 7.57 (1H, d, J=8.8 Hz), 7.32 (1H, s), 7.13 (1H, dd, J=8.4; 2.0 Hz), 6.54 (1H, d, J=3.2 Hz), 5.98 (1H, d, J=9.2 Hz), 4.12 (1H, m), 3.88 (3H, s), 1.82 (2H, m), 0.94 (3H, t, J=7.6 Hz) ppm.

Example 209

Preparation of (R)-6-(1-amino-1-oxobutan-2-ylamino)-2-(1-methyl-1H-indol-4-ylamino)nicotinamide

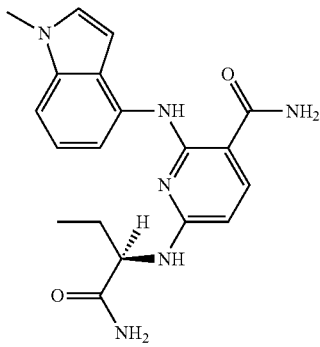 [SMILES: CC[C@@H](Nc1ccc(C(N)=O)c(Nc2cccc3c2ccn3C)n1)C(N)=O]

The title compound was prepared using the same chemistry shown in Example 203. UV: 297 nm. M+H found for $C_{19}H_{22}N_6O_2$: 367.3. NMR (CD$_3$OD): 8.09 (1H, m), 7.42-7.25 (4H, m), 6.42 (1H, m), 6.04 (1H, d, J=8.4 Hz), 4.22 (1H, m), 3.86 (3H, s), 1.84 (2H, m), 0.97 (3H, t, J=7.6 Hz) ppm.

Example 210

Preparation of (R)-6-(1-amino-1-oxobutan-2-ylamino)-2-(3-methylisothiazol-5

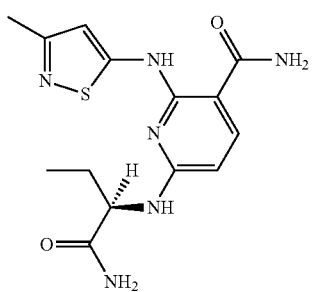 [SMILES: CC[C@@H](Nc1ccc(C(N)=O)c(Nc2cc(C)ns2)n1)C(N)=O]

The title compound was prepared using the same chemistry shown in Example 203. UV: 244, 278, 330 nm. M+H found for $C_{14}H_{18}N_6O_2S$: 335.1. NMR (CD$_3$OD): 8.01 (1H, d, J=8.8 Hz), 6.95 (1H, s), 6.39 (1H, d, J=8.8 Hz), 4.45 (1H, m), 2.55 (3H, s), 2.00 (2H, m), 1.11 (3H, t, J=6.4 Hz) ppm.

Example 211

Preparation of (R)-6-(1-amino-3-cyclopropyl-1-oxo-propan-2-ylamino)-2-(3-methylisothiazol-5-ylamino)nicotinamide

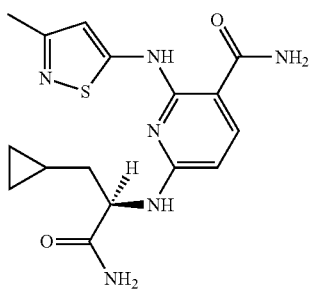 [SMILES: Cc1cc(Nc2nc(N[C@H](CC3CC3)C(N)=O)ccc2C(N)=O)sn1]

The title compound was prepared using the same chemistry shown in Example 203. UV: 244, 278, 330 nm. M+H found for $C_{16}H_{20}N_6O_2S$: 361.1. NMR (CD$_3$OD): 7.80 (1H, d, J=8.4 Hz), 6.73 (1H, s), 6.17 (1H, d, J=8.4 Hz), 4.43 (1H, m), 2.32 (3H, s), 1.75 (1H, m), 1.53 (1H, m), 0.73 (1H, m), 0.29 (2H, m), 0.02 (2H, m) ppm.

Example 212

Preparation of (R)-6-(1-amino-3-cyclopropyl-1-oxo-propan-2-ylamino)-2-(quinolin-3-ylamino)nicotinamide

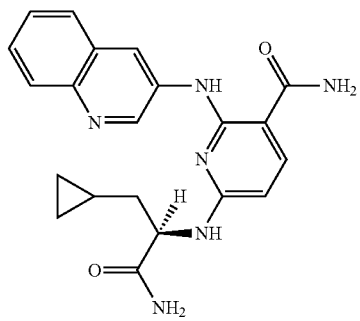 [SMILES: NC(=O)c1ccc(N[C@H](CC2CC2)C(N)=O)nc1Nc1cnc2ccccc2c1]

The title compound was prepared using the same chemistry shown in Example 203. UV: 254, 300 nm M+H found for $C_{21}H_{22}N_6O_2$: 391.2. NMR (CD$_3$OD): 9.54 (1H, s), 9.21 (1H, s), 8.28 (1H, d, J=8.0 Hz), 8.06 (1H, d, J=8.8 Hz), 7.91 (1H, d, J=8.4 Hz), 7.86 (1H, m), 7.80 (1H, m), 6.29 (1H, d, J=9.2 Hz), 4.39 (1H, m), 1.94 (1H, m), 1.70 (1H, m), 0.99 (1H, m), 0.51 (2H, m), 0.21 (2H, m) ppm.

Example 213

Preparation of (R)-6-(1-amino-3-cyclopropyl-1-oxo-propan-2-ylamino)-2-(quinolin-6-ylamino)nicotinamide

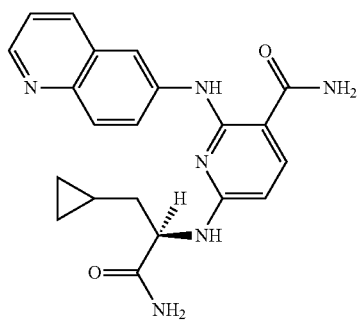

The title compound was prepared using the same chemistry shown in Example 203. UV: 268, 297, 330 nm. M+H found for $C_{21}H_{22}N_6O_2$: 391.2. NMR (CD$_3$OD): 9.26 (1H, d, J=8.0 Hz), 9.06 (1H, s), 8.86 (1H, d, J=5.2 Hz), 8.07 (1H, d, J=9.6 Hz), 8.02 (1H, dd, J=8.8; 2.4 Hz), 7.93 (1H, m), 7.90 (1H, d, J=8.4 Hz), 6.29 (1H, d, J=8.8 Hz), 4.47 (1H, dd, J=8.4; 4.0 Hz), 1.95 (1H, m), 1.73 (1H, m), 1.00 (1H, m), 0.51 (2H, m), 0.20 (2H, m) ppm.

Example 214

Preparation of (R)-6-(1-amino-3-cyclopropyl-1-oxo-propan-2-ylamino)-2-(quinolin-7-ylamino)nicotinamide

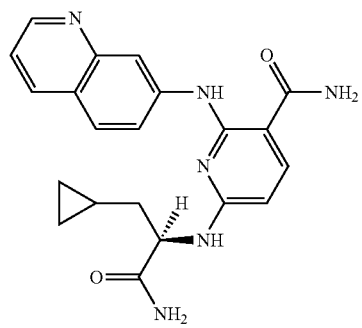 [SMILES: NC(=O)c1ccc(N[C@H](CC2CC2)C(N)=O)nc1Nc1ccc2cccnc2c1]

The title compound was prepared using the same chemistry shown in Example 203. UV: 263, 297 nm. M+H found for $C_{21}H_{22}N_6O_2$: 391.2. NMR (CD$_3$OD): 9.24 (1H, d, J=2.0 Hz), 8.77 (1H, dd, J=6.0; 1.2 Hz), 8.69 (1H, d, J=8.0 Hz), 7.91 (1H, d, J=9.2 Hz), 7.74 (1H, d, J=9.2 Hz), 7.54 (1H, dd, J=7.6; 5.2 Hz), 7.39 (1H, dd, J=8.8; 2.4 Hz), 6.21 (1H, d, J=8.8 Hz), 4.20 (1H, dd, J=8.8; 4.8 Hz), 1.80 (1H, m), 1.60 (1H, m), 0.88 (1H, m), 0.36 (2H, m), 0.05 (2H, m) ppm.

Example 215

(R)-4-(2-amino-1-cyclopropyl-2-oxoethylamino)-5-fluoro-2-(3-methylisothiazol-5-ylamino)benzamide

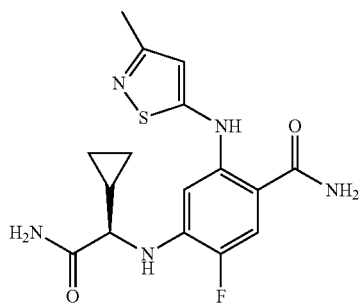 [SMILES: Cc1cc(Nc2cc(N[C@@H](C(N)=O)C3CC3)c(F)cc2C(N)=O)sn1]

Scheme 51:

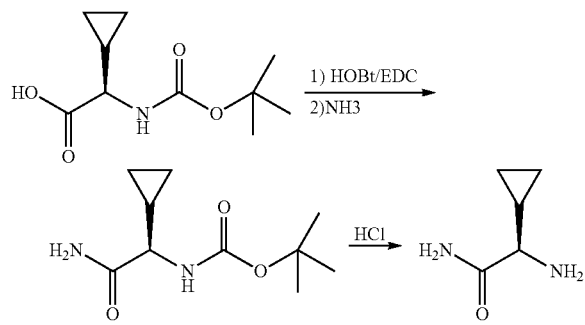

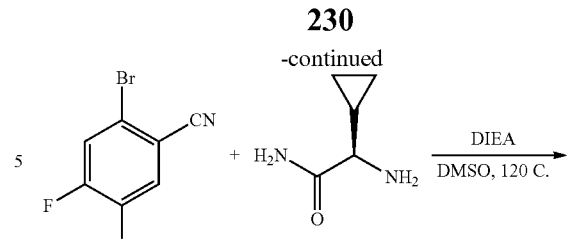

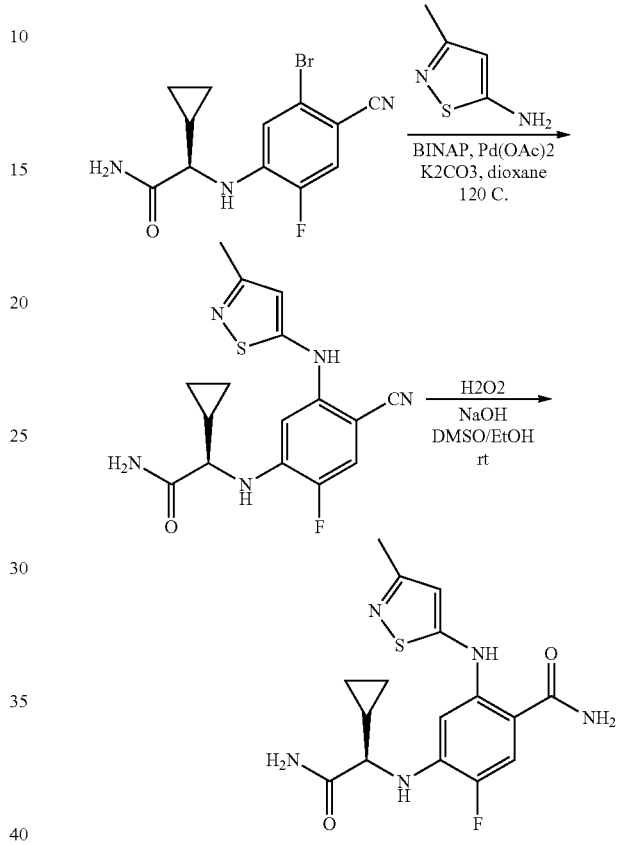

A solution of N-Boc-D-cyclopropylglycine (550 mg, 2.56 mmol), HOBt monohydrate (470 mg, 3.07 mmol) and EDC (638 mg, 3.32 mmol) in DMF (10 mL) was stirred at room temperature for 4 h, conc. NH$_4$OH (0.900 mL, ca. 12.6 mmol) was added. The mixture was stirred for 18 h. Water and EtOAc were added. The organic phase was separated, washed with 5% NaHCO$_3$, dried over Na$_2$SO$_4$, concentrated in vacuo to give (R)-tert-butyl 2-amino-1-cyclopropyl-2-oxoethylcarbamate (300 mg)

A solution of (R)-tert-butyl 2-amino-1-cyclopropyl-2-oxoethylcarbamate (300 mg, 1.40 mmol) in 4N HCl in dioxane (8 mL) was stirred at room temperature for 20 min. It was then concentrated in vacuo to give (R)-2-amino-2-cyclopropylacetamide hydrochloride (225 mg).

A solution of 2-bromo-4,5-difluorobenzonitrile (170 mg, 0.780 mmol), (R)-2-amino-2-cyclopropylacetamide hydrochloride (120 mg, 0.797 mmol) and DIEA (0.500 mL, 2.87 mmol) in DMSO (3 mL) was stirred at 120 C for 18 h. Water and EtOAc were added. The organic phase was separated, dried over Na$_2$SO$_4$, concentrated in vacuo to give (R)-2-(5-bromo-4-cyano-2-fluorophenylamino)-2-cyclopropylacetamide (197 mg)

A mixture of (R)-2-(5-bromo-4-cyano-2-fluorophenylamino)-2-cyclopropylacetamide (87 mg, 0.278 mmol), 5-amino-3-methylisothiazole hydrochloride (63 mg, 0.418 mmol), K₂CO₃ (120 mg, 0.869 mmol), BINAP (40 mg, 0.064 mmol) and Pd(OAc)₂ (20 mg, 0.089 mmol) in dioxane (2 mL) was degassed with argon, then was stirred at 120 C for 18 h. The mixture was concentrated in vacuo. The residue was purified by HPLC to give (R)-2-(4-cyano-2-fluoro-5-(3-methylisothiazol-5-ylamino)phenylamino)-2-cyclopropylacetamide (38 mg).

To a solution of (R)-2-(4-cyano-2-fluoro-5-(3-methylisothiazol-5-ylamino)phenylamino)-2-cyclopropylacetamide (38 mg, 0.110 mmol) in EtOH (1 mL) and DMSO (0.5 mL), aq. 1N NaOH (0.5 mL, 0.50 mmol) and aq. H₂O₂ (50%, 0.5 mL) were added. The mixture was stirred at room temperature for 20 min. HOAc (0.5 mL) was added. The mixture was purified by HPLC to give the titled compound (18 mg). MS 364.2 (M+H); UV 219.3, 280.5, 302.6 nm.

Example 216

2-(3-methylisothiazol-5-ylamino)-4-(2-oxoazepan-3-ylamino)benzamide

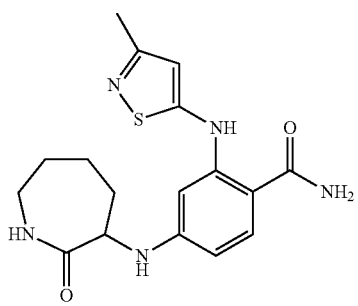

Scheme 52:

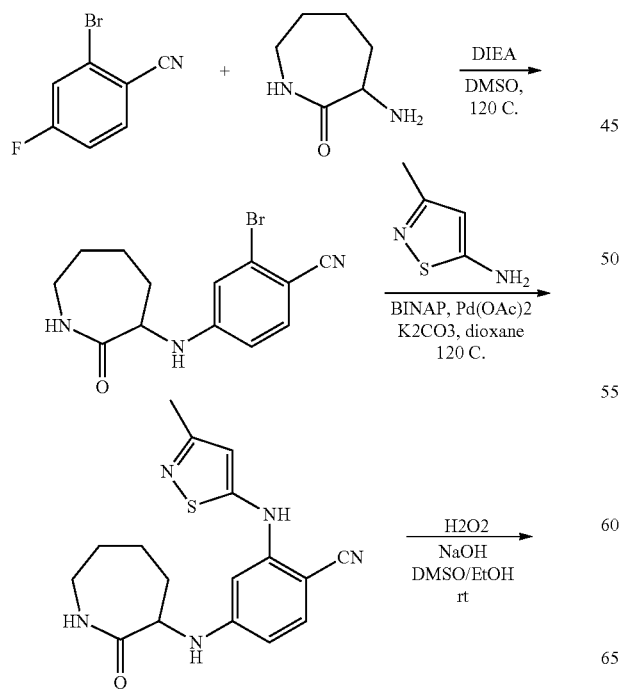

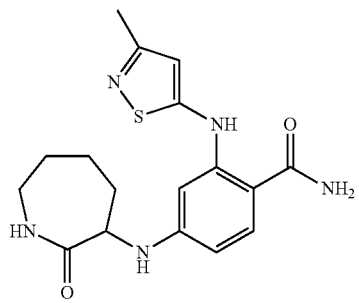 [SMILES: Cc1cc(Nc2cc(NC3CCCCNC3=O)ccc2C(N)=O)sn1]

A solution of 2-bromo-4-fluorobenzonitrile (200 mg, 1.00 mmol), DL-α-amino-ε-caprolactam hydrochloride (173 mg, 1.05 mmol) and DIEA (0.620 mL, 3.56 mmol) in DMSO (3 mL) was stirred at 120 C for 18 h. Water and EtOAc were added. The solid found between the bi-layer was collected by filtration to give 2-bromo-4-(2-oxoazepan-3-ylamino)benzonitrile (155 mg)

A mixture of 2-bromo-4-(2-oxoazepan-3-ylamino)benzonitrile (81 mg, 0.263 mmol), 5-amino-3-methylisothiazole hydrochloride (63 mg, 0.418 mmol), K₂CO₃ (120 mg, 0.869 mmol), BINAP (40 mg, 0.064 mmol) and Pd(OAc)₂ (20 mg, 0.089 mmol) in dioxane (3 mL) was degassed with argon, then was stirred at 120 C for 18 h. Water and EtOAc were added. The organic phase was separated, dried over Na₂SO₄, concentrated in vacuo to give 2-(3-methylisothiazol-5-ylamino)-4-(2-oxoazepan-3-ylamino)benzonitrile (143 mg)

To 2-(3-methylisothiazol-5-ylamino)-4-(2-oxoazepan-3-ylamino)benzonitrile (143 mg, 0.263 mmol) in EtOH (2 mL) and DMSO (1 mL), aq. 1N NaOH (1 mL, 1.0 mmol) and aq. H₂O₂ (50%, 1 mL) were added. The mixture was stirred at room temperature for 3 h. HOAc (1 mL) was added. The mixture was then purified by HPLC to give the titled compound (72 mg). MS 360.3 (M+H); UV 202.1, 300.7 nm.

Example 217

(R)-4-(1-amino-3-(1H-indol-3-yl)-1-oxopropan-2-ylamino)-2-(3-methylisothiazol-5-ylamino)benzamide

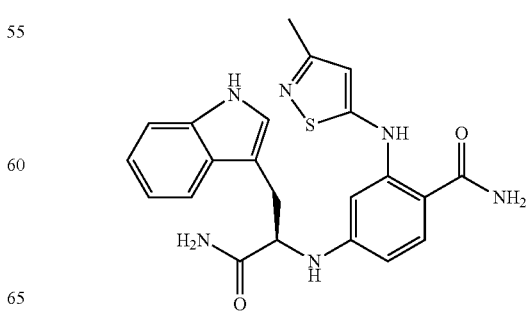

Scheme 53:

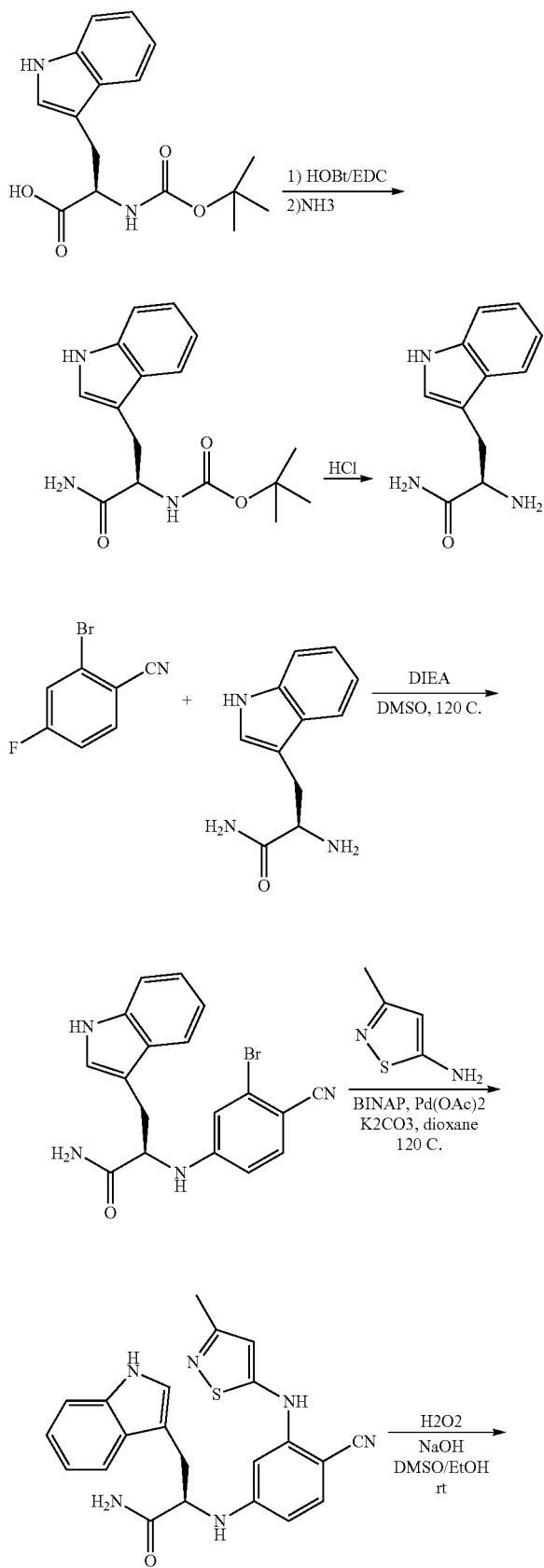

A solution of N-Boc-D-tryptophan (1.00 g, 3.29 mmol), HOBt monohydrate (0.600 g, 3.92 mmol) and EDC (0.820 g, 4.27 mmol) in DMF (12 mL) was stirred at room temperature for 2 h, conc. NH$_4$OH (1.10 mL, ca. 15.4 mmol) was added. The mixture was stirred for 18 h. Water and EtOAc were added. The organic phase was separated, washed with 5% NaHCO$_3$, dried over Na$_2$SO$_4$, concentrated in vacuo to give (R)-tert-butyl 1-amino-3-(1H-indol-3-yl)-1-oxopropan-2-yl-carbamate (0.963 g)

A solution of (R)-tert-butyl 1-amino-3-(1H-indol-3-yl)-1-oxopropan-2-ylcarbamate (0.963 g, 3.18 mmol) in 4N HCl in dioxane (8 mL) was stirred at room temperature for 1 h. It was then concentrated in vacuo. The residue was partitioned between nBuOH and aq. 5% NaHCO$_3$. The nBuOH phase was separated, washed with water, concentrated in vacuo to give (R)-2-amino-3-(1H-indol-3-yl)propanamide as free base (0.324 g).

A solution of 2-bromo-4-fluorobenzonitrile (160 mg, 0.800 mmol), (R)-2-amino-3-(1H-indol-3-yl)propanamide (164 mg, 0.807 mmol) and DIEA (0.300 mL, 1.72 mmol) in DMSO (3 mL) was stirred at 120 C for 18 h. Water and EtOAc were added. The organic phase was separated, dried over Na$_2$SO$_4$, concentrated in vacuo. The residue was purified by a silica gel column, which was eluted with 0-80% EtOAc in hexane to give (R)-2-(3-bromo-4-cyanophenylamino)-3-(1H-indol-3-yl)propanamide (96 mg)

A mixture of (R)-2-(3-bromo-4-cyanophenylamino)-3-(1H-indol-3-yl)propanamide (96 mg, 0.250 mmol), 5-amino-3-methylisothiazole hydrochloride (60 mg, 0.398 mmol), K$_2$CO$_3$ (120 mg, 0.869 mmol), BINAP (40 mg, 0.064 mmol) and Pd(OAc)$_2$ (20 mg, 0.089 mmol) in dioxane (2 mL) was degassed with argon, then was stirred at 120 C for 18 h. Water and EtOAc were added. The organic phase was separated, dried over Na$_2$SO$_4$, concentrated in vacuo to give (R)-2-(4-cyano-3-(3-methylisothiazol-5-ylamino)phenylamino)-3-(1H-indol-3-yl)propanamide (100 mg)

To a solution of (R)-2-(4-cyano-3-(3-methylisothiazol-5-ylamino)phenylamino)-3-(1H-indol-3-yl)propanamide (100 mg, 0.240 mmol) in EtOH (2 mL) and DMSO (1 mL), aq. 1N NaOH (1 mL, 1.0 mmol) and aq. H$_2$O$_2$ (50%, 1 mL) were added. The mixture was stirred at room temperature for 1 h. HOAc (1 mL) was added. The mixture was purified by HPLC to give the titled compound (51 mg). MS 435.2 (M+H); UV 221.7, 292.8 nm.

Example 218

(R)-4-(1-amino-1-oxo-3-(pyridin-2-yl)propan-2-ylamino)-5-fluoro-2-(3-methylisothiazol-5-ylamino)benzamide

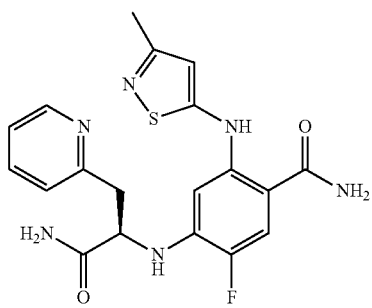 [SMILES: Cc1cc(Nc2cc(N[C@H](Cc3ccccn3)C(N)=O)c(F)cc2C(N)=O)sn1]

Scheme 54:

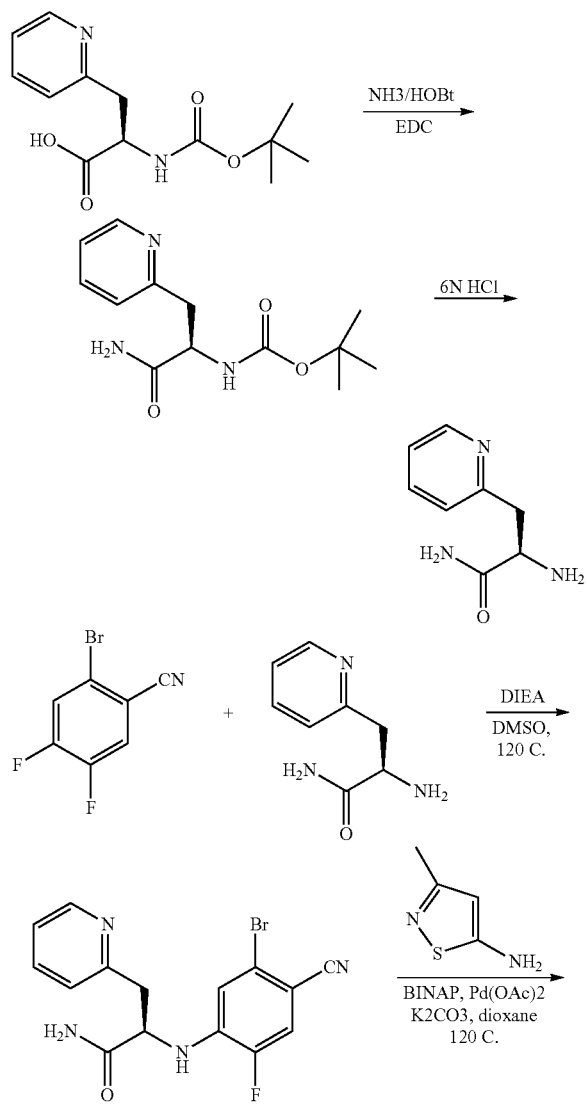

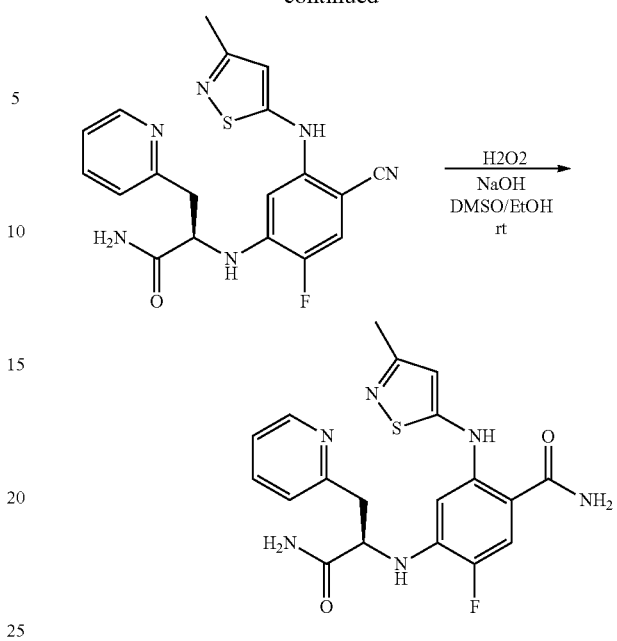

To a solution of N-Boc-D-2-pyridylalanine (266 mg, 1.00 mmol), HOBt monohydrate (184 mg, 1.20 mmol) and conc. NH$_4$OH (0.400 mL, ca. 5.60 mmol) in DMF (5 mL), EDC (288 mg, 1.50 mmol) was added. The mixture was stirred at room temperature for 18 h. Water and nBuOH were added. The nBuOH phase was separated, washed with 5% NaHCO$_3$, concentrated in vacuo. The residue was purified by HPLC to give (R)-tert-butyl 1-amino-1-oxo-3-(pyridin-2-yl)propan-2-ylcarbamate (280 mg)

A solution of (R)-tert-butyl 1-amino-1-oxo-3-(pyridin-2-yl)propan-2-ylcarbamate (280 mg, 0.739 mmol) in aq. 6N HCl (8 mL) was stirred at room temperature for 2 h. It was then concentrated in vacuo to give (R)-2-amino-3-(pyridin-2-yl)propanamide hydrochloride (170 mg).

A solution of 2-bromo-4,5-difluorobenzonitrile (150 mg, 0.688 mmol), (R)-2-amino-3-(pyridin-2-yl)propanamide hydrochloride (170 mg, 0.714 mmol) and DIEA (0.500 mL, 2.87 mmol) in DMSO (4 mL) was stirred at 120 C for 18 h. Water and EtOAc were added. The organic phase was separated, dried over Na$_2$SO$_4$, concentrated in vacuo to give (R)-2-(5-bromo-4-cyano-2-fluorophenylamino)-3-(pyridin-2-yl)propanamide (274 mg)

A mixture of (R)-2-(5-bromo-4-cyano-2-fluorophenylamino)-3-(pyridin-2-yl)propanamide (125 mg, 0.344 mmol), 5-amino-3-methylisothiazole hydrochloride (80 mg, 0.531 mmol), K$_2$CO$_3$ (220 mg, 1.59 mmol), BINAP (40 mg, 0.064 mmol) and Pd(OAc)$_2$ (30 mg, 0.133 mmol) in dioxane (3 mL) was degassed with argon, then was stirred at 120 C for 18 h. The mixture was concentrated in vacuo. The residue was purified by HPLC to give (R)-2-(4-cyano-2-fluoro-5-(3-methylisothiazol-5-ylamino)phenylamino)-3-(pyridin-2-yl)propanamide (53 mg).

To a solution of (R)-2-(4-cyano-2-fluoro-5-(3-methylisothiazol-5-ylamino)phenylamino)-3-(pyridin-2-yl)propanamide (53 mg, 0.133 mmol) in EtOH (1 mL) and DMSO (0.5 mL), aq. 1N NaOH (0.5 mL, 0.50 mmol) and aq. H$_2$O$_2$ (50%, 0.5 mL) were added. The mixture was stirred at room temperature for 15 min. HOAc (0.5 mL) was added. The mixture was purified by HPLC to give the titled compound (16 mg). MS 415.1 (M+H); UV 214.4, 278.0, 302.6 nm.

Example 219

4-(1-amino-4,4,4-trifluoro-1-oxobutan-2-ylamino)-5-fluoro-2-(3-methylisothiazol-5-ylamino)benzamide

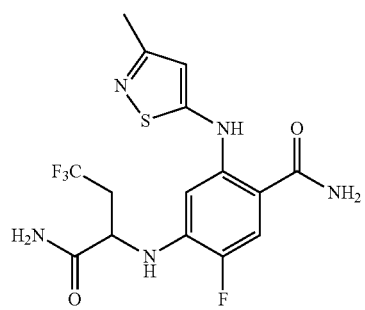 [SMILES: Cc1cc(Nc2cc(NC(CC(F)(F)F)C(N)=O)c(F)cc2C(N)=O)sn1]

Scheme 55:

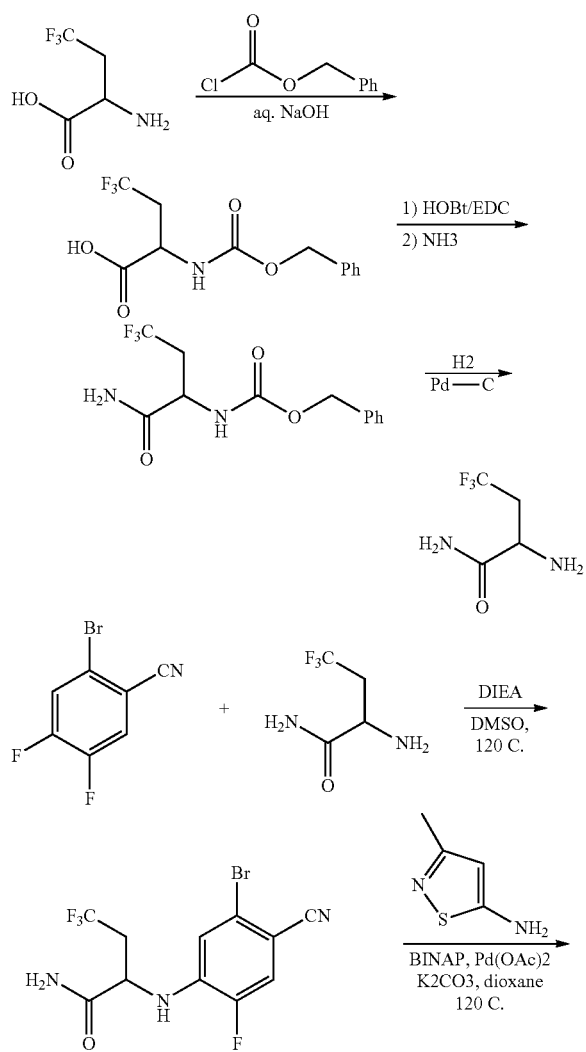

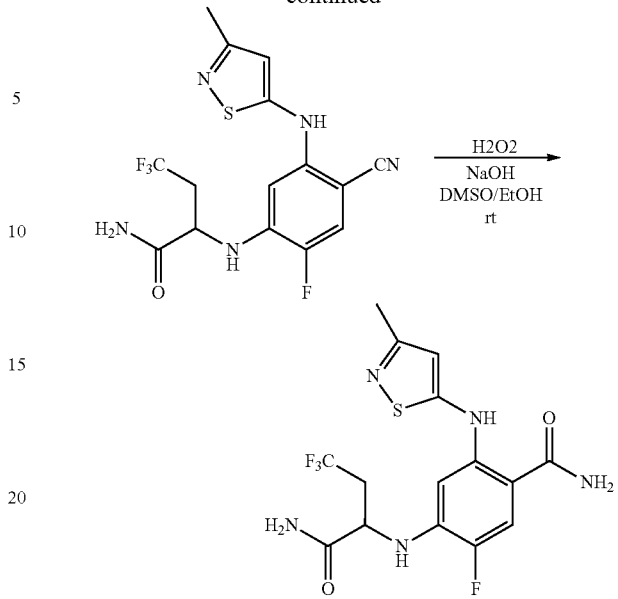

To a solution of 2-amino-4,4,4-trifluorobutyric acid (543 mg, 3.45 mmol) in aq. 1N NaOH (13 mL, 13.0 mmol), a solution of benzyl chloroformate (0.600 mL, 4.26 mmol) in dioxane (5 mL) was added. The mixture was stirred at room temperature for 18 h. It was then washed with EtOAc. The aqueous solution was acidified to pH 1-2 with 6N HCl. The product was extracted with EtOAc. The EtOAc phase was dried over $Na_2SO_4$, concentrated in vacuo to give 2-(benzyloxycarbonylamino)-4,4,4-trifluorobutanoic acid (202 mg).

A solution of 2-(benzyloxycarbonylamino)-4,4,4-trifluorobutanoic acid (200 mg, 0.687 mmol), HOBt monohydrate (137 mg, 0.895 mmol) and EDC (171 mg, 0.890 mmol) in DMF (5 mL) was stirred at room temperature for 15 min, conc. $NH_4OH$ (0.250 mL, ca. 3.50 mmol) was added. The mixture was stirred at room temperature for 18 h. Water and EtOAc were added. The organic phase was separated, washed with 5% $NaHCO_3$, dried over $Na_2SO_4$, concentrated in vacuo to give benzyl 1-amino-4,4,4-trifluoro-1-oxobutan-2-ylcarbamate (175 mg).

A solution of benzyl 1-amino-4,4,4-trifluoro-1-oxobutan-2-ylcarbamate (175 mg, 0.603 mmol) and Pd—C (10%, 55 mg) in MeOH (5 mL) was hydrogenated under balloon hydrogen for 2 h. The mixture was filtered through celite. The filtrate was concentrated in vacuo to give 2-amino-4,4,4-trifluorobutanamide (88 mg).

A solution of 2-bromo-4,5-difluorobenzonitrile (123 mg, 0.564 mmol), 2-amino-4,4,4-trifluorobutanamide (88 mg, 0.564 mmol) and DIEA (0.250 mL, 1.43 mmol) in DMSO (4 mL) was stirred at 120 C for 18 h. Water and EtOAc were added. The organic phase was separated, dried over $Na_2SO_4$, concentrated in vacuo. The residue was purified by a silica gel column, which was eluted with 0-70% EtOAc in hexane to give 2-(5-bromo-4-cyano-2-fluorophenylamino)-4,4,4-trifluorobutanamide (90 mg).

A mixture of 2-(5-bromo-4-cyano-2-fluorophenylamino)-4,4,4-trifluorobutanamide (90 mg, 0.254 mmol), 5-amino-3-methylisothiazole hydrochloride (58 mg, 0.385 mmol), $K_2CO_3$ (200 mg, 1.45 mmol), BINAP (35 mg, 0.056 mmol) and $Pd(OAc)_2$ (23 mg, 0.100 mmol) in dioxane (3 mL) was degassed with argon, then was stirred at 120 C for 18 h. Water and EtOAc were added. The organic phase was separated, dried over $Na_2SO_4$, concentrated in vacuo to give 2-(4-cyano- 2-fluoro-5-(3-methylisothiazol-5-ylamino)phenylamino)-4,4,4-trifluorobutanamide (98 mg).

To a solution of 2-(4-cyano-2-fluoro-5-(3-methylisothiazol-5-ylamino)phenylamino)-4,4,4-trifluorobutanamide (98 mg, 0.250 mmol) in EtOH (2 mL) and DMSO (1 mL), aq. 1N NaOH (1 mL, 1.0 mmol) and aq. $H_2O_2$ (50%, 1 mL) were added. The mixture was stirred at room temperature for 30 min. HOAc (1 mL) was added. The mixture was purified by HPLC to give the titled compound (28 mg). MS 406.1 (M+H); UV 204.7, 287.8 nm.

Example 220

(R)-4-(1-amino-1-oxo-3-(thiophen-2-yl)propan-2-ylamino)-2-(3-methylisothiazol-5-ylamino)benzamide

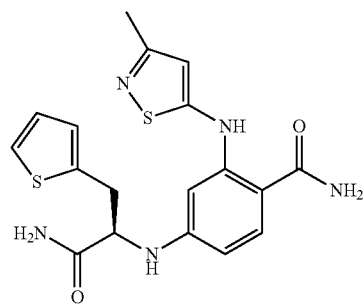 [SMILES: Cc1cc(Nc2cc(N[C@H](Cc3cccs3)C(N)=O)ccc2C(N)=O)sn1]

Scheme 56:

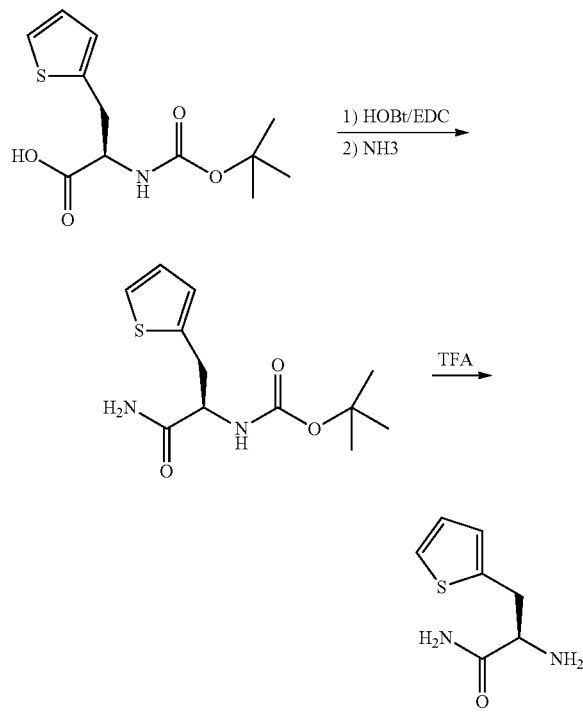

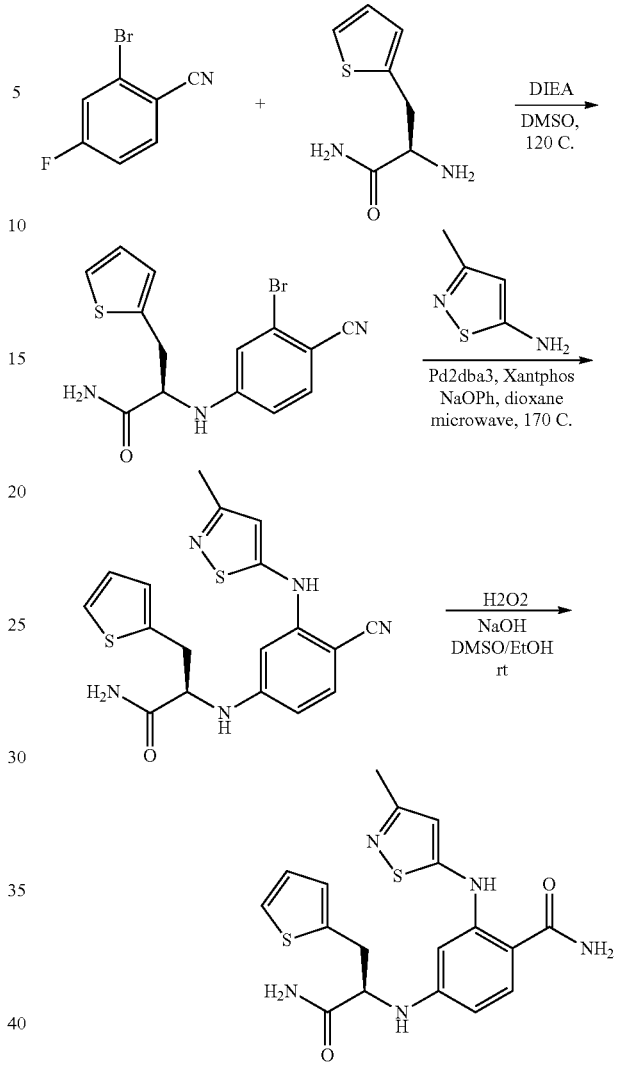

A solution of N-Boc-β-(2-thienyl)-D-alanine (504 mg, 1.86 mmol), HOBt monohydrate (340 mg, 2.22 mmol) and EDC (460 mg, 2.39 mmol) in DMF (6 mL) was stirred at room temperature for 1 h, conc. $NH_4OH$ (0.600 mL, ca. 8.40 mmol) was added. The mixture was stirred for 18 h. Water and EtOAc were added. The organic phase was separated, washed with 5% $NaHCO_3$, dried over $Na_2SO_4$, concentrated in vacuo to give (R)-tert-butyl 1-amino-1-oxo-3-(thiophen-2-yl)propan-2-ylcarbamate (454 mg)

A solution of (R)-tert-butyl 1-amino-1-oxo-3-(thiophen-2-yl)propan-2-ylcarbamate (454 mg, 1.68 mmol) in TFA (4 mL) and $CH_2Cl_2$ (6 mL) was stirred at room temperature for 3 h. It was then concentrated in vacuo. The residue was partitioned between EtOAc and aq. 5% $NaHCO_3$. The EtOAc phase was separated, washed with water, concentrated in vacuo to give (R)-2-amino-3-(thiophen-2-yl)propanamide (93 mg).

A solution of 2-bromo-4-fluorobenzonitrile (120 mg, 0.600 mmol), (R)-2-amino-3-(thiophen-2-yl)propanamide (93 mg, 0.547 mmol) and DIEA (0.200 mL, 1.15 mmol) in DMSO (3 mL) was stirred at 120 C for 4 d. Water and EtOAc were added. The organic phase was separated, dried over $Na_2SO_4$, concentrated in vacuo. The residue was purified by a silica gel column, which was eluted with 0-80% EtOAc in hexane to give (R)-2-(3-bromo-4-cyanophenylamino)-3-(thiophen-2-yl)propanamide (35 mg).

A mixture of (R)-2-(3-bromo-4-cyanophenylamino)-3-(thiophen-2-yl)propanamide (35 mg, 0.100 mmol), 5-amino-3-methylisothiazole hydrochloride (25 mg, 0.166 mmol), sodium phenoxide trihydrate (52 mg, 0.305 mmol), xantphos (14 mg, 0.024 mmol) and Pd$_2$dba$_3$ (10 mg, 0.010 mmol) in dioxane (2 mL) was degassed with argon, then was heated by microwave at 170 C for 30 min. The mixture was concentrated in vacuo. The residue was purified by HPLC to give (R)-2-(4-cyano-3-(3-methylisothiazol-5-ylamino)phenylamino)-3-(thiophen-2-yl)propanamide (13 mg).

To a solution of (R)-2-(4-cyano-3-(3-methylisothiazol-5-ylamino)phenylamino)-3-(thiophen-2-yl)propanamide (13 mg, 0.034 mmol) in EtOH (1 mL) and DMSO (0.5 mL), aq. 1N NaOH (0.5 mL, 0.50 mmol) and aq. H$_2$O$_2$ (50%, 0.5 mL) were added. The mixture was stirred at room temperature for 30 min. HOAc (0.5 mL) was added. The mixture was purified by HPLC to give the titled compound (10 mg). MS 402.1 (M+H); UV 224.1, 302.6 nm.

Example 221

(R)-4-(1-amino-1-oxo-3-(4-(pyridin-4-yl)phenyl)propan-2-ylamino)-5-fluoro-2-(3-methylisothiazol-5-ylamino)benzamide Scheme 57:

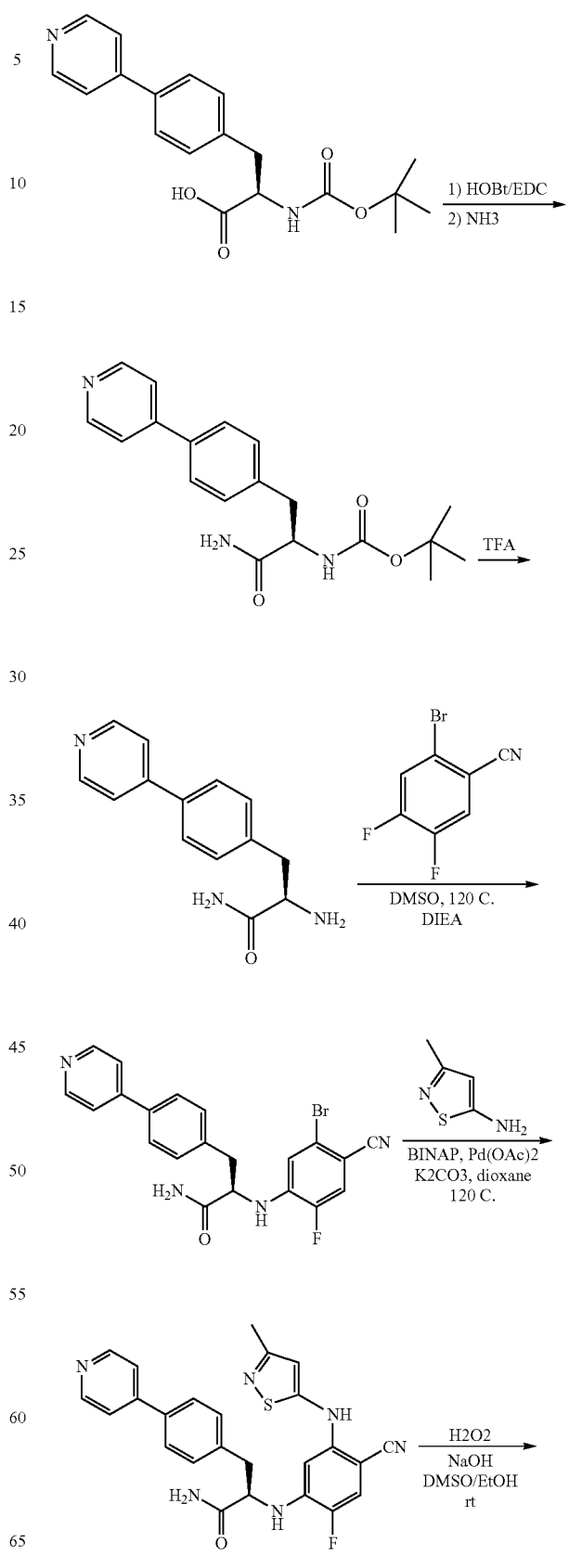

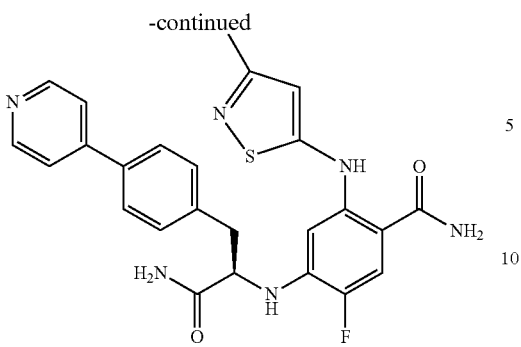

To a mixture of N-Boc-D-iodophenylalanine (1.00 g, 2.55 mmol), pyridine-4-boronic acid (315 mg, 2.56 mmol) and Pd(Ph$_3$P)$_2$Cl$_2$ (90 mg, 0.128 mmol) in dioxane (8 mL), aq. Na$_2$CO$_3$ (600 mg, 5.66 mmol) in water (3 mL) was added. The mixture was stirred at 100 C for 18 h. Water and EtOAc were added, aq. 6N HCl was also added to bring pH to 3-4. The aqueous phase was separated, and concentrated in vacuo. The residue was purified by HPLC to give (R)-2-(tert-butoxycarbonylamino)-3-(4-(pyridin-4-yl)phenyl)propanoic acid (141 mg).

A solution of (R)-2-(tert-butoxycarbonylamino)-3-(4-(pyridin-4-yl)phenyl)propanoic acid (141 mg, 0.412 mmol), HOBt monohydrate (100 mg, 0.653 mmol) and EDC (120 mg, 0.625 mmol) in DMF (2 mL) was stirred at room temperature for 45 min, conc. NH$_4$OH (0.300 mL, ca. 4.20 mmol) was added. The mixture was stirred for 18 h. Water and EtOAc were added. The organic phase was separated, washed with 5% NaHCO$_3$, dried over Na$_2$SO$_4$, concentrated in vacuo to give (R)-tert-butyl 1-amino-1-oxo-3-(4-(pyridin-4-yl)phenyl)propan-2-ylcarbamate (87 mg).

A solution of (R)-tert-butyl 1-amino-1-oxo-3-(4-(pyridin-4-yl)phenyl)propan-2-ylcarbamate (87 mg, 0.255 mmol) in TFA (3 mL) was stirred at room temperature for 1 h. It was then concentrated in vacuo. The residue was dissolved in MeOH (6 mL), MP-carbonate resin (210 mg, ca. 3 mmol/g, 0.63 mmol) was added. After swirling and standing for 2 h, the resin was filtered off. The filtrate was concentrated in vacuo to give (R)-tert-butyl 1-amino-1-oxo-3-(4-(pyridin-4-yl)phenyl)propan-2-ylcarbamate as free base (72 mg).

A solution of 2-bromo-4,5-difluorobenzonitrile (85 mg, 0.390 mmol), (R)-tert-butyl 1-amino-1-oxo-3-(4-(pyridin-4-yl)phenyl)propan-2-ylcarbamate (72 mg, 0.299 mmol) and DIEA (0.200 mL, 1.15 mmol) in DMSO (3 mL) was stirred at 120 C for 18 h. HOAc (0.5 mL) was added. The mixture was purified by HPLC to give (R)-2-(5-bromo-4-cyano-2-fluorophenylamino)-3-(4-(pyridin-4-yl)phenyl)propanamide (62 mg).

A mixture of (R)-2-(5-bromo-4-cyano-2-fluorophenylamino)-3-(4-(pyridin-4-yl)phenyl)propanamide (62 mg, 0.14 mmol), 5-amino-3-methylisothiazole hydrochloride (35 mg, 0.23 mmol), K$_2$CO$_3$ (65 mg, 0.47 mmol), BINAP (25 mg, 0.040 mmol) and Pd(OAc)$_2$ (15 mg, 0.066 mmol) in dioxane (2 mL) and water (0.1 mL) was degassed with argon, then was stirred at 120 C for 18 h. The mixture was purified by HPLC to give (R)-2-(4-cyano-2-fluoro-5-(3-methylisothiazol-5-ylamino)phenylamino)-3-(4-(pyridin-4-yl)phenyl)propanamide (12 mg).

To a solution of (R)-2-(4-cyano-2-fluoro-5-(3-methylisothiazol-5-ylamino)phenylamino)-3-(4-(pyridin-4-yl)phenyl)propanamide (12 mg, 0.025 mmol) in EtOH (1 mL) and DMSO (0.5 mL), aq. 1N NaOH (0.5 mL, 0.50 mmol) and aq. H$_2$O$_2$ (50%, 0.5 mL) were added. The mixture was stirred at room temperature for 30 min. HOAc (0.5 mL) was added. The mixture was purified by HPLC to give the titled compound (6 mg). MS 491.1 (M+H); UV 216.8, 278.0, 312.5 nm.

Example 222

(R)-4-(3-(4-(1H-imidazol-1-yl)phenyl)-1-amino-1-oxopropan-2-ylamino)-5-fluoro-2-(3-methylisothiazol-5-ylamino)benzamide

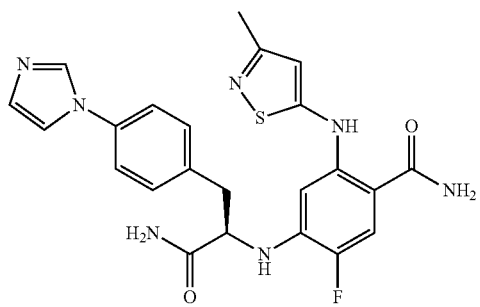 [SMILES: Cc1cc(Nc2cc(N[C@H](Cc3ccc(-n4ccnc4)cc3)C(N)=O)c(F)cc2C(N)=O)sn1]

Scheme 58:

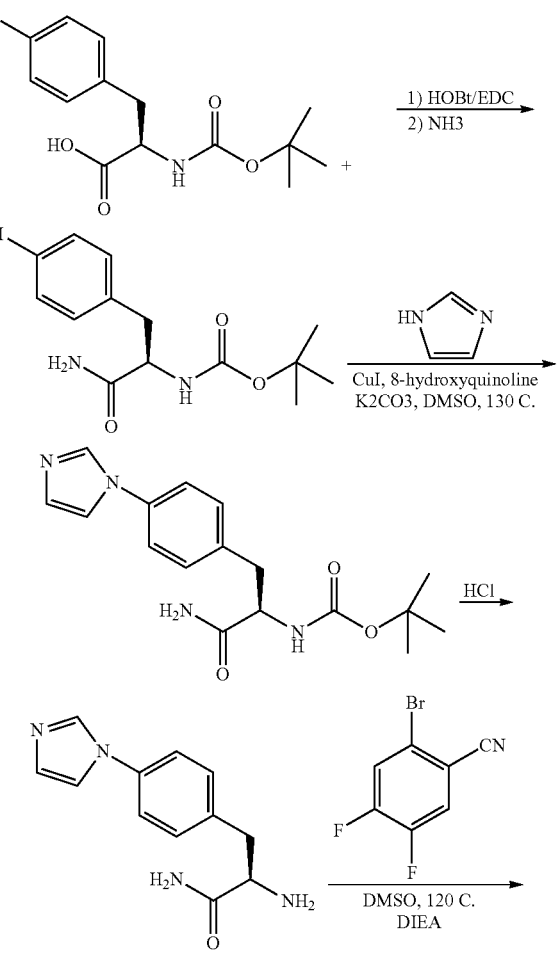

245
-continued

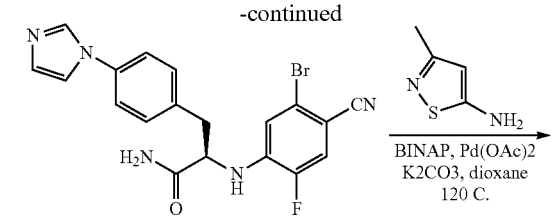

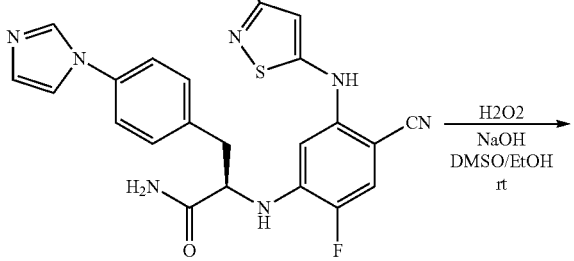

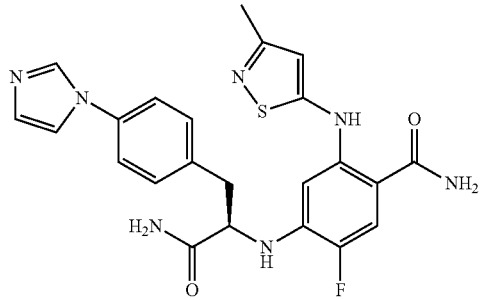 [SMILES: Cc1cc(Nc2cc(N[C@H](Cc3ccc(-n4ccnc4)cc3)C(N)=O)c(F)cc2C(N)=O)sn1]

A solution of N-Boc-D-iodophenylalanine (782 mg, 2.00 mmol), HOBt monohydrate (400 mg, 2.61 mmol) and EDC (500 mg, 2.60 mmol) in DMF (10 mL) was stirred at room temperature for 40 min, conc. NH₄OH (0.800 mL, ca. 11.2 mmol) was added. The mixture was stirred for 18 h. Water and EtOAc were added. The organic phase was separated, washed with 5% NaHCO₃, dried over Na₂SO₄, concentrated in vacuo to give (R)-tert-butyl 1-amino-3-(4-iodophenyl)-1-oxopropan-2-ylcarbamate (743 mg).

A mixture of (R)-tert-butyl 1-amino-3-(4-iodophenyl)-1-oxopropan-2-ylcarbamate (370 mg, 0.948 mmol), imidazole (85 mg, 1.25 mmol), 8-hydroxyquinoline (30 mg, 0.206 mmol), K₂CO₃ (150 mg, 1.08 mmol) and CuI (20 mg, 0.105 mmol) in DMSO (4 mL) was degassed with argon, then was stirred at 130 C for 18 h. The mixture was purified by HPLC to give (R)-tert-butyl 3-(4-(1H-imidazol-1-yl)phenyl)-1-amino-1-oxopropan-2-ylcarbamate (250 mg).

A solution of ((R)-tert-butyl 3-(4-(1H-imidazol-1-yl)phenyl)-1-amino-1-oxopropan-2-ylcarbamate (250 mg, 0.757 mmol) in 4M HCl in dioxane (4 mL) and 6N HCl (4 mL) was stirred at room temperature for 30 min. It was then concentrated in vacuo. The residue was dissolved in MeOH (10 mL), MP-carbonate resin (1.00 g, ca. 3 mmol/g, 3.00 mmol) was added. After swirling and standing for 2 h, the resin was filtered off. The filtrate was concentrated in vacuo to give (R)-3-(4-(1H-imidazol-1-yl)phenyl)-2-aminopropanamide as free base (100 mg).

A solution of 2-bromo-4,5-difluorobenzonitrile (100 mg, 0.458 mmol), ((R)-3-(4-(1H-imidazol-1-yl)phenyl)-2-aminopropanamide (100 mg, 0.434 mmol) and DIEA (0.100 mL, 0.575 mmol) in DMSO (3 mL) was stirred at 120 C for 18 h. The mixture was purified by HPLC to give (R)-3-(4-(1H-imidazol-1-yl)phenyl)-2-(5-bromo-4-cyano-2-fluorophenylamino)propanamide (59 mg).

246

A mixture of (R)-3-(4-(1H-imidazol-1-yl)phenyl)-2-(5-bromo-4-cyano-2-fluorophenylamino)propanamide (59 mg, 0.137 mmol), 5-amino-3-methylisothiazole hydrochloride (35 mg, 0.232 mmol), K₂CO₃ (60 mg, 0.434 mmol), BINAP (25 mg, 0.040 mmol) and Pd(OAc)₂ (15 mg, 0.066 mmol) in dioxane (2 mL) and DMSO (0.3 mL) was degassed with argon, then was stirred at 120 C for 18 h. The mixture was purified by HPLC to give (R)-3-(4-(1H-imidazol-1-yl)phenyl)-2-(4-cyano-2-fluoro-5-(3-methylisothiazol-5-ylamino) phenylamino)propanamide (9 mg).

To a solution of (R)-3-(4-(1H-imidazol-1-yl)phenyl)-2-(4-cyano-2-fluoro-5-(3-methylisothiazol-5-ylamino)phenylamino)propanamide (9 mg, 0.019 mmol) in EtOH (1 mL) and DMSO (0.5 mL), aq. 1N NaOH (0.5 mL, 0.50 mmol) and aq. H₂O₂ (50%, 0.5 mL) were added. The mixture was stirred at room temperature for 30 min. HOAc (0.5 mL) was added. The mixture was purified by HPLC to give the titled compound (5 mg). MS 480.3 (M+H); UV 204.7, 292.8 nm.

Example 223

(R)-4-(1-amino-1-oxo-3-(4-(2-oxopyridin-1(2H)-yl) phenyl)propan-2-ylamino)-5-fluoro-2-(3-methyl-isothiazol-5-ylamino)benzamide

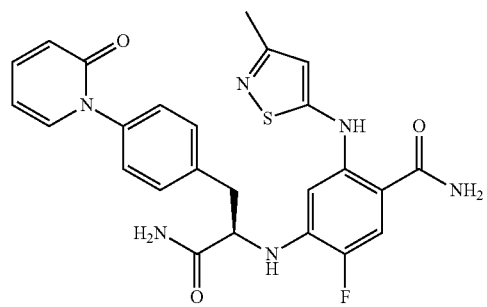 [SMILES: Cc1cc(Nc2cc(N[C@H](Cc3ccc(-n4ccccc4=O)cc3)C(N)=O)c(F)cc2C(N)=O)sn1]

Scheme 59:

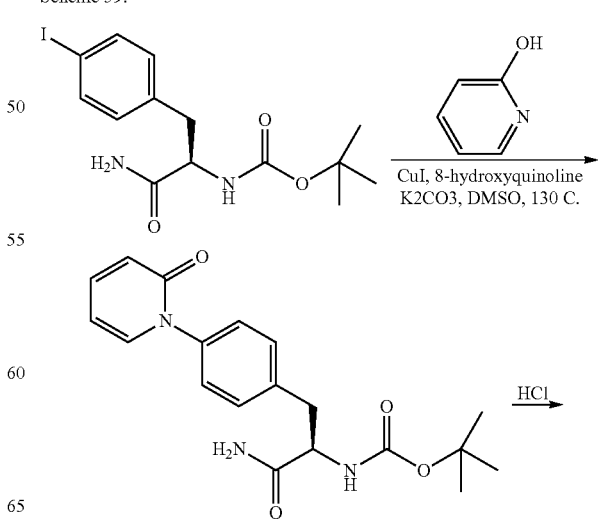

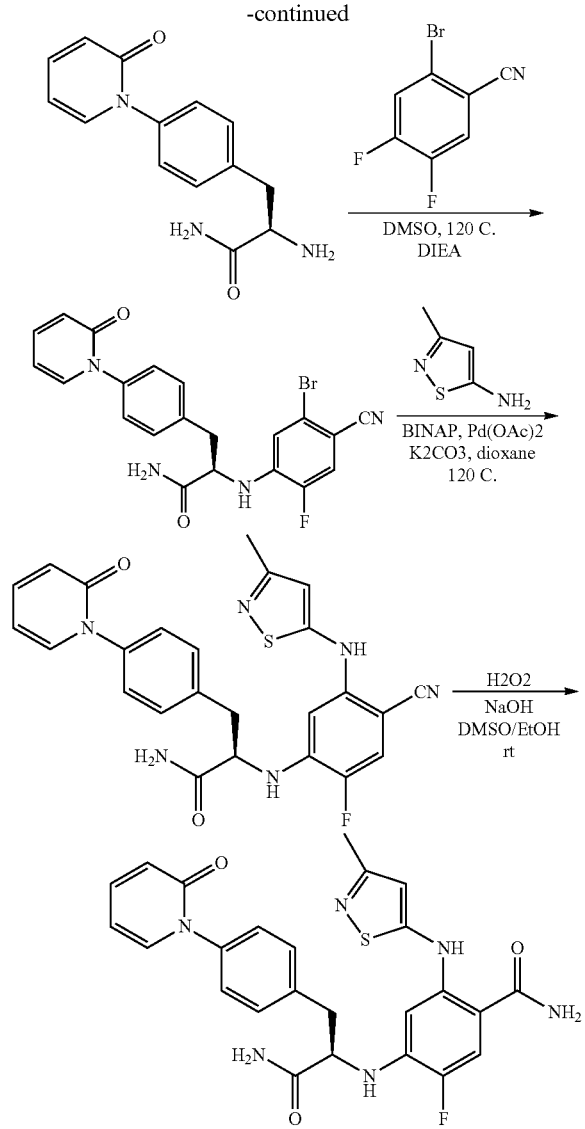

The titled compound (27 mg) was synthesized analogously by the procedures described for Example 284/223, compound (R)-4-(3-(4-(1H-imidazol-1-yl)phenyl)-1-amino-1-oxopropan-2-ylamino)-5-fluoro-2-(3-methylisothiazol-5-ylamino)benzamide. MS 507.3 (M+H); UV 209.5, 297.7 nm.

Example 224

(R)-4-(1-amino-3-(4-(methylsulfonyl)phenyl)-1-oxopropan-2-ylamino)-5-fluoro-2-(3-methylisothiazol-5-ylamino)benzamide

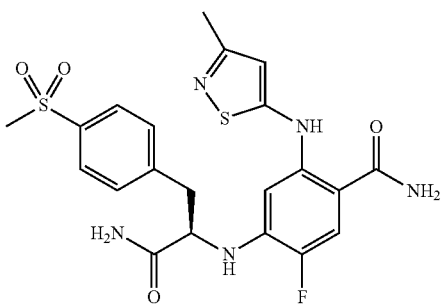 [SMILES: Cc1cc(Nc2cc(N[C@H](Cc3ccc(S(C)(=O)=O)cc3)C(N)=O)c(F)cc2C(N)=O)sn1]

Scheme 60:

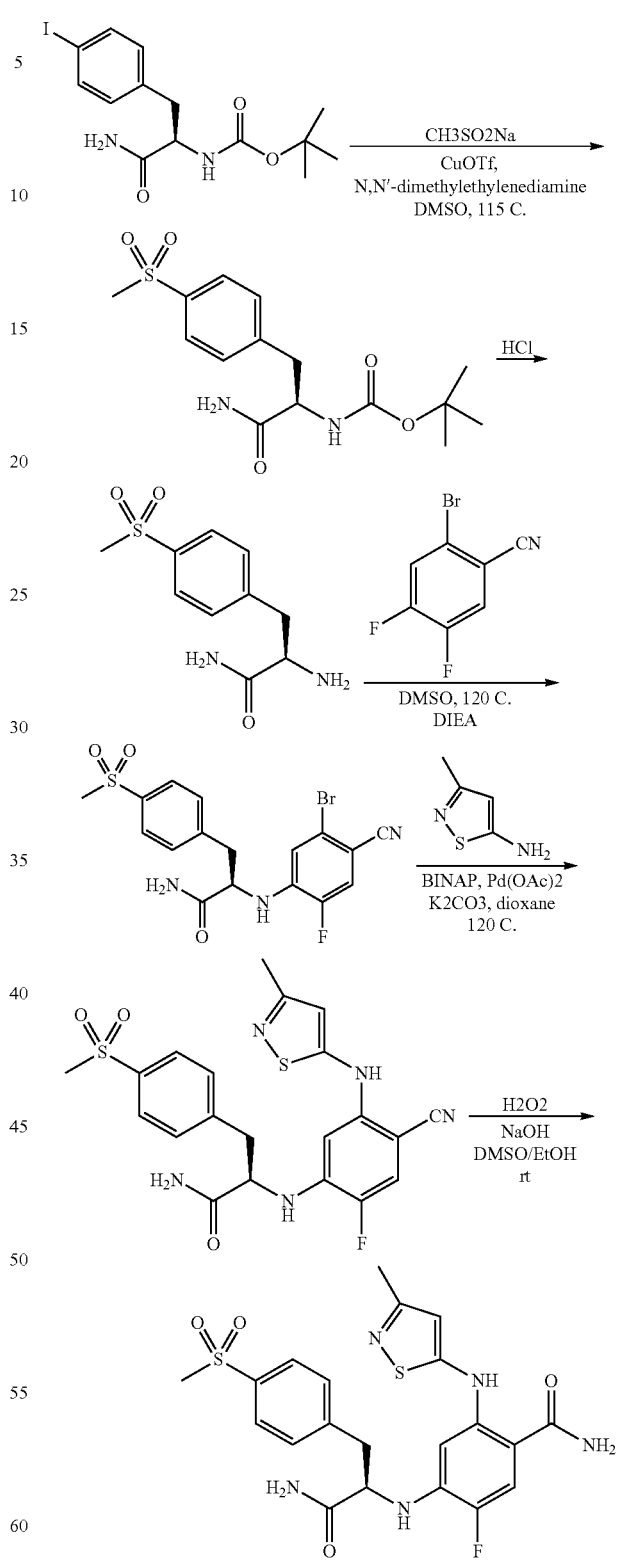

A mixture of (R)-tert-butyl 1-amino-3-(4-iodophenyl)-1-oxopropan-2-ylcarbamate (200 mg, 0.512 mmol), sodium methanesulfinate (200 mg, 85%, 1.66 mmol), CuOTf hemitoluene complex (120 mg, 0.464 mmol) and N,N'-dimethylethylenediamine (0.030 mL, 0.279 mmol) in DMSO (5 mL) was stirred at 115 C for 3 h. Water and EtOAc were added. The organic phase was separated, washed with 5% NaHCO$_3$, dried over Na$_2$SO$_4$, concentrated in vacuo to give (R)-tert-butyl 1-amino-3-(4-(methylsulfonyl)phenyl)-1-oxopropan-2-ylcarbamate (154 mg).

The subsequent procedures were followed analogously to those described in Example 284/223 for (R)-4-(3-(4-(1H-imidazol-1-yl)phenyl)-1-amino-1-oxopropan-2-ylamino)-5-fluoro-2-(3-methylisothiazol-5-ylamino)benzamide, to give the titled compound (6 mg). MS 492.2 (M+H); UV 221.7, 292.8 nm.

Example 225

(R)-4-(1-amino-1-oxo-3-(4-(pyridin-3-yl)phenyl) propan-2-ylamino)-5-fluoro-2-(3-methylisothiazol-5-ylamino)benzamide

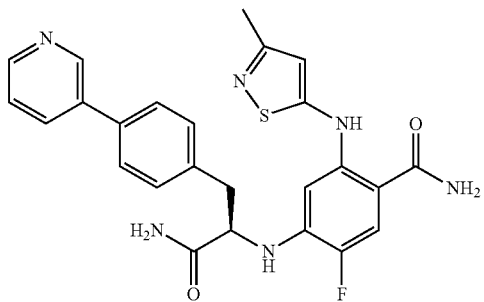 [SMILES: Cc1cc(Nc2cc(N[C@H](Cc3ccc(-c4cccnc4)cc3)C(N)=O)c(F)cc2C(N)=O)sn1]

The titled compound (13 mg) was synthesized analogously by procedures described in the Example for (R)-4-(1-amino-1-oxo-3-(4-(pyridin-4-yl)phenyl)propan-2-ylamino)-5-fluoro-2-(3-methylisothiazol-5-ylamino)benzamide, using pyridine-3-boronic acid in place of pyridine-4-boronic acid. MS 491.5 (M+H); UV 205.2, 244.2, 299.4 nm.

Example 226

(R)-4-(1-amino-1-oxo-3-(4-(pyridin-2-yl)phenyl) propan-2-ylamino)-5-fluoro-2-(3-methylisothiazol-5-ylamino)benzamide

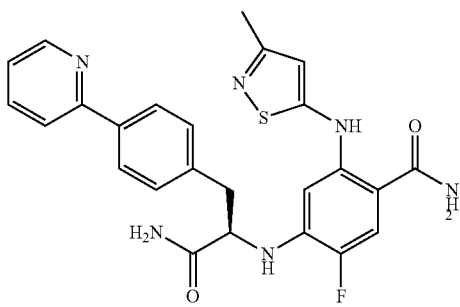 [SMILES: Cc1cc(Nc2cc(N[C@H](Cc3ccc(-c4ccccn4)cc3)C(N)=O)c(F)cc2C(N)=O)sn1]

Scheme 61:

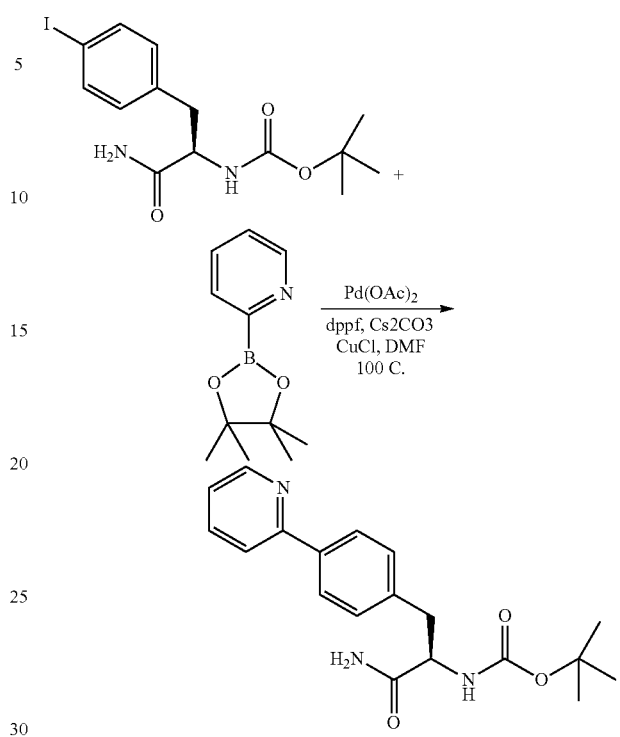

A mixture of (R)-tert-butyl 1-amino-3-(4-iodophenyl)-1-oxopropan-2-ylcarbamate (970 mg, 2.48 mmol), pyridine-2-boronic acid pinacol ester (505 mg, 2.46 mmol), dppf (275 mg, 0.496 mmol), Cs$_2$CO$_3$ (1.00 g, 3.06 mmol), Pd(OAc)$_2$ (56 mg, 0.249 mmol) and CuCl (25 mg, 0.252 mmol) in DMF (10 mL) was degassed with argon, then was stirred at 100 C for 18 h. Water and EtOAc were added. The organic phase was separated, dried over Na$_2$SO$_4$, concentrated in vacuo. The residue was purified by a silica gel column, which was eluted with 20-100% EtOAc in hexane to give (R)-tert-butyl 1-amino-1-oxo-3-(4-(pyridin-2-yl)phenyl)propan-2-ylcarbamate (281 mg).

The subsequent procedures were followed analogously to those described in Example 222 for (R)-4-(3-(4-(1H-imidazol-1-yl)phenyl)-1-amino-1-oxopropan-2-ylamino)-5-fluoro-2-(3-methylisothiazol-5-ylamino)benzamide, to give the titled compound (8 mg). MS 491.5 (M+H); UV 205.2, 244.2, 299.4 nm.

Example 227

Preparation of (R)-6-(1-amino-1-oxobutan-2-ylamino)-5-fluoro-2-(quinolin-3-ylamino)nicotinamide

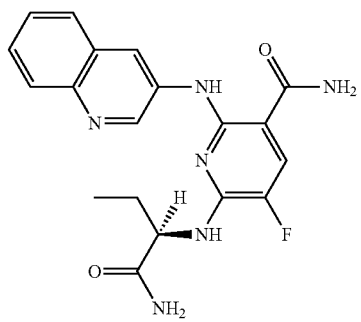 [SMILES: CC[C@@H](Nc1nc(Nc2cnc3ccccc3c2)c(C(N)=O)cc1F)C(N)=O]

Step 1: To the mixture of (R)-(−)-2-aminobutanamide hydrochloride (1.00 g, 7.2 mmol) and 2,6-dichloro-5-fluoro-3-pyridinecarbonitrile (0.92 g, 4.8 mmol) in 40 mL NMP added DIEA (2.5 mL, 14.4 mmol). The mixture was then sent to 100° C. for stirring for 1 h. The mixture was cooled to RT, and to it was poured 300 mL EtOAc. The mixture was washed with brine four times. The organic phase was dried, concentrated and purified using silica flash column (70% EtOAc-30% DCM) to isolate (R)-2-(6-chloro-5-cyano-3-fluoropyridin-2-ylamino)butanamide (1.21 g, 98% yield).

Step 2: The mixture of (R)-2-(6-chloro-5-cyano-3-fluoro-pyridin-2-ylamino)butanamide (120 mg, 0.46 mmol), 3-aminoquinoline (150 mg, 1.0 mmol), Pd(OAc)$_2$ (22 mg, 0.11 mmol), racemic BINAP (68 mg, 0.11 mmol) and fine-powder cesium carbonate (0.50 g, 1.65 mmol) in 20 mL dioxane was degassed using argon stream for 3 min. It was then stirred at 100° C. in argon atmosphere for overnight. The mixture was cooled to RT, concentrated in vacuo, taken into 200 mL EtOAc and 50 mL water. The organic phase was separated and washed with brine. It was dried, concentrated and purified using silica flash column (35% EtOAc in DCM) to give (R)-2-(5-cyano-3-fluoro-6-(quinolin-3-ylamino)pyridin-2-ylamino)butanamide. It was dissolved in 4 mL DMSO. To it were added 2 mL 50% H$_2$O$_2$ and then powder potassium carbonate (91 mg, 0.66 mmol). The mixture was stirred at RT for 30 min. It was diluted with 4 mL 1N HCl. The mixture was subjected to reverse prep HPLC to isolate the title compound as HCl salt (102 mg).

UV: 224, 243, 296, 326 nm. M+H found for C$_{19}$H$_{19}$FN$_6$O$_2$: 383.3. NMR (CD$_3$OD): 9.54 (1H, d, J=2.4 Hz), 9.19 (1H, d, J=2.4 Hz), 8.31 (1H, d, J=6.4 Hz), 8.08 (1H, d, J=8.8 Hz), 7.94-7.81 (3H, m), 4.34-4.30 (1H, m), 2.11-1.91 (2H, m), 1.13 (3H, t, J=7.2 Hz) ppm.

Example 228

Preparation of (R)-6-(1-amino-1-oxobutan-2-ylamino)-5-fluoro-2-(1,8-naphthyridin-3-ylamino)nicotinamide

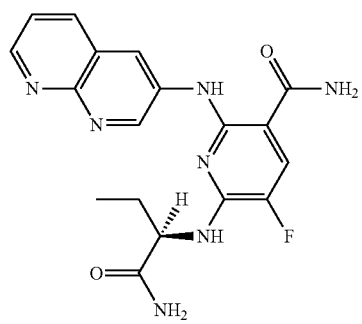 [SMILES: CC[C@@H](Nc1nc(Nc2cnc3ncccc3c2)c(C(N)=O)cc1F)C(N)=O]

The title compound was synthesized analogously according to the procedures described for the preparation of Example 97. However, 3-amino-1,8-naphthyridine was utilized instead of 7-aminoquinoline. UV: 258, 291, 326 nm. M+H found for C$_{18}$H$_{18}$FN$_7$O$_2$: 384.3. NMR (CD$_3$OD): 9.35 (1H, d, J=2.8 Hz), 9.28 (1H, d, J=8.0 Hz), 9.07-9.05 (1H, m), 9.00-8.97 (1H, m), 8.01-7.96 (1H, m), 7.86 (1 h, d, J=11.6 Hz), 4.37-4.33 (1H, m), 2.16-1.94 (2H, m), 1.14 (3H, t, J=7.2 Hz) ppm.

Example 229

Preparation of (R)-6-(1-amino-1-oxobutan-2-ylamino)-5-fluoro-2-(H-imidazo[1,2-a]pyridin-6-ylamino)nicotinamide

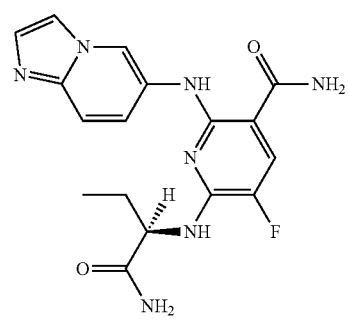 [SMILES: CC[C@@H](Nc1nc(Nc2ccc3nccn3c2)c(C(N)=O)cc1F)C(N)=O]

The title compound was synthesized analogously according to the procedures described for the preparation of Example 97. However, Imidazo[1,2-a]pyridin-6-amine was utilized instead of 7-aminoquinoline. UV: 297 nm. M+H found for C$_{17}$H$_{18}$FN$_7$O$_2$: 372.3. NMR (CD$_3$OD): 11.85 (1H, s), 9.69 (1H, s), 8.39 (1H, s), 7.92-7.60 (4H, m), 7.20-7.10 (1H, m), 4.30-4.23 (1H, m), 2.14-1.92 (2H, m), 1.14 (3H, t, J=7.2 Hz) ppm.

Example 230

Preparation of (R)-6-(1-amino-1-oxobutan-2-ylamino)-5-fluoro-2-(H-imidazo[1,2-a]pyridin-7-ylamino)nicotinamide

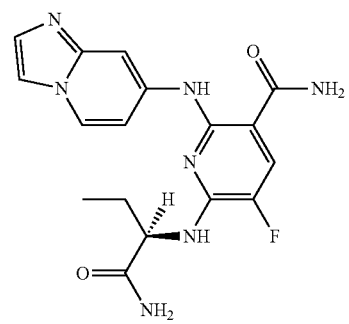 [SMILES: CC[C@@H](Nc1nc(Nc2ccn3ccnc3c2)c(C(N)=O)cc1F)C(N)=O]

The title compound was synthesized analogously according to the procedures described for the preparation of Example 97. However, H-imidazo[1,2-a]pyridin-7-amine was utilized instead of 7-aminoquinoline. UV: 240, 288 nm. M+H found for C$_{17}$H$_{18}$FN$_7$O$_2$: 372.3. NMR (CD$_3$OD): 12.40 (1H, s), 8.58 (1H, s), 8.47 (1H, d, J=7.2 Hz), 7.91-7.85 (2H, m) 7.76 (1H, d, J=2.4 Hz), 7.24-7.17 (2H, m), 4.40-4.32 (1H, m), 2.16-1.93 (2H, m), 1.15 (3H, t, J=7.6 Hz) ppm.

Example 231

Preparation of (R)-6-(1-amino-1-oxobutan-2-ylamino)-5-fluoro-2-(3-methoxyphenylamino)nicotinamide

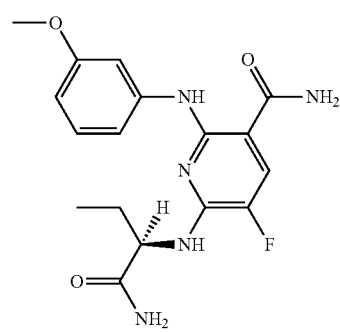 [SMILES: CC[C@@H](Nc1nc(Nc2cccc(OC)c2)c(C(N)=O)cc1F)C(N)=O]

The title compound was synthesized analogously according to the procedures described for the preparation of Example 97. However, 3-methoxyaniline was utilized instead of 7-aminoquinoline. UV: 248, 305 nm. M+H found for $C_{17}H_{20}FN_5O_3$: 362.3. NMR (CD$_3$OD): 7.69 (1H, d, J=12.4 Hz), 7.25-7.13 (3H, m), 6.55-6.51 (1H, m), 4.56 (1H, dd, J=5.2, 8.4 Hz) 2.05-1.84 (2H, m), 1.05 (3H, t, J=7.2 Hz) ppm.

Example 232

Preparation of (R)-6-(1-amino-1-oxobutan-2-ylamino)-5-fluoro-2-(5-methoxypyridin-3-ylamino)nicotinamide

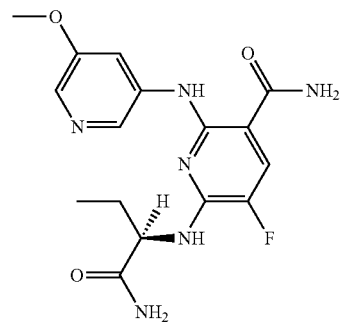 [SMILES: CC[C@@H](Nc1nc(Nc2cncc(OC)c2)c(C(N)=O)cc1F)C(N)=O]

The title compound was synthesized analogously according to the procedures described for the preparation of Example 97. However, 3-amino-5-methoxypyridine was utilized instead of 7-aminoquinoline. UV: 222, 281, 333 nm. M+H found for $C_{16}H_{19}FN_6O_3$: 363.3. NMR (CD$_3$OD): 9.18 (1H, d, J=2.0 Hz), 8.09 (1H, d, J=2.4 Hz), 7.91 (1H, t, J=2.4 Hz), 7.85 (1H, d, J=11.6 Hz), 4.32-4.25 (1H, m), 2.08-1.89 (2H, m), 1.12 (3H, t, J=7.6 Hz) ppm.

Example 233

Preparation of (R)-6-(1-amino-1-oxobutan-2-ylamino)-5-fluoro-2-(naphthalen-2-ylamino)nicotinamide

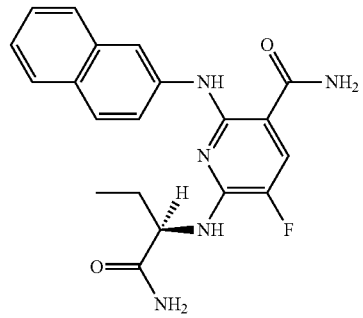 [SMILES: CC[C@@H](Nc1nc(Nc2ccc3ccccc3c2)c(C(N)=O)cc1F)C(N)=O]

The title compound was synthesized analogously according to the procedures described for the preparation of Example 97. However, 2-aminonaphthalene was utilized instead of 7-aminoquinoline. UV: 245, 281, 315 nm. M+H found for $C_{20}H_{20}FN_5O_2$: 382.3. NMR (CD$_3$OD): 8.28 (1H, s), 7.88 (1H, d, J=8.4 Hz), 7.77-7.69 (3H, m), 7.54-7.48 (1H, m), 7.41-7.35 (1H, m), 7.30-7.25 (1H, m), 4.64-4.58 (1H, m), 2.16-1.88 (2H, m), 1.14 (3H, t, J=7.2 Hz) ppm.

Example 234

Preparation of (R)-6-(1-amino-1-oxobutan-2-ylamino)-5-fluoro-2-(benzo[d]thiazol-6-ylamino)nicotinamide

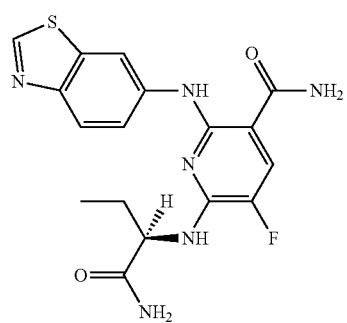 [SMILES: CC[C@@H](Nc1nc(Nc2ccc3ncsc3c2)c(C(N)=O)cc1F)C(N)=O]

The title compound was synthesized analogously according to the procedures described for the preparation of Example 97. However, 6-aminobenzothiazole was utilized instead of 7-aminoquinoline. UV: 259, 330 nm. M+H found for $C_{17}H_{17}FN_6O_2S$: 389.2. NMR (CD$_3$OD): 9.26 (1H, s), 8.72 (1H, d, J=2.0 Hz), 7.92 (1H, d, J=8.8 Hz), 7.75 (1H, d, J=11.6 Hz), 7.51 (1H, dd, J=2.0, 8.8 Hz), 4.42-4.36 (1H, m), 2.16-1.88 (2H, m), 1.14 (3H, t, J=7.2 Hz) ppm.

Example 235

Preparation of (R)-6-(1-amino-1-oxobutan-2-ylamino)-5-fluoro-2-(5-methylpyridin-3-ylamino)nicotinamide

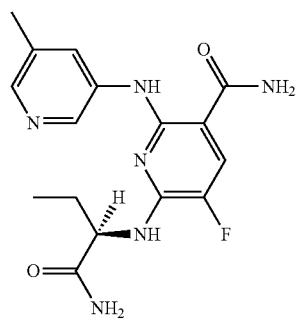 [SMILES: CC[C@@H](Nc1nc(Nc2cncc(C)c2)c(C(N)=O)cc1F)C(N)=O]

The title compound was synthesized analogously according to the procedures described for the preparation of Example 97. However, 3-amino-5-methylpyridine was utilized instead of 7-aminoquinoline. UV: 230, 260, 330 nm. M+H found for $C_{16}H_{19}FN_6O_2$: 347.3. NMR (CD$_3$OD): 9.30-9.25 (1H, m), 8.25-8.15 (2H, m), 7.90-7.80 (1H, m), 4.30-4.20 (1H, m), 3.50 (3H, s), 2.05-1.92 (2H, m), 1.14 (3H, t, J=7.2 Hz) ppm.

Example 236

Preparation of (R)-6-(1-amino-1-oxobutan-2-ylamino)-5-fluoro-2-(1,5-naphthyridin-3-ylamino)nicotinamide

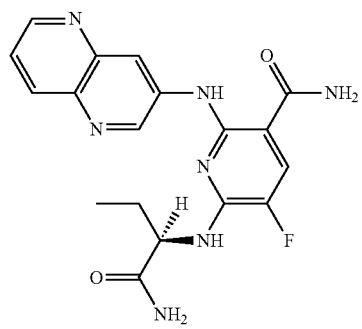 [SMILES: CC[C@@H](Nc1nc(Nc2cnc3cccnc3c2)c(C(N)=O)cc1F)C(N)=O]

The title compound was synthesized analogously according to the procedures described for the preparation of Example 97. However, 3-amino-1,5-naphthyridine was utilized instead of 7-aminoquinoline. UV: 252, 310 nm. M+H found for $C_{18}H_{18}FN_7O_2$: 384.3. NMR (CD$_3$OD): 9.45 (1H, d, J=2.4 Hz), 9.08 (1H, d, J=5.6 Hz), 8.98-8.91 (2H, m), 7.98-7.86 (2H, m), 4.35-4.25 (1H, m), 2.12-1.98 (2H, m), 1.15 (3H, t, J=7.2 Hz) ppm.

Example 237

Preparation of (R)-6-(1-amino-1-oxobutan-2-ylamino)-5-fluoro-2-(benzo[d][1,3]dioxol-5-ylamino)nicotinamide

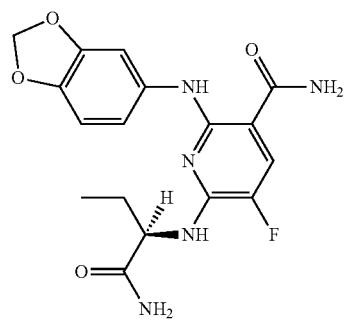

The title compound was synthesized analogously according to the procedures described for the preparation of Example 97. However, 3,4-Methylendioxyaniline was utilized instead of 7-aminoquinoline. UV: 297 nm. M+H found for $C_{17}H_{18}FN_5O_4$: 376.3. NMR (CD$_3$OD): 7.67 (1H, d, J=12.0 Hz), 7.19 (1H, d, J=1.6 Hz), 6.93 (1H, dd, 3=2.0, 8.0 Hz), 6.73 (1H, d, J=8.4 Hz), 5.90 (2H, s), 4.48-4.41 (1H, m), 2.06-1.80 (2H, m), 1.05 (3H, t, J=7.2 Hz) ppm.

Example 238

Preparation of (R)-6-(1-amino-1-oxobutan-2-ylamino)-5-fluoro-2-(benzo[d]thiazol-5-ylamino)nicotinamide

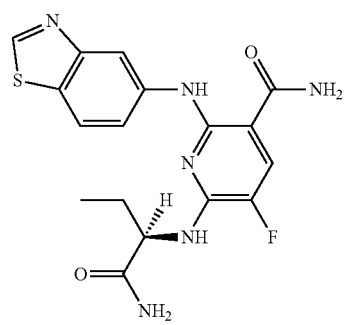 [SMILES: CC[C@@H](Nc1nc(Nc2ccc3scnc3c2)c(C(N)=O)cc1F)C(N)=O]

The title compound was synthesized analogously according to the procedures described for the preparation of Example 97. However, 5-aminobenzothiazole was utilized instead of 7-aminoquinoline. UV: 243, 305 nm. M+H found for $C_{17}H_{17}FN_6O_2$: 389.2. NMR (CD$_3$OD): 9.71 (1H, s), 8.83

(1H, s), 8.01 (1H, d, J=9.2 Hz), 7.81-7.76 (1H, m), 7.54 (1H, d, J=8.8 Hz), 4.60-4.52 (1H, m), 2.14-1.89 (2H, m), 1.09 (3H, t, J=7.2 Hz) ppm.

Example 239

Preparation of (R)-6-(1-amino-1-oxobutan-2-ylamino)-5-fluoro-2-(3-methylisothiazol-5-ylamino)nicotinamide

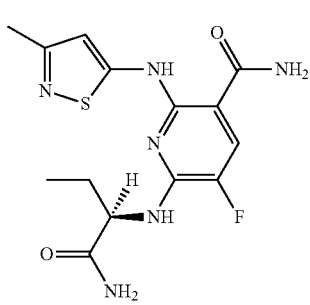 [SMILES: CC[C@@H](Nc1nc(Nc2cc(C)ns2)c(C(N)=O)cc1F)C(N)=O]

The title compound was synthesized analogously according to the procedures described for the preparation of Example 97. However, 5-amino-3-methylisothiazole hydrochloride was utilized instead of 7-aminoquinoline. UV: 243, 305 nm. M+H found for $C_{14}H_{17}FN_6O_2S$: 389.2. NMR (CD$_3$OD): 8.01 (1H, d, J=12.0 Hz), 6.96 (1H, s), 4.66-4.58 (1H, m), 2.56 (3H, s), 2.25-1.91 (2H, m), 1.12 (3H, t, J=7.2 Hz) ppm.

Example 240

Preparation of (R)-6-(1-amino-1-oxobutan-2-ylamino)-5-fluoro-2-(1-methyl-1H-indazol-4-ylamino)nicotinamide

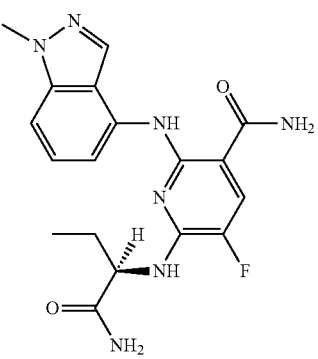 [SMILES: CC[C@@H](Nc1nc(Nc2cccc3c2cnn3C)c(C(N)=O)cc1F)C(N)=O]

The title compound was synthesized analogously according to the procedures described for the preparation of Example 97. However, 4-amino-1-methyl-1H-indazole was utilized instead of 7-aminoquinoline. UV: 264, 333 nm. M+H found for $C_{18}H_{20}FN_7O_2$: 386.5. NMR (DMSO-d$_6$): 12.40 (1H, s), 8.12 (1H, d, J=5.2 Hz), 7.95-7.80 (3H, m), 7.54 (1H, br), 7.40-7.26 (2H, m), 7.15-7.09 (2H, m), 6.95 (1H, d, J=5.2 Hz), 4.45-4.38 (1H, m), 1.96-1.78 (2H, m), 0.95 (3H, t, J=7.2 Hz) ppm.

Example 241

Preparation of (R)-6-(1-amino-1-oxobutan-2-ylamino)-5-fluoro-2-(1-methyl-1H-indazol-5-ylamino)nicotinamide

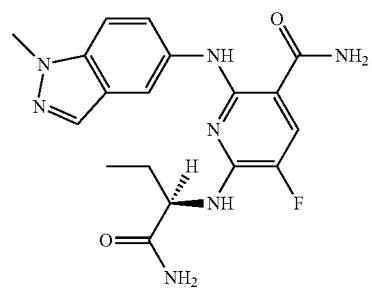 [SMILES: CC[C@@H](Nc1nc(Nc2ccc3c(cnn3C)c2)c(C(N)=O)cc1F)C(N)=O]

The title compound was synthesized analogously according to the procedures described for the preparation of Example 97. However, 4-amino-1-methyl-1H-indazole was utilized instead of 7-aminoquinoline. UV: 243, 295 nm. M+H found for $C_{18}H_{20}FN_7O_2$: 386.5. NMR (DMSO-d$_6$): 11.60 (1H, s), 8.23 (1H, d, J=1.2 Hz), 7.94 (1H, s), 7.85 (1H, d, J=12.4 Hz), 7.70 (1H, br), 7.51-7.45 (2H, m), 7.28 (1H, dd, J=2.0, 8.8 Hz), 7.18 (1H, br), 6.81 (1H, d, J=7.6 Hz), 4.40-4.30 (1H, m), 1.96-1.78 (2H, m), 0.95 (3H, t, J=7.2 Hz) ppm.

Example 242

Preparation of (R)-6-(1-amino-1-oxobutan-2-ylamino)-5-fluoro-2-(quinolin-4-ylamino)nicotinamide

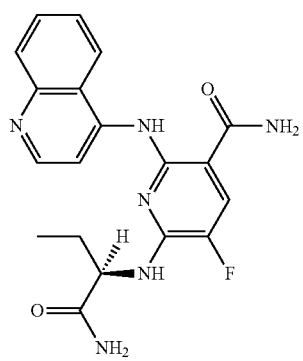 [SMILES: CC[C@@H](Nc1nc(Nc2ccnc3ccccc23)c(C(N)=O)cc1F)C(N)=O]

The title compound was synthesized analogously according to the procedures described for the preparation of Example 97. However, 4-aminoquinoline was utilized instead of 7-aminoquinoline. UV: 228, 264, 326 nm. M+H found for $C_{19}H_{19}FN_6O_2$: 383.5. NMR (DMSO-d$_6$): 8.95 (1H, d, J=6.8 Hz), 8.79 (1H, d, J=6.8 Hz), 8.38 (1H, d, J=8.4 Hz), 8.31 (1H, br), 8.16-8.03 (3H, m), 7.94-7.86 (2H, m), 7.65-7.61 (1H, m), 7.15 (1H, br), 6.81 (1H, d, J=7.6 Hz), 4.40-4.30 (1H, m), 1.99-1.82 (2H, m), 1.01 (3H, t, J=7.2 Hz) ppm.

Example 243

Preparation of (R)-6-(1-amino-1-oxobutan-2-ylamino)-5-fluoro-2-(1-methyl-1H-indol-4-ylamino)nicotinamide

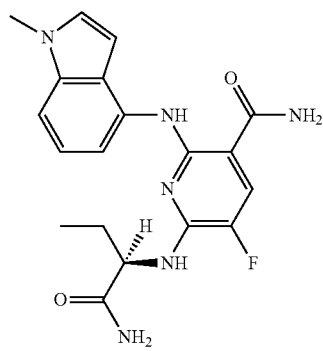 [SMILES: CC[C@@H](Nc1nc(Nc2cccc3c2ccn3C)c(C(N)=O)cc1F)C(N)=O]

The title compound was synthesized analogously according to the procedures described for the preparation of Example 97. However, 4-amino-1-methyl-1H-indole was utilized instead of 7-aminoquinoline. UV: 225, 326 nm. M+H found for $C_{19}H_{21}FN_6O_2$: 385.5. NMR (DMSO-d6): 11.95 (1H, s), 8.04 (1H, d, J=7.6 Hz), 7.82 (1H, d, J=12.4 Hz), 7.68 (1H, br), 7.45 (1H, br), 7.17 (1H, d, J=2.8 Hz), 7.08 (1H, br), 7.08 (1H, t, J=8.0 Hz), 6.92 (1H, d, J=8.4 Hz), 6.74 (1H, d, J=6.8 Hz), 6.42 (1H, d, J=2.8 Hz), 4.43-4.35 (1H, m), 1.99-1.82 (2H, m), 0.94 (3H, t, J=7.2 Hz) ppm.

Example 244

Preparation of (R)-6-(1-amino-1-oxobutan-2-ylamino)-5-fluoro-2-(1-methyl-1H-indol-5-ylamino)nicotinamide

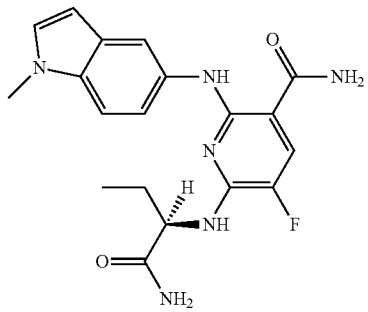 [SMILES: CC[C@@H](Nc1nc(Nc2ccc3c(ccn3C)c2)c(C(N)=O)cc1F)C(N)=O]

The title compound was synthesized analogously according to the procedures described for the preparation of Example 97. However, 5-amino-1-methyl-1H-indole was utilized instead of 7-aminoquinoline. UV: 284 nm. M+H found for $C_{19}H_{21}FN_6O_2$: 385.4. NMR (DMSO-d6): 11.42 (1H, s), 7.91 (1H, d, J=1.6 Hz), 7.82 (1H, d, J=12.4 Hz), 7.65 (1H, br), 7.41 (1H, br), 7.28 (1H, d, J=8.4 Hz), 7.22-7.04 (4H, m), 6.70 (1H, d, J=6.8 Hz), 6.38 (1H, d, J=2.8 Hz), 4.43-4.35 (1H, m), 1.97-1.76 (2H, m), 0.94 (3H, t, J=7.2 Hz) ppm.

Example 245

Preparation of (R)-6-(1-amino-1-oxobutan-2-ylamino)-5-fluoro-2-(quinolin-5-ylamino)nicotinamide

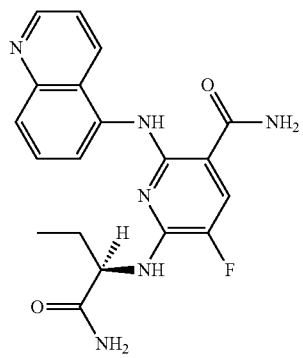 [SMILES: CC[C@@H](Nc1nc(Nc2cccc3ncccc23)c(C(N)=O)cc1F)C(N)=O]

The title compound was synthesized analogously according to the procedures described for the preparation of Example 97. However, 5-aminoquinoline was utilized instead of 7-aminoquinoline. UV: 240, 275 nm. M+H found for $C_{19}H_{19}FN_6O_2$: 383.5. NMR (CD$_3$OD): 9.26 (1H, d, J=8.4 Hz), 9.07 (1H, d, J=5.2 Hz), 8.80 (1H, d, J=8.4 Hz), 8.07 (1H, t, 8.0 Hz), 7.95 (1H, dd, 5.6, 8.0 Hz), 7.86 (1H, d, J=12.0 Hz), 7.71 (1H, d, J=8.4 Hz), 4.33-4.28 (1H, m), 2.06-1.84 (2H, m), 1.07 (3H, t, J=7.2 Hz) ppm.

Example 246

Preparation of (R)-6-(1-amino-4-methyl-1-oxopentan-2-ylamino)-5-fluoro-2-(quinolin-7-ylamino)nicotinamide

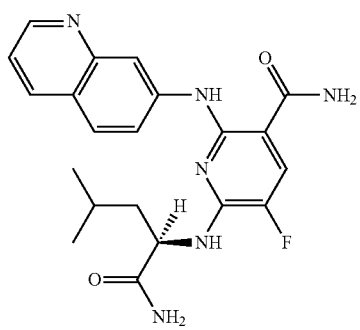 [SMILES: CC(C)C[C@@H](Nc1nc(Nc2ccc3cccnc3c2)c(C(N)=O)cc1F)C(N)=O]

The title compound was synthesized analogously according to the procedures described for the preparation of Example 97. However, (R)-leucinamide hydrochloride was used instead of (R)-(−)-2-aminobutanamide hydrochloride (J16). UV: 262, 293 nm. M+H found for $C_{23}FN_6O_2$: 411.5. NMR (DMSO-d6): 12.67 (1H, s), 9.09 (1H, d, J=4.8 Hz), 8.94 (1H, d, J=8.0 Hz), 8.7 (1H, br), 8.17 (1H, d, J=8.8 Hz), 8.05-7.95 (3H, m), 7.85 (1H, dd, J=2.0, 8.8 Hz), 7.76 (1H, dd, J=2.4, 8.0 Hz), 7.53 (1H, br), 7.47 (1H, br), 7.39 (1H, d, J=7.2

Hz), 4.55-4.46 (1H, m), 1.88-1.65 (3H, m), 0.91 (3H, d, J=6.0 Hz), 0.86 (3H, d, J=6.8 Hz) ppm.

Example 247

Preparation of (R)-6-(1-amino-4-methyl-1-oxopentan-2-ylamino)-5-fluoro-2-(quinolin-3-ylamino)nicotinamide

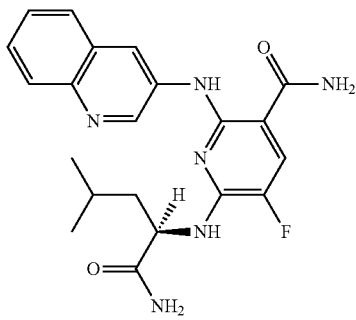 [SMILES: CC(C)C[C@@H](Nc1nc(Nc2cnc3ccccc3c2)c(C(N)=O)cc1F)C(N)=O]

The title compound was synthesized analogously according to the procedures described for the preparation of Example 97. However, 3-aminoquinoline was utilized instead of 7-aminoquinoline, and (R)-leucinamide hydrochloride was used instead of (R)-(−)-2-aminobutanamide hydrochloride (J16). UV: 224, 243, 296, 326 nm. M+H found for $C_{21}H_{23}FN_6O_2$: 411.5. NMR (DMSO-d6): 12.26 (1H, s), 9.17 (1H, s), 9.03 (1H, s), 8.21 (1H, d, J=8.4 Hz), 8.00-7.80 (3H, m), 7.68-7.62 (2H, m), 7.39-7.32 (3H, m), 7.15 (1H, br), 4.50-4.41 (1H, m), 1.88-1.65 (3H, m), 0.91 (3H, d, J=6.0 Hz), 0.81 (3H, d, J=6.4 Hz) ppm.

Example 248

Preparation of (R)-6-(1-amino-4-methyl-1-oxopentan-2-ylamino)-5-fluoro-2-(quinolin-6-ylamino)nicotinamide

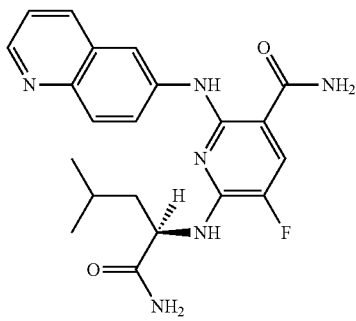 [SMILES: CC(C)C[C@@H](Nc1nc(Nc2ccc3ncccc3c2)c(C(N)=O)cc1F)C(N)=O]

The title compound was synthesized analogously according to the procedures described for the preparation of Example 97. However, 6-aminoquinoline was utilized instead of 7-aminoquinoline, and (R)-leucinamide hydrochloride was used instead of (R)-(−)-2-aminobutanamide hydrochloride (J16). UV: 265, 297, 330 nm. M+H found for $C_{21}H_{23}FN_6O_2$: 411.5. NMR (DMSO-d6): 12.35 (1H, s), 9.15 (1H, br), 9.03-8.80 (2H, m), 8.21-8.05 (1H, m), 8.00-7.83 (4H, m), 7.45-7.30 (3H, m), 7.17 (1H, br), 4.50-4.41 (1H, m), 1.88-1.65 (3H, m), 0.91 (3H, d, J=6.0 Hz), 0.81 (3H, d, J=6.4 Hz) ppm.

Example 249

Preparation of (R)-6-(1-amino-4-methyl-1-oxopentan-2-ylamino)-5-fluoro-2-(1-methyl-1H-indol-5-ylamino)nicotinamide

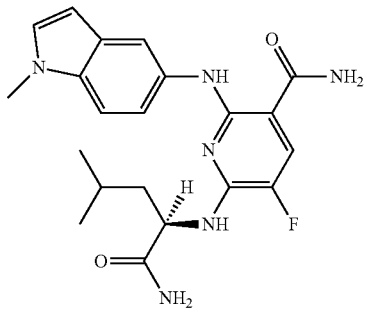 [SMILES: CC(C)C[C@@H](Nc1nc(Nc2ccc3c(ccn3C)c2)c(C(N)=O)cc1F)C(N)=O]

The title compound was synthesized analogously according to the procedures described for the preparation of Example 97. However, 5-amino-1-methyl-1H-indole was utilized instead of 7-aminoquinoline, and (R)-leucinamide hydrochloride was used instead of (R)-(−)-2-aminobutanamide hydrochloride (J16). UV: 284 nm. M+H found for $C_{21}H_{25}FN_6O_2$: 413.3. NMR (DMSO-d6): 11.37 (1H, s), 7.87 (1H, d, J=2.0 Hz), 7.75 (1H, d, J=12.4 Hz), 7.58 (1H, br), 7.20 (1H, d, J=9.2 Hz), 7.17-7.07 (3H, m), 6.97 (1H, br), 6.87 (1H, d, J=8.0 Hz), 6.28 (1H, dd, J=0.8, 6.8 Hz), 4.52-4.44 (1H, m), 1.82-1.54 (3H, m), 0.90 (3H, d, J=6.0 Hz), 0.78 (3H, d, J=6.4 Hz) ppm.

Example 250

Preparation of (R)-6-(1-amino-3-cyclopropyl-1-oxopropan-2-ylamino)-5-fluoro-2-(quinolin-7-ylamino)nicotinamide

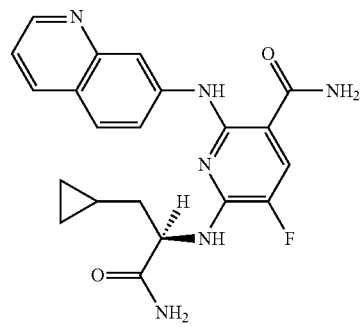 [SMILES: NC(=O)c1cc(F)c(N[C@H](CC2CC2)C(N)=O)nc1Nc1ccc2cccnc2c1]

The title compound was synthesized analogously according to the procedures described for the preparation of Example 97. However, (R)-2-amino-3-cyclopropylpropanamide hydrochloride salt (synthesis detailed in example 35) was used instead of (R)-(+2-aminobutanamide hydrochloride (J16). UV: 217, 262, 293 nm. M+H found for $C_{21}H_{21}FN_6O_2$: 409.5. NMR (DMSO-d6): 12.68 (1H, s), 8.99 (1H, d, J=4.8

Hz), 8.88 (1H, d, J=8.0 Hz), 8.74 (1H, br), 8.11 (1H, d, J=9.2 Hz), 8.00-7.92 (3H, m), 7.74-7.67 (2H, m), 7.49 (1H, br), 7.35 (1H, br), 7.20 (1H, d, J=6.8 Hz), 4.63-4.57 (1H, m), 1.95-1.86 (1H, m), 1.69-1.50 (1H, m), 0.89-0.80 (1H, m), 0.36-0.24 (2H, m), 0.17-0.04 (2H, m) ppm.

Example 251

Preparation of (R)-6-(1-amino-3-cyclopropyl-1-oxo-propan-2-ylamino)-5-fluoro-2-(quinolin-3-ylamino)nicotinamide

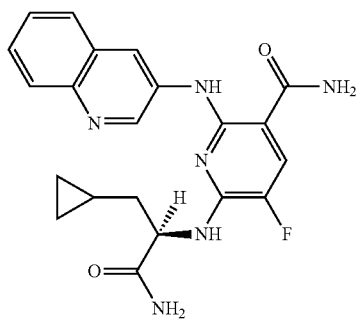 [SMILES: NC(=O)c1cc(F)c(N[C@H](CC2CC2)C(N)=O)nc1Nc1cnc2ccccc2c1]

The title compound was synthesized analogously according to the procedures described for the preparation of Example 97. However, 3-aminoquinoline was utilized instead of 7-aminoquinoline, and (R)-2-amino-3-cyclopropylpropanamide hydrochloride salt (synthesis detailed in example 35) was used instead of (R)-(−)-2-aminobutanamide hydrochloride (J16). UV: 224, 243, 296, 327 nm. M+H found for $C_{21}H_{21}FN_6O_2$: 409.5. NMR (DMSO-d6): 12.19 (1H, s), 9.03 (1H, s), 8.97 (1H, br), 8.12 (1H, d, J=8.4 Hz), 7.95-7.89 (2H, m), 7.82 (1H, br), 7.63-7.53 (2H, m), 7.40 (1H, s), 7.34 (1H, br), 7.19 (1H, d, J=7.2 Hz), 7.12 (1H, br), 4.46-4.39 (1H, m), 1.94-1.85 (1H, m), 1.63-1.53 (1H, m), 0.82-0.74 (1H, m), 0.38-0.24 (2H, m), 0.14-0.07 (1H, m), 0.05-(−) 0.03 (1H, m) ppm.

Example 252

Preparation of (R)-6-(1-amino-3-cyclopropyl-1-oxo-propan-2-ylamino)-5-fluoro-2-(quinolin-6-ylamino)nicotinamide

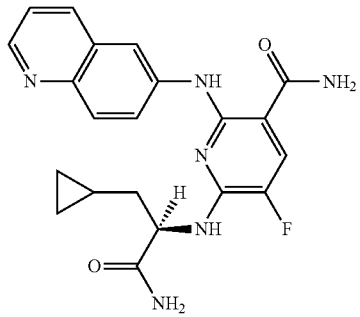

The title compound was synthesized analogously according to the procedures described for the preparation of Example 97. However, 6-aminoquinoline was utilized instead of 7-aminoquinoline, and (R)-2-amino-3-cyclopropylpropanamide hydrochloride salt (synthesis detailed in example 35) was used instead of (R)-(−)-2-aminobutanamide hydrochloride (J16). UV: 265, 297, 330 nm. M+H found for $C_{21}H_{21}FN_6O_2$: 409.5. NMR (DMSO-d6): 12.32 (1H, s), 9.05 (1H, d, J=8.8 Hz), 8.93 (1H, dd, 1.6, 5.2 Hz), 8.81 (1H, d, J=2.0 Hz), 8.11 (1H, d, 9.2 Hz), 7.98-7.83 (4H, m), 7.47 (1H, br), 7.39 (1H, br), 7.29 (1H, d, J=7.2 Hz), 7.12 (1H, br), 4.44-4.36 (1H, m), 1.99-1.90 (1H, m), 1.63-1.56 (1H, m), 0.86-0.81 (1H, m), 0.40-0.30 (2H, m), 0.17-0.12 (1H, m), 0.08-0.01 (1H, m) ppm.

Example 253

Preparation of (R)-6-(1-amino-3-cyclopropyl-1-oxo-propan-2-ylamino)-5-fluoro-2-(3-methylisothiazol-5-ylamino)nicotinamide

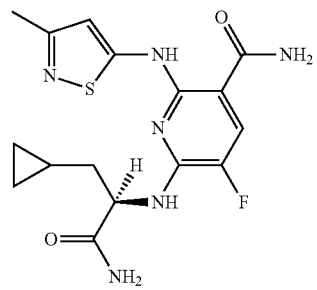 [SMILES: Cc1cc(Nc2nc(N[C@H](CC3CC3)C(N)=O)c(F)cc2C(N)=O)sn1]

The title compound was synthesized analogously according to the procedures described for the preparation of Example 97. However, 5-amino-3-methylisothiazole hydrochloride was utilized instead of 7-aminoquinoline, and (R)-2-amino-3-cyclopropylpropanamide hydrochloride salt (synthesis detailed in example 35) was used instead of (R)-(−)-2-aminobutanamide hydrochloride (J16). UV: 243, 273, 335 nm. M+H found for $C_{16}H_{19}FN_6O_2S$: 379.4. NMR (DMSO-d6): 12.61 (1H, s), 7.92 (1H, d, J=12.0 Hz), 7.83 (1H, br), 7.49 (1H, s), 7.36 (1H, br), 7.14-7.05 (2H, m), 6.66 (1H, s), 4.86-4.78 (1H, m), 2.22 (3H, s), 1.90-1.81 (1H, m), 1.65-1.56 (1H, m), 0.75-0.64 (1H, m), 0.33-0.21 (2H, m), 0.12-(−) 0.04 (2H, m) ppm.

Example 254

Preparation of 6-((1R,2S)-2-aminocyclohexylamino)-2-(2,3-dihydrobenzo[b][1,4]dioxin-6-ylamino)nicotinamide

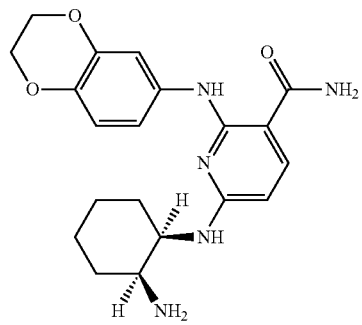 [SMILES: NC(=O)c1ccc(N[C@@H]2CCCC[C@@H]2N)nc1Nc1ccc2c(c1)OCCO2]

The title compound was synthesized analogously according to the procedures described for the preparation of example 157. Conversion of the nitrile to the amide and Boc-deprotection was performed as detailed in scheme 36. UV: 281 nm. M+H found for $C_{20}H_{25}N_5O_3$: 384.3. NMR (CD$_3$OD): 7.78 (1H, d, J=8.8 Hz), 7.26 (1H, s), 6.81-6.77 (2H, m), 6.06 (1H, d, J=9.2 Hz), 4.32-4.20 (5H, m), 3.79-3.72 (1H, m), 1.90-1.48 (8H, m) ppm.

Example 255

Preparation of 6-(1R,2S)-2-aminocyclohexylamino)-2-(benzo[d][1,3]dioxol-5-ylamino)nicotinamide

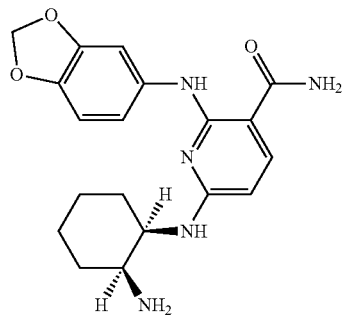

The title compound was synthesized analogously according to the procedures described for the preparation of example 157. Conversion of the nitrile to the amide and Boc-deprotection was performed as detailed in scheme 36. UV: 282 nm. M+H found for $C_{19}H_{23}N_5O_3$: 370.3. NMR (CD$_3$OD): 7.77 (1H, d, J=8.0 Hz), 7.29 (1H, br), 6.79 (1H, br). 6.06 (1H, d, J=8.8 Hz), 5.94 (2H, s), 4.35-4.25 (1H, m), 3.78-3.70 (1H, m), 1.90-1.50 (8H, m)

Example 256

Preparation of 6-(1R,2S)-2-aminocyclohexylamino)-2-(5-methylpyridin-3-ylamino)nicotinamide

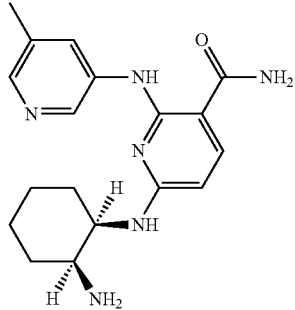

The title compound was synthesized analogously according to the procedures described for the preparation of example 157. Conversion of the nitrile to the amide and Boc-deprotection was performed as detailed in scheme 36. UV: 237, 264, 322 nm. M+H found for $C_{18}H_{24}N_6O$: 341.3. NMR (CD$_3$OD): 9.34-9.29 (1H, m), 8.20-8.15 (2H, m), 7.92-7.88 (1H, m), 6.20 (1H, d, J=8.4 Hz), 4.52-4.44 (1H, m), 3.64-3.55 (1H, m), 1.90-1.50 (8H, m) ppm.

Example 257

Preparation of (S)-2-(3-(2H-1,2,3-triazol-2-yl)phenylamino)-6-(2-aminopropylamino)-5-fluoronicotinamide

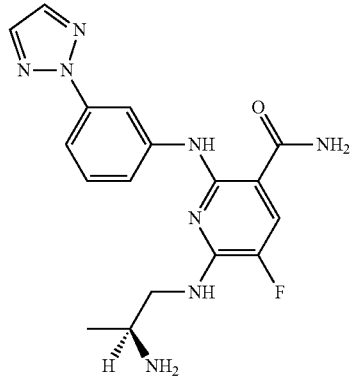 [SMILES: C[C@H](N)CNc1nc(Nc2cccc(-n3nccn3)c2)c(C(N)=O)cc1F]

The title compound was synthesized analogously according to the procedures described for the preparation of Example 97. However, 3-(2H-1,2,3-triazol-2-yl)aniline (J4) was utilized instead of 7-aminoquinoline, and (S)-tert-butyl 1-aminopropan-2-ylcarbamate was used instead of (R)-(−)-2-aminobutanamide hydrochloride (J16). Additionally, a Boc-deprotection according to example 29 (1:1 DCM and TFA mixture) was performed after step 3 of example 97. This gave the TFA salt which was then subjected to preparative reverse phase column chromatography. UV: 267, 305 nm. M+H found for $C_{17}H_{19}FN_8O$: 371.4. NMR (CD$_3$OD): 8.84 (1H, t, J=2.0 Hz), 7.93 (2H, s), 7.77 (1H, d, J=11.6 Hz), 7.68-7.63 (1H, m), 7.40 (1H, t, J=8.0 Hz), 7.23-7.18 (1H, m) 3.92 (1H, dd, J=2.8, 13.2 Hz), 3.74-3.63 (2H, m), 1.21 (3H, d, J=6.4 Hz) ppm.

Example 258

Preparation of (S)-2-(3-(pyrimidin-2-yl)phenylamino)-6-(2-aminopropylamino)-5-fluoronicotinamide

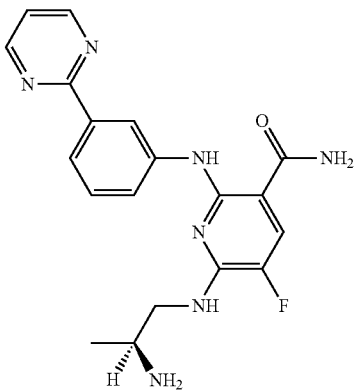 [SMILES: C[C@H](N)CNc1nc(Nc2cccc(-c3ncccn3)c2)c(C(N)=O)cc1F]

The title compound was synthesized analogously according to the procedures described for the preparation of Example 97. However, 3-(pyrimidin-2-yl)aniline was utilized instead of 7-aminoquinoline, and (S)-tert-butyl 1-aminopropan-2-ylcarbamate was used instead of (R)-(−)-2-aminobutanamide hydrochloride (J16). Additionally, a Boc-deprotection according to example 29. (1:1 DCM and TFA mixture) was performed after step 3 of example 97. This gave the TFA salt which was then subjected to preparative reverse phase column chromatography. UV: 263, 303 nm. M+H found for $C_{19}H_{20}FN_7O$: 382.4. NMR ($CD_3OD$): 8.85 (2H, d, J=5.2 Hz), 8.82 (1H, t, J=2.0 Hz), 7.99 (1H, d, J=8.0), 7.74 (1H, d, J=12.0 Hz) 7.51-7.46 (1H, m), 7.43-7.36 (2H, m), 3.93 (1H, dd, J=3.2, 14.0 Hz), 3.72-3.54 (2H, m), 1.15 (3H, d, J=6.8 Hz) ppm.

Example 259

Preparation of (S)-2-(3-(1H-pyrazol-1-yl)phenylamino)-6-(2-aminopropylamino)-5-fluoronicotinamide

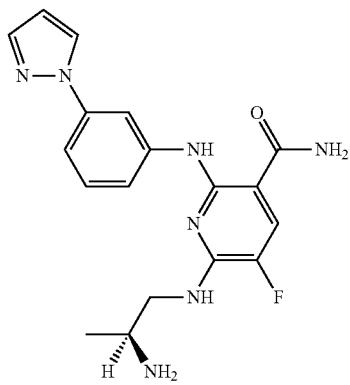 [SMILES: C[C@H](N)CNc1nc(Nc2cccc(-n3cccn3)c2)c(C(N)=O)cc1F]

The title compound was synthesized analogously according to the procedures described for the preparation of Example 97. However, 3-(1H-pyrazol-1-yl)aniline was utilized instead of 7-aminoquinoline, and (S)-tert-butyl 1-aminopropan-2-ylcarbamate was used instead of (R)-(−)-2-aminobutanamide hydrochloride (J16). Additionally, a Boc-deprotection according to example 29 (1:1 DCM and TFA mixture) was performed after step 3 of example 97. This gave the TFA salt which was then subjected to preparative reverse phase column chromatography. UV: 259, 306 nm. M+H found for $C_{18}H_{20}FN_7O$: 370.4. NMR ($CD_3OD$): 8.56 (1H, s), 8.22 (1H, d, J=2.4 Hz), 7.78-7.74 (2H, m), 7.38 (1H, t, J=8.0 Hz) 7.24 (1H, dd, J=1.2, 7.6 Hz), 7.14 (1H, dd, J=1.2, 8.0 Hz), 6.56-6.54 (1H, m), 3.86-3.62 (3H, m), 1.20 (3H, d, J=6.8 Hz) ppm.

Example 260

Preparation of (S)-2-(5-methylpyridin-3-ylamino)-6-(2-aminopropylamino)-5-fluoronicotinamide

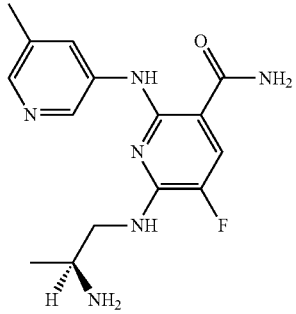 [SMILES: Cc1cncc(Nc2nc(NC[C@H](C)N)c(F)cc2C(N)=O)c1]

The title compound was synthesized analogously according to the procedures described for the preparation of Example 97. However, 3-amino-5-methylpyridine was utilized instead of 7-aminoquinoline, and (S)-tert-butyl 1-aminopropan-2-ylcarbamate was used instead of (R)-(−)-2-aminobutanamide hydrochloride (J16). Additionally, a Boc-deprotection according to scheme 42 (1:1 DCM and TFA mixture) was performed after step 3 of example 97. This gave the TFA salt which was then subjected to preparative reverse phase column chromatography. UV: 229, 261, 330 nm. M+H found for $C_{15}H_{19}FN_6O$: 319.4. NMR ($CD_3OD$): 9.37 (1H, d, J=2.4 Hz), 8.21-8.18 (2H, m), 7.85 (1H, d, J=11.6 Hz), 3.84-3.62 (3H, m), 2.55 (3H, s), 1.17 (3H, d, J=6.8 Hz) ppm.

Example 261

Preparation of (S)-2-(5-fluoropyridin-3-ylamino)-6-(2-aminopropylamino)-5-fluoronicotinamide

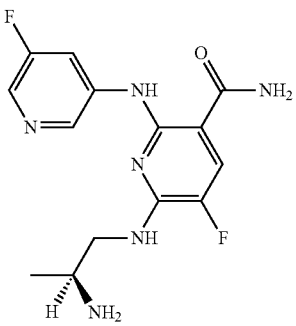 [SMILES: C[C@H](N)CNc1nc(Nc2cncc(F)c2)c(C(N)=O)cc1F]

The title compound was synthesized analogously according to the procedures described for the preparation of Example 97. However, 3-amino-5-fluoropyridine was utilized instead of 7-aminoquinoline, and (S)-tert-butyl 1-aminopropan-2-ylcarbamate was used instead of (R)-(−)-2-aminobutanamide hydrochloride (J16). Additionally, a Boc-deprotection according to scheme 42 (1:1 DCM and TFA mixture) was performed after step 3 of example 97. This gave the TFA salt which was then subjected to preparative reverse phase column chromatography. UV: 229, 259, 328 nm. M+H found for $C_{14}H_{16}F_2N_6O$: 323.3. NMR ($CD_3OD$): 8.67 (1H, dd, J=1.2, 2.0 Hz), 8.18-8.13 (1H, m), 8.07 (1H, d, J=2.0 Hz), 7.81 (1H, d, J=11.6 Hz), 3.83-3.52 (3H, m), 1.37 (3H, d, J=6.8 Hz) ppm.

Example 262

Preparation of (S)-2-(5-fluoropyridin-3-ylamino)-6-(2-aminopropylamino)-5-fluoronicotinamide

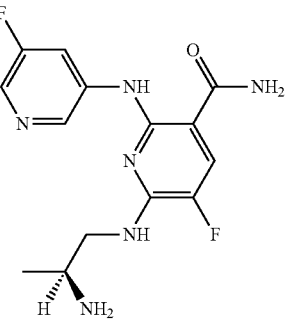

The title compound was synthesized analogously according to the procedures described for the preparation of Example 97. However, 3-amino-5-fluoropyridine was utilized instead of 7-aminoquinoline, and (S)-tert-butyl 1-aminopropan-2-ylcarbamate was used instead of (R)-(−)-2-aminobutanamide hydrochloride (J16). Additionally, a Boc-deprotection according to scheme 42 (1:1 DCM and TFA mixture) was performed after step 3 of example 97. This gave the TFA salt which was then subjected to preparative reverse phase column chromatography. UV: 225, 259, 328 nm. M+H found for $C_{14}H_{17}FN_6O$: 305.4. NMR (CD$_3$OD): 9.46 (1H, d, J=2.4 Hz), 8.44-8.40 (1H, m), 8.33 (1H, d, J=5.2 Hz), 7.89-7.83 (2H, m), 3.86-3.61 (3H, m), 1.37 (3H, d, J=6.8 Hz) ppm.

Example 263

Preparation of (R)-6-(1-amino-1-oxobutan-2-ylamino)-5-fluoro-2-(3-(trifluoromethoxy)phenylamino)nicotinamide

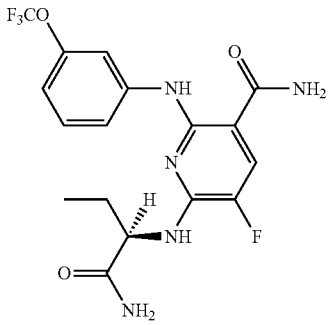 [SMILES: CC[C@@H](Nc1nc(Nc2cccc(OC(F)(F)F)c2)c(C(N)=O)cc1F)C(N)=O]

The title compound was synthesized analogously according to the procedures described for the preparation of Example 97. However, 3-(trifluoromethoxy)aniline was utilized instead of 7-aminoquinoline. UV: 268, 305 nm. M+H found for $C_{17}H_{17}F_4N_5O_3$: 385.4. NMR (CD$_3$OD): 7.78-7.64 (2H, m), 7.43-7.29 (2H, m), 6.85-6.74 (1H, m), 4.54-4.45 (1H, m), 2.16-1.82 (2H, m), 1.02 (3H, t, J=7.2 Hz) ppm.

Example 264

Preparation of (R)-6-(1-amino-1-oxobutan-2-ylamino)-5-fluoro-2-(3-(difluoromethoxy)phenylamino)nicotinamide

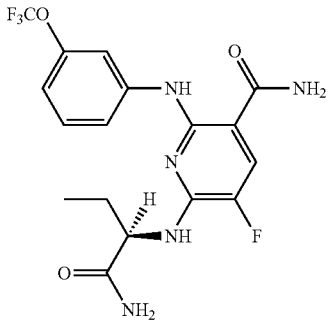 [SMILES: CC[C@@H](Nc1nc(Nc2cccc(OC(F)(F)F)c2)c(C(N)=O)cc1F)C(N)=O]

The title compound was synthesized analogously according to the procedures described for the preparation of Example 97. However, 3-(difluoromethoxy)aniline was utilized instead of 7-aminoquinoline. UV: 269, 309 nm. M+H found for $C_{17}H_{18}F_3N_5O_3$: 385.4. NMR (CD$_3$OD): 7.72 (1H, d, J=12.0 Hz), 7.50-7.45 (1H, m), 7.40 (1H, br), 7.28 (1H, t, J=8.0 Hz), 6.88 (1H, t, J=74.0 Hz), 6.71-6.65 (1H, m), 4.53-4.45 (1H, m), 2.08-1.84 (2H, m), 1.08 (3H, t, J=7.2 Hz) ppm.

Example 265

Preparation of (R)-6-(1-amino-4-methyl-1-oxopentan-2-ylamino)-5-fluoro-2-(3-chlorophenylamino)nicotinamide

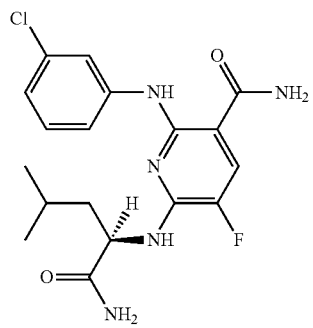 [SMILES: CC(C)C[C@@H](Nc1nc(Nc2cccc(Cl)c2)c(C(N)=O)cc1F)C(N)=O]

The title compound was synthesized analogously according to the procedures described for the preparation of Example 97. However, 3-chloroaniline was utilized instead of 7-aminoquinoline, and (R)-leucinamide hydrochloride was used instead of (R)-(−)-2-aminobutanamide hydrochloride (J16). UV: 269, 306 nm. M+H found for $C_{18}H_{21}ClFN_5O_2$: 394.4. NMR (DMSO-d6): 11.75 (1H, s), 7.87 (1H, d, J=12.4 Hz), 7.76 (1H, br), 7.62 (1H, dd, J=2.0, 2.0 Hz), 7.55 (1H, dd, J=2.0, 7.6 Hz), 7.26-7.19 (3H, m), 7.13 (1H, d, J=8.4 Hz), 7.03 (1H, br), 6.91 (1H, dd, 2.0, 8.0 Hz), 4.52-4.44 (1H, m), 1.82-1.56 (3H, m), 0.94 (3H, d, J=6.0 Hz), 0.84 (3H, d, J=6.4 Hz) ppm.

Example 266

Preparation of (R)-6-(1-amino-4-methyl-1-oxopentan-2-ylamino)-5-fluoro-2-(3-chloro-4-fluorophenylamino)nicotinamide

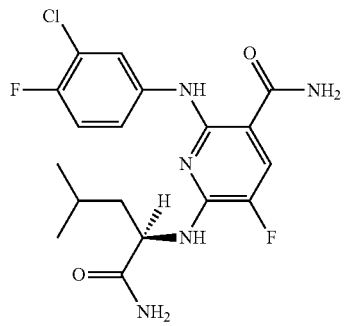 [SMILES: CC(C)C[C@@H](Nc1nc(Nc2ccc(F)c(Cl)c2)c(C(N)=O)cc1F)C(N)=O]

The title compound was synthesized analogously according to the procedures described for the preparation of Example 97. However, 3-chloro-4-fluoroaniline was utilized instead of 7-aminoquinoline, and (R)-leucinamide hydrochloride was used instead of (R)-(+2-aminobutanamide hydrochloride (J16). UV: 299 nm. M+H found for $C_{18}H_{20}ClF_2N_5O_2$: 412.4. NMR (DMSO-d6): 11.64 (1H, s), 7.86 (1H, d, J=12.4 Hz), 7.77-7.72 (2H, m), 7.57 (1H, m), 7.26-7.20 (3H, m), 7.13 (1H, d, J=8.4 Hz), 7.01 (1H, br), 4.46-4.38 (1H, m), 1.83-1.56 (3H, m), 0.90 (3H, d, J=6.0 Hz), 0.78 (3H, d, J=6.4 Hz) ppm.

Example 267

Preparation of (R)-6-(1-amino-4-methyl-1-oxopentan-2-ylamino)-5-fluoro-2-(4-chlorophenylamino)nicotinamide

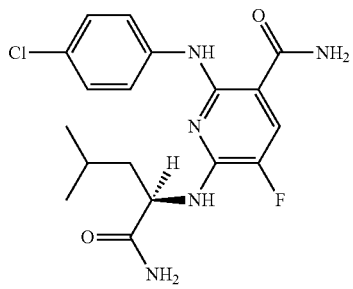 [SMILES: CC(C)C[C@@H](Nc1nc(Nc2ccc(Cl)cc2)c(C(N)=O)cc1F)C(N)=O]

The title compound was synthesized analogously according to the procedures described for the preparation of Example 97. However, 4-chloroaniline was utilized instead of 7-aminoquinoline, and (R)-leucinamide hydrochloride was used instead of (R)-(−)-2-aminobutanamide hydrochloride (J16). UV: 307 nm. M+H found for $C_{18}H_{21}ClFN_5O_2$: 394.4. NMR (DMSO-$d_6$): 11.68 (1H, s), 7.84 (1H, d, J=12.4 Hz), 7.75 (1H, br), 7.64-7.58 (2H, m), 7.39 (1H, br), 7.26-7.20 (3H, m), 7.09-7.04 (2H, m), 4.54-4.45 (1H, m), 1.82-1.65 (2H, m), 1.62-1.53 (1H, m), 0.92 (3H, d, J=6.0 Hz), 0.83 (3H, d, J=6.4 Hz) ppm.

Example 268

Preparation of 6-(1-carbamoylcyclopropylamino)-5-fluoro-2-(quinolin-3-ylamino)nicotinamide

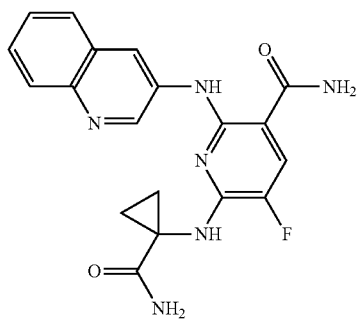 [SMILES: NC(=O)c1cc(F)c(NC2(C(N)=O)CC2)nc1Nc1cnc2ccccc2c1]

The title compound was synthesized analogously according to the procedures described for the preparation of Example 97. However, 3-aminoquinoline was utilized instead of 7-aminoquinoline, and 1-aminocyclopropylcarboxamide was used instead of (R)-(−)-2-aminobutanamide hydrochloride (J16). The 1-aminocyclopropylcarboxamide was prepared analogously according to the procedures described in Example 14 (Scheme 13). UV: 223, 243, 295, 326 nm. M+H found for $C_{19}H_{17}FN_6O_2$: 381.4. NMR (CD$_3$OD): 9.56-9.45 (2H, m), 8.28 (1H, d, J=8.4 Hz), 8.05 (1H, d, J=8.8 Hz), 7.91-7.78 (3H, m), 1.72 (2H, br), 1.21 (2H, br) ppm.

Example 269

Preparation of (R)-6-(1-amino-3-(oxetan-3-yl)-1-oxopropan-2-ylamino)-5-fluoro-2-(quinolin-3-ylamino)nicotinamide

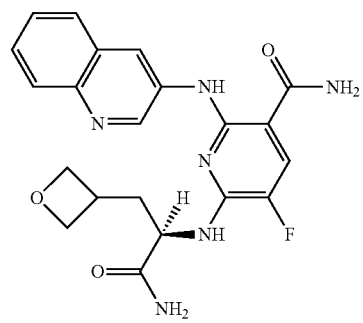 [SMILES: NC(=O)c1cc(F)c(N[C@H](CC2COC2)C(N)=O)nc1Nc1cnc2ccccc2c1]

The title compound can be synthesized analogously according to the procedures described for the preparation of Example 97. However, 3-aminoquinoline can be utilized instead of 7-aminoquinoline, and (R)-2-amino-3-(oxetan-3-yl)propanamide (PBS, Scheme 62) instead of (R)-(−)-2-aminobutanamide hydrochloride (J16).

Scheme 62:

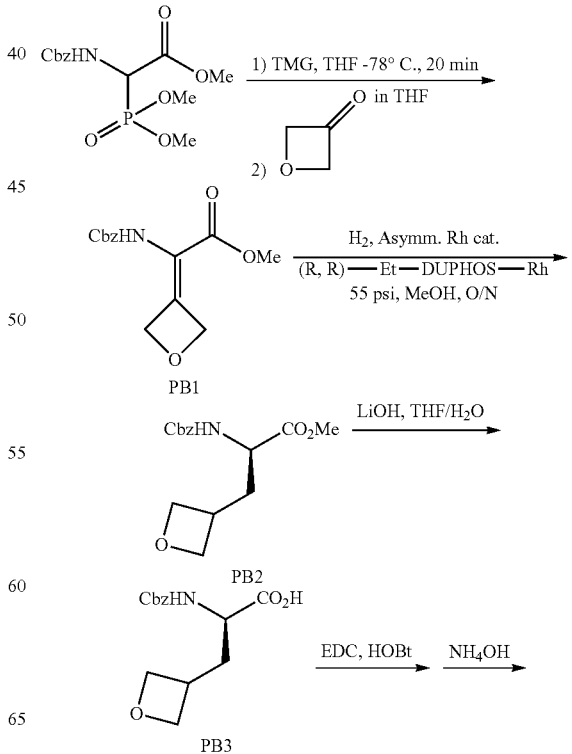

-continued

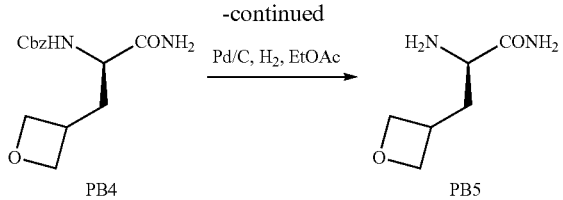

Compound PB1 can be synthesized according to methods described by Moldes et al., Farmaco (2001), 56(8), 609-613. An asymmetric reduction utilizing 1,2-Bis[(2R,5R)-2,5-diethylphospholano]benzene(1,5-cyclooctadiene)rhodium(I) trifluoromethanesulfonate according to Hu et al., Tet Lett (2008), 49(5), 901-902 can give PB2. Saponification of the methyl ester followed by amide formation (see scheme 13) can give PB4. Deprotection of the carbobenzyloxy-protected amine can be carried out using Pd/C, $H_2$ in EtOAc to give PB5.

Example 270

Preparation of (R)-6-(1-amino-4,4-difluoro-1-oxobutan-2-ylamino)-5-fluoro-2-(quinolin-3-ylamino)nicotinamide

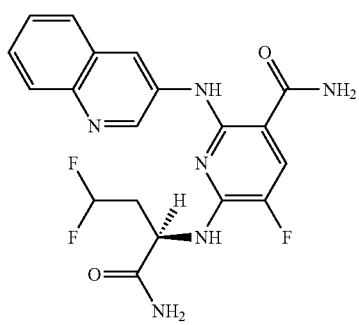 [SMILES: NC(=O)c1cc(F)c(N[C@H](CC(F)F)C(N)=O)nc1Nc1cnc2ccccc2c1]

The title compound can be synthesized analogously according to the procedures described for the preparation of Example 97. However, 3-aminoquinoline can be utilized instead of 7-aminoquinoline, and (R)-2-amino-4,4-difluorobutanamide instead of (R)-(−)-2-aminobutanamide hydrochloride (J16). The synthesis of (R)-2-amino-4,4-difluorobutanamide can be accomplished utilizing analogous chemistry described in Scheme 62 with minor modifications as noted in Hu et al., Tet Lett (2008), 49(5), 901-902.

Examples 271-307 can be synthesized analogously according to the procedures described for the preparation of Example 97 unless otherwise noted. Note that a diamine (or a monoprotected-diamine) is utilized instead of (R)-(−)-2-aminobutanamide hydrochloride (J16). Additionally, a Boc-deprotection utilizing a 1:1 DCM and TFA mixture (according to example 29) or a TFA/H2SO4 mixture (according to scheme 30) was/can be performed after step 3 of example 97. This gives a product which was/can be purified via preparative reverse phase column chromatography.

Example 271

6-((3R,4R)-3-aminotetrahydro-2H-pyran-4-ylamino)-5-fluoro-2-(pyridin-3-ylamino)nicotinamide

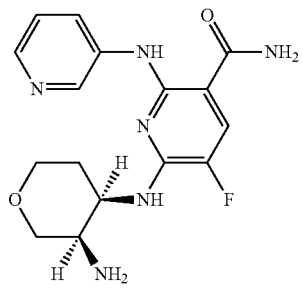

The above example can be synthesized by utilizing J86 (scheme 63, example 279) and 3-aminopyridine.

Example 272

6-((3R,4R)-3-aminotetrahydro-2H-pyran-4-ylamino)-2-(pyridin-3-ylamino)nicotinamide

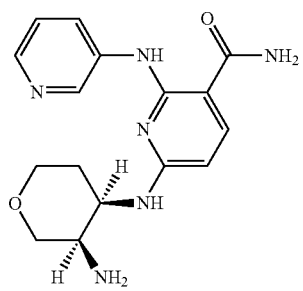 [SMILES: NC(=O)c1ccc(N[C@@H]2CCOC[C@@H]2N)nc1Nc1cccnc1]

The above example can be synthesized with J86 (scheme 63, example 279) and 3-aminopyridine by utilizing analogous chemistry described in example 157.

Example 273

6-((3R,4R)-3-aminotetrahydro-2H-pyran-4-ylamino)-5-fluoro-2-(5-fluoropyridin-3-ylamino)nicotinamide

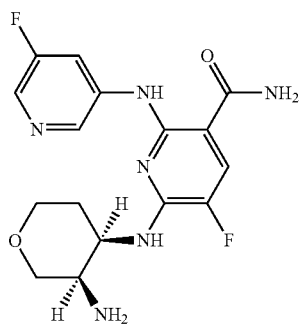 [SMILES: NC(=O)c1cc(F)c(N[C@@H]2CCOC[C@@H]2N)nc1Nc1cncc(F)c1]

The above example can be synthesized by utilizing J86 (scheme 63, example 279) and 3-amino-5-fluoroyridine.

Example 274

6-((3R,4R)-3-aminotetrahydro-2H-pyran-4-ylamino)-2-(5-fluoropyridin-3-ylamino)nicotinamide

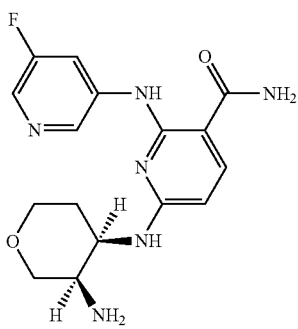 [SMILES: NC(=O)c1ccc(N[C@@H]2CCOC[C@@H]2N)nc1Nc1cncc(F)c1]

The above example can be synthesized with J86 (scheme 63, example 279) and 3-amino-5-fluoropyridine by utilizing analogous chemistry described in example 157.

Example 275

Preparation of 6-((3R,4R)-3-aminotetrahydro-2H-pyran-4-ylamino)-5-fluoro-2-(quinolin-3-ylamino)nicotinamide

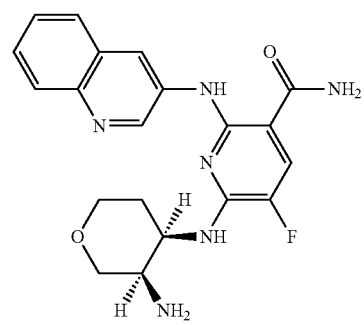

The title compound was synthesized using a procedure similar to that described in Example 279. MS found for C20H21FN6O2 as (M+H)$^+$ 397.3. UV: λ=224, 295, 325 nm. $^1$H NMR: (CD$_3$OD) δ 9.45 (1H, s), 8.99 (1H, s), 8.14-8.10 (2H, m), 7.90-7.80 (3H, m), 4.54 (1H, m), 4.11 (1H, m), 3.84 (1H, d, J=12.0 Hz), 3.76 (1H, m), 3.71 (1H, m), 3.62 (1H, d, J=13.2 Hz), 2.12 (1H, m), 1.94 (1H, m) ppm.

Example 276

6-((3R,4R)-3-aminotetrahydro-2H-pyran-4-ylamino)-2-(quinolin-6-ylamino)nicotinamide

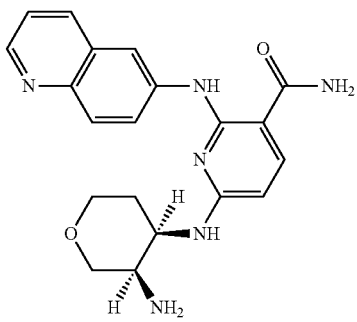

The above example can be synthesized with J86 (scheme 63, example 279) and 6-aminoquinoline by utilizing analogous chemistry described in example 157.

Example 277

Preparation of 6-((3R,4R)-3-aminotetrahydro-2H-pyran-4-ylamino)-5-fluoro-2-(quinolin-6-ylamino)nicotinamide

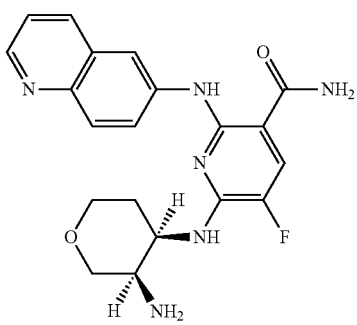

The title compound was synthesized using a procedure similar to that described in Example 279. MS found for C20H21FN6O2 as (M+H)$^+$ 397.3. UV: λ=263, 297, 330 nm. $^1$H NMR: (CD$_3$OD) δ 9.02 (1H, d, J=8.0 Hz), 8.96 (1H, dd, J=5.6; 2.0 Hz), 8.56 (1H, d, J=2.0 Hz), 8.30 (1H, dd, J=8.8; 2.0 Hz), 8.17 (1H, d, J=9.2 Hz), 8.01 (1H, dd, J=8.0; 5.2 Hz), 7.88 (1H, d, J=11.6 Hz), 4.64 (1H, m), 4.14 (1H, m), 3.95 (1H, d, J=13.2 Hz), 3.91 (1H, bs), 3.77 (1H, td, J=9.6; 2.0 Hz), 3.68 (1H, dd, J=12.8; 1.6 Hz), 2.14 (1H, m), 1.97 (1H, m) ppm.

Example 278
6-((3R,4R)-3-aminotetrahydro-2H-pyran-4-ylamino)-2-(quinolin-3-ylamino)nicotinamide
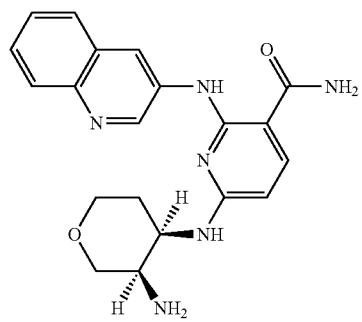
The above example can be synthesized with J86 (scheme 63, example 279) and 3-aminoquinoline by utilizing analogous chemistry described in example 157.
Example 279
Preparation of 2-(3-(2H-1,2,3-triazol-2-yl)phenylamino)-6-((3R,4R)-3-aminotetrahydro-2H-pyran-4-ylamino)-5-fluoronicotinamide
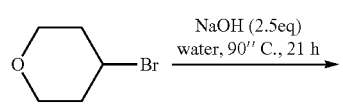
Scheme 63:
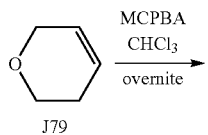
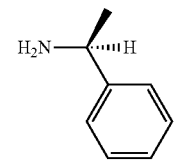
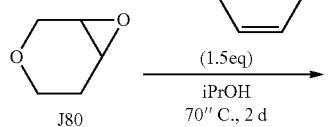
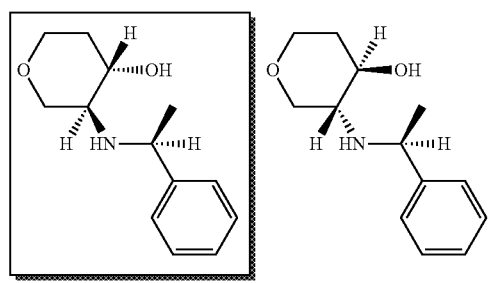
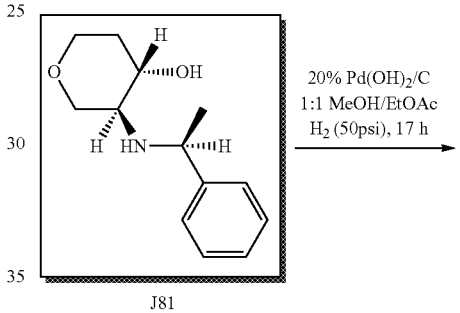
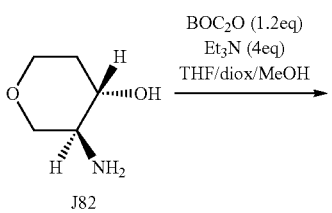
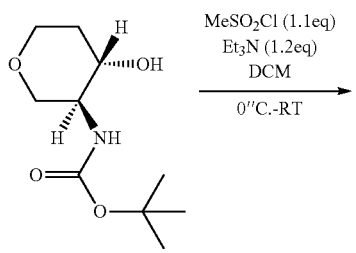
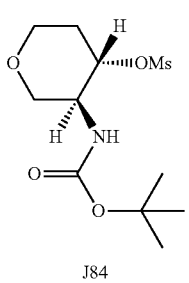

-continued

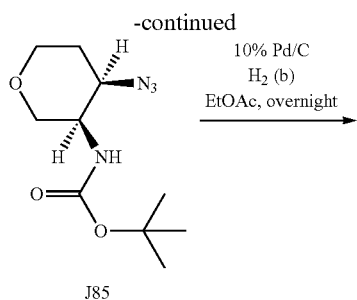
J85

10% Pd/C
H₂ (b)
EtOAc, overnight

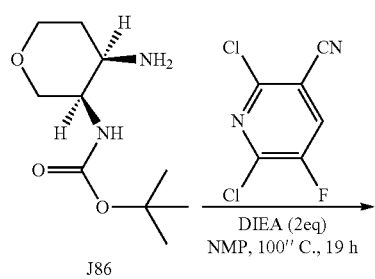
J86

DIEA (2eq)
NMP, 100″ C., 19 h

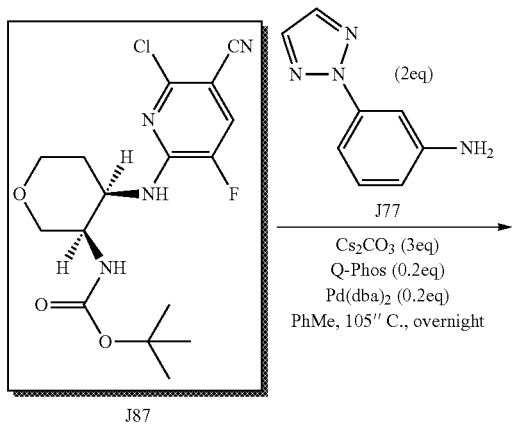
J87

Cs₂CO₃ (3eq)
Q-Phos (0.2eq)
Pd(dba)₂ (0.2eq)
PhMe, 105″ C., overnight

J77

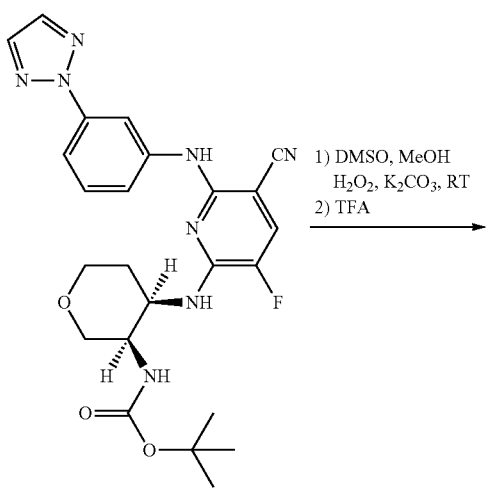

1) DMSO, MeOH
H₂O₂, K₂CO₃, RT
2) TFA

-continued

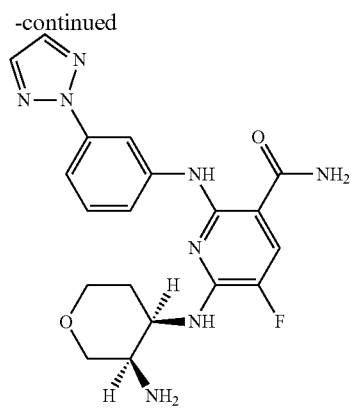

4-Bromotetrahydropyran (Frontier Scientific #B10197, 25.8 g, 156 mmol) was added to the solution of sodium hydroxide (16.0 g, 400 mmol) in 40 mL water. The biphase mixture was stirred in 90° C. with a condenser for 1 day. The mixture was cooled to RT and transferred to a small separatory funnel. The organic phase was carefully separated. It was a mixture of alkene J79 (major) and leftover 4-bromotetrahydropyran. This mixture was dissolved in 100 mL chloroform. To it was added MCPBA (77%, 26.8 g, 120 mmol) in small portions. The mixture was vigorously stirred at RT for overnight. The thick suspension was chilled in ice bath and filtered through celite. The solid cake was washed with ice-chilled chloroform 500 mL×3. All the filtrate and wash solutions were transferred into a big separatory funnel. It was washed with saturated NaHCO₃ solution twice. The organic phase was then dried over anhydrous Na₂SO₃ (30 g). The mixture was filtered and the filtrate was concentrated on a rotary instrument in ice-bath bath (<5° C.) to remove chloroform. A light liquid (J80) with some remaining meta-chlorobenzoic acid solid was obtained. This mixture was dissolved in 100 mL isopropanol. To it was added (S)-(−)-α-methylbenzylamine (15.2 mL, 120 mmol). A gel-like mixture was got initially. The mixture was slowly heated to 70° C. and stirred. A clean solution was then got. The clear solution was stirred for 2 days at 70° C. It was then concentrated in vacuo. The residue was taken into 500 mL EtAOc and washed with saturated Na₂CO₃ solution three times. The organic phase was dried, concentrated and subjected to flash column (0-40% EtOAc in DCM) to isolate desired product J81 (3.52 g) as a cream-colored solid. UV: 259 nm. M+H found for $C_{13}H_{19}NO_2$: 222.2. NMR (DMSO-$d_6$): 7.32-7.25 (4H, m), 7.18 (1H, t), 4.89 (1H, d), 3.86 (1H, m), 3.63 (1H, m), 3.45-3.37 (2H, m, partially obscured by water), 3.19 (1H, m), 2.66 (1H, m), 2.22 (1H, m), 1.92 (1H, m), 1.74 (1H, d), 1.35 (1H, m), 1.22 (3H, d, J=6.4 Hz) ppm.

Compound J81 (3.32 g) was dissolved in 150 mL MeOH and 150 mL EtOAc. To it was added 2.0 g palladium hydroxide (20%, Alfa Aesar #42578). The mixture was treated with 50 psi hydrogen on a Parr shaker for overnight. The mixture was filtered through a celite layer. The solid cake was thoroughly washed with EtOAc and MeOH. The filtrate was concentrated in vacuo to a waxy white solid J82 (2.18 g). It was dissolved in a mixture of 50 mL MeOH, 50 mL dioxane and 100 mL THF. To it were added triethylamine (10.4 mL, 74.5 mmol) and BOC anhydride (4.87 g, 22.3 mmol). The mixture was stirred at RT for overnight. It was concentrated in vacuo and subjected to flash column (0-60% EtOAc in DCM) to isolate compound J83 (2.43 g) as a white solid.

Compound J83 (2.43 g, 11.2 mmol) was dissolved in 60 mL DCM. To it was added triethylamine (1.9 mL, 13.4 mmol). The solution was stirred in ice bath. To it was carefully added dropwise a solution of MsCl (0.97 mL, 12.5 mmol) in 6 mL DCM. The mixture was stirred for 2 h. It was diluted with 300 mL chloroform, washed with water 3×, dried and filtered through a short (0.5-inch) silica plug. The filtrate was concentrated in vacuo to get a white solid J84. This solid was dissolved in 35 mL DMF. To it were added NaN$_3$ (1.44 g, 22 mmol, powder) and NaOAc (1.81 g, 22 mmol, powder). The mixture was stirred at 100° C. for 2 h. It was cooled to RT, diluted with 300 mL EtOAc, washed with water and brine ×2. The organic solution was dried, concentrated and subjected to flash column (0-30% EtOAc in DCM) to isolate compound J85 as a thick oil. It was dissolved in 300 mL EtOAc. To it was added 1.0 g 10% Pd/C. The mixture was stirred at RT under a hydrogen balloon for overnight. The mixture was filtered through celite, and the cake was thoroughly washed with EtOAc. The filtrated was concentrated in vacuo to get a thick oil J86 (1.80 g).

Compound J86 (560 mg, 2.6 mmol) was dissolved in 18 mL NMP. To it were added DIEA (1.4 mL, 7.8 mmol) and 2,6-dichloro-5-fluoronicotinonitrile (500 mg, 2.6 mmol). The mixture was stirred at 80° C. for 4 h. It was diluted with 200 mL EtOAc, washed with brine ×3, dried, concentrated and subjected to flash column to isolate compound J87 (900 mg, 93%). UV=278. M+H found for $C_{16}H_{20}ClFN_4O_3$: 371.2.

A mixture of compound J87 (200 mg, 0.54 mmol), aniline J77 (180 mg, 1.1 mmol), cesium carbonate (fine powder, 530 mg, 1.6 mmol), Q-Phos (Aldrich #675784, 80 mg, 0.11 mmol), Pd(dba)$_2$ (65 mg, 0.11 mmol) in 20 mL toluene was degassed using argon stream and stirred in 105° C. bath under argon atmosphere for overnight. It was concentrated in vacuo, and the residue was taken into 150 mL EtOAc and 50 mL water. The organic phase was separated, dried, concentrated in vacuo, and subjected to flash column to isolate the coupling product (0-30% EtOAc in DCM). This coupling product was dissolved in 10 mL MeOH. To it were added 1 mL DMSO, 100 mg K$_2$CO$_3$ (powder) and 1 mL 50% H$_2$O$_2$. The mixture was stirred for 45 min at RT. It was diluted with 10 mL MeCN and concentrated in vacuo. The residue was then treated with TFA at RT for 1 h. The title compound was isolated from this mixture using reverse phase prep HPLC as HCl salt. UV: 266, 304, 346 nm. M+H found for $C_{19}H_{21}FN_8O_2$: 413.3. NMR (CD$_3$OD): 8.69 (1H, t, J=2.0 Hz), 7.98 (2H, s), 7.80 (1H, d, J=12.0 Hz), 7.70 (1H, dm, J=8.4 Hz), 7.42 (1H, t, J=8.0 Hz), 7.18 (1H, dm, J=8.0 Hz), 4.59 (1H, m), 4.05 (1H, m), 3.90 (1H, m), 3.71-3.47 (3H, m), 2.05 (1H, m), 1.92 (1H, m) ppm.

Example 280

2-(3-(2H-1,2,3-triazol-2-yl)phenylamino)-6-(3R,4R)-3-aminotetrahydro-2H-pyran-4-ylamino)nicotinamide

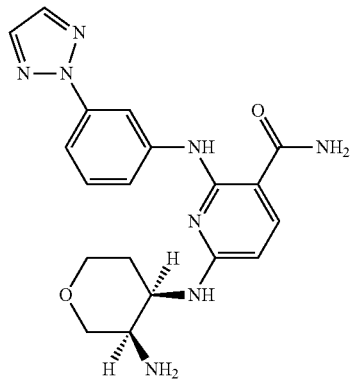 [SMILES: NC(=O)c1ccc(N[C@@H]2CCOC[C@@H]2N)nc1Nc1cccc(-n2nccn2)c1]

The above example can be synthesized with J86 (scheme 63, example 279) and 3-(2H-1,2,3-triazol-2-yl)aniline by utilizing analogous chemistry described in example 157.

Example 281

6-((3R,4R)-3-aminotetrahydro-2H-pyran-4-ylamino)-5-fluoro-2-(3-(pyrimidin-2-yl)phenylamino)nicotinamide

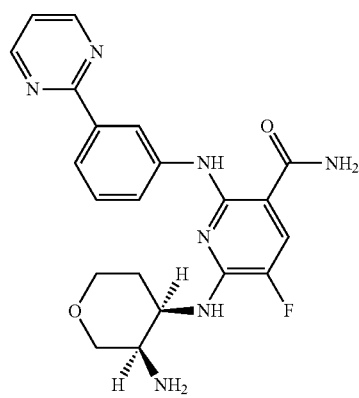

The above example can be synthesized by utilizing J86 and 3-(pyrimidin-2-yl)aniline.

Example 282

6-((3R,4R)-3-aminotetrahydro-2H-pyran-4-ylamino)-2-(3-(pyrimidin-2-yl)phenylamino)nicotinamide

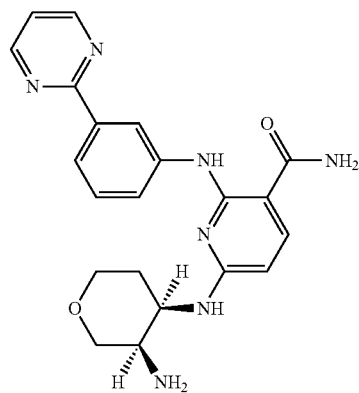 [SMILES: NC(=O)c1ccc(N[C@@H]2CCOC[C@@H]2N)nc1Nc1cccc(-c2ncccn2)c1]

The above example can be synthesized with J86 (scheme 63, example 279) and 3-(pyrimidin-2-yl)aniline by utilizing analogous chemistry described in example 157.

Example 283

Preparation of 2-(3-(1H-pyrazol-1-yephenylamino)-6-(3R,4R)-3-aminotetrahydro-2H-pyran-4-ylamino)-5-fluoronicotinamide

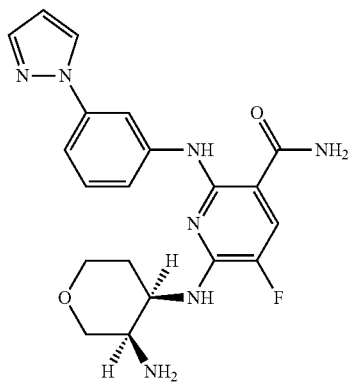 [SMILES: NC(=O)c1cc(F)c(N[C@@H]2CCOC[C@@H]2N)nc1Nc1cccc(-n2cccn2)c1]

The title compound was synthesized using a procedure similar to that described in Example 279. MS found for C20H22FN7O2 as (M+H)+ 412.3. UV: λ=261, 305, 347 nm. ¹H NMR: (CD3OD) δ 8.45 (1H, t, J=2.0 Hz), 8.27 (1H, d, J=2.4 Hz), 7.78 (1H, d, J=12.0 Hz), 7.77 (1H, d, J=2.4 Hz), 7.39 (1H, t, J=8.4 Hz), 7.29 (1H, dm, J=7.6 Hz), 7.14 (1H, dm, J=8.0 Hz), 6.57 (1H, t, J=2.0 Hz), 4.47 (1H, dt, H=11.6; 4.8 Hz), 4.00 (1H, dd, J=12.0; 4.8 Hz), 3.85 (1H, m), 3.63 (1H, d, J=13.2 Hz), 3.52 (1H, td, J=12.0; 2.4 Hz), 3.11 (1H, dd, J=13.2; 1.6 Hz), 2.03 (1H, m), 1.87 (1H, m) ppm.

Example 284

2-(3-(1H-pyrazol-1-yl)phenylamino)-6-((3R,4R)-3-aminotetrahydro-2H-pyran-4-ylamino)nicotinamide

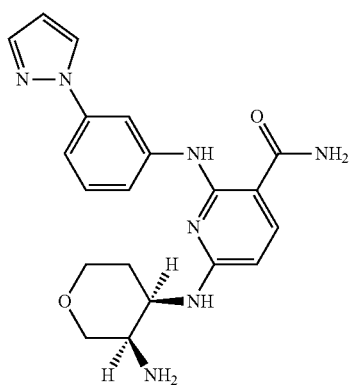 [SMILES: NC(=O)c1ccc(N[C@@H]2CCOC[C@@H]2N)nc1Nc1cccc(-n2cccn2)c1]

The above example can be synthesized with J86 (scheme 63, example 279) and 3-(1H-pyrazol-1-yl)aniline by utilizing analogous chemistry described in example 157.

Example 285

6-((1R,2R)-2-amino-3,3-difluorocyclohexylamino)-5-fluoro-2-(pyridin-3-ylamino)nicotinamide

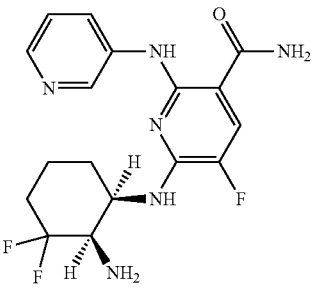 [SMILES: NC(=O)c1cc(F)c(N[C@@H]2CCCC(F)(F)[C@@H]2N)nc1Nc1cccnc1]

The above example can be synthesized by utilizing J69 (scheme 64, example 291) and 3-aminopyridine instead of 6-aminoquinoline as described in example 291.

Example 286

6-((1R,2R)-2-amino-3,3-difluorocyclohexylamino)-2-(pyridin-3-ylamino)nicotinamide

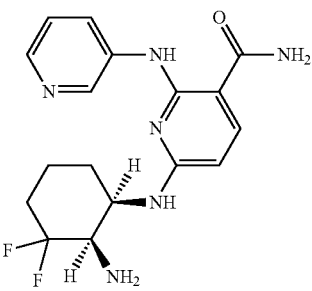 [SMILES: NC(=O)c1ccc(N[C@@H]2CCCC(F)(F)[C@@H]2N)nc1Nc1cccnc1]

The above example can be synthesized with J68 (scheme 64, example 291) and 3-aminopyridine by utilizing analogous chemistry described in example 157. Note that no Boc-deprotection is necessary.

Example 287

6-((1R,2R)-2-amino-3,3-difluorocyclohexylamino)-5-fluoro-2-(5-fluoropyridin-3-ylamino)nicotinamide

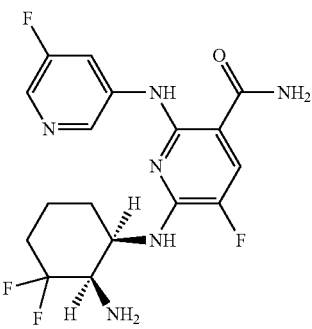 [SMILES: NC(=O)c1cc(F)c(N[C@@H]2CCCC(F)(F)[C@@H]2N)nc1Nc1cncc(F)c1]

The above example can be synthesized by utilizing J69 (scheme 64, example 291) and 3-amino-5-fluoropyridine instead of 6-aminoquinoline as described in example 291.

Example 288

6-((1R,2R)-2-amino-3,3-difluorocyclohexylamino)-2-(5-fluoropyridin-3-ylamino)nicotinamide

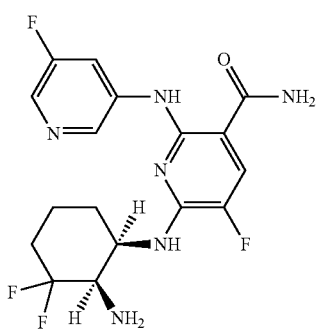 [SMILES: NC(=O)c1cc(F)c(N[C@@H]2CCCC(F)(F)[C@@H]2N)nc1Nc1cncc(F)c1]

The above example can be synthesized with J68 (scheme 64, example 291) and 3-amino-5-fluoropyridine by utilizing analogous chemistry described in example 157. Note that no Boc-deprotection is necessary.

Example 289

Preparation of 6-((1R,2R)-2-amino-3,3-difluorocyclohexylamino)-5-fluoro-2-(quinolin-3-ylamino)nicotinamide

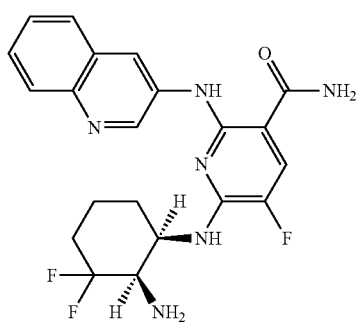 [SMILES: NC(=O)c1cc(F)c(N[C@@H]2CCCC(F)(F)[C@@H]2N)nc1Nc1cnc2ccccc2c1]

The title compound was prepared using the same chemistry shown in Example 291. UV: 297 nm. M+H found for $C_{21}H_{21}F_3N_6O$: 431.4. NMR (CD$_3$OD): 9.27 (1H, d, J=2.0 Hz), 8.85 (1H, s), 8.03 (1H, d, J=8.8 Hz), 8.01 (1H, d, J=8.0 Hz), 7.91 (1H, d, J=11.6 Hz), 7.77 (1H, td, J=8.0; 1.6 Hz), 7.70 (1H, t, J=8.4 Hz), 4.90 (1H, m), 4.16 (1H, m), 2.22-1.84 (6H, m) ppm.

Example 290

6-((1R,2R)-2-amino-3,3-difluorocyclohexylamino)-2-(quinolin-6-ylamino)nicotinamide

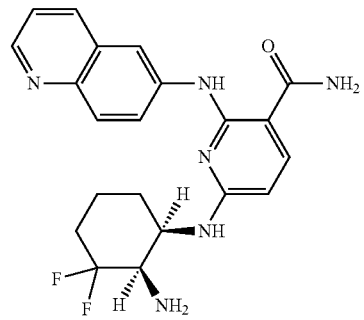 [SMILES: NC(=O)c1ccc(N[C@@H]2CCCC(F)(F)[C@@H]2N)nc1Nc1ccc2ncccc2c1]

The synthesis of the above example is detailed in example 416.

Example 291

Preparation of 6-((1R,2R)-2-amino-3,3-difluorocyclohexylamino)-5-fluoro-2-(quinolin-6-ylamino)nicotinamide

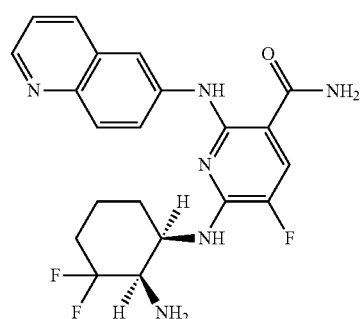

Scheme 64:

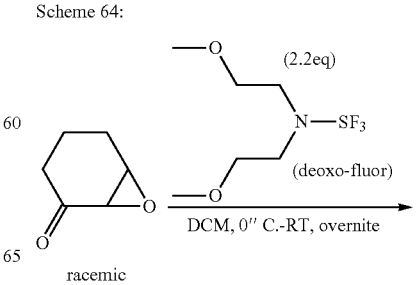

-continued
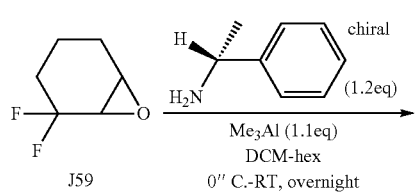
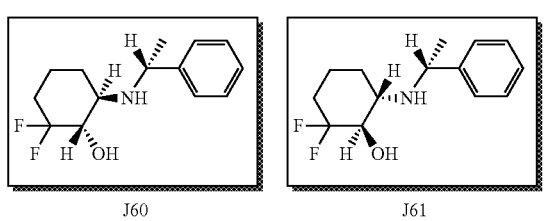
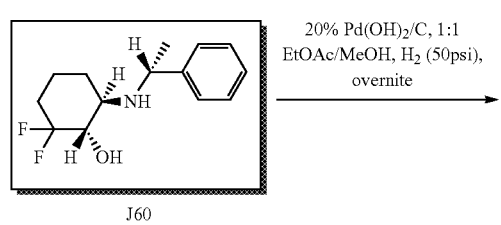
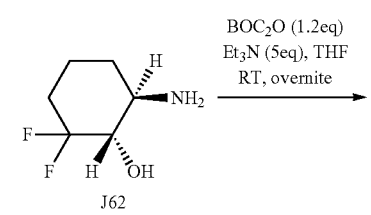
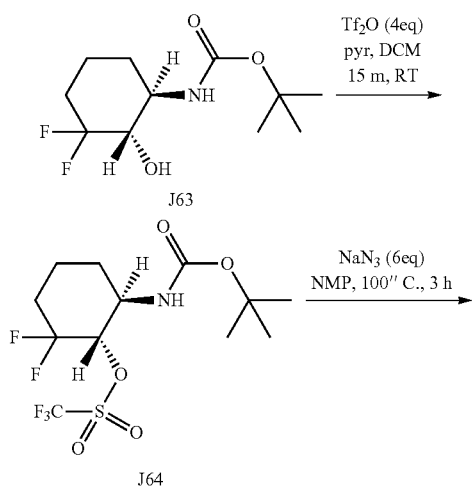
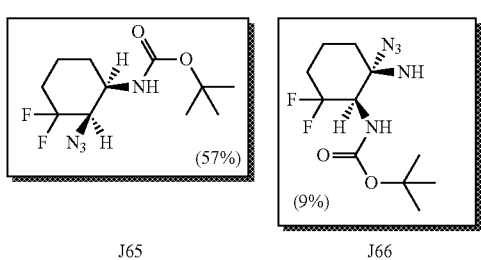
-continued
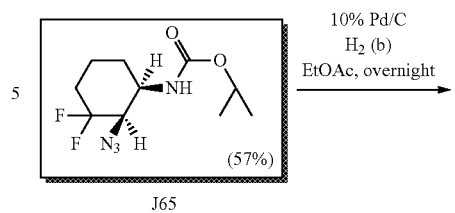
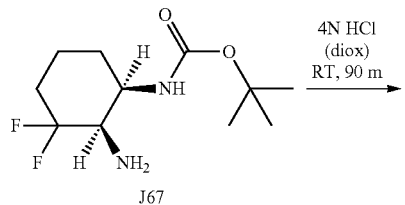
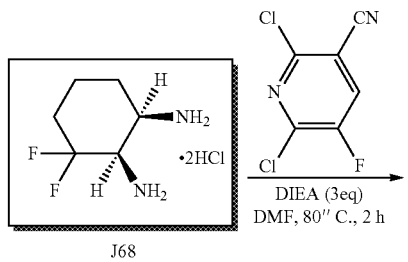
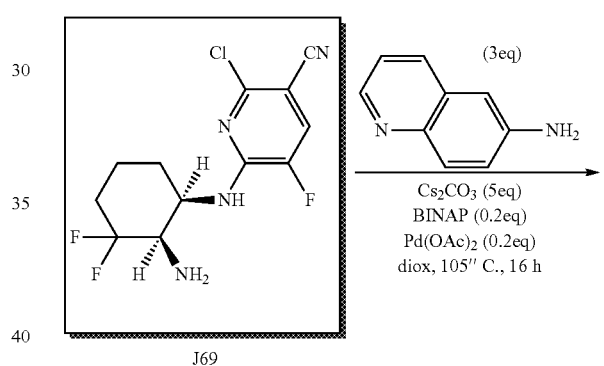
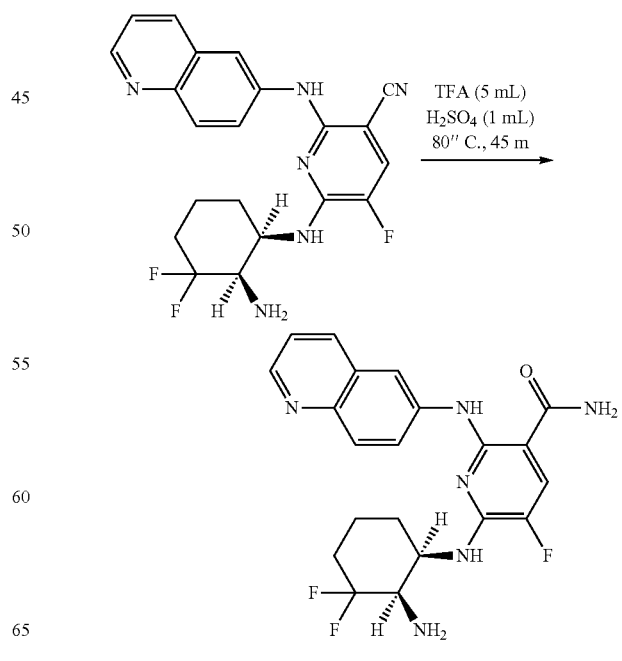

7-Oxabicyclo[4.1.0]heptan-2-one (Aldrich #414522, 8.0 mL, 81 mmol) was dissolved in 40 mL dry DCM and stirred in ice bath. To it was added Deoxo-Fluor (Aldrich #494119, 32.8 mL, 178 mmol) dropwise. The mixture was allowed to warm up to RT and stirred for overnight to give a mixture of compound J59 and some remaining epoxyketone. The mixture was cooled to −20° C. and carefully quenched with 5 mL water dropwise. The mixture was diluted with 600 mL DCM and 200 mL water. The organic phase was separated, dried, filtered through a short (2-inch) silica plug and concentrated in vacuo. The residue was then dissolved in 150 mL DCM.

A solution of (R)-(+)-α-methylbenzylamine (Aldrich #115541, 12.2 mL, 96 mmol) in 50 mL DCM was prepared and stirred in ice bath. To it was added a solution of trimethylaluminum in hexane (Aldrich #268569, 44 mL, 88 mmol). The mixture was stirred for 1 h. To it was then added the 150 mL DCM solution from previous step. The mixture was stirred at RT for over the weekend to give a mixture of J60 and J61 in about 1:1 ratio. The mixture was then cooled in ice bath. Powder NaF (16.8 g, 400 mmol) was added. Then mixture was treated later with ice chips slowly. To it was poured 500 mL DCM. The mixture was stirred for 2 h at RT. It was filtered through celite. The filtrate was concentrated in vacuo and subjected to flash column with 0-2.5% MeOH in DCM to isolate compound J60 (6.67 g) and compound J61 (5.70 g). J60 NMR (CDCl$_3$): 7.39-7.25 (5H, m), 4.00 (1H, q, J=6.8 Hz), 3.53 (1H, ddd), 3.04 (2H, bs), 2.74 (1H, m), 2.11 (1H, m), 1.79 (1H, m), 1.63 (2H, m), 1.44 (3H, d, J=6.4 Hz), 1.40 (1H, m), 1.11 (1H, m) ppm. J61 NMR (CDCl$_3$): 7.36-7.23 (5H, m), 3.95 (1H, q, J=6.4 Hz), 3.48 (1H, ddd), 2.44 (2H, bs), 2.41 (1H, m), 2.09 (2H, m), 1.72-1.55 (2H, m), 1.38 (3H, d, J=6.8 Hz), 1.31 (1H, m), 1.12 (1H, m) ppm.

Compound J60 (6.67 g) was dissolved in 200 mL EtOAc and 200 mL methanol. To the solution was added 20 wt % palladium hydroxide on carbon (Alfa Aesar #212911, 1.65 g). The mixture was shaken on a Parr shaker under 50 psi hydrogen for overnight. The mixture was filtered through celite. The filtrate was concentrated in vacuo to afford compound J62 (4.03 g). It was dissolved in 200 mL THF. To it were added triethylamine (18.1 mL, 130 mmol) and BOC anhydride (6.8 g, 31.2 mmol). The mixture was stirred for overnight, concentrated in vacuo and subjected to flash column (10-20% EtOAc in hexane) to isolate compound J63 (5.34 g).

Compound J63 (1.83 g, 7.3 mmol) was dissolved in 50 mL dry DCM. To it was added 15 mL dry pyridine. The mixture was stirred in ice bath. To it was added Tf$_2$O (4.9 mL, 29 mmol). The reaction was allowed for 15 min and quenched with water. It was further diluted with 100 mL water and 500 mL DCM. The organic phase was separated and washed with water ×3, dried, concentrated in vacuo and pumped to dryness to give crude compound J64. It was dissolved in 30 mL NMP. To it was added sodium azide (2.85 g, 43.8 mmol). The mixture was stirred at 100° C. for 3 h. It was cooled to RT. To it was poured 500 mL EtOAc. The mixture was washed with water ×3, dried, concentrated in vacuo and subjected to flash column (0-20% EtOAc in hexane) to isolate the major product J65 (1.15 g, 57%) and the minor product J66 (0.18 g, 9%). J65 NMR (CDCl$_3$): 4.77 (1H, d, J=6.8 Hz), 3.97 (1H, bs), 3.87 (1H, bm), 1.97-1.86 (2H, m), 1.72-1.63 (2H, m), 1.45 (9H, s), 1.36 (2H, m) ppm. J66 NMR (CDCl$_3$): 4.81 (1H, d, J=8.8 Hz), 3.91 (1H, m), 3.28 (1H, m), 2.21 (1H, m), 2.11 (1H, m), 1.86-1.79 (2H, m), 1.78-1.64 (2H, m), 1.48 (9H, s), 1.43-1.39 (2H, m) ppm.

Compound J65 (1.15 g, 4.16 mmol) was dissolved in 250 mL EtOAc. To it was added 2.0 g of 10% Pd/C. A hydrogen balloon was attached to the reaction flask. The mixture was stirred for overnight. It was filtered through celite. The celite cake was washed thoroughly with EtOAc and methanol. The filtrate was concentrated in vacuo and pumped to dryness to afford a white solid J67. It was then treated with 40 mL 4N HCl in dioxane at RT for 1.5 h to get a thick gel. It was concentrated and pumped overnight to afford compound J68 as a light brown solid.

The mixture of J68 (700 mg, 3.1 mmol), 2,6-dichloro-5-fluoronicotinonitrile (600 mg, 3.1 mmol) and DIEA (1.62 mL, 9.3 mmol) in 20 mL DMF was stirred at 80° C. for 2 h. The mixture was concentrated in vacuo and subjected to flash column (0-10% MeOH in DCM) to isolate compound J69 (885 mg, 93%).

A mixture of compound J69 (80 mg, 0.26 mmol), 6-aminoquinoline (112 mg, 0.78 mmol), cesium carbonate (fine powder, 425 mg, 1.30 mmol), BINAP (33 mg, 0.05 mmol), Pd(OAc)$_2$ (12 mg, 0.05 mmol) in 15 mL dioxane was degassed using argon stream and stirred in 105° C. bath under argon atmosphere for overnight. It was concentrated in vacuo, and the residue was taken into 300 mL EtOAc and 100 mL water. The organic phase was separated, dried, concentrated in vacuo. It was treated with 5 mL TFA and 1 mL conc. H$_2$SO$_4$ at 80° C. for 45 min. The mixture was cooled and to it was added 5 mL water. The mixture was filtered and subjected to reverse phase prep HPLC to isolate the title compound as HCl salt (69 mg). UV: 263, 297 nm. M+H found for C$_{21}$H$_{21}$F$_3$N$_6$O: 431.4. NMR (CD$_3$OD): 8.86 (1H, dd, J=5.2; 1.2 Hz), 8.77 (1H, d, J=7.6 Hz), 8.55 (1H, s), 8.15 (1H, dd, J=9.2; 2.0 Hz), 8.08 (1H, d, J=9.2 Hz), 7.90 (1H, d, J=11.6 Hz), 7.82 (1H, m), 4.91 (1H, m), 4.25 (1H, m), 2.16-1.87 (6H, m) ppm.

Example 292

6-((1R,2R)-2-amino-3,3-difluorocyclohexylamino)-2-(quinolin-6-ylamino)nicotinamide

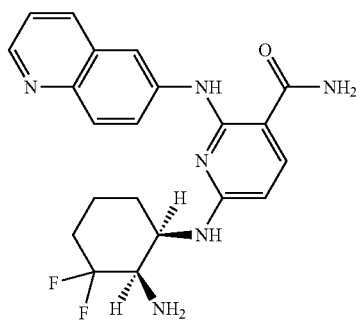 [SMILES: NC(=O)c1ccc(N[C@@H]2CCCC(F)(F)[C@@H]2N)nc1Nc1ccc2ncccc2c1]

Example 293

Preparation of 2-(3-(2H-1,2,3-triazol-2-yl)phenylamino)-6-(1R,2R)-2-amino-3,3-difluorocyclohexylamino)-5-fluoronicotinamide

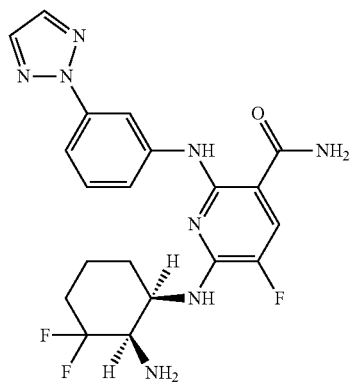 [SMILES: NC(=O)c1cc(F)c(N[C@@H]2CCCC(F)(F)[C@@H]2N)nc1Nc1cccc(-n2nccn2)c1]

The title compound was prepared using the same chemistry shown in Example 291. UV: 263, 301 nm. M+H found for $C_{20}H_{21}F_3N_8O$: 447.4. NMR (CD$_3$OD): 8.85 (1H, s), 7.97 (2H, s), 7.84 (1H, d, J=12.0 Hz), 7.67 (1H, dm, J=8.0 Hz), 7.41 (1H, t, J=8.4 Hz), 7.25 (1H, dm, J=8.0 Hz), 5.20 (1H, m), 4.10 (1H, m), 2.27-1.80 (6H, m) ppm.

Example 294

2-(3-(2H-1,2,3-triazol-2-yl)phenylamino)-6-((1R,2R)-2-amino-3,3-difluorocyclohexylamino)nicotinamide

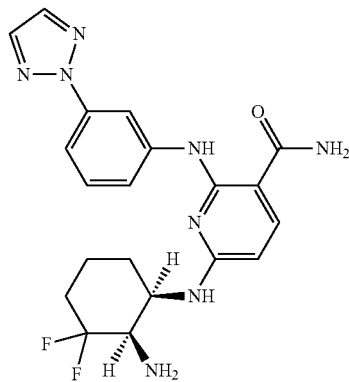 [SMILES: NC(=O)c1ccc(N[C@@H]2CCCC(F)(F)[C@@H]2N)nc1Nc1cccc(-n2nccn2)c1]

The above example can be synthesized with J68 (scheme 64, example 291) and 3-(2H-1,2,3-triazol-2-yl)aniline by utilizing analogous chemistry described in example 157. Note that no Boc-deprotection is necessary.

Example 295

6-((1R,2R)-2-amino-3,3-difluorocyclohexylamino)-5-fluoro-2-(3-(pyrimidin-2-yl)phenylamino)nicotinamide

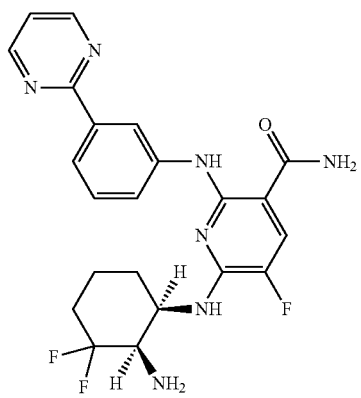 [SMILES: NC(=O)c1cc(F)c(N[C@@H]2CCCC(F)(F)[C@@H]2N)nc1Nc1cccc(-c2ncccn2)c1]

The above example can be synthesized by utilizing J69 (scheme 64, example 291) and 3-(pyrimidin-2-yl)aniline instead of 6-aminoquinoline as described in example 291.

Example 296

6-((1R,2R)-2-amino-3,3-difluorocyclohexylamino)-2-(3-(pyrimidin-2-yl)phenylamino)nicotinamide

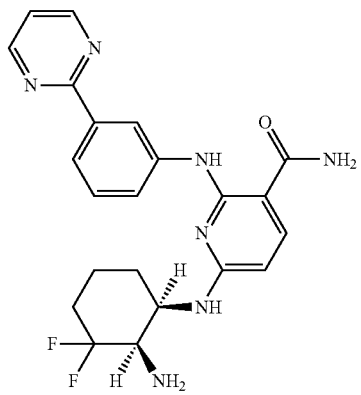 [SMILES: NC(=O)c1ccc(N[C@@H]2CCCC(F)(F)[C@@H]2N)nc1Nc1cccc(-c2ncccn2)c1]

The above example can be synthesized with J68 (scheme 64, example 291) and 3-(pyrimidin-2-yl)aniline by utilizing analogous chemistry described in example 157. Note that no Boc-deprotection is necessary.

Example 297

2-(3-(1H-pyrazol-1-yl)phenylamino)-6-((1R,2R)-2-amino-3,3-difluorocyclohexylamino)-5-fluoronicotinamide

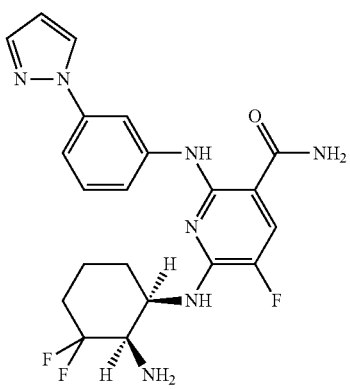 [SMILES: NC(=O)c1cc(F)c(N[C@@H]2CCCC(F)(F)[C@@H]2N)nc1Nc1cccc(-n2cccn2)c1]

The above example can be synthesized by utilizing J69 (scheme 64, example 291) and 3-(1H-pyrazol-1-yl)aniline instead of 6-aminoquinoline as described in example 291.

Example 298

2-(3-(1H-pyrazol-1-yl)phenylamino)-6-((1R,2R)-2-amino-3,3-difluorocyclohexylamino)nicotinamide

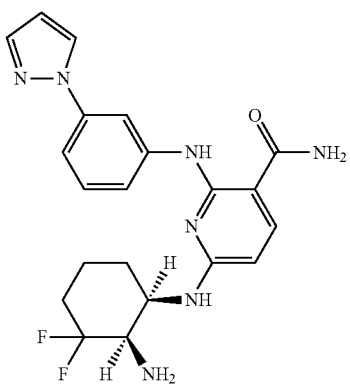 [SMILES: NC(=O)c1ccc(N[C@@H]2CCCC(F)(F)[C@@H]2N)nc1Nc1cccc(-n2cccn2)c1]

The above example can be synthesized with J68 (scheme 64, example 291) and 3-(1H-pyrazol-1-yl)aniline by utilizing analogous chemistry described in example 157. Note that no Boc-deprotection is necessary.

Example 299

Preparation of (R)-6-(1-amino-1-oxopropan-2-ylamino)-5-fluoro-2-(quinolin-3-ylamino)nicotinamide

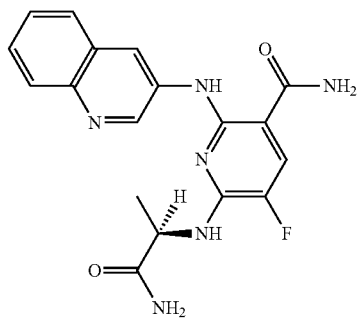 [SMILES: C[C@@H](Nc1nc(Nc2cnc3ccccc3c2)c(C(N)=O)cc1F)C(N)=O]

The title compound was synthesized analogously according to the procedures described for the preparation of Example 97. However, 3-aminoquinoline was utilized instead of 7-aminoquinoline, and (R)-2-aminopropanamide hydrochloride salt (commercially available) was used instead of (R)-(−)-2-aminobutanamide hydrochloride (J16). UV: 224, 243, 296, 326 nm. M+H found for $C_{18}H_{17}FN_6O_2$: 369.4. (CD$_3$OD): 9.53 (1H, d, J=2.4 Hz), 9.14 (1H, d, J=2.4 Hz), 8.29 (1H, d, J=8.0 Hz), 8.07 (1H, d, J=8.4 Hz), 7.89 (1H, dt, J=1.2, 7.2 Hz), 7.84-7.79 (2H, m), 4.44 (1H, q, J=7.2 Hz), 1.60 (3H, d, J=7.2 Hz) ppm.

Example 300

Preparation of (R)-6-(1-amino-3-methyl-1-oxobutan-2-ylamino)-5-fluoro-2-(quinolin-3-ylamino)nicotinamide

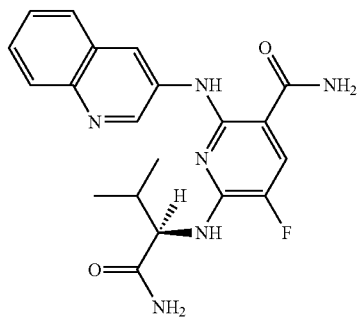 [SMILES: CC(C)[C@@H](Nc1nc(Nc2cnc3ccccc3c2)c(C(N)=O)cc1F)C(N)=O]

The title compound was synthesized analogously according to the procedures described for the preparation of Example 97. However, 3-aminoquinoline was utilized instead of 7-aminoquinoline, and (R)-(−)-2-amino-3-methylbutanamide hydrochloride salt (commercially available) was used instead of (R)-(−)-2-aminobutanamide hydrochloride (J16). UV: 224, 243, 297, 326 nm. M+H found for $C_{20}H_{21}FN_6O_2$: 397.5. NMR (CD$_3$OD): 9.67 (1H, d, J=2.4 Hz), 9.19 (1H, d, J=2.4 Hz), 8.33 (1H, d, J=8.4 Hz), 8.10 (1H, d, J=8.4 Hz), 7.94-7.81 (3H, m), 4.23 (1H, d, J=7.2 Hz), 2.26 (1H, dt, J=6.8, 7.2 Hz), 1.13 (6H, d, J=6.8 Hz) ppm.

Example 301

(R)-6-(1-amino-4,4,4-trifluoro-1-oxobutan-2-ylamino)-5-fluoro-2-(quinolin-3-ylamino)nicotinamide

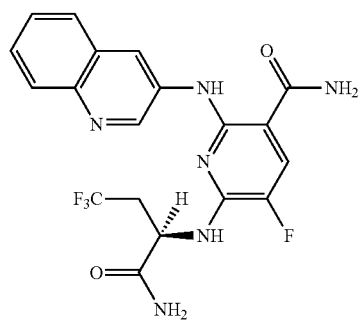 [SMILES: NC(=O)c1cc(F)c(N[C@H](CC(F)(F)F)C(N)=O)nc1Nc1cnc2ccccc2c1]

The title compound can be synthesized analogously according to the procedures described for the preparation of Example 97. However, 3-aminoquinoline can be utilized instead of 7-aminoquinoline, and (R)-2-amino-4,4,4-trifluorobutanamide (see example 219, scheme 55) can be used instead of (R)-(−)-2-aminobutanamide hydrochloride.

Example 302

Preparation of (R)-6-(1-amino-1-oxopropan-2-ylamino)-5-fluoro-2-(quinolin-6-ylamino)nicotinamide

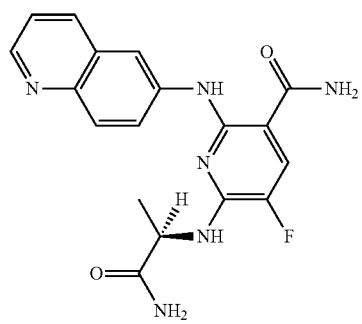 [SMILES: C[C@@H](Nc1nc(Nc2ccc3ncccc3c2)c(C(N)=O)cc1F)C(N)=O]

The title compound was synthesized analogously according to the procedures described for the preparation of Example 97. However, 6-aminoquinoline was utilized instead of 7-aminoquinoline, and (R)-2-aminopropanamide hydrochloride salt (commercially available) was used instead of (R)-(−)-2-aminobutanamide hydrochloride (J16). UV: 265, 297, 328 nm. M+H found for $C_{18}H_{17}FN_6O_2$: 369.3. (CD$_3$OD): 9.27 (1H, d, J=8.4 Hz), 8.95 (1H, d, J=2.4 Hz), 8.86 (1H, dd, J=1.6, 5.6 Hz), 8.06 (1H, d, J=9.2 Hz), 7.99-7.90 (2H, m), 7.84 (1H, d, J=11.6 Hz), 4.53 (1H, q, J=7.2 Hz), 1.63 (3H, d, J=7.2 Hz) ppm.

Example 303

(R)-6-(1-amino-3-methyl-1-oxobutan-2-ylamino)-5-fluoro-2-(quinolin-6-ylamino)nicotinamide

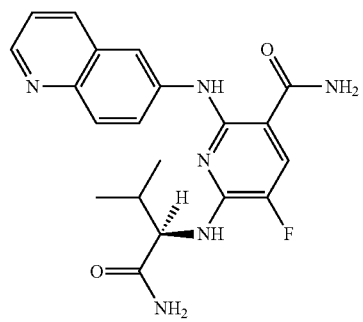 [SMILES: CC(C)[C@@H](Nc1nc(Nc2ccc3ncccc3c2)c(C(N)=O)cc1F)C(N)=O]

The title compound can be synthesized analogously according to the procedures described for the preparation of Example 97. However, 6-aminoquinoline can be utilized instead of 7-aminoquinoline, and D-valinamide hydrochloride salt can be used instead of (R)-(−)-2-aminobutanamide hydrochloride (J16).

Example 304

(R)-6-(1-amino-4,4,4-trifluoro-1-oxobutan-2-ylamino)-5-fluoro-2-(quinolin-6-ylamino)nicotinamide

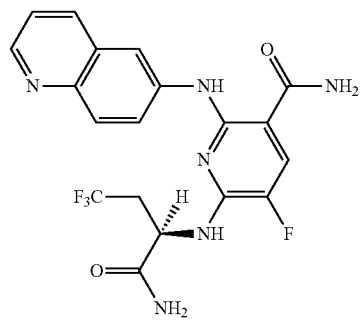 [SMILES: NC(=O)c1cc(F)c(N[C@H](CC(F)(F)F)C(N)=O)nc1Nc1ccc2ncccc2c1]

The title compound can be synthesized analogously according to the procedures described for the preparation of Example 97. However, 6-aminoquinoline can be utilized instead of 7-aminoquinoline, and (R)-2-amino-4,4,4-trifluorobutanamide (see example 219, scheme 55) can be used instead of (R)-(−)-2-aminobutanamide hydrochloride.

Example 305

(R)-6-(1-amino-1-oxopropan-2-ylamino)-5-fluoro-2-(quinolin-7-ylamino)nicotinamide

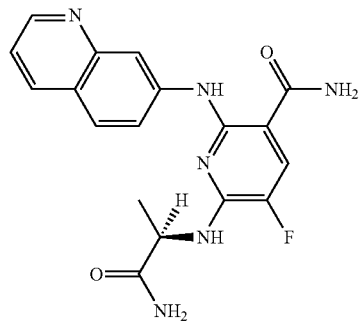 [SMILES: C[C@@H](Nc1nc(Nc2ccc3cccnc3c2)c(C(N)=O)cc1F)C(N)=O]

The title compound can be synthesized analogously according to the procedures described for the preparation of Example 97. However, D-alaninamide (commercially available) can be used instead of (R)-(−)-2-aminobutanamide hydrochloride.

Example 306

(R)-6-(1-amino-3-methyl-1-oxobutan-2-ylamino)-5-fluoro-2-(quinolin-7-ylamino)nicotinamide

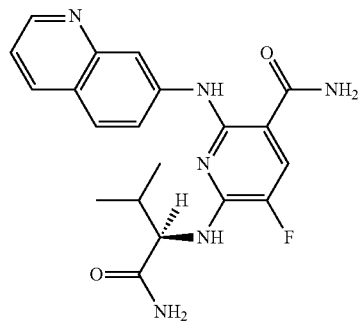 [SMILES: CC(C)[C@@H](Nc1nc(Nc2ccc3cccnc3c2)c(C(N)=O)cc1F)C(N)=O]

The title compound can be synthesized analogously according to the procedures described for the preparation of Example 97. However, D-valinamide hydrochloride salt can be used instead of (R)-(−)-2-aminobutanamide hydrochloride (J16).

Example 307

(R)-6-(1-amino-4,4,4-trifluoro-1-oxobutan-2-ylamino)-5-fluoro-2-(quinolin-7-ylamino)nicotinamide

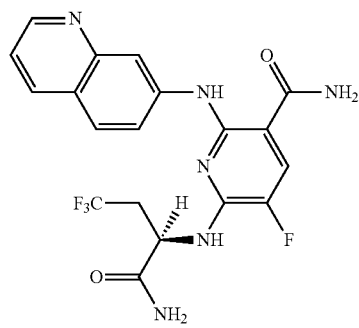 [SMILES: NC(=O)c1cc(F)c(N[C@H](CC(F)(F)F)C(N)=O)nc1Nc1ccc2cccnc2c1]

The title compound can be synthesized analogously according to the procedures described for the preparation of Example 97. However, (R)-2-amino-4,4,4-trifluorobutanamide (see example 219, scheme 55) can be used instead of (R)-(−)-2-aminobutanamide hydrochloride.

Example 308

Preparation of (R)-4-(4-(6-(1-amino-1-oxobutan-2-ylamino)-3-carbamoyl-5-fluoropyridin-2-ylamino)phenyl)-1-methylpiperidine 1-oxide

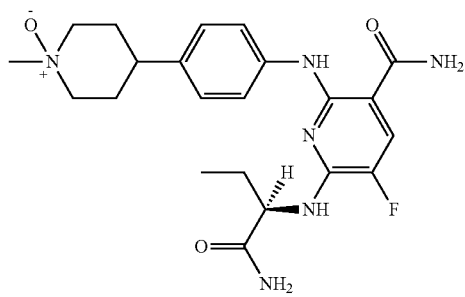

Scheme 65:

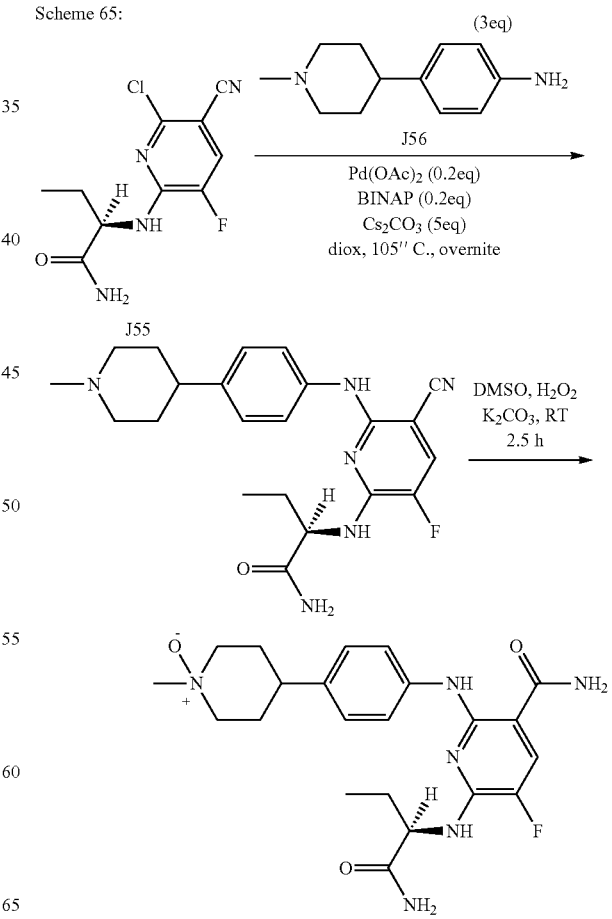

The mixture of compound J55 (100 mg, 0.4 mmol), aniline J56 (228 mg, 1.2 mmol), cesium carbonate (650 mg, 2.0 mmol), BINAP (50 mg, 0.08 mmol) and Pd(OAc)$_2$ (18 mg, 0.08 mmol) in 20 mL dioxane was degassed with Ar. The mixture was stirred under Ar at 105° C. for overnight. It was concentrated in vacuo, taken into EtOAc, washed with brine, dried, and concentrated in vacuo to dryness. This residue was then dissolved in 4 mL DMSO. To it were added 100 mg powder K$_2$CO$_3$ and 2 mL 30% H$_2$O$_2$ in water. The mixture was stirred at RT for 2.5 h. To it was added 4 mL water, the mixture was vigorously stirred and subjected to reverse phase preparative HPLC to isolate the title compound (70 mg, 41% overall yield from J55). UV: 306 nm. M+H found for C$_{22}$H$_{29}$FN$_6$O$_3$: 445.4. NMR (CD$_3$OD): 7.71 (1H, d, J=12.4 Hz), 7.59 (2H, d, J=8.8 Hz), 7.21 (2H, d, J=8.8 Hz), 4.43 (1H, dd, J=8.8; 5.6 Hz), 3.84-3.75 (4H, m), 3.56 (3H, s), 2.86 (1H, m), 2.33 (2H, m), 2.06-2.00 (4H, m), 1.86 (1H, m), 1.06 (3H, t, J=7.2 Hz) ppm.

Example 309

Preparation of 6-((1R,2S)-2-aminocyclohexylamino)-5-fluoro-2-(4-(1-methylpiperidin-4-yl)phenylamino)nicotinamide

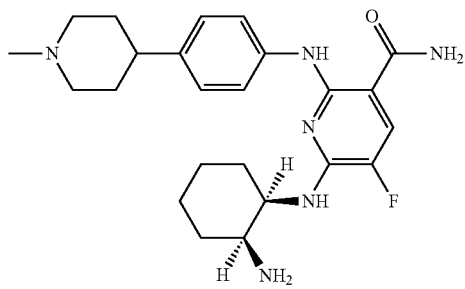 [SMILES: CN1CCC(c2ccc(Nc3nc(N[C@@H]4CCCC[C@@H]4N)c(F)cc3C(N)=O)cc2)CC1]

Scheme 66:

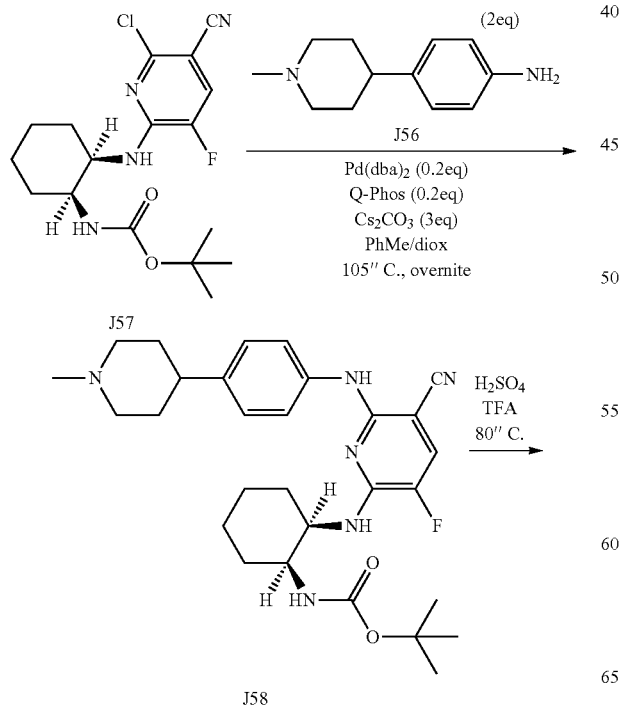

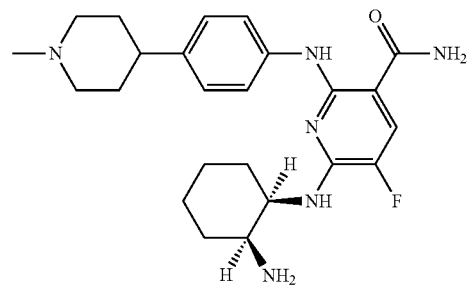

The mixture of compound J57 (100 mg, 0.27 mmol), aniline J56 (103 mg, 0.54 mmol), cesium carbonate (264 mg, 0.81 mmol), Q-Phos (Aldrich #675784, 43 mg, 0.06 mmol) and Pd(dba)$_2$ (35 mg, 0.06 mmol) in 15 mL toluene and 8 mL dioxane was degassed with Argon. The mixture was stirred under Ar at 105° C. for overnight. It was concentrated in vacuo, taken into EtOAc, washed with brine, dried, concentrated in vacuo and subjected to flash column to isolate compound J58 (0 to 10% MeOH in DCM). This compound was then treated in 6 mL TFA and 1 mL conc. H$_2$SO$_4$ at 80° C. for 2 h. The mixture was cooled to RT. It was diluted with 5 mL water. The mixture was stirred, filtered and subjected to reverse phase prep HPLC to isolate the title compound as HCl salt. UV: 301 nm. M+H found for C$_{24}$H$_{33}$FN$_6$O: 441.4. NMR (CD$_3$OD): 7.74 (1H, d, J=12.0 Hz), 7.53 (2H, d, J=8.8 Hz), 7.22 (2H, d, J=8.4 Hz), 4.34 (1H, m), 3.89 (1H, m), 3.61 (2H, m), 3.30 (3H, s), 3.15 (1H, m), 2.11 (2H, m), 1.99 (2H, m), 1.88-1.61 (8H, m) ppm.

Example 310

Preparation of 6-(1R,2S)-2-aminocyclohexylamino)-2-(benzo[d]thiazol-5-ylamino)-5-fluoronicotinamide

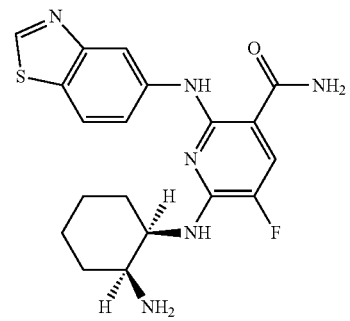

The title compound was prepared using the same chemistry shown in Example 309. UV: 306 nm. M+H found for C$_{19}$H$_{21}$FN$_6$OS: 401.3. NMR (CD$_3$OD): 9.27 (1H, m), 8.68 (1H, d, J=2.0 Hz), 7.96 (1H, d, J=8.4 Hz), 7.80 (1H, d, J=12.4 Hz), 7.40 (1H, dd, J=8.8; 1.6 Hz), 4.49 (1H, m), 3.90 (1H, m), 1.88-1.60 (8H, m) ppm.

Example 311

Preparation of 6-((1R,2S)-2-aminocyclohexylamino)-2-(benzo[d]thiazol-7-ylamino)-5-fluoronicotinamide

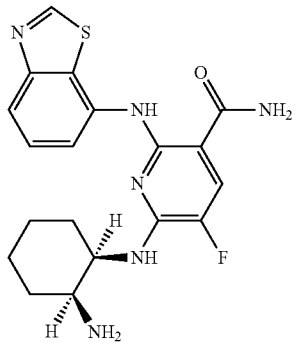 [SMILES: NC(=O)c1cc(F)c(N[C@@H]2CCCC[C@@H]2N)nc1Nc1cccc2ncsc12]

The title compound was prepared using the same chemistry shown in Example 309. UV: 244, 268, 306, 334 nm. M+H found for $C_{19}H_{21}FN_6OS$: 401.3. NMR ($CD_3OD$): 9.25 (1H, s), 7.99 (1H, d, J=8.0 Hz), 7.82 (1H, d, J=8.0 Hz), 7.81 (1H, d, 5=11.6 Hz), 757 (1H, t, J=8.0 Hz), 4.12 (1H, m), 3.63 (1H, m), 1.77 (5H, m), 1.52 (3H, m) ppm.

Example 312

Preparation of 6-((1R,2S)-2-aminocyclohexylamino)-5-fluoro-2-(phenylamino)nicotinamide

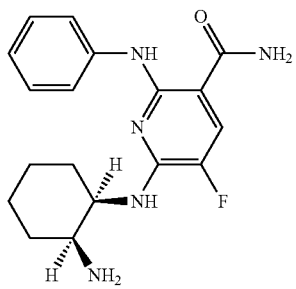 [SMILES: NC(=O)c1cc(F)c(N[C@@H]2CCCC[C@@H]2N)nc1Nc1ccccc1]

Scheme 67:

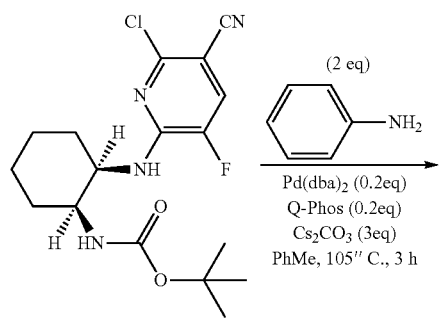

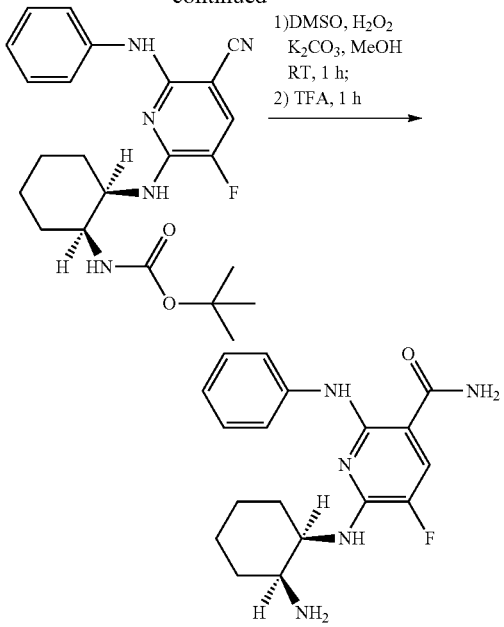

The mixture of compound J57 (100 mg, 0.27 mmol), aniline (50 mg, 0.54 mmol), cesium carbonate (270 mg, 0.81 mmol), Q-Phos (Aldrich #675784, 43 mg, 0.06 mmol) and Pd(dba)$_2$ (35 mg, 0.06 mmol) in 10 mL toluene was degassed with Ar. The mixture was stirred under Ar at 105° C. for 3 h. The reaction mixture was cooled to RT, diluted with 100 mL EtOAc, and rigorously stirred. The slurry was filtered through a short (0.5-inch thick) silica plug. The filtrate was concentrated in vacuo to dryness. This residue was dissolved in 10 mL methanol. To it were added 1 mL DMSO, 100 mg powder $K_2CO_3$ and then 1 mL 50 wt % $H_2O_2$. The mixture was stirred at RT for 1 h, diluted with 30 mL acetonitrile and concentrated in vacuo to dryness. The residue was treated with neat TFA (10 mL) at RT for 1 h. The mixture was concentrated in vacuo and subjected to reverse phase prep HPLC to isolate the title compound. UV: 302, 349 nm. M+H found for $C_{18}H_{22}FN_5O$: 344.4. NMR ($CD_3OD$): 7.73 (1H, d, J=12.0 Hz), 7.52 (2H, d, J=8.0 Hz), 7.30 (2H, t, J=7.2 Hz), 7.00 (1H, t, J=7.6 Hz), 4.33 (1H, m), 3.87 (1H, m), 1.84 (5H, m), 1.61 (3H, m) ppm.

Example 313

Preparation of 6-((1R,2S)-2-aminocyclohexylamino)-5-fluoro-2-(o-tolylamino)nicotinamide

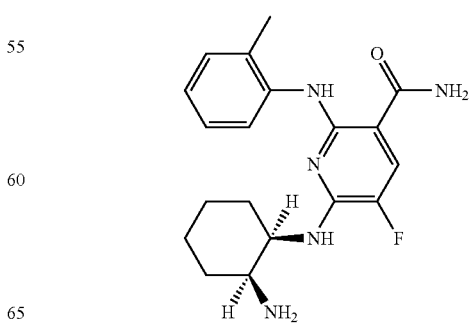

The title compound was prepared using the same chemistry shown in Example 312. UV: 304, 349 nm. M+H found for C₁₉H₂₄FN₅O: 358.4. NMR (CD₃OD): 7.86 (1H, d, J=8.4 Hz), 7.75 (1H, d, J=12.0 Hz), 7.23-7.17 (2H, m), 6.99 (1H, dt, J=7.6; 1.2 Hz), 4.15 (1H, m), 3.72 (1H, m), 2.28 (3H, s), 1.81-1.55 (8H, m) ppm.

Example 314

Preparation of 6-((1R,2S)-2-aminocyclohexy-lamino)-5-fluoro-2-(m-tolylamino)nicotinamide

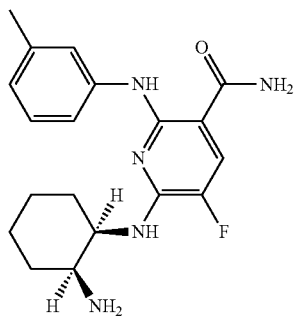 [SMILES: Cc1cccc(Nc2nc(N[C@@H]3CCCC[C@@H]3N)c(F)cc2C(N)=O)c1]

The title compound was prepared using the same chemistry shown in Example 312. UV: 303, 350 nm. M+H found for C₁₉H₂₄FN₅O: 358.4. NMR (CD₃OD): 7.73 (1H, d, J=12.0 Hz), 7.38 (1H, d, J=8.4 Hz), 7.29 (1H, s), 7.18 (1H, t, J=8.4 Hz), 6.83 (1H, d, J=8.0 Hz), 4.36 (1H, m), 3.82 (1H, m), 1.85-1.59 (8H, m) ppm.

Example 315

Preparation of 6-((1R,2S)-2-aminocyclohexy-lamino)-5-fluoro-2-(p-tolylamino)nicotinamide

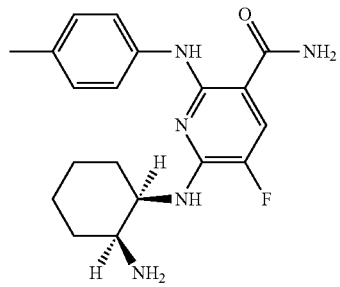 [SMILES: Cc1ccc(Nc2nc(N[C@@H]3CCCC[C@@H]3N)c(F)cc2C(N)=O)cc1]

The title compound was prepared using the same chemistry shown in Example 312. UV: 301, 351 nm. M+H found for C₁₉H₂₄FN₅O: 358.4. NMR (CD₃OD): 7.72 (1H, d, J=11.6 Hz), 7.39 (2H, d, J=8.4 Hz), 7.12 (2H, d, J=8.0 Hz), 4.29 (1H, m), 3.84 (1H, m), 1.83 (5H, m), 1.60 (3H, m) ppm.

Example 316

Preparation of 6-((1R,2S)-2-aminocyclohexy-lamino)-5-fluoro-2-(3-fluorophenylamino)nicotina-mide

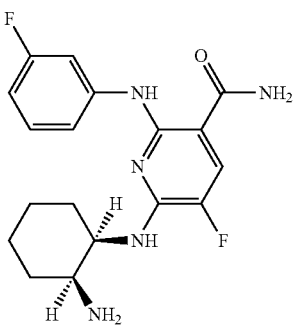

The title compound was prepared using the same chemistry shown in Example 312. UV: 268, 305, 346 nm. M+H found for C₁₈H₂₁F₂N₅O: 362.4. NMR (CD₃OD): 7.77 (1H, d, J=12.0 Hz), 7.73 (1H, dt, J=9.6; 2.4 Hz), 7.26 (1H, q, J=8.4 Hz), 7.07 (1H, dm, J=8.4 Hz), 6.69 (1H, tm, J=7.6 Hz), 4.37 (1H, m), 3.93 (1H, m), 1.93-1.83 (5H, m), 1.61 (3H, m) ppm.

Example 317

Preparation of 6-((1R,2S)-2-aminocyclohexy-lamino)-2-(3-chlorophenylamino)-5-fluoronicotina-mide

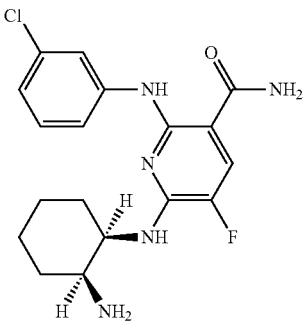 [SMILES: NC(=O)c1cc(F)c(N[C@@H]2CCCC[C@@H]2N)nc1Nc1cccc(Cl)c1]

The title compound was prepared using the same chemistry shown in Example 312. UV: 268, 305, 346 nm. M+H found for C₁₈H₂₁ClFN₅O: 378.3. NMR (CD₃OD): 7.88 (1H, d, J=2.4 Hz), 7.67 (1H, dd, J=12.0; 2.8 Hz), 7.18-7.10 (2H, m), 6.87 (1H, d, J=8.0 Hz), 6.43 (1H, d, J=4.8 Hz), 4.32 (1H, m), 3.77 (1H, m), 1.82-1.78 (5H, m), 1.53 (3H, m) ppm.

Example 318

Preparation of 6-((1R,2S)-2-aminocyclohexylamino)-2-(4-chlorophenylamino)-5-fluoronicotinamide

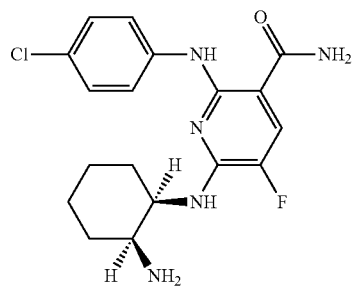 [SMILES: NC(=O)c1cc(F)c(N[C@@H]2CCCC[C@@H]2N)nc1Nc1ccc(Cl)cc1]

The title compound was prepared using the same chemistry shown in Example 312. UV: 306, 347 nm. M+H found for C$_{18}$H$_{21}$ClFN$_5$O: 378.3. NMR (CD$_3$OD): 7.75 (1H, d, J=12.0 Hz), 7.54 (2H, d, J=8.4 Hz), 7.28 (2H, d, J=8.4 Hz), 4.33 (1H, m), 3.87 (1H, m), 1.89-1.81 (5H, m), 1.62 (3H, m) ppm.

Example 319

Preparation of 6-((1R,2S)-2-aminocyclohexylamino)-2-(2,3-dimethylphenylamino)-5-fluoronicotinamide

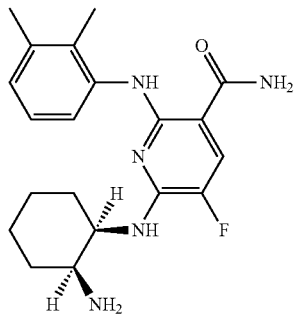 [SMILES: Cc1cccc(Nc2nc(N[C@@H]3CCCC[C@@H]3N)c(F)cc2C(N)=O)c1C]

The title compound was prepared using the same chemistry shown in Example 312. UV: 278, 349 nm. M+H found for C$_{20}$H$_{26}$FN$_5$O: 372.4. NMR (CD$_3$OD): 7.73 (1H, d, J=12.0 Hz), 7.50 (1H, d, J=8.0 Hz), 7.08 (1H, t, J=8.0 Hz), 6.96 (1H, d, J=7.2 Hz), 4.02 (1H, m), 3.59 (1H, m), 2.32 (3H, s), 2.19 (3H, s), 1.76 (4H, m), 1.54 (4H, m) ppm.

Example 320

Preparation of 6-((1R,2S)-2-aminocyclohexylamino)-2-(3,5-dimethylphenylamino)-5-fluoronicotinamide

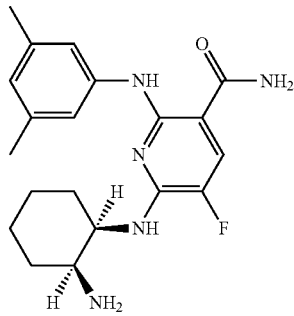 [SMILES: Cc1cc(C)cc(Nc2nc(N[C@@H]3CCCC[C@@H]3N)c(F)cc2C(N)=O)c1]

The title compound was prepared using the same chemistry shown in Example 312. UV: 304, 351 nm. M+H found for C$_{20}$H$_{26}$FN$_5$O: 372.4. NMR (CD$_3$OD): 7.73 (1H, d, J=11.6 Hz), 7.15 (2H, s), 6.68 (1H, s), 4.41 (1H, m), 3.75 (1H, m), 2.30 (6H, s), 1.87-1.57 (8H, m) ppm.

Example 321

Preparation of 6-((1R,2S)-2-aminocyclohexylamino)-5-fluoro-2-(3-fluoro-5-methylphenylamino)nicotinamide

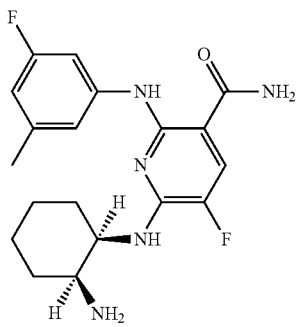

The title compound was prepared using the same chemistry shown in Example 312. UV: 305, 347 nm. M+H found for C$_{19}$H$_{23}$F$_2$N$_5$O: 376.3. NMR (CD$_3$OD): 7.67 (1H, d, J=12.4

Hz), 7.49 (1H, dt, J=11.6; 2.4 Hz), 6.76 (1H, s), 6.44 (1H, d, J=9.2 Hz), 4.30 (1H, m), 3.82 (1H, m), 2.22 (3H, s), 1.83-1.76 (5H, m), 1.53 (3H, m) ppm.

Example 322

Preparation of 6-((1R,2S)-2-aminocyclohexylamino)-5-fluoro-2-(4-fluoro-3-methylphenylamino)nicotinamide

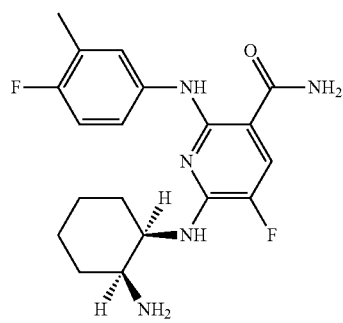 [SMILES: Cc1cc(Nc2nc(N[C@@H]3CCCC[C@@H]3N)c(F)cc2C(N)=O)ccc1F]

The title compound was prepared using the same chemistry shown in Example 312. UV: 296, 349 nm. M+H found for $C_{19}H_{23}F_2N_5O$: 376.3. NMR (CD$_3$OD): 7.73 (1H, d, J=12.0 Hz), 7.36 (1H, m), 7.31 (1H, dd, J=6.8; 2.4 Hz), 6.97 (1H, t, J=8.8 Hz), 4.31 (1H, m), 3.78 (1H, m), 2.26 (3H, s), 1.86-1.74 (5H, m), 1.61 (3H, m) ppm.

Example 323

Preparation of 6-(1R,2S)-2-aminocyclohexylamino)-5-fluoro-2-(3-fluoro-4-methylphenylamino)nicotinamide

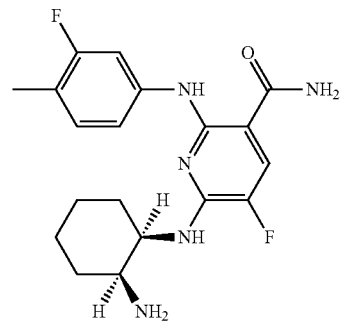 [SMILES: Cc1ccc(Nc2nc(N[C@@H]3CCCC[C@@H]3N)c(F)cc2C(N)=O)cc1F]

The title compound was prepared using the same chemistry shown in Example 312. UV: 305, 349 nm. M+H found for $C_{19}H_{23}F_2N_5O$: 376.4. NMR (CD$_3$OD): 7.66 (1H, d, J=12.0 Hz), 7.55 (1H, dd, J=12.8; 2.0 Hz), 7.02 (1H, t, J=8.4 Hz), 6.88 (1H, dd, J=8.0; 2.4 Hz), 4.27 (1H, m), 3.82 (1H, m), 2.11 (3H, s), 1.82-1.76 (5H, m), 1.52 (3H, m) ppm.

Example 324

Preparation of 6-((1R,2S)-2-aminocyclohexylamino)-2-(3,5-difluorophenylamino)-5-fluoronicotinamide

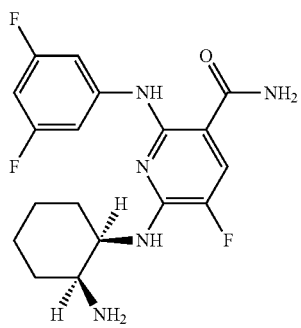 [SMILES: NC(=O)c1cc(F)c(N[C@@H]2CCCC[C@@H]2N)nc1Nc1cc(F)cc(F)c1]

The title compound was prepared using the same chemistry shown in Example 312. UV: 262, 303, 346 nm M+H found for $C_{18}H_{20}F_3N_5O$: 380.3. NMR (CD$_3$OD): 7.79 (1H, d, J=12.4 Hz), 7.28 (2H, dd, J=10.0; 2.4 Hz), 6.50 (1H, tt, J=8.8; 2.4 Hz), 4.39 (1H, m), 3.93 (1H, m), 1.95-1.87 (5H, m), 1.62 (3H, m) ppm.

Example 325

Preparation of 6-((1R,2S)-2-aminocyclohexylamino)-2-(3-chloro-5-fluorophenylamino)-5-fluoronicotinamide

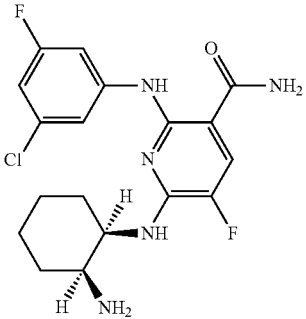 [SMILES: NC(=O)c1cc(F)c(N[C@@H]2CCCC[C@@H]2N)nc1Nc1cc(F)cc(Cl)c1]

The title compound was prepared using the same chemistry shown in Example 312. UV: 262, 306 nm. M+H found for $C_{18}H_{20}ClF_2N_5O$: 396.3. NMR (CD$_3$OD): 7.79 (1H, d, J=12.4

Hz), 7.50 (1H, s), 7.40 (1H, dt, J=11.2; 2.4 Hz), 6.76 (1H, dt, J=8.4; 2.4 Hz), 4.41 (1H, m), 3.89 (1H, m), 1.95-1.87 (5H, m), 1.62 (3H, m) ppm.

Example 326

Preparation of 6-((1R,2S)-2-aminocyclohexylamino)-5-fluoro-2-(3-fluoro-5-methoxyphenylamino)nicotinamide

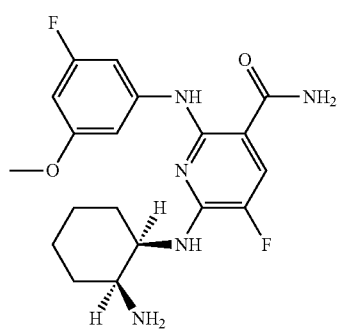 [SMILES: COc1cc(F)cc(Nc2nc(N[C@@H]3CCCC[C@@H]3N)c(F)cc2C(N)=O)c1]

The title compound was prepared using the same chemistry shown in Example 312. UV: 303, 346 nm. M+H found for $C_{19}H_{23}F_2N_5O_2$: 392.4. NMR (CD$_3$OD): 7.76 (1H, d, J=11.6 Hz), 7.17 (1H, dt, J=11.6; 2.0 Hz), 6.85 (1H, s), 6.32 (1H, dt, J=10.8; 2.0 Hz), 4.37 (1H, m), 3.95 (1H, m), 3.78 (3H, s), 1.95-1.86 (5H, m), 1.62 (3H, m) ppm.

Example 327

Preparation of 6-((1R,2R)-2-amino-3,3-difluorocyclohexylamino)-5-fluoro-2-(quinolin-5-ylamino)nicotinamide

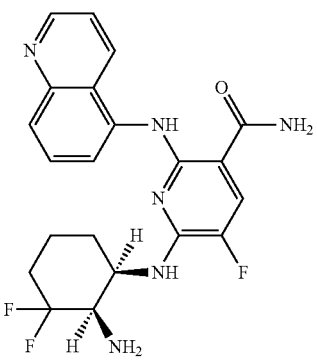 [SMILES: NC(=O)c1cc(F)c(N[C@@H]2CCCC(F)(F)[C@@H]2N)nc1Nc1cccc2ncccc12]

The title compound was prepared using the same chemistry shown in Example 330. UV: 237, 274, 334 nm. M+H found for $C_{21}H_{21}F_3N_6O$: 431.4. NMR (CD$_3$OD): 9.31 (1H, d, J=8.4 Hz), 9.15 (1H, dd, J=5.6; 1.6 Hz), 8.70 (1H, d, J=12.41 Hz), 8.08 (1H, t, J=8.4 Hz), 8.03 (1H, dd, J=9.2; 5.6 Hz), 7.95 (1H, d, J=12.0 Hz), 7.81 (1H, d, J=8.0 Hz), 4.57 (1H, m), 4.09 (1H, m), 2.14 (2H, m), 1.91 (3H, m), 1.72 (1H, m) ppm.

Example 328

Preparation of 6-((1R,2R)-2-amino-3,3-difluorocyclohexylamino)-2-(benzo[d]thiazol-6-ylamino)-5-fluoronicotinamide

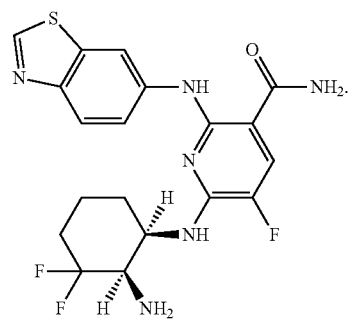 [SMILES: NC(=O)c1cc(F)c(N[C@@H]2CCCC(F)(F)[C@@H]2N)nc1Nc1ccc2ncsc2c1]

The title compound was prepared using the same chemistry shown in Example 330. UV: 259, 325 nm. M+H found for $C_{19}H_{19}F_3N_6OS$: 437.3. NMR (CD$_3$OD): 9.13 (1H, s), 8.39 (1H, d, J=2.0 Hz), 7.96 (1H, d, J=8.8 Hz), 7.83 (1H, d, J=12.0 Hz), 7.66 (1H, dd, J=8.8; 2.0 Hz), 4.82 (1H, m), 4.22 (1H, m), 2.16 (2H, m), 1.94 (3H, m), 1.81 (1H, m) ppm.

Example 329

Preparation of 6-((1R,2R)-2-amino-3,3-difluorocyclohexylamino)-2-(benzo[d]thiazol-7-ylamino)-5-fluoronicotinamide

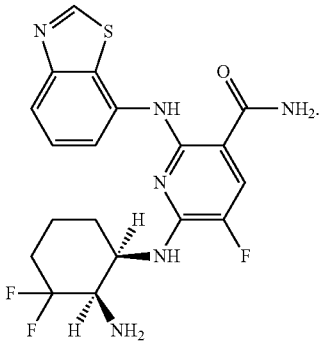 [SMILES: NC(=O)c1cc(F)c(N[C@@H]2CCCC(F)(F)[C@@H]2N)nc1Nc1cccc2ncsc12]

The title compound was prepared using the same chemistry shown in Example 330. UV: 242, 265, 304, 334 nm. M+H found for $C_{19}H_{19}F_3N_6OS$: 437.4. NMR (CD$_3$OD): 9.25 (1H, s), 8.09 (1H, d, J=8.0 Hz), 7.87 (1H, d, J=12.0 Hz), 7.78 (1H, dd, J=8.4; 1.2 Hz), 7.54 (1H, t, J=8.4 Hz), 4.56 (1H, m), 4.08 (1H, m), 2.10 (2H, m), 1.86 (3H, m), 1.71 (1H, m) ppm.

Example 330

Preparation of 6-((1R,2R)-2-amino-3,3-difluorocyclohexylamino)-5-fluoro-2-(1-methyl-1H-indol-4-ylamino)nicotinamide

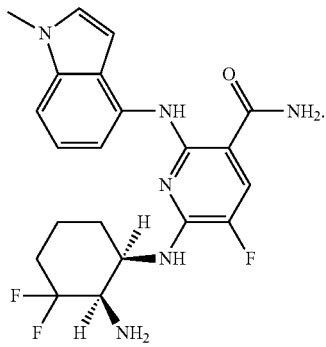 [SMILES: Cn1ccc2c(Nc3nc(N[C@@H]4CCCC(F)(F)[C@@H]4N)c(F)cc3C(N)=O)cccc21]

A mixture of 6-((1R,2R)-2-amino-3,3-difluorocyclohexylamino)-2-chloro-5-fluoronicotinonitrile (compound J69 in Example 203) (150 mg, 0.50 mmol), N-methylindol-4-amine (220 mg, 1.5 mmol), cesium carbonate (fine powder, 820 mg, 2.5 mmol), BINAP (62 mg, 0.10 mmol), Pd(OAc)$_2$ (23 mg, 0.10 mmol) in 20 mL dioxane was degassed using argon stream and stirred in 105° C. bath under argon atmosphere for overnight. The mixture was diluted with 100 mL EtOAc and filtered through a very short (0.5-inch) silica plug. The filtrate was concentrated in vacuo and subjected to flash column (0-10% MeOH in DCM) to isolate 6-((1R,2R)-2-amino-3,3-difluorocyclohexylamino)-5-fluoro-2-(1-methyl-1H-indol-4-ylamino)nicotinonitrile. It was dissolved in 20 mL MeOH. To it were added 2 mL DMSO, 100 mg KOH and then 1 mL 50 wt % H$_2$O$_2$. The mixture was stirred at RT for 90 m and diluted with 20 mL acetonitrile. The mixture was concentrated in vacuo and subjected to reverse phase prep HPLC to isolate the title compound as HCl salt (61 mg). UV: 325 nm. M+H found for C$_{21}$H$_{23}$F$_3$N$_6$O: 433.4. NMR (CD$_3$OD): 7.85 (1H, d, J=8.0 Hz), 7.81 (1H, d, J=12.0 Hz), 7.15 (1H, d, J=8.0 Hz), 7.12 (1H, d, J=3.2 Hz), 7.06 (1H, d, J=7.2 Hz), 6.56 (1H, dd, J=3.2; 0.8 Hz), 4.75 (1H, m), 4.20 (1H, m), 3.79 (3H, s), 2.12 (2H, m), 1.92 (3H, m), 1.77 (1H, m) ppm.

Example 331

Preparation of 6-((1R,2R)-2-amino-3,3-difluorocyclohexylamino)-5-fluoro-2-(1-methyl-1H-indol-5-ylamino)nicotinamide

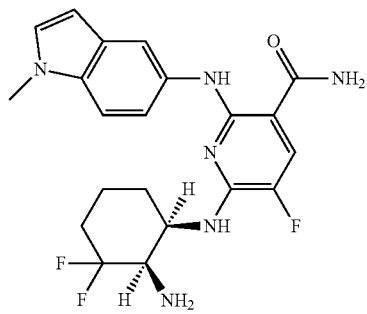 [SMILES: Cn1ccc2cc(Nc3nc(N[C@@H]4CCCC(F)(F)[C@@H]4N)c(F)cc3C(N)=O)ccc21]

The title compound was prepared using the same chemistry shown in Example 330. UV: 282 nm. M+H found for C$_{21}$H$_{23}$F$_3$N$_6$O: 433.4.

Example 332

Preparation of 6-((1R,2R)-2-amino-3,3-difluorocyclohexylamino)-5-fluoro-2-(5-methylpyridin-3-ylamino)nicotinamide

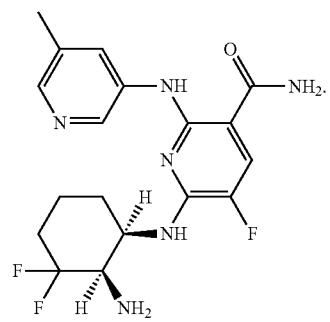 [SMILES: Cc1cncc(Nc2nc(N[C@@H]3CCCC(F)(F)[C@@H]3N)c(F)cc2C(N)=O)c1]

The title compound was prepared using the same chemistry shown in Example 330. UV: 230, 259, 320 nm. M+H found for C$_{18}$H$_{21}$F$_3$N$_6$O: 395.3. NMR (CD$_3$OD): 9.22 (1H, s), 8.34 (1H, s), 824 (1H, s), 7.92 (1H, d, J=11.6 Hz), 4.80 (1H, m), 4.17 (1H, m), 2.53 (3H, s), 2.20 (2H, m), 1.97 (3H, m), 1.84 (1H, m) ppm.

Example 333

Preparation of 6-((1R,2R)-2-amino-3,3-difluorocyclohexylamino)-5-fluoro-2-(3-methylisothiazol-5-ylamino)nicotinamide

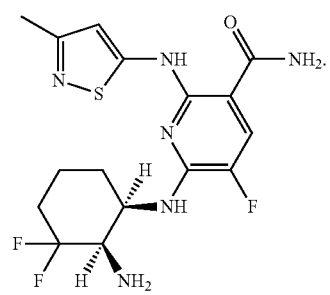 [SMILES: Cc1cc(Nc2nc(N[C@@H]3CCCC(F)(F)[C@@H]3N)c(F)cc2C(N)=O)sn1]

The title compound was prepared using the same chemistry shown in Example 330. UV: 241, 270, 334 nm. M+H found for C$_{16}$H$_{19}$F$_3$N$_6$OS: 401.3. NMR (CD$_3$OD): 7.99 (1 h, d, J=11.6 Hz), 6.79 (1H, s), 5.17 (1H, m), 4.30 (1H, m), 2.43 (3H, s), 2.31-1.86 (6H, m) ppm.

Example 334

Preparation of 6-((1R,2R)-2-amino-3,3-difluorocyclohexylamino)-5-fluoro-2-(p-tolylamino)nicotinamide

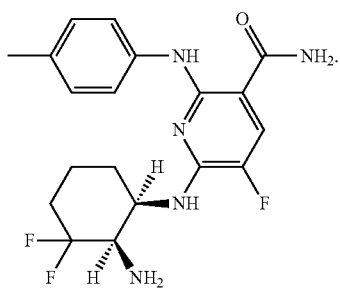 [SMILES: Cc1ccc(Nc2nc(N[C@@H]3CCCC(F)(F)[C@@H]3N)c(F)cc2C(N)=O)cc1]

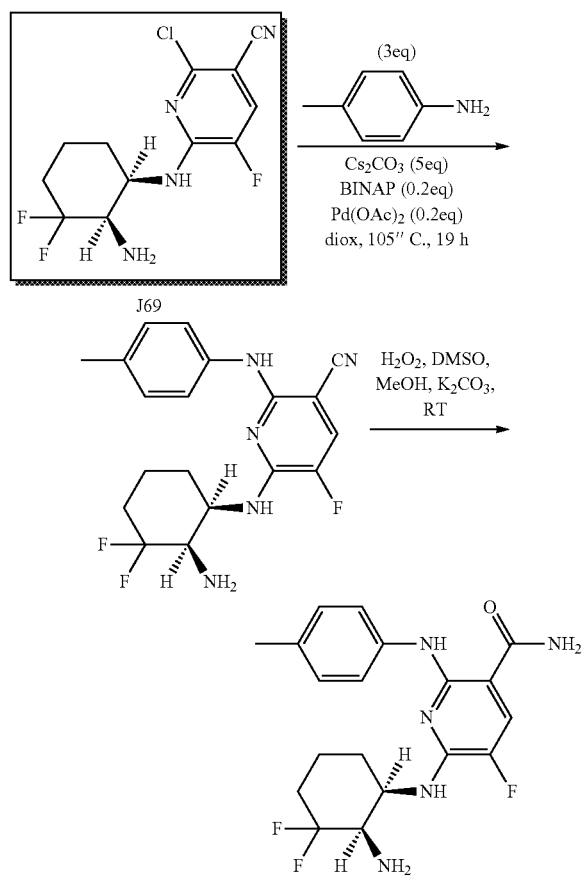

A mixture of compound J69 (60 mg, 0.2 mmol), p-toluidine (65 mg, 0.6 mmol), cesium carbonate (fine powder, 326 mg, 1 mmol), BINAP (25 mg, 0.04 mmol), Pd(OAc)$_2$ (10 mg, 0.04 mmol) in 15 mL dioxane was degassed using argon stream and stirred in 105° C. bath under argon atmosphere for overnight. The mixture was diluted with 100 mL EtOAc and filtered through a very short (0.5-inch) silica plug. The filtrate was concentrated in vacuo to dryness. It was dissolved in 10 mL MeOH. To it were added 1 mL DMSO, 100 mg potassium carbonate powder and then 1 mL 50 wt % H$_2$O$_2$. The mixture was stirred at RT for 1 h and diluted with 20 mL acetonitrile. The mixture was concentrated in vacuo and subjected to reverse phase prep HPLC to isolate the title compound as HCl salt. UV: 302, 352 nm. M+H found for C$_{19}$H$_{22}$F$_3$N$_5$O: 394.4. NMR (CD$_3$OD): 7.77 (1H, d, J=11.6 Hz), 7.41 (2H, d, J=8.4 Hz), 7.10 (2H, d, J=7.6 Hz), 4.69 (1H, m), 4.22 (1H, m), 2.28 (3H, s), 2.12 (2H, m), 1.91 (3H, m), 1.78 (1H, m) ppm.

Example 335

Preparation of 6-((1R,2R)-2-amino-3,3-difluorocyclohexylamino)-5-fluoro-2-(m-tolylamino)nicotinamide

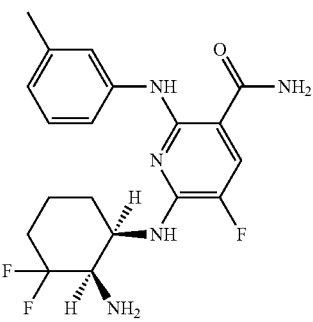

The title compound was prepared using the same chemistry shown in Example 334. UV: 301 nm. M+H found for C$_{19}$H$_{22}$F$_3$N$_5$O: 394.3. NMR (CD$_3$OD): 7.77 (1H, d, J=11.6 Hz), 7.44 (1H, d, J=8.0 Hz), 7.26 (1H, s), 7.16 (1H, t, J=8.0 Hz), 6.81 (1H, d, J=7.6 Hz), 4.77 (1H, m), 4.17 (1H, m), 2.32 (3H, s), 2.16 (2H, m), 1.91 (3H, m), 1.79 (1H, m) ppm.

Example 336

Preparation of 6-((1R,2R)-2-amino-3,3-difluorocyclohexylamino)-2-(3-chlorophenylamino)-5-fluoronicotinamide

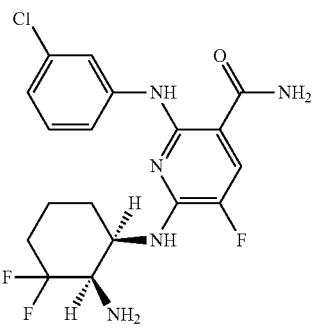

The title compound was prepared using the same chemistry shown in Example 334. UV: 265, 305, 346 nm. M+H found for C$_{18}$H$_{19}$ClF$_3$N$_5$O: 414.3. NMR (CD$_3$OD): 7.81 (1H, d, J=12.0 Hz), 7.78 (1H, s), 7.40 (1H, d, J=8.0 Hz), 7.24 (1H, t, J=8.0 Hz), 6.95 (1H, dm, J=8.0 Hz), 4.77 (1H, m), 4.16 (1H, m), 2.23-1.83 (6H, m) ppm.

Example 337

Preparation of 6-((1R,2R)-2-amino-3,3-difluorocyclohexylamino)-2-(3,5-difluorophenylamino)-5-fluoronicotinamide

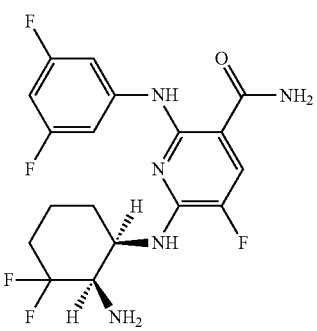 [SMILES: NC(=O)c1cc(F)c(N[C@@H]2CCCC(F)(F)[C@@H]2N)nc1Nc1cc(F)cc(F)c1]

The title compound was prepared using the same chemistry shown in Example 334. UV: 258, 303, 346 nm. M+H found for $C_{18}H_{18}F_5N_5O$: 416.4. NMR ($CD_3OD$): 7.74 (1H, d, J=11.6 Hz), 7.14 (2H, dd, J=9.2; 2.0 Hz), 6.40 (1H, tt, J=9.2; 2.4 Hz), 4.75 (1H, m), 4.10 (1H, m), 2.14-1.72 (6H, m) ppm.

Example 338

Preparation of 6-((1R,2R)-2-amino-3,3-difluorocyclohexylamino)-5-fluoro-2-(3-fluoro-5-methoxyphenylamino)nicotinamide

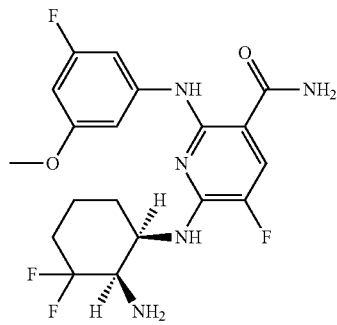 [SMILES: COc1cc(F)cc(Nc2nc(N[C@@H]3CCCC(F)(F)[C@@H]3N)c(F)cc2C(N)=O)c1]

The title compound was prepared using the same chemistry shown in Example 334. UV: 303, 346 nm. M+H found for $C_{19}H_{21}F_4N_5O_2$: 428.4. NMR ($CD_3OD$): 7.81 (1H, d, J=11.2 Hz), 7.16 (1H, dm, J=11.6 Hz), 6.77 (1H, s), 6.31 (1H, dt, J=12.0; 2.0 Hz), 4.85 (1H, m), 4.20 (1H, m), 3.78 (3H, s), 2.22-1.81 (6H, m) ppm.

Example 339

Preparation of 6-((1R,2R)-2-amino-3,3-difluorocyclohexylamino)-5-fluoro-2-(3-fluoro-5-methylphenylamino)nicotinamide

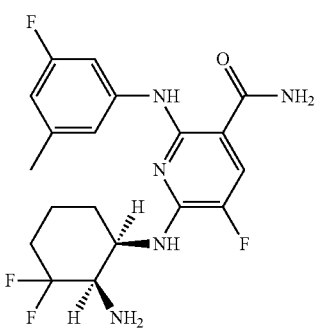

The title compound was prepared using the same chemistry shown in Example 334. UV: 267, 304, 347 nm. M+H found for $C_{19}H_{21}F_4N_5O$: 412.4. NMR ($CD_3OD$): 7.71 (1H, d, J=11.6 Hz), 7.33 (1H, d, J=11.6 Hz), 6.85 (1H, s), 6.43 (1H, d, J=8.8 Hz), 4.75 (1H, m), 4.10 (1H, m), 2.22 (3H, s), 2.20-1.71 (6H, m) ppm.

Example 340

Preparation of 2-(3-(2H-1,2,3-triazol-2-yl)phenylamino)-6-(1S,6S)-6-amino-2,2-difluorocyclohexylamino)-5-fluoronicotinamide

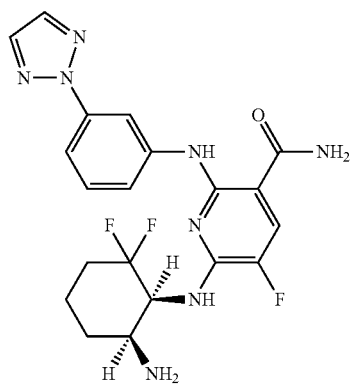 [SMILES: NC(=O)c1cc(F)c(N[C@H]2[C@@H](N)CCCC2(F)F)nc1Nc1cccc(-n2nccn2)c1]

Scheme 69:

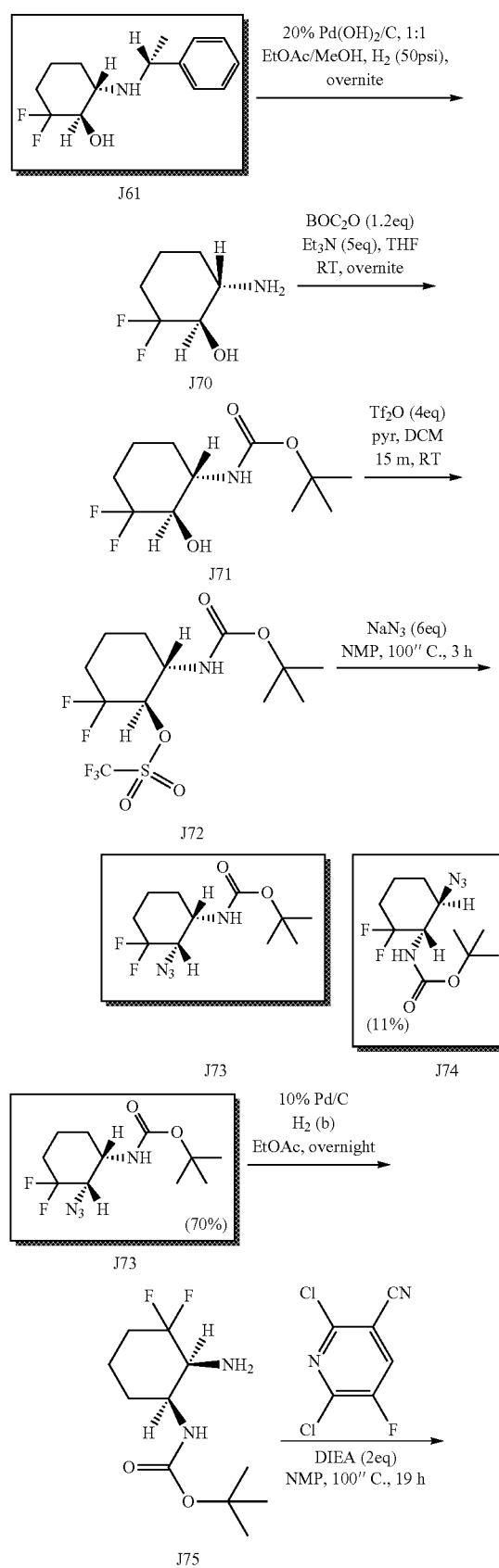

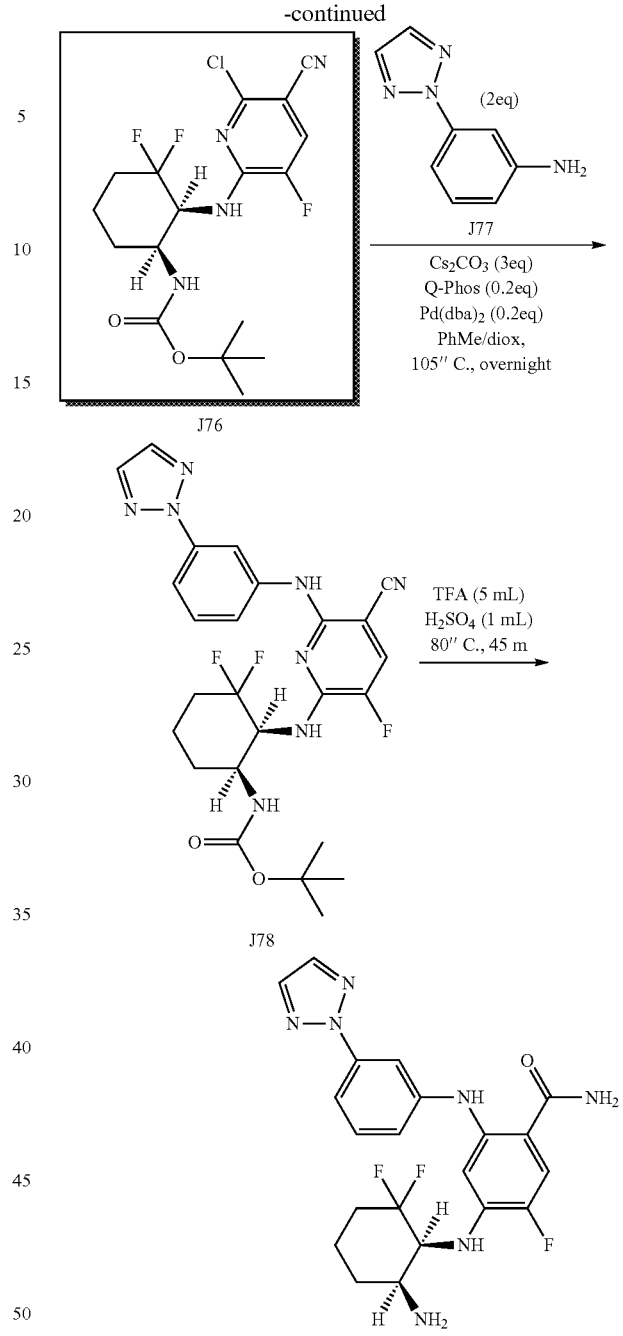

Compound J61 (see Example 291, 5.70 g, 22 mmol) was dissolved in 200 mL and 200 mL methanol. To the solution was added 20 wt % palladium hydroxide on carbon (Alfa Aesar #212911, 1.50 g). The mixture was shaken on a Parr shaker under 40 psi hydrogen for overnight. The mixture was filtered through celite. The filtrate was concentrated in vacuo to afford compound J70. It was dissolved in 200 mL THF. To it were added triethylamine (15.3 mL, 110 mmol) and BOC anhydride (5.8 g, 26.4 mmol). The mixture was stirred for overnight, concentrated in vacuo and subjected to flash column (10-20% EtOAc in hexane) to isolate compound J71 (4.65 g).

Compound J71 (3.00 g, 11.9 mmol) was dissolved in 100 mL dry DCM. To it was added 30 mL dry pyridine. The mixture was stirred in ice bath. To it was added Tf$_2$O (8.0 mL, 47 mmol). The reaction was allowed for 10 min and quenched with water. It was further diluted with 100 mL water and 500 mL DCM. The organic phase was separated and washed with water ×3, dried, concentrated in vacuo and pumped to dryness to give crude compound J72. It was dissolved in 36 mL NMP. To it was added sodium azide (4.64 g, 71.4 mmol). The mixture was stirred at 100° C. for 3 h. It was cooled to RT. To it was poured 500 mL EtOAc. The mixture was washed with water ×3, dried, concentrated in vacuo and subjected to flash column (0-15% EtOAc in hexane) to isolate the major product J73 (2.17 g, 66%) and the minor product J74 (0.42 g, 13%). J65 NMR (CDCl$_3$): 4.92 (1H, d, J=8.8 Hz), 3.91 (1H, m), 3.77 (1H, bm), 1.85 (1H, m), 1.80 (1H, m), 1.64-1.53 (2H, m), 1.36 (9H, s), 1.36-1.27 (2H, m) ppm. J74 NMR (CDCl$_3$): 4.83 (1H, d, J=9.2 Hz), 3.91 (1H, m), 3.28 (1H, m), 2.20 (1H, m), 2.10 (1H, m), 1.84-1.69 (2H, m), 1.47 (9H, s), 1.47-1.42 (2H, m) ppm.

Compound J73 (2.17 g, 7.86 mmol) was dissolved in 250 mL EtOAc. To it was added 0.5 g of 10% Pd/C. A hydrogen balloon was attached to the reaction flask. The mixture was stirred for overnight. It was filtered through celite. The celite cake was washed thoroughly with EtOAc and methanol. The filtrate was concentrated in vacuo and pumped to dryness to afford a white solid J75 (1.61 g, 85%).

The mixture of J75 (790 mg, 3.16 mmol), 2,6-dichloro-5-fluoronicotinonitrile (600 mg, 3.16 mmol) and DIEA (1.1 mL, 6.3 mmol) in 30 mL NMP was stirred at 100° C. for overnight. The mixture was concentrated in vacuo and subjected to flash column (10-35% EtOAc in hexane) to isolate compound J76 (780 mg, 61%).

A mixture of compound J76 (60 mg, 0.15 mmol), aniline J77 (48 mg, 0.30 mmol), cesium carbonate (fine powder, 148 mg, 0.45 mmol), Q-Phos (Aldrich #675784, 22 mg, 0.03 mmol), Pd(dba)$_2$ (18 mg, 0.03 mmol) in 15 mL toluene and 8 mL dioxane was degassed using argon stream and stirred in 105° C. bath under argon atmosphere for overnight. It was concentrated in vacuo, and the residue was taken into 150 mL EtOAc and 50 mL water. The organic phase was separated, dried, concentrated in vacuo. It was treated with 5 mL TFA and 1 mL conc. H$_2$SO$_4$ at 80° C. for 45 min. The mixture was cooled and to it was added 5 mL water. The mixture was filtered and subjected to reverse phase prep HPLC to isolate the title compound as HCl salt (28 mg). UV: 263, 301 nm. M+H found for C$_{20}$H$_{21}$F$_3$N$_8$O: 447.4. NMR (CD$_3$OD): 8.78 (1H, t, J=2.0 Hz), 7.95 (2H, s), 7.88 (1H, d, J=12.0 Hz), 7.69 (1H, dm, J=8.8 Hz), 7.43 (1H, t, J=8.0 Hz), 7.23 (1H, dm, J=8.8 Hz), 5.32 (1H, m), 3.85 (1H, m), 2.28 (1H, m), 2.07 (1H, m), 2.03-1.72 (4H, m) ppm.

Example 341

Preparation of 2-(3-(1H-pyrazol-1-yl)phenylamino)-6-((1S,6S)-6-amino-2,2-difluorocyclohexylamino)-5-fluoronicotinamide

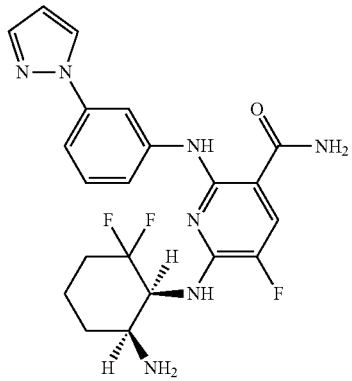 [SMILES: NC(=O)c1cc(F)c(N[C@H]2[C@@H](N)CCCC2(F)F)nc1Nc1cccc(-n2cccn2)c1]

The title compound was prepared using the same chemistry shown in Example 340. UV: 259, 301, 347 nm. M+H found for C$_{21}$H$_{22}$F$_3$N$_7$O: 446.4. NMR (CD$_3$OD): 8.47 (1H, t, J=2.4 Hz), 8.24 (1H, d, J=2.0 Hz), 7.87 (1H, d, J=11.6 Hz), 7.76 (1H, d, J=2.0 Hz), 7.40 (1H, d, J=8.0 Hz), 7.29 (1H, dm, J=8.4 Hz), 7.18 (1H, dm, J=8.0 Hz), 6.55 (1H, t, J=2.0 Hz), 5.22 (1H, m), 3.80 (1H, m), 2.26 (1H, m), 2.02 (1H, m), 1.90 (1H, m), 1.80 (2H, m), 1.69 (1H, m) ppm.

Example 342

Preparation of 6-((1S,6S)-6-amino-2,2-difluorocyclohexylamino)-5-fluoro-2-(3-(pyrimidin-2-yl)phenylamino)nicotinamide

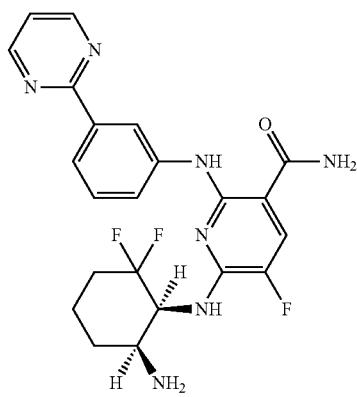 [SMILES: NC(=O)c1cc(F)c(N[C@H]2[C@@H](N)CCCC2(F)F)nc1Nc1cccc(-c2ncccn2)c1]

The title compound was prepared using the same chemistry shown in Example 340. UV: 263, 301, 348 nm. M+H found for C$_{22}$H$_{22}$F$_3$N$_7$O: 458.5. NMR (CD$_3$OD): 8.89 (2H, t, J=8.4 Hz), 8.74 (1H, s), 8.04 (1H, m), 7.87 (1H, d, J=12.0 Hz), 7.55 (1H, m), 7.48-7.41 (2H, m), 5.27 (1H, m), 3.73 (1H, m), 2.23 (1H, m), 2.00-1.69 (5H, m) ppm.

Example 343

Preparation of 6-((1S,6S)-6-amino-2,2-difluorocyclohexylamino)-5-fluoro-2-(quinolin-6-ylamino)nicotinamide

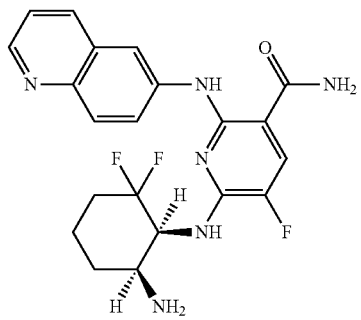 [SMILES: NC(=O)c1cc(F)c(N[C@H]2[C@@H](N)CCCC2(F)F)nc1Nc1ccc2ncccc2c1]

The title compound was prepared using the same chemistry shown in Example 340. UV: 263, 297 nm. M+H found for C$_{21}$H$_{21}$F$_3$N$_6$O: 431.4. NMR (CD$_3$OD): 8.89 (1H, d, J=5.2 Hz), 8.80 (1H, s), 8.76 (1H, d, J=8.0 Hz), 8.09 (1H, d, J=9.2 Hz), 8.04 (1H, dd, J=9.2; 2.4 Hz), 7.95 (1H, d, J=11.6 Hz), 7.87 (1H, dd, J=8.8; 5.2 Hz), 5.42 (1H, m), 3.73 (1H, m), 2.46 (1H, m), 2.17 (1H, m), 2.03-1.94 (3H, m), 1.75 (1H, m) ppm.

Example 344

Preparation of 6-((1S,6S)-6-amino-2,2-difluorocyclohexylamino)-5-fluoro-2-(quinolin-3-ylamino)nicotinamide

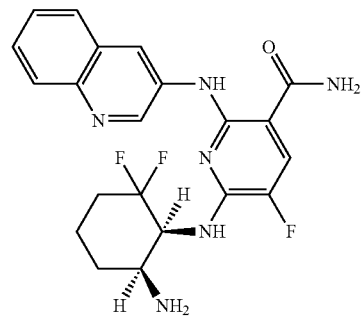 [SMILES: NC(=O)c1cc(F)c(N[C@H]2[C@@H](N)CCCC2(F)F)nc1Nc1cnc2ccccc2c1]

The title compound was prepared using the same chemistry shown in Example 340. UV: 292, 325 nm. M+H found for $C_{21}H_{21}F_3N_6O$: 431.4. NMR (CD$_3$OD): 9.25 (1H, d, J=2.8 Hz), 9.22 (1H, s), 8.09 (1H, s), 8.07 (1H, s), 7.97 (1H, d, J=11.6 Hz), 7.85 (1H, m), 7.78 (1H, m), 5.28 (1H, m), 3.71 (1H, m), 2.29 (1H, m), 2.14 (1H, m), 2.01-1.93 (3H, m), 1.73 (1H, m) ppm.

Example 345

Preparation of 6-((1S,6S)-6-amino-2,2-difluorocyclohexylamino)-2-(benzo[d]thiazol-6-ylamino)-5-fluoronicotinamide

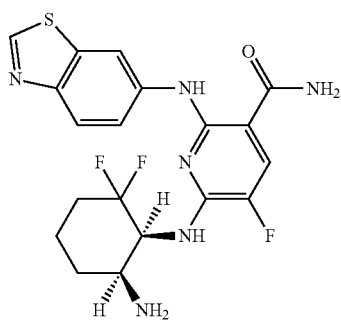 [SMILES: NC(=O)c1cc(F)c(N[C@H]2[C@@H](N)CCCC2(F)F)nc1Nc1ccc2ncsc2c1]

The title compound was prepared using the same chemistry shown in Example 340. UV: 258, 325 nm. M+H found for $C_{19}H_{19}F_3N_6OS$: 437.3. NMR (CD$_3$OD): 9.10 (1H, s), 8.54 (1H, d, J=2.0 Hz), 7.95 (1H, d, J=8.8 Hz), 7.87 (1H, d, J=12.0 Hz), 7.53 (1H, dd, J=9.2; 2.4 Hz), 5.25 (1H, m), 3.72 (1H, m), 2.27 (1H, m), 2.12 (1H, m), 1.98-1.86 (3H, m), 1.74 (1H, m) ppm.

Example 346

Preparation of 6-(1S,6S)-6-amino-2,2-difluorocyclohexylamino)-5-fluoro-2-(p-tolylamino)nicotinamide

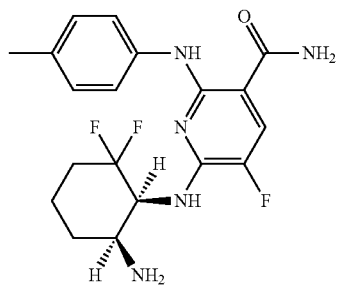 [SMILES: Cc1ccc(Nc2nc(N[C@H]3[C@@H](N)CCCC3(F)F)c(F)cc2C(N)=O)cc1]

Scheme 70:

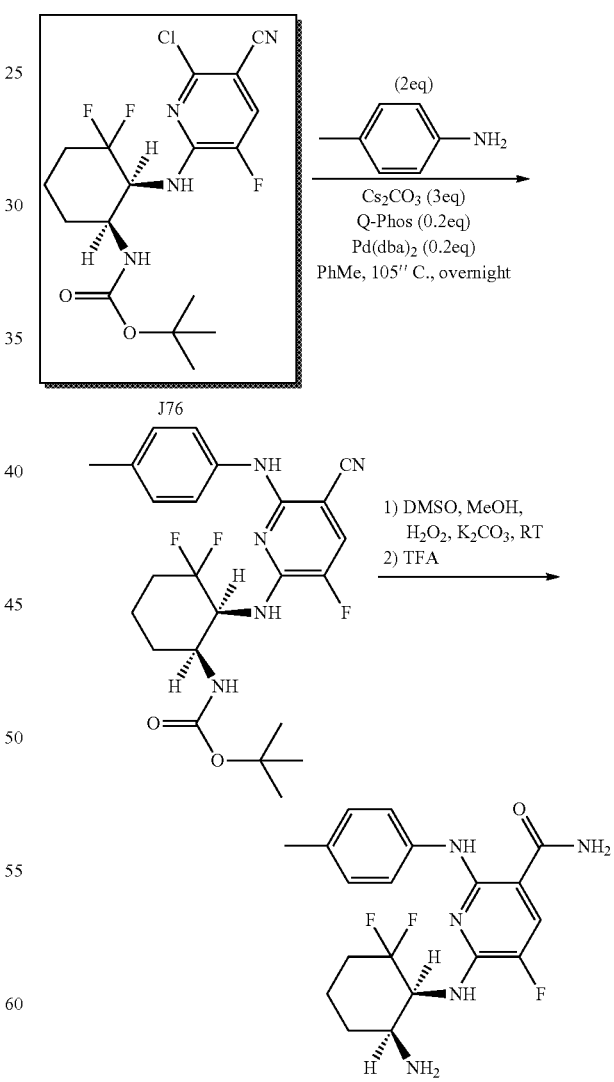

A mixture of compound J76 (55 mg, 0.14 mmol), p-toluidine (30 mg, 0.28 mmol), cesium carbonate (fine powder, 140 mg, 0.42 mmol), Q-Phos (Aldrich #675784, 22 mg, 0.03 mmol), Pd(dba)$_2$ (18 mg, 0.03 mmol) in 15 mL toluene was degassed using argon stream and stirred in 105° C. bath under argon atmosphere for overnight. It was concentrated in vacuo, and the residue was taken into 150 mL EtOAc and 50 mL water. The organic phase was separated, dried, concentrated in vacuo. It was dissolved in 10 mL MeOH. To it were added 1 mL DMSO, 100 mg K$_2$CO$_3$ (powder) and 1 mL 50% H$_2$O$_2$. The mixture was stirred for 2 h at RT. It was diluted with 10 mL MeCN and concentrated in vacuo. The residue was then treated with TFA at RT for 30 min. The title compound was isolated from this mixture using reverse phase prep HPLC as HCl salt. UV: 244, 300, 352 nm. M+H found for C$_{19}$H$_{22}$F$_3$N$_5$O: 394.4. NMR (CD$_3$OD): 7.80 (1H, d, J=12.0 Hz), 7.39 (2H, d, J=8.0 Hz), 7.11 (2H, d, J=8.0 Hz), 5.12 (1H, m), 3.72 (1H, m), 2.30 (3H, s), 2.25 (1H, m), 2.08 (1H, m), 1.89 (3H, m), 1.75 (1H, m) ppm.

Example 347

Preparation of 6-((1S,6S)-6-amino-2,2-difluorocyclohexylamino)-5-fluoro-2-(pyridin-3-ylamino)nicotinamide

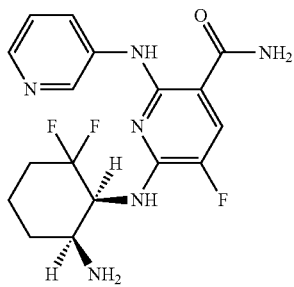 [SMILES: NC(=O)c1cc(F)c(N[C@H]2[C@@H](N)CCCC2(F)F)nc1Nc1cccnc1]

The title compound was prepared using the same chemistry shown in Example 346. UV: 255, 304, 327 nm. M+H found for C$_{17}$H$_{19}$F$_3$N$_6$O: 381.3. NMR (CD$_3$OD): 9.28 (1H, d, J=2.4 Hz), 8.61 (1H, dm, J=8.8 Hz), 8.37 (1H, d, J=5.6 Hz), 7.98 (1H, d, J=11.6 Hz), 7.93 (1H, dd, J=8.4; 5.2 Hz), 5.18 (1H, m), 3.76 (1H, m), 2.26 (1H, m), 2.12 (1H, m), 1.99 (3H, m), 1.74 (1H, m) ppm.

Example 348

Preparation of 6-(1S,6S)-6-amino-2,2-difluorocyclohexylamino)-5-fluoro-2-(5-fluoropyridin-3-ylamino)nicotinamide

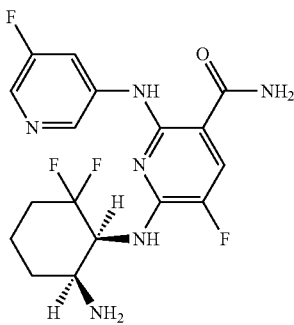 [SMILES: NC(=O)c1cc(F)c(N[C@H]2[C@@H](N)CCCC2(F)F)nc1Nc1cncc(F)c1]

The title compound was prepared using the same chemistry shown in Example 346. UV: 255, 327 nm. M+H found for C$_{17}$H$_{18}$F$_4$N$_6$O: 399.3. NMR (CD$_3$OD): 8.73 (1H, s), 8.53 (1H, d, J=10.0 Hz), 8.29 (1H, s), 7.96 (1H, d, J=12.4 Hz), 5.19 (1H, m), 3.76 (1H, m), 2.27 (1H, m), 2.12 (1H, m), 1.96 (3H, m), 1.74 (1H, m) ppm.

Example 349

Preparation of 6-((3R,4R)-3-aminotetrahydro-2H-pyran-4-ylamino)-5-fluoro-2-(p-tolylamino)nicotinamide

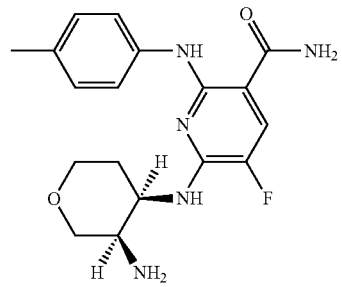

The title compound was prepared using the same chemistry shown in Example 279. UV: 300, 351 nm. M+H found for C$_{18}$H$_{22}$FN$_5$O$_2$: 360.3. NMR (CD$_3$OD): 7.72 (1H, d, J=11.6 Hz), 7.36 (2H, d, J=8.4 Hz), 7.12 (2H, d, J=8.4 Hz), 4.30 (1H, m), 4.08 (1H, m), 3.90 (2H, m), 3.65 (2H, m), 2.04 (1H, m), 1.86 (1H, m) ppm.

Example 350

Preparation of (S)-6-(piperidin-3-ylamino)-2-(quinolin-6-ylamino)nicotinamide

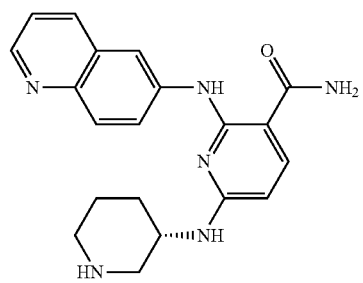 [SMILES: NC(=O)c1ccc(N[C@H]2CCCNC2)nc1Nc1ccc2ncccc2c1]

The title compound can be prepared using the same chemistry shown in Scheme 36 in Example 132.

Example 351

Preparation of (R)-5-fluoro-6-(pyrrolidin-3-ylamino)-2-(quinolin-6-ylamino)nicotinamide

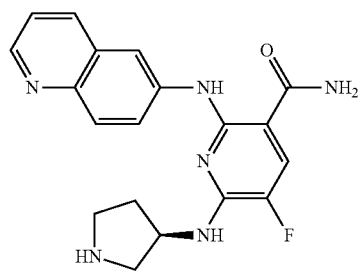 [SMILES: NC(=O)c1cc(F)c(N[C@@H]2CCNC2)nc1Nc1ccc2ncccc2c1]

The title compound can be prepared by methods described in example 90. However (R)-tert-butyl 3-aminopyrrolidine-1-carboxylate hydrochloride salt can be utilized instead of J20 and 6-aminoquinoline instead of 3-(2H-1,2,3-triazol-2-yl)aniline.

Examples 352-366

The title compounds was prepared using the same chemistry as shown in Example 279 above unless otherwise noted.

| EXAMPLE NO. | STRUCTURE |
|---|---|
| 352 | 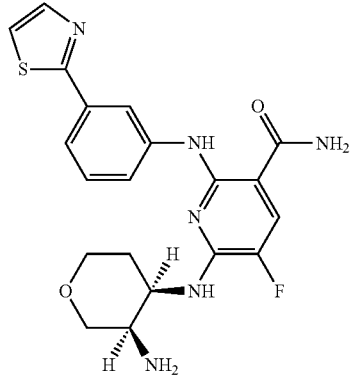 [SMILES: NC(=O)c1cc(F)c(N[C@@H]2CCOC[C@@H]2N)nc1Nc1cccc(-c2nccs2)c1] |
| 353 | 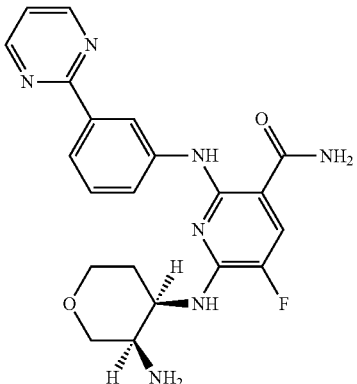 |
| 356 | 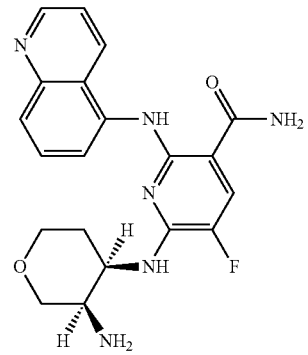 [SMILES: NC(=O)c1cc(F)c(N[C@@H]2CCOC[C@@H]2N)nc1Nc1cccc2ncccc12] |
| 357 | 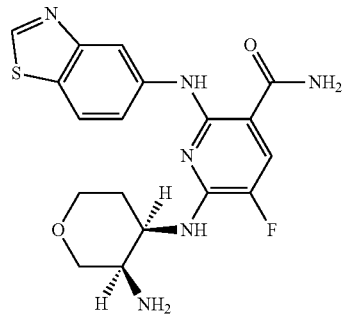 [SMILES: NC(=O)c1cc(F)c(N[C@@H]2CCOC[C@@H]2N)nc1Nc1ccc2scnc2c1] |
| 359 | 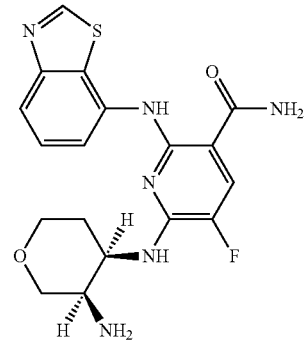 [SMILES: NC(=O)c1cc(F)c(N[C@@H]2CCOC[C@@H]2N)nc1Nc1cccc2ncsc12] |
| 360 | 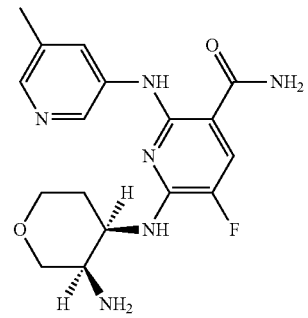 |

-continued
| EXAMPLE NO. | STRUCTURE |
|---|---|
| 361 | 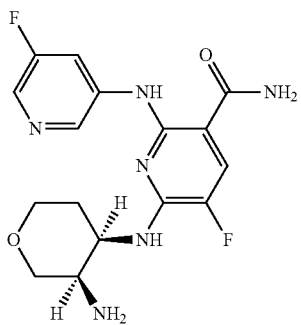 [SMILES: NC(=O)c1cc(F)c(N[C@@H]2CCOC[C@@H]2N)nc1Nc1cncc(F)c1] |
| 362 | 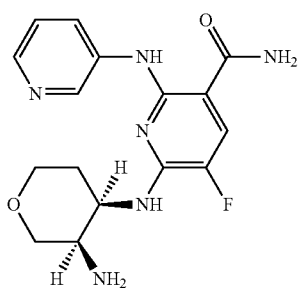 |
| 364 | 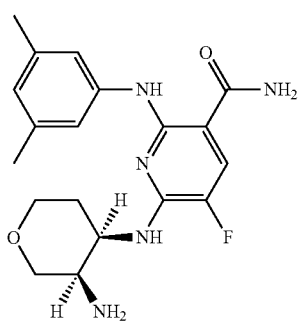 [SMILES: Cc1cc(C)cc(Nc2nc(N[C@@H]3CCOC[C@@H]3N)c(F)cc2C(N)=O)c1] |
| 366 | 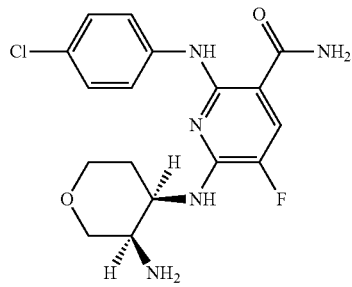 |
Example 368
Preparation of 6-((1R,2R)-2-amino-3,3-difluorocyclohexylamino)-5-fluoro-2-(1-methyl-1H-indazol-5-ylamino)nicotinamide
| EXAMPLE NO. | STRUCTURE |
|---|---|
| 368 | 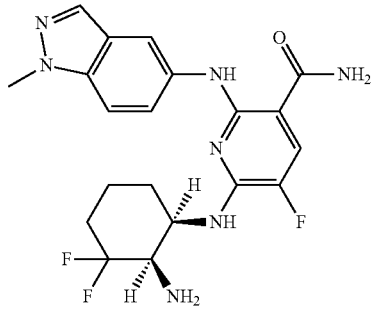 [SMILES: Cn1ncc2cc(Nc3nc(N[C@@H]4CCCC(F)(F)[C@@H]4N)c(F)cc3C(N)=O)ccc21] |
The title compound was prepared using the same chemistry as shown in Example 291.
Example 369
(S)-6-(1-(1-aminocyclopropyl)propylamino)-5-fluoro-2-(m-tolylamino)nicotinamide
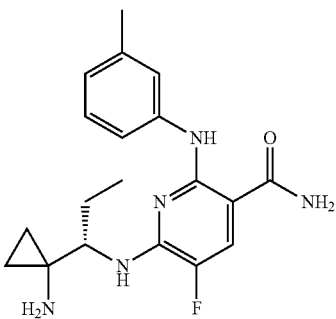 [SMILES: CC[C@H](Nc1nc(Nc2cccc(C)c2)c(C(N)=O)cc1F)C1(N)CC1]
Scheme 71
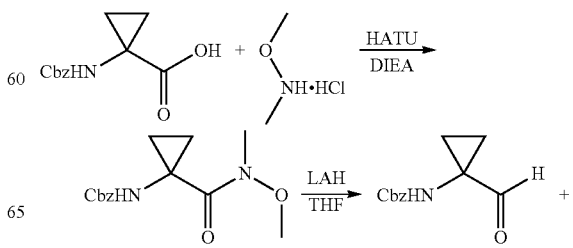

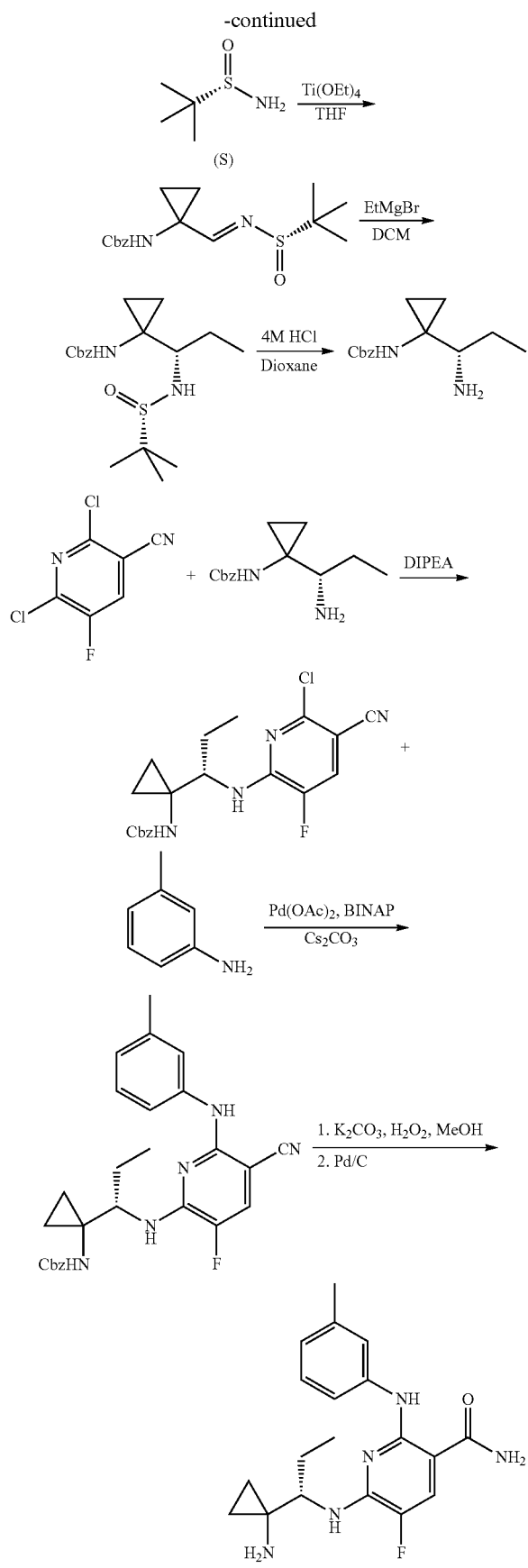

I. Synthesis of
(S)-benzyk-1-(1-aminopropyl)cyclopropylcarbamate

Step 1: To a solution of Z-cyclopropylcarboxylic acid (3.5 g, 14.9 mmol) and N,O-dimethylamine hydrochloride salt (1.60 g, 16.4 mmol) in DMF (25 mL) was added HATU (6.80 g, 17.87 mmol) and DIPEA (13.26 mL, 74.5 mmol). After stirred at room temperature for 2 h, the mixture was diluted with EtOAc, and poured to 1N NaOH, the aqueous layer was separated and extracted with EtOAc, organic layer was combined, washed with brine, dried and concentrated to give crude oil. Purification by flash chromatography gave benzyl 1-(methoxy(methyl)carbamoyl)cyclopropylcarbamate (2.7 g).

Step 2: To a solution of benzyl 1-(methoxy(methyl)carbamoyl)cyclopropylcarbamate (1.34 g, 4.82 mmol) in THF (25 mL) at 0° C. was added LiAlH$_4$ (366 mg, 9.64 mmol). After stirred at 0° C. for 30 min, it was poured to a solution of KHSO$_4$ (1.9 g) in water (30 mL), extracted with EtOAc, organic layer was separated, washed with brine, dried and concentrated to give benzyl 1-formylcyclopropylcarbamate (820 mg).

Step 3: To a solution of benzyl 1-formylcyclopropylcarbamate (820 mg, 3.76 mmol) in THF (12 mL) was added (S)-2-methylpropane-2-sulfinamide (546 mg, 4.51 mmol) and Ti(OEt)4 (1.72 g, 7.52 mmol). After stirred at room temperature for 4 h, the mixture was added brine, the precipitate was filtered off, the filter cake was washed with EtOAc, the filtrate was washed with brine, dried and concentrated to give crude oil, which was purified by flash chromatography (DCM/EtOAc=100:0 to 65:35) to give (S)-benzyl-1-((tert-butylsufinylimino)methyl)cyclopropylcarbamate (757 mg).

After stirred at 0° C. for 30 min, it was diluted with DCM, washed with Sat. NH$_4$Cl, brine, dried and concentrated to give crude oil, which was purified by preparative HPLC to give benzyl 1-((S)-1-((S)-1,1-dimethylethylsulfinamido)propyl)cyclopropylcarbamate (320 mg).

Step 5: To a solution of 1-(S)-1-(S)-1,1-dimethylethylsulfinamido)propyl)cyclopropylcarbamate (320 mg) in MeOH (6 mL) was added HCl (4 N in dioxane, 0.6 mL). After stirred at room temperature for 1 h, it was concentrated to give (S)-benzyl-1-(1-aminopropyl)cyclopropylcarbamate as HCl salt (281 mg).

II. Synthesis of (S)-6-(1-(1-aminocyclopropyl)propylamino)-5-fluoro-2-(m-tolylamino)nicotinamide Step 1: To a solution of 2,6-dichloro-5-fluoronicotinamide (124 mg, 0.65 mmol) in NMP (3.0 mL) was added (S)-benzyk-1-(1-aminopropyl)cyclopropylcarbamate hydrochloride salt (187 mg, 0.66 mmol) and DIPEA (0.231 mL, 1.3 mmol). After heated at 70° C. for 4 h, the mixture was diluted with EtOAc, organic layer was washed brine, dried and concentrated to give (S)-benzyl 1-(1-(6-chloro-5-cyano-3-fluoropyridin-2-ylamino)propyl)cyclopropylcarbamate (220 mg).

Step 2: To a solution of (S)-benzyl 1-(1-(6-chloro-5-cyano-3-fluoropyridin-2-ylamino)propyl)cyclopropylcarbamate (60 mg, 0.15 mmol) in dioxane (1 mL) was added m-toluidine (19 mg, 0.18 mmol), BINAP (18.7 mg, 0.03 mmol), Pd(OAc)$_2$ (6.7 mg, 0.03 mmol) and Cs$_2$CO$_3$ (146 mg, 0.45 mmol). After degassed with Argon, the mixture was heated at 80° C. for 15 h. The mixture was diluted with dioxane, precipitate was filtered off, filter cake was washed with ACN, the filtrate was concentrated and purified by column to give of (S)-benzyl 1-(1-(5-cyano-3-fluoro-6-(m-tolylamino)pyridin-2-ylamino)propyl)cyclopropylcarbamate (55 mg).

Step 3: To a solution of (S)-benzyl 1-(1-(5-cyano-3-fluoro-6-(m-tolylamino)pyridin-2-ylamino)propyl)cyclopropylcarbamate (55 mg, 0.12 mmol) in MeOH (1 mL) was added K$_2$CO$_3$ (40 mg) and H$_2$O$_2$ (50%, 10 drops). After stirred at room temperature for 2 h, it was diluted with EtOAc, washed with water, brine, dried and concentrated to give 1-(1-(5-carbamoyl-3-fluoro-6-(m-tolylamino)pyridin-2-ylamino)propyl)cyclopropylcarbamate, which was diluted with MeOH (1 mL) and THF (1 mL), added Pd/C (40 mg), charged with H$_2$ (1 atm). After stirred for 1 h, Pd/C was filtered off, and the filtrate was concentrated and purified by preparative HPLC to give (S)-6-(1-(1-aminocyclopropyl)propyl amino)-5-fluoro-2-(m-tolylamino)nicotinamide (11 mg). MS found for C$_{19}$H$_{24}$FN$_5$O as (M+H)$^+$ 358.5. λ=302.1.

Example 370

(S)-6-(1-(1-aminocyclopropyl)propylamino)-5-fluoro-2-(p-tolylamino)nicotinamide

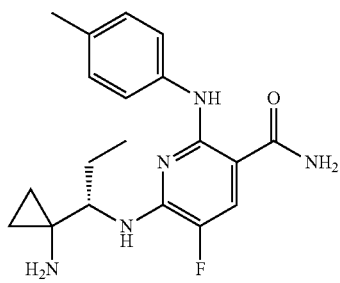 [SMILES: CC[C@H](Nc1nc(Nc2ccc(C)cc2)c(C(N)=O)cc1F)C1(N)CC1]

The title compound was synthesized similar to Example 369 in Scheme 71 using p-toluidine to replace m-toluidine. MS found for C$_{19}$H$_{24}$FN$_5$O as (M+H)$^+$ 358.5. λ=298.5.

Example 371

(S)-6-(1-(1-aminocyclopropyl)propylamino)-5-fluoro-2-(pyridin-3-ylamino)nicotinamide

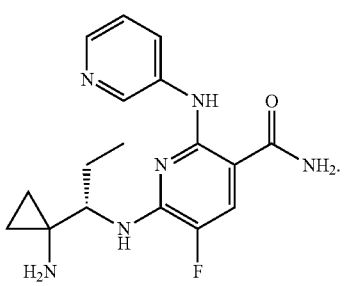 [SMILES: CC[C@H](Nc1nc(Nc2cccnc2)c(C(N)=O)cc1F)C1(N)CC1]

The title compound was synthesized similar to Example 369 in Scheme 71 using 3-aminopyridine to replace m-toluidine. MS found for C$_{17}$H$_{21}$FN$_6$O as (M+H)$^+$ 345.5. λ=260.5, 328.3.

Example 372

(R)-6-(1-(1-aminocyclopropyl)propylamino)-5-fluoro-2-(p-tolylamino)nicotinamide

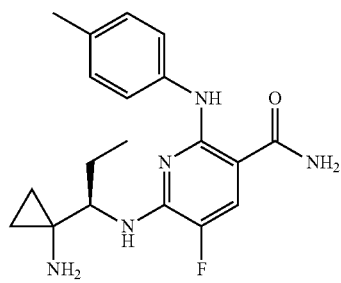 [SMILES: CC[C@@H](Nc1nc(Nc2ccc(C)cc2)c(C(N)=O)cc1F)C1(N)CC1]

Scheme 72

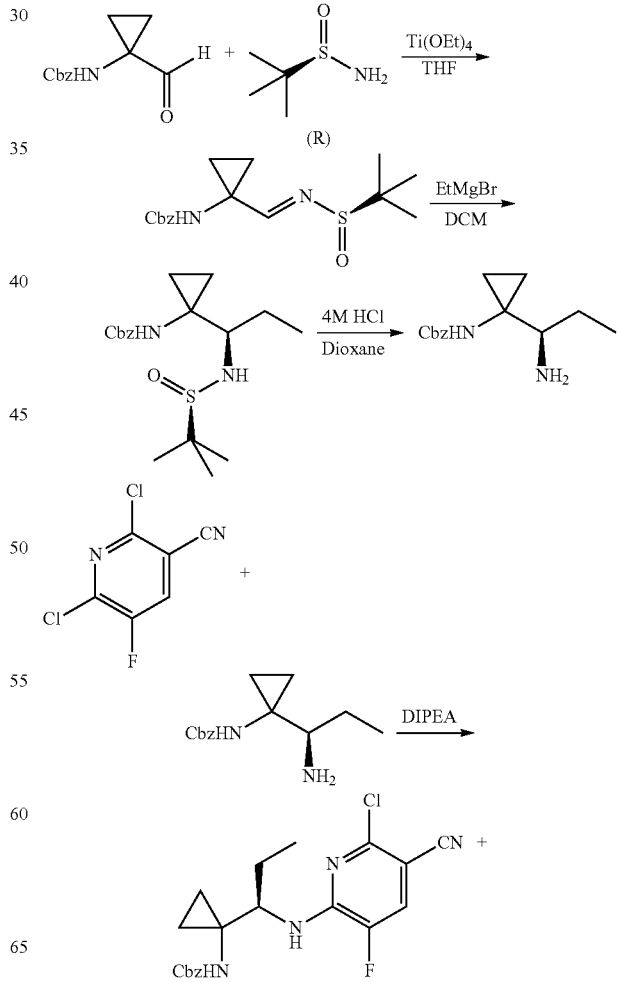

333

-continued

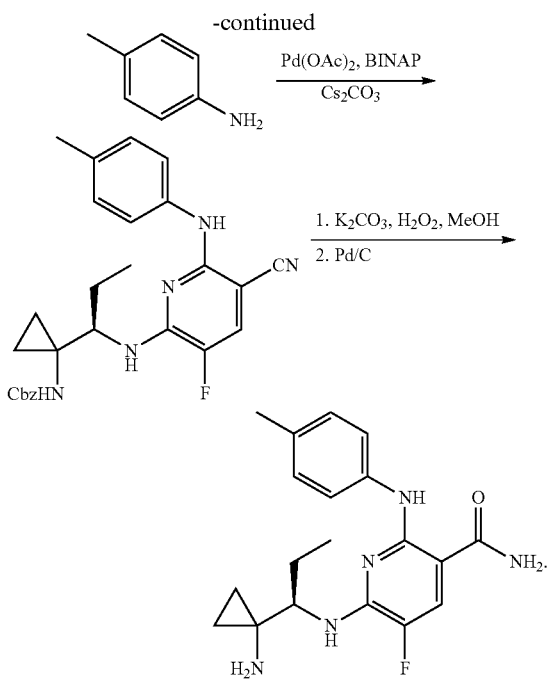

Step 1: To a solution of benzyl 1-formylcyclopropylcarbamate (1.37 g) in THF (20 mL) was added (R)-2-methylpropane-2-sulfinamide (912 mg) and Ti(OEt)₄ (2.87 g). After stirred at room temperature for 4 h, the mixture was added brine, the precipitate was filtered off, the filter cake was washed with EtOAc, the filtrate was washed with brine, dried and concentrated to give crude oil, which was purified by flash chromatography (DCM/EtOAc=2:1) to give (R)-benzyl-1-((tert-butylsufinylimino)methyl)cyclopropylcarbamate (1.26 g).

Step 2: To a solution of (R)-benzyl-1-((tert-butylsufinylimino)methyl)cyclopropylcarbamate (1.26 g) in DCM (18 mL) at 0° C. was added EtMgBr (3M in ether, 4 mL). After stirred at 0° C. for 30 min, it was diluted with DCM, washed with Sat. NH₄Cl, brine, dried and concentrated to give crude oil, which was purified by preparative HPLC to give benzyl 1-((R)-1-((R)-1,1-dimethylethylsulfinamido)propyl)cyclopropylcarbamate (900 mg).

After stirred at room temperature for 1 h, it was concentrated to give (R)-benzyl-1-O-aminopropyl)cyclopropylcarbamate as HCl salt (557 mg).

II. Synthesis of (R)-6-(1-(1-aminocyclopropyl)propylamino)-5-fluoro-2-(p-tolylamino)nicotinamide Step 1: To a solution of 2,6-dichloro-5-fluoronicotinamide (233 mg, 1.22 mmol) in NMP (5.0 mL) was added (R)-benzyl-1-(1-aminopropyl)cyclopropylcarbamate hydrochloride salt (350 mg, 1.23 mmol) and DIPEA (0.434 mL, 2.44 mmol). After heated at 80° C. for 4 h, the mixture was diluted with EtOAc, organic layer was washed brine, dried and concentrated to give (R)-benzyl 1-(1-(6-chloro-5-cyano-3-fluoropyridin-2-ylamino)propyl)cyclopropylcarbamate (220 mg).

Step 2: To a solution of (R)-benzyl 1-(1-(6-chloro-5-cyano-3-fluoropyridin-2-ylamino)propyl)cyclopropylcarbamate (100 mg, 0.25 mmol) in dioxane (1.5 mL) was added p-toluidine (32 mg, 0.30 mmol), BINAP (31 mg, 0.05 mmol), Pd(OAc)₂ (11.2 mg, 0.05 mmol) and Cs₂CO₃ (244.5 mg, 0.75 mmol). After degassed with Argon, the mixture was heated at

334

80° C. for 5 h. The mixture was diluted with dioxane, precipitate was filtered off, filter cake was washed with ACN, the filtrate was concentrated and purified by column to give of (R)-benzyl 1-(1-(5-cyano-3-fluoro-6-(p-tolylamino)pyridin-2-ylamino)propyl)cyclopropylcarbamate (80 mg).

Step 3: To a solution of (R)-benzyl 1-(1-(5-cyano-3-fluoro-6-(p-tolylamino)pyridin-2-ylamino)propyl)cyclopropylcarbamate (80 mg) in MeOH (1.5 mL) was added K₂CO₃ (80 mg) and H₂O₂ (50%, 10 drops). After stirred at room temperature for 2 h, it was diluted with EtOAc, washed with water, brine, dried and concentrated to give (R)-1-(1-(5-carbamoyl-3-fluoro-6-(p-tolylamino)pyridin-2-ylamino)propyl)cyclopropylcarbamate, which was diluted with MeOH (1 mL) and THF (1 mL), added Pd/C (50 mg), charged with H2 (1 atm). After stirred for 1 h, Pd/C was filtered off, and the filtrate was concentrated and purified by preparative HPLC to give (R)-6-(1-(1-aminocyclopropyl)propylamino)-5-fluoro-2-(p-tolylamino)nicotinamide (11 mg). MS found for C₁₉H₂₄FN₅O as (M+H)⁺ 358.5. λ=300.1.

Example 372

(R)-6-(1-(1-aminocyclopropyl)propylamino)-5-fluoro-2-(m-tolylamino)nicotinamide

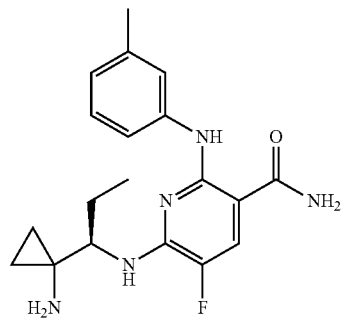 [SMILES: CC[C@@H](Nc1nc(Nc2cccc(C)c2)c(C(N)=O)cc1F)C1(N)CC1]

The title compound was synthesized similar to Example 372 in Scheme 72 using m-toluidine to replace p-toluidine. MS found for C₁₉H₂₄FN₅O as (M+H)⁺ 358.5. λ=303.2.

Example 373

(R)-6-(1-(1-aminocyclopropyl)propylamino)-5-fluoro-2-(5-fluoropyridin-3-ylamino)nicotinamide

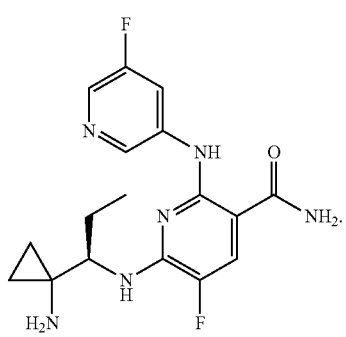 [SMILES: CC[C@@H](Nc1nc(Nc2cncc(F)c2)c(C(N)=O)cc1F)C1(N)CC1]

The title compound was synthesized similar to Example 372 in Scheme 72 using 3-amino-5-fluoropyridine to replace p-toluidine. MS found for $C_{17}H_{21}FN_6O$ as $(M+H)^+$ 363.5. λ=260.5, 327.1.

Example 374

6-(((1R,2S)-2-aminocyclohexylamino)-5-fluoro-2-(3-methylisoxazol-5-ylamino)nicotinamide

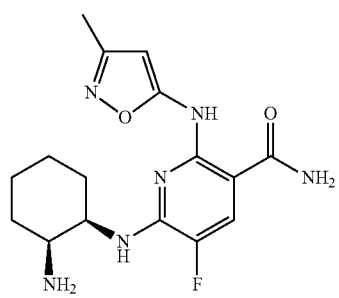 [SMILES: Cc1cc(Nc2nc(N[C@@H]3CCCC[C@@H]3N)c(F)cc2C(N)=O)on1]

Scheme 73

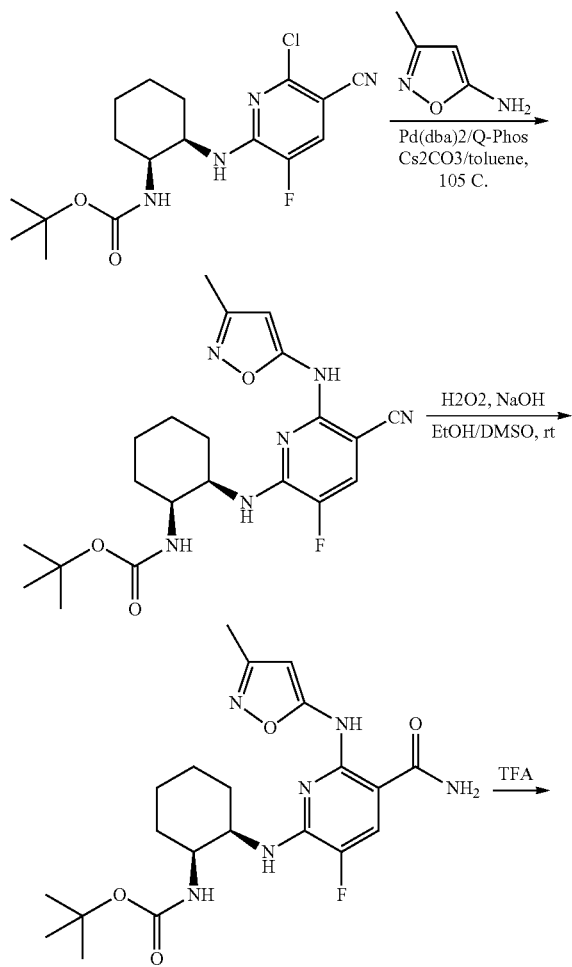

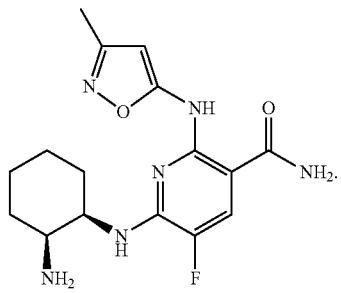

Water and EtOAc were added. The organic phase was separated, dried over $Na_2SO_4$, concentrated in vacuo to give a crude tert-butyl (1S,2R)-2-(5-cyano-3-fluoro-6-(3-methylisoxazol-5-ylamino)pyridin-2-ylamino)cyclohexylcarbamate (259 mg).

To a solution of the crude tert-butyl (1S,2R)-2-(5-cyano-3-fluoro-6-(3-methylisoxazol-5-ylamino)pyridin-2-ylamino)cyclohexylcarbamate in EtOH (2 mL) and DMSO (2 mL), aq. 1N NaOH (1 mL) and aq. H2O2 (50%, 1 mL) were added. The mixture was stirred at room temperature for 15 min. Water and EtOAc were added. The organic phase was separated, dried over $Na_2SO_4$, concentrated in vacuo to give crude tert-butyl (1S,2R)-2-(5-carbamoyl-3-fluoro-6-(3-methylisoxazol-5-ylamino)pyridin-2-ylamino)cyclohexylcarbamate, which was then dissolved in TFA (4 mL). After 10 min, excess TFA was removed in vacuo. The residue was purified by HPLC to give the titled compound (18 mg). MS 349.3 (M+H); UV 201.0, 259.0, 295.8, 333.5 nm; t 0.450 min.

Example 375

(R)-4-(1-amino-3-cyclopropyl-1-oxopropan-2-ylamino)-5-fluoro-2-(3-phenylisoxazol-5-ylamino)benzamide

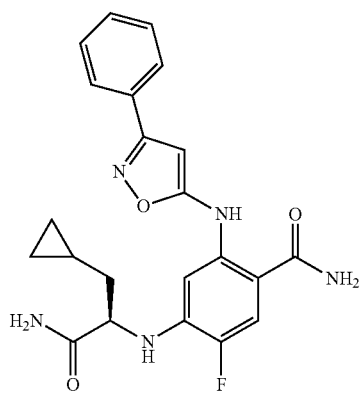 [SMILES: NC(=O)c1cc(F)c(N[C@H](CC2CC2)C(N)=O)cc1Nc1cc(-c2ccccc2)no1]

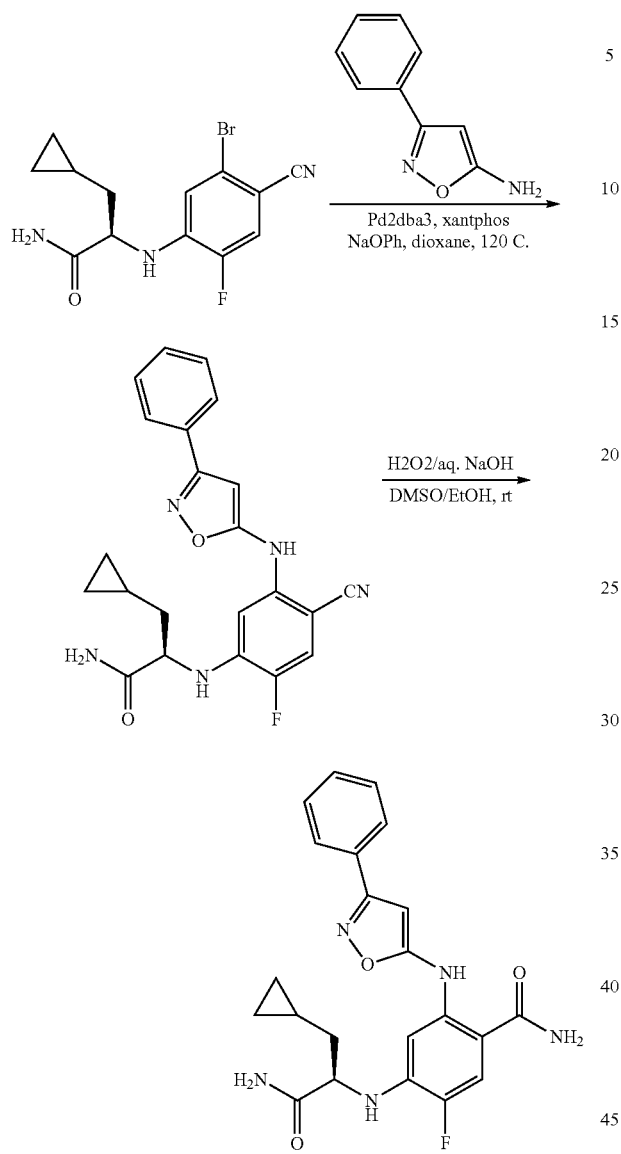

give the titled compound (13 mg). MS 424.4 (M+H); UV 201.0, 244.9, 289.1 nm; t 0.668 min.

Example 376

6-(1-carbamoylcyclopentylamino)-5-fluoro-2-(quinolin-3-ylamino)nicotinamide

A mixture of (R)-2-(5-bromo-4-cyano-2-fluorophenylamino)-3-cyclopropylpropanamide (150 mg, 0.460 mmol), 5-amino-3-phenylisoxazole (100 mg, 0.625 mmol), sodium phenoxide trihydrate (100 mg, 0.588 mmol), xantphos (60 mg, 0.103 mmol) and Pd2 dba3 (40 mg, 0.043 mmol) in dioxane (3 mL) was degassed with Ar, then was stirred at 120 C for 18 h. HOAc (0.5 mL) was added. The mixture was concentrated in vacuo. The residue was purified by HPLC to give (R)-2-(4-cyano-2-fluoro-5-(3-phenylisoxazol-5-ylamino)phenylamino)-3-cyclopropylpropanamide (75 mg).

To a solution of (R)-2-(4-cyano-2-fluoro-5-(3-phenylisoxazol-5-ylamino)phenylamino)-3-cyclopropylpropanamide (75 mg) in EtOH (1 mL) and DMSO (0.5 mL) at room temperature, aq. 1N NaOH (0.5 mL) and aq. H2O2 (50%, 0.5 mL) were added. The mixture was stirred at room temperature for 15 min. HOAc (0.5 mL) was added. After being concentrated in vacuo, the residue was purified by HPLC to

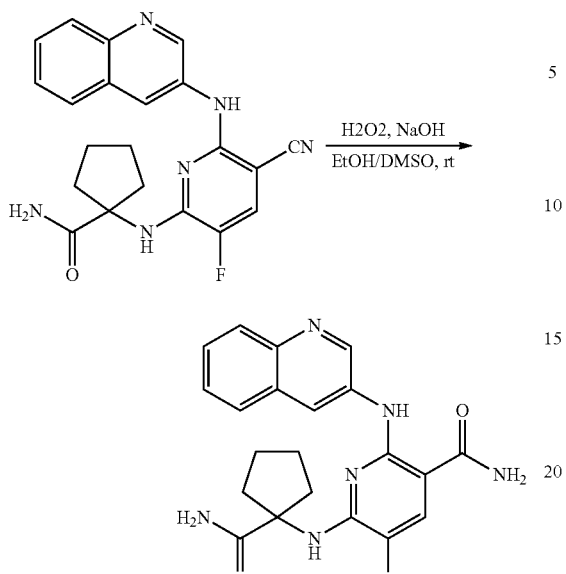

vacuo. The residue was purified by HPLC to give the titled compound (41 mg). MS 409.4 (M+H); UV 224.1, 243.7, 302.6, 324.8 nm; t 0.495 min.

Example 377

6-(1-amino-4,4,4-trifluoro-1-oxobutan-2-ylamino)-5-fluoro-2-(quinolin-3-ylamino)nicotinamide

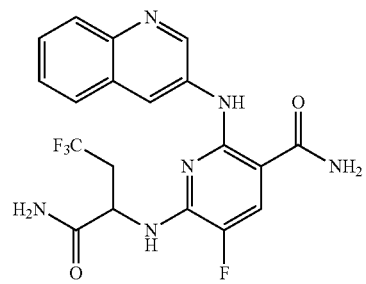 [SMILES: NC(=O)c1cc(F)c(NC(CC(F)(F)F)C(N)=O)nc1Nc1cnc2ccccc2c1]

To a solution of N-Boc-1-amino-1-cyclopentane carboxylic acid (518 mg, 2.26 mmol) and HOBt hydrate (416 mg, 2.71 mmol) in DMF (5 mL), EDC (522 mg, 2.71 mmol) was added. After being stirred at room temperature for 1 h, conc. NH4OH (14 N, 0.900 mL, 12.6 mmol) was added. The mixture was stirred for 18 h. Water and EtOAc were added. The organic phase was washed with 5% NaHCO3, dried over Na2SO4, concentrated in vacuo to give tert-butyl 1-carbamoylcyclopentylcarbamate (305 mg).

A solution of tert-butyl 1-carbamoylcyclopentylcarbamate (305 mg, 1.33 mmol) in 4N HCl in dioxane (5 mL) and aq. 6N HCl (3 mL) was stirred at room temperature for 3 h. It was then concentrated in vacuo to give 1-aminocyclopentanecarboxamide hydrochloride as a solid (214 mg).

A solution of 2,6-dichloro-3-cyano-5-fluoropyridine (250 mg, 1.30 mmol), 1-aminocyclopentanecarboxamide hydrochloride (214 mg, 1.30 mmol) and DIEA (0.650 mL, 3.73 mmol) in DMSO (3 mL) was stirred at 95 C for 4 h. Water and EtOAc were added. The organic phase was separated, dried over Na2SO4, concentrated in vacuo. The residue was purified by a silica gel column, eluted with 50-100% EtOAc in hexane to give 1-(6-chloro-5-cyano-3-fluoropyridin-2-ylamino)cyclopentanecarboxamide (180 mg).

A mixture of 1-(6-chloro-5-cyano-3-fluoropyridin-2-ylamino)cyclopentanecarboxamide (90 mg, 0.318 mmol), 3-aminoquinoline (58 mg, 0.402 mmol), sodium phenoxide trihydrate (85 mg, 0.500 mmol), xantphos (30 mg, 0.051 mmol) and Pd2 dba3 (20 mg, 0.021 mmol) in dioxane (2 mL) was degassed with Ar, then was stirred at 110 C for 4 h. Water and EtOAc were added. The organic phase was washed with aq. 1N NaOH, dried over Na2SO4, concentrated in vacuo to give crude 1-(5-cyano-3-fluoro-6-(quinolin-3-ylamino)pyridin-2-ylamino)cyclopentanecarboxamide.

To a solution of crude 1-(5-cyano-3-fluoro-6-(quinolin-3-ylamino)pyridin-2-ylamino)cyclopentanecarboxamide in EtOH (2 mL) and DMSO (1 mL), aq. 1N NaOH (1 mL) and aq. H2O2 (50%, 1 mL) were added. The mixture was stirred for 1 h. HOAc (0.5 mL) was added. It was concentrated in Scheme 76

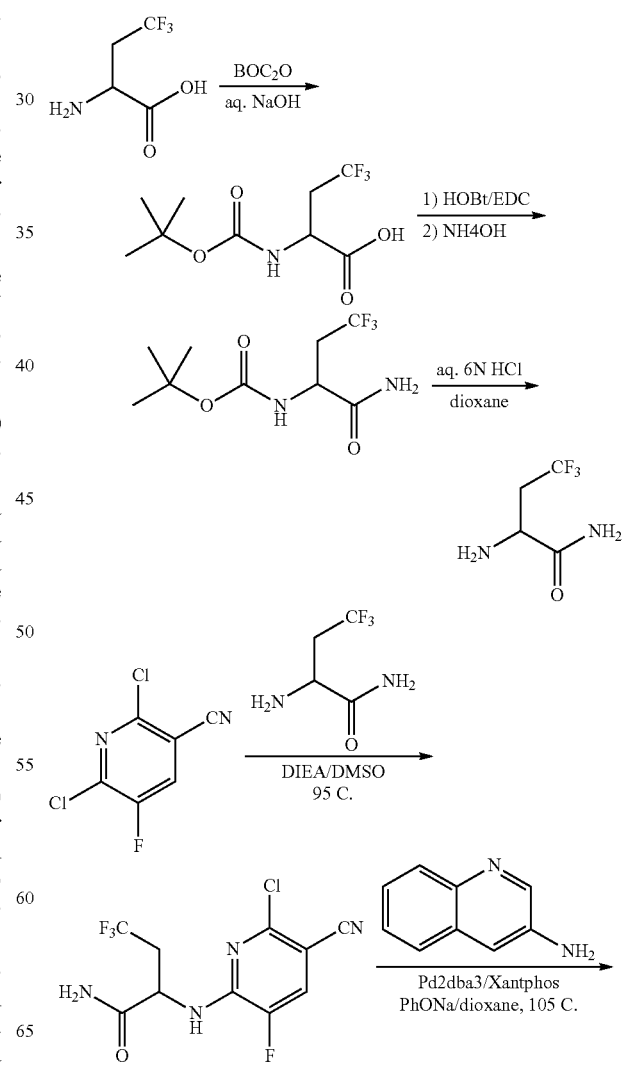

-continued

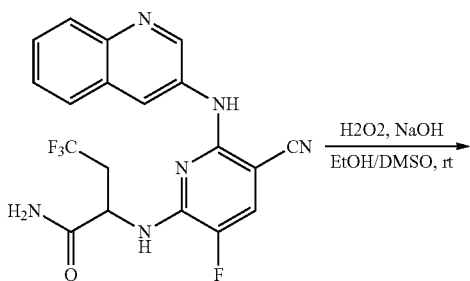

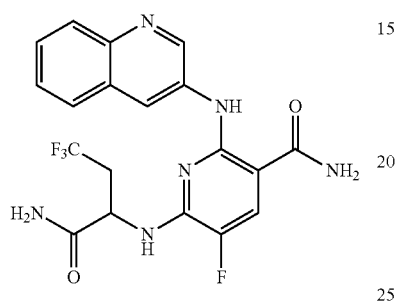

To a solution of 2-amino-4,4,4-trifluorobutyric acid (453 mg, 2.88 mmol) in aq. 1N NaOH (12 mL, 12.0 mmol), a solution of Boc2O (693 mg, 3.17 mmol) in dioxane (5 mL) was added. The mixture was stirred for 18 h. More Boc2O (479 mg, 2.19 mmol) in dioxane (4 mL) was added. After being stirred for 3 h, water was added. The aqueous solution was washed with Et2O twice, then was acidified to pH 1-2 with 1N HCl. The product was extracted with EtOAc twice. The combined EtOAc solution was dried over $Na_2SO_4$, concentrated in vacuo to give 2-(tert-butoxycarbonylamino)-4,4,4-trifluorobutanoic acid as a solid (672 mg).

To a solution of 2-(tert-butoxycarbonylamino)-4,4,4-trifluorobutanoic acid (370 mg, 1.43 mmol) and HOBt hydrate (264 mg, 1.72 mmol) in DMF (5 mL), EDC (332 mg, 1.72 mmol) was added. After being stirred at room temperature for 1 h, conc. NH4OH (14 N, 0.600 mL, 8.40 mmol) was added. The mixture was stirred for 18 h. Water and EtOAc were added. The organic phase was washed with 5% NaHCO3, dried over $Na_2SO_4$, concentrated in vacuo to give tert-butyl 1-amino-4,4,4-trifluoro-1-oxobutan-2-ylcarbamate as a solid.

A solution of the solid tert-butyl 1-amino-4,4,4-trifluoro-1-oxobutan-2-ylcarbamate in dioxane (4 mL) and aq. 6N HCl (6 mL) was stirred at room temperature for 1 h. It was then concentrated in vacuo to give 2-amino-4,4,4-trifluorobutanamide hydrochloride as a solid (135 mg).

A solution of 2,6-dichloro-3-cyano-5-fluoropyridine (134 mg, 0.701 mmol), 2-amino-4,4,4-trifluorobutanamide hydrochloride (135 mg, 0.701 mmol) and DIEA (0.365 mL, 2.10 mmol) in DMSO (3 mL) was stirred at 95 C for 3 h. Water and EtOAc were added. The organic phase was separated, dried over $Na_2SO_4$, concentrated in vacuo to give crude 2-(6-chloro-5-cyano-3-fluoropyridin-2-ylamino)-4,4,4-trifluorobutanamide (218 mg).

A mixture of the crude 2-(6-chloro-5-cyano-3-fluoropyridin-2-ylamino)-4,4,4-trifluorobutanamide (109 mg, 0.350 mmol), 3-aminoquinoline (52 mg, 0.361 mmol), sodium phenoxide trihydrate (85 mg, 0.500 mmol), xantphos (30 mg, 0.051 mmol) and Pd2 dba3 (20 mg, 0.021 mmol) in dioxane (2 mL) was degassed with Ar, then was stirred at 105 C for 3 h. Water and EtOAc were added. The organic phase was washed with aq. 1N NaOH, dried over $Na_2SO_4$, concentrated in vacuo to give crude 2-(5-cyano-3-fluoro-6-(quinolin-3-ylamino)pyridin-2-ylamino)-4,4,4-trifluorobutanamide (180 mg).

To a solution of crude 2-(5-cyano-3-fluoro-6-(quinolin-3-ylamino)pyridin-2-ylamino)-4,4,4-trifluorobutanamide (180 mg) in EtOH (2 mL) and DMSO (1 mL), aq. 1N NaOH (1 mL) and aq. H2O2 (50%, 1 mL) were added. The mixture was stirred for 20 min. HOAc (0.5 mL) was added. It was concentrated in vacuo. The residue was purified by HPLC to give the titled compound (44 mg). MS 437.3 (M+H); UV 202.2, 224.1, 295.2 nm; t 0.482 min.

Example 378

6-(1-carbamoylcyclohexylamino)-5-fluoro-2-(quinolin-3-ylamino)nicotinamide

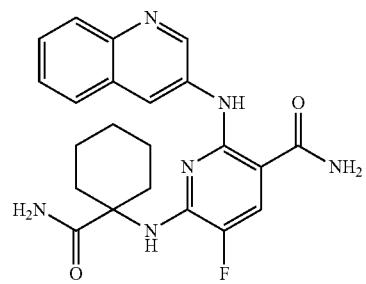 [SMILES: NC(=O)c1cc(F)c(NC2(C(N)=O)CCCCC2)nc1Nc1cnc2ccccc2c1]

The titled compound is synthesized analogously according to the procedures described in Example of 6-(1-carbamoylcyclopentylamino)-5-fluoro-2-(quinolin-3-ylamino)nicotinamide.

Example 379

6-(1-carbamoylcyclobutylamino)-5-fluoro-2-(quinolin-3-ylamino)nicotinamide

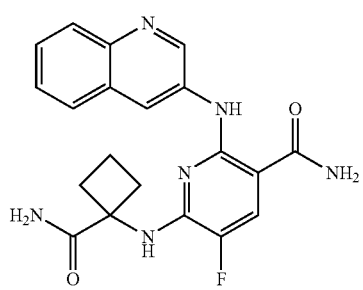 [SMILES: NC(=O)c1cc(F)c(NC2(C(N)=O)CCC2)nc1Nc1cnc2ccccc2c1]

The titled compound is synthesized analogously according to the procedures described in Example of 6-(1-carbamoylcyclopentylamino)-5-fluoro-2-(quinolin-3-ylamino)nicotinamide.

Example 380

Preparation of (S)-2-(m-toluidino)-6-(2-amino-4,4-difluorobutylamino)-5-fluoronicotinamide

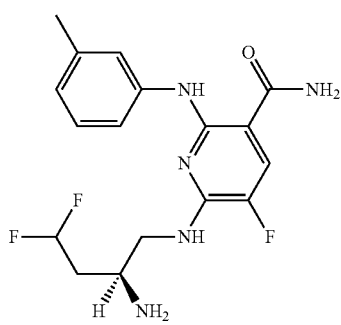 [SMILES: Cc1cccc(Nc2nc(NC[C@@H](N)CC(F)F)c(F)cc2C(N)=O)c1]

Example 380 was synthesized as seen in Schemes 77 and 78.

Step 1: To 10.2 g (30.8 mmol) of N-(Benzyloxycarbonyl)phosphonoglycine trimethyl ester in ~120 mL of THF at −78° C. was added 4.25 mL 1,1,3,3-tetra-methyl-guanidine. The reaction was stirred at −78° C. for 20 minutes and then 4.27 g (33.9 mmol) of 1-Ethoxy-2,2-difluoroethanol in ~15 mL THF was added dropwise. The reaction was stirred at −78° C. for 30 minutes and then was warmed to room temperature. The THF was removed in vacuo and then the resulting residue was dissolved in EtOAc. The organic layer was washed with cold H$_2$O and the aqueous layer was further extracted with EtOAc. The combined organics were concentrated in vacuo. The resulting crude product (9.2 g) was subjected to normal phase silica chromatography eluting with gradient starting at 10% EtOAc in hexanes, finishing at 20% EtOAc in hexanes. The product B51A (5.20 g) was isolated as a mixture of E and Z isomers. An NMR in CDCl$_3$ matched spectra reported by Hu et al. (for ref. see Example PB44).

Step 2: To 4.77 g of B51A in 125 mL MeOH was added 146 mg 1,2-Bis[(2R,5R)-2,5-diethylphospholano]benzene (1,5-cyclooctadiene)rhodium(I)trifluoromethanesulfonate. The resulting solution was degassed with Ar for 5 minutes and then subjected to H$_2$ at 150 psi for 12 h. The MeOH was removed to give 4.81 g of crude B51B which was run through a short silica column using 30% EtOAc in hexanes. Isolated product was massed to be 4.72 g.

Step 3: To 4.72 g (16.4 mmol) of B51B in ~50 mL THF at 0° C. was added LiBH$_4$ (716 mg (32.9 mmol). The reaction was allowed to warm to room temperature and was stirred for an additional 30 minutes. The reaction was quenched with saturated NH$_4$Cl (aq) and EtOAc was added to extract product. The combined organics were washed with brine and concentrated to give 4.23 g of B51C which was used without further purification.

Steps 4 and 5: Conversion of B51C to mesylate (B51D) followed by conversion to the azide (B51E) was achieved utilizing chemistry described in example 279.

Step 6: To 4.16 g (14.5 mmol) of B51E in ~40 mL THF was added 5.72 g (21.8 mmol) PPh$_3$ and 6 mL H$_2$O. The reaction was stirred at 60° C. for 3 hours and then volatiles were removed to give 10.4 g of crude. The crude reaction mixture was subjected to normal phase silica chromatography using a gradient of MeOH in DCM from 0 to 20%, resulting in 3.07 g of pure B51F.

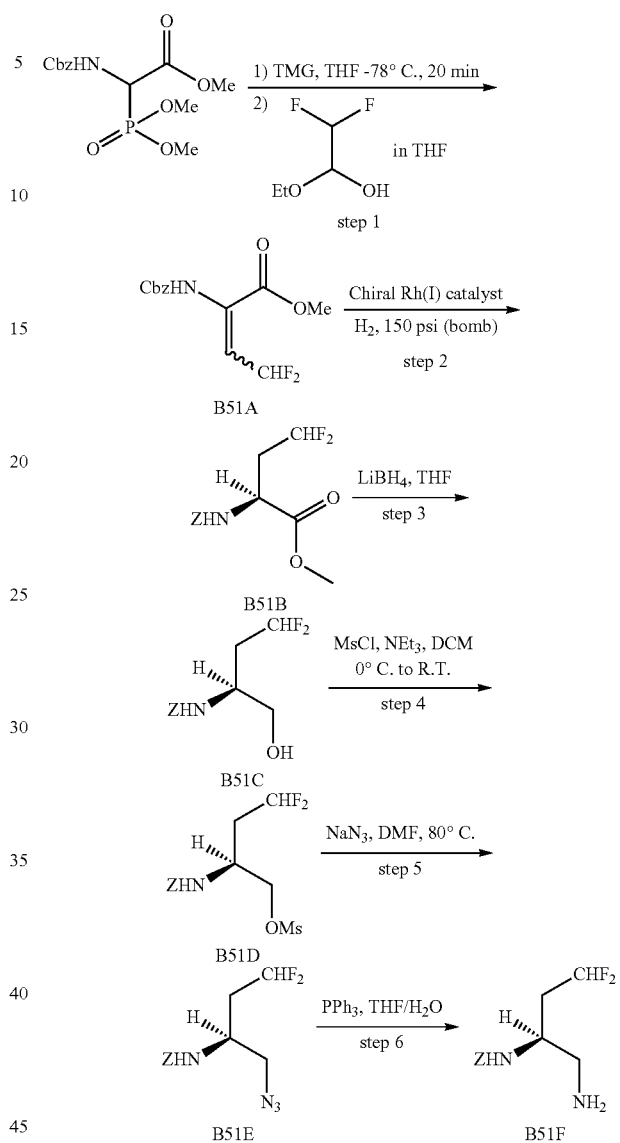

The amine (B51F) was reacted with 2,6-Dichloro-5-fluoro-3-pyridinecarbonitrile (J1) as seen below in Scheme 78, utilizing chemistry previously described in Example 97. In the final step, deprotection of the carbobenzyloxy-protected amine was carried out using BBr$_3$ in dichloromethane at 0° C. to give the title compound which was purified by rpHPLC.

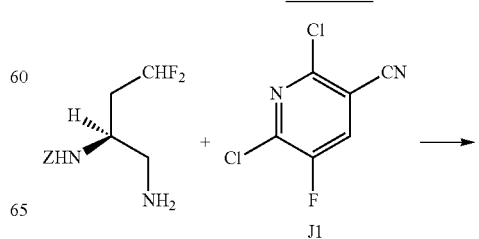

-continued

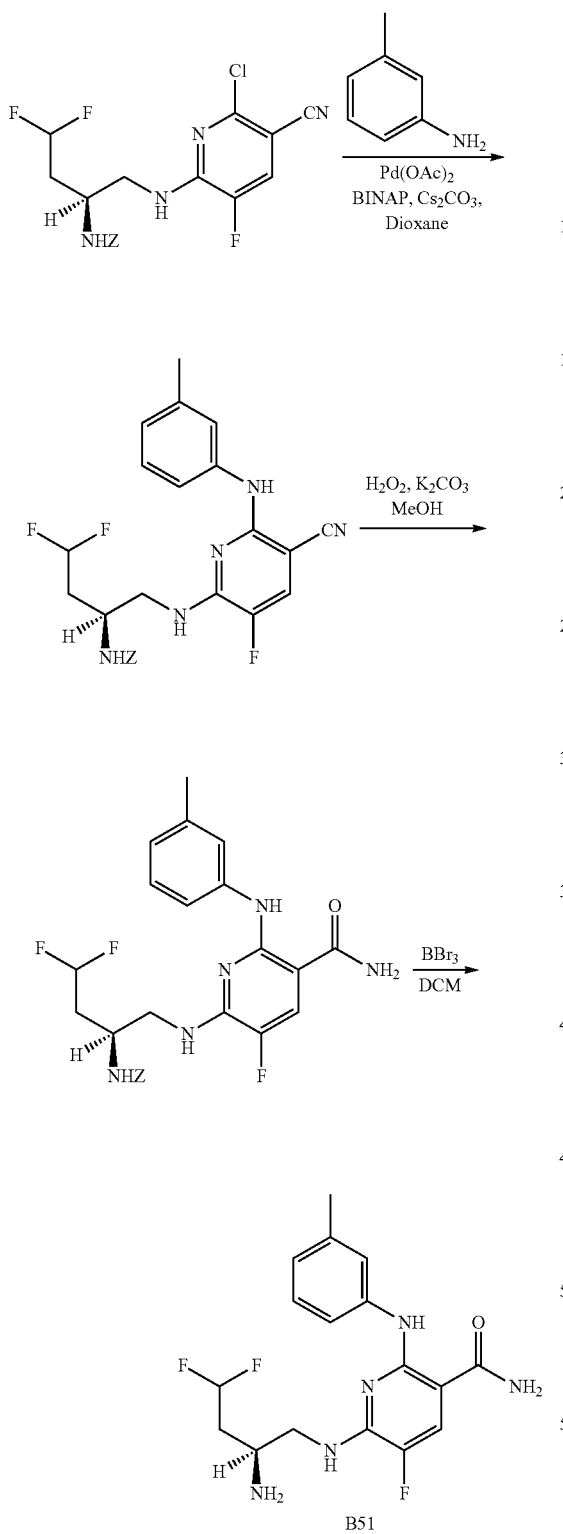

UV: 302 nm. M+H found for $C_{17}H_{20}F_3N_5O$: 368.5. NMR (CD$_3$OD): 7.75 (1H, dd, J=2.8, 12.0 Hz), 7.43 (1H, d, J=8.0 Hz), 7.24-7.16 (2H, m), 6.87 (1H, d, J=7.2 Hz), 5.97 (1H, t, J=55.2 Hz), 3.81-3.57 (3H, m), 2.34 (3H, s), 2.31-2.10 (2H, m) ppm.

Example 381

Preparation of (S)-2-(p-toluidino)-6-(2-amino-4,4-difluorobutylamino)-5-fluoronicotinamide

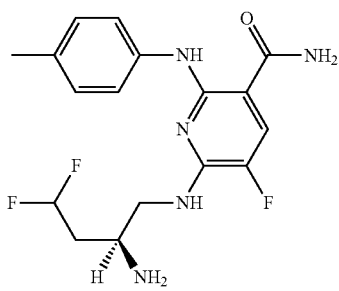 [SMILES: Cc1ccc(Nc2nc(NC[C@@H](N)CC(F)F)c(F)cc2C(N)=O)cc1]

Example 381 was synthesized analogously according to the procedures described for the preparation of Example 380. However, in Scheme 78, p-toluidine was utilized instead of m-toluidine. UV: 299 nm. M+H found for $C_{17}H_{20}F_3N_5O$: 368.5. NMR (CD$_3$OD): 7.74 (1H, dd, J=2.0, 12.0 Hz), 7.34 (2H, d, J=6.8 Hz), 7.15 (2H, J=7.2 Hz), 5.93 (1H, tt, J=3.2, 55.2 Hz), 3.81-3.72 (2H, m), 3.57-3.48 (1H, m), 2.31 (3H, s), 2.29-2.10 (2H, m) ppm.

Example 382

Preparation of (S)-6-(2-amino-4,4-difluorobutylamino)-5-fluoro-2-(5-fluoropyridin-3-ylamino)nicotinamide

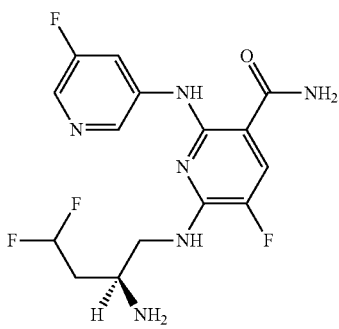 [SMILES: NC(=O)c1cc(F)c(NC[C@@H](N)CC(F)F)nc1Nc1cncc(F)c1]

Example 382 was synthesized analogously according to the procedures described for the preparation of Example 364. However, in Scheme 78, 3-Amino-5-fluoropyridine was utilized instead of m-toluidine. UV: 299 nm. M+H found for $C_{15}H_{16}F_4N_6O$: 373.5. NMR (CD$_3$OD): 8.70 (1H, s), 8.08-7.99 (2H, m), 7.85-7.82 (1H, m), 6.13 (1H, tt, J=4.0, 55.6 Hz), 3.87-3.81 (2H, m), 3.72-3.64 (1H, m), 2.42-2.17 (2H, m) ppm.

Example 383

Preparation of (R)-6-(pyrrolidin-3-ylamino)-2-(quinolin-6-ylamino)nicotinamide

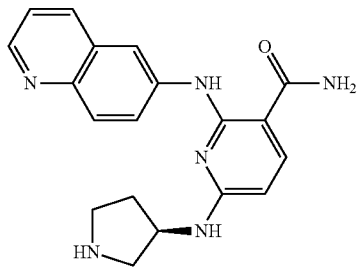 [SMILES: NC(=O)c1ccc(N[C@@H]2CCNC2)nc1Nc1ccc2ncccc2c1]

The title compound can be prepared using the same chemistry shown in Scheme 36 in Example 132.

Example 384

Preparation of 6-((3R,4R)-3-aminotetrahydro-2H-pyran-4-ylamino)-2-(benzo[d]thiazol-6-ylamino)-5-fluoronicotinamide

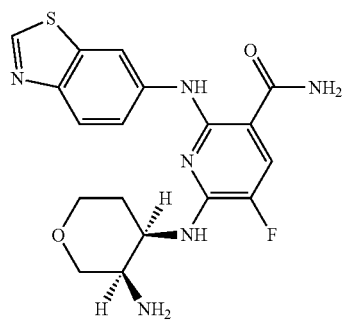 [SMILES: NC(=O)c1cc(F)c(N[C@@H]2CCOC[C@@H]2N)nc1Nc1ccc2ncsc2c1]

The title compound was synthesized using a procedure similar to that described in Example 279. MS found for C18H19FN6O2S as (M+H)+ 403.2. UV: λ=258, 325 nm. $^1$H NMR: (CD$_3$OD) δ 9.10 (1H, s), 8.45 (1H, d, J=2.0 Hz), 7.98 (1H, d, J=8.4 Hz), 7.80 (1H, d, J=11.6 Hz), 7.56 (1H, dd, J=8.8; 2.0 Hz), 4.46 (1H, m), 4.16 (1H, m), 3.90-3.85 (2H, m), 3.70-3.64 (2H, m), 2.07 (1H, m), 1.90 (1H, m) ppm.

Example 385

Preparation of 6-((3R,4R)-3-aminotetrahydro-2H-pyran-4-ylamino)-5-fluoro-2-(m-tolylamino)nicotinamide

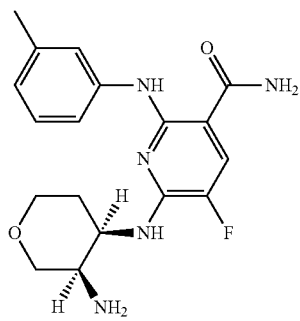 [SMILES: Cc1cccc(Nc2nc(N[C@@H]3CCOC[C@@H]3N)c(F)cc2C(N)=O)c1]

The title compound was synthesized using a procedure similar to that described in Example 279. MS found for C$_{18}$H$_{22}$FN$_5$O$_2$ as (M+H)+ 360.3. UV: λ=303, 349 nm. $^1$H NMR: (CD$_3$OD) δ 7.74 (1H, d, J=11.6 Hz), 7.41 (1H, dm, J=8.4 Hz), 7.20 (1H, d, J=2.8 Hz), 7.17 (1H, d, J=8.0 Hz), 6.84 (1H, d, J=7.2 Hz), 4.62 (1H, s), 4.33 (1H, m), 4.08 (1H, m), 3.92-3.89 (2H, m), 3.66-3.60 (2H, m), 2.33 (3H, s), 2.05 (1H, m), 1.88 (1H, m) ppm.

Example 386

Preparation of 6-((3R,4R)-3-aminotetrahydro-2H-pyran-4-ylamino)-2-(3-chlorophenylamino)-5-fluoronicotinamide

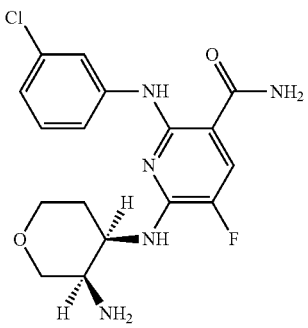 [SMILES: NC(=O)c1cc(F)c(N[C@@H]2CCOC[C@@H]2N)nc1Nc1cccc(Cl)c1]

The title compound was synthesized using a procedure similar to that described in Example 279. MS found for C17H19ClFN5O2 as (M+H)+ 380.3. UV: λ=266, 305, 347 nm. $^1$H NMR: (CD$_3$OD) δ 7.96 (1H, t, J=2.0 Hz), 7.78 (1H, d, J=11.6 Hz), 7.26 (1H, t, J=8.0 Hz), 7.17 (1H, dm, J=9.2 Hz), 6.98 (1H, dm, J=8.4 Hz), 4.43 (1H, m), 4.10 (1H, m), 3.97 (1H, d, J=12.0 Hz), 3.87-3.84 (2H, m), 3.66 (1H, td, J=12.0; 2.4 Hz), 2.08 (1H, m), 1.90 (1H, m) ppm.

Example 387

Preparation of 6-((1R,2R)-2-amino-3,3-difluorocyclohexylamino)-5-fluoro-2-(1-methyl-1H-indazol-4-ylamino)nicotinamide

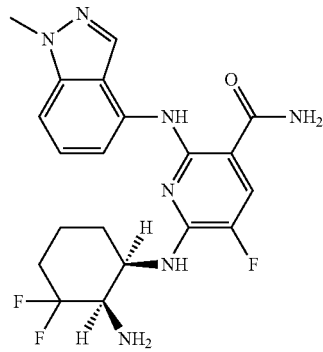 [SMILES: Cn1ncc2c(Nc3nc(N[C@@H]4CCCC(F)(F)[C@@H]4N)c(F)cc3C(N)=O)cccc21]

The title compound was synthesized using a procedure similar to that described in Example 291. MS found for C20H22F3N7O as (M+H)+ 434.3. UV: λ=261, 335 nm. $^1$H NMR: (CD$_3$OD) δ 8.07 (1H, d, J=0.8 Hz), 7.94 (1H, d, J=7.2 Hz), 7.86 (1H, d, J=11.6 Hz), 7.35 (1H, t, J=8.4 Hz), 7.13 (1H, d, J=8.8 Hz), 4.74 (1H, m), 4.24 (1H, m), 4.04 (3H, s), 2.16 (2H, m), 1.93 (3H, m), 1.78 (1H, m) ppm.

Example 388

Preparation of 6-((1S,6S)-6-amino-2,2-difluorocyclohexylamino)-2-(3-chlorophenylamino)-5-fluoronicotinamide

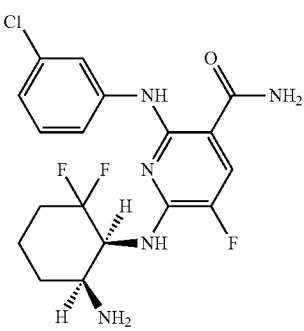 [SMILES: NC(=O)c1cc(F)c(N[C@H]2[C@@H](N)CCCC2(F)F)nc1Nc1cccc(Cl)c1]

The title compound was synthesized using a procedure similar to that described in Example 340. MS found for C18H19ClF3N5O as (M+H)+ 414.3. UV: λ=303, 347 nm. $^1$H NMR: (CD$_3$OD) δ 7.75 (1H, d, J=11.6 Hz), 7.75 (1H, t, J=2.4 Hz), 7.19-7.12 (2H, m), 6.87 (1H, dt, J=7.6; 2.4 Hz), 5.07 (1H, m), 3.67 (1H, m), 2.16 (1H, m), 1.98 (1H, m), 1.86 (3H, m), 1.68 (1H, m) ppm.

Example 389

Preparation of 6-((1S,6S)-6-amino-2,2-difluorocyclohexylamino)-5-fluoro-2-(1-methyl-1H-indazol-4-ylamino)nicotinamide

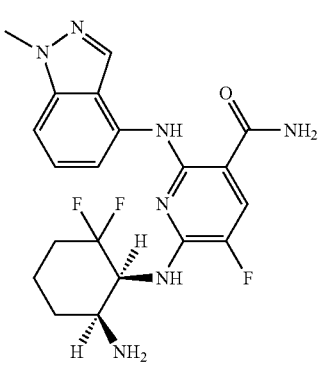 [SMILES: Cn1ncc2c(Nc3nc(N[C@H]4[C@@H](N)CCCC4(F)F)c(F)cc3C(N)=O)cccc21]

The title compound was synthesized using a procedure similar to that described in Example 340. MS found for C20H22F3N7O as (M+H)+ 434.3. UV: λ=261, 281, 332 nm. $^1$H NMR: (CD$_3$OD) δ 8.06 (1H, d, J=0.8 Hz), 7.90 (1H, d, J=11.6 Hz), 7.89 (1H, d, J=7.2 hz), 7.38 (1H, dd, J=8.4; 7.6 Hz), 7.16 (1H, d, J=8.8 Hz), 5.20 (1H, m), 4.05 (3H, s), 3.77 (1H, m), 2.28 (1H, m), 2.09 (1H, m), 1.90 (3H, m), 1.77 (1H, m) ppm.

Example 390

Preparation of 6-((1R,2R)-2-amino-3,3-difluorocyclohexylamino)-2-(1-ethyl-1H-indol-4-ylamino)-5-fluoronicotinamide

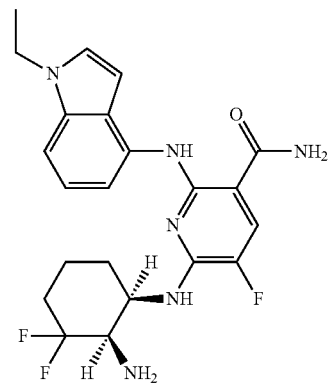 [SMILES: CCn1ccc2c(Nc3nc(N[C@@H]4CCCC(F)(F)[C@@H]4N)c(F)cc3C(N)=O)cccc21]

The title compound was synthesized using a procedure similar to that described in Example 291. MS found for C22H25F3N6O as (M+H)+ 447.3. UV: λ=325 nm. $^1$H NMR: (CD$_3$OD) δ 7.88 (1H, d, J=7.6 Hz), 7.81 (1H, d, J=11.6 Hz), 7.19 (1H, d, J=3.2 Hz), 7.14-7.06 (2H, m), 6.59 (1H, d, J=3.2 Hz), 4.76 (1H, m), 4.23 (1H, m), 4.20 (2H, d, J=7.2 Hz), 2.13 (2H, m), 1.93 (3H, m), 1.78 (1H, m), 1.43 (3H, t, J=7.2 Hz) ppm.

Example 391

Preparation of 6-((1R,2R)-2-amino-3,3-difluorocyclohexylamino)-5-fluoro-2-(1-isopropyl-1H-indol-4-ylamino)nicotinamide

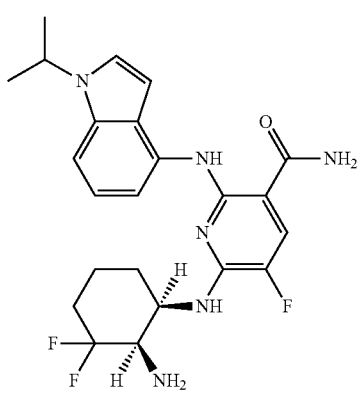 [SMILES: CC(C)n1ccc2c(Nc3nc(N[C@@H]4CCCC(F)(F)[C@@H]4N)c(F)cc3C(N)=O)cccc21]

The title compound was synthesized using a procedure similar to that described in Example 291. MS found for C23H27F3N6O as (M+H)+ 461.3. UV: λ=325 nm. $^1$H NMR: (CD$_3$OD) δ 7.91 (1H, m), 7.80 (1H, d, J=12.0 Hz), 7.31 (1H, d, J=3.6 Hz), 7.11-7.10 (2H, m), 6.63 (1H, d, J=3.2 Hz), 4.75

(1H, m), 4.72 (1H, m), 4.16 (1H, m), 2.13 (2H, m), 1.91 (3H, m), 1.77 (1H, m), 1.52 (6H, d, J=6.4 Hz) ppm.

Example 392

Preparation of 6-((1R,2R)-2-amino-3,3-difluorocyclohexylamino)-5-fluoro-2-(1-isobutyl-1H-indol-4-ylamino)nicotinamide

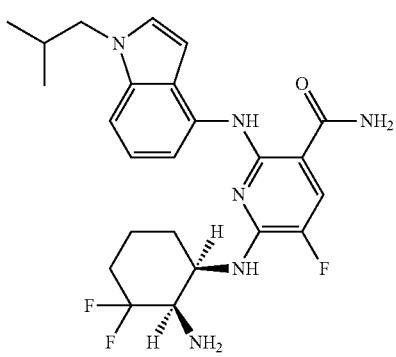 [SMILES: CC(C)Cn1ccc2c(Nc3nc(N[C@@H]4CCCC(F)(F)[C@@H]4N)c(F)cc3C(N)=O)cccc21]

The title compound was synthesized using a procedure similar to that described in Example 291. MS found for C24H29F3N6O as (M+H)+ 475.4. UV: λ=325 nm. ¹H NMR: (CD₃OD) δ 7.90 (1H, d, J=7.2 Hz), 7.81 (1H, d, J=11.6 Hz), 7.15 (1H, d, J=3.2 Hz), 7.11 (1H, t, J=7.2 Hz), 7.05 (1H, d, J=8.4 Hz), 6.59 (1H, d, J=3.2 Hz), 4.76 (1H, m), 4.21 (1H, m), 3.95 (2H, d, J=7.2 Hz), 2.23-2.11 (3H, m), 1.93 (3H, m), 1.79 (1H, m), 0.91 (6H, d, J=6.8 Hz) ppm.

Example 393

Preparation of 6-(1R,2S)-2-aminocyclohexylamino)-5-fluoro-2-(thieno[2,3-b]pyridin-3-ylamino)nicotinamide

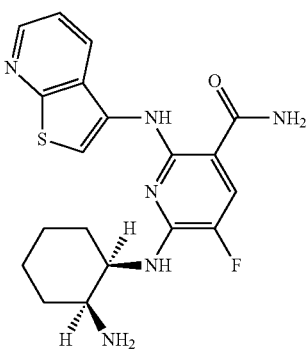 [SMILES: NC(=O)c1cc(F)c(N[C@@H]2CCCC[C@@H]2N)nc1Nc1csc2ncccc12]

The title compound was synthesized using a procedure similar to that described in Example 78. MS found for C19H21FN6OS as (M+H)+ 401.3. UV: λ=226, 266, 347 nm. ¹H NMR: (CD₃OD) δ 8.59 (1H, dd, J=4.8; 2.4 Hz), 8.23 (1H, dd, J=8.0; 1.6 Hz), 7.85 (1H, d, J=11.6 Hz), 7.85 (1H, s), 7.52 (1H, dd, J=8.0; 4.8 Hz), 4.38 (1H, m), 3.82 (1H, m), 1.85-1.61 (8H, m) ppm.

Example 394

Preparation of 6-((1R,2S)-2-aminocyclohexylamino)-5-fluoro-2-(thieno[3,2-c]pyridin-3-ylamino)nicotinamide

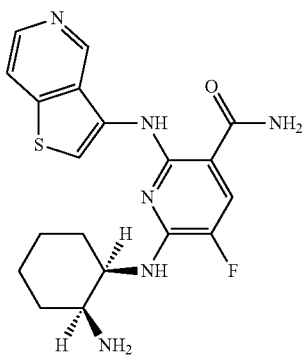 [SMILES: NC(=O)c1cc(F)c(N[C@@H]2CCCC[C@@H]2N)nc1Nc1csc2ccncc12]

The title compound was synthesized using a procedure similar to that described in Example 78. MS found for C19H21FN6OS as (M+H)+ 401.3. UV: λ=216, 240, 282, 344 nm. ¹H NMR: (CD₃OD) δ 9.16 (1H, s), 8.53 (1H, d, J=6.0 Hz), 8.36 (1H, d, J=5.2 Hz), 8.10 (1H, s), 7.89 (1H, d, J=11.6 Hz), 4.45 (1H, m), 3.79 (1H, m), 1.87-1.62 (8H, m) ppm.

Example 395

Preparation of 6-((1R,2R)-2-amino-3,3-difluorocyclohexylamino)-5-fluoro-2-(1-methyl-2-oxoindolin-4-ylamino)nicotinamide

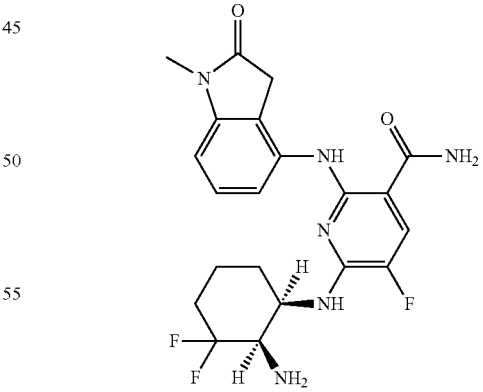

The title compound was found and isolated as a major byproduct during the preparation of 6-((1R,2R)-2-amino-3,3-difluorocyclohexylamino)-5-fluoro-2-(1-methyl-1H-indol-4-ylamino)nicotinamide (Example 330). MS found for C21H23F3N6O2 as (M+H)+ 449.3. UV: λ=244, 301, 347 nm. ¹H NMR: (CD₃OD) δ 7.91 (1H, d, J=8.8 Hz), 7.80 (1H, d, J=11.6 Hz), 7.25 (1H, t, J=8.0 Hz), 6.65 (1H, d, J=7.2 Hz), 4.69 (1H, m), 4.23 (1H, m), 3.47 (2H, d, J=11.6 Hz), 3.20 (3H, s), 2.15 (2H, m), 1.91 (3H, m), 1.78 (1H, m) ppm.

Example 396

Preparation of 6-((1R,2S)-2-aminocyclohexylamino)-2-(1-methyl-1H-indol-4-ylamino)nicotinamide

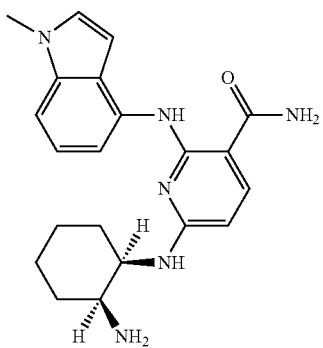 [SMILES: Cn1ccc2c(Nc3nc(N[C@@H]4CCCC[C@@H]4N)ccc3C(N)=O)cccc21]

The title compound was synthesized using a procedure similar to that described in Example 157. MS found for C21H26N6O as (M+H)+ 379.4. UV: λ=283, 335 nm. $^1$H NMR: (CD$_3$OD) δ 8.01 (1H, m), 7.61 (1H, m), 7.26-7.22 (3H, m), 6.51 (1H, m), 6.21 (1H, m), 4.28 (1H, m), 4.07 (3H, s), 3.55 (1H, m), 1.93-1.52 (8H, m) ppm.

Example 397

Preparation of 6-((1R,2S)-2-aminocyclohexylamino)-2-(1-methyl-1H-indol-5-ylamino)nicotinamide

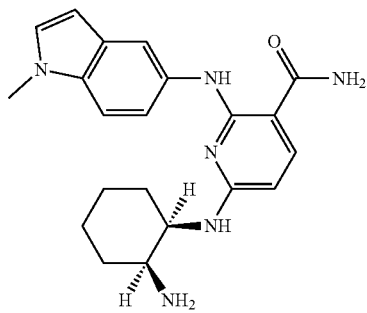 [SMILES: Cn1ccc2cc(Nc3nc(N[C@@H]4CCCC[C@@H]4N)ccc3C(N)=O)ccc21]

The title compound was synthesized using a procedure similar to that described in Example 157. MS found for C21H26N6O as (M+H)+ 379.3. UV: λ=278, 354 nm. $^1$H NMR: (CD$_3$OD) δ 7.66 (1H, m), 7.49 (1H, m), 7.26 (1H, m), 7.19 (1H, m), 7.17 (1H, m), 6.49 (1H, m), 6.16 (1H, m), 4.22 (1H, m), 3.88 (3H, s), 3.48 (1H, m), 1.79-1.50 (8H, m) ppm.

Example 398

Preparation of 6-((1R,2S)-2-aminocyclohexylamino)-2-(1-methyl-1H-indazol-4-ylamino)nicotinamide

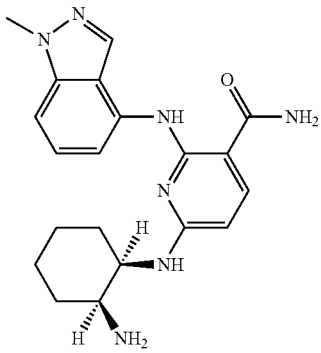 [SMILES: Cn1ncc2c(Nc3nc(N[C@@H]4CCCC[C@@H]4N)ccc3C(N)=O)cccc21]

The title compound was synthesized using a procedure similar to that described in Example 157. MS found for C20H25N7O as (M+H)+ 380.3. UV: λ=276, 335 nm. $^1$H NMR: (CD3OD) δ 8.08 (1H, s), 7.94 (1H, d, J=7.2 Hz), 7.86 (1H, d, J=8.4 Hz), 7.40 (1H, t, J=8.0 Hz), 7.16 (1H, d, J=8.8 Hz), 6.17 (1H, d, J=8.8 Hz), 4.40 (1H, m), 4.05 (3H, s), 3.76 (1H, m), 1.83-1.61 (8H, m) ppm.

Example 399

Preparation of 6-((1R,2S)-2-aminocyclohexylamino)-2-(1-methyl-1H-indazol-5-ylamino)nicotinamide

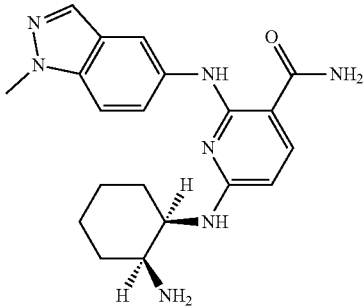 [SMILES: Cn1ncc2cc(Nc3nc(N[C@@H]4CCCC[C@@H]4N)ccc3C(N)=O)ccc21]

The title compound was synthesized using a procedure similar to that described in Example 157. MS found for C20H25N7O as (M+H)+ 380.3. UV: λ=278, 349 nm. $^1$H NMR: (CD₃OD) δ 8.08-7.96 (4H, m), 7.65 (1H, m), 7.45 (1H, m), 4.24 (1H, m), 4.10 (3H, s), 3.55 (1H, m), 1.81-1.58 (8H, m) ppm.

Example 400

Preparation of 6-((1R,2S)-2-aminocyclohexylamino)-2-(benzo[d]thiazol-5-ylamino)nicotinamide

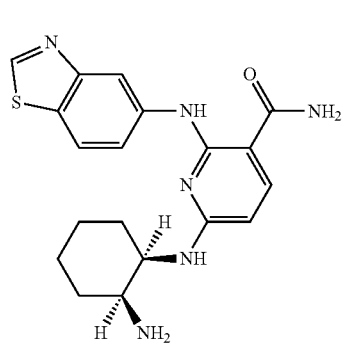 [SMILES: NC(=O)c1ccc(N[C@@H]2CCCC[C@@H]2N)nc1Nc1ccc2scnc2c1]

The title compound was synthesized using a procedure similar to that described in Example 157. MS found for C19H22N6OS as (M+H)⁺ 383.3. UV: λ=268, 301 nm. ¹H NMR: (CD3OD) δ 9.25 (1H, s), 8.74 (1H, d, J=2.0 Hz), 7.97 (1H, d, J=8.4 Hz), 7.85 (1H, d, J=8.4 Hz), 7.41 (1H, dd, J=8.8; 1.6 Hz), 6.17 (1H, d, J=8.8 Hz), 4.51 (1H, m), 3.77 (1H, m), 1.90-1.65 (8H, m) ppm.

Example 401

Preparation of 6-((1R,2S)-2-aminocyclohexylamino)-2-(benzo[d]thiazol-7-ylamino)nicotinamide

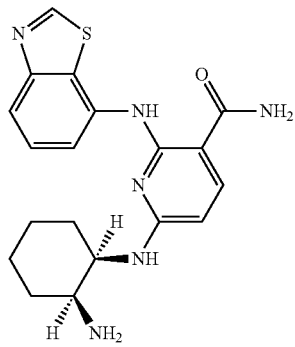 [SMILES: NC(=O)c1ccc(N[C@@H]2CCCC[C@@H]2N)nc1Nc1cccc2ncsc12]

The title compound was synthesized using a procedure similar to that described in Example 157. MS found for C19H22N6OS as (M+H)⁺ 383.3. UV: λ=244, 268, 330 nm. ¹H NMR: (CD3OD) δ 9.25 (1H, s), 8.05 (1H, d, J=8.0 Hz), 7.86 (1H, d, J=8.8 Hz), 7.82 (1H, dd, J=8.4; 1.2 Hz), 7.58 (1H, t, J=8.4 Hz), 6.17 (1H, d, J=8.8 Hz), 4.16 (1H, m), 3.54 (1H, m), 1.74-1.51 (8H, m) ppm.

Example 402

Preparation of 6-((1R,2S)-2-aminocyclohexylamino)-2-(thieno[2,3-b]pyridin-3-ylamino)nicotinamide

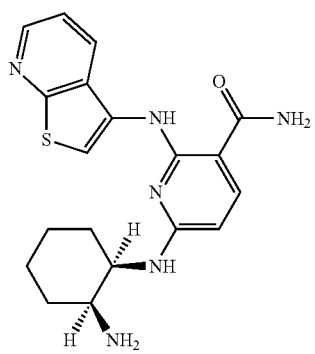 [SMILES: NC(=O)c1ccc(N[C@@H]2CCCC[C@@H]2N)nc1Nc1csc2ncccc12]

The title compound was synthesized using a procedure similar to that described in Example 157. MS found for C19H22N6OS as (M+H)⁺ 383.3. UV: λ=230, 263, 332 nm. ¹H NMR: (CD3OD) δ 8.64 (1H, dd, J=4.4; 1.6 Hz), 8.34 (1H, dd, J=8.4; 1.6 Hz), 7.99 (1H, s), 7.90 (1H, d, J=8.4 Hz), 7.60 (1H, dd, J=8.0; 4.8 Hz), 6.21 (1H, d, J=9.2 Hz), 4.44 (1H, m), 3.69 (1H, m), 1.84-1.56 (8H, m) ppm.

Example 403

Preparation of 6-((1R,2S)-2-aminocyclohexylamino)-2-(benzo[d]thiazol-6-ylamino)nicotinamide

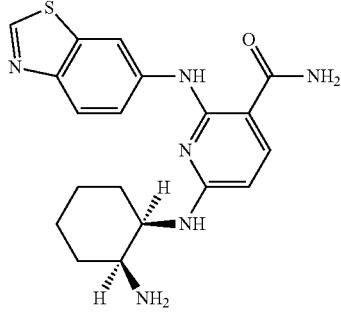 [SMILES: NC(=O)c1ccc(N[C@@H]2CCCC[C@@H]2N)nc1Nc1ccc2ncsc2c1]

The title compound was synthesized using a procedure similar to that described in Example 157. MS found for C19H22N6OS as (M+H)⁺ 383.3. UV: λ=259, 332 nm. ¹H NMR: (CD3OD) δ 9.18 (1H, s), 8.52 (1H, d, J=1.6 Hz), 8.02

(1H, d, J=8.8 Hz), 7.90 (1H, d, J=8.0 Hz), 7.62 (1H, dd, J=9.2; 2.0 Hz), 6.19 (1H, d, J=8.8 Hz), 4.38 (1H, m), 3.72 (1H, m), 1.82-1.58 (8H, m) ppm.

Example 404

Preparation of 6-((1R,2S)-2-aminocyclohexylamino)-2-(2-hydroxybenzo[d]thiazol-6-ylamino)nicotinamide

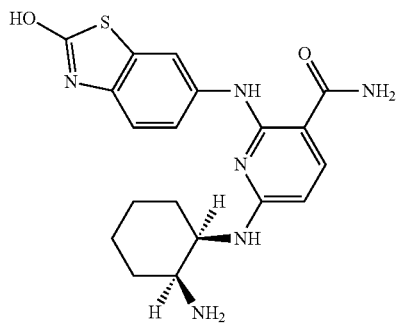 [SMILES: NC(=O)c1ccc(N[C@@H]2CCCC[C@@H]2N)nc1Nc1ccc2nc(O)sc2c1]

The title compound was found and isolated as a minor byproduct during the preparation of 6-((1R,2S)-2-aminocyclohexylamino)-2-(benzo[d]thiazol-6-ylamino)nicotinamide (Example 412). MS found for C19H22N6O2S as (M+H)+ 399.3. UV: λ=281, 347 nm. $^1$H NMR: (CD3OD) δ 7.90 (1H, s), 7.73 (1H, s), 7.20 (1H, dd, J=8.8; 2.0 Hz), 7.09 (1H, d, J=8.8 Hz), 6.11 (1H, d, J=8.4 Hz), 4.17 (1H, m), 3.53 (1H, m), 1.70-1.45 (8H, m) ppm.

Example 405

Preparation of 6-((1R,2R)-2-amino-3,3-difluorocyclohexylamino)-5-fluoro-2-(thieno[2,3-b]pyridin-3-ylamino)nicotinamide

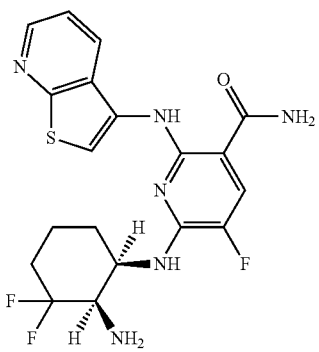 [SMILES: NC(=O)c1cc(F)c(N[C@@H]2CCCC(F)(F)[C@@H]2N)nc1Nc1csc2ncccc12]

The title compound was synthesized using a procedure similar to that described in Example 291. MS found for C19H19F3N6OS as (M+H)+ 437.3. UV: λ=226, 263, 347 nm. $^1$H NMR: (CD3OD) δ 8.58 (1H, d, J=4.8 Hz), 8.24 (1H, d, J=8.4 Hz), 7.90 (1H, d, J=11.6 Hz), 7.89 (1H, s), 7.51 (1H, ddd, J=8.0; 4.8; 0.8 Hz), 4.81 (1H, m), 4.24 (1H, m), 2.17-1.79 (6H, m) ppm.

Example 406

Preparation of 2-(1,6-naphthyridin-3-ylamino)-6-((1R,2S)-2-aminocyclohexylamino)nicotinamide

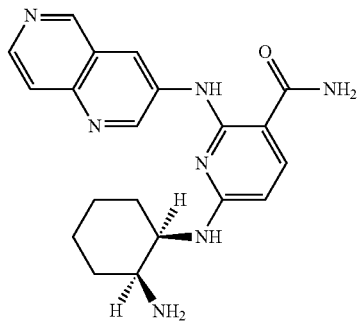 [SMILES: NC(=O)c1ccc(N[C@@H]2CCCC[C@@H]2N)nc1Nc1cnc2ccncc2c1]

The title compound was synthesized using a procedure similar to that described in Example 157. MS found for C20H23N7O as (M+H)+ 378.4. UV: λ=266, 332 nm. $^1$H NMR: (CD3OD) δ 9.77 (1H, s), 9.54 (1H, s), 9.23 (1H, s), 8.62 (1H, d, J=6.4 Hz), 8.38 (1H, d, J=6.4 Hz), 7.92 (1H, d, J=8.8 Hz), 6.37 (1H, d, J=8.8 Hz), 4.59 (1H, m), 3.74 (1H, m), 1.92-1.60 (8H, m) ppm.

Example 407

Preparation of 2-(1H-pyrrolo[3,2-b]pyridin-6-ylamino)-6-(1R,2S)-2-aminocyclohexylamino)nicotinamide

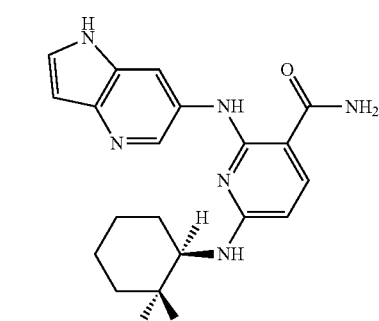

The title compound was synthesized using a procedure similar to that described in Example 157. MS found for C19H23N7O as (M+H)+ 366.4. UV: λ=282, 325 nm. $^1$H NMR: (CD3OD) δ 9.10 (1H, m), 8.72 (1H, m), 8.04 (1H, m), 7.93 (1H, m), 6.92 (1H, m), 6.31 (1H, m), 4.43 (1H, m), 3.61 (1H, m), 1.85-1.63 (8H, m) ppm.

Example 408

Preparation of 3-(6-((1R,2S)-2-aminocyclohexylamino)-3-carbamoyl-5-fluoropyridin-2-ylamino)-5-fluoropyridine 1-oxide

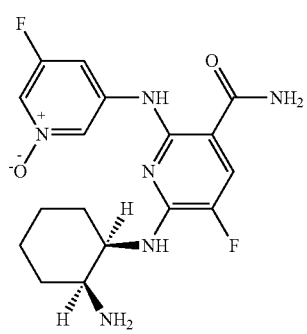

Compound tert-butyl (1S,2R)-2-(5-cyano-3-fluoro-6-(5-fluoropyridin-3-ylamino)pyridin-2-ylamino)cyclohexylcarbamate was synthesized using a procedure similar to that described in Example 41. This compound (175 mg, 0.40 mmol) was dissolved in 10 mL MeOH and 2 mL DMSO. To it were added 100 mg KOH and then 1 mL $H_2O_2$ (50 wt %). The mixture was stirred at RT for 40 m and quenched with acetonitrile. It was diluted with EtOAc and washed with brine three times. The organic phase was dried and concentrated in vacuo to dryness. It was dissolved in 8 mL DMF. To it was added MCPBA (400 mg) and the mixture was stirred at RT for overnight. It was diluted with EtOAc and washed with 1N NaOH solution three times. The organic phase was dried and concentrated in vacuo. The residue was then treated with 2:1 DCM/TFA at RT for 15 m. The mixture was concentrated in vacuo and subjected to reverse phase HPLC to isolate the title compound. MS found for $C_{17}H_{20}F_2N_6O_2$ as $(M+H)^+$ 379.3. UV: λ=263, 306, 332 nm. $^1$H NMR: (CD3OD) δ 9.15 (1H, s), 8.07 (1H, m), 7.86 (1H, d, J=11.6 Hz), 7.52 (1H, dt, J=9.6; 2.0 Hz), 4.46 (1H, m), 3.83 (1H, m), 2.08-1.63 (8H, m) ppm.

Example 411

Preparation or 6-((1R,2S)-2-aminocyclohexylamino)-5-fluoro-2-(1-methyl-1H-pyrrolo[2,3-b]pyridin-4-ylamino)nicotinamide

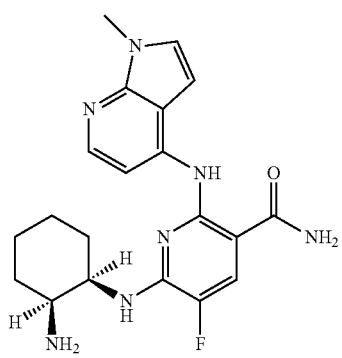 [SMILES: Cn1ccc2c(Nc3nc(N[C@@H]4CCCC[C@@H]4N)c(F)cc3C(N)=O)ccnc21]

The title compound was synthesized using a procedure similar to that described in the Scheme B2.

Scheme B2.

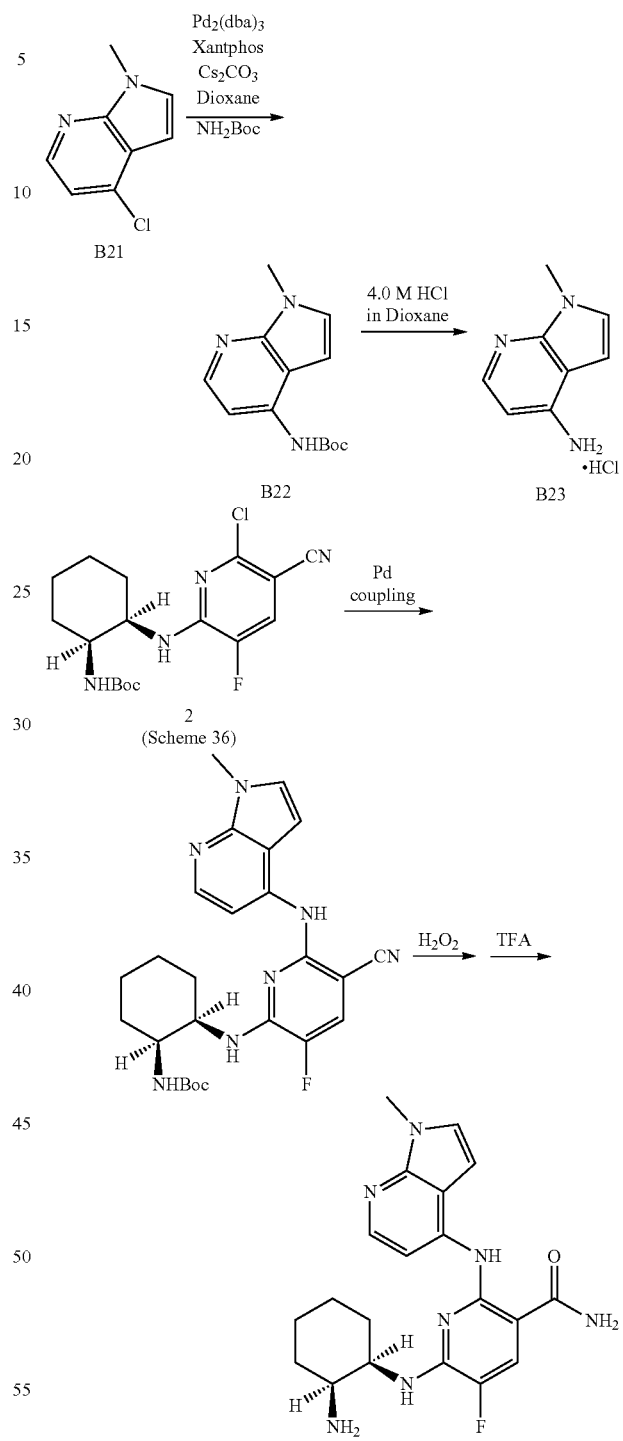

Commercially available 4-chloro-1-methyl-1H-pyrrolo[2,3-b]pyridine (B21) was converted to B22 as described in example 183. Boc-deprotection using 4.0 M HCl in dioxane provided B23 which was reacted with 2 as described in Scheme 43 (Pd(dba)$_2$, Q-Phos). Subsequent hydration of the nitrile (scheme 43) and Boc deprotection (TFA in DCM) afforded crude product that was purified via reverse phase HPLC. MS found for $C_{20}H_{24}FN_7O$ as $(M+H)^+$ 398.3. UV: λ=205, 263, 284, 351 nm. $^1$H NMR: (CD3OD) δ 8.48 (1H, d, J=6.4 Hz), 8.24 (1H, d, 6.8 Hz), 7.96 (1H, d, J=12 Hz), 7.42 (1H, d, 3.6 Hz), 6.85 (1H, d, 3.2 Hz), 4.81-4.74 (1H, m), 3.95-3.90 (4H, m), 2.05-1.64 (8H, m) ppm.

Example 412

Preparation of 6-((1S,6S)-6-amino-2,2-difluorocyclohexylamino)-2-(thieno[2,3-b]pyridin-3-ylamino)nicotinamide

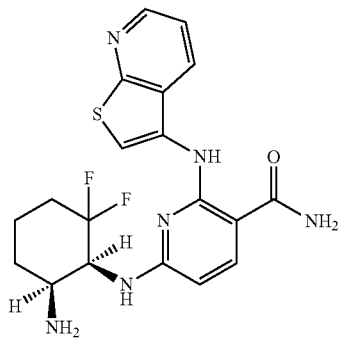 [SMILES: NC(=O)c1ccc(N[C@H]2[C@@H](N)CCCC2(F)F)nc1Nc1csc2ncccc12]

The title compound was synthesized using a procedure similar to that described in Example 132. Intermediate J75 (see scheme 69) was reacted with 2,6-dichloropyridine-3-carbonitrile with DIEA in DMF. After work-up, the resulting mixture was purified via normal phase chromatography. The appropriate regioisomeric product was coupled with 3-aminothieno[2,3-b]pyridine in a manner described in scheme 43 (Pd(dba)$_2$ and Q-Phos). Subsequent Boc deprotection (TFA in DCM) followed by hydration of the nitrile (scheme 43) afforded crude product that was purified via reverse phase HPLC. MS found for C19H20F2N6SO as (M+H)$^+$ 419.3. UV: λ=226, 263, 331 nm. $^1$H NMR: (CD3OD) δ 8.58 (1H, dd, J=1.6, 4.8 Hz), 8.23 (1H, dd, J=1.6, 8.0 Hz), 7.98 (1H, s), 7.94 (1H, d, J=8.4 Hz), 7.51 (1H, dd, J=4.8, 8.0 Hz), 6.28 (1H, d, J=8.4 Hz), 5.07-5.00 (1H, m), 3.79-3.72 (1H, m), 2.28-1.75 (6H, m) ppm.

Example 413

Preparation of 6-((1S,6S)-6-amino-2,2-difluorocyclohexylamino)-2-(3-(thiazol-2-yl)phenylamino)nicotinamide

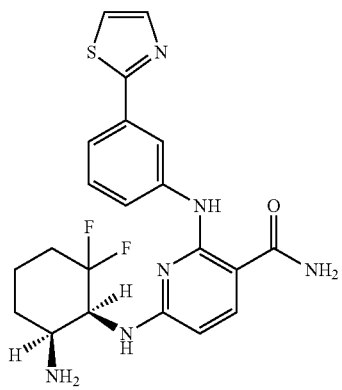 [SMILES: NC(=O)c1ccc(N[C@H]2[C@@H](N)CCCC2(F)F)nc1Nc1cccc(-c2nccs2)c1]

The title compound was synthesized using a procedure similar to that described in Example 132. Intermediate J75 (see scheme 69) was reacted with 2,6-dichloropyridine-3-carbonitrile with DIEA in DMF. After work-up, the resulting mixture was purified via normal phase chromatography. The appropriate regioisomeric product was coupled with 3-(thiazol-2-yl)aniline (see example 189) in a manner described in scheme 43 (Pd(dba)$_2$ and Q-Phos). Subsequent Boc deprotection (TFA in DCM) followed by hydration of the nitrile (scheme 43) afforded crude product that was purified via reverse phase HPLC. MS found for C21H22F2N6SO as (M+H)$^+$ 445.3. UV: k=302 nm. $^1$H NMR: (CD3OD) δ 8.65 (1H, dd, J=0.8, 1.2 Hz), 7.90 (1H, d, J=1.2 Hz), 7.88 (1H, d, J=4.0 Hz), 7.64 (1H, d, J=3.6 Hz), 7.54-7.49 (1H, m), 7.43-7.39 (1H, m), 6.26 (1H, d, J=8.4 Hz), 5.20-5.10 (1H, m), 3.78-3.70 (1H, m), 2.38-1.65 (6H, m) ppm.

Example 414

Preparation of 2-(3-(2H-1,2,3-triazol-2-yl)phenylamino)-6-((1S,6S)-6-amino-2,2-difluorocyclohexylamino)nicotinamide

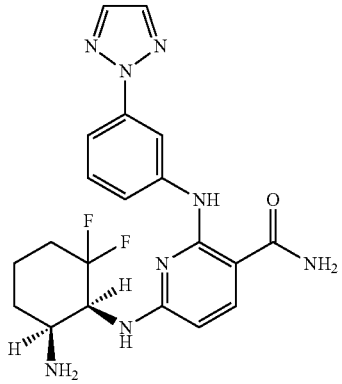 [SMILES: NC(=O)c1ccc(N[C@H]2[C@@H](N)CCCC2(F)F)nc1Nc1cccc(-n2nccn2)c1]

The title compound was synthesized using a procedure similar to that described in Example 132. Intermediate J75 (see scheme 69) was reacted with 2,6-dichloropyridine-3-carbonitrile with DIEA in DMF. After work-up, the resulting mixture was purified via normal phase chromatography. The appropriate regioisomeric product was coupled with 3-(2H-1,2,3-triazol-2-yl)aniline in a manner described in scheme 43 (Pd(dba)$_2$ and Q-Phos). Subsequent Boc deprotection (TFA in DCM) followed by hydration of the nitrile (scheme 43) afforded crude product that was purified via reverse phase HPLC. MS found for C20H22F2N8O as (M+H)$^+$ 429.3. UV: λ=264, 305 nm. $^1$H NMR: (CD3OD) δ 8.91 (1H, dd, J=2.0, 2.4 Hz), 7.95 (2H, s), 7.90 (1H, d, J=8.4 Hz), 7.71-7.65 (1H, m), 7.43 (1H, t, J=8.0 Hz), 7.27-7.22 (1H, m), 6.27 (1H, d, J=8.4 Hz), 5.32-5.26 (1H, m), 3.82-3.74 (1H, m), 2.30-1.70 (6H, m) ppm.

Example 415

Preparation of 6-((1S,6S)-6-amino-2,2-difluorocyclohexylamino)-2-(quinolin-6-ylamino)nicotinamide

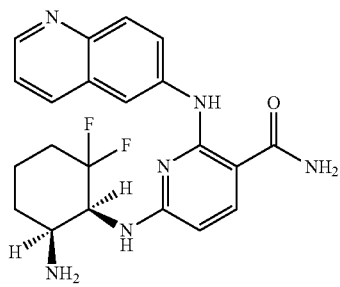 [SMILES: NC(=O)c1ccc(N[C@H]2[C@@H](N)CCCC2(F)F)nc1Nc1ccc2ncccc2c1]

The title compound was synthesized using a procedure similar to that described in Example 132. Intermediate J75 (see scheme 69) was reacted with 2,6-dichloropyridine-3-carbonitrile with DIEA in DMF. After work-up, the resulting mixture was purified via normal phase chromatography. The appropriate regioisomeric product was coupled with 6-aminoquinoline in a manner described in scheme 43 (Pd(dba)2 and Q-Phos). Subsequent Boc deprotection (TFA in DCM) followed by hydration of the nitrile (scheme 43) afforded crude product that was purified via reverse phase HPLC. MS found for C21H22F2N6O as (M+H)$^+$ 413.3. UV: $\lambda$=263, 296, 325 nm. $^1$H NMR: (CD3OD) $\delta$ 8.82 (1H, dd, J=1.2, 4.8 Hz), 8.76 (1H, d, 1.2 Hz), 8.62 (1H, d, J=8.8 Hz), 8.08-7.98 (2H, m), 7.95 (1H, d, J=9.2 Hz), 7.75 (1H, dd, 4.8, 8.4 Hz), 6.36 (1H, d, J=8.8 Hz), 5.36-5.29 (1H, m), 3.75-3.68 (1H, m), 2.25-1.71 (6H, m) ppm.

Example 416

Preparation of 6-((1R,2R)-2-amino-3,3-difluorocyclohexylamino)-2-(quinolin-6-ylamino)nicotinamide

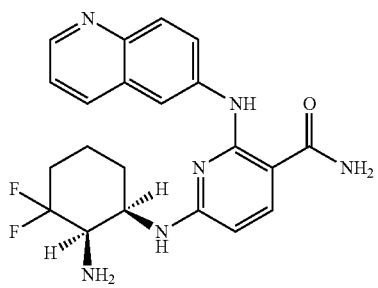 [SMILES: NC(=O)c1ccc(N[C@@H]2CCCC(F)(F)[C@@H]2N)nc1Nc1ccc2ncccc2c1]

The title compound was synthesized using a procedure similar to that described in Example 132. Intermediate J68 (see scheme 64) was reacted with 2,6-dichloropyridine-3-carbonitrile with DIEA in DMF. After work-up, the resulting mixture was purified via normal phase chromatography. The appropriate regioisomeric product was coupled with 6-aminoquinoline in a manner described in scheme 43 (Pd(dba)2 and Q-Phos). Subsequent hydration of the nitrile (scheme 43) afforded crude product that was purified via reverse phase HPLC. MS found for C21H22F2N6O as (M+H)$^+$ 413.2. UV: $\lambda$=265, 297, 328 nm. $^1$H NMR: (CD3OD) $\delta$ 8.89 (1H, d, J=5.2 Hz), 8.86-8.79 (1H, m), 8.62 (1H, s), 8.22 (1H, dd, J=2.4, 9.2 Hz), 8.09 (1H, d, J=9.2 Hz), 7.92 (1H, d, J=9.2 Hz), 7.89-7.83 (1H, m), 6.15 (1H, d, J=9.2 Hz), 5.01-4.95 (1H, m), 4.28-4.20 (1H, m), 2.38-1.80 (6H, m) ppm.

Example 417

Preparation of 6-((1R,2R)-2-amino-3,3-difluorocyclohexylamino)-2-(quinolin-7-ylamino)nicotinamide

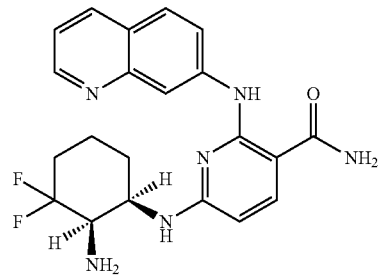 [SMILES: NC(=O)c1ccc(N[C@@H]2CCCC(F)(F)[C@@H]2N)nc1Nc1ccc2cccnc2c1]

The title compound was synthesized using a procedure similar to that described in Example 132. Intermediate J68 (see scheme 64) was reacted with 2,6-dichloropyridine-3-carbonitrile with DIEA in DMF. After work-up, the resulting mixture was purified via normal phase chromatography. The appropriate regioisomeric product was coupled with 7-aminoquinoline in a manner described in scheme 43 (Pd(dba)2 and Q-Phos). Subsequent hydration of the nitrile (scheme 43) afforded crude product that was purified via reverse phase HPLC. MS found for C21H22F2N6O as (M+H)$^+$ 413.3. UV: $\lambda$=263, 294 nm. $^1$H NMR: (CD3OD) $\delta$ 8.72 (1H, dd, J=1.6, 4.4 Hz), 8.29-8.22 (2H, m), 8.09 (1H, br), 7.81 (2H, dd, J=3.2, 8.8 Hz), 7.34 (1H, dd, J=4.0, 8.0 Hz), 6.09 (1H, d, J=9.2 Hz), 4.65-4.59 (1H, m), 4.51-4.43 (1H, m) 3.58-3.48 (2H, m), 2.20-2.02 (2H, m), 1.95-1.63 (4H, m) ppm.

Example 418

Preparation of 6-((1R,2R)-2-amino-3,3-difluorocyclohexylamino)-2-(1-methyl-1H-indol-4-ylamino)nicotinamide

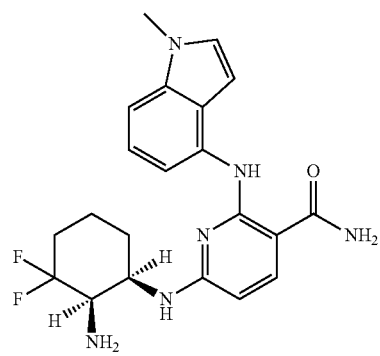 [SMILES: Cn1ccc2c(Nc3nc(N[C@@H]4CCCC(F)(F)[C@@H]4N)ccc3C(N)=O)cccc21]

The title compound was synthesized using a procedure similar to that described in Example 132. Intermediate J68 (see scheme 64) was reacted with 2,6-dichloropyridine-3-carbonitrile with DIEA in DMF. After work-up, the resulting mixture was purified via normal phase chromatography. The appropriate regioisomeric product was coupled with 4-amino-N-methylindole in a manner described in scheme 43 (Pd(dba)$_2$ and Q-Phos). Subsequent hydration of the nitrile (scheme 43) afforded crude product that was purified via reverse phase HPLC. MS found for C21H24F2N6O as (M+H)$^+$ 415.4. UV: λ=220, 278, 327 nm. $^1$H NMR: (CD3OD) δ 7.90-7.79 (2H, m), 7.23-7.10 (3H, m), 6.58 (1H, br), 6.12 (1H, d, J=8.0 Hz), 4.18-4.07 (1H, m), 3.80 (3H, s), 2.20-1.76 (6H, m) ppm.

Example 419

Preparation of 6-((1R,2S)-2-aminocyclohexy-lamino)-2-(pyrazolo[1,5-a]pyridin-3-ylamino)nicotinamide

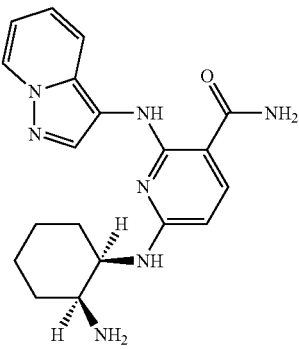 [SMILES: NC(=O)c1ccc(N[C@@H]2CCCC[C@@H]2N)nc1Nc1cnn2ccccc12]

The title compound was synthesized using a procedure similar to that described in Example 157. MS found for C19H23N7O as (M+H)$^+$ 366.4. UV: λ=278, 349 nm. $^1$H NMR: (CD3OD) δ 8.57 (1H, m), 8.15 (2H, m), 7.59 (1H, d, J=8.8 Hz), 7.32 (1H, m), 7.00 (1H, m), 6.27 (1H, m), 4.16 (1H, m), 3.47 (1H, m), 1.77-1.52 (8H, m) ppm.

Example 420

Preparation of 6-((1R,2R)-2-amino-3,3-difluorocyclohexylamino)-5-fluoro-2-(pyrazolo[1,5-a]pyridin-3-ylamino)nicotinamide

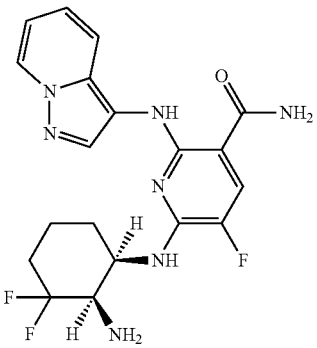 [SMILES: NC(=O)c1cc(F)c(N[C@@H]2CCCC(F)(F)[C@@H]2N)nc1Nc1cnn2ccccc12]

The title compound was synthesized using a procedure similar to that described in Example 291. MS found for C19H20F3N7O as (M+H)$^+$ 420.3. UV: λ=278, 347 nm. $^1$H NMR: (CD3OD) δ 8.44 (1H, m), 8.20 (1H, m), 7.80 (1H, m), 7.52 (1H, m), 7.21 (1H, m), 6.90 (1H, m), 4.46 (1H, m), 3.92 (1H, m), 2.06 (2H, m), 1.80 (3H, m), 1.65 (1H, m) ppm.

Example 421

Preparation of 6-((1R,2S)-2-aminocyclohexy-lamino)-4-(pyrazolo[1,5-a]pyridin-3-ylamino)nicotinamide

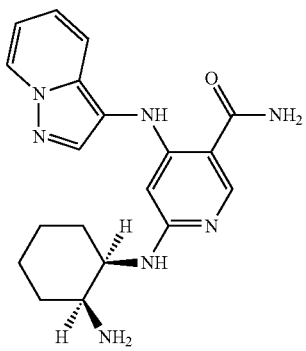

The title compound was synthesized using a procedure similar to that described in Example 194. MS found for C19H23N7O as (M+H)$^+$ 366.4. UV: λ=226, 244 nm. $^1$H NMR: (CD3OD) δ 8.58 (1H, d, J=7.6 Hz), 8.33 (1H, s), 8.06 (1H, s), 7.51 (1H, d, J=8.8 Hz), 7.32 (1H, t, J=8.8 Hz), 7.00 (1H, t, J=8.0 Hz), 5.93 (1H, s), 4.04 (1H, m), 3.46 (1H, m), 1.79-1.52 (8H, m) ppm.

Example 422

Preparation of 6-(1R,2S)-2-aminocyclohexylamino)-4-(thieno[2,3-b]pyridin-3-ylamino)nicotinamide

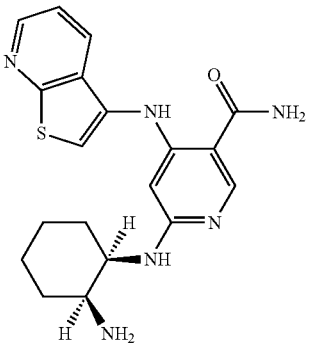

The title compound was synthesized using a procedure similar to that described in Example 194. MS found for C19H22N6OS as (M+H)$^+$ 383.3. UV: λ=249 nm. $^1$H NMR: (CD3OD) δ 8.65 (1H, d, J=4.4 Hz), 8.38 (1H, s), 8.12 (1H, d, J=8.4 Hz), 7.81 (1H, s), 7.51 (1H, m), 6.23 (1H, s), 4.08 (1H, m), 3.49 (1H, m), 1.82-1.54 (8H, m) ppm.

Example 423

Preparation of (R)-6-(1-amino-1-oxobutan-2-ylamino)-5-fluoro-2-(thieno[2,3-b]pyridin-3-ylamino)nicotinamide

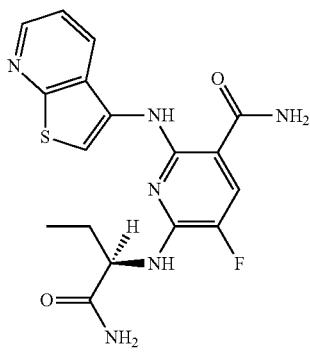 [SMILES: CC[C@@H](Nc1nc(Nc2csc3ncccc23)c(C(N)=O)cc1F)C(N)=O]

The title compound was synthesized using a procedure similar to that described in Example 97. MS found for C17H17FN6O2S as (M+H)+ 389.3. UV: λ=227, 281, 347 nm. $^1$H NMR: (CD3OD) δ 8.68 (1H, dd, J=4.8; 1.6 Hz), 8.45 (1H, dd, J=8.4; 1.6 Hz), 8.11 (1H, s), 7.82 (1H, d, J=12.0 Hz), 7.68 (1H, dd, J=8.0; 4.8 Hz), 4.46 (1H, m), 2.03 (1H, m), 1.93 (1H, m), 1.09 (3H, t, J=7.2 Hz) ppm.

Example 424

Preparation of (R)-6-(1-amino-1-oxobutan-2-ylamino)-5-fluoro-2-(pyrazolo[1,5-a]pyridin-3-ylamino)nicotinamide

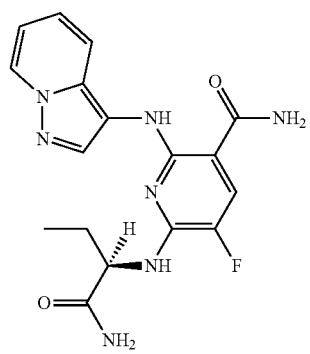 [SMILES: CC[C@@H](Nc1nc(Nc2cnn3ccccc23)c(C(N)=O)cc1F)C(N)=O]

The title compound was synthesized using a procedure similar to that described in Example 97. MS found for C17H18FN7O2 as (M+H)+ 372.3. UV: λ=283, 349 nm. $^1$H NMR: (CD3OD) δ 8.52-8.38 (2H, m), 7.80-7.70 (2H, m), 7.60 (1H, m), 7.28 (1H, m), 6.91 (1H, m), 4.37 (1H, m), 1.93 (1H, m), 1.79 (1H, m), 0.97 (3H, t, J=7.2 Hz) ppm.

Example 425

Preparation of (R)-6-(1-amino-1-oxobutan-2-ylamino)-2-(thieno[2,3-b]pyridin-3-ylamino)nicotinamide

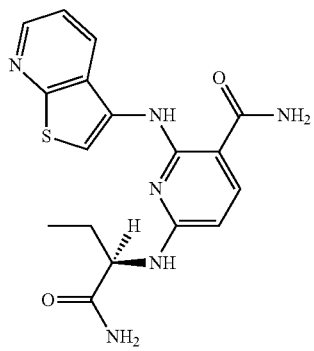 [SMILES: CC[C@@H](Nc1ccc(C(N)=O)c(Nc2csc3ncccc23)n1)C(N)=O]

The title compound was synthesized using a procedure similar to that described in Example 97. MS found for C17H18N6O2S as (M+H)+ 371.3. UV: λ=231, 278, 332 nm. $^1$H NMR: (CD3OD) δ 8.63 (1H, d, J=5.2 Hz), 8.37 (1H, d, J=7.6 Hz), 8.16 (1H, s), 7.88 (1H, d, J=9.2 Hz), 7.60 (1H, dd, J=8.0; 4.8 Hz), 6.14 (1H, d, J=4.8 Hz), 4.33 (1H, m), 1.98 (1H, m), 1.85 (1H, m), 1.09 (3H, t, 7.6 Hz) ppm.

Example 426

Preparation of 6-(1-(aminomethyl)cyclopropylamino)-2-(quinolin-6-ylamino)nicotinamide

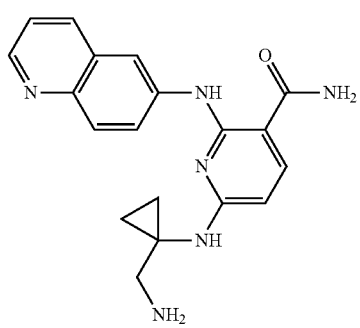 [SMILES: NCC1(Nc2ccc(C(N)=O)c(Nc3ccc4ncccc4c3)n2)CC1]

The title compound can be synthesized according to example 132 utilizing tert-butyl (1-aminocyclopropyl)methylcarbamate instead of tert-butyl (1S,2R)-2-aminocyclohexylcarbamate and 6-aminoquinoline instead of 3-(2H-1,2,3-triazol-2-yl)aniline.

Example 427

Preparation of 6-((1R,2S)-2-aminocyclohexylamino)-5-fluoro-2-(1-isopropyl-1H-pyrazol-4-ylamino)nicotinamide

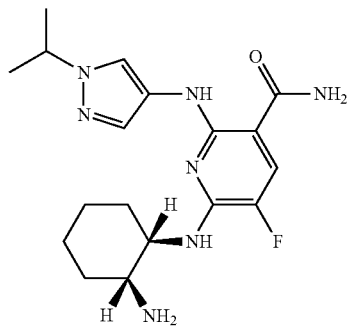 [SMILES: CC(C)n1cc(Nc2nc(N[C@@H]3CCCC[C@@H]3N)c(F)cc2C(N)=O)cn1]

The title compound was prepared using the same chemistry shown in Example 312. UV: 281 nm. M+H found C18H26FN7O: 376.4. NMR (CD3OD): 7.82 (1H, s), 7.65 (1H, d, J=12.0 Hz), 7.63 (1H, s), 4.47 (1H, m), 4.30 (1H, m), 3.41 (1H, m), 1.82-1.52 (8H, m), 1.49 (6H, d, J=6.8 Hz) ppm.

This example illustrates methods for evaluating the compounds of the invention, along with results obtained for such assays. The in vitro and in vivo human Syk activities of the inventive compounds can be determined by various procedures known in the art, such as a test for their ability to inhibit the activity of human plasma Syk. The potent affinities for human Syk inhibition exhibited by the inventive compounds can be measured by an $IC_{50}$ value (in nM). The $IC_{50}$ value is the concentration (in nM) of the compound required to provide 50% inhibition of human Syk proteolytic activity. The smaller the $IC_{50}$ value, the more active (potent) is a compound for inhibiting Syk activity.

An in vitro assay for detecting and measuring inhibition activity against Syk is as follows:
Inhibition of Syk Tyrosine Phosphorylation Activity Potency of candidate molecules for inhibiting Syk tyrosine phosphorylation activity is assessed by measuring the ability of a test compound to inhibit Syk-mediated tyrosine phosphorylation of a Syk-specific substrate.

SYK tyrosine phosphorylation activity is measured using the LANCE™ Technology developed by Perkin Elmer Life and Analytical Sciences (Boston, Mass.). LANCE™ refers to homogeneous time resolved fluorometry applications using techniques such as time-resolved fluorescence resonance energy transfer assay (TR-FRET) (see generally for procedures in Perkin Elmer Application Note—How to Optimize a Tyrosine Kinase Assay Using Time Resolved Fluorescence-Based LANCE Detection, wwww.perkinelmer.com/lifesciences). The assay principle involves detection of a phosphorylated substrate using energy transfer from a phosphospecific europium-labeled antibody to streptavidin-allophycocyanin as an acceptor.

To test the ability of candidate molecules to inhibit SYK tyrosine phosphorylation activity, molecules are reconstituted in 30% DMSO and serially diluted 1:3 with the final dilution containing DMSO in the absence of the candidate molecule. The final DMSO concentration in the assay is 3%. Kinase assays are performed as a two part reaction. The first reaction is a kinase reaction and which comprises of a candidate molecule, full length active recombinant SYK enzyme (Millipore, Calif.) and biotin-labeled SYK-specific substrate biotin-DEEDYESP-OH. The second reaction involves termination of the kinase reaction and the simultaneous addition of the detection reagents—europium-labeled anti-phosphotyrosine reagent (Eu-W1024-PY100, Perkin Elmer, Boston, Mass.) and Streptavidin-Allophycocyanin detection reagent (SA-APC, Prozyme, Calif.). The kinase reaction is performed in a black U-bottom 96-well microtitre plate. The final reaction volume is 50 μL and contains a final concentration of 1 nM active SYK enzyme, 550 nM SYK-substrate, and 100 μM ATP diluted in a buffer containing 50 mM Tris pH 7.5, 5 mM $MgCl_2$, and 1 mM DTT. The reaction is allowed to proceed for 1 hour at room temperature. The quench buffer contains 100 mM Tris pH 7.5, 300 mM $NaCl_2$, 20 mM EDTA, 0.02% Brij35, and 0.5% BSA. The detection reagents are added to the reaction mixture at the following dilutions-1:500 for Eu-W1024-PY100 and 1:250 for SA-APC. The kinase reaction is terminated by the addition of 50 μL quench buffer containing the detection reagents. The detection is allowed to proceed for 1 hr at room temperature. Detection of the phosphorylated substrate in the absence and presence of inhibitors is measured in the TR-FRET instrument, Analyst HT (Molecular Probes, Sunnyvale, Calif.) and the condition for measurements are set up using CriterionHost Release 2.0 (Molecular Probes, Sunnyvale, Calif.). The settings used are a follows: excitation 360 nm, emission 665-7.5 nm, beam splitter 350 nm 50/50, flash 100 pulses, delay 60 us, integration 400 us, z-height 2 mm. Inhibition of SYK-tyrosine kinase activity is calculated as the maximum response observed in the presence of inhibitor, compared to that in the absence of inhibitor. $IC_{50}$s were derived by non-linear regression analysis.

Intracellular phospho-flow cytometry was used to test compound inhibition of Syk activity in the non-Hodgkin's lymphoma cell line Ramos. $1 \times 10^6$ cells in log phase growth were aliquoted; Syk kinase is activated by incubating cells for 10 minutes with 3 μg/ml antibody specific to the B cell receptor. Directly following, cells are fixed in 1% paraformaldehyde for 5 minutes at room temperature, washed in phosphate buffered saline, and then permeablized by incubation for 2 hours in ice cold methanol. Cells are again washed in phosphate buffered saline, then incubated for 30 minutes with antibody specific for phosphorylated Erk (Y204), which are indicators of Syk kinase activity. All antibodies used are purchased from BD Pharmingen (San Jose, Calif.). After incubation with antibodies, cells are again washed and subjected to flow cytometry.

The anti-proliferative effects of compounds on non-Hodgkin's lymphoma B cell lines SUDHL-4, SUDHL-6, and Toledo was also assessed. SUDHL-4 and SUDHL-6 require B cell receptor signaling for growth and survival, while the Toledo cell line (serving here as a negative control) does not. Cells were aliquoted into each well of a 96-well plate and incubated with increasing concentrations of compound for 72 hours, after which cell survival and proliferation was determined using the MTT assay (Chemicon International, Inc., Temecula, Calif.) following protocols supplied by the manufacturer. Data are detailed in the Tables and Figures herein as $IC_{50}$ values plus or minus standard deviations from 5 or 6 independent experiments.

Induction of apoptosis in non-Hodgkin's lymphoma B cell lines SUDHL-4, SUDHL-6, and Toledo was assessed by measuring the apoptotis marker Caspase 3. Cells were incubated with 1, 3, or 10 µM compound for 24, 48, and 72 hours. At the conclusion of each time point, cells were processed for flow cytometry analysis using the Monoclonal Rabbit Anti-Active Caspase-3 Antibody Kit and related protocols (BD Pharmingen). Data from two independent experiments are presented in Table 1, representing the percent of total cells undergoing apoptosis following incubation with compounds under the indicated conditions.

Syk activity is not only required for B cell signaling, proliferation, and survival, as shown, but is also critical for cellular activation upon cross-linking of the B cell receptor. B cell activation leads to increased cell surface expression of several proteins involved in cell signaling, antigen presentation, and adhesion. Among these, CD80, CD86, and CD69 are commonly measured to determine B cell activation status. Therefore, primary mouse B cells isolated from spleen were aliquoted and incubated with increasing concentrations of compound (0.05 to 2 µM) in the presence of goat anti-mouse IgD (eBiosciences, Inc., San Diego, Calif.) for 20 hours to cross-link the B cell receptor. Following, cells were washed and incubated for 30 minutes on ice with antibodies specific for the CD80, CD86, and CD69 B cell activation markers. B cells were identified from the pooled population by staining with the B cell marker CD45RO. All antibodies were purchased from BD Pharmingen. Table 1 depicts the $IC_{50}$ range in which these compounds inhibited B cell receptor induced activation of mouse primary B cells In the table below, activity in the Syk assays is provided as follows: +++++=$IC_{50}$<0.0010 µM; ++++=0.0010 µM<$IC_{50}$<0.010 µM, +++=0.010 µM<$IC_{50}$<0.10 µM, ++=0.10 µM<$IC_{50}$<1 µM, +=$IC_{50}$>1 µM.

TABLE 1

| Example No. | Syk IC50 | Syk B-Cell Percent Inhibition at 0.050 uM | Syk B-Cell Percent Inhibition at 0.25 uM |
|---|---|---|---|
| 1 | + | — | — |
| 2 | ++ | — | — |
| 3 | + | — | — |
| 4 | ++ | — | — |
| 5 | ++ | — | — |
| 6 | +++ | +++ | +++++ |
| 7 | +++ | +++ | +++++ |
| 8 | + | — | — |
| 9 | +++ | +++ | +++++ |
| 10 | ++ | — | — |
| 11 | ++ | — | — |
| 12 | ++ | — | — |
| 13 | ++ | — | — |
| 14 | +++ | — | — |
| 15 | ++ | — | — |
| 16 | ++ | — | — |
| 17 | +++ | — | — |
| 18 | ++ | — | — |
| 19 | + | — | — |
| 20 | +++ | ++++ | +++++ |
| 21 | +++ | ++ | +++++ |
| 22 | +++ | — | — |
| 23 | + | — | — |
| 24 | ++++ | +++ | ++++ |
| 25 | +++ | +++ | ++++ |
| 26 | +++ | +++ | ++++ |
| 27 | +++ | +++ | ++++ |
| 28 | ++ | + | ++ |
| 29 | ++ | — | — |
| 30 | ++ | — | — |
| 31 | +++ | ++ | ++++ |
| 32 | ++ | — | — |
| 33 | +++ | — | — |
| 34 | +++ | — | — |
| 35 | +++ | ++ | +++ |
| 36 | +++ | ++ | +++ |
| 37 | +++ | ++ | +++ |
| 38 | ++ | + | ++ |
| 39 | ++ | ++ | ++ |
| 40 | +++ | ++ | ++ |
| 41 | ++++ | ++++ | +++++ |
| 42 | ++++ | +++++ | +++++ |
| 43 | ++++ | +++++ | +++++ |
| 44 | ++++ | +++++ | +++++ |
| 45 | ++++ | ++++ | +++++ |
| 46 | ++++ | +++++ | +++++ |
| 47 | ++++ | ++ | +++++ |
| 48 | +++ | ++ | +++++ |
| 49 | +++ | +++ | +++++ |
| 50 | ++++ | ++++ | +++++ |
| 51 | ++++ | +++++ | +++++ |
| 52 | ++++ | +++++ | +++++ |
| 53 | +++ | ++ | ++++ |
| 54 | +++ | ++ | +++++ |
| 55 | ++++ | ++++ | +++++ |
| 56 | ++++ | +++++ | +++++ |
| 57 | ++++ | ++++ | +++++ |
| 58 | ++++ | ++++ | +++++ |
| 59 | ++++ | +++++ | +++++ |
| 60 | +++++ | +++++ | +++++ |
| 61 | ++++ | ++++ | +++++ |
| 62 | ++++ | ++ | +++++ |
| 63 | ++++ | +++++ | +++++ |
| 64 | +++++ | +++++ | +++++ |
| 65 | ++ | + | ++ |
| 66 | +++++ | +++++ | +++++ |
| 67 | +++++ | +++++ | +++++ |
| 68 | ++++ | +++++ | +++++ |
| 69 | ++++ | ++++ | +++++ |
| 70 | ++++ | +++++ | +++++ |
| 71 | ++++ | +++ | +++++ |
| 72 | ++++ | +++++ | +++++ |
| 73 | ++++ | +++ | +++++ |
| 74 | ++++ | +++++ | +++++ |
| 75 | ++ | + | ++ |
| 76 | ++++ | +++++ | +++++ |
| 77 | +++ | +++ | +++++ |
| 78 | ++++ | +++++ | +++++ |
| 79 | ++++ | ++++ | +++++ |
| 80 | ++++ | +++ | +++++ |
| 81 | +++ | ++++ | +++++ |
| 82 | ++++ | ++++ | +++++ |
| 83 | +++ | ++ | ++++ |
| 84 | ++ | + | ++ |
| 85 | ++++ | ++++ | +++++ |
| 86 | ++++ | +++ | +++++ |
| 87 | ++++ | +++++ | +++++ |
| 88 | ++++ | +++++ | +++++ |
| 89 | ++++ | +++ | +++++ |
| 90 | ++++ | ++++ | +++++ |
| 91 | ++++ | ++++ | +++++ |
| 92 | +++ | +++ | +++++ |
| 93 | ++++ | +++ | +++++ |
| 94 | ++++ | ++++ | +++++ |
| 95 | +++ | +++ | ++++ |
| 96 | +++ | ++ | ++++ |
| 97 | +++ | ++ | ++++ |
| 98 | +++ | +++ | +++++ |
| 99 | +++ | ++++ | +++++ |
| 100 | +++ | ++++ | +++++ |
| 101 | — | — | — |
| 102 | ++++ | — | — |
| 103 | ++ | — | — |
| 104 | ++ | — | — |
| 105 | ++ | — | — |
| 106 | ++++ | +++++ | +++++ |
| 107 | ++++ | +++++ | +++++ |
| 108 | +++ | ++++ | +++++ |
| 109 | +++ | — | — |
| 110 | ++++ | ++++ | ++++ |

TABLE 1-continued

| Example No. | Syk IC50 | Syk B-Cell Percent Inhibition at 0.050 uM | Syk B-Cell Percent Inhibition at 0.25 uM |
|---|---|---|---|
| 111 | ++ | — | — |
| 112 | +++ | +++ | +++++ |
| 113 | ++++ | +++++ | +++++ |
| 114 | +++ | ++++ | +++++ |
| 115 | ++++ | +++++ | +++++ |
| 116 | ++ | — | — |
| 117 | ++++ | +++++ | +++++ |
| 118 | ++++ | +++++ | +++++ |
| 119 | +++ | — | — |
| 120 | ++++ | ++++ | +++++ |
| 121 | +++ | +++ | +++++ |
| 122 | ++++ | +++++ | +++++ |
| 123 | ++++ | +++++ | +++++ |
| 124 | +++ | +++++ | +++++ |
| 125 | ++ | — | — |
| 126 | + | — | — |
| 127 | +++ | +++ | +++++ |
| 128 | ++++ | +++++ | +++++ |
| 129 | ++++ | +++++ | +++++ |
| 130 | ++++ | ++++ | +++++ |
| 131 | ++++ | ++++ | +++++ |
| 132 | ++++ | ++++ | +++++ |
| 133 | +++ | +++ | +++++ |
| 134 | ++++ | +++++ | +++++ |
| 135 | ++++ | +++++ | +++++ |
| 136 | ++++ | +++++ | +++++ |
| 137 | ++++ | +++++ | +++++ |
| 138 | ++++ | +++++ | +++++ |
| 139 | ++++ | +++++ | +++++ |
| 140 | +++ | ++ | +++++ |
| 141 | ++++ | ++++ | +++++ |
| 142 | + | — | — |
| 143 | + | — | — |
| 144 | — | — | — |
| 145 | — | — | — |
| 147 | ++ | — | — |
| 150 | ++++ | ++++ | +++++ |
| 151 | ++++ | ++ | +++++ |
| 152 | ++ | ++ | +++ |
| 153 | ++++ | +++ | +++++ |
| 154 | ++++ | +++++ | +++++ |
| 155 | + | ++ | +++ |
| 156 | ++++ | +++ | +++++ |
| 157 | +++ | +++ | +++++ |
| 158 | ++++ | ++++ | +++++ |
| 159 | ++++ | +++ | +++++ |
| 160 | +++ | ++ | +++++ |
| 161 | ++++ | +++++ | +++++ |
| 162 | ++++ | +++++ | +++++ |
| 163 | ++++ | ++++ | +++++ |
| 164 | ++++ | +++ | +++++ |
| 165 | ++++ | +++ | ++++ |
| 166 | ++ | + | + |
| 174 | ++++ | +++++ | +++++ |
| 175 | +++ | +++++ | +++++ |
| 176 | +++ | — | — |
| 177 | + | — | — |
| 178 | +++ | — | — |
| 179 | ++++ | +++ | +++++ |
| 180 | ++++ | +++++ | +++++ |
| 181 | ++++ | ++++ | +++++ |
| 182 | ++++ | +++++ | +++++ |
| 183 | ++++ | +++ | +++++ |
| 184 | ++++ | +++ | +++++ |
| 185 | ++++ | ++++ | +++++ |
| 186 | ++++ | ++ | +++++ |
| 187 | ++++ | +++ | +++++ |
| 188 | ++++ | + | ++++ |
| 189 | ++++ | +++++ | +++++ |
| 190 | +++ | ++ | +++++ |
| 192 | ++++ | ++ | ++++ |
| 196 | +++ | ++++ | +++++ |
| 198 | +++ | +++++ | +++++ |
| 199 | ++++ | ++++ | +++++ |
| 200 | +++ | +++++ | +++++ |
| 201 | ++ | — | — |
| 202 | +++ | +++++ | +++++ |
| 203 | ++++ | +++ | +++++ |
| 204 | +++ | ++ | +++++ |
| 205 | ++++ | ++++ | +++++ |
| 206 | +++ | ++ | +++++ |
| 207 | +++ | ++ | +++++ |
| 208 | +++ | — | — |
| 209 | +++ | — | — |
| 210 | +++ | ++ | +++++ |
| 211 | +++ | — | — |
| 212 | ++++ | +++ | +++++ |
| 213 | ++++ | ++++ | +++++ |
| 214 | +++ | ++ | +++++ |
| 215 | +++ | ++ | +++++ |
| 227 | +++ | +++ | +++++ |
| 228 | +++ | +++ | ++ |
| 229 | +++ | + | + |
| 230 | ++ | + | + |
| 231 | +++ | — | — |
| 232 | ++ | — | — |
| 233 | ++++ | ++ | ++++ |
| 234 | +++ | + | +++ |
| 235 | +++ | — | + |
| 236 | ++ | — | — |
| 237 | ++ | — | — |
| 239 | +++ | +++ | +++++ |
| 240 | ++ | — | — |
| 241 | +++ | +++++ | +++++ |
| 242 | +++ | — | — |
| 243 | +++ | +++ | +++++ |
| 244 | ++ | — | — |
| 245 | +++ | + | +++ |
| 246 | +++ | ++ | +++++ |
| 247 | +++ | +++ | +++++ |
| 248 | ++++ | +++++ | +++++ |
| 249 | +++ | — | — |
| 250 | +++ | ++ | ++++ |
| 251 | ++++ | ++ | ++++ |
| 252 | ++++ | +++ | +++++ |
| 253 | +++ | +++ | +++++ |
| 254 | ++++ | ++ | +++++ |
| 255 | ++++ | ++ | +++++ |
| 255 | +++ | — | — |
| 256 | ++++ | ++++ | +++++ |
| 257 | ++++ | +++++ | +++++ |
| 258 | +++ | ++++ | +++++ |
| 259 | ++++ | +++++ | +++++ |
| 260 | +++ | — | — |
| 261 | ++ | — | — |
| 262 | ++ | — | — |
| 263 | ++ | — | — |
| 264 | ++ | — | — |
| 265 | +++ | + | +++++ |
| 266 | +++ | — | — |
| 275 | +++ | +++++ | +++++ |
| 276 | ++++ | — | — |
| 279 | ++++ | — | — |
| 289 | ++ | — | — |
| 291 | +++ | +++++ | +++++ |
| 293 | ++ | — | — |
| 300 | +++ | — | — |
| 301 | +++ | — | — |
| 302 | +++ | — | — |
| 308 | ++ | — | — |
| 309 | +++ | +++++ | +++++ |
| 310 | ++++ | +++++ | +++++ |
| 312 | ++++ | — | — |
| 313 | +++ | + | ++++ |
| 314 | ++++ | +++++ | +++++ |
| 315 | ++++ | — | — |
| 316 | ++++ | +++++ | +++++ |
| 317 | ++++ | ++++ | +++++ |
| 318 | +++ | ++ | +++++ |
| 319 | +++ | ++ | +++++ |

TABLE 1-continued

| Example No. | Syk IC50 | Syk B-Cell Percent Inhibition at 0.050 uM | Syk B-Cell Percent Inhibition at 0.25 uM |
|---|---|---|---|
| 320 | ++++ | +++++ | +++++ |
| 321 | +++++ | +++++ | +++++ |
| 322 | ++++ | ++++ | +++++ |
| 323 | ++++ | +++ | +++++ |
| 324 | ++++ | +++++ | +++++ |
| 325 | ++++ | +++ | +++++ |
| 326 | +++++ | +++++ | +++++ |
| 327 | ++ | — | — |
| 328 | +++ | +++++ | +++++ |
| 329 | ++ | — | — |
| 330 | +++ | ++++ | +++++ |
| 331 | +++ | — | — |
| 332 | ++ | — | — |
| 333 | ++ | — | — |
| 334 | ++ | — | — |
| 335 | +++ | ++ | +++++ |
| 336 | ++ | — | — |
| 337 | ++ | — | — |
| 338 | ++ | — | — |
| 339 | +++ | — | — |
| 340 | ++++ | +++++ | +++++ |
| 341 | ++++ | +++++ | +++++ |
| 342 | +++ | — | — |
| 343 | ++++ | +++++ | +++++ |
| 344 | ++++ | +++++ | +++++ |
| 345 | ++++ | +++++ | +++++ |
| 346 | +++ | ++++ | +++++ |
| 347 | +++ | — | — |
| 348 | +++ | — | — |
| 349 | +++ | +++++ | +++++ |
| 351 | +++ | +++++ | +++++ |
| 358 | ++++ | +++++ | +++++ |
| 363 | ++++ | +++++ | +++++ |
| 365 | ++++ | +++++ | +++++ |
| 367 | ++ | — | — |
| 369 | ++ | — | — |
| 370 | + | — | — |
| 371 | + | — | — |
| 372 | +++ | +++ | ++++ |
| 373 | +++ | — | — |
| 376 | ++ | — | — |
| 377 | +++ | — | — |
| 378 | + | — | — |
| 379 | ++ | — | — |
| 380 | +++ | — | — |
| 381 | ++ | — | — |
| 382 | ++ | — | — |
| 383 | + | ++ | ++ |
| 384 | ++++ | +++++ | +++++ |
| 385 | ++++ | +++++ | +++++ |
| 386 | ++++ | +++++ | +++++ |
| 387 | ++ | — | — |
| 388 | ++++ | +++++ | +++++ |
| 389 | ++++ | +++++ | +++++ |
| 390 | +++ | + | +++++ |
| 391 | +++ | +++ | ++++ |
| 392 | ++ | — | — |
| 393 | ++++ | +++++ | +++++ |
| 394 | +++ | — | — |
| 395 | + | — | — |
| 396 | ++++ | +++++ | +++++ |
| 397 | ++++ | ++++ | +++++ |
| 398 | ++++ | +++++ | +++++ |
| 399 | ++++ | +++++ | +++++ |
| 400 | ++++ | +++++ | +++++ |
| 401 | ++++ | +++++ | +++++ |
| 402 | +++++ | +++++ | +++++ |
| 403 | ++++ | +++++ | +++++ |
| 404 | ++++ | +++++ | +++++ |
| 405 | +++ | — | — |
| 406 | +++ | ++++ | +++++ |
| 407 | +++ | + | +++ |
| 408 | ++ | — | — |
| 409 | + | + | ++ |
| 419 | ++++ | +++++ | +++++ |
| 420 | +++ | — | — |
| 421 | + | — | — |
| 422 | + | — | — |
| 423 | +++ | ++++ | +++++ |
| 424 | +++ | — | — |
| 425 | +++ | ++++ | +++++ |

Example 426

Millipore Upstate KinaseProfiler™ Screening

This assay is a direct measurement of the effect of compound on the catalytic activity of JAK3. Purified human JAK3 (GenBank AF513860) sequence (residue 781—C terminus) was obtained from insect cells. The catalytic hydrolysis of ATP is measured using a radiometric filter binding method. Incubation of kinase with $^{33}$[P]ATP and substrate leads to incorporation of $^{33}$[P] into the substrate which can then be separated from the other reaction components by filtration. Assays were performed using 10 μM ATP and in the absence or presence of 1, 0.3, or 0.1 μM compound. Activity was expressed as % of inhibition of control.

Example 376 IL4 Assay

Inhibition of IL4-induced phospho STAT6 formation was measured by pre-incubating 0.5 million Ramos B lymphocytes (ATCC) with 5 μl compound or DMSO vehicle for 1 hour at 37° C./5% CO2. Cells were activated by addition of 1 ng/ml [f] IL4 (R & D Research Systems) for 10 min at 37° C./5% CO2 and then fixed by addition of 1.6% [f] PFA (Electron Microscopy Services). Following a PBS wash step and permaeabilization with 100% methanol, cells were incubated with ALEXA-conjugated anti-phosphoSTAT6 (Y641) antibody (BD 612600). The extent of cell associated-fluorescence was determined by flow cytometry and data expressed as mean fluorescent intensity. The extent of inhibition of the IL4-induced signal was then calculated.

Example 427 Kinase Assay Protocols:

JAK and TYK2 tyrosine phosphorylation activity is measured using the Z'-LYTE™ Technology developed by Invitrogen Corporation (Carlsbad, Calif.). For JAK1, JAK2 and JAK3 the Z'-LYTE™ Kinase Assay Kit-Tyr6 Peptide (part number PV4122) was used. For TYK2 the Z'-LYTE™ Kinase Assay Kit-Tyr6 Peptide (part number PV3192) was used. The Z'-LYTE™ biochemical assay employs a fluorescence resonance energy transfer (FRET) coupled-enzyme format and is based on the differential sensitivity of phosphorylated and non-phosphorylated peptides to proteolitic cleavage. The assay uses a synthetic peptide substrate that is labelled with a donor fluorophore (coumarin) and an acceptor fluorophore (fluorescein) that make up a FRET pair. In the primary reaction (the Kinase Reaction), the kinase transfers the γ-phosphate of ATP to a single tyrosine residue on the substrate, while the presence of a kinase inhibitor in the primary reaction suppresses phosphorylation. In the secondary reaction (the Development Reaction), a site-specific protease (the Development Reagent) is added. The development buffer quenches the Kinase Reaction, while the protease recognizes and cleaves non-phosphorylated Z'-LYTE™ peptide substrate. Cleavage disrupts FRET between the donor and acceptor fluorophores on the non-phosphorylated substrate, while uncleaved, phosphorylated substrate maintains FRET.

To test the ability of candidate molecules to inhibit JAK tyrosine phosphorylation activity, molecules are reconstituted in 100% DMSO and serially diluted 1:10 in polypropylene v-bottom microtiter plates. The candidate molecules are then diluted 1:25 into kinase buffer and 2.5 µl transferred into duplicate wells of a 384 well low volume black microtiter assay plate (Corning, USA). The final DMSO concentration in the assay is 1%. The kinase reaction contains 2.5 µl of a candidate molecule, 50 of catalytic domain recombinant Kinase enzyme+Tyr peptide substrate (Invitrogen, CA) and 2.5 µl ATP (Invitrogen, CA). The kinase reaction is allowed to proceed for 1 hour at room temperature. The protease reaction is initiated by the addition of 5 µl Development Reagent (Invitrogen, CA). After 1 hour incubation at room temperature the fluorescence is measured using a FlexStation plate reader (Molecular Devices, Sunnyvale, Calif.). The reader settings used are as follows: Fluorescence mode, endpoint, top read, excitation 400 nm, emission 445 nm and 520 nm, Auto Cutoff 435 nm and 515 nm, PMT sensitivity high, 6 reads per well. Inhibition of JAK activity is calculated as the percent phosphorylation of substrate in the presence of inhibitor compared to the percent phosphorylation of substrate in the absence of inhibitor. IC50's were derived using XIfit 4.3 (IDBS, UK), 4 parameter logistic model 205: $Y=(A+((B-A)/(1+((C/x)^D))))$.

Inhibition of IL4-induced phospho STAT6 formation was measured by pre-incubating 0.5 million Ramos B lymphocytes (ATCC) with 5 µl compound or DMSO vehicle for 1 hour at 37° C./5% $CO_2$. Cells were activated by addition of 1 ng/ml [f] IL4 (R & D Research Systems) for 10 min at 37° C./5% $CO_2$ and then fixed by addition of 1.6% [f] PFA (Electron Microscopy Services). Following a PBS wash step and permaeabilization with 100% methanol, cells were incubated with ALEXA-conjugated anti-phosphoSTAT6 (Y641) antibody (BD 612600). The extent of cell associated-fluorescence was determined by flow cytometry and data expressed as mean fluorescent intensity. The extent of inhibition of the IL4-induced signal was then calculated.

Example 428 SYK Kinase Screening Assay

Phosphorylation of a peptide substrate by purified SYK kinase was measured using a FRET method. Following dilution in 30% DMSO, 5 µl compound was added to 45 ul reaction mix such that the final concentrations were 50 mM Tris pH 7.5, 5 mM $MgCl_2$, 4.7 nM syk enzyme (ProQuinase), 100 µM DDT, 100 µM ATP, and 545 nM biotin-DEEDYESP-OH substrate. Plates were incubated at room temperature for 1 hour and 50 µl detection buffer (100 mM Tris, pH 7.5, 300 mM $NaCl_2$, 20 mM EDTA, 0.02% Brij 35, 0.05% BSA (Sigma), 46 nM SureLight Allophycocyanin-Streptavidin (Perkin Elmer), and 21 nM LANCE Eu-W 1024 Anti-phosphotyrosine (Perkin Elmer)) added. Plates were incubated for a further 1 hour at room temperature and substrate phosphorylation determined using an Analyst (Molecular Devices) with the settings at Ex 360, Em 665, 60 µsec delay.

Example 429 Ramos B Cell SYK Screening

Formation of pERK downstream of SYK was measured using flow cytometry. Following dilution in 20% DMSO, 5 µl compound was added to 195 µl cells (2.5 million/ml) in RPMI 1940 media, 10% FBS, 1% penicillin-streptomycin and incubated for 1 hour at 37° C. Cells were stimulated through the B cell receptor by incubating with 3 µg/ml (final) donkey anti-human IgM antibody (Jackson Labs) for 10 min at 37° C. Reactions were terminated by addition of 16% PFA and cells incubated for 10 min at room temperature. Following addition of 2 ml cold PBS, cells were centrifuged (5 min at 365×g, RT) and the supernatant removed. Cells were resuspended in 2 ml 50% methanol/PBS (precooled to −20° C.) and incubated at 4° C. for 1 hr.

Methanol-treated cells were diluted by addition of 2 ml PBS and pelleted by centrifugation (5 min at 365×g, RT). Cells were washed once more in 2 ml PBS/1% BSA and resuspended in 100 ul 1/100 dilution of rabbit anti phosphoERK1/2 (Cell Signaling). Following incubation for 30 min at room temperature, cells were washed in 2 ml PBS/1% BSA and resuspended in 100 ul 1/100 dilution of APC conjugated goat anti rabbit IgG (Jackson Labs) in PBS/1% BSA.

Cells were incubated for 30 min at room temperature in the dark, washed in 2 ml PBS/1% BSA, and resuspended in 300 µl PBS. The geometric mean of the APC fluorescing population was measured using a FacsCaliber (Becton Dickinson).

As detailed herein, Syk has been implicated experimentally in B cell development, proliferation, and survival. Moreover, Syk is implicated as an oncogene. Expression of constitutively active Syk in adoptively transferred bone marrow cells induces leukemia in mice, and over-activity of Syk is associated with a variety of lymphomas in humans Given the role of Syk in B cell biology, its selective inhibition may be sufficient to provide clinical benefit in B cell proliferative disorders, while reducing toxicities that may arise due to suppression of other off-target kinases.

The present invention provides a number of embodiments. It is apparent that the examples may be altered to provide other embodiments of this invention. Therefore, it will be appreciated that the scope of this invention is to be defined by the appended claims rather than by the specific embodiments, which have been represented by way of example.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety. From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A compound of having the formula (I):

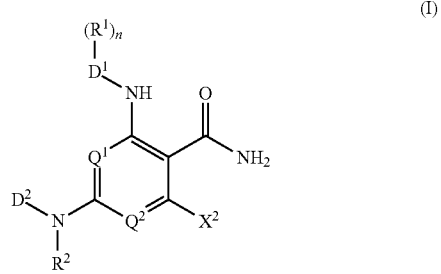

or a tautomer thereof or a pharmaceutically acceptable salt or hydrate thereof, wherein:
$Q^1$ is $CX^1$; $Q^2$ is $CX^1$ or N;
each $X^1$ is independently selected from the group consisting of: hydrogen, $C_{1-8}$ alkyl, halogen, cyano, and aminocarbonyl;
$X^2$ is H or halogen;

$D^1$ is selected from the group consisting of:
(a) aryl;
(b) heteroaryl; and
(c) heterocyclyl;
each $R^1$ is independently selected from the group consisting of $C_{1-8}$ alkyl, $C_{2-8}$ alkenyl, $C_{2-8}$alkynyl, $C_{1-8}$alkoxy, $C_{1-8}$alkylthio, aminocarbonyl, $C_{1-8}$alkoxycarbonylC$_{1-8}$ alkylene, $C_{1-8}$alkoxycarbonylC$_{1-8}$alkoxy, $C_{1-8}$alkoxycarbonylamino, oxo, halo, cyano, haloC$_{1-8}$alkyl, haloC$_{1-8}$alkoxy, aminosulfonyl, heteroarylsulfinyl; amino, hydroxyl, $C_{1-8}$arylalkylene, phenyl, aminoC$_{1-8}$alkyl, aminoC$_{3-8}$cycloalkyl, heterocyclyl, heteroaryl, heterocyclylC$_{1-8}$alkylene and hydroxyC$_{1-8}$alkylene;
$D^2$ is selected from the group consisting of:

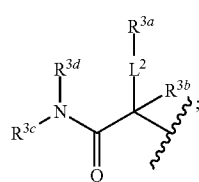

(a)

$R^{3a}$ is selected from the group consisting of: H, $C_{1-8}$alkyl, $C_{1-8}$alkenyl, $C_{1-8}$alkynyl, hydroxyl, oxo, amino, thio, halo, carboxy, aminocarbonyl, $C_{1-8}$alkoxy, haloC$_{1-8}$alkoxy, $C_{1-8}$alkylamino, diC$_{1-8}$alkylamino, cyano, $C_{1-8}$alkylthio, $C_{1-8}$alkylsulfonyl, aminocarbonyl, $C_{1-8}$alkoxycarbonylamino, $C_{1-8}$ alkylC$_{3-8}$cycloalkyl, $C_{3-8}$cycloalkyl, $C_{3-8}$cycloalkyloxy, $C_{3-8}$cycloalkylamino, $C_{3-8}$cycloalkylthio, heteroaryl, heteroarylalkoxy, aryl, arylalkoxy, heterocyclyl and heterocyclyloxy; wherein the aryl is optionally substituted by hydroxyl, $C_{1-8}$alkyl, $C_{1-8}$alkoxy, halo, haloC$_{1-8}$alkyl, $C_{1-8}$alkylsulfonyl or heteroaryl;
$R^{3b}$ is selected from the group consisting of: H and $C_{1-8}$alkyl; or may be combined with $R^{3a}$ to form a 3 to 8 membered carbocyclic or heterocyclic ring;
$R^{3c}$ is selected from the group consisting of: H, $C_{1-8}$alkyl and $C_{3-8}$cycloalkyl; or taken together with $R^{3d}$ and the atoms to which they are attached to form a heterocyclyl ring;
$R^{3d}$ is selected from the group consisting of: H, $C_{1-8}$alkyl and $C_{3-8}$cycloalkyl;
$L^2$ is selected from the group consisting of a bond and $C_{1-8}$alkylene;

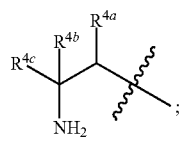

(b)

$R^{4a}$ is independently selected from the group consisting of: $C_{1-8}$alkyl, hydroxyC$_{1-8}$alkyl, $C_{1-8}$haloalkyl, amino, $C_{1-8}$alkylamino, $C_{1-8}$ alkoxycarbonylaminoC$_{1-8}$ alkylene, $C_{3-8}$cycloalkyl, heteroaryl, $C_{1-8}$ alkylC$_{3-8}$cycloalkyl, $C_{1-8}$alkylthioC$_{1-8}$ alkyl, $C_{1-8}$alkylsulfonylC$_{1-8}$ alkylene, aminocarbonyl, $C_{1-8}$alkoxyC$_{1-8}$alkyl, $C_{1-8}$alkoxyC$_{1-8}$alkoxy, haloC$_{1-8}$alkyl, aryl and heterocyclyl; wherein the aryl is optionally substituted by hydroxyl, $C_{1-8}$alkoxy, halo or haloC$_{1-8}$alkyl; or taken together with $R^{4b}$ and the atoms to which they are attached to form a $C_{3-8}$ cycloalkyl or heterocycloalkyl ring;
$R^{4b}$ is selected from the group consisting of $C_{1-8}$alkyl, $C_{1-8}$alkylamino, amino, aminoC$_{1-8}$alkyl, carboxy, $C_{1-8}$alkylaminoC$_{1-8}$alkyl, $C_{1-8}$alkoxyC$_{1-8}$alkyl, hydroxyC$_{1-8}$alkyl; carboxyC$_{1-8}$alkyl, $C_{3-8}$cycloalkylC$_{1-8}$ alkyl, aryloxyC$_{1-8}$alkyl, arylC$_{1-8}$alkyl, heteroarylC$_{1-8}$alkyl, and hydroxyC$_{1-8}$alkoxy; or may be combined with $R^{4a}$ or $R^{4c}$ and the atoms to which they are attached to form a $C_{3-8}$ cycloalkyl or heterocyclyl ring;
$R^{4c}$ is H or alkyl or may be combined with $R^{4b}$ and the atoms to which they are attached to form a $C_{3-8}$ cycloalkyl or heterocyclyl ring;
(c) $C_{3-8}$cycloalkyl; optionally substituted with from 1 to 3 substituents, $R^{6a}$, independently selected from the group consisting of $C_{1-8}$alkyl, $C_{1-8}$alkoxyC$_{1-8}$alkyl, aminocarbonyl-, hydroxy, oxo, halogen, $C_{1-8}$alkoxy and $C_{1-8}$alkylsulfonyl;
(d) heterocycloalkyl; optionally substituted with from 1 to 3 substituents, $R^{6a}$, independently selected from the group consisting of $C_{1-8}$alkyl, $C_{1-8}$alkoxyC$_{1-8}$alkyl, aminocarbonyl-, hydroxy, oxo, halogen, $C_{1-8}$alkoxy and $C_{1-8}$alkylsulfonyl; and
(e) arylalkylene; optionally substituted with from 1 to 3 substituents, $R^{6a}$, independently selected from the group consisting of $C_{1-8}$alkyl, $C_{1-8}$alkoxyC$_{1-8}$alkyl, aminocarbonyl-, hydroxy, oxo, halogen, $C_{1-8}$alkoxy and $C_{1-8}$alkylsulfonyl;
each $R^2$ is independently selected from the group consisting of H and $C_{1-8}$ alkyl;
the subscript n is 0, 1, 2, 3 or 4; and
the wavy line indicates the point of attachment to the rest of the molecule.

2. The compound of claim 1 having formula (Ia):

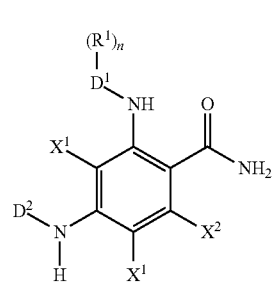

(Ia)

or a tautomer thereof or a pharmaceutically acceptable salt or hydrate thereof.

3. The compound of claim 1 having formula (Ib) or (Ic):

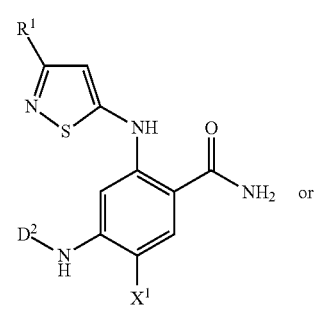

(Ib)

-continued

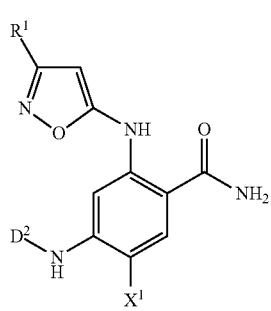

(Ic)

or a tautomer thereof or a pharmaceutically acceptable salt or hydrate thereof.

4. The compound of claim 1 having formula (Ie):

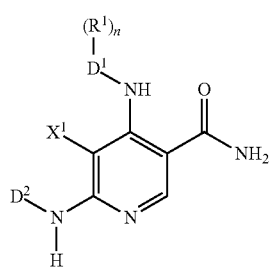

(Ie)

or a tautomer thereof or a pharmaceutically acceptable salt or hydrate thereof.

5. The compound of claim 1 wherein the compound has the formula (If):

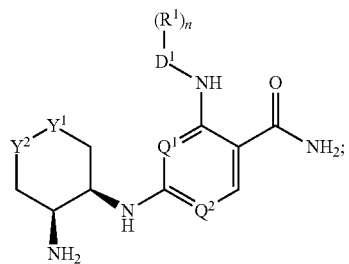

(If)

wherein each $Y^1$ and $Y^2$ is each independently selected from the group consisting of: O, $CR_2$, NH, $NCOCH_3$ and S.

6. The compound of claim 1 wherein the compound has the formula (Ig):

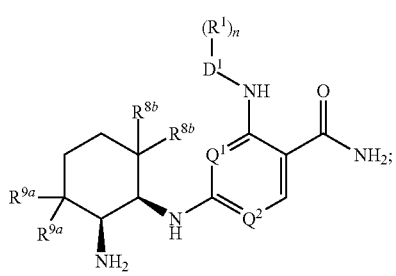

(Ig)

Wherein each $R^{9a}$ and $R^{8b}$ is independently H or F.

7. A compound of claim 6 wherein $D^1$ is selected from the group consisting of:

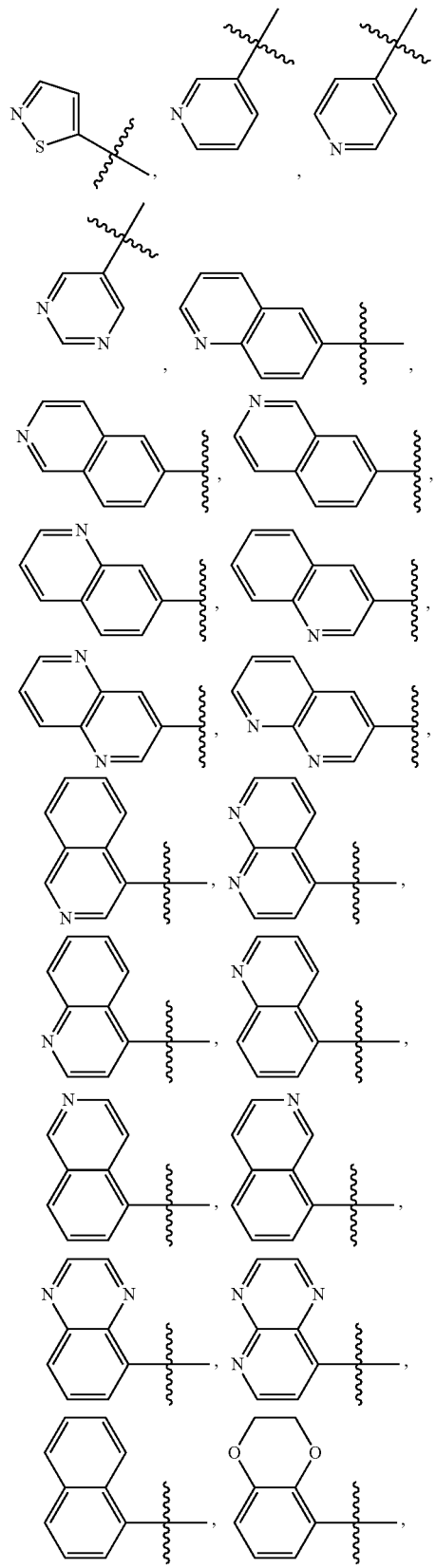

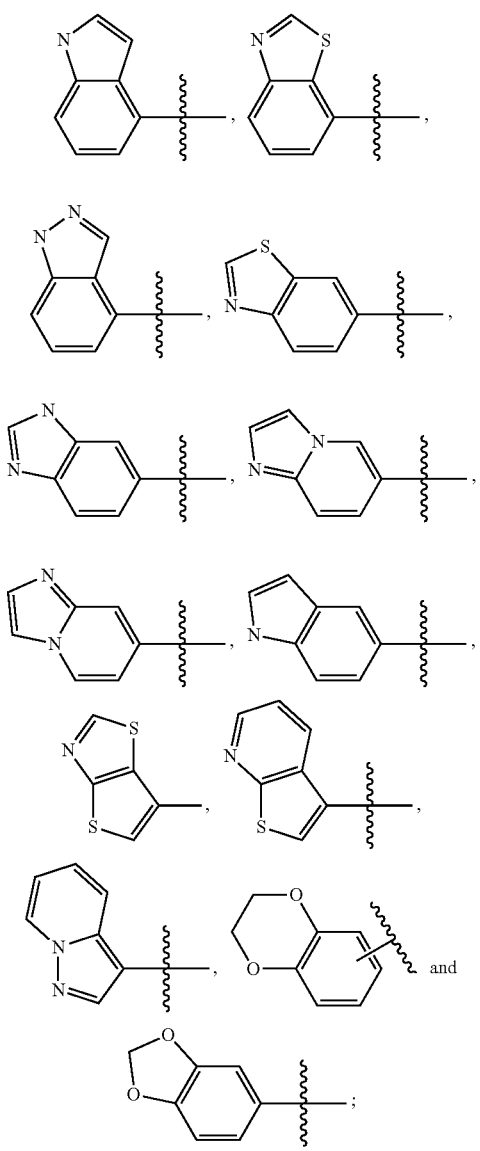

and

R¹ is alkyl, alkoxy or halo.

8. The compound of claim 6 wherein the compound has the formula (Ih):

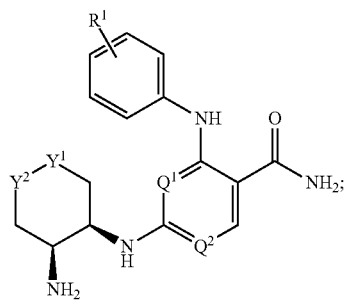

(Ih)

wherein each Y¹ and Y² is each independently selected from the group consisting of: O, CR₂, NH, NCOCH₃ and S.

9. The compound of claim 6 wherein the compound has the formula (Ii):

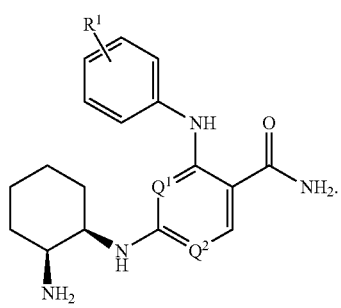

(Ii)

10. The compound of claim 6 wherein the compound has the formulae (Ija-la):

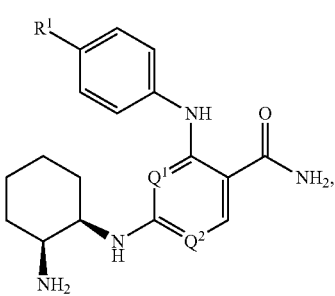

(Ija)

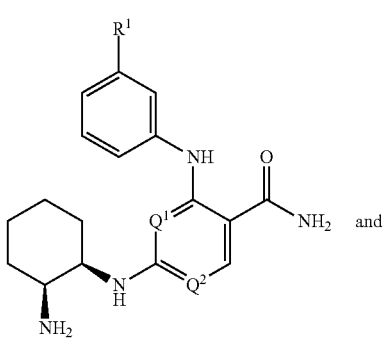

(Ika) and

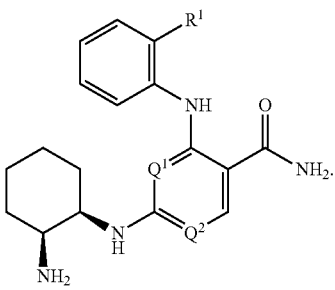

(Ila)

11. The compound of claim 6 wherein the wherein the compound has the formula (Im):

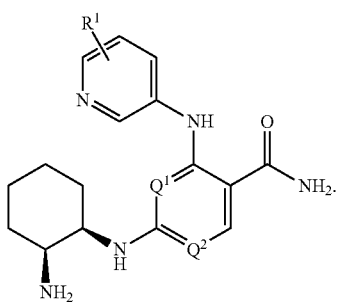
(Im)

12. The compound of claim 6 wherein the a compound, wherein the compound has the formulae (In-p):

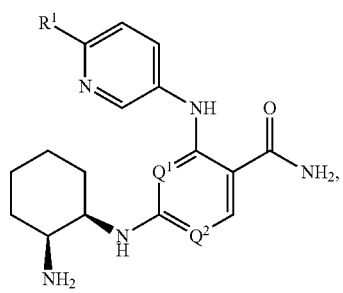
(In)

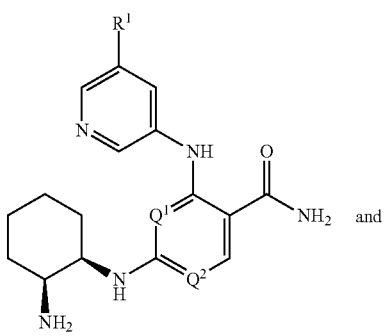
(Io)

and

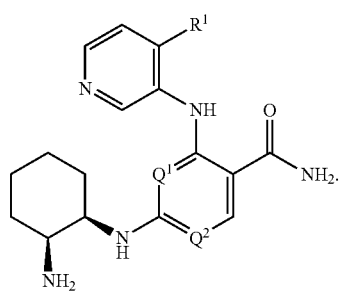
(Ip)

13. The compound of claim 6 wherein the a compound, wherein the compound has the formula (Iq):

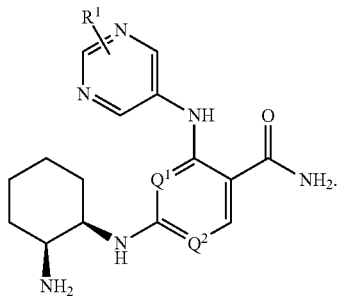
(Iq)

14. The compound of claim 6 wherein a compound, wherein the compound has the formulae (Ir):

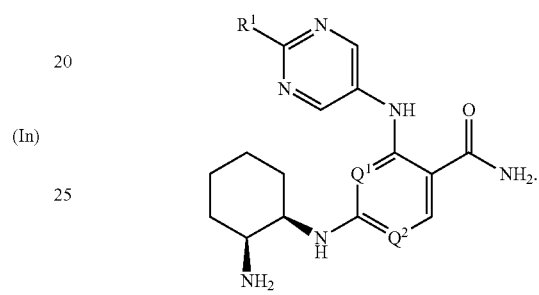
(Ir)

15. The compound of claim 6 wherein a compound, wherein the compound has the formulae (Is):

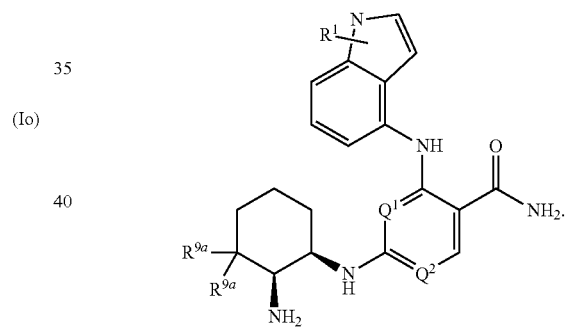
(Is)

16. The compound of claim 6 wherein a compound, wherein the compound has the formulae (It):

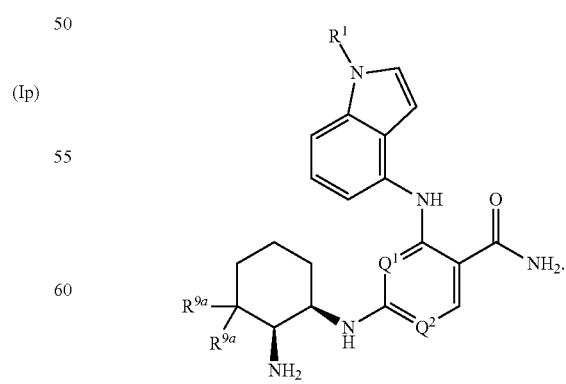
(It)

17. The compound of claim 6 wherein $R^1$ is selected from the group methyl or fluoro.

18. The compound of claim 1 wherein a compound having the formula (Im):

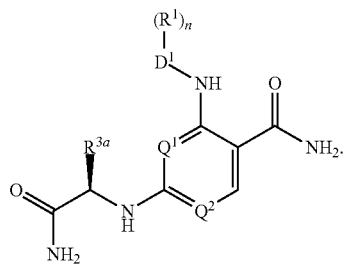
(Iu)

19. The compound of claim 18 wherein the compound has the formula (In):

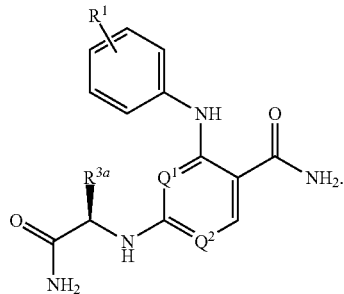
(Iv)

20. The compound of claim 18 wherein the compound has a formula selected from the group consisting of:

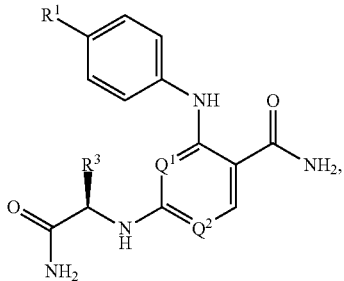
(Iw)

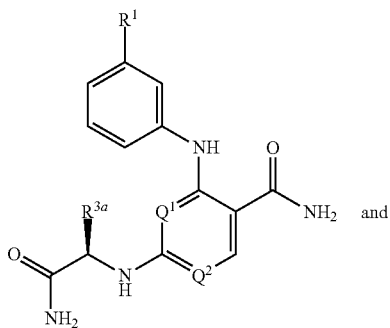
(Ix)

and

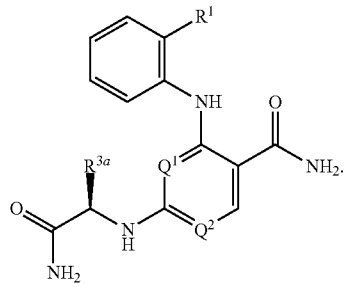
(Iy)

21. The compound of claim 20 wherein $R^{3a}$ is selected from the group consisting of $C_{1-8}$alkyl, $C_{3-8}$cycloalkyl, aryl, heteroaryl and heterocyclyl.

22. The compound of claim 20 wherein $R^{3a}$ is selected from the group consisting of methyl, ethyl, isopropyl, isobutyl, benzyl, benzyloxymethyl, hydroxymethyl, methoxymethyl, cyclohexylmethyl, phenyl, cyclopropyl, cyclohexyl, cyclopropylmethyl, ethyl, 4-fluorophenylmethyl, 3-fluorophenylmethyl, 4-pyridinylmethyl, 3-pyridinylmethyl, 4-hydroxyphenylmethyl, 4-methoxyphenylmethyl.

23. A composition comprising a compound of claim 1 in combination with a pharmaceutically acceptable carrier or diluent.

24. A method for inhibiting Syk kinase or a signal transduction pathway mediated at least in part by Syk kinase activity comprising the step of contacting a cell with a compound of claim 1.

25. A kit comprising a composition of claim 23, packaging and instructions for use.

26. The compound of claim 1 selected from the group consisting of:
  4-((1R,2S)-2-aminocyclohexylamino)-2-(m-tolylamino)benzamide;
  4-((1R,2S)-2-aminocyclohexylamino)-2-(1-methyl-1H-indol-4-ylamino)benzamide;
  4-((1R,2S)-2-aminocyclohexylamino)-2-(4-fluorophenylamino)benzamide;
  4-((1R,2S)-2-aminocyclohexylamino)-2-(3,5-dimethylphenylamino)benzamide;
  2-(3-(2H-1,2,3-triazol-2-yl)phenylamino)-4-((1R,2S)-2-aminocyclohexylamino)benzamide;
  4-((1R,2S)-2-aminocyclohexylamino)-2-(3-methylisothiazol-5-ylamino)benzamide;
  4-((1R,2S)-2-aminocyclohexylamino)-2-(3-phenylisoxazol-5-ylamino)benzamide;
  4-((1R,2S)-2-aminocyclohexylamino)-2-(1-methyl-1H-pyrazol-4-ylamino)benzamide;
  (R)-4-(1-amino-4-methyl-1-oxopentan-2-ylamino)-2-(3-methylisothiazol-5-ylamino)benzamide;
  (R)-4-(1-amino-1-oxopropan-2-ylamino)-2-(3-methylisothiazol-5-ylamino)benzamide;
  (R)-4-(1-amino-3-methyl-1-oxobutan-2-ylamino)-2-(3-methylisothiazol-5-ylamino)benzamide;
  (R)-4-(1-amino-4-methyl-1-oxopentan-2-ylamino)-2-(5-methylisoxazol-3-ylamino)benzamide;
  (R)-4-(1-amino-4-methyl-1-oxopentan-2-ylamino)-2-(3-methylisoxazol-5-ylamino)benzamide;
  (R)-4-(1-amino-1-oxo-3-phenylpropan-2-ylamino)-2-(3-methylisothiazol-5-ylamino)benzamide;
  (R)-4-(1-amino-3-(benzyloxy)-1-oxopropan-2-ylamino)-2-(3-methylisothiazol-5-ylamino)benzamide;
  (R)-4-(1-amino-3-hydroxy-1-oxopropan-2-ylamino)-2-(3-methylisothiazol-5-ylamino)benzamide;

(R)-4-(1-amino-3-cyclohexyl-1-oxopropan-2-ylamino)-2-(3-methylisothiazol-5-ylamino)benzamide;
(R)-4-(2-amino-2-oxo-1-phenylethylamino)-2-(3-methylisothiazol-5-ylamino)benzamide;
(R)-4-(1-amino-4-methyl-1-oxopentan-2-ylamino)-2-fluoro-6-(3-methylisothiazol-5-ylamino)benzamide;
(R)-4-(1-amino-4-methyl-1-oxopentan-2-ylamino)-5-fluoro-2-(3-methylisothiazol-5-ylamino)benzamide;
4-((1R,2S)-2-aminocyclohexylamino)-5-fluoro-2-(3-methylisothiazol-5-ylamino)benzamide;
(R)-4-(2-amino-1-cyclohexyl-2-oxoethylamino)-2-(3-methylisothiazol-5-ylamino)benzamide;
(R)-4-(1-amino-4-methyl-1-oxopentan-2-ylamino)-3-fluoro-2-(3-methylisothiazol-5-ylamino)benzamide;
(R)-4-(1-amino-1-oxo-3-phenylpropan-2-ylamino)-5-fluoro-2-(3-methylisothiazol-5-ylamino)benzamide;
(R)-4-(1-amino-3-cyclopropyl-1-oxopropan-2-ylamino)-5-fluoro-2-(3-methylisothiazol-5-ylamino)benzamide;
(R)-4-(1-amino-1-oxobutan-2-ylamino)-5-fluoro-2-(3-methylisothiazol-5-ylamino)benzamide;
(R)-4-(1-amino-3-(4-fluorophenyl)-1-oxopropan-2-ylamino)-5-fluoro-2-(3-methylisothiazol-5-ylamino)benzamide;
(R)-4-(1-amino-3-(4-hydroxyphenyl)-1-oxopropan-2-ylamino)-5-fluoro-2-(3-methylisothiazol-5-ylamino)benzamide;
(R)-4-(2-amino-3-methoxypropylamino)-2-(3-methylisothiazol-5-ylamino)benzamide;
(S)-4-(2-aminobutylamino)-2-(3-methylisothiazol-5-ylamino)benzamide;
(S)-4-(2-aminopropylamino)-2-(3-methylisothiazol-5-ylamino)benzamide;
(S)-4-(2-amino-4-methylpentylamino)-2-(3-methylisothiazol-5-ylamino)benzamide;
(R)-4-(1-amino-1-oxobutan-2-ylamino)-2-(3-methylisothiazol-5-ylamino)benzamide;
(R)-4-(1-amino-1-oxobutan-2-ylamino)-2-(3-methylisothiazol-5-ylamino)benzamide;
(R)-4-(1-amino-3-cyclopropyl-1-oxopropan-2-ylamino)-2-(3-methylisothiazol-5-ylamino)benzamide;
(R)-4-(1-amino-3-(4-methoxyphenyl)-1-oxopropan-2-ylamino)-5-fluoro-2-(3-methylisothiazol-5-ylamino)benzamide;
(R)-4-(1-amino-3-(3-fluorophenyl)-1-oxopropan-2-ylamino)-5-fluoro-2-(3-methylisothiazol-5-ylamino)benzamide;
(R)-4-(1-amino-1-oxo-3-(pyridin-4-yl)propan-2-ylamino)-5-fluoro-2-(3-methylisothiazol-5-ylamino)benzamide;
(R)-4-(1-amino-1-oxo-3-(pyridin-3-yl)propan-2-ylamino)-5-fluoro-2-(3-methylisothiazol-5-ylamino)benzamide;
(R)-4-(1-amino-3-methoxy-1-oxopropan-2-ylamino)-5-fluoro-2-(3-methylisothiazol-5-ylamino)benzamide;
6-(cis-2-aminocyclohexylamino)-4-(3-toluidino)nicotinamide;
6-(cyclopentylamino)-4-(4-morpholinophenylamino)nicotinamide;
4-(4-carbamoylphenylamino)-6-(cyclopentylamino)nicotinamide;
4-((1R,2S)-2-aminocyclohexylamino)-5-fluoro-2-(3-phenylisoxazol-5-ylamino)benzamide;
4-((1R,2S)-2-aminocyclohexylamino)-2-(3-methylisoxazol-5-ylamino)benzamide;
4-((1R,2S)-2-aminocyclohexylamino)-5-fluoro-2-(3-methylisoxazol-5-ylamino)benzamide;
(R)-4-(1-amino-3-(2-fluorophenyl)-1-oxopropan-2-ylamino)-5-fluoro-2-(3-methylisothiazol-5-ylamino)benzamide;
4-(3-(2H-1,2,3-triazol-2-yl)phenylamino)-6-((1R,2S)-2-aminocyclohexylamino)nicotinamide;
6-((1R,2S)-2-aminocyclohexylamino)-4-(3-methylisothiazol-5-ylamino)nicotinamide;
(R)-4-(2-amino-1-cyclopropyl-2-oxoethylamino)-5-fluoro-2-(3-methylisothiazol-5-ylamino)benzamide;
2-(3-methylisothiazol-5-ylamino)-4-(2-oxoazepan-3-ylamino)benzamide;
(R)-4-(1-amino-3-(1H-indol-3-yl)-1-oxopropan-2-ylamino)-2-(3-methylisothiazol-5-ylamino)benzamide;
(R)-4-(1-amino-1-oxo-3-(pyridin-2-yl)propan-2-ylamino)-5-fluoro-2-(3-methylisothiazol-5-ylamino)benzamide;
4-(1-amino-4,4,4-trifluoro-1-oxobutan-2-ylamino)-5-fluoro-2-(3-methylisothiazol-5-ylamino)benzamide;
(R)-4-(1-amino-1-oxo-3-(thiophen-2-yl)propan-2-ylamino)-2-(3-methylisothiazol-5-ylamino)benzamide;
(R)-4-(1-amino-1-oxo-3-(4-(pyridin-4-yl)phenyl)propan-2-ylamino)-5-fluoro-2-(3-methylisothiazol-5-ylamino)benzamide;
(R)-4-(3-(4-(1H-imidazol-1-yl)phenyl)-1-amino-1-oxopropan-2-ylamino)-5-fluoro-2-(3-methylisothiazol-5-ylamino)benzamide;
(R)-4-(1-amino-1-oxo-3-(4-(2-oxopyridin-1(2H)-yl)phenyl)propan-2-ylamino)-5-fluoro-2-(3-methylisothiazol-5-ylamino)benzamide;
(R)-4-(1-amino-3-(4-(methylsulfonyl)phenyl)-1-oxopropan-2-ylamino)-5-fluoro-2-(3-methylisothiazol-5-ylamino)benzamide;
(R)-4-(1-amino-1-oxo-3-(4-(pyridin-3-yl)phenyl)propan-2-ylamino)-5-fluoro-2-(3-methylisothiazol-5-ylamino)benzamide;
(R)-4-(1-amino-3-cyclopropyl-1-oxopropan-2-ylamino)-5-fluoro-2-(3-phenylisoxazol-5-ylamino)benzamide;
6-((1R,2S)-2-aminocyclohexylamino)-4-(pyrazolo[1,5-a]pyridin-3-ylamino)nicotinamide; and,
6-((1R,2S)-2-aminocyclohexylamino)-4-(thieno[2,3-b]pyridin-3-ylamino)nicotinamide, and pharmaceutically acceptable salts thereof.

* * * * *